US012351577B2

(12) United States Patent
Schiller et al.

(10) Patent No.: US 12,351,577 B2
(45) Date of Patent: Jul. 8, 2025

(54) INHIBITING CYCLIC AMP-RESPONSIVE ELEMENT-BINDING PROTEIN (CREB)

(71) Applicant: FORMA Therapeutics, Inc., Watertown, MA (US)

(72) Inventors: Shawn E. R. Schiller, Haverhill, MA (US); Torsten Herbertz, Watertown, MA (US); Hongbin Li, Madison, CT (US); Bradford Graves, Watertown, MA (US); Steven Mischke, Waltham, MA (US); Angela V. West, Watertown, MA (US); Anna Ericsson, Shrewsbury, MA (US); Jennifer R. Downing, Watertown, MA (US)

(73) Assignee: FORMA Therapeutics, Inc., Watertown, MA (US)

( * ) Notice: Subject to any disclaimer, the term of this patent is extended or adjusted under 35 U.S.C. 154(b) by 594 days.

(21) Appl. No.: 17/439,646

(22) PCT Filed: Mar. 13, 2020

(86) PCT No.: PCT/US2020/022818
§ 371 (c)(1),
(2) Date: Sep. 15, 2021

(87) PCT Pub. No.: WO2020/190791
PCT Pub. Date: Sep. 24, 2020

(65) Prior Publication Data
US 2022/0213089 A1 Jul. 7, 2022

Related U.S. Application Data

(60) Provisional application No. 62/819,108, filed on Mar. 15, 2019.

(51) Int. Cl.
*C07D 471/04* (2006.01)
(52) U.S. Cl.
CPC .................. *C07D 471/04* (2013.01)
(58) Field of Classification Search
None
See application file for complete search history.

(56) References Cited

U.S. PATENT DOCUMENTS

| | | | |
|---|---|---|---|
| 6,011,029 A | 1/2000 | Ding et al. |
| 7,101,869 B2 | 9/2006 | Blumenkopf et al. |
| 7,709,489 B2 | 5/2010 | Aranyi et al. |
| 9,211,333 B2 | 12/2015 | Zhang et al. |
| 9,763,922 B2 | 9/2017 | Adler et al. |
| 9,975,896 B2 | 5/2018 | Marineau et al. |
| 10,336,722 B2 | 7/2019 | Bair et al. |
| 10,562,916 B2 | 2/2020 | Campbell et al. |
| 10,870,648 B2 | 12/2020 | Schiller et al. |
| 2004/0214825 A1 | 10/2004 | McCall et al. |
| 2006/0106020 A1 | 5/2006 | Rodgers et al. |
| 2006/0167047 A1 | 7/2006 | Timmers et al. |
| 2007/0179165 A1 | 8/2007 | Gyorkos et al. |
| 2007/0203236 A1 | 8/2007 | Smith et al. |
| 2007/0254961 A1 | 11/2007 | Tapas et al. |
| 2009/0326020 A1 | 12/2009 | Yan et al. |
| 2010/0166781 A1 | 7/2010 | Setiadi et al. |
| 2010/0179325 A1 | 7/2010 | Suzuki et al. |
| 2010/0216853 A1 | 8/2010 | Marmorstein et al. |
| 2010/0267672 A1 | 10/2010 | Jung et al. |
| 2011/0257196 A1 | 10/2011 | Yan et al. |
| 2012/0108581 A1 | 5/2012 | Ashikawa et al. |
| 2012/0258953 A1 | 10/2012 | Aay et al. |
| 2013/0158003 A1 | 6/2013 | Campbell et al. |
| 2013/0324580 A1 | 12/2013 | Zhang et al. |
| 2016/0158207 A1 | 9/2016 | Adler et al. |
| 2016/0257692 A1 | 9/2016 | Bair et al. |
| 2020/0216445 A1 | 7/2020 | Schiller et al. |

FOREIGN PATENT DOCUMENTS

| | | |
|---|---|---|
| EP | 2 412 710 A1 | 1/2012 |
| JP | 2013-526615 | 6/2013 |
| JP | 2016-540831 | 12/2016 |
| JP | 2017-537100 | 12/2017 |
| WO | WO 1995/020589 A1 | 8/1995 |
| WO | WO 2002/040614 A1 | 5/2002 |
| WO | WO 2003/033517 A1 | 4/2003 |
| WO | WO 2003/045929 A1 | 6/2003 |
| WO | WO 2004/043392 A2 | 5/2004 |
| WO | WO 2005/066162 A1 | 7/2005 |

(Continued)

OTHER PUBLICATIONS

Herdemann. Journal of Organic Chemistry, 2002, 67, 1890-1897 (Year: 2002).*
Extended European Search Report from corresponding application EP 19 18 3741 (dated Aug. 1, 2019).
International Search Report from related application PCT/US2018/051235 (dated Feb. 25, 2019).
International Search Report from related application PCT/US2018/051214 (dated Dec. 4, 2018).
International Search Report from related application PCT/US2017/034320 (dated Nov. 15, 2017).
International Search Report from related application PCT/US2014/066198 (dated May 18, 2015).
International Search Report from related Application No. PCT/US2019/039936 (dated Sep. 23, 2019).
International Search Report from related Application No. PCT/US2020/022783 (dated Jun. 10, 2020).

(Continued)

*Primary Examiner* — Noble E Jarrell
(74) *Attorney, Agent, or Firm* — Tara A. Nealey; Polsinelli LLP

(57) ABSTRACT

The present disclosure is directed to inhibitors of the CBP/p300 family of bromodomains. The compounds can be useful in the treatment of disease or disorders associated with the inhibition of the CBP/p300 family of bromodomains. For instance, the disclosure is concerned with compounds and compositions for inhibition of the CBP/p300 family of bromodomains, methods of treating diseases or disorders associated with the inhibition of CBP/p300 family of bromodomains (e.g., certain forms of cancer), and methods of synthesis of these compounds.

19 Claims, 85 Drawing Sheets

(56) References Cited

FOREIGN PATENT DOCUMENTS

| | | |
|---|---|---|
| WO | WO 2007/120339 A1 | 10/2007 |
| WO | WO 2007/133653 A2 | 11/2007 |
| WO | WO 2008/009348 A1 | 1/2008 |
| WO | WO 2009/000413 A1 | 12/2008 |
| WO | WO 2009/064251 A1 | 5/2009 |
| WO | WO 2009/152072 A1 | 12/2009 |
| WO | WO 2010/110380 A1 | 9/2010 |
| WO | WO 2010/118208 A1 | 10/2010 |
| WO | WO 2010/138490 A1 | 12/2010 |
| WO | WO 2011/085039 A2 | 7/2011 |
| WO | WO 2011/109059 A1 | 9/2011 |
| WO | WO 2011/150156 A2 | 12/2011 |
| WO | WO 2012/019093 A1 | 2/2012 |
| WO | WO 2012/080729 A2 | 6/2012 |
| WO | WO 2012/082837 A1 | 6/2012 |
| WO | WO 2012/116135 A1 | 8/2012 |
| WO | WO 2013/004995 A1 | 1/2013 |
| WO | WO 2013/006485 A1 | 1/2013 |
| WO | WO 2013/148114 A1 | 10/2013 |
| WO | WO 2014/045305 A1 | 3/2014 |
| WO | WO 2014/133414 A2 | 9/2014 |
| WO | WO 2014/182929 A1 | 11/2014 |
| WO | WO 2015/002754 A2 | 1/2015 |
| WO | WO 2015/004533 A2 | 1/2015 |
| WO | WO 2015/013635 A1 | 1/2015 |
| WO | WO 2015/022322 A1 | 2/2015 |
| WO | WO 2015/073763 A1 | 5/2015 |
| WO | WO 2015/074064 A2 | 5/2015 |
| WO | WO 2015/074081 A1 | 5/2015 |
| WO | WO 2016/044694 A1 | 3/2016 |
| WO | WO 2016/086200 A1 | 6/2016 |
| WO | WO 2016/110821 A1 | 7/2016 |
| WO | WO 2016/128908 A1 | 8/2016 |
| WO | WO 2016/170323 A1 | 10/2016 |
| WO | WO 2016/170324 A1 | 10/2016 |
| WO | WO 2017/197056 A1 | 11/2017 |
| WO | WO 2017/197240 A1 | 11/2017 |
| WO | WO 2017/205536 A2 | 11/2017 |
| WO | WO 2018/073586 A1 | 4/2018 |
| WO | WO 2018/073587 A1 | 4/2018 |
| WO | WO 2019/055869 A1 | 3/2019 |
| WO | WO 2019/055877 A1 | 3/2019 |

OTHER PUBLICATIONS

International Search Report from related Application No. PCT/US2020/022818 (dated Jun. 15, 2020).

International Search Report from related Application No. PCT/US2020/022823 (dated Jun. 15, 2020).

PubChem CID: 138472436, create date, Aug. 20, 2019, p. 2 formula.

PubChem CID 136574372, deposited Jan. 24, 2019, pp. 1-8, p. 2.

"AR: Androgen Receptor", Depmap Portal, https://depmap.org/portal/gene/AR?tab=characterization (release 19Q2).

"Gene Set: Hallmark_Androgen Response", Gene Set Enrichment Analysis, http://software.broadinstitute.org/gsea/msigdb/cards/HALLMARK_ANDROGEN_RESPONSE.html.

Bowers, et al. Virtual Ligand Screening of the p300/CBP Histone Acetyltransferase: Identification of a Selective Small Molecule Inhibitor, Chemistry & Biology 17, pp. 471-482, May 28, 2010.

Chekler, Eugene L. et al. "Transcriptional Profiling of a Selective CREB Binding Protein Bromodomain Inhibitor Highlights Therapeutic Opportunities", Chemistry and Biology, 2015, 22(12), 1588-1596.

Crawford et al. "Discovery of a Potent and Selective Vivo Probe (GNE-272) for the Bromodomains fo CBP/EP300", J. Med. Chem., 2016, 56 pgs.

Duncan, A. Hay et al. "Discovery and Optimization of Small Molecule Ligands for the CBP/p300 Bromodomains", J. Am. Chem. Soc., 2014, 136(26), 9308-9319.

Fan et al. "p300 Modulates the BRCA1 Inhibition of Estrogen Receptor Activity", Cancer Research, 2002, 62, 141-151.

Garcia-Carpizo et al. "CREBBP/EP300 bromodomain inhibition affects the proliferation of AR positive breast cancer cell lines", Molecular Cancer Research, 2019.

Goff, Corinne Le et al. "Synthesis of some novel fused tetracyclic quinolonecarboxylic acids via 7-methyl-6,7,8,9-tetrahydro-3H-imidazo[4,5-f]quinoline and 6-methyl-5,6,7,8-tetrahydro-1H-imidazo[4,5-g]quinoline", Journal of Heterocyclic Chemistry, 1994, 31(1), 153-160.

Hammitzsch, "CBP30, a selective CBP/p300 bromodomain inhibitor, suppresses human Th 17 responses," Proceedings of the National Academy of Sciences 112.34 (2015): 10768-10773.

Jiang et al., "Small molecule Nas-e targeting cAMP response element binding protein (CREB) and CREB-binding protein interaction inhibits breast cancer bone metastasis" Journal of Cellular and Molecular Medicine, Nov. 20, 2018, vol. 23, pp. 1224-1234.

Jin et al. "Therapeutic Targeting of the CBP/p300 Bromodomain Blocks the Growth of Castration-Resistant Prostate Cancer", Cancer Research, 2017, 77(20), 5564-5575.

Kumar et al. "Androgen Receptor Immunohistochemistry as a Companion Diagnostic Approach to Predict Clinical Response to Enzalutamide in Triple-Negative Breast Cancer", JCO Precision Oncology, 2017, DOI: 10.1200/PO.17.00075.

Lasko et al. "Discovery of a selective catalytic p300/CBP inhibitor that targets lineage-specific tumours", Nature, 2017, vol. 000, 17 pgs.

Robinson et al., "Androgen receptor driven transcription in molecular apocrine breast cancer is mediated by FoxA1", The EMBO Journal, 2011, 30, 3019-3027.

Safarpour, Damoun et al. "Androgen receptor (AR) expression in 400 breast carcinomas: is routine AR assessment justified?", Am J Cancer Res, 2014, 4(4), 353-368.

Scher, Howard et al. "Association of AR-V7 on Circulating Tumor Cells as a Treatment-Specific Biomarker With Outcomes and Survival in Castration-Resistant Prostate Cancer", JAMA Oncology, 2016, 2(11), 1441-1449.

Scher et al. "Assessment of the Validity of Nuclear-Localized Androgen Receptor Splice Variant 7 in Circulating Tumor Cells as a Predictive Biomarker for Castration-Resistant Prostate Cancer" JAMA Oncology, 2018, 4(9), 1179-1186.

Snow et al., "Discovery of 2-Phenylamino-imidazo[4,5-h]isoquinolin-9-ones: a New Class of Inhibitors of Lck Kinase", Journal of Medicinal Chemistry, vol. 45, pp. 3394-3405.

Solankee et al. "Synthesis and evaluation of some novel S-triazine based chalcones and their derivatives", Der Pharma Chemica, 2011, 3(6), 317-324.

Traina et al. "Enzalutamide for the Treatment of Androgen Receptor-Expressing Triple-Negative Breast Cancer" Journal of Clinical Oncology, 2018, 36(9), 884-890.

Tucci, Marcello et al. "Enzalutamide-resistant castration-resistant prostate cancer: challenges and solutions", Onco Targets and Therapy, 2018, 11, 7353-7368.

Wong et al. "Anti-tumor activity of targeted and cytotoxic agents in murine subcutaneous tumor models correlates with clinical response", Clinical Cancer Research, 2012.

European Search Report from corresponding application EP 20 77 3477 (dated Nov. 21, 2022).

Moustakim et al.,, "Discovery of a PCAF Bromodomain Chemical Probe", Angewandte chemie, Dec. 14, 2016 , pp. 845-849, vol. 129.

\* cited by examiner

| Structure | Compound name | MS (ESI, m/z) [M+H]+ | $^1$H-NMR δ (ppm) |
|---|---|---|---|
| 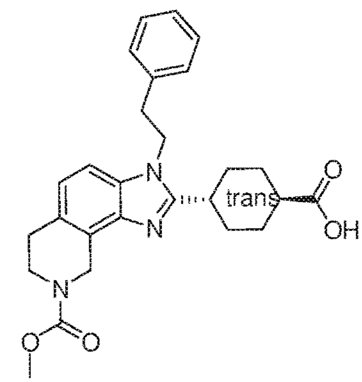 | trans-4-[8-(methoxycarbonyl)-3-(2-phenylethyl)-3H,6H,7H,8H,9H-imidazo[4,5-h]isoquinolin-2-yl]cyclohexane-1-carboxylic acid | 462 | 1H-NMR (CD3OD, 400 MHz) δ (ppm): 7.35 (d, J = 8.4 Hz, 1H), 7.24-7.15 (m, 3H), 7.07 (d, J = 8.4 Hz, 1H), 6.92-6.84 (m, 2H), 4.96 (s, 2H), 4.49 (t, J = 6.4 Hz, 2H), 3.82-3.69 (m, 5H), 3.11 (t, J = 6.4 Hz, 2H), 2.95 (t, J = 6.0 Hz, 2H), 2.38-2.21 (m, 2H), 2.03-1.89 (m, 2H), 1.67-1.52 (m, 2H), 1.47-1.26 (m, 4H). |
| 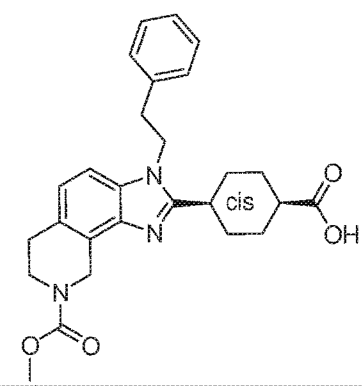 | cis-4-[8-(methoxycarbonyl)-3-(2-phenylethyl)-3H,6H,7H,8H,9H-imidazo[4,5-h]isoquinolin-2-yl]cyclohexane-1-carboxylic acid | 462 | 1H-NMR (CD3OD, 400 MHz) δ (ppm): 7.34 (d, J = 8.0 Hz, 1H), 7.22-7.20 (m, 3H), 7.07 (d, J = 7.2 Hz, 1H), 6.92-6.91 (m, 2H), 5.12-4.98 (m, 2H), 4.51-4.47 (m, 2H), 3.82-3.71 (m, 5H), 3.16-3.09 (m, 2H), 2.97-2.91 (m, 2H), 2.62-2.56 (m, 1H), 2.39-2.27 (m, 1H), 2.27-2.15 (m, 2H), 1.82-1.73 (m, 2H), 1.48-1.42 (m, 2H), 1.34-1.31 (m, 2H). |
| 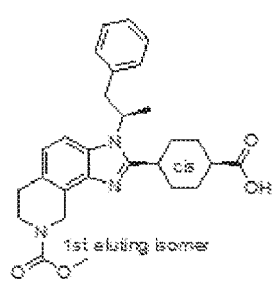 | cis-4-[8-(methoxycarbonyl)-3-[(2R)-1-phenylpropan-2-yl]-3H,6H,7H,8H,9H-imidazo[4,5-h]isoquinolin-2-yl]cyclohexane-1-carboxylic acid | 476 | 1H-NMR (CD3OD, 400 MHz) δ (ppm): 7.68 (d, J = 7.6 Hz, 1H), 7.18-7.06 (m, 4H), 6.79 (d, J = 3.2 Hz, 2H), 5.00-4.89 (m, 2H), 4.88-4.84 (m, 1H), 3.84-3.73 (m, 5H), 3.54-3.39 (m, 1H), 3.21-3.11 (m, 1H), 3.00-2.91 (m, 2H), 2.68-2.56 (m, 1H), 2.53-2.34 (m, 1H), 2.27-2.19(m, 1H), 2.18-2.08 (m, 1H), 1.81 (d, J = 6.8 Hz, 3H), 1.75-1.53 (m, 4H), 0.99-0.84 (m, 1H), 0.84-0.68 (m, 1H). |

FIGURE 1

| | | | |
|---|---|---|---|
| 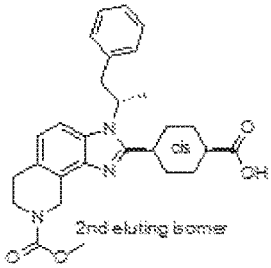<br>2nd eluting isomer | cis-4-[8-(methoxycarbonyl)-3-[(2S)-1-phenylpropan-2-yl]-3H,6H,7H,8H,9H-imidazo[4,5-h]isoquinolin-2-yl]cyclohexane-1-carboxylic acid | 476 | 1H-NMR (CD3OD, 400 MHz) δ (ppm): 7.68 (d, $J$ = 7.6 Hz, 1H), 7.17-7.05 (m, 4H), 6.79 (d, $J$ = 3.6 Hz, 2H), 5.01-4.92 (m, 2H), 4.85-4.78 (m, 1H), 3.82-3.69 (m, 5H), 3.53-3.40 (m, 1H), 3.23-3.11 (m, 1H), 2.97-2.92 (m, 2H), 2.69-2.53 (m, 1H), 2.53-2.33 (m, 1H), 2.28-2.19 (m, 1H), 2.18-2.07 (m, 1H), 1.81 (d, $J$ = 7.2 Hz, 3H), 1.76-1.54 (m, 4H), 1.46-1.34 (m, 1H), 0.88-0.66 (m, 1H). |
| 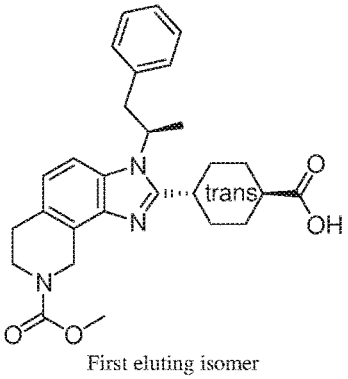<br>First eluting isomer | trans-4-[8-(methoxycarbonyl)-3-[(2R)-1-phenylpropan-2-yl]-3H,6H,7H,8H,9H-imidazo[4,5-h]isoquinolin-2-yl]cyclohexane-1-carboxylic acid | 476 | 1H-NMR (CD3OD, 400 MHz) δ (ppm): 7.68 (d, $J$ = 8.4 Hz, 1H), 7.19-7.00 (m, 4H), 6.86-6.71 (m, 2H), 4.96 (d, $J$ = 2.8 Hz, 2H), 4.88-4.83 (m, 1H), 3.82-3.73 (m, 5H), 3.52-3.41 (m, 1H), 3.22-3.11 (m, 1H), 2.98 (t, $J$ = 5.6 Hz, 2H), 2.48-2.34 (m, 1H), 2.31-2.22 (m, 1H), 2.11-1.96 (m, 1H), 1.92-1.76 (m, 5H), 1.65-1.43 (m, 3H), 1.32-1.14 (m, 1H), 0.92-0.72 (m, 1H). |
| 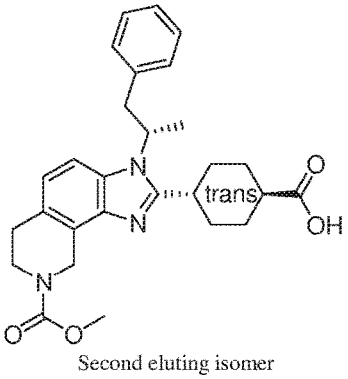<br>Second eluting isomer | trans-4-[8-(methoxycarbonyl)-3-[(2S)-1-phenylpropan-2-yl]-3H,6H,7H,8H,9H-imidazo[4,5-h]isoquinolin-2-yl]cyclohexane-1-carboxylic acid | 476 | 1H-NMR (CD3OD, 400 MHz) δ (ppm): 7.69 (d, $J$ = 8.2 Hz, 1H), 7.16-7.05 (m, 4H), 6.82-6.75 (m, 2H), 4.96 (d, $J$ = 2.4 Hz, 2H), 4.88-4.83 (m, 1H), 3.84-3.73 (m, 5H), 3.50-3.41 (m, 1H), 3.22-3.09 (m, 1H), 2.98 (t, $J$ = 5.2 Hz, 2H), 2.47-2.34 (m, 1H), 2.31-2.22 (m, 1H), 2.12-2.01 (m, 1H), 1.94-1.77 (m, 5H), 1.65-1.47 (m, 3H), 1.35-1.14 (m, 1H), 0.87-0.72 (m, 1H). |

FIGURE 1 (continued)

| Structure | Name | MW | NMR |
|---|---|---|---|
| 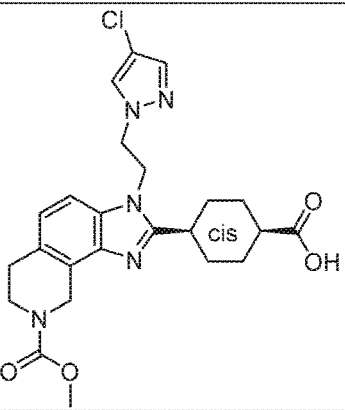 | (1r,4r)-4-[3-[2-(4-chloro-1H-pyrazol-1-yl)ethyl]-8-(methoxycarbonyl)-3H,6H,7H,8H,9H-imidazo[4,5-h]isoquinolin-2-yl]cyclohexane-1-carboxylic acid | 486 | 1H-NMR (CD3OD, 400 MHz) δ (ppm): 7.65 (s, 1H), 7.57 (d, J = 8.4 Hz, 1H), 7.46 (s, 1H), 7.40 (d, J = 8.4 Hz, 1H), 4.97-4.94 (m, 4H), 4.68-4.65 (m, 2H), 3.83-3.80 (m, 5H), 3.06-3.03 (m, 2H), 2.77-2.75 (m, 1H), 2.46-2.40 (m, 1H), 2.20-2.16 (m, 2H), 1.92-1.80 (m, 2H), 1.80-1.73 (m, 2H), 1.63-1.53 (m, 2H). |
| 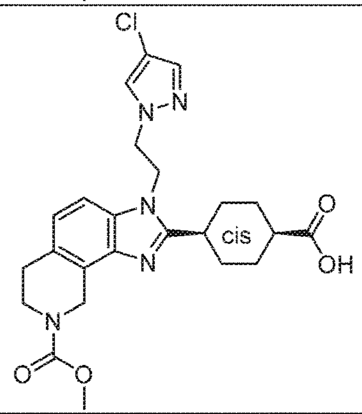 | (1s,4s)-4-[3-[2-(4-chloro-1H-pyrazol-1-yl)ethyl]-8-(methoxycarbonyl)-3H,6H,7H,8H,9H-imidazo[4,5-h]isoquinolin-2-yl]cyclohexane-1-carboxylic acid | 486 | 1H-NMR (CD3OD, 400 MHz) δ (ppm): 7.51 (s, 1H), 7.25 (d, J = 8.4 Hz, 1H), 7.24 (s, 1H), 7.06 (d, J = 8.4 Hz, 1H), 4.99 (s, 2H), 4.64-4.61 (m, 2H), 4.51-4.54 (m, 2H), 3.78-3.64 (m, 5H), 2.96-2.93 (m, 2H), 2.61-2.53 (m, 1H), 2.33-2.21 (m, 3H), 1.94-1.84 (m, 2H), 1.60-1.54 (m, 4H) |
| 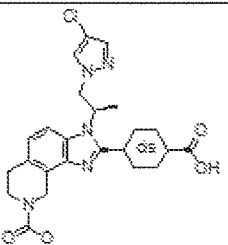First eluting isomer | (1s,4s)-4-[3-[(2R)-1-(4-chloro-1H-pyrazol-1-yl)propan-2-yl]-8-(methoxycarbonyl)-3H,6H,7H,8H,9H-imidazo[4,5-h]isoquinolin-2-yl]cyclohexane-1-carboxylic acid | | |
| 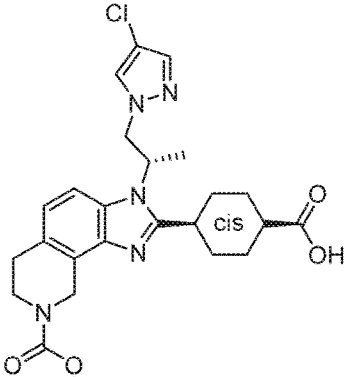Second eluting isomer | (1s,4s)-4-[3-[(2S)-1-(4-chloro-1H-pyrazol-1-yl)propan-2-yl]-8-(methoxycarbonyl)-3H,6H,7H,8H,9H-imidazo[4,5-h]isoquinolin-2-yl]cyclohexane-1-carboxylic acid | 500 | 1H-NMR (CD3OD, 400 MHz) δ (ppm): 7.60 (d, J = 8.0 Hz, 1H), 7.43 (s, 1H), 7.09 (d, J = 8.4 Hz, 1H), 7.00 (s, 1H), 5.13-5.05 (m, 1H), 4.97 (s, 2H), 4.85-4.80 (m, 1H), 4.59-4.55 (m, 1H), 3.81-3.73 (m, 5H), 2.97-2.95 (m, 2H), 2.72-2.64 (m, 1H), 2.59-2.49 (m, 1H), 2.34-2.21 (m, 2H), 1.98-1.90 (m, 1H), 1.78-1.55 (m, 7H), 1.36-1.32 (m, 1H). |

FIGURE 1 (continued)

| Structure | Name | # | NMR |
|---|---|---|---|
| 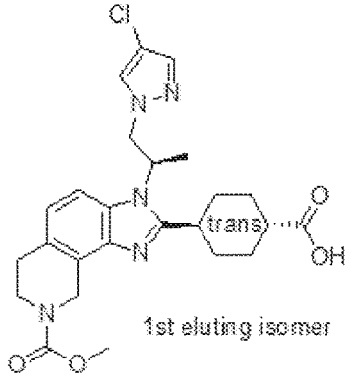 1st eluting isomer | methyl 3-[(2R)-1-(4-chloro-1H-pyrazol-1-yl)propan-2-yl]-2-[trans-4-(methoxycarbonyl)cyclohexyl]-3H,6H,7H,8H,9H-imidazo[4,5-h]isoquinoline-8-carboxylate | 500 | (CD3OD, 400MHz) δ (ppm): 7.62 (d, $J$ = 7.6 Hz, 1H), 7.43 (s, 1H), 7.11 (d, $J$ = 8.0 Hz, 1H), 7.03 (s, 1H), 5.14-5.07 (m, 1H), 4.98 (s, 2H), 4.84-4.82 (m, 1H), 4.60-4.55 (m, 1H), 3.80-3.78 (m, 5H), 2.98-2.96 (m, 2H), 2.56-2.50 (m, 1H), 2.38-2.35 (m, 1H), 2.11-2.05 (m, 2H), 1.92-1.82 (m, 2H), 1.78 (d, $J$ = 7.2 Hz, 3H), 1.67-1.61 (m, 2H), 1.52-1.43 (m, 2H). |
| 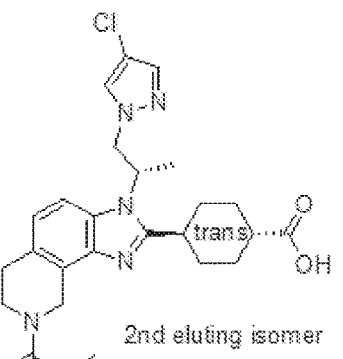 2nd eluting isomer | methyl 3-[(2S)-1-(4-chloro-1H-pyrazol-1-yl)propan-2-yl]-2-[trans-4-(methoxycarbonyl)cyclohexyl]-3H,6H,7H,8H,9H-imidazo[4,5-h]isoquinoline-8-carboxylate | 502 | (CD3OD, 400MHz) δ (ppm): 7.62 (d, $J$ = 7.2 Hz, 1H), 7.43 (s, 1H), 7.11 (d, $J$ = 8.4 Hz, 1H), 7.03 (s, 1H), 5.14-5.07 (m, 1H), 4.98 (s, 2H), 4.84-4.82 (m, 1H), 4.60-4.55 (m, 1H), 3.83-3.78 (m, 5H), 2.99-2.96 (m, 2H), 2.57-2.52 (m, 1H), 2.38-2.36 (m, 1H), 2.11-2.05 (m, 2H), 1.92-1.83 (m, 2H), 1.78 (d, $J$ = 7.2 Hz, 3H), 1.67-1.59 (m, 2H), 1.57-1.45 (m, 2H). |
| 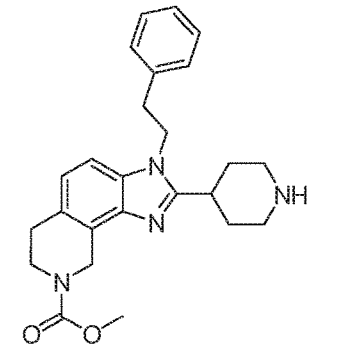 | methyl 3-(2-phenylethyl)-2-(piperidin-4-yl)-3H,6H,7H,8H,9H-imidazo[4,5-h]isoquinoline-8-carboxylate | 419 | 1H-NMR (CD3OD, 400 MHz) δ (ppm): 7.41 (d, $J$ = 8.4 Hz, 1H), 7.27-7.04 (m, 4H), 6.96-6.84 (m, 2H), 4.95 (s, 2H), 4.55 (t, $J$ = 6.2 Hz, 2H), 3.80-3.75 (m, 5H), 3.40-3.36 (m, 1H), 3.36-3.32 (m, 1H), 3.14 (t, $J$ = 6.4 Hz, 2H), 2.96 (t, $J$ = 5.6 Hz, 2H), 2.92-2.78 (m, 2H), 2.74-2.61 (m, 1H), 1.95-1.76 (m, 2H), 1.48-1.39 (m, 2H). |

FIGURE 1 (continued)

| | Name | MW | NMR |
|---|---|---|---|
|  | methyl 2-(1,1-dioxo-1lambda6-thietan-3-yl)-3-(2-phenylethyl)-3H,6H,7H,8H,9H-imidazo[4,5-h]isoquinoline-8-carboxylate | 440 | 1H-NMR (CD3OD, 400 MHz) δ (ppm): 7.41 (d, J = 8.4 Hz, 1H), 7.29-7.20 (m, 3H), 7.15 (d, J = 8.4 Hz, 1H), 6.91-6.82 (m, 2H), 5.00 (s, 2H), 4.51 (t, J = 6.4 Hz, 2H), 4.42-4.32 (m, 2H), 4.07-3.96 (m, 2H), 3.87-3.70 (m, 5H), 3.59-3.44 (m, 1H), 3.17-3.11 (m, 2H), 3.01-2.92 (m, 2H). |
|  | trans-4-(3-[[4-(difluoromethoxy)phenyl]methyl]-8-(methoxycarbonyl)-3H,6H,7H,8H,9H-imidazo[4,5-h]isoquinolin-2-yl)cyclohexane-1-carboxylic acid | 514 | 1H-NMR (CD3OD, 400 MHz) δ (ppm): 7.25 (d, J = 8.4 Hz, 1H), 7.18-7.08 (m, 4H), 7.05 (d, J = 8.4 Hz, 1H), 7.02-6.55 (m, 1H), 5.53 (s, 2H), 5.03 (s, 2H), 3.85-3.69 (m, 5H), 3.03-2.88 (m, 3H), 2.45-2.33 (m, 1H), 2.17-2.01 (m, 2H), 1.93-1.79 (m, 4H), 1.60-1.41 (m, 2H). |
| 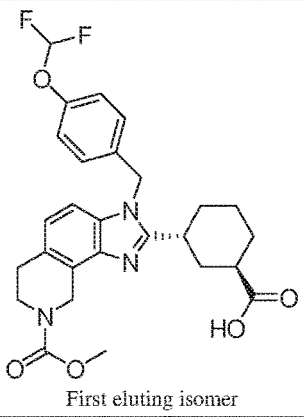<br>First eluting isomer | (1R,3R)-3-(3-[[4-(difluoromethoxy)phenyl]methyl]-8-(methoxycarbonyl)-3H,6H,7H,8H,9H-imidazo[4,5-h]isoquinolin-2-yl)cyclohexane-1-carboxylic acid | 514 | 1H-NMR (CD3OD, 400 MHz) δ (ppm): 7.24 (d, J = 8.0 Hz, 1H), 7.17-7.11 (m, 2H), 7.11-7.02 (m, 3H), 6.98-6.58 (m, 1H), 5.54 (s, 2H), 5.03 (s, 2H), 3.84-3.70 (m, 5H), 3.34-3.33 (m, 1H), 2.95 (t, J = 5.6 Hz, 2H), 2.93-2.82 (m, 1H), 2.36-2.16 (m, 2H), 2.00-1.85 (m, 2H), 1.84-1.74 (m, 2H), 1.73-1.62 (m, 1H), 1.58-1.42 (m, 1H). |

FIGURE 1 (continued)

| Structure | Name | m/z | 1H-NMR |
|---|---|---|---|
| 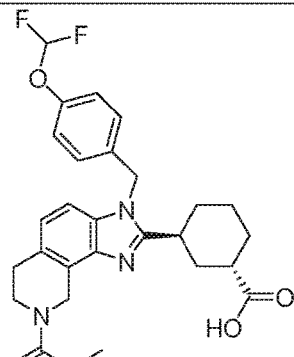 Second eluting isomer | (1S,3S)-3-(3-[[4-(difluoromethoxy)phenyl]methyl]-8-(methoxycarbonyl)-3H,6H,7H,8H,9H-imidazo[4,5-h]isoquinolin-2-yl)cyclohexane-1-carboxylic acid | 514 | 1H-NMR (CD3OD, 400 MHz) δ (ppm): 7.23 (d, $J$ = 8.4 Hz, 1H), 7.18-7.00 (m, 5H), 7.00- 6.55 (m, 1H), 5.54 (s, 2H), 5.03 (s, 2H), 3.85-3.72 (m, 5H), 3.34-3.33 (m, 1H), 2.95 (t, $J$ = 5.6 Hz, 2H), 2.89-2.81 (m, 1H), 2.37-2.15 (m, 2H), 1.98-1.84 (m, 2H), 1.83-1.75 (m, 2H), 1.74-1.60 (m, 1H), 1.69-1.42 (m, 1H). |
| 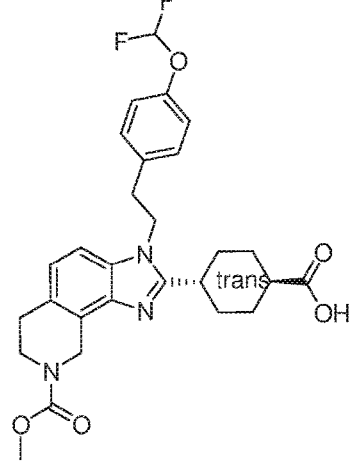 | (1r,4r)-4-(3-[2-[4-(difluoromethoxy)phenyl]ethyl]-8-(methoxycarbonyl)-3H,6H,7H,8H,9H-imidazo[4,5-h]isoquinolin-2-yl)cyclohexane-1-carboxylic acid | 528 | 1H-NMR (CD3OD, 400 MHz) δ (ppm): 7.37 (d, J=8.0 Hz, 1H), 7.10 (d, J=8.0 Hz, 1H), 7.04-6.98 (m, 2H), 6.98-6.43 (m, 3H), 4.98 (s, 2H), 4.62-4.47 (m, 2H), 3.93-3.69 (m, 5H), 3.22-3.08 (m, 2H), 3.03-2.92 (m, 2H), 2.44-2.23 (m, 2H), 2.12-1.93 (m, 2H), 1.77-1.60 (m, 2H), 1.57-1.43 (m, 2H), 1.42-1.27 (m, 2H). |
| 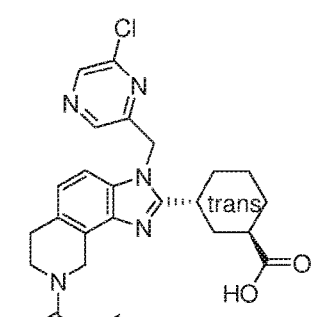 First eluting isomer | (1R,3R)-3-[3-[(6-chloropyrazin-2-yl)methyl]-8-(methoxycarbonyl)-3H,6H,7H,8H,9H-imidazo[4,5-h]isoquinolin-2-yl]cyclohexane-1-carboxylic acid | 484, 486 | 1H-NMR (CD3OD, 400 MHz) δ (ppm): 8.58 (s, 1H), 8.51 (s, 1H), 7.28 (d, $J$ = 8.4 Hz, 1H), 7.04 (d, $J$ = 8.4 Hz, 1H), 5.75-5.64 (m, 2H), 5.04 (s, 2H), 3.86 -3.69 (m, 5H), 3.46-3.36 (m, 1H), 2.95 (t, $J$ = 6.0 Hz, 2H), 2.91-2.81 (m, 1H), 2.37-2.17 (m, 2H), 2.03-1.89 (m, 3H), 1.89-1.78 (m, 1H), 1.78-1.66 (m, 1H), 1.66-1.47 (m, 1H). |

FIGURE 1 (continued)

| Structure | Name | MS | 1H-NMR |
|---|---|---|---|
| 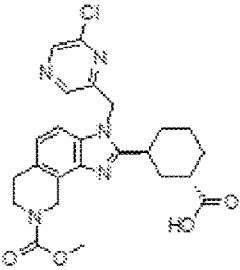<br>Second eluting isomer | (1S,3S)-3-[3-[(6-chloropyrazin-2-yl)methyl]-8-(methoxycarbonyl)-3H,6H,7H,8H,9H-imidazo[4,5-h]isoquinolin-2-yl]cyclohexane-1-carboxylic acid | 484, 486 | 1H-NMR (CD3OD, 400 MHz) δ (ppm): 8.58 (s, 1H), 8.51 (s, 1H), 7.28 (d, J = 8.4 Hz, 1H), 7.04 (d, J = 8.4 Hz, 1H), 5.75-5.66 (m, 2H), 5.03 (s, 2H), 3.84-3.67 (m, 5H), 3.48-3.36 (m, 1H), 2.95 (t, J = 6.0 Hz, 2H), 2.91-2.83 (m, 1H), 2.35-2.17 (m, 2H), 2.01-1.87 (m, 3H), 1.87-1.79 (m, 1H), 1.79-1.66 (m, 1H), 1.62-1.46 (m, 1H). |
| 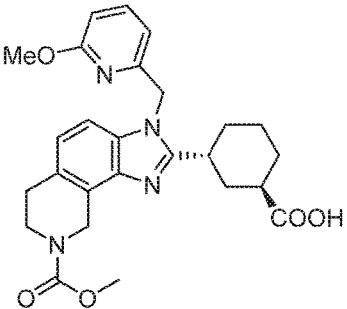<br>First eluting isomer | (1R,3R)-3-(8-(methoxycarbonyl)-3-((6-methoxypyridin-2-yl)methyl)-6,7,8,9-tetrahydro-3H-imidazo[4,5-h]isoquinolin-2-yl)cyclohexane-1-carboxylic acid | 479 | 1H-NMR (CD3OD, 400 MHz) δ (ppm): 7.58 (t, J = 7.6 Hz, 1H), 7.29 (d, J = 8.4 Hz, 1H), 7.01 (d, J = 8.4 Hz, 1H), 6.76 (d, J = 7.2 Hz, 1H), 6.64 (d, J = 8.0 Hz, 1H), 5.56-5.44 (m, 2H), 5.02 (s, 2H), 3.79-3.74 (m, 8H), 3.56-3.50 (m, 1H), 2.95-2.92 (m, 3H), 2.40-2.36 (m, 1H), 2.25-2.21 (m, 1H), 1.98-1.92 (m, 3H), 1.89-1.88 (m, 1H), 1.83-1.80 (m, 1H), 1.79-1.71 (m, 1H). |
| 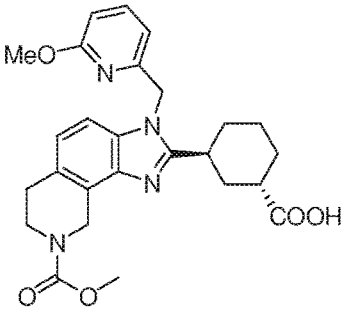<br>Second eluting isomer | (1S,3S)-3-(8-(methoxycarbonyl)-3-((6-methoxypyridin-2-yl)methyl)-6,7,8,9-tetrahydro-3H-imidazo[4,5-h]isoquinolin-2-yl)cyclohexane-1-carboxylic acid | 479 | 1H-NMR (CD3OD, 400 MHz) δ (ppm): 7.57 (t, J = 7.6 Hz, 1H), 7.28 (d, J = 8.4 Hz, 1H), 7.00 (d, J = 8.0 Hz, 1H), 6.76 (d, J = 7.2 Hz, 1H), 6.63 (d, J = 8.0 Hz, 1H), 5.55-5.43 (m, 2H), 5.01 (s, 2H), 3.78-3.73 (m, 8H), 3.55-3.50 (m, 1H), 2.92-2.88 (m, 3H), 2.39-2.36 (m, 1H), 2.24-2.21 (m, 1H), 2.01-1.91 (m, 3H), 1.88-1.83 (m, 1H), 1.79-1.73 (m, 1H), 1.70-1.68 (m, 1H). |

FIGURE 1 (continued)

| Structure | Name | m/z | 1H-NMR |
|---|---|---|---|
| 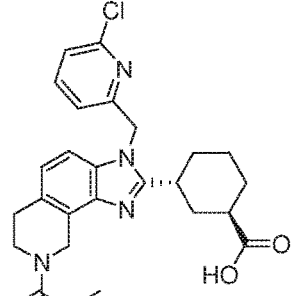<br>First eluting isomer | (1R,3R)-3-[3-[(6-chloropyridin-2-yl)methyl]-8-(methoxycarbonyl)-3H,6H,7H,8H,9H-imidazo[4,5-h]isoquinolin-2-yl]cyclohexane-1-carboxylic acid | 483, 485 | 1H-NMR (CD3OD, 400 MHz) δ (ppm): 7.71 (t, J = 7.8 Hz, 1H), 7.33 (d, J = 8.0 Hz, 1H), 7.21 (d, J = 8.0 Hz, 1H), 7.01 (t, J = 8.0 Hz, 2H), 5.65-5.52 (m, 2H), 5.03 (s, 2H), 3.83-3.70 (m, 5H), 3.49-3.36 (m, 1H), 3.00-2.84 (m, 3H), 2.39-2.28 (m, 1H), 2.28-2.16 (m, 1H), 2.02-1.87 (m, 3H), 1.87-1.77 (m, 1H), 1.77-1.64 (m, 1H), 1.64-1.44 (m, 1H). |
| 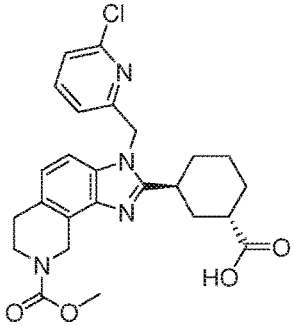<br>Second eluting isomer | (1S,3S)-3-[3-[(6-chloropyridin-2-yl)methyl]-8-(methoxycarbonyl)-3H,6H,7H,8H,9H-imidazo[4,5-h]isoquinolin-2-yl]cyclohexane-1-carboxylic acid | 483, 485 | 1H-NMR (CD3OD, 400 MHz) δ (ppm): 7.71 (t, J = 7.6 Hz, 1H), 7.33 (d, J = 8.0 Hz, 1H), 7.21 (d, J = 8.4 Hz, 1H), 7.04-6.95 (m, 2H), 5.63-5.57 (m, 2H), 5.03 (s, 2H), 3.83-3.70 (m, 5H), 3.49-3.36 (m, 1H), 3.00-2.84 (m, 3H), 2.39-2.28 (m, 1H), 2.28-2.16 (m, 1H), 2.02-1.87 (m, 3H), 1.87-1.77 (m, 1H), 1.77-1.64 (m, 1H), 1.64-1.44 (m, 1H). |
| 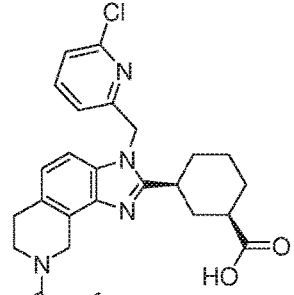<br>Third eluting isomer | (1R,3S)-3-[3-[(6-chloropyridin-2-yl)methyl]-8-(methoxycarbonyl)-3H,6H,7H,8H,9H-imidazo[4,5-h]isoquinolin-2-yl]cyclohexane-1-carboxylic acid | 483, 485 | 1H-NMR (CD3OD, 400 MHz) δ (ppm): 7.73 (t, J = 8.0 Hz, 1H), 7.35 (d, J = 8.0 Hz, 1H), 7.26 (d, J = 8.4 Hz, 1H), 7.05 (t, J = 8.0 Hz, 2H), 5.57 (s, 2H), 5.03 (s, 2H), 3.83-3.71 (m, 5H), 3.28-3.11 (m, 1H), 3.00-2.87 (m, 2H), 2.55-2.38 (m, 1H), 2.25-2.14 (m, 1H), 2.14-2.03 (m, 1H), 2.03-1.87 (m, 3H), 1.87-1.71 (m, 1H), 1.62-1.44 (m, 2H). |

FIGURE 1 (continued)

| | Compound | m/z | NMR |
|---|---|---|---|
| 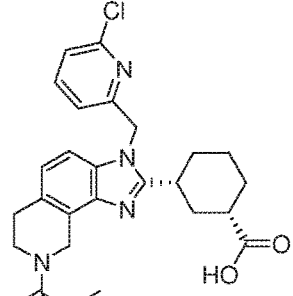<br>Fourth eluting isomer | (1S,3R)-3-[3-[(6-chloropyridin-2-yl)methyl]-8-(methoxycarbonyl)-3H,6H,7H,8H,9H-imidazo[4,5-h]isoquinolin-2-yl]cyclohexane-1-carboxylic acid | 483, 485 | 1H-NMR (CD3OD, 400 MHz) δ (ppm): 7.73 (t, *J* = 7.6 Hz, 1H), 7.35 (d, *J* = 8.0 Hz, 1H), 7.26 (d, *J* = 8.0 Hz, 1H), 7.11-7.02 (m, 2H), 5.57 (s, 2H), 5.03 (s, 2H), 3.83-3.71 (m, 5H), 3.28-3.11 (m, 1H), 3.00-2.87 (m, 2H), 2.55-2.38 (m, 1H), 2.25-2.14 (m, 1H), 2.14-2.03 (m, 1H), 2.03-1.87 (m, 3H), 1.87-1.71 (m, 1H), 1.62-1.44 (m, 2H). |
| 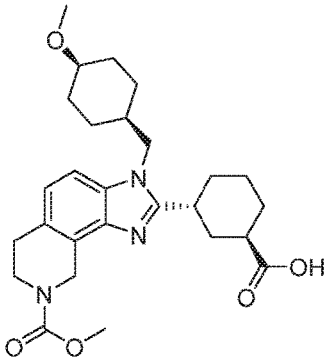<br>First eluting isomer | (1R,3R)-3-(8-(methoxycarbonyl)-3-(((1s,4S)-4-methoxycyclohexyl)methyl)-6,7,8,9-tetrahydro-3H-imidazo[4,5-h]isoquinolin-2-yl)cyclohexane-1-carboxylic acid | 484 | : 1H NMR (400 MHz, CD3OD) δ (ppm): 7.31 (d, *J* = 8.8 Hz, 1H), 7.06 (d, *J* = 8.4 Hz, 1H), 5.18 (s, 2H), 4.20-4.15 (m, 1H), 4.11-4.05 (m, 1H), 3.82-3.73 (m, 5H), 3.50-3.48 (m, 1H), 3.47-3.46 (m, 1H), 3.15-3.04 (m, 1H), 2.95-2.92 (m, 3H), 2.34-2.28 (m, 2H), 2.05-1.84 (m, 6H), 1.79-1.62 (m, 4H), 1.58-1.20 (m, 7H). |
| 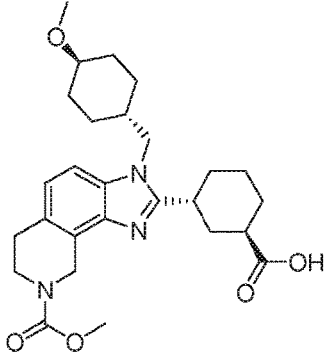<br>Second eluting isomer | (1S,3S)-3-(8-(methoxycarbonyl)-3-(((1r,4S)-4-methoxycyclohexyl)methyl)-6,7,8,9-tetrahydro-3H-imidazo[4,5-h]isoquinolin-2-yl)cyclohexane-1-carboxylic acid | 484 | 1H NMR (400 MHz, CD3OD) δ (ppm): 7.35 (d, *J* = 8.4 Hz, 1H), 7.10 (d, *J* = 8.4 Hz, 1H), 4.99 (s, 2H), 4.23-4.08 (m, 2H), 3.82-3.72 (m, 5H), 3.63-3.60 (m, 1H), 3.49-3.37 (m, 1H), 3.09-3.04 (m, 1H), 2.95-2.92 (m, 3H), 2.30-2.27 (m, 2H), 1.96-1.84 (m, 7H), 1.75-1.69 (m, 1H), 1.60-1.46 (m, 9H). |

FIGURE 1 (continued)

| Structure | Name | MW | 1H NMR |
|---|---|---|---|
| 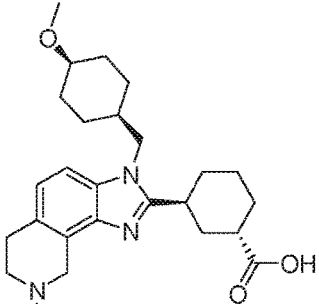 Third eluting isomer | (1R,3R)-3-(8-(methoxycarbonyl)-3-(((1s,4S)-4-methoxycyclohexyl)methyl)-6,7,8,9-tetrahydro-3H-imidazo[4,5-h]isoquinolin-2-yl)cyclohexane-1-carboxylic acid | 484 | 1H NMR (400 MHz, CD3OD) δ (ppm): 7.55-7.48 (m, 1H), 7.27-7.21 (m, 1H), 5.15-5.10 (m, 2H), 4.31-4.17 (m, 2H), 3.81-3.75 (m, 5H), 3.54-3.43 (m, 1H), 3.20-3.17 (m, 2H), 3.09-2.91 (m, 3H), 2.35-2.29 (m, 2H), 2.11-2.04 (m, 2H), 1.99-1.87 (m, 5H), 1.75-1.73 (m, 2H), 1.63-1.56 (m, 2H), 1.50-1.07 (m, 6H). |
| 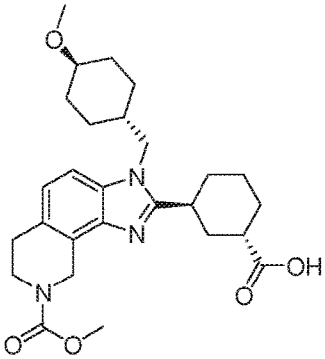 Fourth eluting isomer | (1S,3S)-3-(8-(methoxycarbonyl)-3-(((1r,4S)-4-methoxycyclohexyl)methyl)-6,7,8,9-tetrahydro-3H-imidazo[4,5-h]isoquinolin-2-yl)cyclohexane-1-carboxylic acid | 484 | 1H NMR (400 MHz, CD3OD) δ (ppm): 7.30 (d, J = 8.8 Hz, 1H), 7.06 (d, J = 8.0 Hz, 1H), 5.07 (s, 2H), 4.22-4.11 (m, 1H), 4.09-4.06 (m, 1H), 3.80-3.72 (m, 5H), 3.50-3.33 (m, 1H), 3.25-3.19 (m, 1H), 3.09-3.04 (m, 1H), 2.95-2.90 (m, 3H), 2.34-2.21 (m, 4H), 2.08-1.82 (m, 5H), 1.72-1.69 (m, 2H), 1.64-1.56 (m, 2H), 1.34-1.27 (m, 2H), 1.24-0.92 (m, 4H). |
| 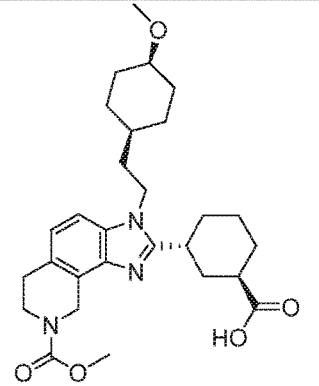 First eluting isomer | (1R,3R)-3-[8-(methoxycarbonyl)-3-[2-[(1s,4s)-4-methoxycyclohexyl]ethyl]-3H,6H,7H,8H,9H-imidazo[4,5-h]isoquinolin-2-yl]cyclohexane-1-carboxylic acid | 498 | 1H-NMR (CD3OD, 400 MHz) δ (ppm): 7.29 (d, J = 8.4 Hz, 1H), 7.06 (d, J = 8.0 Hz, 1H), 5.00 (s, 2H), 4.38-4.26 (m, 2H), 3.81-3.73 (m, 5H), 3.36 (s, 3H), 3.27-3.17 (m, 1H), 2.95-2.91 (m, 3H), 2.28-2.24 (m, 2H), 2.09-2.03 (m, 2H), 1.99-1.87 (m, 6H), 1.72-1.59 (m, 4H), 1.49-1.26 (m, 2H), 1.22-1.02 (m, 4H). |

FIGURE 1 (continued)

| Structure | Name | MW | NMR |
|---|---|---|---|
| 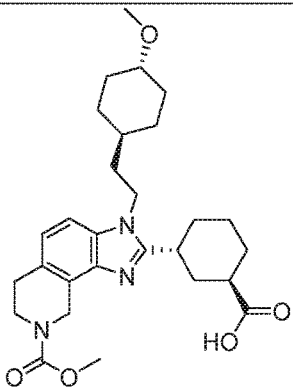<br>Second eluting isomer | (1R,3R)-3-[8-(methoxycarbonyl)-3-[2-[(1r,4r)-4-methoxycyclohexyl]ethyl]-3H,6H,7H,8H,9H-imidazo[4,5-h]isoquinolin-2-yl]cyclohexane-1-carboxylic acid | 498 | 1H-NMR (CD3OD, 400 MHz) δ (ppm): 7.29 (d, $J$ = 8.0 Hz, 1H), 7.06 (d, $J$ = 8.0 Hz, 1H), 5.00 (s, 2H), 4.33-4.25 (m, 2H), 3.81-3.79 (m, 5H), 3.35 (s, 3H), 3.20-3.12 (m, 1H), 2.95-2.82 (m, 3H), 2.28-2.24 (m, 2H), 2.08-2.03 (m, 2H), 1.99-1.87 (m, 6H), 1.72-1.58 (m, 4H), 1.46-1.28 (m, 2H), 1.22-1.04 (m, 4H). |
| 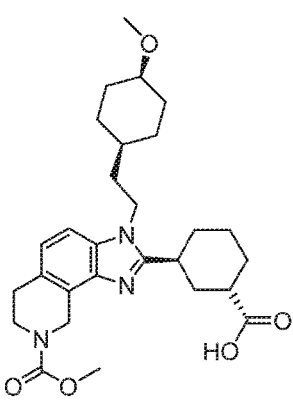<br>Third eluting isomer | (3S)-3-[8-(methoxycarbonyl)-3-[2-[(1s,4s)-4-methoxycyclohexyl]ethyl]-3H,6H,7H,8H,9H-imidazo[4,5-h]isoquinolin-2-yl]cyclohexane-1-carboxylic acid | 498 | 1H-NMR (CD3OD, 400 MHz) δ (ppm): 7.29 (d, $J$ = 8.0 Hz, 1H), 7.06 (d, $J$ = 8.4 Hz, 1H), 5.00 (s, 2H), 4.37-4.26 (m, 2H), 3.82-3.79 (m, 5H), 3.35 (s, 3H), 3.21-3.14 (m, 1H), 3.08-2.95 (m, 3H), 2.57-2.41 (m, 1H), 2.36-2.18 (m, 1H), 2.11-2.09 (m, 2H), 2.01-1.84 (m, 4H), 1.70-1.68 (m, 2H), 1.57-1.46 (m, 2H), 1.33-1.24 (m, 4H), 1.22-1.06 (m, 3H), 1.00-0.90 (m, 1H). |
| 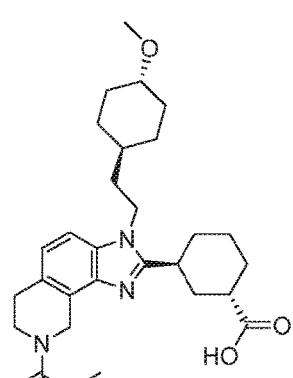<br>Fourth eluting isomer | (1S,3S)-3-[8-(methoxycarbonyl)-3-[2-[(1r,4r)-4-methoxycyclohexyl]ethyl]-3H,6H,7H,8H,9H-imidazo[4,5-h]isoquinolin-2-yl]cyclohexane-1-carboxylic acid | 498 | 1H-NMR (CD3OD, 400 MHz) δ (ppm): 7.29 (d, $J$ = 8.4 Hz, 1H), 7.07 (d, $J$ = 8.4 Hz, 1H), 5.00 (s, 2H), 4.29-4.26 (m, 2H), 3.81-3.79 (m, 5H), 3.35 (s, 3H), 3.21-3.14 (m, 1H), 3.09-3.04 (m, 2H), 2.95-2.91 (m, 2H), 2.58-2.40 (m, 1H), 2.20-2.18 (m, 1H), 2.12-2.09 (m, 2H), 2.01-1.96 (m, 2H), 1.93-1.84 (m, 3H), 1.72-1.66 (m, 2H), 1.61-1.51 (m, 2H), 1.31-1.24 (m, 3H), 1.23-1.05 (m, 3H). |

FIGURE 1 (continued)

| Structure | Name | MW | 1H-NMR |
|---|---|---|---|
| 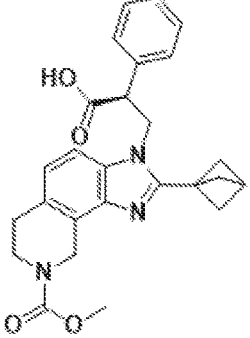<br>First eluting isomer | (2S)-3-(2-{bicyclo[1.1.1]pentan-1-yl}-8-(methoxycarbonyl)-3H,6H,7H,8H,9H-imidazo[4,5-h]isoquinolin-3-yl)-2-phenylpropanoic acid | 498 | 1H-NMR (Methanol-d4, 400 MHz) δ (ppm): 7.32-7.21 (m, 3H), 7.17-7.11 (m, 3H), 6.99 (d, J = 8.0 Hz, 1H), 5.02-4.93 (m, 3H), 4.66-4.54 (m, 1H), 4.17-4.10 (m, 1H), 3.81-3.72 (m, 5H), 2.95-2.89 (m, 2H), 2.55 (s, 1H), 2.33 (s, 6H). |
| 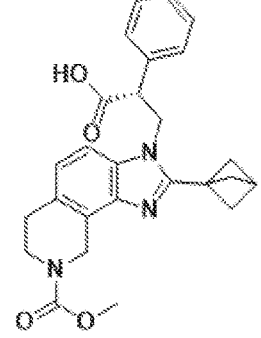<br>Second eluting isomer | (2R)-3-(2-{bicyclo[1.1.1]pentan-1-yl}-8-(methoxycarbonyl)-3H,6H,7H,8H,9H-imidazo[4,5-h]isoquinolin-3-yl)-2-phenylpropanoic acid | 498 | 1H-NMR (Methanol-d4, 400 MHz) δ (ppm): 7.32-7.24 (m, 3H), 7.17-7.11 (m, 3H), 7.00 (d, J = 8.4 Hz, 1H), 4.96 (m, 3H), 4.66-4.54 (m, 1H), 4.17-4.10 (m, 1H), 3.81-3.71 (m, 5H), 2.95-2.89 (m, 2H), 2.56 (s, 1H), 2.36 (s, 6H). |
| 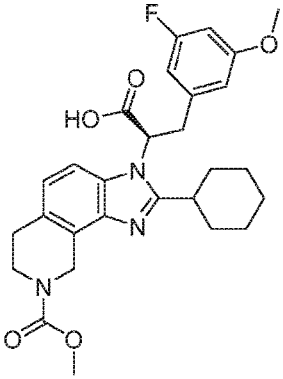<br>First eluting isomer | (R)-2-(2-cyclohexyl-8-(methoxycarbonyl)-6,7,8,9-tetrahydro-3H-imidazo[4,5-h]isoquinolin-3-yl)-3-(3-fluoro-5-methoxyphenyl)propanoic acid | 510 | 1H-NMR (CD3OD, 400 MHz) δ (ppm): 7.45 (d, J = 7.6 Hz, 1H), 7.16 (d, J = 8.0 Hz, 1H), 6.63-6.60 (m, 1H), 6.55-6.52 (m, 1H), 6.47 (s, 1H), 4.97 (s, 2H), 4.87-4.86 (m, 1H), 4.65-4.59 (m, 1H), 4.13-4.09 (m, 1H), 3.78 (s, 3H), 3.77-3.70 (m, 2H), 3.69 (s, 3H), 2.98 (t, J = 5.2 Hz, 2H), 2.80-2.60 (m, 1H), 1.95-1.83 (m, 2H), 1.82-1.74 (m, 2H), 1.71-1.54 (m, 2H), 1.51-1.38 (m, 1H), 1.33-1.12 (m, 3H). |

FIGURE 1 (continued)

| | | | |
|---|---|---|---|
| 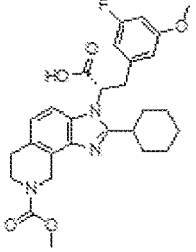 Second eluting isomer | (S)-2-(2-cyclohexyl-8-(methoxycarbonyl)-6,7,8,9-tetrahydro-3H-imidazo[4,5-h]isoquinolin-3-yl)-3-(3-fluoro-5-methoxyphenyl)propanoic acid | 510 | 1H-NMR (CD3OD, 400 MHz) δ (ppm): 7.44 (d, J = 8.4 Hz, 1H), 7.16 (d, J = 8.4 Hz, 1H), 6.63-6.60 (m, 1H), 6.54-6.52 (m, 1H), 6.47 (s, 1H), 4.97 (s, 2H), 4.88-4.82(m, 1H), 4.71-4.56 (m, 1H), 4.16-4.05 (m, 1H), 3.78 (s, 3H), 3.77-3.73 (m, 2H), 3.69 (s, 3H), 2.98 (t, J = 5.2 Hz, 2H), 2.78-2.62 (m, 1H), 2.61-1.83 (m, 2H), 1.82-1.52 (m, 4H), 1.51-1.12 (m, 4H) |
| 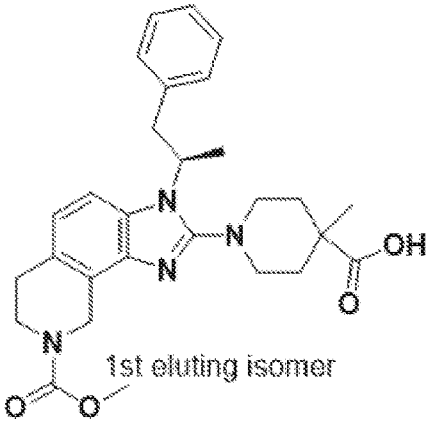 1st eluting isomer | 1-[8-(methoxycarbonyl)-3-[(2R)-1-phenylpropan-2-yl]-3H,6H,7H,8H,9H-imidazo[4,5-h]isoquinolin-2-yl]-4-methylpiperidine-4-carboxylic acid | 491 | (DMSO-d6, 400 MHz) δ (ppm): 12.41 (br, 1H), 7.57 (d, J = 8.4 Hz, 1H), 7.17 – 7.09 (m, 3H), 6.95 – 6.92 (m, 3H), 4.71 (s, 3H), 3.71 – 3.58 (m, 5H), 3.33 – 3.27 (m, 2H), 3.16 – 3.11 (m, 1H), 2.96 (d, J = 13.6 Hz, 1H), 2.86 – 2.72 (m, 2H), 2.72 – 2.62 (m, 2H), 2.01 – 1.93 (m, 2H), 1.57 (d, J = 6.8 Hz, 3H), 1.51 – 1.38 (m, 2H), 1.17 (s, 3H). |
| 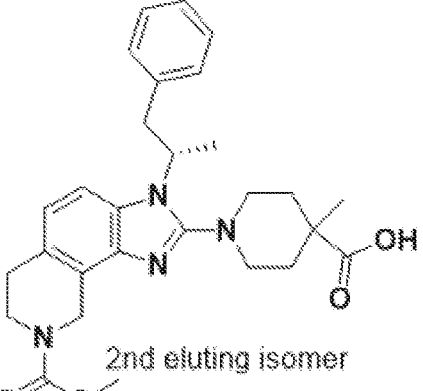 2nd eluting isomer | 1-[8-(methoxycarbonyl)-3-[(2S)-1-phenylpropan-2-yl]-3H,6H,7H,8H,9H-imidazo[4,5-h]isoquinolin-2-yl]-4-methylpiperidine-4-carboxylic acid | 491 | 1H-NMR (DMSO-d6, 400 MHz) δ (ppm): 12.42 (br, 1H), 7.57 (d, J = 8.4 Hz, 1H), 7.17-7.11 (m, 3H), 6.95-6.92 (m, 3H), 4.75-4.62 (m, 3H), 3.69-3.61 (m, 5H), 3.27-3.25 (m, 2H), 3.17-3.11 (m, 1H), 2.98-2.92 (m, 1H), 2.87-2.81 (m, 2H), 2.76-2.52 (m, 2H), 2.01-1.88 (m, 2H), 1.57 (d, J = 6.8 Hz, 3H), 1.52-1.35 (m, 2H) 1.17 (s, 3H). |

FIGURE 1 (continued)

| Structure | Name | MW | 1H-NMR |
|---|---|---|---|
| 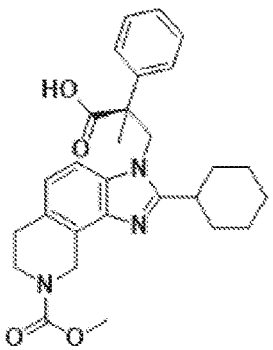First eluting isomer | (2S)-3-[2-cyclohexyl-8-(methoxycarbonyl)-3H,6H,7H,8H,9H-imidazo[4,5-h]isoquinolin-3-yl]-2-methyl-2-phenylpropanoic acid | 476 | 1H-NMR (Methanol-d4, 400 MHz) δ (ppm): 7.37-7.29 (m, 3H), 7.22 (d, J = 6.8 Hz, 2H), 7.13 (d, J = 8.0 Hz, 1H), 6.97 (d, J = 8.4 Hz, 1H), 4.97 (s, 2H), 4.85-4.81 (m, 1H), 4.77-4.71 (m, 1H), 3.81-3.72 (m, 5H), 2.96-2.90 (m, 2H), 2.17-2.06 (m, 1H), 1.76-1.71 (m, 1H), 1.70-1.62 (m, 4H), 1.61-1.53 (m, 3H), 1.48-1.35 (m, 1H), 1.31-1.20 (m, 3H), 1.15-1.02 (m, 1H). |
| 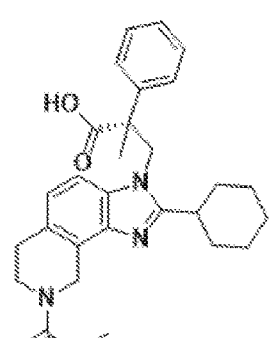Second eluting isomer | (2R)-3-[2-cyclohexyl-8-(methoxycarbonyl)-3H,6H,7H,8H,9H-imidazo[4,5-h]isoquinolin-3-yl]-2-methyl-2-phenylpropanoic acid | 476 | 1H-NMR (Methanol-d4, 400 MHz) δ (ppm): 7.38-7.31 (m, 3H), 7.22 (d, J = 7.2 Hz, 2H), 7.14 (d, J = 8.4 Hz, 1H), 6.97 (d, J = 8.4 Hz, 1H), 4.97 (s, 2H), 4.85-4.80 (m, 1H), 4.76-4.71 (m, 1H), 3.82-3.73 (m, 5H), 2.97-2.90 (m, 2H), 2.18-2.12 (m, 1H), 1.78-1.73 (m, 1H), 1.69-1.62 (m, 4H), 1.59-1.55 (m, 3H), 1.51-1.36 (m, 1H), 1.34-1.17 (m, 3H), 1.15-0.98 (m, 1H). |
| 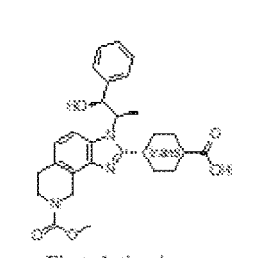First eluting isomer | (trans)-4-{3-[(1S,2R)-1-hydroxy-1-phenylpropan-2-yl]-8-(methoxycarbonyl)-3H,6H,7H,8H,9H-imidazo[4,5-h]isoquinolin-2-yl}cyclohexane-1-carboxylic acid | 492 | 1H-NMR (CD3OD, 400 MHz) δ (ppm): 7.79 (d, J = 8.0 Hz, 1H), 7.35-7.30 (m, 5H), 7.05 (d, J = 8.0 Hz, 1H), 5.19 (d, J = 7.2 Hz, 1H), 4.99 (s, 2H), 4.78-4.79 (m, 1H), 3.79 (s, 3H), 3.78-3.72 (m, 2H), 2.96-2.92 (m, 2H), 2.78-2.73 (m, 1H), 2.38-2.21 (m, 1H), 2.07-1.95 (m, 2H), 1.91-1.79 (m, 2H), 1.78-1.56 (m, 6H), 1.54-1.43 (m, 1H). |

FIGURE 1 (continued)

| | | | |
|---|---|---|---|
| 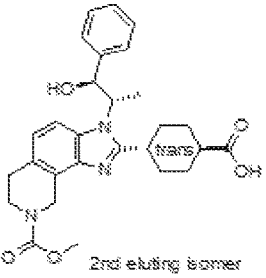 | (trans)-4-{3-[(1S,2S)-1-hydroxy-1-phenylpropan-2-yl]-8-(methoxycarbonyl)-3H,6H,7H,8H,9H-imidazo[4,5-h]isoquinolin-2-yl}cyclohexane-1-carboxylic acid | 492 | 1H-NMR (CD3OD, 400 MHz) δ (ppm): 7.64 (d, J = 8.0 Hz, 1H), 7.18-7.11 (m, 4H), 6.97-6.91 (m, 2H), 5.26-5.21 (m, 1H), 4.90 (s, 2H), 4.63-4.61 (m, 1H), 3.78 (s, 3H), 3.77-3.71 (m, 2H), 3.02-2.94 (m, 2H), 2.37-2.27 (m, 2H), 2.05-2.02 (m, 1H), 1.94-1.88 (m, 5H), 1.66-1.51 (m, 3H), 1.40-1.20 (m, 1H), 0.80-0.70 (m, 1H). |
| 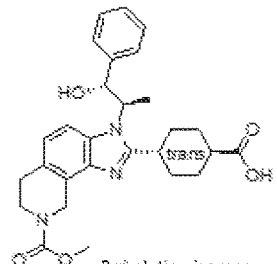 | (trans)-4-{3-[(1R,2R)-1-hydroxy-1-phenylpropan-2-yl]-8-(methoxycarbonyl)-3H,6H,7H,8H,9H-imidazo[4,5-h]isoquinolin-2-yl}cyclohexane-1-carboxylic acid | 492 | 1H-NMR (CD3OD, 400 MHz) δ (ppm): 7.64 (d, J = 8.4 Hz, 1H), 7.18-7.09 (m, 4H), 6.98-6.91 (m, 2H), 5.28-5.22 (m, 1H), 4.90 (s, 2H), 4.63-4.61 (m, 1H), 3.78 (s, 3H), 3.77-3.72 (m, 2H), 2.99-2.71 (m, 2H), 2.37-2.29 (m, 2H), 2.25-2.05 (m, 1H), 1.94-1.85 (m, 5H), 1.66-1.51 (m, 3H), 1.40-1.20 (m, 1H), 0.80-0.70 (m, 1H). |
| 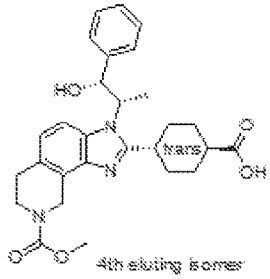 | (trans)-4-{3-[(1R,2S)-1-hydroxy-1-phenylpropan-2-yl]-8-(methoxycarbonyl)-3H,6H,7H,8H,9H-imidazo[4,5-h]isoquinolin-2-yl}cyclohexane-1-carboxylic acid | 492 | 1H-NMR (CD3OD, 400 MHz) δ (ppm): 7.80 (d, J = 8.4 Hz, 1H), 7.35-7.30 (m, 5H), 7.05 (d, J = 8.4 Hz, 1H), 5.19 (d, J = 6.8 Hz, 1H), 4.90 (s, 2H), 4.80-4.73 (m, 1H), 3.79 (s, 3H), 3.78-3.72 (m, 2H), 2.98-2.92 (m, 2H), 2.79-2.74 (m, 1H), 2.41-2.36 (m, 1H), 2.12-2.06 (m, 2H), 1.95-1.81 (m, 2H), 1.73-1.72 (m, 3H), 1.67 (d, J= 11.6 Hz, 3H), 1.63-1.58 (m, 1H). |

FIGURE 1 (continued)

| Structure | Name | MW | 1H-NMR |
|---|---|---|---|
| 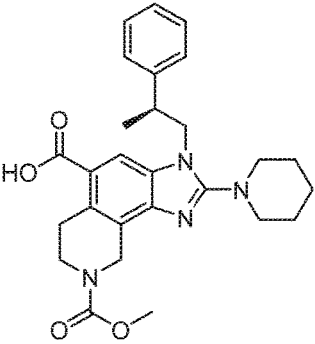 First eluting isomer | 8-(methoxycarbonyl)-3-[(2S)-2-phenylpropyl]-2-(piperidin-1-yl)-3H,6H,7H,8H,9H-imidazo[4,5-h]isoquinoline-5-carboxylic acid | 477 | 1H-NMR (CD3OD, 400 MHz) δ (ppm): 7.72 (s, 1H), 7.21-7.10 (m, 3H), 7.00 (d, $J$ = 7.2 Hz, 2H), 4.87-4.85 (m, 2H), 4.32-4.15 (m, 2H), 3.85-3.68 (m, 5H), 3.54-3.40 (m, 1H), 3.30-3.20 (m, 2H), 3.19-3.00 (m, 2H), 2.90-2.80 (m, 2H), 1.80-1.50 (m, 6H), 1.40-1.20 (m, 3H). |
| 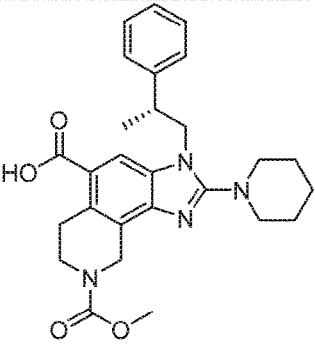 Second eluting isomer | 5,8-dimethyl 3-(2-phenylpropyl)-2-(piperidin-1-yl)-3H,6H,7H,8H,9H-imidazo[4,5-h]isoquinoline-5,8-dicarboxylate | 477 | 1H-NMR (CD3OD, 400 MHz) δ (ppm): 7.75 (s, 1H), 7.24-7.09 (m, 3H), 7.00 (d, $J$ = 7.2 Hz, 2H), 4.87-4.85 (m, 2H), 4.40-4.20 (m, 2H), 3.78 (s, 3H), 3.74-3.66 (m, 2H), 3.54-3.40 (m, 1H), 3.29-3.22 (m, 2H), 3.18-3.00 (m, 2H), 2.91-2.80 (m, 2H), 1.80-1.56 (m, 6H), 1.39-1.25 (m, 3H). |
| 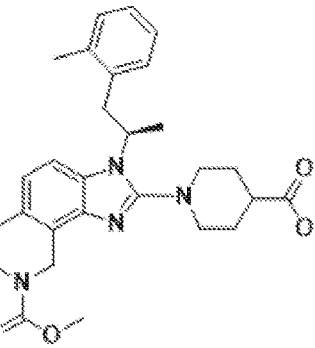 First eluting isomer | 1-[8-(methoxycarbonyl)-3-[(2R)-1-(2-methylphenyl)propan-2-yl]-3H,6H,7H,8H,9H-imidazo[4,5-h]isoquinolin-2-yl]piperidine-4-carboxylic acid | 491 | 1H-NMR (Methanol-$d_4$, 400 MHz) δ (ppm): 7.62 (d, $J$ = 8.4 Hz, 1H), 7.14-7.06 (m, 2H), 7.04-6.97 (m, 1H), 6.79-6.73 (m, 1H), 6.27 (d, $J$ = 7.6 Hz, 1H), 4.87-4.78 (m, 2H), 3.87-3.68 (m, 6H), 3.22-3.14 (m, 2H), 2.97-2.92 (m, 2H), 2.82-2.66 (m, 2H), 2.48-2.26 (m, 6H), 1.96-1.91 (m, 1H), 1.88-1.75 (m, 5H), 1.50-1.48 (m, 1H). |
| 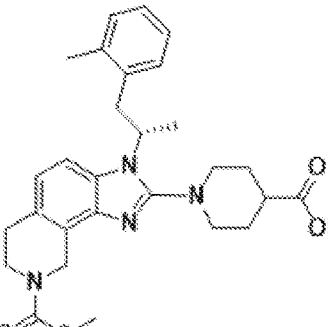 Second eluting isomer | 1-[8-(methoxycarbonyl)-3-[(2S)-1-(2-methylphenyl)propan-2-yl]-3H,6H,7H,8H,9H-imidazo[4,5-h]isoquinolin-2-yl]piperidine-4-carboxylic acid | 491 | 1H-NMR (Methanol-$d_4$, 400 MHz) δ (ppm): 7.61 (d, $J$ = 8.4 Hz, 1H), 7.14-7.06 (m, 2H), 7.04-6.97 (m, 1H), 6.74 (m, 1H), 6.27 (d, $J$ = 7.6 Hz, 1H), 4.87 (s, 2H), 3.87-3.68 (m, 6H), 3.24-3.14 (m, 2H), 2.97-2.92 (m, 2H), 2.82-2.66 (m, 2H), 2.48-2.26 (m, 6H), 1.96-1.91 (m, 1H), 1.88-1.75 (m, 5H), 1.59-1.47 (m, 1H). |

FIGURE 1 (continued)

| Structure | Name | MS | NMR |
|---|---|---|---|
| 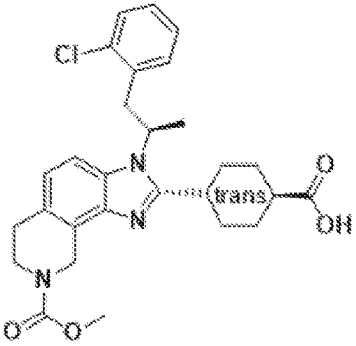<br>First eluting isomer | (trans)-4-{3-[(2R)-1-(2-chlorophenyl)propan-2-yl]-8-(methoxycarbonyl)-3H,6H,7H,8H,9H-imidazo[4,5-h]isoquinolin-2-yl}cyclohexane-1-carboxylic acid | 510, 512 | 1H-NMR (Methanol-d4, 400 MHz) δ (ppm): 7.73 (d, J = 8.4 Hz, 1H), 7.41 (d, J = 7.6 Hz, 1H), 7.22-7.09 (m, 2H), 6.99-6.90 (m, 1H), 6.51 (d, J = 6.8 Hz, 1H), 5.11-4.98 (m, 1H), 4.95 (s, 2H), 3.84-3.75 (m, 5H), 3.58-3.39 (m, 2H), 3.05-2.93 (m, 2H), 2.53-2.42 (m, 1H), 2.38-2.27 (m, 1H), 2.16-2.09 (m, 1H), 2.02-1.81 (m, 5H), 1.71-1.44 (m, 3H), 1.38-1.23 (m, 1H), 0.88-0.78 (m, 1H). |
| 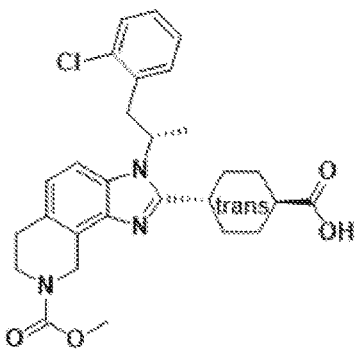<br>Second eluting isomer | (trans)-4-{3-[(2S)-1-(2-chlorophenyl)propan-2-yl]-8-(methoxycarbonyl)-3H,6H,7H,8H,9H-imidazo[4,5-h]isoquinolin-2-yl}cyclohexane-1-carboxylic acid | 510, 512 | 1H-NMR (Methanol-d4, 400 MHz) δ (ppm): 7.73 (d, J = 8.4 Hz, 1H), 7.41 (d, J = 8.0 Hz, 1H), 7.24-7.09 (m, 2H), 6.99-6.90 (m, 1H), 6.51 (d, J = 6.4 Hz, 1H), 5.11-4.98 (m, 1H), 4.95 (s, 2H), 3.84-3.75 (m, 5H), 3.59-3.39 (m, 2H), 3.05-2.93 (m, 2H), 2.56-2.42 (m, 1H), 2.40-2.28 (m, 1H), 2.15-2.07 (m, 1H), 1.99-1.77 (m, 5H), 1.71-1.44 (m, 3H), 1.38-1.23 (m, 1H), 0.91-0.78 (m, 1H). |
| 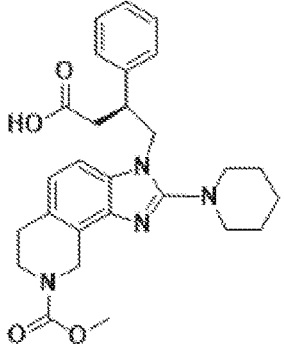<br>First eluting isomer | (3S)-4-[8-(methoxycarbonyl)-2-(piperidin-1-yl)-3H,6H,7H,8H,9H-imidazo[4,5-h]isoquinolin-3-yl]-3-phenylbutanoic acid | 477 | 1H-NMR (Methanol-d4, 400 MHz) δ (ppm): 7.43 (d, J = 8.4 Hz, 1H), 7.21-7.11 (m, 3H), 7.05 (d, J = 7.6 Hz, 1H), 6.92 (d, J = 7.6 Hz, 2H), 4.87-4.85 (m, 2H), 4.50-4.24 (m, 2H), 3.84-3.68 (s, 6H), 3.37 (s, 1H), 3.13-3.08 (m, 2H), 3.01-2.90 (m, 2H), 2.89-2.69 (m, 4H), 1.76-1.56 (m, 6H). |

FIGURE 1 (continued)

| Structure | Name | MW | 1H-NMR |
|---|---|---|---|
| 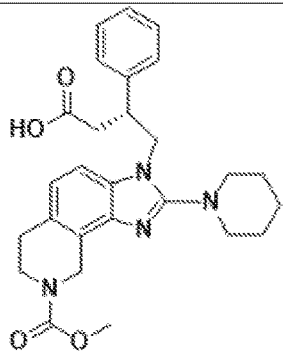Second eluting isomer | (3R)-4-[8-(methoxycarbonyl)-2-(piperidin-1-yl)-3H,6H,7H,8H,9H-imidazo[4,5-h]isoquinolin-3-yl]-3-phenylbutanoic acid | 477 | 1H-NMR (Methanol-d4, 400 MHz) δ (ppm): 7.46 (d, J = 8.0 Hz, 1H), 7.21-7.11 (m, 3H), 7.02 (d, J = 8.4 Hz, 1H), 6.96-6.90 (m, 2H), 4.90-4.85 (m, 2H), 4.45-4.20 (m, 2H), 3.84-3.68 (s, 6H), 3.08-2.99 (m, 2H), 2.96-2.92 (m, 2H), 2.89-2.69 (m, 4H), 1.76-1.56 (m, 6H). |
| 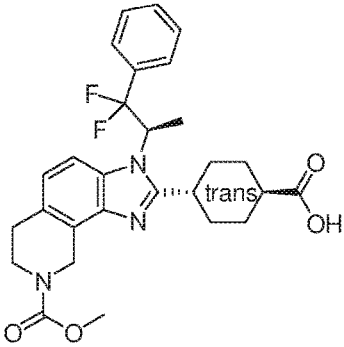First eluting isomer | (1r,4r)-4-[3-[(2R)-1,1-difluoro-1-phenylpropan-2-yl]-8-(methoxycarbonyl)-3H,6H,7H,8H,9H-imidazo[4,5-h]isoquinolin-2-yl]cyclohexane-1-carboxylic acid | 512 | 1H-NMR (CD3OD, 400 MHz) δ (ppm): 7.94 (d, J = 8.4 Hz, 1H), 7.55-7.41 (m, 4H), 7.35 (d, J = 7.6 Hz, 2H), 5.77-5.72 (m, 1H), 4.95-4.94 (m, 2H), 3.86-3.75 (m, 5H), 3.07-2.89 (m, 3H), 2.43-2.32 (m, 1H), 2.16-2.11 (m, 1H), 2.05-1.98 (m, 5H), 1.74-1.62 (m, 3H), 1.48-1.32 (m, 1H), 0.96-0.88 (m, 1H). |
| 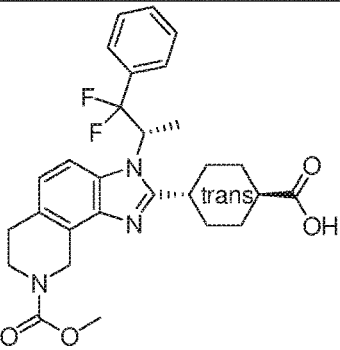Second eluting isomer | (1r,4r)-4-[3-[(2S)-1,1-difluoro-1-phenylpropan-2-yl]-8-(methoxycarbonyl)-3H,6H,7H,8H,9H-imidazo[4,5-h]isoquinolin-2-yl]cyclohexane-1-carboxylic acid | 512 | 1H-NMR (CD3OD, 400 MHz) δ (ppm): 7.86-7.84 (m, 1H), 7.59-7.40 (m, 3H), 7.39-7.26 (m, 3H), 5.72-5.55 (m, 1H), 4.89-4.85 (m, 2H), 3.84-3.73 (m, 5H), 3.04-2.97 (m, 2H), 2.89-2.78 (m, 1H), 2.44-2.31 (m, 1H), 2.13-1.89 (m, 6H), 1.73-1.56 (m, 3H), 1.42-1.25 (m, 1H), 0.98-0.84 (m, 1H). |

FIGURE 1 (continued)

| Structure | Name | MW | 1H-NMR |
|---|---|---|---|
| 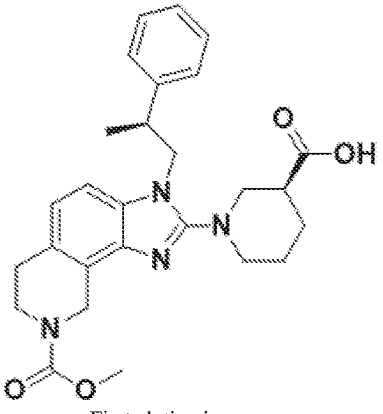<br>First eluting isomer | (3S)-1-[8-(methoxycarbonyl)-3-[(2S)-2-phenylpropyl]-3H,6H,7H,8H,9H-imidazo[4,5-h]isoquinolin-2-yl]piperidine-3-carboxylic acid | 477 | 1H-NMR (Methanol-$d4$, 400 MHz) δ (ppm): 7.29-7.12 (m, 4H), 7.08-6.98 (m, 3H), 4.38-4.30 (m, 1H), 4.24-4.17 (m, 1H), 3.86-3.68 (m, 5H), 3.48-3.38 (m, 2H), 3.28-3.22 (m, 2H), 3.20-3.10 (m, 1H), 3.01-2.83 (m, 4H), 2.79-2.67 (m, 1H), 2.09-2.01 (m, 1H), 1.87-1.57 (m, 3H), 1.28 (d, $J = 7.2$ Hz, 3H). |
| 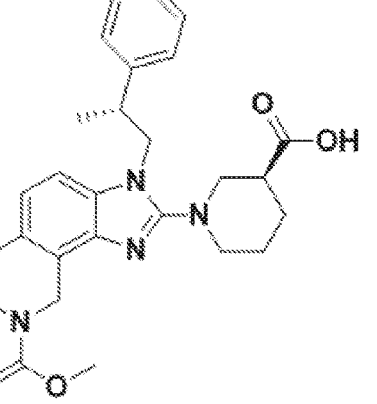<br>Second eluting isomer | (3S)-1-[8-(methoxycarbonyl)-3-[(2R)-2-phenylpropyl]-3H,6H,7H,8H,9H-imidazo[4,5-h]isoquinolin-2-yl]piperidine-3-carboxylic acid | 477 | 1H-NMR (Methanol-$d4$, 400 MHz) δ (ppm): 7.28 (d, $J = 8.0$ Hz, 1H), 7.19-7.08 (m, 3H), 7.03 (d, $J = 8.0$ Hz, 1H), 6.91 (d, $J = 6.4$ Hz, 2H), 4.38-4.30 (m, 1H), 4.24-4.17 (m, 1H), 3.86-3.68 (m, 5H), 3.48-3.38 (m, 1H), 3.31-3.20 (m, 3H), 3.16-3.08 (m, 1H), 2.97-2.88 (m, 3H), 2.72-2.64 (m, 1H), 2.62-2.51 (m, 1H), 1.97-1.91 (m, 1H), 1.88-1.79 (m, 2H), 1.73-1.62 (m, 1H), 1.36 (d, $J = 6.8$ Hz, 3H). |
| 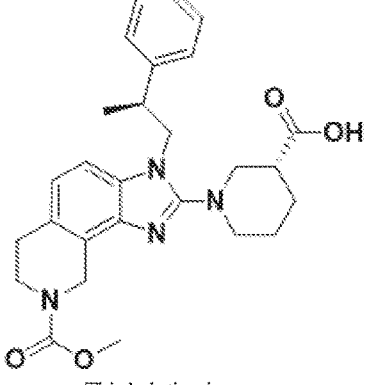<br>Third eluting isomer | (3R)-1-[8-(methoxycarbonyl)-3-[(2S)-2-phenylpropyl]-3H,6H,7H,8H,9H-imidazo[4,5-h]isoquinolin-2-yl]piperidine-3-carboxylic acid | 477 | 1H-NMR (Methanol-$d4$, 400 MHz) δ (ppm): 7.26-7.11 (m, 4H), 7.09-6.94 (m, 3H), 4.38-4.30 (m, 1H), 4.24-4.17 (m, 1H), 3.81-3.73 (m, 5H), 3.47-3.39 (m, 2H), 3.28-3.22 (m, 2H), 3.18-3.06 (m, 1H), 3.00-2.81 (m, 4H), 2.79-2.70 (m, 1H), 2.09-1.98 (m, 1H), 1.85-1.55 (m, 3H), 1.28 (d, $J = 7.2$ Hz, 3H). |

FIGURE 1 (continued)

| Structure | Name | MW | 1H-NMR |
|---|---|---|---|
| 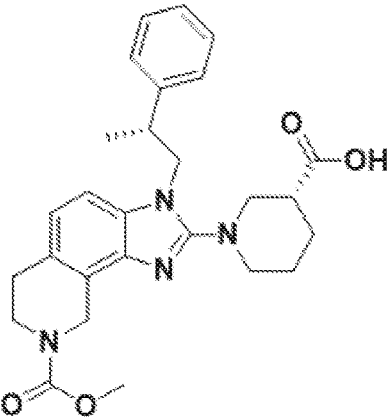 Fourth eluting isomer | (3R)-1-[8-(methoxycarbonyl)-3-[(2R)-2-phenylpropyl]-3H,6H,7H,8H,9H-imidazo[4,5-h]isoquinolin-2-yl]piperidine-3-carboxylic acid | 477 | 1H-NMR (Methanol-$d_4$, 400 MHz) δ (ppm): 7.29 (d, $J$ = 8.0 Hz, 1H), 7.19-7.08 (m, 3H), 7.04 (d, $J$ = 8.0 Hz, 1H), 6.96-6.83 (m, 2H), 4.38-4.30 (m, 1H), 4.24-4.17 (m, 1H), 3.85-3.64 (m, 5H), 3.55-3.36 (m, 2H), 3.29-3.21 (m, 2H), 3.19-3.08 (m, 1H), 2.95-2.87 (m, 3H), 2.72-2.64 (m, 1H), 2.57-2.52 (m, 1H), 1.94-1.76 (m, 3H), 1.74-1.61 (m, 1H), 1.36 (d, $J$ = 6.8 Hz, 3H). |
| 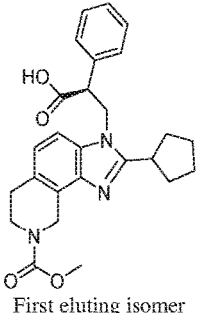 First eluting isomer | (2S)-3-[2-cyclopentyl-8-(methoxycarbonyl)-3H,6H,7H,8H,9H-imidazo[4,5-h]isoquinolin-3-yl]-2-phenylpropanoic acid | 448 | 1H-NMR (CD3OD, 400 MHz) δ (ppm): 7.46-7.33 (m, 1H), 7.33-7.23 (m, 3H), 7.23-7.13 (m, 2H), 7.13-7.00 (m, 1H), 4.96 (s, 2H), 4.95-4.91 (m, 1H), 4.69-4.51 (m, 1H), 4.25-4.08 (m, 1H), 3.87-3.68 (m, 5H), 3.20-3.05 (m, 1H), 3.00-2.90 (m, 2H), 2.25-2.08 (m, 1H), 2.00-1.80 (m, 3H), 1.80-1.69 (m, 2H), 1.69-1.49 (m, 2H). |
| 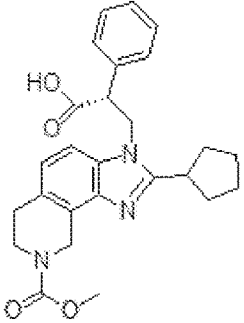 Second eluting isomer | (2R)-3-[2-cyclopentyl-8-(methoxycarbonyl)-3H,6H,7H,8H,9H-imidazo[4,5-h]isoquinolin-3-yl]-2-phenylpropanoic acid | 448 | 1H-NMR (CD3OD, 400 MHz) δ (ppm): 7.39-7.29 (m, 1H), 7.29-7.20 (m, 3H), 7.20-7.11 (m, 2H), 7.07 (d, $J$=8.4 Hz, 1H), 4.97 (s, 2H), 4.90-4.85 (m, 1H), 4.68-4.42 (m, 1H), 4.18-4.05 (m, 1H), 3.88-3.69 (m, 5H), 3.10-3.00 (m, 1H), 3.00-2.89 (m, 2H), 2.22-2.01 (m, 1H), 1.95-1.65 (m, 5H), 1.65-1.51 (m, 2H). |
| 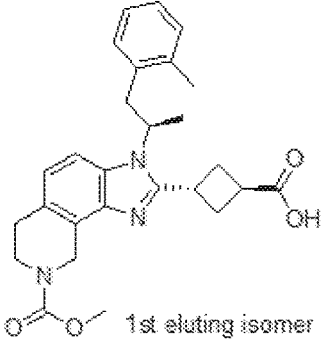 1st eluting isomer | trans-3-[8-(methoxycarbonyl)-3-[(2R)-1-(2-methylphenyl)propan-2-yl]-3H,6H,7H,8H,9H-imidazo[4,5-h]isoquinolin-2-yl]cyclobutane-1-carboxylic acid | 462 | 1H-NMR (Methanol-$d_4$, 400 MHz) δ (ppm): 8.10-8.05 (m, 1H), 7.58-7.47 (m, 1H), 7.31-7.15 (m, 1H), 7.15-7.02 (m, 1H), 6.95-6.85 (m, 1H), 6.50-6.25 m, 1H), 5.03-4.92 (m, 3H), 3.97-3.75 (m, 5H), 3.72-3.50 (m, 2H), 3.45-3.35 (m, 2H), 3.35-3.12 (m, 1H), 3.12-1.02 (m, 2H), 2.62-2.42 (m, 2H), 2.30 (s, 3H), 2.20-1.95 (m, 2H), 1.92 (d, $J$=6.4 Hz, 3H). |

FIGURE 1 (continued)

| | | | |
|---|---|---|---|
| 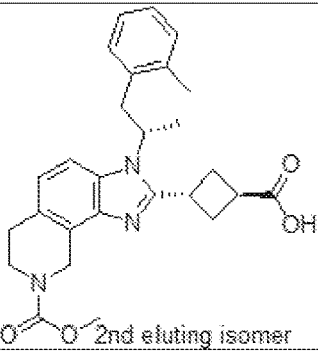 2nd eluting isomer | trans-3-[8-(methoxycarbonyl)-3-[(2S)-1-(2-methylphenyl)propan-2-yl]-3H,6H,7H,8H,9H-imidazo[4,5-h]isoquinolin-2-yl]cyclobutane-1-carboxylic acid | 462 | 1H-NMR (Methanol-$d4$, 400 MHz) δ (ppm): 8.12-8.06 (m, 1H), 7.58-7.47 (m, 1H), 7.31-7.15 (m, 1H), 7.15-7.02 (m, 1H), 6.95-6.85 (m, 1H), 6.41-6.35 (m, 1H), 4.99-4.91 (m, 3H), 3.92-3.82 (m, 2H), 3.82-3.78 (m, 3H), 3.72-3.42 (m, 2H), 3.28-3.13 (m, 2H), 3.13-3.02 (m, 2H), 2.85-2.55 (m, 2H), 2.32 (s, 3H), 2.23-2.01 (m, 2H), 1.92 (d, $J=6.4$ Hz, 3H). |
| 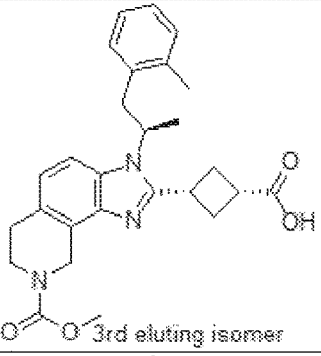 3rd eluting isomer | cis-3-[8-(methoxycarbonyl)-3-[(2R)-1-(2-methylphenyl)propan-2-yl]-3H,6H,7H,8H,9H-imidazo[4,5-h]isoquinolin-2-yl]cyclobutane-1-carboxylic acid | 462 | 1H-NMR (Methanol-$d4$, 400 MHz) δ (ppm): 8.12-8.03 (m, 1H), 7.58-7.47 (m, 1H), 7.31-7.15 (m, 1H), 7.15-7.02 (m, 1H), 6.95-6.85 (m, 1H), 6.42-6.33 (m, 1H), 5.02-4.97 (m, 3H), 4.02-3.65 (m, 6H), 3.55-3.35 (m, 2H), 3.30-3.21(m, 3H), 3.00-2.65 (m, 2H), 2.31 (s, 3H), 2.23-2.11 (m, 2H), 1.91 (d, $J = 6.4$ Hz, 3H). |
| 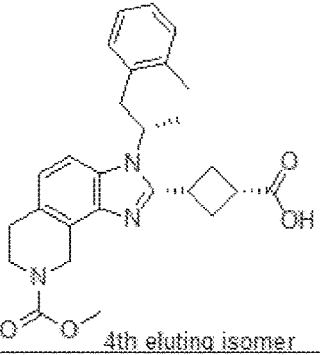 4th eluting isomer | cis-3-[8-(methoxycarbonyl)-3-[(2S)-1-(2-methylphenyl)propan-2-yl]-3H,6H,7H,8H,9H-imidazo[4,5-h]isoquinolin-2-yl]cyclobutane-1-carboxylic acid | 462 | 1H-NMR (Methanol-$d4$, 400 MHz) δ (ppm): 8.10 (s, 1H), 7.58-7.47 (m, 1H), 7.31-7.15 (m, 1H), 7.15-7.02 (m, 1H), 6.95-6.85 (m, 1H), 6.50-6.25(s, 1H), 5.00 (s, 3H), 4.02-3.65 (m, 6H), 3.55-3.35 (m, 2H), 3.30-3.21(m, 3H), 3.00-2.65 (m, 2H), 3.65-2.42 (s, 3H), 2.30-2.00 (s, 2H), 2.00-1.85 (d, $J = 4$ Hz, 3H). |
| 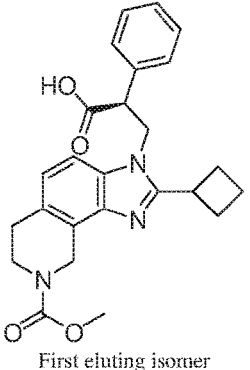 First eluting isomer | (2R)-3-[2-cyclobutyl-8-(methoxycarbonyl)-3H,6H,7H,8H,9H-imidazo[4,5-h]isoquinolin-3-yl]-2-phenylpropanoic acid | 434 | 1H-NMR (CD3OD, 400 MHz) δ (ppm): 7.47-7.25 (m, 4H), 7.25-7.15 (m, 2H), 7.09 (d, J=8.4 Hz, 1H), 5.00 (s, 2H), 4.88-4.78 (m, 1H), 4.53-4.42 (m, 1H), 4.13-4.09 (m, 1H), 3.84-3.77 (m, 5H), 3.66-3.50 (m, 1H), 3.02-2.92 (m, 2H), 2.58-2.36 (m, 3H), 2.18-2.02 (m, 2H), 2.01-1.88 (m, 1H) |

FIGURE 1 (continued)

| Structure | Name | MW | 1H-NMR |
|---|---|---|---|
| 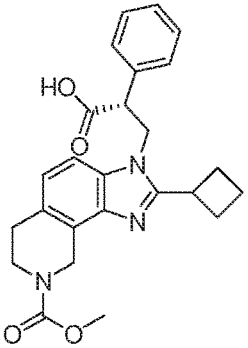<br>Second eluting isomer | (2S)-3-[2-cyclobutyl-8-(methoxycarbonyl)-3H,6H,7H,8H,9H-imidazo[4,5-h]isoquinolin-3-yl]-2-phenylpropanoic acid | 434 | 1H-NMR (CD3OD, 400 MHz) δ (ppm): 7.34-7.22 (m, 4H), 7.22-7.12 (m, 2H), 7.08 (d, J=8.4 Hz, 1H), 5.00 (s, 2H), 4.88-4.77 (m, 1H), 4.51-4.40 (m, 1H), 4.15-4.07 (m, 1H), 4.85-4.72 (m, 5H), 3.65-3.50 (m, 1H), 3.13-2.89 (m, 2H), 2.60-2.32 (m, 3H), 2.17-2.02 (m, 2H), 2.01-1.85 (m, 1H). |
| 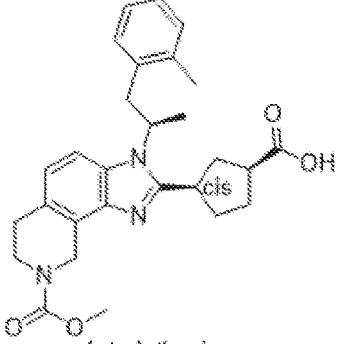<br>1st eluting isomer | (1S,3R)-3-[8-(methoxycarbonyl)-3-[(2R)-1-(2-methylphenyl)propan-2-yl]-3H,6H,7H,8H,9H-imidazo[4,5-h]isoquinolin-2-yl]cyclopentane-1-carboxylic acid | 476 | 1H-NMR (Methanol-d4, 400 MHz) δ (ppm): 7.82-7.70 (m, 1H), 7.18-7.03 (m, 3H), 6.91-6.82 (m, 1H), 6.49-6.42 (m, 1H), 5.05-4.95 (m, 2H), 4.90-4.80 (m, 1H), 3.95-3.65 (m, 5H), 3.55-3.35 (m, 1H), 3.33-3.21 (m, 1H), 3.05-2.95 (m, 2H), 2.94-2.78 (m, 2H), 2.17 (s, 3H), 2.10-1.90 (m, 4H), 1.90-1.75 (m, 4H), 1.75-1.51(m, 1H). |
| 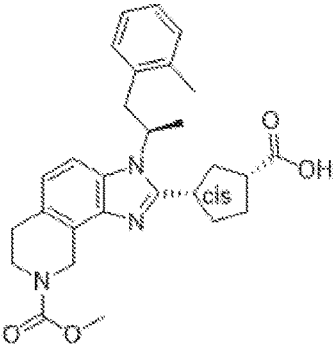<br>2th eluting isomer | (1R,3S)-3-[8-(methoxycarbonyl)-3-[(2R)-1-(2-methylphenyl)propan-2-yl]-3H,6H,7H,8H,9H-imidazo[4,5-h]isoquinolin-2-yl]cyclopentane-1-carboxylic acid | 476 | 1H-NMR (Methanol-d4, 400 MHz) δ (ppm): 8.17-8.08 (m, 1H), 7.53-7.44 (m, 1H), 7.55-7.45 (m, 1H), 7.15-7.02 (m, 1H), 6.98-6.82 (m, 1H), 6.45-6.40 (m, 1H), 5.25-5.05 (m, 1H), 5.02-4.95(m, 2H), 3.90-3.81 (m, 2H), 3.80 (s, 3H), 3.70-3.50 (m, 1H), 3.45-3.35 (m, 2H), 3.20-2.90 (m, 3H), 2.57-2.35 (m, 1H), 2.28 (s, 3H), 2.25-2.05 (m, 1H), 2.07-1.85 (m, 5H), 1.45-1.05 (m, 2H). |
| 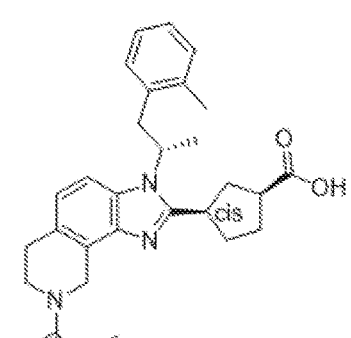<br>3th eluting isomer | (1S,3R)-3-[8-(methoxycarbonyl)-3-[(2S)-1-(2-methylphenyl)propan-2-yl]-3H,6H,7H,8H,9H-imidazo[4,5-h]isoquinolin-2-yl]cyclopentane-1-carboxylic acid | 476 | 1H-NMR (Methanol-d4, 400 MHz) δ (ppm): 7.79-7.71 (m, 1H), 7.25-7.10 (m, 2H), 7.10-7.00 (m, 1H), 6.90-6.75 (m, 1H), 6.49-6.42 (m, 1H), 5.00 (s, 2H), 4.95-4.80 (m, 1H), 3.90-3.70 (m, 5H), 3.62-3.45 (m, 1H), 3.32-3.25 (m, 1H), 3.24-3.10 (m, 1H), 3.05-2.95 (m, 2H), 2.94-2.82 (m, 1H), 2.42-2.30 (m, 1H), 2.29 (s, 3H), 2.27-2.08 (m, 1H), 1.95-1.70 (m, 5H), 1.45-1.21 (m, 1H), 1.20-1.10 (m, 1H). |

FIGURE 1 (continued)

| Structure | Name | MW | NMR |
|---|---|---|---|
| 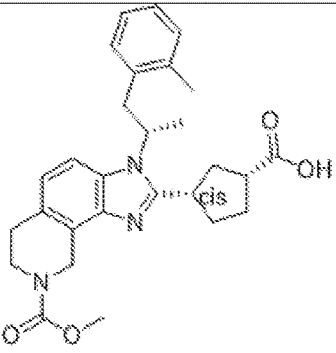<br>4th eluting isomer | (1R,3S)-3-[8-(methoxycarbonyl)-3-[(2S)-1-(2-methylphenyl)propan-2-yl]-3H,6H,7H,8H,9H-imidazo[4,5-h]isoquinolin-2-yl]cyclopentane-1-carboxylic acid | 476 | 1H-NMR (Methanol-d4, 400 MHz) δ (ppm): 8.17-8.08 (m, 1H), 7.55-7.46 (m, 1H), 7.22-7.17 (m, 1H), 7.15-7.02 (m, 1H), 6.98-6.82 (m, 1H), 6.52-6.43 (m, 1H), 5.25-5.05 (m, 1H), 5.02-4.95 (m, 2H), 3.92-3.85 (m, 2H), 3.80 (s, 3H), 3.62-3.45 (m, 1H), 3.45-3.35 (m, 1H), 3.30-3.15 (m, 1H), 3.15-3.02 (m, 2H), 2.98-2.75 (m, 1H), 2.35-2.20 (m, 4H), 2.18-2.02 (m, 2H), 2.01-1.85 (m, 4H), 1.85-1.60 (m, 1H), 1.50-1.25 (m, 1H). |
| 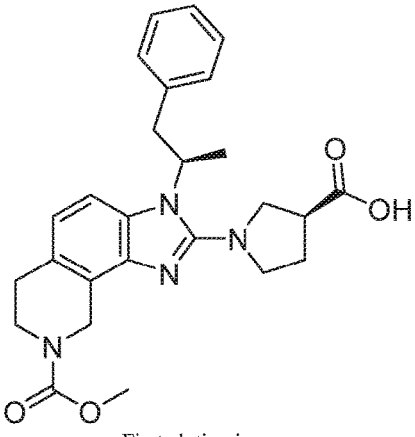<br>First eluting isomer | (3S)-1-[8-(methoxycarbonyl)-3-[(2R)-1-phenylpropan-2-yl]-6H,7H,9H-imidazo[4,5-h]isoquinolin-2-yl]pyrrolidine-3-carboxylic acid | 463 | 1H-NMR (CD3OD, 400 MHz) δ (ppm): 7.54 (d, J=8.4 Hz, 1H), 7.25-7.02 (m, 4H), 6.82-6.89 (m, 2H), 4.87-4.80 (m, 3H), 3.88-3.69 (m, 5H), 3.60-3.45 (m, 3H), 3.44-3.35 (m, 1H), 3.27-3.03 (m, 3H), 2.98-2.90 (m, 2H), 2.26-2.18 (m, 1H), 2.17-2.05 (m, 1H), 1.76 (d, J=6.8 Hz, 3H). |
| 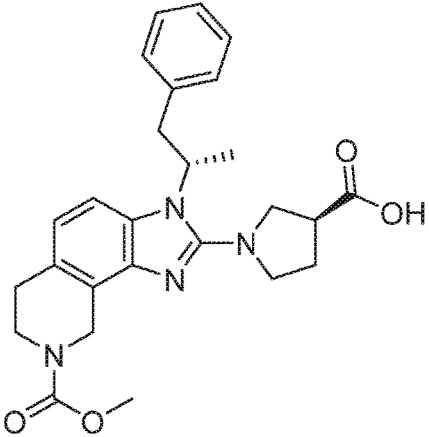<br>Second eluting isomer | (3S)-1-[8-(methoxycarbonyl)-3-[(2S)-1-phenylpropan-2-yl]-6H,7H,9H-imidazo[4,5-h]isoquinolin-2-yl]pyrrolidine-3-carboxylic acid | 463 | 1H-NMR (CD3OD, 400 MHz) δ (ppm): 7.57 (d, J=8.0 Hz, 1H), 7.28-7.03 (m, 4H), 6.90-6.73 (m, 2H), 5.05-4.95 (m, 1H), 4.82 (s, 2H), 3.90-3.53 (m, 6H), 3.52-3.33 (m, 3H), 3.28-3.02 (m, 3H), 2.99-2.88 (m, 2H), 2.39-2.18 (m, 1H), 2.17-2.02 (m, 1H), 1.82 (d, J=6.8 Hz, 3H). |

FIGURE 1 (continued)

| Structure | Name | MW | 1H-NMR |
|---|---|---|---|
| 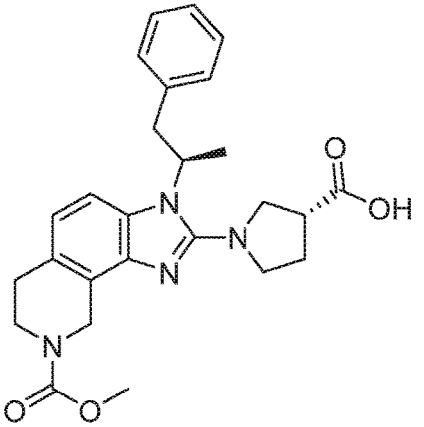<br>Third eluting isomer | (3R)-1-[8-(methoxycarbonyl)-3-[(2R)-1-phenylpropan-2-yl]-6H,7H,9H-imidazo[4,5-h]isoquinolin-2-yl]pyrrolidine-3-carboxylic acid | 463 | 1H-NMR (CD3OD, 400 MHz) δ (ppm): 7.56 (d, *J*=8.4 Hz, 1H), 7.14-7.01 (m, 4H), 6.85-6.78 (m, 2H), 5.01-4.96 (m, 1H), 4.83 (s, 2H), 3.80 (s, 3H), 3.79-3.66 (m, 3H), 3.53-3.32 (m, 3H), 3.23-3.00 (m, 3H), 2.99-2.91 (m, 2H), 2.32-2.18 (m, 1H), 2.17-2.02 (m, 1H), 1.80 (d, *J*=6.8 Hz, 3H). |
| 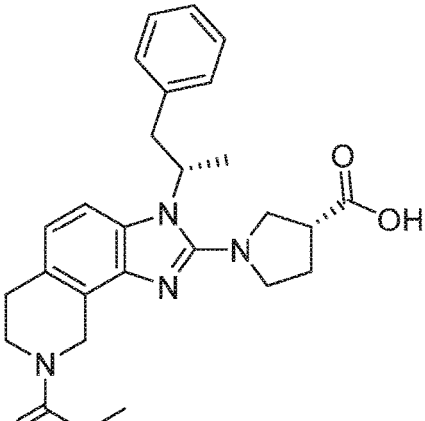<br>Fourth eluting isomer | (3R)-1-[8-(methoxycarbonyl)-3-[(2S)-1-phenylpropan-2-yl]-6H,7H,9H-imidazo[4,5-h]isoquinolin-2-yl]pyrrolidine-3-carboxylic acid | 463 | 1H-NMR (CD3OD, 400 MHz) δ (ppm): 7.54 (d, *J*=8.0 Hz, 1H), 7.15-6.94 (m, 4H), 6.92-6.71 (m, 2H), 4.87-4.78 (m, 3H), 3.81-3.65 (m, 5H), 3.57-3.38 (m, 4H), 3.23-3.06 (m, 3H), 3.00-2.85 (m, 2H), 2.29-2.04 (m, 2H), 1.85 (d, *J*=6.8 Hz, 3H). |
| 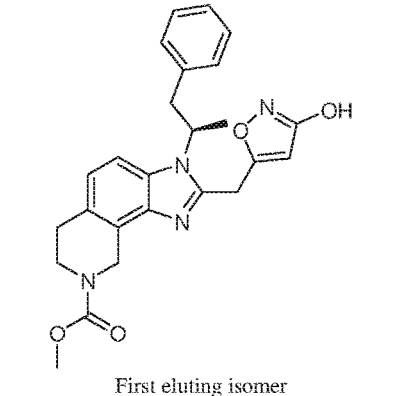<br>First eluting isomer | Methyl 2-[(3-hydroxy-1,2-oxazol-5-yl)methyl]-3-[(2S)-1-phenylpropan-2-yl]-6H,7H,9H-imidazo[4,5-h]isoquinoline-8-carboxylate | 447 | 1H-NMR (CD3OD, 400 MHz) δ (ppm): 7.71 (d, *J*=8.4 Hz, 1H), 7.38-7.00 (m, 4H), 7.00-6.63 (m, 2H), 5.66 (s, 1H), 4.95 (s, 2H), 4.82-4.70 (m, 1H), 4.05-3.87 (m, 1H), 3.87-3.68 (m, 6H), 3.45-3.35 (m, 1H), 3.28-3.14 (m, 1H), 3.02-2.92 (m, 2H), 1.71 (d, *J*=6.8 Hz, 3H). |

FIGURE 1 (continued)

| | | | |
|---|---|---|---|
| 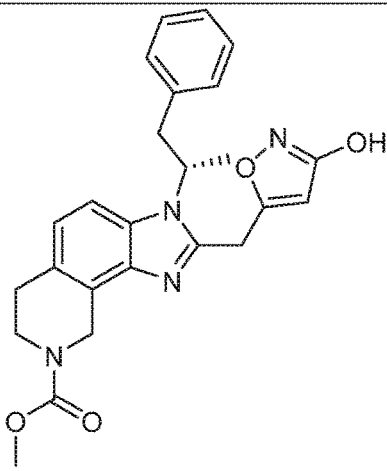<br>Second eluting isomer | methyl 2-[(3-hydroxy-1,2-oxazol-5-yl)methyl]-3-[(2R)-1-phenylpropan-2-yl]-6H,7H,9H-imidazo[4,5-h]isoquinoline-8-carboxylate | 447 | 1H-NMR (CD3OD, 400 MHz) δ (ppm): 7.71 (d, J=8.4 Hz, 1H), 7.34-7.03 (m, 4H), 7.02-6.69 (m, 2H), 5.65 (s, 1H), 4.95 (s, 2H), 4.82-4.67 (m, 1H), 4.05-3.92 (m, 1H), 3.89-3.66 (m, 6H), 3.44-3.34 (m, 1H), 3.28-3.14 (m, 1H), 3.05-2.91 (m, 2H), 1.72 (d, J=6.8 Hz, 3H). |
| 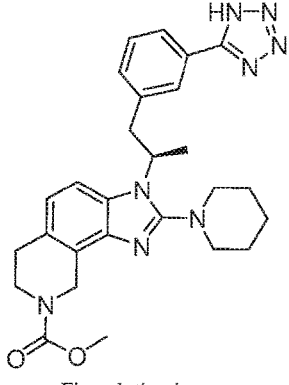<br>First eluting isomer | Methyl 2-(piperidin-1-yl)-3-[(2R)-1-[3-(1H-1,2,3,4-tetrazol-5-yl)phenyl]propan-2-yl]-3H,6H,7H,8H,9H-imidazo[4,5-h]isoquinoline-8-carboxylate | 501 | 1H NMR (400 MHz, CD3OD-d4) δ(ppm): 7.74 (d, J= 7.6 Hz, 1H), 7.66 (d, J= 8.0 Hz, 1H), 7.28 (s, 1H), 7.25-7.21 (m, 1H), 7.16 (d, J= 8.0 Hz, 1H), 6.84 (d, J= 7.6 Hz, 1H), 4.84 4.79 (m, 2H), 4.89-4.45 (m, 1H), 3.89-3.62 (m, 5H), 3.50-3.39 (m, 1H), 3.26-3.16 (m, 1H), 3.12-3.05 (m, 2H), 3.00-2.95 (m, 2H), 2.80-2.59(m, 2H), 1.91(d, J= 6.8 Hz, 3H), 1.69-1.45(m, 6H). |
| 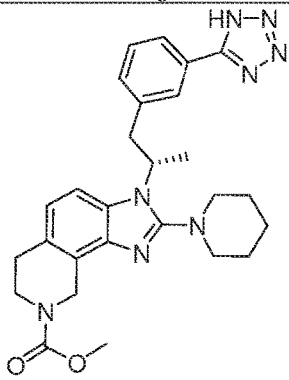<br>Second eluting isomer | methyl 2-(piperidin-1-yl)-3-[(2S)-1-[3-(1H-1,2,3,4-tetrazol-5-yl)phenyl]propan-2-yl]-3H,6H,7H,8H,9H-imidazo[4,5-h]isoquinoline-8-carboxylate | 501 | 1H NMR (400 MHz, CD3OD-d4) δ(ppm): 7.74 (d, J = 8.0 Hz, 1H), 7.66 (d, J = 8.4 Hz, 1H), 7.28 (s, 1H), 7.25-7.21 (m, 1H), 7.17 (d, J = 8.4 Hz, 1H), 6.61 (d, J = 7.2 Hz, 1H), 4.84-4.79 (m, 2H), 4.55-4.52 (m, 1H), 3.86-3.70 (m, 5H), 3.48-3.40 (m, 1H), 3.27-3.20 (m, 1H), 3.20-3.00 (m, 2H), 3.00-2.94 (m, 2H), 2.79-2.64 (m, 2H), 1.91 (d, J = 7.2 Hz, 3H), 1.69-1.47 (m, 6H). |

FIGURE 1 (continued)

| | Name | MW | 1H NMR |
|---|---|---|---|
| 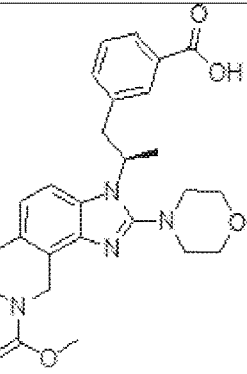<br>First eluting isomer | 3-[(2R)-2-[8-(methoxycarbonyl)-2-(morpholin-4-yl)-3H,6H,7H,8H,9H-imidazo[4,5-h]isoquinolin-3-yl]propyl]benzoic acid | 479 | 1H NMR (400 MHz, CD3OD-d4) δ(ppm): 7.73 (d, J = 8.0 Hz, 1H), 7.61 (d, J = 8.4 Hz, 1H), 7.47 (s, 1H), 7.15-7.08 (m, 2H), 6.90 (d, J = 7.6 Hz, 1H), 4.93-4.91 (m, 1H), 4.89-4.83 (m, 2H), 3.78-3.71 (m, 7H), 3.70-3.63 (m, 2H), 3.44-3.32 (m, 1H), 3.20-3.15 (m, 1H), 3.09-3.03 (m, 2H), 2.98-2.95 (m, 2H), 2.55-2.51 (m, 2H), 1.84 (d, J = 7.2 Hz, 3H). |
| 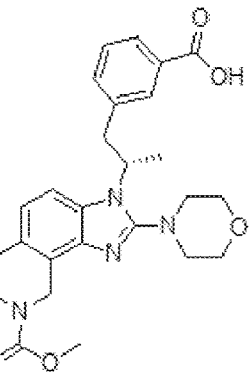<br>Second eluting isomer | 3-[(2S)-2-[8-(methoxycarbonyl)-2-(morpholin-4-yl)-3H,6H,7H,8H,9H-imidazo[4,5-h]isoquinolin-3-yl]propyl]benzoic acid | 479 | 1H NMR (400 MHz, CD3OD-d4) δ(ppm): 7.73 (d, J = 7.6 Hz, 1H), 7.60 (d, J = 8.4 Hz, 1H), 7.48 (s, 1H), 7.15-7.08 (m, 2H), 6.89 (d, J = 7.6 Hz, 1H), 4.98-4.89 (m, 1H), 4.88-4.84 (m, 2H), 3.82-3.71 (m, 7H), 3.70-3.62 (m, 2H), 3.44-3.39 (m, 1H), 3.20-3.11 (m, 1H), 3.08-3.02 (m, 2H), 2.98-2.92 (m, 2H), 2.55-2.50 (m, 2H), 1.84 (d, J = 7.2 Hz, 3H). |
| 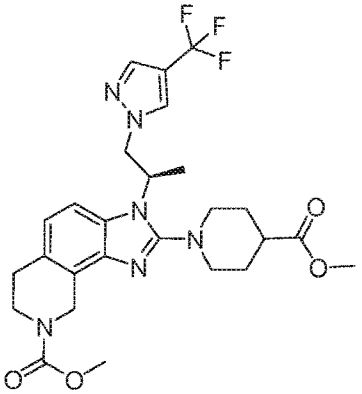<br>First eluting isomer | 1-[8-(methoxycarbonyl)-3-[(2R)-1-[4-(trifluoromethyl)pyrazol-1-yl]propan-2-yl]-6H,7H,9H-imidazo[4,5-h]isoquinolin-2-yl]piperidine-4-carboxylic acid | 535 | 1H-NMR (CD3OD, 400 MHz) δ (ppm): 7.65(s, 1H), 7.52-7.50 (d, J=8.4 Hz, 1H), 7.27-7.21(m, 1H), 7.07 (d, J = 8.4 Hz, 1H), 5.06-4.92 (m, 1H), 4.89 (s, 2H), 4.88-4.79 (m, 1H), 4.62-4.54 (m, 1H), 3.82-3.73 (m, 5H), 3.37-3.27 (m, 1H), 2.98-2.91 (m, 3H), 2.87-2.82 (m, 2H), 2.53-2.35 (m, 1H), 2.05-1.85 (m, 3H), 1.79 (d, J=7.2 Hz, 3H), 1.78-1.64 (m, 1H). |

FIGURE 1 (continued)

| Structure | Name | Mass | NMR |
|---|---|---|---|
| 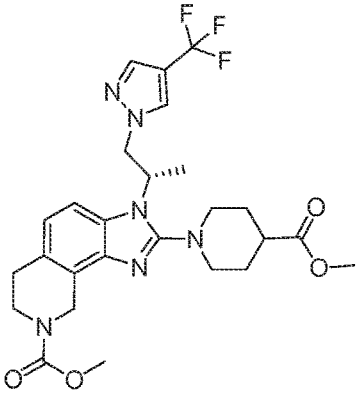<br>Second eluting isomer | 1-[8-(methoxycarbonyl)-3-[(2S)-1-[4-(trifluoromethyl)pyrazol-1-yl]propan-2-yl]-6H,7H,9H-imidazo[4,5-h]isoquinolin-2-yl]piperidine-4-carboxylic acid | 535 | 1H-NMR (CD3OD, 400 MHz) δ (ppm): 7.65 (s, 1H), 7.51 (d, $J$ = 8.4 Hz, 1H), 7.30-7.15 (m, 1H), 7.087 (d, $J$ = 8.4 Hz, 1H), 5.04-4.92 (m, 1H), 4.89 (s, 2H), 4.87-4.79 (m, 1H), 4.59-4.52 (m, 1H), 3.82-3.71 (m, 5H), 3.33-3.21 (m, 1H), 3.02-2.90 (m, 3H), 2.89-2.75 (m, 2H), 2.55-2.43 (m, 1H), 2.04-1.85 (m, 3H), 1.79 (d, $J$ = 6.8 Hz, 3H), 1.78-1.63 (m, 1H). |
| 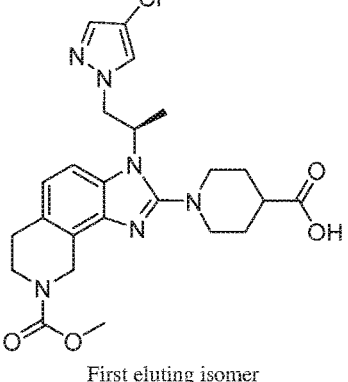<br>First eluting isomer | 1-[3-[(2R)-1-(4-chloro-1H-pyrazol-1-yl)propan-2-yl]-8-(methoxycarbonyl)-3H,6H,7H,8H,9H-imidazo[4,5-h]isoquinolin-2-yl]piperidine-4-carboxylic acid | 501, 503 | 1H-NMR (CD3OD, 400 MHz) δ (ppm): 7.74 (d, J=8.4Hz, 1H), 7.36 (s, 1H), 7.33 (d, J=8.4Hz, 1H), 7.26 (s, 1H), 4.94-4.72 (m, 4H), 4.61-4.49 (m, 1H), 4.87-4.69 (m, 5H), 4.69-4.51 (m, 1H), 3.44-3.33 (m, 2H), 3.28-3.17 (m, 1H), 3.02 (s, 2H), 2.72-2.59 (m, 1H), 2.20-1.91 (m, 3H), 1.83 (d, J=7.6Hz, 3H), 1.82-1.71(m, 1H). |
| 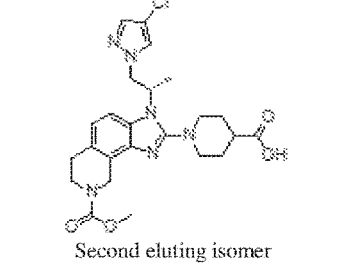<br>Second eluting isomer | 1-[3-[(2S)-1-(4-chloro-1H-pyrazol-1-yl)propan-2-yl]-8-(methoxycarbonyl)-3H,6H,7H,8H,9H-imidazo[4,5-h]isoquinolin-2-yl]piperidine-4-carboxylic acid | 501, 503 | 1H-NMR (CD3OD, 400 MHz) δ (ppm): 7.74 (d, J=8.4Hz, 1H), 7.36 (s, 1H), 7.32 (d, J=8.8Hz, 1H), 7.27 (s, 1H), 4.88-4.66 (m, 4H), 4.65-4.49 (m, 1H), 3.88-3.65 (m, 5H), 3.62-3.52 (m, 1H), 3.44-3.35 (m, 2H), 3.29-3.18 (m, 1H), 3.09-2.90 (m, 2H), 2.72-2.51 (m, 1H), 2.21-1.95 (m, 3H), 1.83 (d, J=7.2Hz, 3H), 1.82-1.71 (m, 1H). |
| 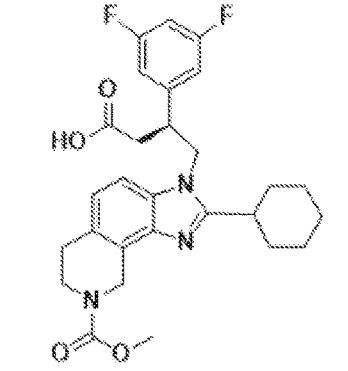<br>First eluting isomer | (3S)-4-[2-cyclohexyl-8-(methoxycarbonyl)-3H,6H,7H,8H,9H-imidazo[4,5-h]isoquinolin-3-yl]-3-(3,5-difluorophenyl)butanoic acid | 512 | 1H-NMR (Methanol-$d$4, 400 MHz) δ (ppm): 7.79 (d, $J$ = 8.4 Hz, 1H), 7.37 (d, $J$ = 8.4 Hz, 1H), 6.95-6.73 (m, 3H), 4.96 (s, 2H), 4.87-4.80 (m, 1H), 4.74-4.64 (m, 1H), 3.88-3.69 (m, 6H), 3.17-3.03 (m, 3H), 3.00-2.80 (m, 2H), 2.08-1.97 (m, 1H), 1.96-1.87 (m, 1H), 1.84-1.75 (m, 2H), 1.74-1.44 (m, 3H), 1.39-1.22 (m, 2H), 1.07-0.99 (m, 1H). |

FIGURE 1 (continued)

| Structure | Name | MW | 1H-NMR |
|---|---|---|---|
| 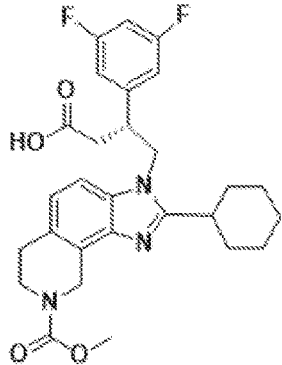<br>Second eluting isomer | (3R)-4-[2-cyclohexyl-8-(methoxycarbonyl)-3H,6H,7H,8H,9H-imidazo[4,5-h]isoquinolin-3-yl]-3-(3,5-difluorophenyl)butanoic acid | 512 | 1H-NMR (Methanol-d4, 400 MHz) δ (ppm): 7.77 (d, J = 8.4Hz, 1H), 7.36 (d, J = 8.4 Hz, 1H), 6.93-6.82 (m, 1H), 6.79 (d, J = 6.8 Hz, 2H), 4.96 (s, 2H), 4.87-4.78 (m, 1H), 4.74-4.64 (m, 1H), 3.88-3.69 (m, 6H), 3.16-2.99 (m, 3H), 3.00-2.80 (m, 2H), 2.04-1.89 (m, 2H), 1.87-1.80 (m, 2H), 1.73-1.46 (m, 3H), 1.39-1.22 (m, 2H), 1.07-0.98 (m, 1H). |
| 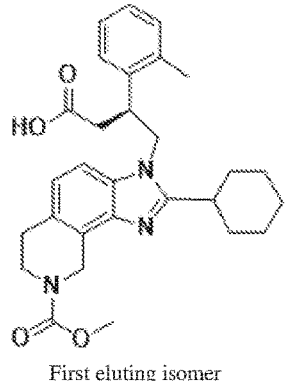<br>First eluting isomer | (3S)-4-[2-cyclohexyl-8-(methoxycarbonyl)-3H,6H,7H,8H,9H-imidazo[4,5-h]isoquinolin-3-yl]-3-(2-methylphenyl)butanoic acid | 490 | 1H-NMR (Methanol-d4, 400 MHz) δ (ppm): 7.88-7.82 (m, 1H), 7.58 (d, J = 7.6 Hz, 1H), 7.39-7.28 (m, 2H), 7.37-7.28 (m, 1H), 6.98 (d, J = 7.6 Hz, 1H), 4.95 (s, 2H), 4.86-4.75 (m, 1H), 4.71-4.57 (m, 1H), 4.14-4.03 (m, 1H), 3.87-3.72 (m, 5H), 3.16-3.06 (m, 1H), 3.06-2.97 (m, 2H), 2.85-2.76 (m, 1H), 2.71-2.63 (m, 1H), 1.94-1.81 (m, 2H), 1.81-1.62 (m, 2H), 1.57-1.36 (m, 6H), 1.36-1.22 (m, 1H), 1.21-1.07 (m, 1H), 0.77-0.63 (m, 1H). |
| 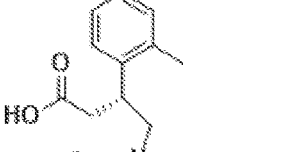<br>Second eluting isomer | (3R)-4-[2-cyclohexyl-8-(methoxycarbonyl)-3H,6H,7H,8H,9H-imidazo[4,5-h]isoquinolin-3-yl]-3-(2-methylphenyl)butanoic acid | 490 | 1H-NMR (Methanol-d4, 400 MHz) δ (ppm): 7.89-7.82 (m, 1H), 7.57 (d, J = 7.6 Hz, 1H), 7.39-7.28 (m, 2H), 7.37-7.28 (m, 1H), 6.98 (d, J = 7.6 Hz, 1H), 4.95 (s, 2H), 4.86-4.73 (m, 1H), 4.71-4.57 (m, 1H), 4.15-4.03 (m, 1H), 3.87-3.72 (m, 5H), 3.16-3.06 (m, 1H), 3.06-2.97 (m, 2H), 2.85-2.76 (m, 1H), 2.72-2.57 (m, 1H), 1.94-1.81 (m, 2H), 1.81-1.62 (m, 2H), 1.62-1.36 (m, 6H), 1.36-1.22 (m, 1H), 1.21-1.07 (m, 1H), 0.78-0.66 (m, 1H). |

FIGURE 1 (continued)

| Structure | Name | MW | 1H-NMR |
|---|---|---|---|
| 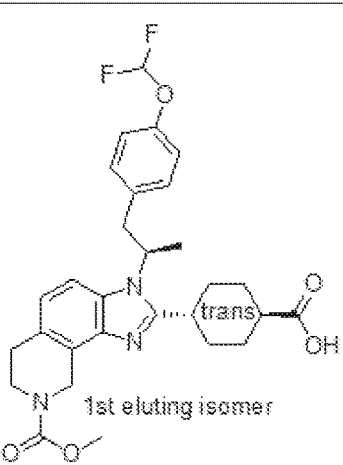 1st eluting isomer | trans-4-[3-[(2R)-1-[4-(difluoromethoxy)phenyl]propan-2-yl]-8-(methoxycarbonyl)-3H,6H,7H,8H,9H-imidazo[4,5-h]isoquinolin-2-yl]cyclohexane-1-carboxylic acid | 542 | 1H-NMR (CD3OD, 400 MHz) δ (ppm): 7.69 (d, $J$ = 8.4 Hz, 1H), 7.11 (d, $J$ = 8.4 Hz, 1H), 6.92-6.81 (m, 2H), 6.70-6.51 (m, 3H), 5.02-4.91 (m, 2H), 4.87-4.78 (m, 1H), 3.81-3.78 (m, 5H), 3.51-3.45 (m, 1H), 3.19-3.16 (m, 1H), 2.99-2.96 (m, 2H), 2.42 (br s, 1H), 3.34-2.28 (m, 1H), 2.08-2.05 (m, 1H), 1.95-1.81 (m, 5H), 1.70-1.52 (m, 3H), 1.30-1.26 (m, 1H), 0.89-0.86 (m, 1H). |
| 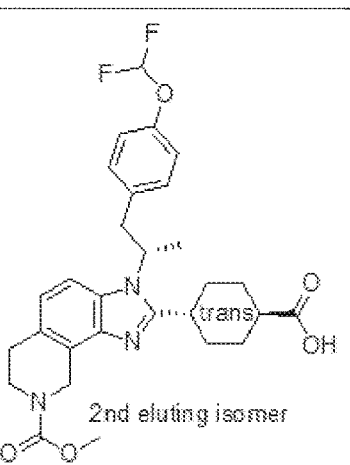 2nd eluting isomer | trans-4-[3-[(2S)-1-[4-(difluoromethoxy)phenyl]propan-2-yl]-8-(methoxycarbonyl)-3H,6H,7H,8H,9H-imidazo[4,5-h]isoquinolin-2-yl]cyclohexane-1-carboxylic acid | 542 | 1H-NMR (CD3OD, 400 MHz) δ (ppm): 7.69 (d, $J$ = 7.6 Hz, 1H), 7.11 (d, $J$ = 8.4 Hz, 1H), 6.92-6.83 (m, 2H), 6.81-6.51 (m, 3H), 5.02-4.92 (m, 2H), 4.87-4.81 (m, 1H), 3.81-3.78 (m, 5H), 3.51-3.45 (m, 1H), 3.20-3.16 (m, 1H), 2.99-2.96 (m, 2H), 2.43 (br s, 1H), 2.34-2.28 (m, 1H), 2.08-2.05 (m, 1H), 1.95-1.81 (m, 5H), 1.67-1.52 (m, 3H), 1.31-1.27 (m, 1H), 0.89-0.86 (m, 1H). |
| 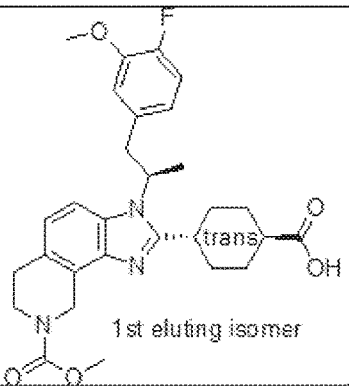 1st eluting isomer | trans-4-[3-[(2R)-1-(4-fluoro-3-methoxyphenyl)propan-2-yl]-8-(methoxycarbonyl)-3H,6H,7H,8H,9H-imidazo[4,5-h]isoquinolin-2-yl]cyclohexane-1-carboxylic acid | 524 | 1H-NMR (CD3OD, 400 MHz) δ (ppm): 7.70 (d, $J$ = 7.6 Hz, 1H), 7.13 (d, $J$ = 8 Hz, 1H), 6.86-6.81 (m, 1H), 6.42 (s, 1H), 6.22 (d, $J$ = 6 Hz, 1H), 4.96 (s, 2H), 4.85-4.76 (m, 1H), 3.81-3.78 (m, 5H), 3.46-3.40 (m, 4H), 3.17-3.10 (m, 1H), 2.99-2.96 (m, 2H), 2.45 (br s, 1H), 2.35-2.29 (br s, 1H), 2.08-2.05 (m, 1H), 1.98-1.95 (m, 1H), 1.89-1.79 (m, 4H), 1.70-1.56 (m, 3H), 1.34-1.25 (m, 1H), 0.94-0.91 (m, 1H). |

FIGURE 1 (continued)

| Structure | Name | MW | 1H-NMR |
|---|---|---|---|
| 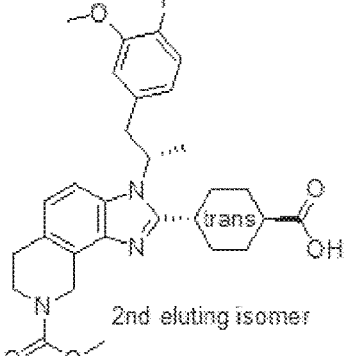 2nd eluting isomer | trans-4-[3-[(2S)-1-(4-fluoro-3-methoxyphenyl)propan-2-yl]-8-(methoxycarbonyl)-3H,6H,7H,8H,9H-imidazo[4,5-h]isoquinolin-2-yl]cyclohexane-1-carboxylic acid | 524 | 1H-NMR (CD3OD, 400 MHz) δ (ppm): 7.70 (d, J = 7.6 Hz, 1H), 7.13 (d, J = 8.4 Hz, 1H), 6.86-6.81 (m, 1H), 6.43 (s, 1H), 6.23 (d, J = 6.8 Hz, 1H), 4.97 (s, 2H), 4.88-4.85 (m, 1H), 3.78-3.77 (m, 5H), 3.46-3.40 (m, 4H), 3.15-3.10 (m, 1H), 2.99-2.96 (m, 2H), 2.44 (br s, 1H), 2.35-2.29 (br s, 1H), 2.08-2.05 (br s, 1H), 1.98-1.95 (m, 1H), 1.89-1.83 (m, 4H), 1.71-1.56 (m, 3H), 1.32-1.25 (m, 1H), 0.96-0.88 (m, 1H). |
| 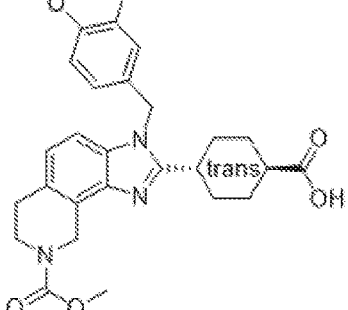 | (trans)-4-{3-[(3-fluoro-4-methoxyphenyl)methyl]-8-(methoxycarbonyl)-3H,6H,7H,8H,9H-imidazo[4,5-h]isoquinolin-2-yl}cyclohexane-1-carboxylic acid | 496 | 1H-NMR (CD3OD, 400 MHz) δ (ppm): 7.26-7.24 (m, 1H), 7.05-7.01 (m, 2H), 6.87-6.79 (m, 2H), 5.44 (s, 2H), 5.02 (s, 2H), 3.84 (s, 3H), 3.79 (s, 5H), 3.02-2.95 (m, 3H), 2.41-2.35 (m, 1H), 2.10-2.07 (m, 2H), 1.92-1.84 (m, 4H), 1.59-1.49 (m, 2H). |
| 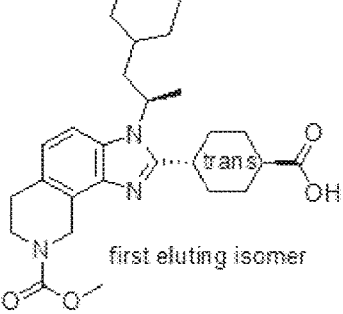 first eluting isomer | Trans-4-[8-(methoxycarbonyl)-3-[(2R)-1-(oxan-4-yl)propan-2-yl]-3H,6H,7H,8H,9H-imidazo[4,5-h]isoquinolin-2-yl]cyclohexane-1-carboxylic acid | 484 | 1H-NMR (DMSO-d6, 400 MHz) δ (ppm): 7.50 (br s, 1H), 7.03 (d, J = 8.4 Hz, 1H), 5.00 (s, 2H), 3.92 (d, J = 9.6 Hz, 1H), 3.82-3.76 (m, 6H), 3.27-3.21 (m, 2H), 3.08-3.03 (m, 1H), 2.96-2.93 (m, 2H), 2.50-2.44 (m, 1H), 2.21-2.19 (m, 3H), 2.08-1.92 (m, 3H), 1.90-1.87 (m, 2H), 1.74-1.58 (m, 6H), 1.40-1.21 (m, 5H). |
| 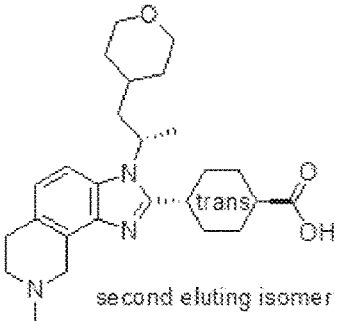 second eluting isomer | trans-4-[8-(methoxycarbonyl)-3-[(2S)-1-(oxan-4-yl)propan-2-yl]-3H,6H,7H,8H,9H-imidazo[4,5-h]isoquinolin-2-yl]cyclohexane-1-carboxylic acid | 484 | 1H-NMR (DMSO-d6, 400 MHz) δ (ppm): 7.49 (br s, 1H), 7.03 (d, J = 8.4 Hz, 1H), 5.00 (s, 2H), 3.91 (d, J = 9.6 Hz, 1H), 3.82-3.76 (m, 6H), 3.27-3.21 (m, 2H), 3.07-3.00 (m, 1H), 2.96-2.93 (m, 2H), 2.50-2.44 (m, 1H), 2.21-2.18 (m, 3H), 2.07-2.01 (m, 3H), 1.92-1.83 (m, 2H), 1.74-1.66 (m, 6H), 1.40-1.21 (m, 5H). |

FIGURE 1 (continued)

| | Name | MW | NMR |
|---|---|---|---|
| 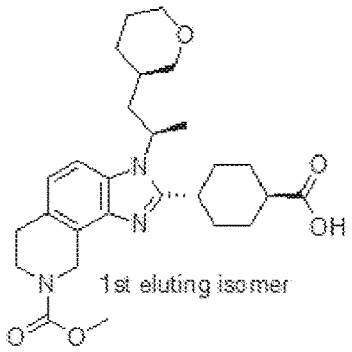 1st eluting isomer | (trans)-4-[8-(methoxycarbonyl)-3-[(2R)-1-[(3R)-oxan-3-yl]propan-2-yl]-3H,6H,7H,8H,9H-imidazo[4,5-h]isoquinolin-2-yl]cyclohexane-1-carboxylic acid | 484 | 1H-NMR (Methanol-d4, 400 MHz) δ (ppm): 7.49 (d, J = 7.2 Hz, 1H), 7.03 (d, J = 7.6 Hz, 1H), 4.99 (s, 2H), 4.86-4.79 (m, 1H), 3.78-3.72 (m, 6H), 3.40-3.33 (m, 2H), 3.09-3.04 (m, 1H), 2.99-2.94 (m, 3H), 2.50-2.44 (m, 1H), 2.21-2.15 (m, 3H), 2.09-1.94 (m, 4H), 1.91-1.52 (m, 8H), 1.47 (br s, 1H), 1.37-1.15 (m, 2H). |
| 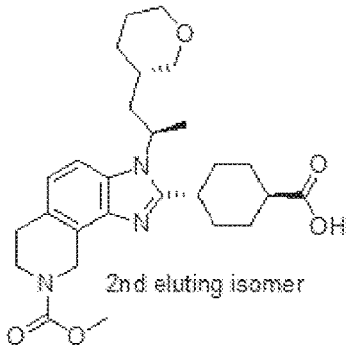 2nd eluting isomer | (trans)-4-[8-(methoxycarbonyl)-3-[(2R)-1-[(3S)-oxan-3-yl]propan-2-yl]-3H,6H,7H,8H,9H-imidazo[4,5-h]isoquinolin-2-yl]cyclohexane-1-carboxylic acid | 484 | 1H-NMR (Methanol-d4, 400 MHz) δ (ppm): 7.50 (br s, 1H), 7.03 (d, J = 8.4 Hz, 1H), 4.99 (s, 2H), 4.90-4.79 (m, 1H), 3.91-3.88 (m, 1H), 3.79-3.75 (m, 6H), 3.37-3.33 (m, 1H), 3.18-3.13 (m, 1H), 3.07-3.02 (m, 1H), 2.95-2.92 (m, 2H), 2.47 (br s, 1H), 2.21-2.12 (m, 2H), 2.04 (br s, 4H), 1.89-1.83 (m, 2H), 1.70-1.62 (m, 5H), 1.52-1.41 (m, 3H), 1.11 (br s, 1H), 0.88 (br s, 1H). |
| 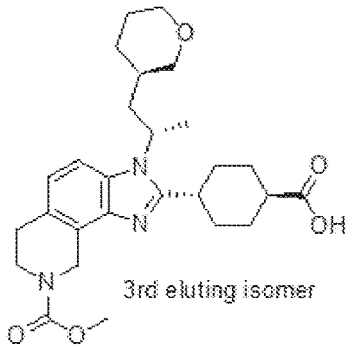 3rd eluting isomer | (trans)-4-[8-(methoxycarbonyl)-3-[(2S)-1-[(3R)-oxan-3-yl]propan-2-yl]-3H,6H,7H,8H,9H-imidazo[4,5-h]isoquinolin-2-yl]cyclohexane-1-carboxylic acid | 484 | 1H-NMR (Methanol-d4, 400 MHz) δ (ppm): 7.49 (br s, 1H), 7.03 (d, J = 8.8 Hz, 1H), 4.99 (s, 2H), 4.82-4.79 (m, 1H), 3.91-3.88 (m, 1H), 3.78 (br s, 6H), 3.38-3.35 (m, 1H), 3.19-3.13 (m, 1H), 3.06 (br s, 1H), 2.94 (s, 2H), 2.50-2.44 (m, 1H), 2.21-2.15 (m, 2H), 2.04 (br s, 4H), 1.90-1.84 (m, 2H), 1.76-1.63 (m, 5H), 1.52-1.40 (m, 3H), 1.32 (br s, 1H), 1.11 (br s, 1H). |
| 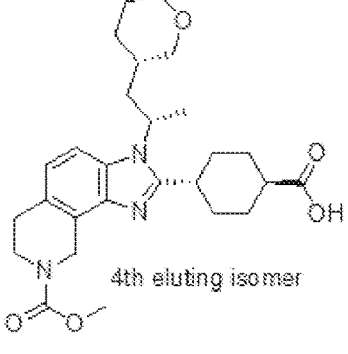 4th eluting isomer | (trans)-4-[8-(methoxycarbonyl)-3-[(2S)-1-[(3S)-oxan-3-yl]propan-2-yl]-3H,6H,7H,8H,9H-imidazo[4,5-h]isoquinolin-2-yl]cyclohexane-1-carboxylic acid | 484 | 1H-NMR (Methanol-d4, 400 MHz) δ (ppm): 7.49 (d, J = 7.2 Hz, 1H), 7.03 (d, J = 8.4 Hz, 1H), 4.99 (s, 2H), 4.83-4.78 (m, 1H), 3.78-3.73 (m, 6H), 3.40-3.38 (m, 2H), 3.09-3.3 (m, 1H), 2.99-2.92 (m, 3H), 2.47-2.44 (m, 1H), 2.21-2.15 (m, 3H), 2.09-1.90 (m, 4H), 1.84-1.63 (m, 1H), 1.80-1.52 (m, 7H), 1.47 (s, 1H), 1.39-1.12 (m, 2H). |

FIGURE 1 (continued)

| Structure | Name | MW | 1H-NMR |
|---|---|---|---|
| 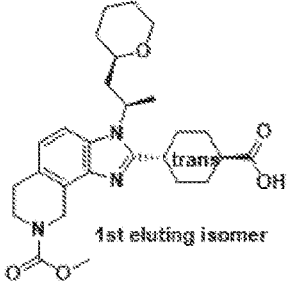 1st eluting isomer | Trans -4-[8-(methoxycarbonyl)-3-[(2R)-1-[(2R)-oxan-2-yl]propan-2-yl]-3H,6H,7H,8H,9H-imidazo[4,5-h]isoquinolin-2-yl]cyclohexane-1-carboxylic acid | 484 | 1H-NMR (CD3OD, 400 MHz) δ (ppm): 7.47 (d, J = 8.8Hz, 1H), 7.02 (d, J = 8.8Hz, 1H), 5.01 (s, 2H), 4.88(br s, 1H), 3.98-3.91 (m, 1H), 3.87-3.79 (m, 5H), 3.17-3.15 (m, 2H), 2.96-2.94 (m, 2H), 2.55-2.41 (m, 3H), 2.24-2.13 (m,4H), 2.00 (br s, 1H), 1.91-1.79(m, 1H), 1.67-1.52 (m,7H), 1.47-1.23 (m, 5H). |
| 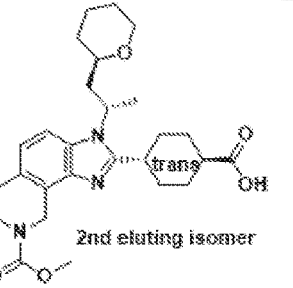 2nd eluting isomer | Trans -4-[8-(methoxycarbonyl)-3-[(2S)-1-[(2R)-oxan-2-yl]propan-2-yl]-3H,6H,7H,8H,9H-imidazo[4,5-h]isoquinolin-2-yl]cyclohexane-1-carboxylic acid | 484 | 1H-NMR (CD3OD, 400 MHz) δ (ppm): δ7.44 (d, J = 8.4 Hz, 1H), 7.02 (d, J = 8.4 Hz, 1H), 4.99 (s, 2H), 4.94-4.88 (m, 1H), 3.94-3.91 (m, 1H), 3.79-3.75 (m, 5H), 3.42 (br s, 2H), 3.09-3.03 (m, 1H), 2.95-2.93 (m, 2H), 2.47-2.42 (m, 1H), 2.24-2.11 (m, 4H), 2.06-1.81 (m, 5H), 1.71-1.59 (m, 6H), 1.55-1.51 (m, 3H), 1.22-1.17 (m, 1H). |
| 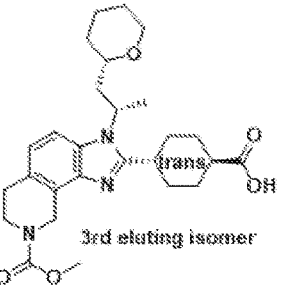 3rd eluting isomer | Trans -4-[8-(methoxycarbonyl)-3-[(2S)-1-[(2S)-oxan-2-yl]propan-2-yl]-3H,6H,7H,8H,9H-imidazo[4,5-h]isoquinolin-2-yl]cyclohexane-1-carboxylic acid | 484 | 1H-NMR (CD3OD, 400 MHz) δ (ppm): 7.45 (d, J = 8.8 Hz, 1H), 7.02 (d, J = 8.8 Hz, 1H), 5.01 (s, 2H), 1.89 (br s, 1H), 3.99-3.95 (m, 1H), 3.79-3.76 (m, 5H), 3.20-3.15 (m, 2H), 2.96-2.93 (m, 2H), 2.57-2.43 (m, 3H), 2.24-1.90 (m, 6H), 1.71-1.59 (m, 7H), 1.52-1.26 (m, 7H). |
| 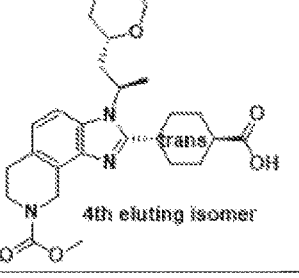 4th eluting isomer | Trans -4-[8-(methoxycarbonyl)-3-[(2R)-1-[(2S)-oxan-2-yl]propan-2-yl]-3H,6H,7H,8H,9H-imidazo[4,5-h]isoquinolin-2-yl]cyclohexane-1-carboxylic acid | 484 | 1H-NMR (CD3OD, 400 MHz) δ (ppm): 7.46 (d, J = 8.4 Hz, 1H), 7.02 (d, J = 8.4 Hz, 1H),4.99 (s, 2H), 4.92-4.89 (m, 1H), 3.94-3.91 (m, 1H), 3.78-3.76 (m, 5H), 3.42-3.34 (m, 2H), 3.09-3.04 (m, 1H), 2.95-2.93 (m, 2H), 2.47-2.42 (m, 1H), 2.23-2.06 (m, 4H), 2.04-1.80 (m, 5H), 1.71-1.51 (m, 9H), 1.20-1.67 (m, 1H). |
| 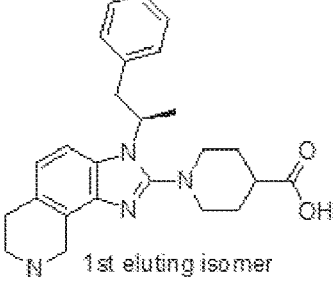 1st eluting isomer | methyl 1-[8-(methoxycarbonyl)-3-[(2R)-1-phenylpropan-2-yl]-3H,6H,7H,8H,9H-imidazo[4,5-h]isoquinolin-2-yl]piperidine-4-carboxylate | 477 | 1H-NMR-PH-FMA-PJ00200-008-0A (CD3OD, 400MHz) δ (ppm): 7.59 (d, J = 8.0 Hz, 1H), 7.10-7.06 (m, 4H), 6.78-6.76 (m, 2H), 4.88 (s, 2H), 4.85-4.81 (m, 1H), 3.80-3.75 (m, 5H), 3.42-3.39 (m, 1H), 3.22-3.08 (m, 2H), 2.97 (s, 2H), 2.81-2.75 (m, 2H), 2.44-2.40 (m, 2H), 1.96-1.94 (m, 1H), 1.86-1.77 (m, 5H), 1.64-1.57 (m, 1H). |

FIGURE 1 (continued)

| Structure | Name | MW | 1H NMR |
|---|---|---|---|
| 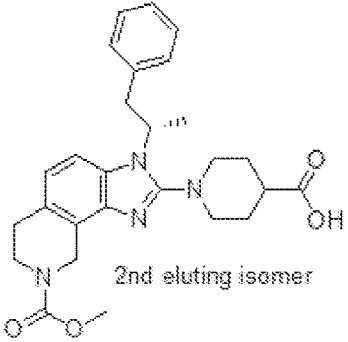 | methyl 1-[8-(methoxycarbonyl)-3-[(2S)-1-phenylpropan-2-yl]-3H,6H,7H,8H,9H-imidazo[4,5-h]isoquinolin-2-yl]piperidine-4-carboxylate<br>2nd eluting isomer | 477 | 1H-NMR-PH-FMA-PJ00200-008-0B (CD3OD, 400MHz) δ (ppm): 7.59 (d, J = 8.0 Hz, 1H), 7.10-7.06 (m, 4H), 6.78-6.76 (m, 2H), 4.89 (s, 2H), 4.85-4.81 (m, 1H), 3.79-3.75 (m, 5H), 3.42-3.38 (m, 1H), 3.18-3.08 (m, 2H), 2.97 (s, 2H), 2.81-2.75 (m, 2H), 2.44-2.40 (m, 2H), 1.96-1.94 (m, 1H), 1.86-1.77 (m, 5H), 1.64-1.57 (m, 1H). |
| 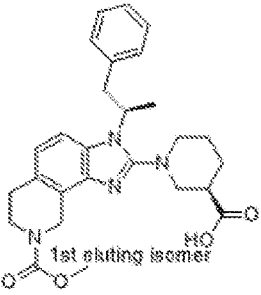 | (3R)-1-[8-(methoxycarbonyl)-3-[(2R)-1-phenylpropan-2-yl]-3H,6H,7H,8H,9H-imidazo[4,5-h]isoquinolin-2-yl]piperidine-3-carboxylic acid<br>1st eluting isomer | 477 | 1H-NMR-PH-FMA-PJ00200-009-0A (DMSO, 400MHz) δ (ppm): 12.43 (br s, 1H), 7.57 (d, J = 8.4 Hz, 1H), 7.13-7.06 (m, 3H), 6.95 (d, J = 8.4 Hz, 1H), 6.88-6.85 (m, 2H), 4.85-4.79 (m, 1H), 4.71 (s, 2H), 3.73 -3.59 (m, 5H), 3.27-3.22 (m, 1H), 3.12-3.07 (m, 1H), 3.00-2.90 (m, 2H), 2.88-2.78 (m, 3H), 2.51 (br s, 2H), 1.82 (br s, 1H), 1.69-1.61 (m, 6H) |
| 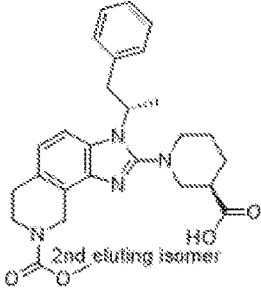 | (3R)-1-[8-(methoxycarbonyl)-3-[(2S)-1-phenylpropan-2-yl]-3H,6H,7H,8H,9H-imidazo[4,5-h]isoquinolin-2-yl]piperidine-3-carboxylic acid<br>2nd eluting isomer | 477 | 1H-NMR-PH-FMA-PJ00200-009-0B (DMSO, 400MHz) δ (ppm): 7.58 (d, J = 8.0 Hz, 1H), 7.18-7.10 (m, 3H), 6.98-6.94 (m, 3H), 4.72 (s, 3H), 3.71-3.59 (m, 5H), 3.26-3.13 (m, 3H), 2.85-2.82 (m, 3H), 2.62-2.51 (m, 3H), 1.94 (br s, 1H), 1.63 (br s, 1H), 1.56 (d, J = 7.2 Hz, 3H), 1.51-1.46 (m, 2H). |
| 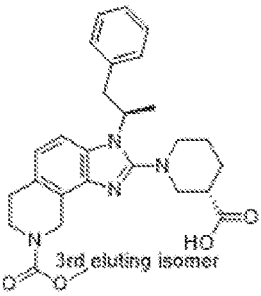 | (3S)-1-[8-(methoxycarbonyl)-3-[(2R)-1-phenylpropan-2-yl]-3H,6H,7H,8H,9H-imidazo[4,5-h]isoquinolin-2-yl]piperidine-3-carboxylic acid<br>3rd eluting isomer | 477 | 1H-NMR-PH-FMA-PJ00200-009-0C (DMSO, 400MHz) δ (ppm): 7.58 (d, J = 8.0 Hz, 1H), 7.13-7.06 (m, 3H), 6.95 (d, J = 8.4 Hz, 1H), 6.88 (d, J = 7.2 Hz, 2H), 4.85-4.81 (m, 1H), 4.71 (s, 2H), 3.74-3.59 (m, 5H), 3.27-3.22 (m, 1H), 3.12-3.07 (m, 1H), 2.97-2.90 (m, 2H), 2.88-2.79 (m, 3H), 2.51-2.54 (m, 2H), 1.82 (br s, 1H), 1.69 – 1.60 (m, 6H). |

FIGURE 1 (continued)

| | Structure | Name | MW | NMR |
|---|---|---|---|---|
| | 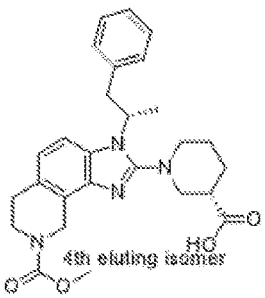 4th eluting isomer | (3S)-1-[8-(methoxycarbonyl)-3-[(2S)-1-phenylpropan-2-yl]-3H,6H,7H,8H,9H-imidazo[4,5-h]isoquinolin-2-yl]piperidine-3-carboxylic acid | 477 | 1H-NMR-PH-FMA-PJ00200-009-0D (DMSO, 400MHz) δ (ppm): 12.38 (br s, 1H), 7.58 (d, $J$ = 8.0 Hz, 1H), 7.18-7.10 (m, 3H), 6.98-6.94 (m, 3H), 4.72 (br s, 3H), 3.70-3.59 (m, 5H), 3.26-3.24 (m, 2H), 3.18-3.13 (m, 1H), 2.86-2.83 (m, 3H), 2.64 (br s, 2H), 2.57-2.51 (m, 1H), 1.94 (br s, 1H), 1.63 (s, 1H), 1.56 (d, $J$ = 6.8 Hz, 3H), 1.51-1.49 (m, 2H). |
| | 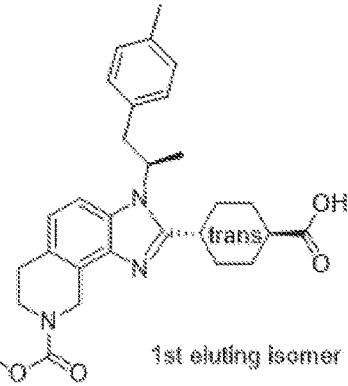 1st eluting isomer | (trans)-4-[8-(methoxycarbonyl)-3-[(2R)-1-(4-methylphenyl)propan-2-yl]-3H,6H,7H,8H,9H-imidazo[4,5-h]isoquinolin-2-yl]cyclohexane-1-carboxylic acid | 490 | 1H-NMR (CD3OD, 400 MHz) δ (ppm): 7.67 (d, $J$ = 7.2 Hz, 1H), 7.10 (d, $J$ = 8.8 Hz, 1H), 6.93 (d, $J$ = 7.6 Hz, 2H), 6.66 (d, $J$ = 7.6 Hz, 2H), 4.96 (s, 2H), 4.84-4.81(m, 1H), 3.80-3.78 (m, 5H), 3.43-3.40 (m, 1H), 3.14-3.10 (m, 1H), 2.99-2.96 (m, 2H), 2.38-2.27 (m, 2H), 2.22 (s, 3H), 2.07-2.03 (m, 1H), 1.91-1.79 (m, 5H), 1.65-1.47 (m, 3H), 1.30-1.24 (m, 1H), 0.83-0.81 (m, 1H). |
| | 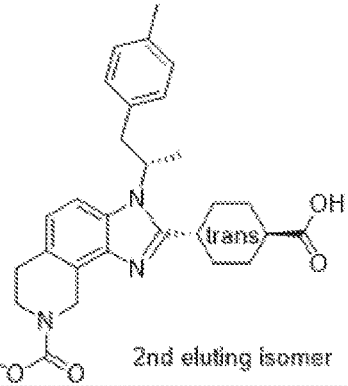 2nd eluting isomer | (trans)-4-[8-(methoxycarbonyl)-3-[(2S)-1-(4-methylphenyl)propan-2-yl]-3H,6H,7H,8H,9H-imidazo[4,5-h]isoquinolin-2-yl]cyclohexane-1-carboxylic acid | 490 | 1H-NMR (CD3OD, 400 MHz) δ (ppm): 7.67 (d, $J$ = 8.0 Hz, 1H), 7.10 (d, $J$ = 8.0 Hz, 1H), 6.93 (d, $J$ = 7.6 Hz, 2H), 6.71-6.65 (m, 2H), 4.96 (s, 2H), 4.87-4.81 (m, 1H), 3.80-3.78 (m, 5H), 3.43-3.40 (m, 1H), 3.14-3.10 (m, 1H), 2.97-2.94 (m, 2H), 2.38-2.27 (m, 2H), 2.22 (s, 3H), 2.07-2.04 (m, 1H), 1.91-1.79 (m, 5H), 1.65-1.47 (m, 3H), 1.30-1.24 (m, 1H), 0.83-0.81 (m, 1H). |
| | 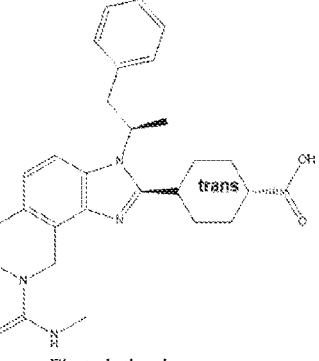 First eluting isomer | (trans)-4-[8-(methylcarbamoyl)-3-[(2R)-1-phenylpropan-2-yl]-3H,6H,7H,8H,9H-imidazo[4,5-h]isoquinolin-2-yl]cyclohexane-1-carboxylic acid | 475 | 1H-NMR-PH-FMA-PJ00200-013-0A (CD3OD, 400MHz) δ (ppm): 7.79 (d, $J$ = 7.2 Hz, 1H), 7.13-7.11 (m, 4H), 6.80 (s, 2H), 4.94-4.81 (m, 3H), 3.80-3.67 (m, 2H), 3.51-3.45 (m, 1H), 3.20-3.16 (m, 1H), 2.98 (s, 2H), 2.81 (s, 3H), 2.43-2.41 (m, 1H), 2.28-2.26 (m, 1H), 2.06 (d, $J$ = 8.0 Hz, 1H), 1.88-1.82 (m, 5H), 1.64-1.57 (m, 3H), 1.32-1.20 (m, 1H), 0.89-0.80 (m, 1H). |

FIGURE 1 (continued)

| Structure | Name | MW | NMR |
|---|---|---|---|
| 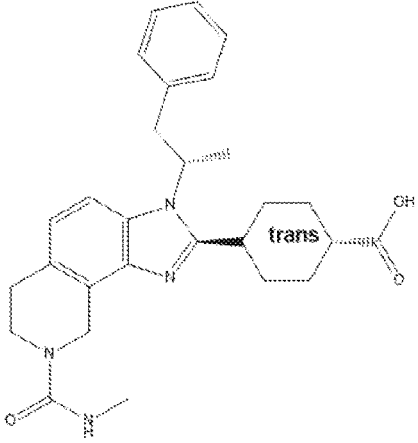 Second eluting isomer | (trans)-4-[8-(methylcarbamoyl)-3-[(2S)-1-phenylpropan-2-yl]-3H,6H,7H,8H,9H-imidazo[4,5-h]isoquinolin-2-yl]cyclohexane-1-carboxylic acid | 475 | 1H-NMR-PH-FMA-PJ00200-013-0B (CD3OD, 400MHz) δ (ppm): 7.70 (d, J = 8.0 Hz, 1H), 7.13-7.11 (m, 4H), 6.80 (d, J = 2.8 Hz, 1H), 4.91-4.81 (m, 3H), 3.81-3.67 (m, 2H), 3.51-3.45 (m, 1H), 3.20-3.16 (m, 1H), 2.94 (s, 2H), 2.81 (s, 3H), 2.41 (s, 1H), 2.28-2.26 (m, 1H), 2.06 (d, J = 10.0 Hz, 1H), 1.88-1.82 (m, 5H), 1.60-1.54 (m, 3H), 1.31-1.22 (m, 1H), 0.89-0.80 (m, 1H). |
| 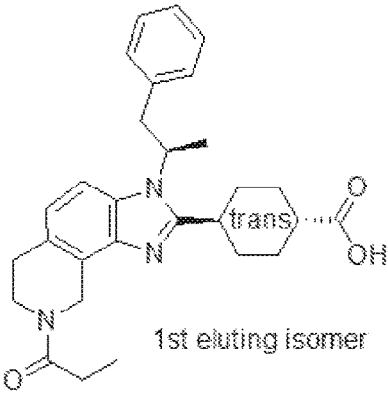 1st eluting isomer | trans-4-[3-[(2R)-1-phenylpropan-2-yl]-8-propanoyl-3H,6H,7H,8H,9H-imidazo[4,5-h]isoquinolin-2-yl]cyclohexane-1-carboxylic acid | 474 | (CD3OD, 400MHz) δ (ppm): 7.73 (s, 1H), 7.14-7.09 (m, 4H), 6.80 (s, 2H), 5.12-5.00 (m, 2H), 4.87-4.84 (m, 1H), 3.92-3.83 (m, 2H), 3.51-3.44 (m, 1H), 3.20-3.16 (m, 1H), 3.06-3.04 (m, 1H), 2.99-2.96 (m, 1H), 2.63-2.54 (m, 2H), 2.53-2.35 (m, 1H), 2.34-2.27 (m, 1H), 2.07-2.05 (m, 1H), 1.87-1.82 (m, 5H), 1.57-1.48 (m, 3H), 1.31-1.17 (m, 4H), 0.92-0.83 (m, 1H). |
| 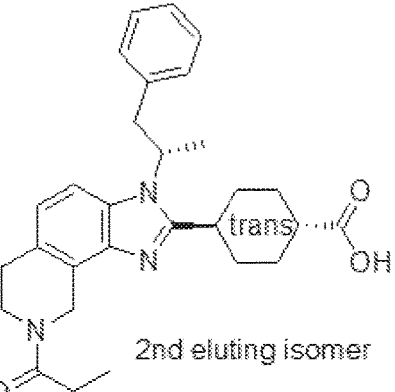 2nd eluting isomer | trans-4-[3-[(2S)-1-phenylpropan-2-yl]-8-propanoyl-3H,6H,7H,8H,9H-imidazo[4,5-h]isoquinolin-2-yl]cyclohexane-1-carboxylic acid | 474 | (CD3OD, 400MHz) δ (ppm): 7.71 (s, 1H), 7.15-7.11 (m, 4H), 6.80 (s, 2H), 5.12-5.01 (m, 2H), 4.87 (s, 1H), 3.92-3.83 (m, 2H), 3.51-3.44 (m, 1H), 3.20-3.16 (m, 1H), 3.06 (s, 1H), 2.99-2.96 (m, 1H), 2.63-2.54 (m, 2H), 2.43-2.41 (m, 1H), 2.29-2.26 (m, 1H), 2.07-2.05 (m, 1H), 1.97-1.82 (m, 5H), 1.66-1.51 (m, 3H), 1.39-1.17 (m, 4H), 0.84-0.83 (m, 1H). |

FIGURE 1 (continued)

| Structure | Name | MW | NMR |
|---|---|---|---|
| 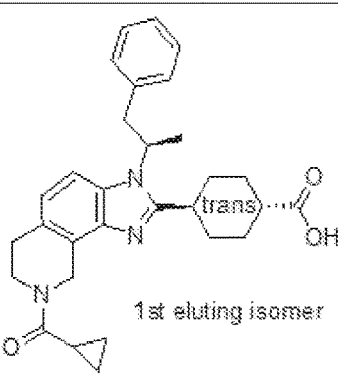 | trans-4-[8-cyclopropanecarbonyl-3-[(2R)-1-phenylpropan-2-yl]-3H,6H,7H,8H,9H-imidazo[4,5-h]isoquinolin-2-yl]cyclohexane-1-carboxylic acid | 486 | CD3OD, 400MHz) δ (ppm): 7.72 (s, 1H), 7.15-7.12 (m, 4H), 6.81 (s, 2H), 5.32 (s, 1H), 5.07 (d, J = 8.0 Hz,1H), 4.87 (s, 1H), 4.09 (s, 1H), 3.92 (d, J = 6.0 Hz,1H), 3.51-3.45 (m, 1H), 3.20-3.06 (m, 2H), 2.97 (s, 1H), 2.68-2.29 (m, 2H), 2.18-2.05 (m, 2H), 1.88-1.83 (m, 5H), 1.68-1.51 (m, 3H), 1.31-1.25 (m, 1H), 0.99-0.80 (m, 5H). |
| 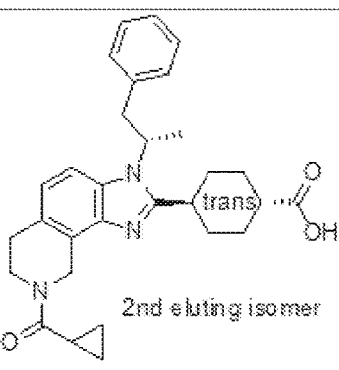 | trans-4-[8-cyclopropanecarbonyl-3-[(2S)-1-phenylpropan-2-yl]-3H,6H,7H,8H,9H-imidazo[4,5-h]isoquinolin-2-yl]cyclohexane-1-carboxylic acid | 486 | (CD3OD, 400MHz) δ (ppm): 7.72 (s, 1H), 7.16-7.12 (m, 4H), 6.81 (s, 2H), 5.27 (s, 1H), 5.07 (d, J = 7.2 Hz,1H), 4.87 (s, 1H), 4.09 (s, 1H), 3.92 (d, J = 6.0 Hz,1H), 3.52-3.45 (m, 1H), 3.20-3.11 (m, 2H), 2.97 (s, 1H), 2.68-2.29 (m, 2H), 2.18-2.05 (m, 2H), 1.88-1.83 (m, 5H), 1.77-1.55 (m, 3H), 1.40-1.19 (m, 1H), 0.96-0.90 (m, 5H). |
| 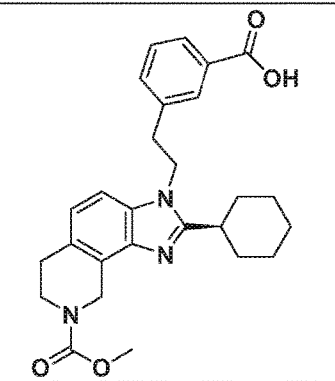 | 3-{2-[2-cyclohexyl-8-(methoxycarbonyl)-3H,6H,7H,8H,9H-imidazo[4,5-h]isoquinolin-3-yl]ethyl}benzoic acid | 462 | 1H-NMR (Methanol-d4, 400 MHz) δ (ppm): 7.86 (d, J = 8 Hz, 1H), 7.69 (s, 1H), 7.37 (d, J = 8.4 Hz, 1H), 7.32-7.28 (m, 1H), 7.11-7.05 (m, 2H), 4.98 (s, 2H), 4.56-4.53 (m, 2H), 3.78-3.76 (m, 5H), 3.22-3.19 (m, 2H), 2.98-2.95 (m, 2H), 2.43-2.37 (m, 1H), 1.76-1.70 (m, 3H), 1.64-1.54 (m, 2H), 1.43-1.37 (m, 2H), 1.32-1.17 (m, 3H). |
| 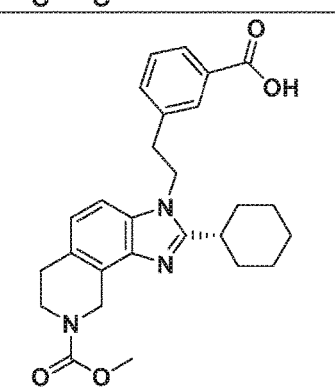 | 2-[2-[2-cyclohexyl-8-(methoxycarbonyl)-6H,7H,9H-imidazo[4,5-h]isoquinolin-3-yl]ethyl]benzoic acid | 462 | 1H-NMR (DMSO-d6, 400 MHz) δ (ppm): 13.24 (br s, 1H), 7.88 (s, 1H), 7.48 (d, J = 8 Hz, 1H), 7.32 (br s, 2H), 6.98 (d, J = 8.4 Hz, 1H), 6.88 (br s, 1H), 4.80 (s, 2H), 4.47-4.44 (m, 2H), 3.68-3.66 (m, 5H), 2.88-2.86 (m, 2H) 2.58-2.51 (m, 1H), 1.71-1.62 (m, 3H), 1.60-1.46 (m, 5H), 1.28-1.17 (m, 4H). |

FIGURE 1 (continued)

| Structure | Name | # | NMR |
|---|---|---|---|
| 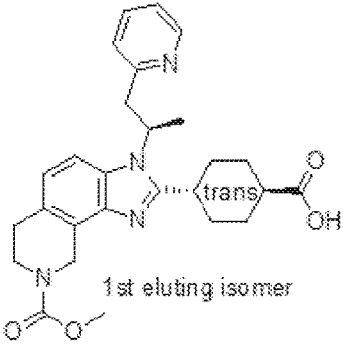 1st eluting isomer | Trans-4-[8-(methoxycarbonyl)-3-[(2R)-1-(pyridin-2-yl)propan-2-yl]-3H,6H,7H,8H,9H-imidazo[4,5-h]isoquinolin-2-yl]cyclohexane-1-carboxylic acid | 477 | 1H-NMR (CD3OD, 400 MHz) δ (ppm): 8.52 (d, J = 4 Hz, 1H), 7.71 (d, J = 5.6 Hz, 1H), 7.52-7.48 (m, 1H), 7.23-7.20 (m, 1H), 7.11 (d, J = 7.6 Hz, 1H), 6.66 (d, J = 6 Hz, 1H), 5.13 (br s, 1H), 4.94 (s, 2H), 3.78-3.66 (m, 6H), 3.37-3.35 (m, 1H), 2.96-2.92 (m, 2H), 2.63 (br s, 1H), 2.33 (br s, 1H), 2.10-1.92 (m, 3H), 1.82 (d, J = 6.8 Hz, 3H), 1.76-1.62 (m, 3H), 1.48-1.41 (m, 1H), 1.09 (br s, 1H). |
| 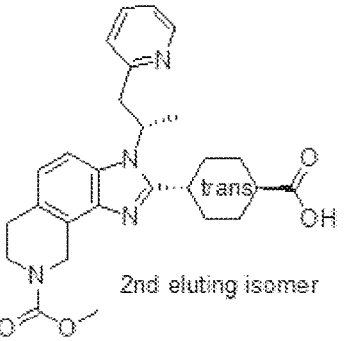 2nd eluting isomer | trans-4-[8-(methoxycarbonyl)-3-[(2S)-1-(pyridin-2-yl)propan-2-yl]-3H,6H,7H,8H,9H-imidazo[4,5-h]isoquinolin-2-yl]cyclohexane-1-carboxylic acid | 477 | 1H-NMR (CD3OD, 400 MHz) δ (ppm): 8.52 (d, J = 4.4 Hz, 1H), 7.71 (d, J = 5.6 Hz, 1H), 7.52-7.48 (m, 1H), 7.23-7.20 (m, 1H), 7.11 (d, J = 8.4 Hz, 1H), 6.66 (d, J = 6 Hz, 1H), 5.13 (br s, 1H), 4.98 (s, 2H), 3.78-3.66 (m, 6H), 2.96 (d, J = 5.6 Hz, 2H), 2.64 (br s, 1H), 2.32 (br s, 1H), 2.10-1.92 (m, 3H), 1.82 (d, J = 6.8 Hz, 3H), 1.79-1.62 (m, 3H), 1.48-1.40 (m, 1H), 1.09 (br s, 1H). |
| 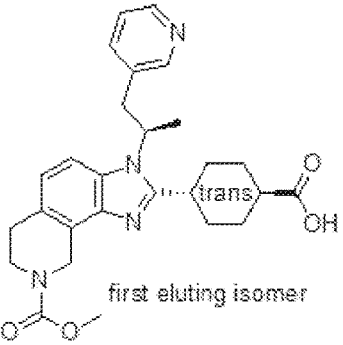 first eluting isomer | Trans-4-[8-(methoxycarbonyl)-3-[(2R)-1-(pyridin-3-yl)propan-2-yl]-3H,6H,7H,8H,9H-imidazo[4,5-h]isoquinolin-2-yl]cyclohexane-1-carboxylic acid | 477 | 1H-NMR (CD3OHD, 400 MHz) δ (ppm): 8.30 (d, J = 3.6 Hz, 1H), 7.94 (s, 1H), 7.72 (d, J = 7.2 Hz, 1H), 7.32 (s, 1H), 7.24-7.21 (m, 1H), 7.13 (d, J = 8.4 Hz, 1H), 5.00 (s, 3H), 3.82-3.78 (m, 5H), 3.60-3.54 (m, 1H), 3.32-3.24 (m, 1H), 2.99-2.93 (m, 2H), 2.46 (br s, 1H), 2.32-2.30 (m, 1H), 2.07 (d, J = 10 Hz, 1H), 1.96 (d, J = 10.8 Hz, 1H), 1.90-1.84 (m, 4H), 1.68-1.55 (m, 3H), 1.37-1.31 (m, 1H), 0.89 (d, J = 9.6 Hz, 1H). |
| 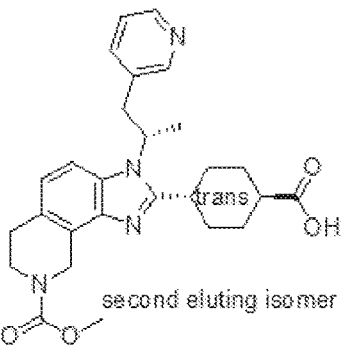 second eluting isomer | trans-4-[8-(methoxycarbonyl)-3-[(2S)-1-(pyridin-3-yl)propan-2-yl]-3H,6H,7H,8H,9H-imidazo[4,5-h]isoquinolin-2-yl]cyclohexane-1-carboxylic acid | 477 | 1H-NMR (CD3OHD, 400 MHz) δ (ppm): 8.30 (d, J = 4.4 Hz, 1H), 7.94 (s, 1H), 7.72 (d, J = 6.4 Hz, 1H), 7.32 (s, 1H), 7.24-7.21 (m, 1H), 7.13 (d, J = 8.4 Hz, 1H), 5.00 (s, 3H), 3.84-3.81 (m, 5H), 3.60-3.54 (m, 1H), 3.32-3.23 (m, 1H), 3.00-2.98 (m, 2H), 2.48 (br s, 1H), 2.32-2.98 (m, 1H), 2.07 (d, J = 10.4 Hz, 1H), 1.96 (d, J = 11.2 Hz, 1H), 1.86-1.84 (m, 4H), 1.68-1.52 (m, 3H), 1.38-1.31 (m, 1H), 0.89 (d, J = 10 Hz, 1H). |

FIGURE 1 (continued)

| Structure | Name | # | NMR |
|---|---|---|---|
| 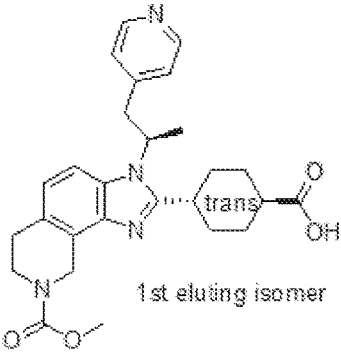 1st eluting isomer | trans-4-[8-(methoxycarbonyl)-3-[(2R)-1-(pyridin-4-yl)propan-2-yl]-3H,6H,7H,8H,9H-imidazo[4,5-h]isoquinolin-2-yl]cyclohexane-1-carboxylic acid | 477 | (CD3OD, 400MHz) δ (ppm): 8.30 (d, J = 4.8 Hz, 2H), 7.74 (s, 1H), 7.16 (d, J = 8.0 Hz, 1H), 6.94 (s, 2H), 5.05-4.96 (m, 3H), 3.79 (s, 5H), 3.62-3.56 (m, 1H), 3.26 (m, 1H), 2.99-2.94 (m, 2H), 2.55-2.47 (m, 1H), 2.38-2.29 (m, 1H), 2.12-2.07 (m, 1H), 1.99-1.81 (m, 5H), 1.79-1.59 (m, 3H), 1.42-1.28 (m, 2H), 0.94-0.83 (m, 1H). |
| 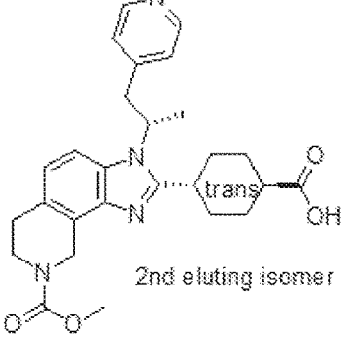 2nd eluting isomer | trans-4-[8-(methoxycarbonyl)-3-[(2R)-1-(pyridin-4-yl)propan-2-yl]-3H,6H,7H,8H,9H-imidazo[4,5-h]isoquinolin-2-yl]cyclohexane-1-carboxylic acid | 477 | (CD3OD, 400MHz) δ (ppm): 8.89 (d, J = 4.8 Hz, 2H), 7.72-7.71 (m, 1H), 7.13 (d, J = 4.8 Hz, 1H), 6.93 (s, 2H), 5.01-4.92 (m, 3H), 3.78 (s, 5H), 3.61-3.54 (m, 1H), 3.28-3.25 (m, 1H), 3.05-2.98 (m, 2H), 2.51-2.47 (m, 1H), 2.33-2.27 (m, 1H), 2.09-1.84 (m, 6H), 1.74-1.58 (m, 3H), 1.42-1.27 (m, 2H), 0.95-0.86 (m, 1H) |
| 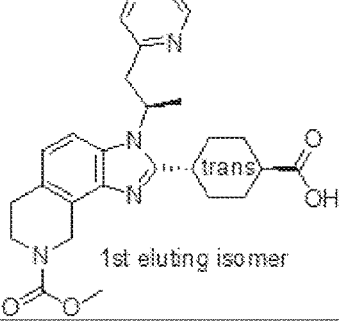 1st eluting isomer | trans-4-[8-(methoxycarbonyl)-3-[(2R)-1-(pyrazin-2-yl)propan-2-yl]-3H,6H,7H,8H,9H-imidazo[4,5-h]isoquinolin-2-yl]cyclohexane-1-carboxylic acid | 478 | 1H-NMR (Methanol-d4, 400 MHz) δ (ppm): 8.54 (s, 1H), 8.37 (s, 1H), 8.05 (br s, 1H), 7.75 (br s, 1H), 7.16 (d, J = 8.8 Hz, 1H), 5.32 (br s, 1H), 4.93 (s, 2H), 3.77 (s, 6H), 3.50-3.45 (m, 1H), 2.98-2.91 (m, 3H), 2.39 (br s, 1H), 2.13-2.10 (m, 2H), 1.99 (s, 1H), 1.85-1.80 (m, 4H), 1.77-1.51(m, 3H), 1.38 (br s, 1H) |
| 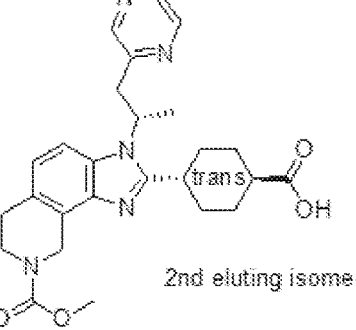 2nd eluting isomer | trans-4-[8-(methoxycarbonyl)-3-[(2S)-1-(pyrazin-2-yl)propan-2-yl]-3H,6H,7H,8H,9H-imidazo[4,5-h]isoquinolin-2-yl]cyclohexane-1-carboxylic acid | 478 | 1H-NMR (Methanol-d4, 400 MHz) δ (ppm): 8.55 (s, 1H), 8.37 (s, 1H), 8.00 (br s, 1H), 7.71 (br s, 1H), 7.11 (d, J = 8 Hz, 1H), 5.29-5.24 (m, 1H), 4.97 (s, 2H), 3.77-3.75 (m, 6H), 3.47-3.44 (m, 1H), 2.97-2.94 (m, 2H), 2.82 (br s, 1H), 2.38 (br s, 1H), 2.11-2.05 (m, 2H), 1.96 (s, 1H), 1.84-1.76 (m, 4H), 1.67-1.58 (m, 2H), 1.56-1.46 (m, 1H), 1.36-1.27 (m, 1H). |

FIGURE 1 (continued)

| Structure | Name | MW | 1H-NMR |
|---|---|---|---|
| 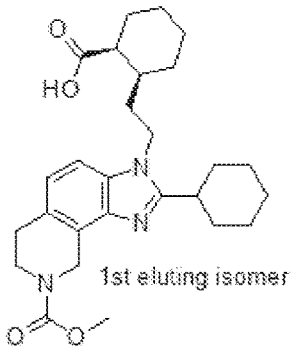 1st eluting isomer | (1S,2S)-2-{2-[2-cyclohexyl-8-(methoxycarbonyl)-3H,6H,7H,8H,9H-imidazo[4,5-h]isoquinolin-3-yl]ethyl}cyclohexane-1-carboxylic acid | 468 | 1H-NMR (Methanol-$d4$, 400 MHz) δ (ppm): 7.30 (d, $J$ = 8 Hz, 1H), 7.05 (d, $J$ = 8 Hz, 1H), 5.00 (s, 2H), 4.28-4.24 (m, 2H), 3.78-3.75 (m, 5H), 3.05-2.93 (m, 3H), 2.63 (br s, 1H), 2.02 (br s, 1H), 1.93-1.82 (m, 10H), 1.76-1.63 (m, 3H), 1.60-1.41 (m, 7H |
| 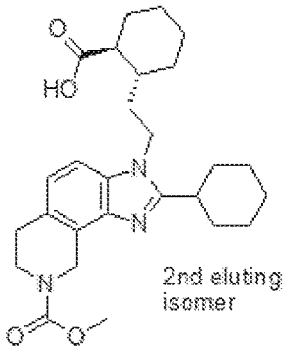 2nd eluting isomer | (1S,2R)-2-{2-[2-cyclohexyl-8-(methoxycarbonyl)-3H,6H,7H,8H,9H-imidazo[4,5-h]isoquinolin-3-yl]ethyl}cyclohexane-1-carboxylic acid | 468 | 1H-NMR (Methanol-$d4$, 400 MHz) δ (ppm): 7.29 (d, $J$ = 8 Hz, 1H), 7.05 (d, $J$ = 8 Hz, 1H), 4.99 (s, 2H), 4.36-4.22 (m, 2H), 3.78-3.75 (m, 5H), 2.99-2.94 (m, 3H), 2.16-2.11 (m, 1H), 2.03-1.94 (m, 6H), 1.86-1.82 (m, 5H), 1.74-1.14 (m, 10H) |
| 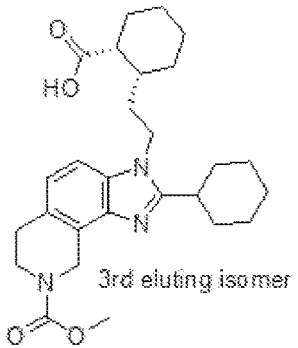 3rd eluting isomer | (1R,2R)-2-{2-[2-cyclohexyl-8-(methoxycarbonyl)-3H,6H,7H,8H,9H-imidazo[4,5-h]isoquinolin-3-yl]ethyl}cyclohexane-1-carboxylic acid | 468 | 1H-NMR (Methanol-$d4$, 400 MHz) δ (ppm): 7.29 (d, J = 8 Hz, 1H), 7.05 (d, $J$ = 8.4 Hz, 1H), 4.99 (s, 2H), 4.27-4.23 (m, 2H), 3.78-3.75 (m, 5H), 3.00-2.93 (m, 3H), 2.61 (s, 1H), 2.03 (br s, 1H), 1.92-1.82 (m, 10H), 1.72-1.69 (m, 3H), 1.59-1.41 (m, 7H). |
| 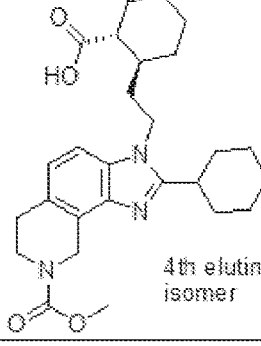 4th eluting isomer | (1R,2S)-2-{2-[2-cyclohexyl-8-(methoxycarbonyl)-3H,6H,7H,8H,9H-imidazo[4,5-h]isoquinolin-3-yl]ethyl}cyclohexane-1-carboxylic acid | 468 | 1H-NMR (Methanol-$d4$, 400 MHz) δ (ppm): 7.29 (d, J = 8.4 Hz, 1H), 7.03 (d, $J$ = 8.4 Hz, 1H), 4.99 (s, 2H), 4.34-4.24 (m, 2H), 3.78-3.74 (m, 5H), 2.99-2.93 (m, 3H), 2.06-1.92 (m, 7H), 1.88-1.79 (m, 7H), 1.69-1.25 (m, 7H), 1.18-1.09 (m, 1H). |

FIGURE 1 (continued)

| Structure | Name | MW | 1H-NMR |
|---|---|---|---|
| 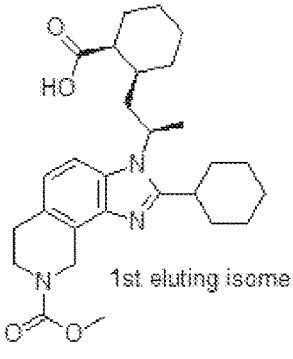 1st eluting isomer | (1S,2S)-2-[(2R)-2-[2-cyclohexyl-8-(methoxycarbonyl)-3H,6H,7H,8H,9H-imidazo[4,5-h]isoquinolin-3-yl]propyl]cyclohexane-1-carboxylic acid | 482 | 1H-NMR (Methanol-$d_4$, 400 MHz) δ (ppm): 7.47 (d, $J = 7.2$ Hz, 1H), 7.01 (d, $J = 8.4$ Hz, 1H), 4.99 (s, 2H), 4.76-4.74 (m, 1H), 3.78-3.74 (m, 5H), 3.08 (br s, 1H), 2.94-2.91 (m, 2H), 2.56 (s, 1H), 2.24 (br s, 1H), 2.05-1.84 (m, 7H), 1.81-1.55 (m, 9H), 1.54-1.36 (m, 4H), 1.33-1.18 (m, 3H). |
| 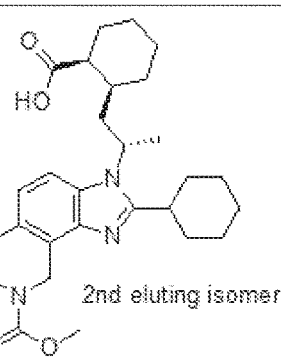 2nd eluting isomer | (1S,2S)-2-[(2S)-2-[2-cyclohexyl-8-(methoxycarbonyl)-3H,6H,7H,8H,9H-imidazo[4,5-h]isoquinolin-3-yl]propyl]cyclohexane-1-carboxylic acid | 482 | 1H-NMR (Methanol-$d_4$, 400 MHz) δ (ppm): 7.41 (d, $J = 8$ Hz, 1H), 7.01 (d, $J = 8$ Hz, 1H), 5.00 (s, 2H), 4.79-4.75 (m, 1H), 3.78-3.75 (m, 5H), 3.11-3.08 (m, 1H), 2.95-2.92 (m, 2H), 2.18-1.86 (m, 8H), 1.83-1.71 (m, 4H), 1.65-1.41 (m, 10H), 1.31-1.16 (m, 2H), 0.89-0.81 (m, 1H). |
| 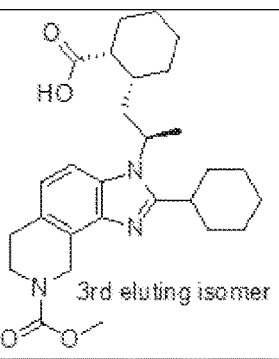 3rd eluting isomer | (1R,2R)-2-[(2R)-2-[2-cyclohexyl-8-(methoxycarbonyl)-3H,6H,7H,8H,9H-imidazo[4,5-h]isoquinolin-3-yl]propyl]cyclohexane-1-carboxylic acid | 482 | 1H-NMR (Methanol-$d_4$, 400 MHz) δ (ppm): 7.44 (d, $J = 7.6$ Hz, 1H), 6.99 (d, $J = 8.8$ Hz, 1H), 4.99 (s, 2H), 4.79-4.75 (m, 1H), 3.78-3.75 (m, 5H), 3.13-3.03 (m, 2H), 2.95-2.92 (m, 2H), 2.24-2.19 (m, 1H), 2.02-1.89 (m, 7H), 1.86-1.71 (m, 4H), 1.67-1.40 (m, 10H), 1.23-1.14 (m, 2H), 0.84-0.79 (m, 1H). |
| 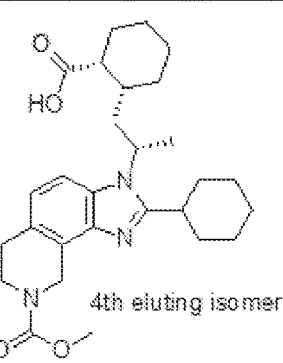 4th eluting isomer | (1R,2R)-2-[(2S)-2-[2-cyclohexyl-8-(methoxycarbonyl)-3H,6H,7H,8H,9H-imidazo[4,5-h]isoquinolin-3-yl]propyl]cyclohexane-1-carboxylic acid | 482 | 1H-NMR (Methanol-$d_4$, 400 MHz) δ (ppm): 7.47 (d, $J = 6.8$ Hz, 1H), 7.02 (d, $J = 8$ Hz, 1H), 5.00 (s, 2H), 4.82-4.74 (m, 1H), 3.78-3.75 (m, 5H), 3.08-3.05 (m, 1H), 2.95-2.92 (m, 2H), 2.56 (s, 1H), 2.24 (br s, 1H), 2.05-1.91 (m, 6H), 1.85-36 (m, 13H), 1.30-1.21 (m, 4H). |

FIGURE 1 (continued)

| | | | |
|---|---|---|---|
| 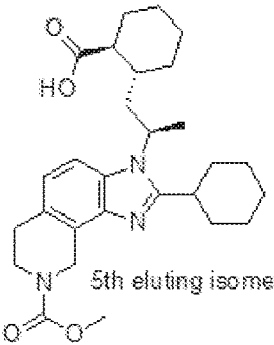 5th eluting isomer | (1S,2R)-2-[(2R)-2-[2-cyclohexyl-8-(methoxycarbonyl)-3H,6H,7H,8H,9H-imidazo[4,5-h]isoquinolin-3-yl]propyl]cyclohexane-1-carboxylic acid | 482 | 1H-NMR (Methanol-$d4$, 400 MHz) δ (ppm): 7.44 (br s, 1H), 7.02 (br s, 1H), 5.00 (s, 2H), 3.79-3.76 (m, 5H), 3.17-3.05 (m, 1H), 2.94 (br s, 2H), 2.54-2.39 (m, 1H), 2.02-1.89 (m, 7H), 1.82-1.48 (m, 12H), 1.39-1.02 (m, 7H). |
| 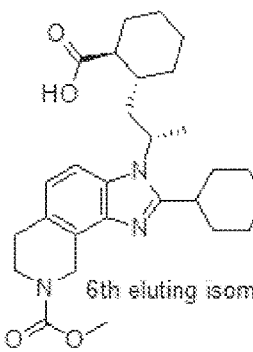 6th eluting isomer | (1S,2R)-2-[(2S)-2-[2-cyclohexyl-8-(methoxycarbonyl)-3H,6H,7H,8H,9H-imidazo[4,5-h]isoquinolin-3-yl]propyl]cyclohexane-1-carboxylic acid | 482 | 1H-NMR (Methanol-$d4$, 400 MHz) δ (ppm): 7.46 (d, $J = 6.8$ Hz, 1H), 7.01 (d, $J = 8$ Hz, 1H), 5.00 (s, 2H), 4.80 (br s, 1H), 3.78-3.76 (m, 5H), 3.02-2.99 (m, 1H), 2.93 (s, 1H), 2.40 (s, 1H), 2.23 (br s, 1H), 2.11-2.02 (m, 1H), 1.93-1.28 (m, 23H). |
| 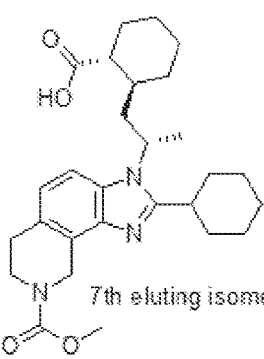 7th eluting isomer | (1R,2S)-2-[(2S)-2-[2-cyclohexyl-8-(methoxycarbonyl)-3H,6H,7H,8H,9H-imidazo[4,5-h]isoquinolin-3-yl]propyl]cyclohexane-1-carboxylic acid | 482 | 1H-NMR (Methanol-$d4$, 400 MHz) δ (ppm): 7.78 (d, $J = 8.4$ Hz, 1H), 7.36 (d, $J = 8.4$ Hz, 1H), 5.17 (s, 1H), 4.99 (s, 2H), 3.81-3.79 (m, 5H), 3.45-3.39 (m, 1H), 3.03-2.99 (m, 2H), 2.46-2.40 (m, 1H), 2.06-1.93 (m, 7H), 1.84-1.43 (m, 13H), 1.28-1.15 (m, 5H). |
| 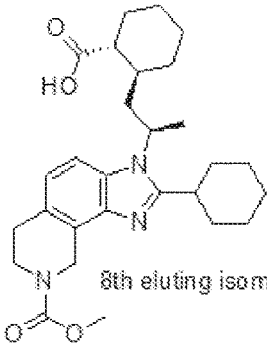 8th eluting isomer | (1R,2S)-2-[(2R)-2-[2-cyclohexyl-8-(methoxycarbonyl)-3H,6H,7H,8H,9H-imidazo[4,5-h]isoquinolin-3-yl]propyl]cyclohexane-1-carboxylic acid | 482 | 1H-NMR (Methanol-$d4$, 400 MHz) δ (ppm): 7.44 (br s, 1H), 7.01 (d, $J = 8$ Hz, 1H), 4.99 (s, 2H), 4.80-4.76 (m, 1H), 3.78-3.75 (m, 5H), 3.02-2.99 (m, 1H), 2.93 (s, 2H), 2.40 (s, 1H), 2.23 (br s, 1H), 2.16-2.06 (m, 1H), 0.20-1.32 (m, 23H). |

FIGURE 1 (continued)

| Structure | Name | MW | 1H-NMR |
|---|---|---|---|
| 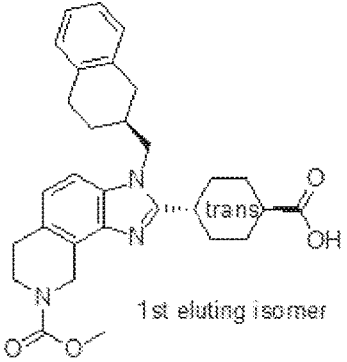 1st eluting isomer | Trans-4-[8-(methoxycarbonyl)-3-[[(2S)-1,2,3,4-tetrahydronaphthalen-2-yl]methyl]-3H,6H,7H,8H,9H-imidazo[4,5-h]isoquinolin-2-yl]cyclohexane-1-carboxylic acid | 502 | 1H-NMR (CD3OD, 400 MHz) δ (ppm): 7.33 (d, *J* = 8.4 Hz, 1H), 7.08-7.05 (m, 4H), 6.99-6.98 (m, 1H), 5.02 (s, 2H), 4.29-4.26 (m, 2H), 3.79-3.77 (m, 5H), 2.97-2.87 (m, 4H), 2.76-2.71 (m, 2H), 2.59-2.53 (m, 1H), 2.44-2.32 (m, 2H), 2.15-2.12 (m, 2H), 2.02-1.86 (m, 5H), 1.69-1.54 (m, 3H). |
| 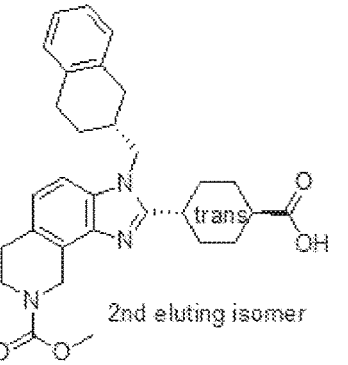 2nd eluting isomer | trans-4-[8-(methoxycarbonyl)-3-[[(2R)-1,2,3,4-tetrahydronaphthalen-2-yl]methyl]-3H,6H,7H,8H,9H-imidazo[4,5-h]isoquinolin-2-yl]cyclohexane-1-carboxylic acid | 502 | 1H-NMR (CD3OD, 400 MHz) δ (ppm): 7.33 (d, *J* = 8 Hz, 1H), 7.08-7.06 (m, 4H), 7.00-6.98 (m, 1H), 5.02 (s, 2H), 4.29-4.27 (m, 2H), 3.79-3.77 (m, 5H), 2.97-2.88 (m, 4H), 2.78-2.71 (m, 2H), 2.59-2.53 (m, 1H), 2.44-2.32 (m, 2H), 2.15-2.13 (m, 2H), 2.02-1.87 (m, 5H), 1.69-1.55 (m, 3H). |
| 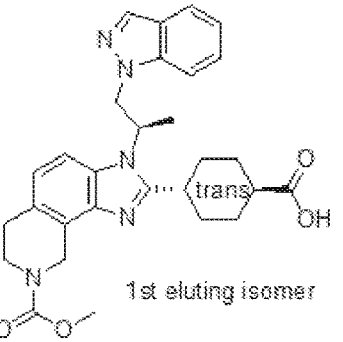 1st eluting isomer | Trans-4-[3-[(2R)-1-(1H-indazol-1-yl)propan-2-yl]-8-(methoxycarbonyl)-3H,6H,7H,8H,9H-imidazo[4,5-h]isoquinolin-2-yl]cyclohexane-1-carboxylic acid | 516 | 1H-NMR (CD3OD, 400 MHz) δ (ppm): 7.96-7.94 (m, 2H), 7.68 (d, *J* = 8 Hz, 1H), 7.35 (s, 1H), 7.15-7.06 (m, 2H), 6.92 (s, 1H), 5.38-5.24 (m, 2H), 4.86-4.82 (m, 3H), 3.80-3.78 (m, 5H), 3.03 (s, 2H), 2.35-2.24 (m, 2H), 2.05-2.01 (m, 1H), 1.96 (d, J = 6.8 Hz, 3H), 1.88-1.85 (m, 2H), 1.53-1.48 (m, 3H), 1.15-1.09 (m, 1H), 0.64 (d, *J* = 12.8 Hz, 1H). |
| 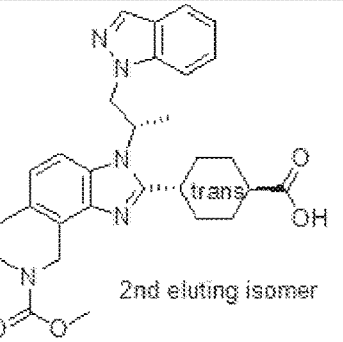 2nd eluting isomer | trans-4-[3-[(2S)-1-(1H-indazol-1-yl)propan-2-yl]-8-(methoxycarbonyl)-3H,6H,7H,8H,9H-imidazo[4,5-h]isoquinolin-2-yl]cyclohexane-1-carboxylic acid | 516 | 1H-NMR (CD3OD, 400 MHz) δ (ppm): 7.97-7.94 (m, 2H), 7.67 (d, *J* = 8 Hz, 1H), 7.30 (s, 1H), 7.12-7.05 (m, 2H), 6.85 (s, 1H), 5.28-5.20 (m, 2H), 4.86-4.82 (m, 3H), 3.79-3.77 (m, 5H), 3.01 (s, 2H), 2.27-2.20 (m, 2H), 2.10-1.85 (m, 6H), 1.49-1.47 (m, 3H), 1.16-1.06 (m, 1H), 0.64 (d, *J* = 12.8 Hz, 1H). |

FIGURE 1 (continued)

| Structure | Name | MW | NMR |
|---|---|---|---|
| 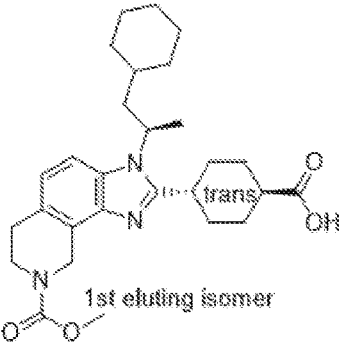 | (trans)-4-{3-[(2R)-1-cyclohexylpropan-2-yl]-8-(methoxycarbonyl)-3H,6H,7H,8H,9H-imidazo[4,5-h]isoquinolin-2-yl}cyclohexane-1-carboxylic acid | 496 | 0A (CD3OD, 400 MHz) δ (ppm): 7.49 (d, J = 6.8 Hz, 1H), 7.02 (d, J = 8.8 Hz, 1H), 5.00 (s, 2H), 4.88-4.83 (m, 1H), 3.79-3.71 (m, 5H), 3.10-3.05 (m, 1H), 2.99-2.93 (m, 2H), 2.50-2.44 (m, 1H), 2.19-2.16 (m, 3H), 2.07-1.96 (m, 3H), 1.88-1.68 (m, 5H), 1.64-1.51 (m, 6H), 1.46-1.44 (m, 1H), 1.16-1.05 (m, 3H), 1.03-0.87 (m, 3H). |
| 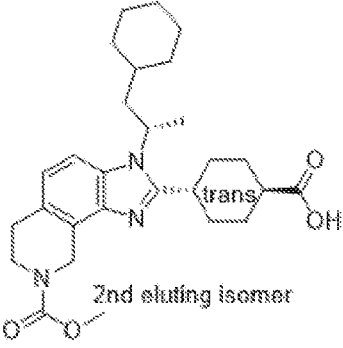 | (trans)-4-{3-[(2S)-1-cyclohexylpropan-2-yl]-8-(methoxycarbonyl)-3H,6H,7H,8H,9H-imidazo[4,5-h]isoquinolin-2-yl}cyclohexane-1-carboxylic acid | 496 | (CD3OD, 400 MHz) δ (ppm): 7.53-7.45 (m, 1H), 7.02 (d, J = 8.8 Hz, 1H), 5.00 (s, 2H), 4.89-4.82 (m, 1H), 3.85-3.79 (m, 5H), 3.05-3.01 (m, 1H), 2.95 (s, 2H), 2.50-2.44 (m, 1H), 2.21-2.17 (m, 3H), 2.07-1.93 (m, 3H), 1.88-1.62 (m, 5H), 1.53-1.51 (m, 6H), 1.46-1.40 (m, 1H), 1.17-1.03 (m, 3H), 0.96-0.94 (m, 3H). |
| 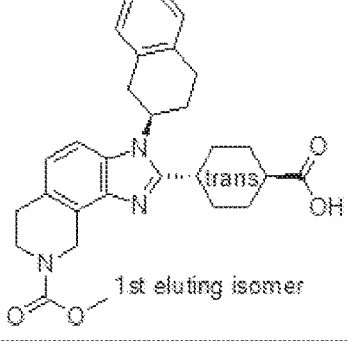 | trans-4-[8-(methoxycarbonyl)-3-[(2R)-1,2,3,4-tetrahydronaphthalen-2-yl]-3H,6H,7H,8H,9H-imidazo[4,5-h]isoquinolin-2-yl]cyclohexane-1-carboxylic acid | 488 | (CD3OD, 400MHz) δ (ppm): 7.41 (d, J = 8.4 Hz, 1H), 7.22-7.14 (m, 4H), 6.99 (d, J = 8.4 Hz, 1H), 5.01 (s, 2H), 4.93-4.88 (m, 1H), 3.79-3.72 (m, 5H), 3.69-3.65 (m, 1H), 3.18-3.05 (m, 4H), 2.95-2.92 (m, 2H), 2.75-2.71 (m, 1H), 2.47-2.40 (m, 1H), 2.17-2.07 (m, 5H), 1.96-1.92 (m, 2H), 1.67-1.61 (m, 2H), 1.34-1.31 (m, 1H). |
| 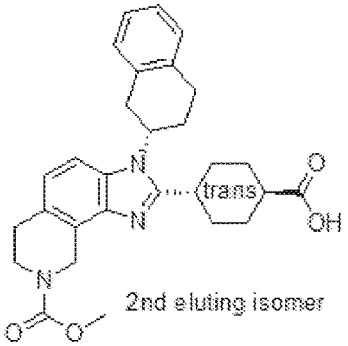 | trans-4-[8-(methoxycarbonyl)-3-[(2S)-1,2,3,4-tetrahydronaphthalen-2-yl]-3H,6H,7H,8H,9H-imidazo[4,5-h]isoquinolin-2-yl]cyclohexane-1-carboxylic acid | 488 | (CD3OD, 400MHz) δ (ppm): 7.41 (d, J = 8.4 Hz, 1H), 7.22-7.15 (m, 4H), 6.99 (d, J = 8.4 Hz, 1H), 5.01 (s, 2H), 4.93-4.90 (m, 1H), 3.79-3.72 (m, 5H), 3.69-3.65 (m, 1H), 3.18-3.05 (m, 4H), 2.95-2.92 (m, 2H), 2.73-2.70 (m, 1H), 2.45-2.41 (m, 1H), 2.17-2.07 (m, 5H), 1.95-1.92 (m, 2H), 1.67-1.61 (m, 2H), 1.34-1.30 (m, 2H) |

FIGURE 1 (continued)

| Structure | Name | MW | 1H-NMR |
|---|---|---|---|
| 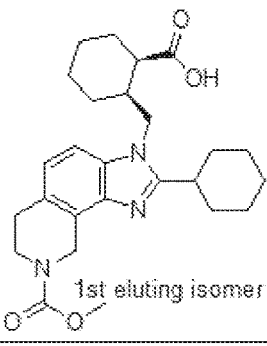 1st eluting isomer | (1R,2S)-2-[[2-cyclohexyl-8-(methoxycarbonyl)-3H,6H,7H,8H,9H-imidazo[4,5-h]isoquinolin-3-yl]methyl]cyclohexane-1-carboxylic acid | 454 | 1H-NMR (CD3OD, 400 MHz) δ (ppm): 7.43 (d, $J$ = 7.6 Hz, 1H), 7.04 (d, $J$ = 6 Hz, 1H), 5.00 (s, 2H), 4.31-4.27 (m, 1H), 3.99-3.93 (m, 1H), 3.78-3.72 (m, 5H), 3.11-3.05 (m, 1H), 2.94 (s, 2H), 2.25-2.06 (m, 3H), 1.91-1.77 (m, 8H), 1.68-1.27 (m, 7H), 1.09 (br s, 2H). |
| 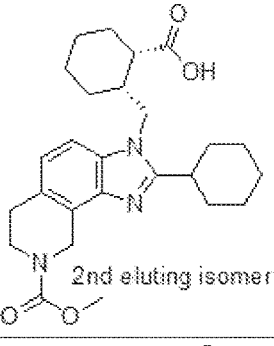 2nd eluting isomer | (1S,2R)-2-[[2-cyclohexyl-8-(methoxycarbonyl)-3H,6H,7H,8H,9H-imidazo[4,5-h]isoquinolin-3-yl]methyl]cyclohexane-1-carboxylic acid | 454 | 1H-NMR (CD3OD, 400 MHz) δ (ppm): 7.43 (d, $J$ = 7.2 Hz, 1H), 7.03 (br s, 1H), 4.99 (s, 2H), 4.31-4.28 (m, 1H), 3.98-3.92 (m, 1H), 3.78-3.75 (m, 5H), 3.15-3.07 (m, 1H), 2.93 (s, 2H), 2.31-2.06 (m, 3H), 1.90-1.76 (m, 8H), 1.67-1.24 (m, 6H), 1.11 (br s, 2H). |
| 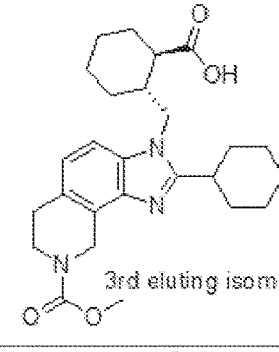 3rd eluting isomer | (1R,2R)-2-[[2-cyclohexyl-8-(methoxycarbonyl)-3H,6H,7H,8H,9H-imidazo[4,5-h]isoquinolin-3-yl]methyl]cyclohexane-1-carboxylic acid | 454 | 1H-NMR (CD3OD, 400 MHz) δ (ppm): 7.35 (d, $J$ = 8.4 Hz, 1H), 7.06 (d, $J$ = 8.4 Hz, 1H), 5.00 (s, 2H), 4.446-4.40 (m, 1H), 4.31-4.26 (m, 1H), 3.769-3.76 (m, 5H), 3.05 (br s, 1H), 2.97-2.94 (m, 2H), 2.67-2.65 (m, 1H), 2.35 (br s, 1H), 1.93-1.76 (m, 10H), 1.74-1.36 (m, 7H) |
| 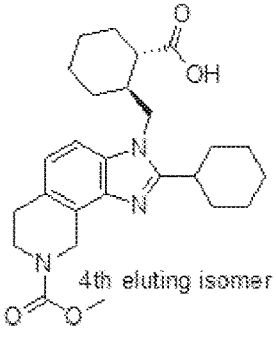 4th eluting isomer | (1S,2S)-2-[[2-cyclohexyl-8-(methoxycarbonyl)-3H,6H,7H,8H,9H-imidazo[4,5-h]isoquinolin-3-yl]methyl]cyclohexane-1-carboxylic acid | 454 | 1H-NMR (CD3OD, 400 MHz) δ (ppm): 7.35 (d, $J$ = 8.4 Hz, 1H), 7.05 (d, $J$ = 8.4 Hz, 1H), 5.00 (s, 2H), 4.46-4.40 (m, 1H), 4.29-4.25 (m, 1H), 3.78-3.76 (m, 5H), 3.05 (br s, 1H), 2.96-2.93 (m, 2H), 2.64-2.62 (m, 1H), 2.35 (br s, 1H), 1.98-1.63 (m, 11H), 1.56-1.30 (m, 7H). |

FIGURE 1 (continued)

| Structure | Name | MW | NMR |
|---|---|---|---|
| (1st eluting isomer) | (1s,4s)-4-{2-[2-cyclohexyl-8-(methoxycarbonyl)-3H,6H,7H,8H,9H-imidazo[4,5-h]isoquinolin-3-yl]ethyl}cyclohexane-1-carboxylic acid | 468 | (DMSO-$d6$, 400MHz) δ (ppm): 7.29 (d, $J$ = 8 Hz, 1H), 6.97 (d, $J$ = 8.4 Hz, 1H), 4.81 (s, 2H), 4.20-4.16 (m, 2H), 3.68-3.65 (m, 5H), 2.92-2.84 (m, 3H), 2.48-2.45 (m, 1H), 1.88-1.81 (m, 6H), 1.75-1.50 (m, 7H), 1.48-1.17 (m, 8H). |
| (2nd eluting isomer) | (1r,4r)-4-{2-[2-cyclohexyl-8-(methoxycarbonyl)-3H,6H,7H,8H,9H-imidazo[4,5-h]isoquinolin-3-yl]ethyl}cyclohexane-1-carboxylic acid | 468 | (DMSO-$d6$, 400MHz) δ (ppm): 7.29 (d, $J$ = 8.4 Hz, 1H), 6.97 (d, $J$ = 8.4 Hz, 1H), 4.81 (s, 2H), 4.21-4.18 (m, 2H), 3.68-3.65 (m, 5H), 2.92-2.86 (m, 3H), 2.17-2.11 (m, 1H), 1.92-1.81 (m, 8H), 1.73-1.64 (m, 3H), 1.56 (d, $J$ = 7.2 Hz, 2H), 1.48-1.21 (m, 6H), 1.07-0.97 (m, 2H) |
| (1st eluting isomer) | (1S,3S)-3-{2-[2-cyclohexyl-8-(methoxycarbonyl)-3H,6H,7H,8H,9H-imidazo[4,5-h]isoquinolin-3-yl]ethyl}cyclohexane-1-carboxylic acid | 468 | 1H-NMR (CD3OD, 400 MHz) δ (ppm): δ 7.30 (d, $J$ = 8.4 Hz, 1H), 7.07 (d, $J$ = 8.4 Hz, 1H), 5.00 (s, 2H), 4.28-4.25 (m, 5H), 2.96-2.94 (m, 3H), 2.67-2.65 (m, 1H), 2.07-2.04 (m, 1H), 1.95-1.73 (m, 11H), 1.65-1.46 (m, 7H), 1.33-1.21 (m, 2H) |

FIGURE 1 (continued)

| Structure | Name | MW | 1H-NMR |
|---|---|---|---|
| 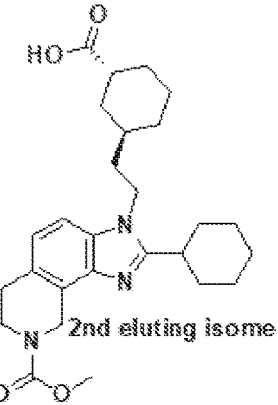 2nd eluting isomer | (1R,3R)-3-{2-[2-cyclohexyl-8-(methoxycarbonyl)-3H,6H,7H,8H,9H-imidazo[4,5-h]isoquinolin-3-yl]ethyl}cyclohexane-1-carboxylic acid | 468 | 1H-NMR (CD3OD, 400 MHz) δ (ppm): 7.30 (d, J = 8.4 Hz, 1H), 7.07 (d, J = 8.4 Hz, 1H), 5.00 (s, 2H), 4.28-4.24 (m, 2H), 3.79-3.76 (m, 5H), 2.98-2.94 (m, 3H), 2.66-2.64 (m, 1H), 2.08-2.05 (m, 1H), 1.94-1.75 (m, 11H), 1.65-1.46 (m, 7H), 1.34-1.21 (m, 2H) |
| 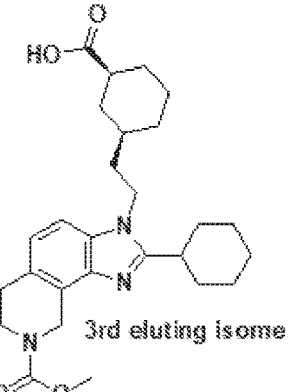 3rd eluting isomer | (1S,3R)-3-{2-[2-cyclohexyl-8-(methoxycarbonyl)-3H,6H,7H,8H,9H-imidazo[4,5-h]isoquinolin-3-yl]ethyl}cyclohexane-1-carboxylic acid | 468 | 1H-NMR (CD3OD, 400 MHz) δ (ppm): 7.30 (d, J = 8.4 Hz, 1H), 7.07 (d, J = 8.4 Hz, 1H), 5.00 (s, 2H), 4.28-4.26 (m, 2H), 3.79-3.76 (m, 5H), 2.97-2.94 (m, 3H), 2.31-2.23 (m, 1H), 2.11-2.04 (m, 1H), 1.96-1.82 (m, 9H), 1.75-1.70 (m, 2H), 1.57-1.31 (m, 9H) |
| 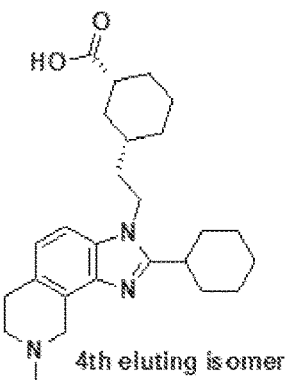 4th eluting isomer | (1R,3S)-3-{2-[2-cyclohexyl-8-(methoxycarbonyl)-3H,6H,7H,8H,9H-imidazo[4,5-h]isoquinolin-3-yl]ethyl}cyclohexane-1-carboxylic acid | 468 | 1H-NMR (CD3OD, 400 MHz) δ (ppm): 7.30 (d, J = 8.4 Hz, 1H), 7.07 (d, J = 8.4 Hz, 1H), 5.00 (s, 2H), 4.31-4.27 (m, 2H), 3.78-3.76 (m, 5H), 2.99-2.94 (m, 3H), 2.29-2.23 (m, 1H), 2.11-2.06 (m, 1H), 1.96-1.82 (m, 9H), 1.75-1.69 (m, 2H), 1.55-1.29 (m, 7H), 1.22-0.92 (m, 2H) |

FIGURE 1 (continued)

| Structure | Name | MW | 1H-NMR |
|---|---|---|---|
| 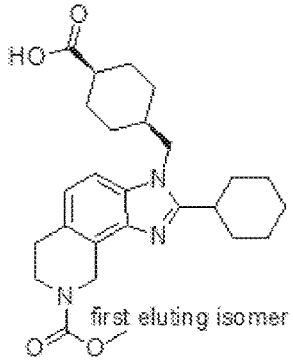 | 4-[[2-cyclohexyl-8-(methoxycarbonyl)-3H,6H,7H,8H,9H-imidazo[4,5-h]isoquinolin-3-yl]methyl]cyclohexane-1-carboxylic acid<br>first eluting isomer | 454 | 1H-NMR (DMSO-*d6*, 400 MHz) δ (ppm): 12.14 (br s, 1H), 7.16 (d, *J* = 8 Hz, 1H), 6.95 (d, *J* = 8.4 Hz, 1H), 4.80 (s, 2H), 4.04 (d, *J* = 7.2 Hz, 2H), 3.67-3.64 (m, 5H), 2.89-2.83 (m, 3H), 2.49-2.42 (m, 1H), 1.94 (d, *J* = 9.2 Hz, 2H), 1.83-1.64 (m, 8H), 1.46-1.33 (m, 7H), 1.25-1.20 (m, 2H). |
| 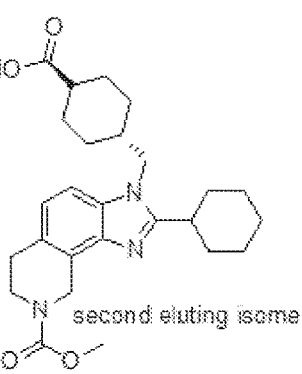 | 4-[[2-cyclohexyl-8-(methoxycarbonyl)-3H,6H,7H,8H,9H-imidazo[4,5-h]isoquinolin-3-yl]methyl]cyclohexane-1-carboxylic acid<br>second eluting isomer | 454 | 1H-NMR (DMSO-*d6*, 400 MHz) δ (ppm): 7.33 (d, *J* = 8.4 Hz, 1H), 6.95 (d, *J* = 8 Hz, 1H), 4.80 (s, 2H), 4.03 (d, *J* = 7.2 Hz, 2H), 3.67-3.64 (m, 5H), 2.93-2.83 (m, 3H), 2.17-2.11 (m, 1H), 1.88-1.82 (m, 6H), 1.72-1.64 (m, 4H), 1.53-1.39 (m, 5H), 1.23-1.09 (m, 4H) |
| 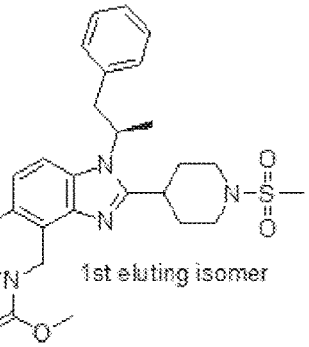 | Methyl 2-(1-methanesulfonylpiperidin-4-yl)-3-[(2R)-1-phenylpropan-2-yl]-3H,6H,7H,8H,9H-imidazo[4,5-h]isoquinoline-8-carboxylate<br>1st eluting isomer | 511 | 1H-NMR (Methanol-*d4*, 400 MHz) δ (ppm): 7.69 (d, *J* = 6.8 Hz, 1H), 7.13-7.11 (m, 4H), 6.79 (s, 2H), 4.96 (s, 2H), 4.93-4.91 (s, 1H), 3.78 (br s, 6H), 3.65-3.62 (m, 1H), 3.52-3.46 (m, 1H), 3.19-3.15 (m, 1H), 2.97-2.94 (m, 2H), 2.87-2.79 (m, 4H), 2.60-2.55 (m, 2H), 1.86-1.74 (m, 6H), 0.78-0.76 (m, 1H). |
| 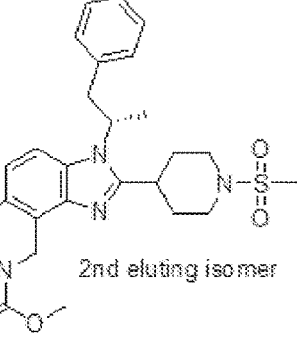 | methyl 2-(1-methanesulfonylpiperidin-4-yl)-3-[(2S)-1-phenylpropan-2-yl]-3H,6H,7H,8H,9H-imidazo[4,5-h]isoquinoline-8-carboxylate<br>2nd eluting isomer | 511 | 1H-NMR (Methanol-*d4*, 400 MHz) δ (ppm): 7.68 (d, *J* = 7.6 Hz, 1H), 7.12-7.10 (m, 4H), 6.79 (d, *J* = 3.2 Hz, 2H), 4.95 (s, 2H), 4.89-4.85 (m, 1H), 3.77-3.73 (m, 6H), 3.65-3.60 (m, 2H), 3.50-3.44 (m, 1H), 3.18-3.14 (m, 1H), 2.96 (s, 2H), 2.86-2.80 (m, 4H), 2.60-2.55 (m, 2H), 1.85-1.70 (m, 6H), 0.78-0.74 (m, 1H). |

FIGURE 1 (continued)

| Structure | Name | m/z | 1H-NMR |
|---|---|---|---|
| 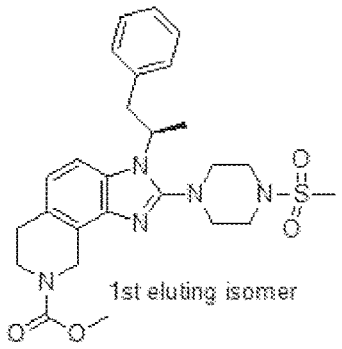 1st eluting isomer | methyl 2-(4-methanesulfonylpiperazin-1-yl)-3-[(2R)-1-phenylpropan-2-yl]-3H,6H,7H,8H,9H-imidazo[4,5-h]isoquinoline-8-carboxylate | 512 | 1H-NMR-PH-FMA-PJ00200-034-0A (CD3OD, 400MHz) δ (ppm): 7.62 (d, *J* = 8.4 Hz, 1H), 7.10 (d, *J* = 5.2 Hz, 4H), 6.78 (d, *J* = 4.4 Hz, 2H), 4.93 (s, 2H), 3.83-3.70 (m, 5H), 3.59-3.45 (m, 2H), 3.41-3.21 (m, 4H), 3.18-2.97 (m, 5H), 2.92 (s, 3H), 2.60-2.58 (m, 2H), 1.79 (d, *J* = 7.2 Hz, 3H). |
| 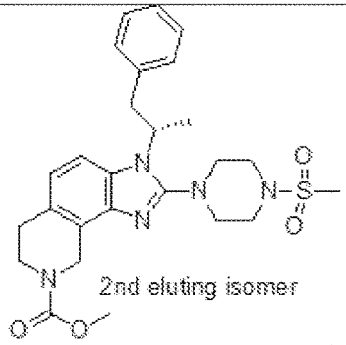 2nd eluting isomer | methyl 2-(4-methanesulfonylpiperazin-1-yl)-3-[(2S)-1-phenylpropan-2-yl]-3H,6H,7H,8H,9H-imidazo[4,5-h]isoquinoline-8-carboxylate | 512 | 1H-NMR-PH-FMA-PJ00200-034-0B (CD3OD, 400MHz) δ (ppm): 7.62 (d, *J* = 8.0 Hz, 1H), 7.10 (d, *J* = 5.6 Hz, 4H), 6.78 (d, *J* = 4.8 Hz, 2H), 4.88 (s, 2H), 3.78-3.73 (m, 5H), 3.50-3.45 (m, 1H), 3.41-3.18 (m, 5H), 3.14-2.97 (m, 5H), 2.92 (s, 3H), 2.60-2.58 (m, 2H), 1.79 (d, *J* = 7.2 Hz, 3H). |
| 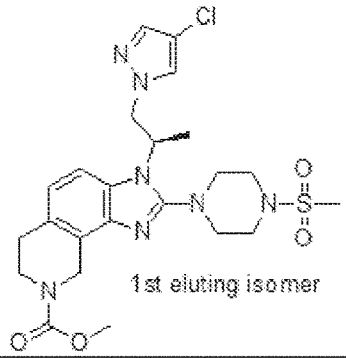 1st eluting isomer | Methyl 3-[(2R)-1-(4-chloro-1H-pyrazol-1-yl)propan-2-yl]-2-(4-methanesulfonylpiperazin-1-yl)-3H,6H,7H,8H,9H-imidazo[4,5-h]isoquinoline-8-carboxylate | 536, 538 | 1H-NMR (Methanol-*d4*, 400 MHz) δ (ppm): 7.54 (d, *J* = 8 Hz, 1H), 7.40 (s, 1H), 7.09 (d, *J* = 8.4 Hz, 1H), 6.96 (s, 1H), 5.07-4.97 (m, 1H), 4.91 (s, 2H), 4.79-4.73 (m, 1H), 4.53-4.48 (m, 1H), 3.82-3.74 (m, 5H), 3.46-3.39 (m, 2H), 3.32-3.31 (m, 2H), 3.24-3.19 (m, 2H), 2.96-2.90 (m, 7H), 1.76 (d, *J* = 7.2 Hz, 3H) |
| 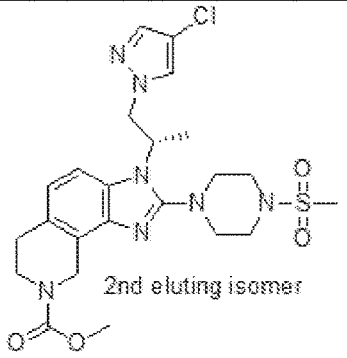 2nd eluting isomer | methyl 3-[(2S)-1-(4-chloro-1H-pyrazol-1-yl)propan-2-yl]-2-(4-methanesulfonylpiperazin-1-yl)-3H,6H,7H,8H,9H-imidazo[4,5-h]isoquinoline-8-carboxylate | 536, 538 | 1H-NMR (Methanol-*d4*, 400 MHz) δ (ppm): 7.54 (d, *J* = 8 Hz, 1H), 7.40 (s, 1H), 7.09 (d, *J* = 8.4 Hz, 1H), 6.96 (s, 1H), 5.04-4.97 (m, 1H), 4.91 (s, 2H), 4.79-4.73 (m, 1H), 4.53-4.48 (m, 1H), 3.80-3.73 (m, 5H), 3.44-3.39 (m, 2H), 3.33-3.31 (m, 2H), 3.24-3.20 (m, 2H), 2.95-2.88 (m, 7H), 1.76 (d, *J* = 7.2 Hz, 3H |

FIGURE 1 (continued)

| Structure | Name | MW | 1H-NMR |
|---|---|---|---|
| 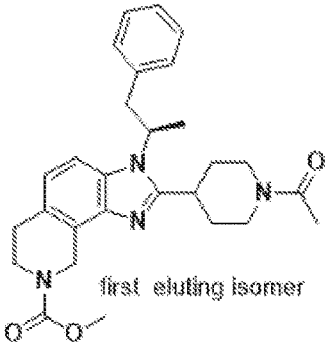 first eluting isomer | methyl 2-(1-acetylpiperidin-4-yl)-3-[(2R)-1-phenylpropan-2-yl]-3H,6H,7H,8H,9H-imidazo[4,5-h]isoquinoline-8-carboxylate | 475 | 1H-NMR-PH-FMA-PJ00200-038-0A (CD3OD, 400 MHz) δ (ppm): 7.70 (d, J = 8.4 Hz, 1H), 7.13-7.11 (m, 4H), 6.81 (d, J = 3.2 Hz, 2H), 4.99-4.91 (m, 3H), 4.59-4.39 (m, 1H), 4.00-3.96 (m, 1H), 3.86-3.78 (m, 5H), 3.54-3.45 (m, 1H), 3.20-2.92 (m, 4H), 2.74-2.68 (m, 2H), 2.11 (d, J = 2.8 Hz, 3H), 1.85-1.82 (m, 4H), 1.77-1.51 (m, 2H), 0.76-0.66 (m, 1H). |
| 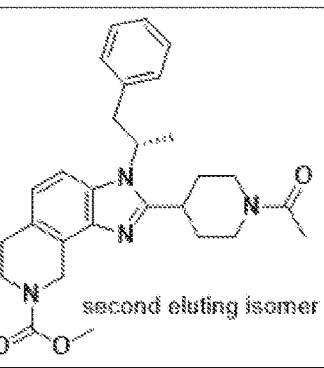 second eluting isomer | methyl 2-(1-acetylpiperidin-4-yl)-3-[(2S)-1-phenylpropan-2-yl]-3H,6H,7H,8H,9H-imidazo[4,5-h]isoquinoline-8-carboxylate | 475 | 1H-NMR-PH-FMA-PJ00200-038-0B (CD3OD, 400 MHz) δ (ppm): 7.70 (d, J = 6.8 Hz, 1H), 7.13-7.11 (m, 4H), 6.81 (s, 2H), 4.99-4.91 (m, 3H), 4.59-4.39 (m, 1H), 4.00-3.96 (m, 1H), 3.86-3.78 (m, 5H), 3.54-3.45 (m, 1H), 3.20-2.98 (m, 4H), 2.74-2.68 (m, 2H), 2.11 (d, J = 2.4 Hz, 3H), 1.85-1.82 (m, 4H), 1.78-1.31 (m, 2H), 0.81-0.62 (m, 1H). |
| 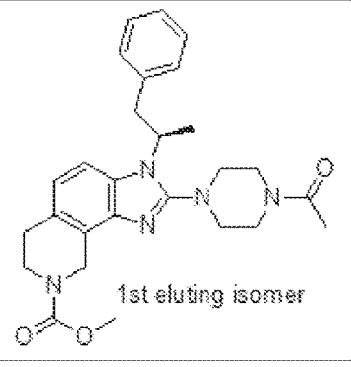 1st eluting isomer | methyl 2-(4-acetylpiperazin-1-yl)-3-[(2R)-1-phenylpropan-2-yl]-3H,6H,7H,8H,9H-imidazo[4,5-h]isoquinoline-8-carboxylate | 476 | 1H-NMR-PH-FMA-PJ00200-039-0A (DMSO-d6, 400MHz) δ (ppm): 7.61 (d, J = 8.0 Hz, 1H), 7.17-7.11 (m, 3H), 6.98 (d, J = 8.0 Hz, 1H), 6.93 (d, J = 6.8 Hz, 2H), 4.80-4.67 (m, 3H), 3.72-3.61 (m, 5H), 3.59-3.47 (m, 4H), 3.43-3.29 (m, 1H), 3.17-3.12 (m, 1H), 2.96-2.92 (m, 1H), 2.87-2.79 (m, 3H), 2.79-2.68 (m, 1H), 2.51-2.47 (m, 1H), 2.03 (s, 3H), 1.63 (d, J = 4.0 Hz, 3H). |
| 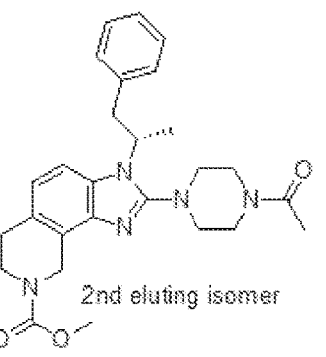 2nd eluting isomer | methyl 2-(4-acetylpiperazin-1-yl)-3-[(2S)-1-phenylpropan-2-yl]-3H,6H,7H,8H,9H-imidazo[4,5-h]isoquinoline-8-carboxylate | 476 | 1H-NMR-PH-FMA-PJ00200-039-0B (DMSO-d6, 400MHz) δ (ppm): 7.61 (d, J = 8.0 Hz, 1H), 7.16-7.12 (m, 3H), 6.98 (d, J = 8.4 Hz, 1H), 6.93 (d, J = 7.2 Hz, 2H), 4.79-4.72 (m, 3H), 3.72-3.62 (m, 5H), 3.60-3.49 (m, 4H), 3.33-3.27 (m, 1H), 3.17-3.12 (m, 1H), 2.94-2.92 (m, 1H), 2.88-2.79 (m, 3H), 2.68-2.63 (m, 1H), 2.51-2.47 (m, 1H), 2.03 (s, 3H), 1.63 (d, J = 4.0 Hz, 3H). |

FIGURE 1 (continued)

| Structure | Name | MW | 1H-NMR |
|---|---|---|---|
| 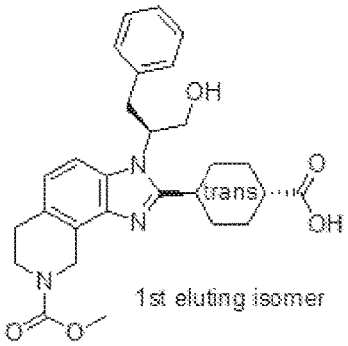 | Trans-4-[3-[(2S)-1-hydroxy-3-phenylpropan-2-yl]-8-(methoxycarbonyl)-3H,6H,7H,8H,9H-imidazo[4,5-h]isoquinolin-2-yl]cyclohexane-1-carboxylic acid | 492 | 1H-NMR (CD3OD, 400 MHz) δ (ppm): 7.67 (d, $J$ = 8.4 Hz, 1H), 7.14-7.11 (m, 4H), 6.83 (d, $J$ = 3.6 Hz, 2H), 4.97 (s, 2H), 4.73-4.69 (m, 1H), 4.37-4.31 (m, 1H), 4.14-4.10 (m, 1H), 3.81-3.75 (m, 5H), 3.45-3.39 (m, 1H), 3.25-3.21 (m, 1H), 2.98 (s, 2H), 2.46-2.40 (m, 1H), 2.32-2.26 (m, 1H), 2.07-1.98 (m, 2H), 1.88 (d, $J$ = 13.6 Hz, 1H), 1.66-1.48 (m, 3H), 1.30-1.21 (m, 1H), 0.79 (d, $J$ = 12.4 Hz, 1H). |
| 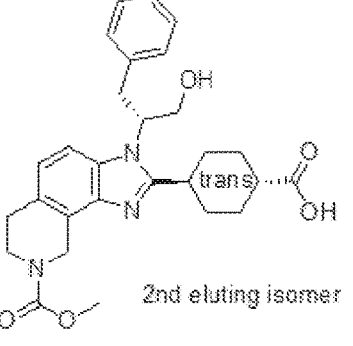 | trans-4-[3-[(2R)-1-hydroxy-3-phenylpropan-2-yl]-8-(methoxycarbonyl)-3H,6H,7H,8H,9H-imidazo[4,5-h]isoquinolin-2-yl]cyclohexane-1-carboxylic acid | 492 | 1H-NMR (CD3OD, 400 MHz) δ (ppm): 7.67 (d, $J$ = 8.4 Hz, 1H), 7.14-7.11 (m, 4H), 6.83 (d, $J$ = 3.6 Hz, 2H), 4.97 (s, 2H), 4.72-4.71 (m, 1H), 4.37-4.32 (m, 1H), 4.14-4.10 (m, 1H), 3.81-3.75 (m, 5H), 3.46-3.39 (m, 1H), 3.25-3.21 (m, 1H), 2.98 (s, 2H), 2.43-2.40 (m, 1H), 2.32-2.26 (m, 1H), 2.06-1.98 (m, 2H), 1.87 (d, $J$ = 14 Hz, 1H), 1.66-1.48 (m, 3H), 1.30-1.21 (m, 1H), 0.79 (d, $J$ = 13.6 Hz, 1H). |
| 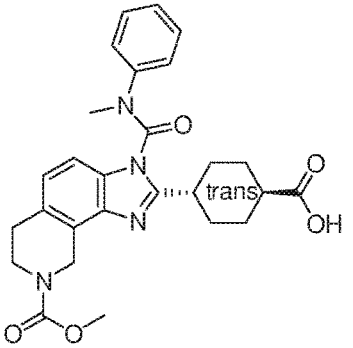 | trans-4-[8-(methoxycarbonyl)-3-[methyl(phenyl)carbamoyl]-3H,6H,7H,8H,9H-imidazo[4,5-h]isoquinolin-2-yl]cyclohexane-1-carboxylic acid | 491 | 1H-NMR (CD3OD, 400 MHz) δ (ppm): 7.34 (d, $J$ = 8.4 Hz, 1H), 7.24-7.13 (m, 5H), 7.05 (d, $J$ = 8.4 Hz, 1H), 4.93-4.83 (m, 2H), 3.76-3.72 (m, 5H), 3.63 (s, 3H), 3.00-2.96 (m, 1H), 2.90-2.89 (m, 2H), 2.41-2.40 (m, 1H), 2.21-2.11 (m, 3H), 1.96-1.86 (m, 1H), 1.65-1.57 (m, 4H). |
| 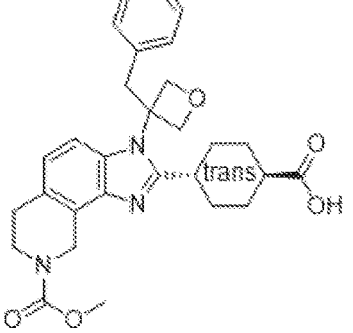 | (Trans)-4-[3-(3-benzyloxetan-3-yl)-8-(methoxycarbonyl)-3H,6H,7H,8H,9H-imidazo[4,5-h]isoquinolin-2-yl]cyclohexane-1-carboxylic acid | 504 | 1H-NMR (DMSO-$d$6, 400 MHz) δ (ppm): 7.19-7.15 (m, 3H), 6.91 (d, $J$ = 8.4 Hz, 1H), 6.83-6.80 (m, 3H), 5.05 (br s, 4H), 4.79 (br s, 2H), 3.68 (br s, 6H), 3.45 (br s, 1H), 2.85 (s, 2H), 2.18 (br s, 1H), 1.92 (br s, 2H), 1.71 (br s, 1H), 1.50 (br s, 3H), 1.24 (br s, 1H), 0.94 (br s, 1H), 0.61 (br s, 1H). |

FIGURE 1 (continued)

| Structure | Name | MW | 1H-NMR |
|---|---|---|---|
| 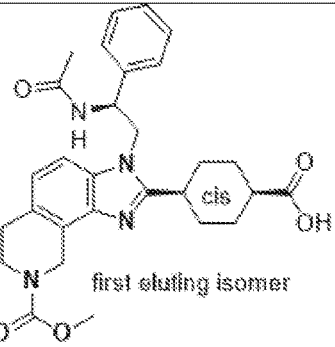 first eluting isomer | (cis)-4-{3-[(2S)-2-acetamido-2-phenylethyl]-8-(methoxycarbonyl)-3H,6H,7H,8H,9H-imidazo[4,5-h]isoquinolin-2-yl}cyclohexane-1-carboxylic acid | 519 | 1H-NMR- PH-FMA-PJ00200-045-0A (Methanol-$d4$, 400 MHz) δ (ppm): 7.41-7.31 (m, 3H), 7.28 (d, $J$ = 7.6 Hz, 2H), 7.02-7.00 (m, 1H), 6.94-6.92 (m, 1H), 6.09-6.05 (m, 1H), 5.01 (s, 2H), 4.49-4.44 (m, 1H), 4.00-3.94 (m, 1H), 3.79-3.76 (m, 5H), 2.95-2.90 (m, 3H), 2.44-2.38 (m, 1H), 2.13-1.88 (m, 5H), 1.82 (s, 3H), 1.74-1.71 (m, 1H), 1.64-1.60 (m, 1H), 1.56-1.44 (m, 1H). |
| 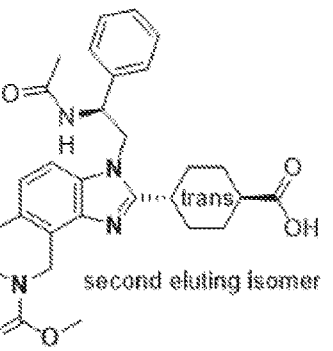 second eluting isomer | (trans)-4-{3-[(2S)-2-acetamido-2-phenylethyl]-8-(methoxycarbonyl)-3H,6H,7H,8H,9H-imidazo[4,5-h]isoquinolin-2-yl}cyclohexane-1-carboxylic acid | 519 | 1H-NMR- PH-FMA-PJ00200-045-0B (Methanol-$d4$, 400 MHz) δ (ppm): 7.54 (d, $J$ = 8.0 Hz, 1H), 7.34-7.32 (m, 3H), 7.18-7.17 (m, 2H), 7.10 (d, $J$ = 8.4 Hz, 1H), 5.37-5.34 (m, 1H), 4.97 (s, 2H), 4.64-4.58 (m, 1H), 4.51-4.46 (m, 1H), 3.78 (s, 5H), 2.98-2.95 (m, 2H), 2.50-2.44 (m, 1H), 2.37-2.31 (m, 1H), 2.09-2.06 (m, 1H), 2.00-1.95 (m, 4H), 1.90-1.87 (m, 1H), 1.71-1.63 (m, 2H), 1.57-1.51 (m, 1H), 1.34-1.31 (m, 1H), 1.16-1.13 (m, 1H). |
| 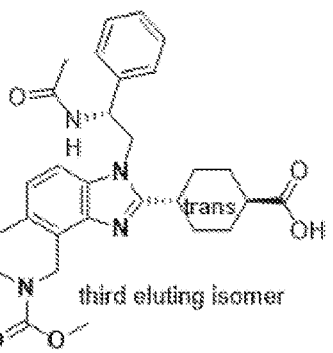 third eluting isomer | (trans)-4-{3-[(2R)-2-acetamido-2-phenylethyl]-8-(methoxycarbonyl)-3H,6H,7H,8H,9H-imidazo[4,5-h]isoquinolin-2-yl}cyclohexane-1-carboxylic acid | 519 | 1H-NMR- PH-FMA-PJ00200-045-0C (Methanol-$d4$, 400 MHz) δ (ppm): 7.54 (d, $J$ = 8.0 Hz, 1H), 7.34-7.32 (m, 3H), 7.18-7.17 (m, 2H), 7.10 (d, $J$ = 8.4 Hz, 1H), 5.37-5.34 (m, 1H), 4.97 (s, 2H), 4.63-.58 (m, 1H), 4.51-4.46 (m, 1H), 3.78-3.76 (m, 5H), 2.98-2.95 (m, 2H), 2.50-2.44 (m, 1H), 2.37-2.31 (m, 1H), 2.09-2.06 (m, 1H), 2.00-1.95 (m, 4H), 1.90-1.87 (m, 1H), 1.71-1.63 (m, 2H), 1.55-1.51 (m, 1H), 1.35-1.31 (m, 1H), 1.17-1.13 (m, 1H). |
| 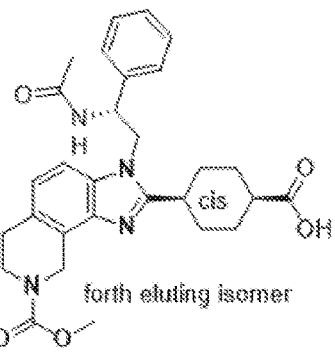 forth eluting isomer | (cis)-4-{3-[(2R)-2-acetamido-2-phenylethyl]-8-(methoxycarbonyl)-3H,6H,7H,8H,9H-imidazo[4,5-h]isoquinolin-2-yl}cyclohexane-1-carboxylic acid | 519 | 1H-NMR- PH-FMA-PJ00200-045-0D (Methanol-$d4$, 400 MHz) δ (ppm): 7.41-7.33 (m, 3H), 7.28 (d, $J$ = 7.2 Hz, 2H), 7.02-7.00 (m, 1H), 6.94-6.92 (m, 1H), 6.10-6.05 (m, 1H), 5.01 (s, 2H), 4.49-4.44 (m, 1H), 4.00-3.94 (m, 1H), 3.79-3.76 (m, 5H), 2.96-2.90 (m, 3H), 2.44-2.41 (m, 1H), 2.13-1.94 (m, 4H), 1.90-1.82 (m, 4H), 1.74-1.57 (m, 2H), 1.46-1.31 (m, 1H). |

FIGURE 1 (continued)

| Structure | Name | MW | NMR |
|---|---|---|---|
| 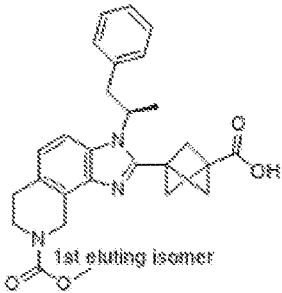 | 3-[8-(methoxycarbonyl)-3-[(2R)-1-phenylpropan-2-yl]-3H,6H,7H,8H,9H-imidazo[4,5-h]isoquinolin-2-yl]bicyclo[1.1.1]pentane-1-carboxylic acid | 460 | 1H-NMR-PH-FMA-PJ00200-046-0A (CD3OD, 400MHz) δ (ppm): 7.72 (d, J = 8.4 Hz, 1H), 7.18-7.12 (m, 4H), 6.73 (d, J = 6.4 Hz, 2H), 5.03-4.93 (m, 3H), 3.82-3.79 (m, 5H), 3.62-3.55 (m, 1H), 3.17-3.13 (m, 1H), 3.00-2.98 (m, 2H), 2.28-2.21 (m, 6H), 1.78 (d, J = 6.8 Hz, 3H). |
| 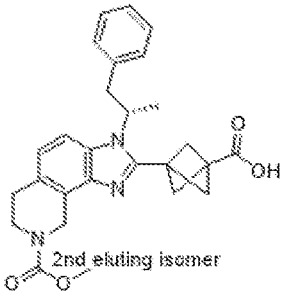 | 3-[8-(methoxycarbonyl)-3-[(2S)-1-phenylpropan-2-yl]-3H,6H,7H,8H,9H-imidazo[4,5-h]isoquinolin-2-yl]bicyclo[1.1.1]pentane-1-carboxylic acid | 460 | 1H-NMR-PH-FMA-PJ00200-046-0B (CD3OD, 400MHz) δ (ppm): 7.72 (d, J = 8.4 Hz, 1H), 7.18-7.12 (m, 4H), 6.73 (d, J = 6.4 Hz, 2H), 5.03-4.93 (m, 3H), 3.82-3.79 (m, 5H), 3.62-3.55 (m, 1H), 3.17-3.13 (m, 1H), 3.00-2.98 (m, 2H), 2.28-2.21 (m, 6H), 1.78 (d, J = 7.2 Hz, 3H). |
| 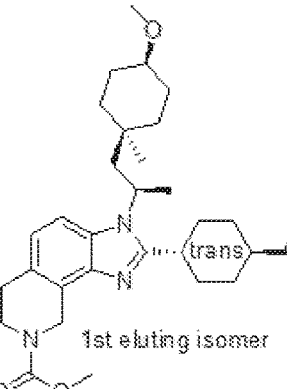 | (1r,4r)-4-[8-(methoxycarbonyl)-3-[(2R)-1-[(1s,4s)-4-methoxy-1-methylcyclohexyl]propan-2-yl]-3H,6H,7H,8H,9H-imidazo[4,5-h]isoquinolin-2-yl]cyclohexane-1-carboxylic acid | 526 | DMSO-d6, 400MHz δ (ppm): 12.16 (br s, 1H), 7.50 (d, J = 8.4 Hz, 1H), 6.94 (d, J = 7.2 Hz, 1H), 4.80-4.71 (m, 3H), 3.86 (br s, 5H), 3.32 (br s, 2H), 3.15 (br s, 2H), 2.99 (br s, 1H), 2.84 (br s, 2H), 2.35 (br s, 1H), 2.18-2.11 (m, 1H), 2.08-1.85 (m, 6H), 1.68-1.36 (m, 10H), 1.31-1.16 (m, 2H), 1.13-1.02 (m, 1H), 1.00-0.89 (m, 1H), 0.87-0.65 (m, 3H). |
| 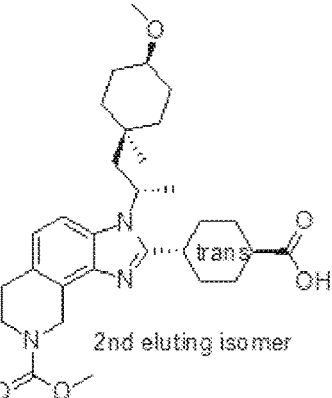 | (1r,4r)-4-[8-(methoxycarbonyl)-3-[(2S)-1-[(1s,4s)-4-methoxy-1-methylcyclohexyl]propan-2-yl]-3H,6H,7H,8H,9H-imidazo[4,5-h]isoquinolin-2-yl]cyclohexane-1-carboxylic acid | 526 | (DMSO-d6, 400MHz) δ (ppm): 12.08 (br s, 1H), 7.48 (d, J = 8.0 Hz, 1H), 6.93 (d, J = 8.0 Hz, 1H), 4.85-4.70 (m, 3H), 3.75-3.58 (s, 5H), 3.17 (s, 3H), 3.05-2.92 (m, 2H), 2.90-2.80 (m, 2H), 2.40-2.27 (m, 1H), 2.15-1.85 (m, 7H), 1.75-1.66 (m, 1H), 1.65-1.39 (m, 8H), 1.35-1.11 (m, 4H), 1.15-0.91 (m, 1H), 0.90-0.71 (m, 3H). |

FIGURE 1 (continued)

| Structure | Name | MW | NMR |
|---|---|---|---|
| 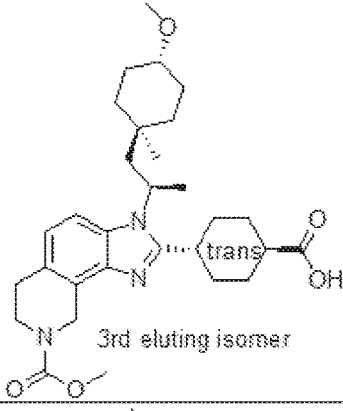 3rd eluting isomer | (1r,4r)-4-[8-(methoxycarbonyl)-3-[(2R)-1-[(1r,4r)-4-methoxy-1-methylcyclohexyl]propan-2-yl]-3H,6H,7H,8H,9H-imidazo[4,5-h]isoquinolin-2-yl]cyclohexane-1-carboxylic acid | 526 | (DMSO-$d_6$, 400MHz) δ (ppm): 12.08 (br s, 1H), 7.50 (d, $J$ = 7.6 Hz, 1H), 6.94 (d, $J$ = 7.6 Hz, 1H), 4.80-4.71 (m, 3H), 3.86 (br s, 5H), 3.15-3.02 (m, 4H), 2.99 (br s, 1H), 2.88-2.79 (m, 2H), 2.41-2.29 (m, 1H), 2.21-2.12 (m, 1H), 2.10-1.81 (m, 6H), 1.66-1.35 (m, 10H), 1.34-1.16 (m, 2H), 1.13-1.02 (m, 1H), 1.00-0.89 (m, 1H), 0.87-0.65 (m, 3H) |
| 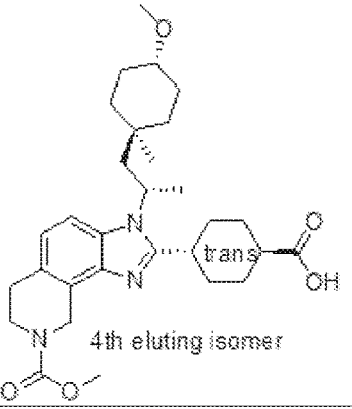 4th eluting isomer | (1r,4r)-4-[8-(methoxycarbonyl)-3-[(2S)-1-[(1r,4r)-4-methoxy-1-methylcyclohexyl]propan-2-yl]-3H,6H,7H,8H,9H-imidazo[4,5-h]isoquinolin-2-yl]cyclohexane-1-carboxylic acid | 526 | (DMSO-$d_6$, 400MHz) δ (ppm): 11.89 (br s, 1H), 7.48 (d, $J$ = 8.4 Hz, 1H), 6.93 (d, $J$ = 8.8 Hz, 1H), 4.85-4.70 (m, 3H), 3.75-3.58 (s, 5H), 3.17 (s, 3H), 3.05-2.92 (m, 2H), 2.90-2.79 (m, 2H), 2.40-2.27 (m, 1H), 2.15 – 1.85 (m, 7H), 1.75-1.66 (m, 1H), 1.65 – 1.39 (m, 8H), 1.35-1.11 (m, 4H), 1.15-0.91 (m, 1H), 0.90-0.71 (m, 3H). |
| 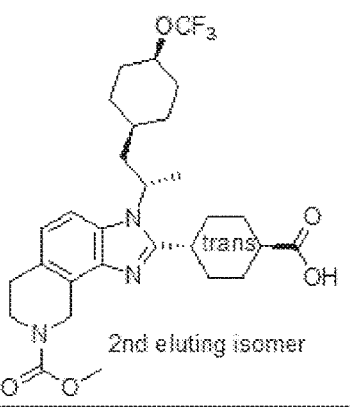 2nd eluting isomer | trans-4-[8-(methoxycarbonyl)-3-[(2S)-1-[4-(trifluoromethoxy)cyclohexyl]propan-2-yl]-3H,6H,7H,8H,9H-imidazo[4,5-h]isoquinolin-2-yl]cyclohexane-1-carboxylic acid | 566 | 1H-NMR (CD3OD, 400 MHz) δ (ppm): 7.49 (s, 1H), 7.03 (d, $J$ = 8.4 Hz, 1H), 5.00 (s, 2H), 4.82-4.76 (m, 1H), 4.19-4.14 (m, 1H), 3.78-3.76 (m, 5H), 3.09-3.05 (m, 1H), 2.95 (s, 2H), 2.50-2.44 (m, 1H), 2.22-1.96 (m, 9H), 1.87-1.80 (m, 2H), 1.73-1.55 (m, 6H), 1.40-1.21 (m, 2H), 1.21-1.03 (m, 3H). |

FIGURE 1 (continued)

| Structure | Name | MW | NMR |
|---|---|---|---|
| 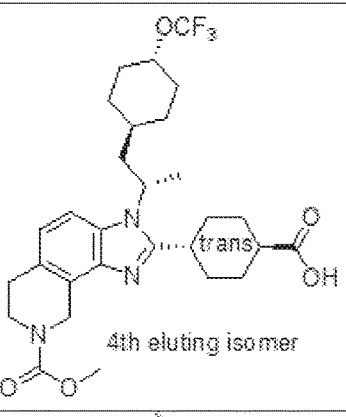 4th eluting isomer | trans-4-[8-(methoxycarbonyl)-3-[(2R)-1-[4-(trifluoromethoxy)cyclohexyl]propan-2-yl]-3H,6H,7H,8H,9H-imidazo[4,5-h]isoquinolin-2-yl]cyclohexane-1-carboxylic acid | 566 | 1H-NMR (CD3OD, 400 MHz) δ (ppm): 7.48 (s, 1H), 7.03 (d, $J$ = 7.6 Hz, 1H), 5.00 (s, 2H), 4.82-4.76 (m, 1H), 4.20-4.10 (m, 1H), 3.79-3.76 (m, 5H), 3.09-3.02 (m, 1H), 2.95 (s, 2H), 2.50-2.42 (m, 1H), 2.22-1.96 (m, 9H), 1.88-1.63 (m, 6H), 1.59-1.41 (m, 2H), 1.37-1.31 (m, 2H), 1.28-1.02 (m, 3H). |
| 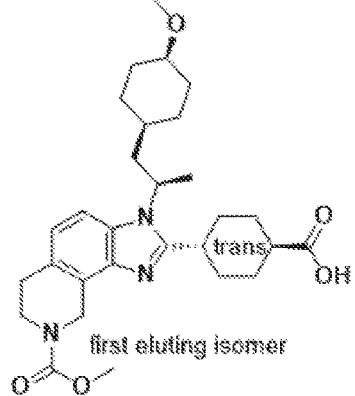 first eluting isomer | (trans)-4-[8-(methoxycarbonyl)-3-[(2R)-1-[(1s,4s)-4-methoxycyclohexyl]propan-2-yl]-3H,6H,7H,8H,9H-imidazo[4,5-h]isoquinolin-2-yl]cyclohexane-1-carboxylic acid | 512 | (Methanol-$d4$, 400 MHz) δ (ppm): 7.49 (s, 1H), 7.00 (d, $J$ = 8.4 Hz, 1H), 5.00 (s, 2H), 4.83-4.82 (m, 1H), 3.79-3.76 (m, 5H), 3.37 (s, 1H), 3.26 (s, 3H), 3.07-3.05 (m, 1H), 2.96-2.93 (m, 2H), 2.48-2.43 (m, 1H), 2.21-2.16 (m, 3H), 2.07-2.00 (m, 3H), 1.88-1.78 (m, 4H), 1.72-1.57 (m, 6H), 1.39-1.23 (m, 5H), 1.05 (s, 1H) |
| 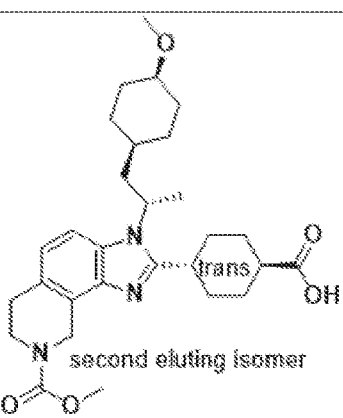 second eluting isomer | (trans)-4-[8-(methoxycarbonyl)-3-[(2S)-1-[(1s,4s)-4-methoxycyclohexyl]propan-2-yl]-3H,6H,7H,8H,9H-imidazo[4,5-h]isoquinolin-2-yl]cyclohexane-1-carboxylic acid | 512 | (Methanol-$d4$, 400 MHz) δ (ppm): 7.48 (s, 1H), 7.02 (d, $J$ = 8.0 Hz, 1H), 5.00 (s, 2H), 4.82 (br s, 1H), 3.79-3.76 (m, 5H), 3.27 (s, 3H), 3.13-3.04 (m, 2H), 2.96-2.93 (m, 2H), 2.50-2.45 (m, 1H), 2.21-2.16 (m, 3H), 2.07-1.96 (m, 6H), 1.92-1.80 (m, 2H), 1.73-1.51 (m, 5H), 1.34-1.30 (m, 1H), 1.06-0.96 (m, 5H). |

FIGURE 1 (continued)

| Structure | Name | MW | NMR |
|---|---|---|---|
| 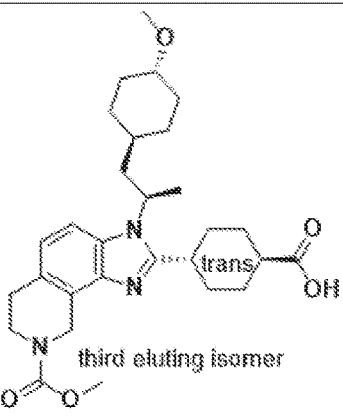 third eluting isomer | (trans)-4-[8-(methoxycarbonyl)-3-[(2R)-1-[(1r,4r)-4-methoxycyclohexyl]propan-2-yl]-3H,6H,7H,8H,9H-imidazo[4,5-h]isoquinolin-2-yl]cyclohexane-1-carboxylic acid | 512 | (Methanol-d4, 400 MHz) δ (ppm): 7.49 (s, 1H), 7.03 (d, J = 8.4 Hz, 1H), 5.00 (s, 2H), 4.85-4.83 (m, 1H), 3.79-3.76 (m, 5H), 3.37 (s, 1H), 3.28 (s, 3H), 3.09-3.03 (m, 1H), 2.96-2.93 (m, 2H), 2.47-2.44 (m, 1H), 2.21-2.17 (m, 3H), 2.07-2.01 (m, 3H), 1.87-1.78 (m, 4H), 1.75-1.57 (m, 6H), 1.39-1.23 (m, 5H), 1.05 (s, 1H). |
| 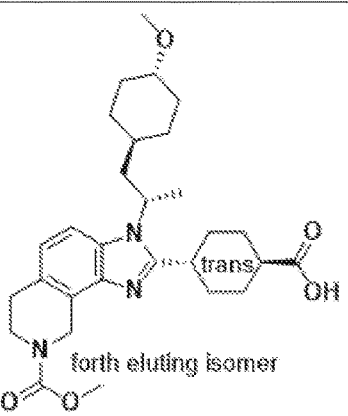 forth eluting isomer | (trans)-4-[8-(methoxycarbonyl)-3-[(2S)-1-[(1r,4r)-4-methoxycyclohexyl]propan-2-yl]-3H,6H,7H,8H,9H-imidazo[4,5-h]isoquinolin-2-yl]cyclohexane-1-carboxylic acid | 512 | (Methanol-d4, 400 MHz) δ (ppm): 7.48 (s, 1H), 7.02 (d, J = 8.4 Hz, 1H), 5.00 (s, 2H), 4.80 (s, 1H), 3.79-3.76 (m, 5H), 3.27 (s, 3H), 3.10-3.05 (m, 2H), 2.96-2.93 (m, 2H), 2.50-2.44 (m, 1H), 2.21-2.16 (m, 3H), 2.07-1.96 (m, 6H), 1.92-1.79 (m, 2H), 1.73-1.51 (m, 5H), 1.32-1.30 (m, 1H) 1.07-0.96 (m, 5H). |
| 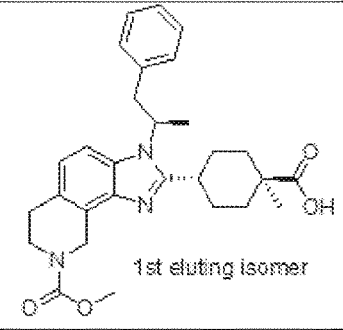 1st eluting isomer | 4-[8-(methoxycarbonyl)-3-(1-phenylpropan-2-yl)-3H,6H,7H,8H,9H-imidazo[4,5-h]isoquinolin-2-yl]-1-methylcyclohexane-1-carboxylic acid (stereocenters not assigned) | 490 | 1H-NMR (CD3OD, 400 MHz) δ (ppm): 7.70-7.66 (m, 1H), 7.20-7.18 (m, 4H), 6.80 (s, 2H), 5.03-4.98 (m, 2H), 4.83-4.81 (m, 1H), 3.82-3.79 (m, 5H), 3.51-3.45 (m, 1H), 3.17 (d, J = 12.4 Hz, 1H), 2.99 (s, 2H), 2.42-2.37 (m, 1H), 1.86-1.47 (m, 10H), 1.30 (s, 3H), 0.65-0.57 (m, 1H). |
| 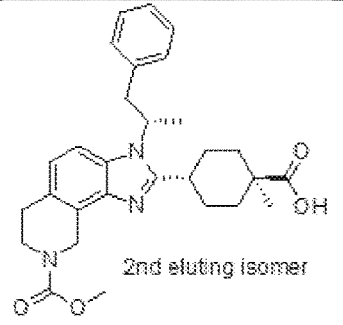 2nd eluting isomer | 4-[8-(methoxycarbonyl)-3-(1-phenylpropan-2-yl)-3H,6H,7H,8H,9H-imidazo[4,5-h]isoquinolin-2-yl]-1-methylcyclohexane-1-carboxylic acid (stereocenters not assigned) | 490 | 1H-NMR (CD3OD, 400 MHz) δ (ppm): 7.69 (br s, 1H), 7.17-7.12 (m, 4H), 6.80 (s, 2H), 5.00-4.97 (m, 2H), 4.83-4.81 (m, 1H), 3.82-3.79 (m, 5H), 3.50-3.45 (m, 1H), 3.20 (d, J = 8 Hz, 1H), 2.99 (s, 2H), 2.36-2.29 (m, 1H), 1.83-1.49 (m, 10H), 1.30 (s, 3H), 0.65-0.57 (m, 1H). |

FIGURE 1 (continued)

| Structure | Name | MW | 1H-NMR |
|---|---|---|---|
| 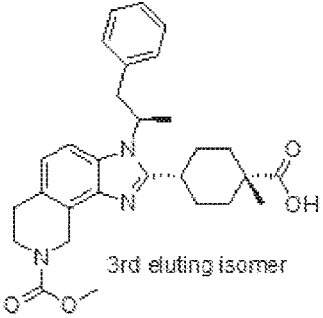 3rd eluting isomer | 4-[8-(methoxycarbonyl)-3-(1-phenylpropan-2-yl)-3H,6H,7H,8H,9H-imidazo[4,5-h]isoquinolin-2-yl]-1-methylcyclohexane-1-carboxylic acid (stereocenters not assigned) | 490 | 1H-NMR (CD3OD, 400 MHz) δ (ppm): 7.68-7.64 (m, 1H), 7.16-7.08 (m, 4H), 6.80 (s, 2H), 5.00-4.96 (m, 2H), 4.87-4.83 (m, 1H), 3.81-3.77 (m, 5H), 3.50-3.44 (m, 1H), 3.17 (d, J = 10.4 Hz, 1H), 2.97 (s, 2H), 2.42-2.21 (m, 2H), 2.12 (d, J = 13.2 Hz, 1H), 1.81 (d, J = 6.8 Hz, 3H), 1.72-1.62 (m, 3H), 1.39-1.27 (m, 1H), 1.18 (s, 3H), 1.06-0.96 (m, 1H), 0.80-0.72 (m, 1H). |
| 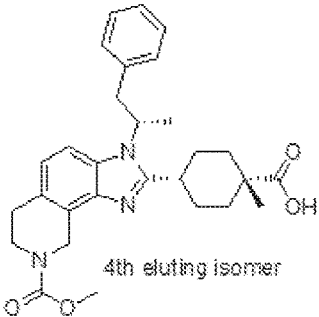 4th eluting isomer | 4-[8-(methoxycarbonyl)-3-(1-phenylpropan-2-yl)-3H,6H,7H,8H,9H-imidazo[4,5-h]isoquinolin-2-yl]-1-methylcyclohexane-1-carboxylic acid (stereocenters not assigned) | 490 | 1H-NMR (CD3OD, 400 MHz) δ (ppm): 7.69-7.67 (m, 1H), 7.13-7.09 (m, 4H), 6.80 (s, 2H), 5.01-4.96 (m, 2H), 4.87-4.83 (m, 1H), 3.81-3.77 (m, 5H), 3.50-3.44 (m, 1H), 3.17 (d, J = 12.4 Hz, 1H), 2.97 (s, 2H), 2.37-2.24 (m, 2H), 2.12 (d, J = 12.8 Hz, 1H), 1.81 (d, J = 6.8 Hz, 3H), 1.72-1.62 (m, 3H), 1.34-1.27 (m, 1H), 1.18 (s, 3H), 1.06-0.96 (m, 1H), 0.80-0.72 (m, 1H). |
| 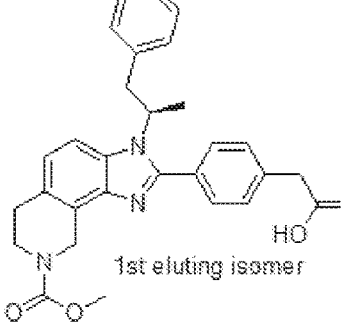 1st eluting isomer | 2-{4-[8-(methoxycarbonyl)-3-[(2R)-1-phenylpropan-2-yl]-3H,6H,7H,8H,9H-imidazo[4,5-h]isoquinolin-2-yl]phenyl}acetic acid | 484 | 1H-NMR (DMSO-d6, 400 MHz) δ (ppm): 12.42 (br s, 1H), 7.82 (d, J = 8.8 Hz, 1H), 7.30 (d, J = 8.4 Hz, 2H), 7.16-7.11 (m, 4H), 7.10-7.03 (m, 2H), 6.75-6.73 (m, 2H), 4.83 (s, 2H), 4.64-4.59 (m, 1H), 3.76-3.64 (m, 7H), 3.47-3.42 (m, 1H), 3.16-3.11 (m, 1H), 2.93-2.87 (, 2H), 1.64 (d, J = 6.8 Hz, 3H) |
| 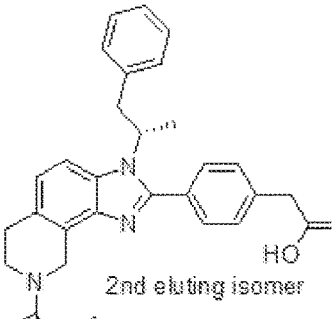 2nd eluting isomer | 2-{4-[8-(methoxycarbonyl)-3-[(2S)-1-phenylpropan-2-yl]-3H,6H,7H,8H,9H-imidazo[4,5-h]isoquinolin-2-yl]phenyl}acetic acid | 484 | 1H-NMR (DMSO-d6, 400 MHz) δ (ppm): 12.42 (br s, 1H), 7.82 (d, J = 8.4 Hz, 1H), 7.31 (d, J = 8 Hz, 2H), 7.17-7.11 (m, 4H), 7.10-7.01 (m, 2H), 6.75-6.73 (m, 2H), 4.83 (s, 2H), 4.64-4.59 (m, 1H), 3.77-3.64 (m, 7H), 3.47-3.42 (m, 1H), 3.16-3.11 (m, 1H), 2.93-2.87 (m, 2H), 1.64 (d, J = 6.8 Hz, 3H) |

FIGURE 1 (continued)

| Structure | Name | MW | 1H-NMR |
|---|---|---|---|
| 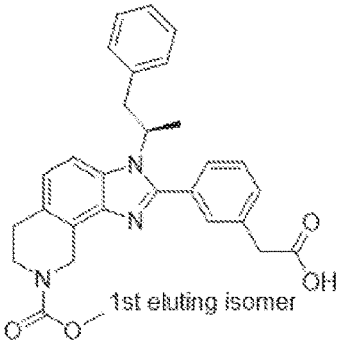 | 2-{3-[8-(methoxycarbonyl)-3-(1-phenylpropan-2-yl)-3H,6H,7H,8H,9H-imidazo[4,5-h]isoquinolin-2-yl]phenyl}acetic acid<br>1st eluting isomer | 484 | 1H-NMR (CD3OD, 400 MHz) δ (ppm): δ 7.82 (d, *J* = 8.4 Hz, 1H), 7.45-7.36 (m, 2H), 7.23 (d, *J* = 8.4 Hz, 1H), 7.17-7.14 (m, 1H), 7.08-7.04 (m, 2H), 6.97 (d, *J* = 7.2 Hz, 1H), 6.74 (s, 1H), 6.59 (d, *J* = 7.2 Hz, 2H), 5.02-4.89 (m, 2H), 4.71-4.66 (m, 1H), 3.88-3.79 (m, 2H), 3.77 (s, 3H), 3.65-3.50 (m, 3H), 3.06-3.01 (m, 3H), 1.80 (d, *J* = 7.2 Hz, 3H). |
| 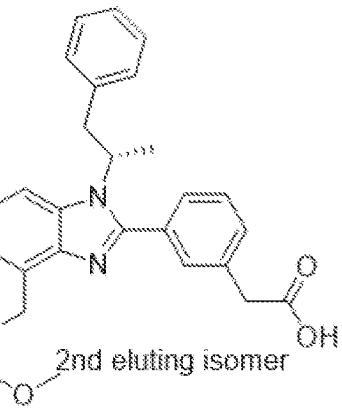 | 2-{3-[8-(methoxycarbonyl)-3-(1-phenylpropan-2-yl)-3H,6H,7H,8H,9H-imidazo[4,5-h]isoquinolin-2-yl]phenyl}acetic acid<br>2nd eluting isomer | 484 | %). 1H-NMR (CD3OD, 400 MHz) δ (ppm): δ7.81 (d, *J* = 8.4 Hz, 1H), 7.44-7.36 (m, 2H), 7.22 (d, *J* = 8.4Hz, 1H), 7.17-7.13 (m, 1H), 7.07-7.04 (m, 2H), 6.97 (d, *J* = 7.2 Hz, 1H), 6.74 (s, 1H), 6.59 (d, *J* = 7.2 Hz, 2H), 5.01-4.89 (m, 2H), 4.71-4.64 (m, 1H), 3.88-3.79 (m, 2H), 3.77 (s, 3H), 3.66-3.49 (m, 3H), 3.06-3.01 (m, 3H), 1.80 (d, *J* = 6.8 Hz, 3H). |
| 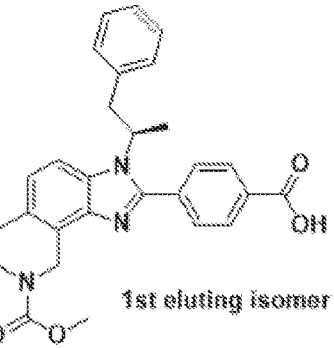 | 4-[8-(methoxycarbonyl)-3-[(2R)-1-phenylpropan-2-yl]-3H,6H,7H,8H,9H-imidazo[4,5-h]isoquinolin-2-yl]benzoic acid<br>1st eluting isomer | 470 | 1H-NMR (CD3OD, 400 MHz) δ (ppm): 8.02 (d, *J* = 7.6 Hz, 2H), 7.84 (d, *J* = 8.4 Hz, 1H), 7.25 (d, *J* = 8.4 Hz, 1H), 7.18-7.14 (m, 1H), 7.07-7.03 (m, 4H), 6.55 (d, *J* = 7.6 Hz, 2H), 5.04-4.92 (m, 2H), 4.70-4.61 (m, 1H), 3.90-3.80 (m, 2H), 3.78 (s, 3H), 3.54-3.48 (m, 1H), 3.07-2.99 (m, 3H), 1.87 (d, *J* = 7.2 Hz, 3H). |
|  | 4-[8-(methoxycarbonyl)-3-[(2S)-1-phenylpropan-2-yl]-3H,6H,7H,8H,9H-imidazo[4,5-h]isoquinolin-2-yl]benzoic acid<br>2nd eluting isomer | 470 | 1H-NMR (CD3OD, 400 MHz) δ (ppm): 8.02 (d, *J* = 7.6 Hz, 2H), 7.84 (d, *J* = 8.4 Hz, 1H), 7.25 (d, *J* = 8.4 Hz, 1H), 7.18-7.14 (m, 1H), 7.07-7.03 (m, 4H), 6.55 (d, *J* = 7.6 Hz, 2H), 5.03-4.97 (m, 2H), 4.68-4.63 (m, 1H), 3.90-3.80 (m, 2H), 3.77 (s, 3H), 3.54-3.48 (m, 1H), 3.07-3.03 (m, 3H), 1.87 (d, *J* = 6.8 Hz, 3H). |

FIGURE 1 (continued)

| Structure | Name | MW | 1H-NMR |
|---|---|---|---|
| 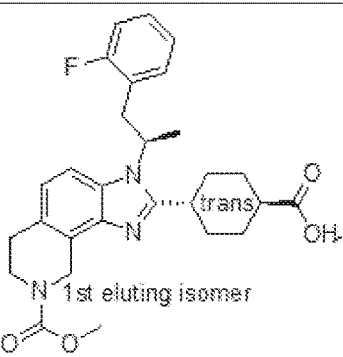 | (trans)-4-{3-[(2R)-1-(2-fluorophenyl)propan-2-yl]-8-(methoxycarbonyl)-3H,6H,7H,8H,9H-imidazo[4,5-h]isoquinolin-2-yl}cyclohexane-1-carboxylic acid | 494 | 1H-NMR (DMSO-d6, 400 MHz) δ (ppm): 12.09 (br s, 1H), 7.66 (d, J = 6.8 Hz, 1H), 7.24-7.19 (m, 1H), 7.13-7.08 (m, 1H), 7.02-6.98 (m, 3H), 7.85-4.72 (m, 3H), 3.70-3.61 (m, 5H), 3.40-3.23 (m, 3H), 2.86-2.80 (m, 2H), 2.28-2.22 (m, 1H), 1.98-1.95 (m, 1H), 1.88-1.81 (m, 2H), 1.65 (d, J = 6.8 Hz, 3H), 1.58-1.42 (m, 3H), 1.31-1.24 (m, 1H), 1.10-1.03 (m, 1H). |
| 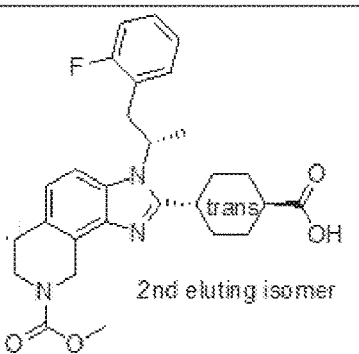 | (trans)-4-{3-[(2S)-1-(2-fluorophenyl)propan-2-yl]-8-(methoxycarbonyl)-3H,6H,7H,8H,9H-imidazo[4,5-h]isoquinolin-2-yl}cyclohexane-1-carboxylic acid | 494 | 1H-NMR (DMSO-d6, 400 MHz) δ (ppm): 12.14 (br s, 1H), 7.66 (d, J = 6.8 Hz, 1H), 7.24-7.22 (m, 1H), 710-7.08 (m, 1H), 7.02-6.98 (m, 3H), 4.85-4.77 (m, 3H), 3.72-3.61 (m, 5H), 3.37-3.23 (m, 3H), 2.86-2.82 (m, 2H), 2.28-2.22 (m, 1H), 1.94-1.91 (m, 1H), 1.88-1.80 (m, 1H), 1.65 (d, J = 6.8 Hz, 3H), 1.58-1.40 (m, 3H), 1.30-1.21 (m, 1H), 1.10-1.04 (m, 1H) |
| 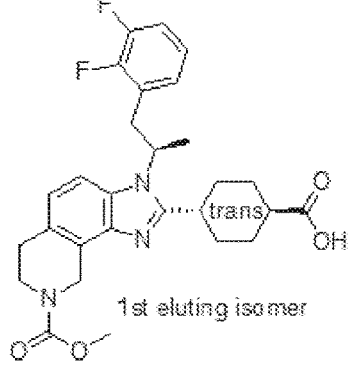 | Trans-4-[3-[(2R)-1-(2,3-difluorophenyl)propan-2-yl]-8-(methoxycarbonyl)-3H,6H,7H,8H,9H-imidazo[4,5-h]isoquinolin-2-yl]cyclohexane-1-carboxylic acid | 512 | 1H-NMR (CD3OD, 400 MHz) δ (ppm): 7.68 (s, 1H), 7.11-7.05 (m, 2H), 6.91-6.86 (m, 1H), 6.54 (s, 1H), 5.02-4.96 (m, 3H), 3.78 (br s, 5H), 3.57-3.51 (m, 1H), 3.39-3.38 (m, 1H), 2.97 (s, 2H), 2.58 (br s, 1H), 2.38-2.32 (m, 1H), 2.12-1.99 (m, 2H), 1.92 (d, J = 12.8 Hz, 1H), 1.83 (d, J = 6.8 Hz, 1H), 1.76-1.53 (m, 3H), 1.39-1.35 (m, 1H), 1.09-1.06 (m, 1H). |
| 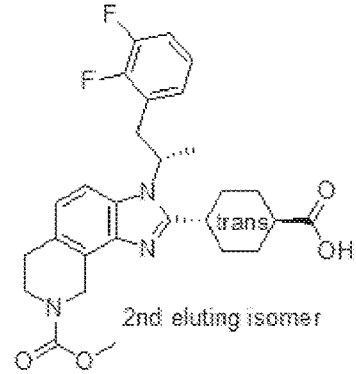 | trans-4-[3-[(2S)-1-(2,3-difluorophenyl)propan-2-yl]-8-(methoxycarbonyl)-3H,6H,7H,8H,9H-imidazo[4,5-h]isoquinolin-2-yl]cyclohexane-1-carboxylic acid | 512 | 1H-NMR (CD3OD, 400 MHz) δ (ppm): 7.68 (s, 1H), 7.11-7.05 (m, 2H), 6.91-6.86 (m, 1H), 6.54 (br s, 1H), 5.02-4.96 (m, 3H), 3.78 (s, 5H), 3.57-3.51 (m, 1H), 3.39-3.38 (m, 1H), 2.97 (s, 2H), 2.58 (br s, 1H), 2.38-2.35 (m, 1H), 2.12-1.99 (m, 2H), 1.92 (d, J = 12 Hz, 1H), 1.83 (d, J = 6.8 Hz, 1H), 1.76-1.56 (m, 3H), 1.39-1.36 (m, 1H), 1.09-1.06 (m, 1H). |

FIGURE 1 (continued)

| Structure | Name | MW | 1H-NMR |
|---|---|---|---|
| 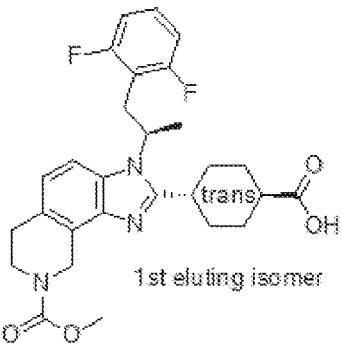 | trans-4-{3-[(2R)-1-(2,6-difluorophenyl)propan-2-yl]-8-(methoxycarbonyl)-3H,6H,7H,8H,9H-imidazo[4,5-h]isoquinolin-2-yl}cyclohexane-1-carboxylic acid<br>1st eluting isomer | 512 | 1H-NMR (Methanol-$d4$, 400 MHz) δ (ppm): 7.65 (s, 1H), 7.28-7.24 (m, 1H), 7.07 (d, $J$ = 6.8 Hz, 1H), 6.91-6.87 (m, 2H), 4.96 (br s, 3H), 3.78-3.76 (m, 5H), 3.60-3.50 (m, 1H), 3.29-3.26 (m, 1H), 2.96 (s, 2H), 2.62 (br s, 1H), 2.37-2.34 (m, 1H), 2.14-2.11 (m, 1H), 2.04-1.86 (m, 2H), 1.81 (d, $J$ = 6.8 Hz, 3H), 1.77-1.70 (m, 2H), 1.61-1.51 (m, 1H), 1.41-1.33 (m, 1H), 1.20-1.15 (m, 1H) |
| 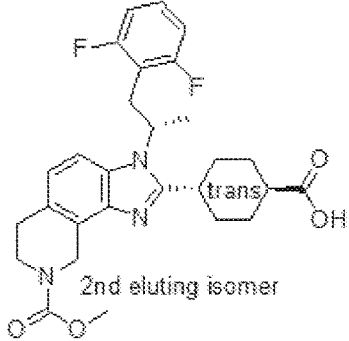 | trans-4-{3-[(2S)-1-(2,6-difluorophenyl)propan-2-yl]-8-(methoxycarbonyl)-3H,6H,7H,8H,9H-imidazo[4,5-h]isoquinolin-2-yl}cyclohexane-1-carboxylic acid<br>2nd eluting isomer | 512 | 1H-NMR (Methanol-$d4$, 400 MHz) δ (ppm): 7.64 (s, 1H), 7.28-7.23 (m, 1H), 7.07 (d, $J$ = 8.8 Hz, 1H), 6.91-6.87 (m, 2H), 4.96 (br s, 3H), 3.78 (br s, 5H), 3.60-3.50 (m, 1H), 3.34-3.30 (m, 1H), 2.96 (s, 2H), 2.62 (s, 1H), 2.39-2.35 (m, 1H), 2.14-1.90 (m, 3H), 1.81 (d, $J$ = 6.8 Hz, 3H), 1.76-1.67 (m, 2H), 1.61-1.52 (m, 1H), 1.42-1.39 (m, 1H), 1.20-1.11 (m, 1H). |
| 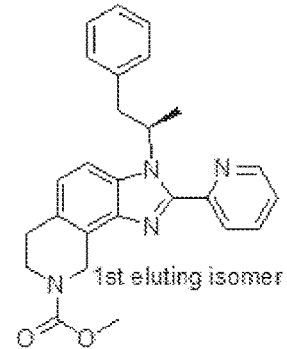 | methyl 3-[(2R)-1-phenylpropan-2-yl]-2-(pyridin-2-yl)-3H,6H,7H,8H,9H-imidazo[4,5-h]isoquinoline-8-carboxylate<br>1st eluting isomer | 427 | 1H-NMR (DMSO-$d6$, 400 MHz) δ (ppm): 8.75 (d, $J$ = 4 Hz, 1H), 7.93-7.89 (m, 1H), 7.83-7.81 (m, 2H), 7.52-7.49 (m, 1H), 7.13 (d, $J$ = 8.4 Hz, 1H), 7.06-7.03 (m, 3H), 6.86 (d, $J$ = 3.6 Hz, 2H), 6.05-5.98 (m, 1H), 4.92-4.88 (m, 2H), 3.77-3.65 (m, 5H), 3.41-3.25 (m, 1H), 3.23-3.20 (m, 1H), 2.97-2.92 (m, 2H), 1.69 (d, $J$ = 7.2 Hz, 3H). |
| 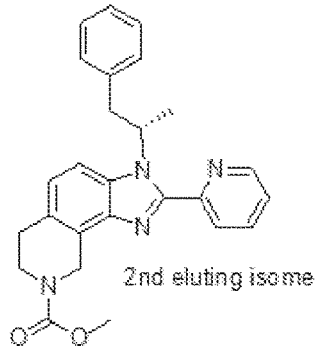 | methyl 3-[(2S)-1-phenylpropan-2-yl]-2-(pyridin-2-yl)-3H,6H,7H,8H,9H-imidazo[4,5-h]isoquinoline-8-carboxylate<br>2nd eluting isomer | 427 | 1H-NMR (DMSO-$d6$, 400 MHz) δ (ppm): 8.75 (d, $J$ = 3.6 Hz, 1H), 7.93-7.91 (m, 1H), 7.89-7.81 (m, 2H), 7.52-7.49 (m, 1H), 7.13 (d, $J$ = 8.4 Hz, 1H), 7.07-7.05 (m, 3H), 6.86 (d, $J$ = 3.6 Hz, 2H), 6.05-6.99 (m, 1H), 4.92-4.88 (m, 2H), 3.77-3.65 (m, 5H), 3.41-3.35 (m, 1H), 3.23-3.20 (m, 1H), 2.92-2.88 (m, 2H), 1.69 (d, $J$ = 7.2 Hz, 3H) |

FIGURE 1 (continued)

| | Name | # | 1H-NMR |
|---|---|---|---|
| 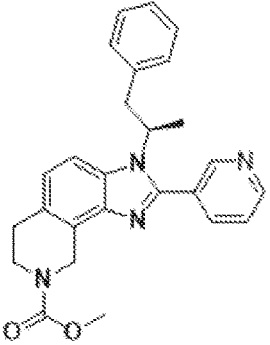<br>First eluting isomer | Methyl 3-[(2R)-1-phenylpropan-2-yl]-2-(pyridin-3-yl)-3H,6H,7H,8H,9H-imidazo[4,5-h]isoquinoline-8-carboxylate | 427 | 1H-NMR (Methanol-d4, 400 MHz) δ (ppm): 8.67-8.66 (m, 1H), 8.23 (s, 1H), 7.86 (d, J = 8.4 Hz, 1H), 7.47-7.45 (m, 1H), 7.16-7.12 (m, 2H), 7.09-7.05 (m, 2H), 6.64 (d, J = 6.8 Hz, 2H), 4.89-4.85 (m, 1H), 4.58-4.52 (m, 1H), 3.78-3.75 (m, 1H), 3.70-3.63 (m, 4H), 3.44-3.32 (m, 1H), 3.12-3.08 (m, 1H), 2.95-2.91 (m, 2H), 1.73 (d, J = 7.2 Hz, 3H) |
| 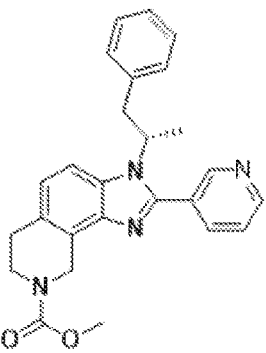<br>Second eluting isomer | methyl 3-[(2S)-1-phenylpropan-2-yl]-2-(pyridin-3-yl)-3H,6H,7H,8H,9H-imidazo[4,5-h]isoquinoline-8-carboxylate | 427 | 1H-NMR (Methanol-d4, 400 MHz) δ (ppm): 8.67-8.66 (m, 1H), 8.23 (s, 1H), 7.86 (d, J = 2.8 Hz, 1H), 7.47-7.44 (m, 2H), 7.16-7.12 (m, 2H), 7.09-7.05 (m, 2H), 6.64 (d, J = 7.2 Hz, 2H), 4.89-4.85 (m, 2H), 4.58-4.52 (m, 1H), 3.78-3.73 (m, 1H), 3.70-3.63 (m, 4H), 3.44-3.32 (m, 1H), 3.12-3.08 (m, 1H), 2.95-2.91 (m, 2H), 1.73 (d, J = 7.2 Hz, 3H). |
| 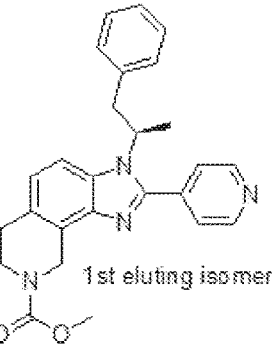<br>1st eluting isomer | Methyl 3-[(2R)-1-phenylpropan-2-yl]-2-(pyridin-4-yl)-3H,6H,7H,8H,9H-imidazo[4,5-h]isoquinoline-8-carboxylate | 427 | 1H-NMR (Methanol-d4, 400 MHz) δ (ppm): 8.58 (d, J = 5.2 Hz, 2H), 7.86 (d, J = 8.4 Hz, 1H), 7.28 (d, J = 8.4 Hz, 1H), 7.18-7.14 (m, 1H), 7.06-7.02 (m, 4H), 6.53 (d, J = 7.6 Hz, 2H), 5.04-4.93 (m, 2H), 4.70-4.63 (m, 1H), 3.90-80 (m, 2H), 3.78 (s, 3H), 3.52-3.46 (m, 1H), 3.08-2.99 (m, 3H), 1.91 (d, J = 7.2 Hz, 3H). |
| 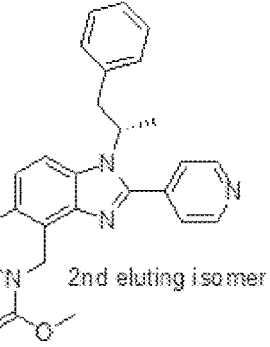<br>2nd eluting isomer | methyl 3-[(2S)-1-phenylpropan-2-yl]-2-(pyridin-4-yl)-3H,6H,7H,8H,9H-imidazo[4,5-h]isoquinoline-8-carboxylate | 427 | 1H-NMR (Methanol-d4, 400 MHz) δ (ppm): 8.58 (d, J = 5.2 Hz, 2H), 7.86 (d, J = 8.4 Hz, 1H), 7.28 (d, J = 8.4 Hz, 1H), 7.18-7.14 (m, 1H), 7.06-7.02 (m, 4H), 6.53 (d, J = 7.2 Hz, 2H), 5.04-4.92 (m, 2H), 4.72-4.64 (m, 1H), 3.93-3.80 (m, 2H), 3.78 (s, 3H), 3.53-3.46 (m, 1H), 3.08-2.99 (m, 3H), 1.91 (d, J = 6.8 Hz, 3H). |

FIGURE 1 (continued)

| | Name | # | NMR |
|---|---|---|---|
| 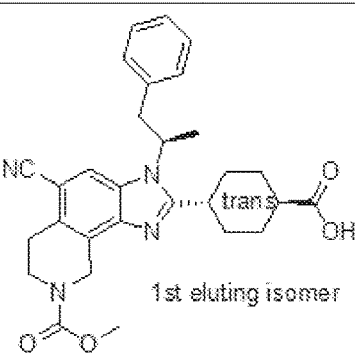 | (trans)-4-[5-cyano-8-(methoxycarbonyl)-3-[(2R)-1-phenylpropan-2-yl]-3H,6H,7H,8H,9H-imidazo[4,5-h]isoquinolin-2-yl]cyclohexane-1-carboxylic acid | 501 | 1H-NMR (Methanol-$d_4$, 400 MHz) δ (ppm): 8.24 (s, 1H), 7.18-7.08 (m, 3H), 6.82 (s, 2H), 4.96 (s, 3H), 3.91-3.83 (m, 2H), 3.79 (s, 3H), 3.49-3.38 (m, 1H), 3.22-3.18 (m, 1H), 3.12 (s, 2H), 2.46 (s, 1H), 2.30 (s, 1H), 2.07 (d, $J$ = 10.7 Hz, 1H), 1.84 (d, $J$ = 6.9 Hz, 5H), 1.63-1.46 (m, 3H), 1.27 (d, $J$ = 13.4 Hz, 1H), 0.84 (s, 1H). |
| 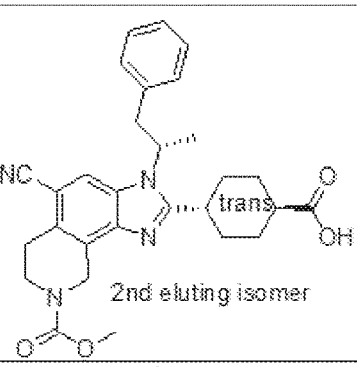 | (trans)-4-[5-cyano-8-(methoxycarbonyl)-3-[(2S)-1-phenylpropan-2-yl]-3H,6H,7H,8H,9H-imidazo[4,5-h]isoquinolin-2-yl]cyclohexane-1-carboxylic acid | 501 | 1H-NMR (Methanol-$d_4$, 400 MHz) δ (ppm): 8.24 (s, 1H), 7.14-7.13 (m, 3H), 6.83 (s, 2H), 5.01-4.92 (m, 3H), 3.88-3.85 (m, 2H), 3.79 (s, 3H), 3.46-3.40 (m, 1H), 3.25-3.20 (m, 1H), 3.12 (s, 2H), 2.46-2.44 (m, 1H), 2.32-2.27 (m, 1H), 2.08-2.5 (m, 1H), 1.92-1.83 (m, 5H), 1.63-1.54 (m, 3H), 1.34-1.25 (m, 1H), 0.85-0.77 (m, 1H). |
| 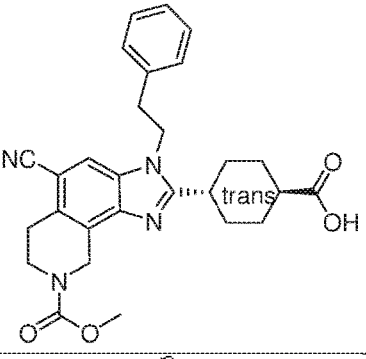 | trans-4-[5-cyano-8-(methoxycarbonyl)-3-(2-phenylethyl)-3H,6H,7H,8H,9H-imidazo[4,5-h]isoquinolin-2-yl]cyclohexane-1-carboxylic acid | 524 | 1H-NMR (CD3OD, 400 MHz) δ (ppm): 7.84 (s, 1H), 7.24 – 7.21 (m, 3H), 6.93– 6.91 (m, 2H), 4.98 (s, 2H), 4.59-4.56 (m, 2H), 3.86-3.85 (m, 2H), 3.79 (s, 3H), 3.15-3.09 (m, 4H), 2.45-2.30 (m, 2H), 2.02-1.99 (m, 2H), 1.69-1.60 (m, 2H), 1.52-1.34 (m, 4H). |
| 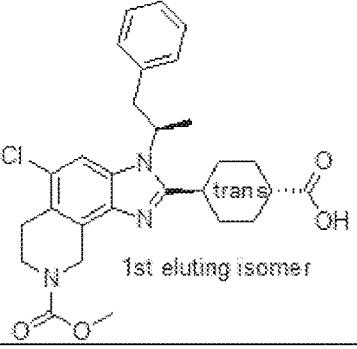 | (trans)-4-[5-chloro-8-(methoxycarbonyl)-3-[(2R)-1-phenylpropan-2-yl]-6H,7H,9H-imidazo[4,5-h]isoquinolin-2-yl]cyclohexane-1-carboxylic acid | 510, 512 | 1H-NMR (DMSO-$d_6$, 400 MHz) δ (ppm): 12.10 (br s, 1H), 7.88 (s, 1H), 7.18-7.11 (m, 3H), 6.93 (d, $J$ = 6.4 Hz, 2H), 4.83-4.74 (m, 3H), 3.73-3.67 (m, 5H), 3.30-3.26 (m, 1H), 3.19-3.15 (m, 1H), 2.88-2.80 (m, 2H), 2.45 (br s, 1H), 2.21 (br s, 1H), 1.93 (br s, 1H), 1.83-1.76 (m, 2H), 1.65 (d, $J$ = 6.8 Hz, 3H), 1.45-1.42 (m, 3H), 1.26-1.17 (m, 1H), 0.97-0.92 (m, 1H) |

FIGURE 1 (continued)

| Structure | Name | MS | 1H-NMR |
|---|---|---|---|
| 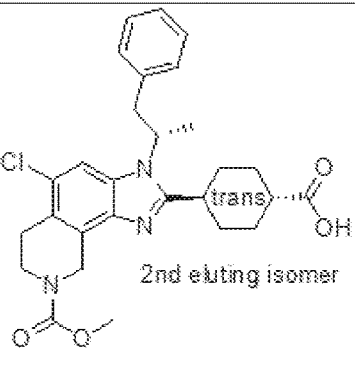 | (trans)-4-[5-chloro-8-(methoxycarbonyl)-3-[(2R)-1-phenylpropan-2-yl]-6H,7H,9H-imidazo[4,5-h]isoquinolin-2-yl]cyclohexane-1-carboxylic acid | 510, 512 | 1H-NMR (DMSO–$d_6$, 400 MHz) δ (ppm): 12.10 (br s, 1H), 7.88 (s, 1H), 7.22-7.13 (m, 3H), 6.93 (d, J = 6.8 Hz, 2H), 4.84-4.75 (m, 3H), 3.73-3.67 (m, 5H), 3.32-3.26 (m, 1H), 3.19-3.16 (m, 1H), 2.84-2.80 (m, 2H), 2.45 (br s, 1H), 2.21 (br s, 1H), 1.93 (br s, 1H), 1.83-1.70 (m, 2H), 1.65 (d, J = 6.8 Hz, 3H), 1.45-1.40 (m, 3H), 1.27-1.18 (m, 1H), 0.98-0.90 (m, 1H) |
| 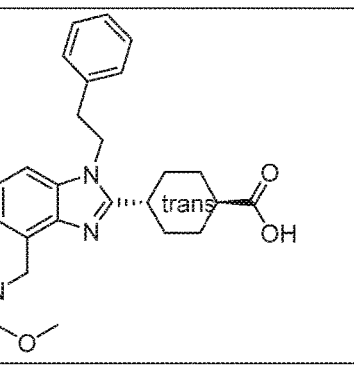 | (trans)-4-[5-chloro-8-(methoxycarbonyl)-3-(2-phenylethyl)-3H,5H,5aH,6H,7H,8H,9H-imidazo[4,5-h]isoquinolin-2-yl]cyclohexane-1-carboxylic acid | 496, 498 | 1H-NMR (CD3OD-$d_4$, 400 MHz) δ (ppm): 7.51 (s, 1H), 7.26-7.21 (m, 3H), 6.92 (d, J = 6.4 Hz, 2H), 4.99 (s, 2H), 4.58-4.50 (m, 2H), 3.82-3.73 (m, 5H), 3.12 (s, 2H), 2.96 (s, 2H), 2.37-2.22 (m, 2H), 2.01-1.92 (m, 2H), 1.68-1.58 (m, 2H), 1.50-1.44 (m, 2H), 1.42-1.32 (m, 2H). |
| 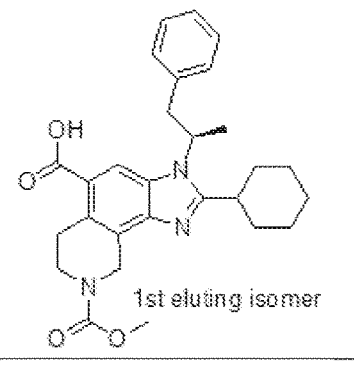 | 2-cyclohexyl-8-(methoxycarbonyl)-3-[(2R)-1-phenylpropan-2-yl]-3H,6H,7H,8H,9H-imidazo[4,5-h]isoquinoline-5-carboxylic acid | 476 | 1H-NMR (CD3OD-$d_4$, 400 MHz) δ (ppm): 8.35 (s, 1H), 7.12 (s, 3H), 6.82 (s, 2H), 5.04 (s, 2H), 4.99 (br s, 2H), 3.79-3.76 (m, 5H), 3.50-3.42 (m, 1H), 3.25-3.21 (m, 1H), 2.45 (br s, 1H), 1.85-1.78 (m, 5H), 1.74-1.67 (m, 2H), 1.55-1.53 (m, 2H), 1.45-1.12 (m, 4H), 0.86-0.83 (m, 1H). |
| 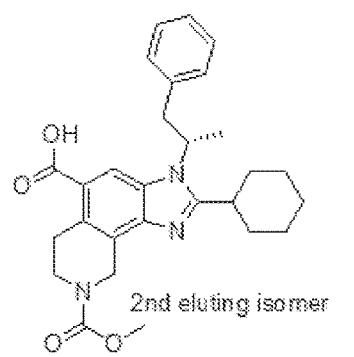 | 2-cyclohexyl-8-(methoxycarbonyl)-3-[(2S)-1-phenylpropan-2-yl]-3H,6H,7H,8H,9H-imidazo[4,5-h]isoquinoline-5-carboxylic acid | 476 | 1H-NMR (CD3OD-$d_4$, 400 MHz) δ (ppm): 8.35 (s, 1H), 7.12 (s, 3H), 6.82 (s, 2H), 5.04 (s, 2H), 4.99 (br s, 2H), 3.79-3.76 (m, 5H), 3.48-3.42 (m, 1H), 3.25-3.21 (m, 1H), 2.45 (br s, 1H), 1.85-1.78 (m, 5H), 1.74-1.67 (m, 2H), 1.55-1.53 (m, 2H), 1.45-1.12 (m, 4H), 0.86-0.83 (m, 1H). |

FIGURE 1 (continued)

| Structure | Name | MW | NMR |
|---|---|---|---|
| 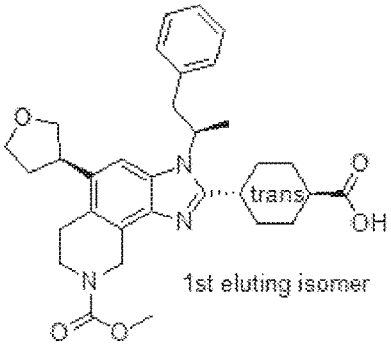 1st eluting isomer | (trans)-4-[8-(methoxycarbonyl)-5-[(3R)-oxolan-3-yl]-3-[(2R)-1-phenylpropan-2-yl]-3H,6H,7H,8H,9H-imidazo[4,5-h]isoquinolin-2-yl]cyclohexane-1-carboxylic acid | 546 | 1H-NMR (Methanol-*d*4, 400 MHz) δ (ppm): 7.64 (s, 1H), 7.12 (br s, 3H), 6.79 (br s, 2H), 4.97 (s, 2H), 4.19-4.12 (m, 2H), 4.03-3.87 (m, 2H), 3.85-3.78 (m, 6H), 3.47-3.41 (m, 1H), 3.21-3.18 (m, 1H), 3.00 (s, 2H), 2.55-2.29 (m, 3H), 2.10-2.04 (m, 2H), 1.91-1.82 (m, 5H), 1.61-1.51 (m, 3H), 1.40-1.18 (m, 2H), 0.85-0.80 (m, 1H). LCMS (ES, *m/z*) 546[M+H]+. |
| 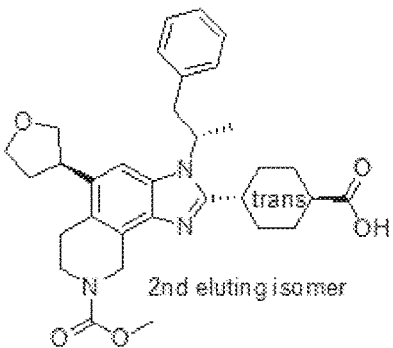 2nd eluting isomer | (trans)-4-[8-(methoxycarbonyl)-5-[(3R)-oxolan-3-yl]-3-[(2S)-1-phenylpropan-2-yl]-3H,6H,7H,8H,9H-imidazo[4,5-h]isoquinolin-2-yl]cyclohexane-1-carboxylic acid | 546 | 1H-NMR (Methanol-*d*4, 400 MHz) δ (ppm): 7.63 (s, 1H), 7.12 (br s, 3H), 6.79 (s, 2H), 5.03-4.91 (m, 2H), 4.21-4.14 (m, 2H), 4.02-3.95 (m, 2H), 3.89-3.73 (m, 6H), 3.48-3.39 (m, 1H), 3.24-3.18 (m, 1H), 3.00 (s, 2H), 2.48-2.28 (m, 3H), 2.04-2.01 (m, 2H), 1.87-1.81 (m, 5H), 1.61-1.49 (m, 3H), 1.31-1.25 (m, 2H), 0.85-0.81 (m, 1H |
| 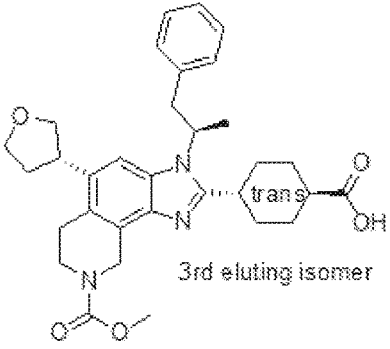 3rd eluting isomer | (trans)-4-[8-(methoxycarbonyl)-5-[(3S)-oxolan-3-yl]-3-[(2S)-1-phenylpropan-2-yl]-3H,6H,7H,8H,9H-imidazo[4,5-h]isoquinolin-2-yl]cyclohexane-1-carboxylic acid | 546 | 1H-NMR (Methanol-*d*4, 400 MHz) δ (ppm): 7.64 (s, 1H), 7.13 (br s, 3H), 6.79 (s, 2H), 4.97 (s, 2H), 4.19-4.12 (m, 2H), 4.03-3.95 (m, 2H), 3.88-3.78 (m, 6H), 3.50-3.41 (m, 1H), 3.21-3.15 (m, 1H), 3.00 (br s, 2H), 2.52-2.29 (m, 3H), 2.10-2.06 (m, 2H), 1.87-1.81 (m, 5H), 1.61-1.48 (m, 3H), 1.31-1.25 (m, 2H), 0.85-0.81 (m, 1H). |
| 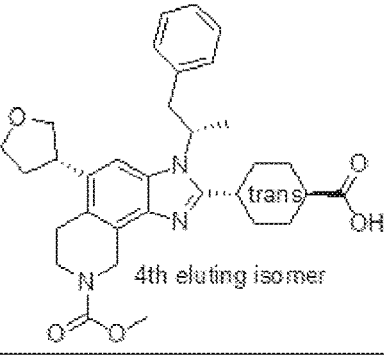 4th eluting isomer | (trans)-4-[8-(methoxycarbonyl)-5-[(3S)-oxolan-3-yl]-3-[(2R)-1-phenylpropan-2-yl]-3H,6H,7H,8H,9H-imidazo[4,5-h]isoquinolin-2-yl]cyclohexane-1-carboxylic acid | 546 | 1H-NMR (Methanol-*d*4, 400 MHz) δ (ppm): 7.64 (br s, 1H), 7.12(br s, 3H), 6.80 (br s, 2H), 5.03-4.91 (m, 2H), 4.21-4.11 (m, 2H), 4.02-3.98 (m, 2H), 3.89-3.75 (m, 6H), 3.48-3.42 (m, 1H), 3.21-3.16 (m, 1H), 3.05-2.94 (m, 2H), 2.48-2.19 (m, 3H), 2.06 (br s, 2H), 1.91-1.81 (m, 5H), 1.69-1.43 (m, 3H), 1.37-1.15 (m, 2H), 0.84-0.80 (m, 1H) |

FIGURE 1 (continued)

| | Name | MW | NMR |
|---|---|---|---|
| 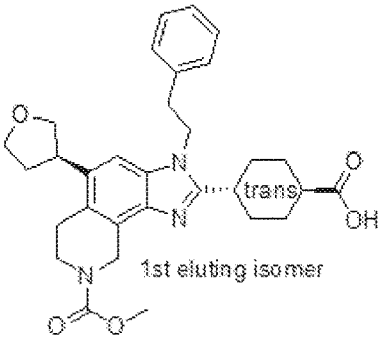 | trans-4-[8-(methoxycarbonyl)-5-[(3R)-oxolan-3-yl]-3-(2-phenylethyl)-3H,6H,7H,8H,9H-imidazo[4,5-h]isoquinolin-2-yl]cyclohexane-1-carboxylic acid | 532 | 1H-NMR (CD3OD, 400 MHz) δ (ppm): 7.21-7.18 (m, 4H), 6.91 (d, J = 7.2 Hz, 2H), 4.99 (s, 2H), 4.53-4.50 (m, 2H), 4.15-4.07 (m, 2H), 3.99-3.93 (m, 1H), 3.86-3.71 (m, 7H), 3.14-3.11 (m, 2H), 2.97 (s, 2H), 2.45-2.32 (m, 3H), 2.03-1.96 (m, 3H), 1.72-1.53 (m, 4H), 1.45-1.36 (m, 2H) |
| 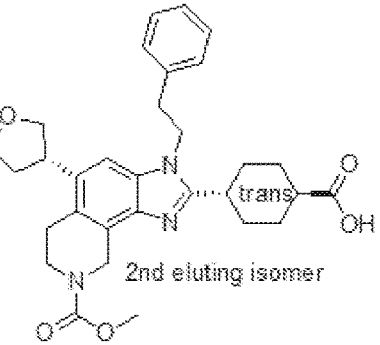 | trans-4-[8-(methoxycarbonyl)-5-[(3S)-oxolan-3-yl]-3-(2-phenylethyl)-3H,6H,7H,8H,9H-imidazo[4,5-h]isoquinolin-2-yl]cyclohexane-1-carboxylic acid | 532 | 1H-NMR (CD3OD, 400 MHz) δ (ppm): 7.21-7.19 (m, 4H), 6.91 (d, J = 7.6 Hz, 2H), 4.99 (s, 2H), 4.53-4.51 (m, 2H), 4.15-4.11 (m, 2H), 3.99-3.93 (m, 1H), 3.86-3.72 (m, 7H), 3.14-3.11 (m, 2H), 2.97 (s, 2H), 2.45-2.33 (m, 3H), 2.05-1.98 (m, 3H), 1.72-1.63 (m, 2H), 1.56-1.53 (m, 2H), 1.45-1.36 (m, 2H). |
| 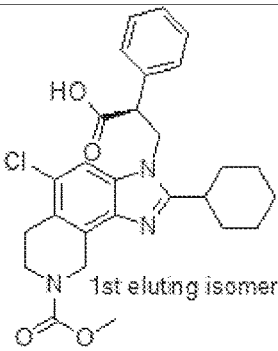 | (2S)-3-[5-chloro-2-cyclohexyl-8-(methoxycarbonyl)-3H,6H,7H,8H,9H-imidazo[4,5-h]isoquinolin-3-yl]-2-phenylpropanoic acid | 496, 498 | 1H-NMR (CD3OD, 400 MHz) δ (ppm): 7.52 (s, 1H), 7.34-7.29 (m, 3H), 7.15 (d, J = 7.2 Hz, 2H), 4.97 (s, 2H), 4.86-4.82 (m, 1H), 4.58-4.52 (m, 1H), 4.11-4.07 (m, 1H), 3.82-3.78 (m, 5H), 2.96-2.93 (m, 2H), 2.59-2.53 (m, 1H), 1.86-1.83 (m, 2H), 1.76-1.74 (m, 2H), 1.62-1.55 (m, 2H), 1.47-1.12 (m, 4H). |
| 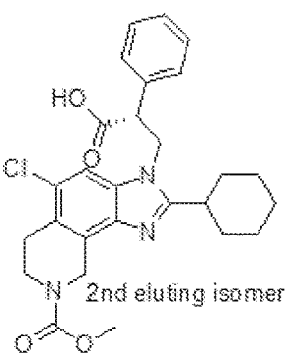 | (2R)-3-[5-chloro-2-cyclohexyl-8-(methoxycarbonyl)-3H,6H,7H,8H,9H-imidazo[4,5-h]isoquinolin-3-yl]-2-phenylpropanoic acid | 496, 498 | 1H-NMR (CD3OD, 400 MHz) δ (ppm): 7.52 (s, 1H), 7.30 – 7.28 (m, 3H), 7.15 (d, J = 7.2 Hz, 2H), 4.97 (s, 2H), 4.86-4.82 (m, 1H), 4.58-4.52 (m, 1H), 4.11-4.07 (m, 1H), 3.82-3.78 (m, 5H), 2.96-2.93 (m, 2H), 2.59-2.53 (m, 1H), 1.86-1.83 (m, 2H), 1.76-1.74 (m, 2H), 1.66-1.58 (m, 2H), 1.46-1.12 (m, 4H). |

FIGURE 1 (continued)

| Structure | Name | MW | 1H-NMR |
|---|---|---|---|
| 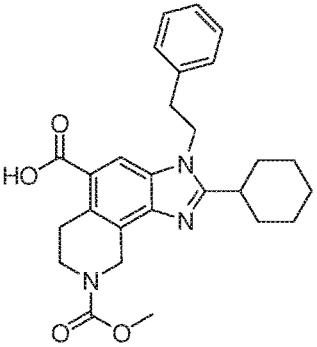 | 2-cyclohexyl-8-(methoxycarbonyl)-3-(2-phenylethyl)-3H,6H,7H,8H,9H-imidazo[4,5-h]isoquinoline-5-carboxylic acid | 462 | 1H-NMR (CD3OD, 400 MHz) δ (ppm): 7.97 (s, 1H), 7.22-7.17 (m, 3H), 6.92 (d, J = 7.2 Hz, 2H), 5.01 (s, 2H), 4.54-4.51 (m, 2H), 3.79 (s, 3H), 3.75-3.72 (m, 2H), 3.30-3.28 (m, 2H), 3.15-3.13 (tm, 2H), 2.41-2.35 (m, 1H), 1.77-1.71 (m, 3H), 1.63-1.54 (m, 2H), 1.45-1.42 (m, 2H), 1.34-1.22 (m, 3H). |
| <br>1st eluting isomer | methyl 2-(1-acetylpiperidin-4-yl)-3-[(2R)-1-(pyridin-3-yl)propan-2-yl]-3H,6H,7H,8H,9H-imidazo[4,5-h]isoquinoline-8-carboxylate | 476 | 1H-NMR (DMSO-d6, 400 MHz) δ (ppm): 8.33 (s, 1H), 8.01 (s, 1H), 7.78-7.76 (m, 1H), 7.35-7.34 (m, 1H), 7.26-7.22 (m, 1H), 7.19-7.17 (m, 1H), 5.03-4.97 (m, 1H), 4.93 (s, 2H), 4.60-4.48 (m, 1H), 4.02-3.91 (m, 1H), 3.81-3.74 (m, 5H), 3.62-3.56 (m, 1H), 3.29-3.25 (m, 1H), 3.05-2.99 (m, 3H), 2.95-2.85 (m, 1H), 2.81-2.55 (m, 1H), 2.12 (s, 3H), 1.88-1.83 (m, 5H), 1.69-1.63 (m, 1H), 0.90-0.70 (m, 1H). |
| 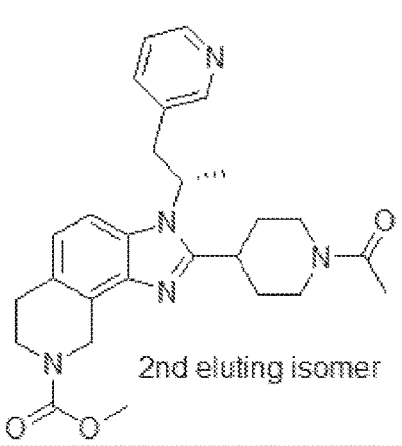<br>2nd eluting isomer | methyl 2-(1-acetylpiperidin-4-yl)-3-[(2S)-1-(pyridin-3-yl)propan-2-yl]-3H,6H,7H,8H,9H-imidazo[4,5-h]isoquinoline-8-carboxylate | 476 | 1H-NMR (DMSO-d6, 400 MHz) δ (ppm): 8.30 (s, 1H), 7.99 (s, 1H), 7.76-7.74 (m, 1H), 7.32-7.30 (m, 1H), 7.23-7.20 (m, 1H), 7.16-7.14 (m, 1H), 5.01-4.98 (m, 1H), .93 (s, 2H), 4.56-4.47 (m, 1H), 3.98-3.90 (m, 1H), 3.82-3.75 (m, 5H), 3.61-3.57 (m, 1H), 3.27-3.04 (m, 2H), 2.98-2.95 (m, 2H), 2.87-2.50 (m, 2H), 2.12 (s, 3H), 1.87-1.70 (m, 5H), 1.65-1.62 (m, 1H), 0.90-0.70 (m, 1H). |

FIGURE 1 (continued)

| Structure | Name | MW | 1H-NMR |
|---|---|---|---|
| 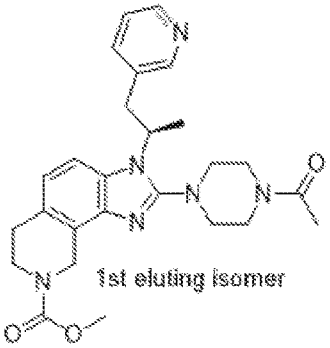 | methyl 2-(4-acetylpiperazin-1-yl)-3-[(2R)-1-(pyridin-3-yl)propan-2-yl]-3H,6H,7H,8H,9H-imidazo[4,5-h]isoquinoline-8-carboxylate | 477 | 1H-NMR (CD3OD, 400 MHz) δ (ppm): 8.25 (s, 1H), 7.88 (s, 1H), 7.62 (d, $J$ = 8.0 Hz, 1H), 7.24 (br s, 1H), 7.18-7.16 (m, 1H), 7.10 (d, $J$ = 8.4 Hz, 1H), 4.95-4.91 (m, 1H), 4.84 (s, 2H), 3.82-3.67 (m, 8H), 3.53-3.40 (m, 2H), 3.20-3.15 (m, 1H), 3.11-3.04 (m, 2H), 2.97-2.94 (m, 2H), 2.60-2.54 (m, 2H), 2.15 (s, 3H), 1.88 (d, $J$ = 6.8 Hz, 3H). |
| 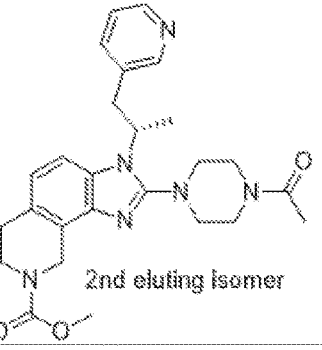 | methyl 2-(4-acetylpiperazin-1-yl)-3-[(2S)-1-(pyridin-3-yl)propan-2-yl]-3H,6H,7H,8H,9H-imidazo[4,5-h]isoquinoline-8-carboxylate | 477 | 1H-NMR (CD3OD, 400 MHz) δ (ppm): 8.25 (s, 1H), 7.88 (br s, 1H), 7.62 (d, $J$ = 8.4 Hz, 1H), 7.24 (br s, 1H), 7.19-7.15 (m, 1H), 7.10 (d, $J$ = 8.4 Hz, 1H), 4.95-4.91 (m, 1H), 4.84 (s, 2H), 3.82-3.67 (m, 8H), 3.53-3.40 (m, 2H), 3.20-3.15 (m, 1H), 3.11-3.04 (m, 2H), 2.97-2.94 (m, 1H), 2.60-2.54 (m, 2H), 2.15 (s, 3H), 1.88 (d, $J$ = 7.2 Hz, 3H). |
| 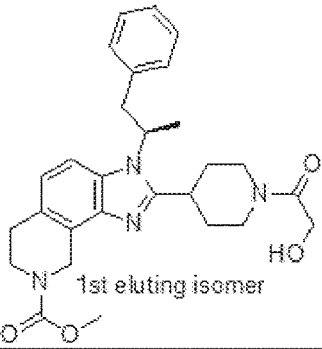 | methyl 2-[1-(2-hydroxyacetyl)piperidin-4-yl]-3-[(2R)-1-phenylpropan-2-yl]-3H,6H,7H,8H,9H-imidazo[4,5-h]isoquinoline-8-carboxylate | 491 | 1H-NMR (DMSO-$d$6, 400 MHz) δ (ppm): 7.68 (s, 1H), 7.16-7.14 (m, 3H), 7.01 (d, $J$ = 8 Hz, 1H), 6.94 (d, $J$ = 6.4 Hz, 2H), 4.87 (br s, 1H), 4.80-4.76 (m, 2H), 4.49-4.47 (m, 1H), 4.40-4.23 (m, 1H), 4.15-4.04 (m, 2H), 3.70-3.51 (m, 3H), 3.33-3.08 (m, 6H), 2.88-2.72 (m, 4H), 1.77-1.65 (m, 5H), 1.49-1.34 (m, 1H, ), 0.90-0.81 (m, 1H) |
| 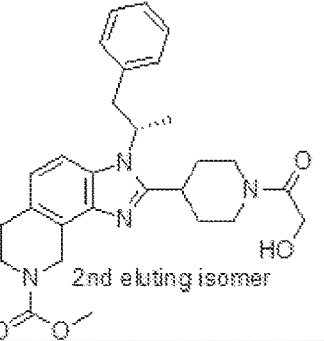 | methyl 2-[1-(2-hydroxyacetyl)piperidin-4-yl]-3-[(2S)-1-phenylpropan-2-yl]-3H,6H,7H,8H,9H-imidazo[4,5-h]isoquinoline-8-carboxylate | 491 | 1H-NMR (DMSO-d6, 400 MHz) δ (ppm): 7.68 (s, 1H), 7.16-7.14 (m, 3H), 7.01 (d, $J$ = 8 Hz, 1H), 6.94 (d, $J$ = 6.4 Hz, 2H), 4.88 (br s, 1H), 4.81-4.76 (m, 2H), 4.49-4.47 (m, 1H), 4.39-4.23 (m, 1H), 4.15-4.04 (m, 2H), 3.70-3.62 (m, 6H), 3.36-3.22 (m, 2H), 3.21-3.17 (m, 1H), 2.92-2.68 (m, 4H), 1.74-1.61 (m, 5H), 1.55-1.26 (m, 1H), 0.88 (br s, 1H) |

FIGURE 1 (continued)

| Structure | Name | MW | 1H-NMR |
|---|---|---|---|
| 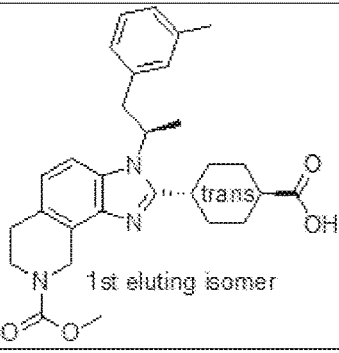 1st eluting isomer | (trans)-4-[8-(methoxycarbonyl)-3-[(2R)-1-(3-methylphenyl)propan-2-yl]-3H,6H,7H,8H,9H-imidazo[4,5-h]isoquinolin-2-yl]cyclohexane-1-carboxylic acid | 490 | 1H-NMR (DMSO-$d6$, 400 MHz) δ (ppm): 12.14 (br s, 1H), 7.65 (d, $J$ = 8.4 Hz, 1H), 7.01-6.93 (m, 3H), 6.87 (s, 1H), 6.59 (d, $J$ = 6 Hz, 1H), 4.81-4.72 (m, 3H), 3.72-3.61 (m, 5H), 3.26-3.11 (m, 2H), 2.91-2.82 (m, 2H), 2.45 (br s, 1H), 2.23-2.18 (m, 4H), 1.95-1.78 (m, 3H), 1.64 (d, $J$ = 6.8 Hz, 3H), 1.56-1.42 (m, 3H), 1.32-1.19 (m, 1H), 1.06-0.95 (m, 1H) |
| 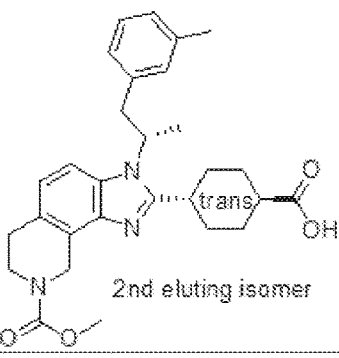 2nd eluting isomer | (trans)-4-[8-(methoxycarbonyl)-3-[(2S)-1-(3-methylphenyl)propan-2-yl]-3H,6H,7H,8H,9H-imidazo[4,5-h]isoquinolin-2-yl]cyclohexane-1-carboxylic acid | 490 | 1H-NMR (DMSO-$d6$, 400 MHz) δ (ppm): 12.06 (br s, 1H), 7.65 (d, $J$ = 8.4 Hz, 1H), 7.01-6.93 (m, 3H), 6.87 (s, 1H), 6.59 (d, $J$ = 5.2 Hz, 1H), 4.81-4.71 (m, 3H), 3.72-3.60 (m, 5H), 3.26-3.11 (m, 2H), 2.91-2.82 (m, 2H), 2.45 (br s, 1H), 2.23-2.18 (m, 4H), 1.95-1.78 (m, 3H), 1.64 (d, $J$ = 6.8 Hz, 3H), 1.54-1.41 (m, 3H), 1.32-1.18 (m, 1H), 1.06-0.96 (m, 1H) |
| 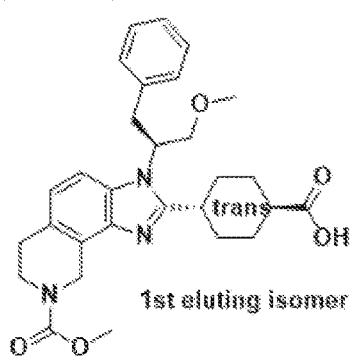 1st eluting isomer | Trans-4-{3-[(2S)-1-methoxy-3-phenylpropan-2-yl]-8-(methoxycarbonyl)-3H,6H,7H,8H,9H-imidazo[4,5-h]isoquinolin-2-yl}cyclohexane-1-carboxylic acid | 506 | 1H-NMR (CD3OD, 400 MHz) δ (ppm): δ 7.69 (d, $J$ = 8.8 Hz, 1H), 7.13-7.10 (m, 4H), 6.83 (d, $J$ = 2.8 Hz, 2H), 5.01-4.92 (m, 2H), 4.88 (br s, 1H), 4.22-4.17 (m, 1H), 3.99-3.96 (m, 1H), 3.78 (br s, 5H), 3.47-3.41 (m, 1H), 3.28 (s, 3H), 3.22-3.20 (m, 1H), 2.98 (br s, 2H), 2.43-2.25 (m, 2H), 2.06-1.86 (m, 3H), 1.65-1.47 (m, 3H), 1.29-1.18 (m, 1H), 0.81-0.77 (m, 1H). |
| 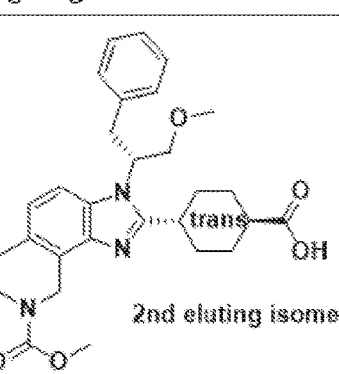 2nd eluting isomer | trans-4-{3-[(2R)-1-methoxy-3-phenylpropan-2-yl]-8-(methoxycarbonyl)-3H,6H,7H,8H,9H-imidazo[4,5-h]isoquinolin-2-yl}cyclohexane-1-carboxylic acid | 506 | 1H-NMR (CD3OD, 400 MHz) δ (ppm): δ 7.70 (d, $J$ = 8.4 Hz, 1H), 7.14-7.11 (m, 4H), 6.84 (d, $J$ = 3.6 Hz, 2H), 5.01-4.92 (m, 2H), 4.87 (br s, 1H), 4.22-4.17 (m, 1H), 3.99-3.96 (m, 1H), 3.78-3.74 (m, 5H), 3.47-3.41 (m, 1H), 3.28 (s, 3H), 3.23-3.20 (m, 1H), 2.98 (br s, 2H), 2.44-2.26 (m, 2H), 2.06-1.86 (m, 3H), 1.65-1.48 (m, 3H), 1.28-1.18 (m, 1H), 0.80-0.76 (m, 1H). |

FIGURE 1 (continued)

| Structure | Name | MW | 1H-NMR |
|---|---|---|---|
| (1st eluting isomer) | (trans)-4-[3-[(2S)-2-methoxy-2-phenylethyl]-8-(methoxycarbonyl)-6H,7H,9H-imidazo[4,5-h]isoquinolin-2-yl]cyclohexane-1-carboxylic acid | 492 | 1H-NMR (DMSO-$d6$, 400 MHz) δ (ppm): 12.09 (br s, 1H), 7.41-7.29 (m, 6H), 6.98 (d, $J$ = 8 Hz, 1H), 4.81 (m, 2H), 4.56-4.44 (m, 2H), 4.37-4.33 (m, 1H), 3.68 (br s, 5H), 3.07 (s, 3H), 2.88-2.86 (m, 2H), 2.64-2.63 (m, 1H), 2.32-2.26 (m, 1H), 1.98-1.92 (m, 2H), 1.79-1.76 (m, 1H), 1.68-1.52 (m, 3H), 1.46-1.35 (m, 2H) |
| (2nd eluting isomer) | (trans)-4-[3-[(2R)-2-methoxy-2-phenylethyl]-8-(methoxycarbonyl)-6H,7H,9H-imidazo[4,5-h]isoquinolin-2-yl]cyclohexane-1-carboxylic acid | 492 | 1H-NMR (DMSO-$d6$, 400 MHz) δ (ppm): 12.08 (br s, 1H), 7.41-7.29 (m, 6H), 6.98 (d, $J$ = 8.4 Hz, 1H), 4.81 (m, 2H), 4.56-4.44 (m, 2H), 4.37-4.33 (m, 1H), 3.68 (br s, 5H), 3.07 (s, 3H), 2.88-2.86 (m, 2H), 2.64-2.63 (m, 1H), 2.32-2.26 (m, 1H), 1.98-1.92 (m, 2H), 1.79-1.76 (m, 1H), 1.68-1.52 (m, 3H), 1.45-1.36 (m, 2H) |
| 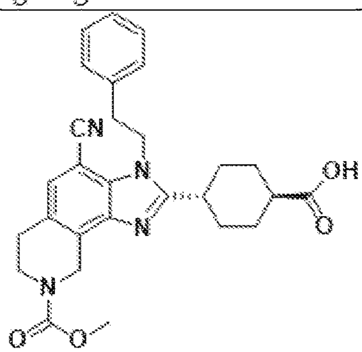 | Trans-4-[4-cyano-8-(methoxycarbonyl)-3-(2-phenylethyl)-3H,6H,7H,8H,9H-imidazo[4,5-h]isoquinolin-2-yl]cyclohexane-1-carboxylic acid | 487 | 1H-NMR (CD3OD, 400 MHz) δ (ppm): 7.53 (s, 1H), 7.28-7.22 (m, 3H), 7.00-6.98 (m, 2H), 5.03 (s, 2H), 4.78-4.75 (m, 2H), 3.82-3.79 (m, 5H), 3.22-3.19 (m, 2H), 3.02-2.99 (m, 2H), 2.38-2.28 (m, 2H), 2.03-1.99 (m, 2H), 1.67-1.53 (m, 4H), 1.39-1.33 (m, 2H). |
| 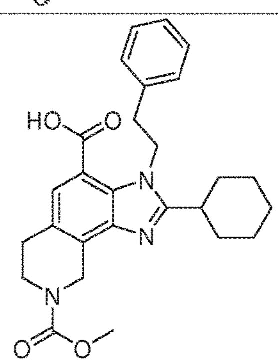 | 2-cyclohexyl-8-(methoxycarbonyl)-3-(2-phenylethyl)-3H,6H,7H,8H,9H-imidazo[4,5-h]isoquinoline-4-carboxylic acid | 462 | 1H-NMR (CD3OD-$d4$, 400 MHz) δ (ppm): 7.61 (s, 1H), 7.21-7.19 (m, 3H), 6.91-6.89 (m, 2H), 5.02 (s, 2H), 3.81-3.79 (m, 5H), 3.01-2.96 (m, 4H), 2.59-2.54 (m, 1H), 2.05 (s, 2H), 1.79-1.75 (m, 3H), 1.63-1.52 (m, 4H), 1.31 (br s, 3H). |

FIGURE 1 (continued)

| | Name | MW | NMR |
|---|---|---|---|
| 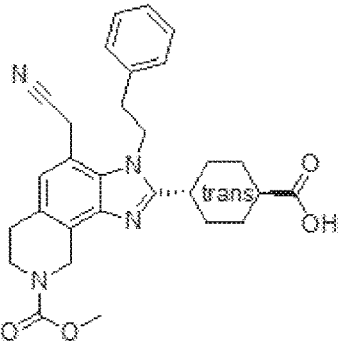 | (1r,4r)-4-[4-(cyanomethyl)-8-(methoxycarbonyl)-3-(2-phenylethyl)-3H,6H,7H,8H,9H-imidazo[4,5-h]isoquinolin-2-yl]cyclohexane-1-carboxylic acid | 501 | 1H NMR (DMSO-$d6$, 400 MHz) δ (ppm): 11.94 (br s, 1H), 7.30-7.22 (m, 3H), 7.07 – 7.03 (m, 3H), 4.78 (s, 2H), 4.55 (s, 2H), 4.48 (s, 2H), 3.67 (br s,5H), 3.08 – 2.95 (m, 2H), 2.87 (s, 2H), 2.39-2.37 (m, 1H), 2.27-2.21 (m, 1H), 1.89 (d, $J$ = 12.7 Hz, 2H), 1.54-1.52 (m, 4H), 1.34-1.21 (m, 2H). |
| 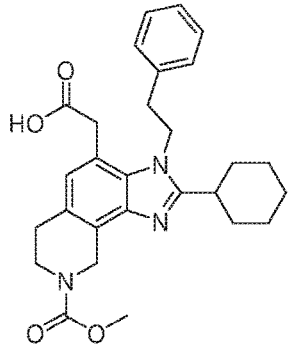 | 2-[2-cyclohexyl-8-(methoxycarbonyl)-3-(2-phenylethyl)-3H,6H,7H,8H,9H-imidazo[4,5-h]isoquinolin-4-yl]acetic acid | 476 | 1H-NMR (CD3OD-$d4$, 400 MHz) δ (ppm): 7.27-7.25 (m, 3H), 6.98 (s, 3H), 4.98 (s, 2H), 4.66 (s, 2H), 4.01 (s, 2H), 3.79 (br s, 5H), 3.09 (br s, 2H), 2.95 (br s, 2H), 2.40-2.38 (m, 1H), 1.78-1.72 (m, 3H), 1.68-1.49 (m, 4H), 1.31-1.26 (m, 3H). |
| 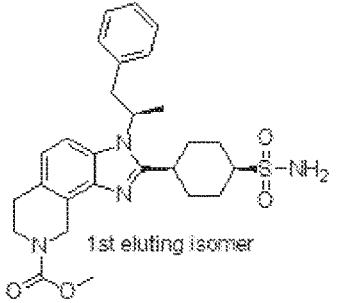 | methyl 3-[(2R)-1-phenylpropan-2-yl]-2-[(1s,4s)-4-sulfamoylcyclohexyl]-3H,6H,7H,8H,9H-imidazo[4,5-h]isoquinoline-8-carboxylate<br>1st eluting isomer | 511 | 1H-NMR (CD3OD, 400 MHz) δ (ppm): 7.71 (d, $J$ = 8.0 Hz, 1H), 7.21-7.12 (m, 4H), 6.79 (d, $J$ = 3.2 Hz, 2H), 5.02-4.92 (m, 2H), 4.87-4.82 (m, 1H), 3.78-3.77 (m, 5H), 3.53-3.47 (m, 1H), 3.19-3.16 (m, 1H), 3.07-3.04 (m, 1H), 2.98 (s, 2H), 2.68 (br s, 1H), 2.41-2.35 (m, 1H), 2.31-2.26 (m, 1H), 2.11-1.99 (m, 1H), 1.97-1.88 (m, 1H), 1.86-1.79 (m, 4H), 1.75-1.65 (m, 2H), 1.15-1.06 (m, 1H). |
| 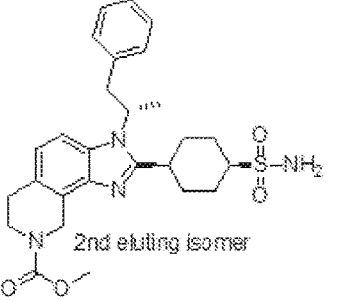 | methyl 3-[(2S)-1-phenylpropan-2-yl]-2-[(1s,4s)-4-sulfamoylcyclohexyl]-3H,6H,7H,8H,9H-imidazo[4,5-h]isoquinoline-8-carboxylate<br>2nd eluting isomer | 511 | 1H-NMR (CD3OD, 400 MHz) δ (ppm): 7.66 (d, $J$ = 8.4 Hz, 1H), 7.12-7.08 (m, 4H), 6.79 (s, 2H), 5.02-4.96 (m, 2H), 4.85-4.78 (m, 1H), 3.78 (br s, 5H), 3.53-3.47 (m, 1H), 3.16-3.14 (m, 1H), 3.04-2.97 (m, 3H), 2.64 (br s, 1H), 2.38 (br s, 1H), 2.24 (br s, 1H), 2.04 (br s, 1H), 1.93 (br s, 1H), 1.80-1.69 (m, 6H), 1.20-1.11 (m, 1H). |

FIGURE 1 (continued)

| Structure | Name | MW | NMR |
|---|---|---|---|
| 3rd eluting isomer | methyl 3-[(2R)-1-phenylpropan-2-yl]-2-[(1r,4r)-4-sulfamoylcyclohexyl]-3H,6H,7H,8H,9H-imidazo[4,5-h]isoquinoline-8-carboxylate | 511 | 1H-NMR (CD3OD, 400 MHz) δ (ppm): 7.72 (d, $J$ = 6.8 Hz, 1H), 7.19-7.13 (m, 4H), 6.81 (s, 2H), 5.01-4.91 (m, 2H), 4.90 (br s, 1H), 3.79-3.77 (m, 5H), 3.52-3.46 (m, 1H), 3.20-3.17 (m, 1H), 2.99-2.89 (m, 3H), 2.47 (br s, 1H), 2.31 (br s, 1H), 2.15-2.12 (m, 1H), 1.96 (br s, 1H), 1.84 (d, $J$ = 6.8 Hz, 3H), 1.68-1.53 (m, 3H), 1.38-1.29 (m, 1H), 0.86-0.78 (m, 1H). |
| 4th eluting isomer | methyl 3-[(2S)-1-phenylpropan-2-yl]-2-[(1r,4r)-4-sulfamoylcyclohexyl]-3H,6H,7H,8H,9H-imidazo[4,5-h]isoquinoline-8-carboxylate | 511 | : 1H-NMR (CD3OD, 400 MHz) δ (ppm): 7.69 (d, $J$ = 6 Hz, 1H), 7.23 (s, 4H), 6.80 (s, 2H), 5.01-4.96 (m, 2H), 4.88 (br s, 1H), 3.84-3.78 (m, 5H), 3.51-3.42 (m, 1H), 3.19-3.16 (m, 1H), 2.98-2.93 (m, 3H), 2.43 (br s, 1H), 2031 (br s, 1H), 2.14-2.11 (m, 1H), 1.95 (br s, 1H), 1.83 (d, $J$ = 6.8 Hz, 3H), 1.82-1.54 (m, 3H), 1.38-1.28 (m, 1H), 0.84-0.79 (m, 1H) |
| 1st eluting isomer | methyl 2-[1-(acetamidosulfonyl)piperidin-4-yl]-3-[(2R)-1-phenylpropan-2-yl]-3H,6H,7H,8H,9H-imidazo[4,5-h]isoquinoline-8-carboxylate | 554 | 1H-NMR (CD3OD, 400 MHz) δ (ppm): 7.70 (d, $J$ = 6Hz, 1H), 7.12-7.11 (m, 4H), 6.79 (m, 2H), 4.96 (s, 2H), 4.91-4.97 (m, 1H), 3.85-3.78 (m, 6H), 3.71-3.68 (m, 1H) 3.52-3.45 (m, 1H), 3.18-3.15 (m, 1H), 2.98-2.94 (m, 3H), 2.73-2.67 (m, 1H), 2.54 (br s, 1H), 2.08 (s, 3H), 1.83-1.81 (m, 5H), 1.76-1.68 (m, 1H), 0.73-0.71 (m, 1H) |
| 2nd eluting isomer | methyl 2-[1-(acetamidosulfonyl)piperidin-4-yl]-3-[(2S)-1-phenylpropan-2-yl]-3H,6H,7H,8H,9H-imidazo[4,5-h]isoquinoline-8-carboxylate | 554 | 1H-NMR (CD3OD, 400 MHz) δ (ppm): 7.70 (d, $J$ = 7.6 Hz, 1H), 7.13-7.11 (m, 4H), 6.79 (s, 2H), 4.96 (s, 2H), 4.91-4.87 (m, 1H), 3.88-3.78 (m, 6H), 3.71-3.68 (m, 1H) 3.52-3.49 (m, 1H), 3.18-3.15 (m, 1H), 2.98-2.94 (m, 3H), 2.73-2.67 (m, 1H), 2.54 (br s, 1H), 2.08 (s, 3H), 1.83-1.82 (m, 5H), 1.76-1.68 (m, 1H), 0.73-0.70 (m, 1H). |

FIGURE 1 (continued)

| Structure | Name | MW | NMR |
|---|---|---|---|
| 1st eluting isomer | methyl 3-[(2R)-1-phenylpropan-2-yl]-2-[(1s,4s)-4-(acetamidosulfonyl)cyclohexyl]-3H,6H,7H,8H,9H-imidazo[4,5-h]isoquinoline-8-carboxylate | 553 | 1H-NMR (CD3OD-d4, 400 MHz) δ (ppm): 7.67 (d, J = 7.6 Hz, 1H), 7.16-7.09 (m, 4H), 6.79 (d, J = 3.2 Hz, 2H), 5.03-4.96 (m, 2H), 4.79-4.77 (m, 1H), 3.78-3.76 (m, 1H), 3.61 (br s, 1H), 3.53-3.47 (m, 1H), 3.17-3.13 (m, 1H), 2.98-2.94 (m, 2H), 2.61 (br s, 1H), 2.30-2.23 (m, 2H), 2.08-2.02 (m, 3H), 1.96-1.79 (m, 6H), 1.70-1.65 (m, 2H), 1.06-1.01 (m, 1H) |
| 2nd eluting isomer | methyl 3-[(2S)-1-phenylpropan-2-yl]-2-[(1s,4s)-4-(acetamidosulfonyl)cyclohexyl]-3H,6H,7H,8H,9H-imidazo[4,5-h]isoquinoline-8-carboxylate | 553 | 1H-NMR (CD3OD-d4, 400 MHz) δ (ppm): 7.70 (d, J = 6.4 Hz, 1H), 7.13-7.12 (m, 4H), 6.8 (br s, 2H), 5.00-4.95 (m, 2H), 4.88-4.84 (m, 1H), 3.78-3.76 (m, 5H), 3.50-3.40 (m, 2H), 3.18-3.16 (m, 1H), 2.98-2.95 (m, 2H), 2.44 (br s, 1H), 2.24-2.20 (m, 1H), 2.09-1.95 (m, 5H), 1.83 (d, J = 6.8 Hz, 3H), 1.78-1.47 (m, 4H), 0.84-0.78 (m, 1H) |
| 3rd eluting isomer | methyl 3-[(2R)-1-phenylpropan-2-yl]-2-[(1r,4r)-4-(acetamidosulfonyl)cyclohexyl]-3H,6H,7H,8H,9H-imidazo[4,5-h]isoquinoline-8-carboxylate | 553 | 1H-NMR (CD3OD-d4, 400 MHz) δ (ppm): 7.67 (d, J = 8 Hz, 1H), 7.12-7.09 (m, 4H), 6.78 (d, J = 3.2 Hz, 2H), 5.03-4.92 (m, 2H), 4.87-4.77 (m, 1H), 3.84-3.77 (m, 5H), 3.61 (br s, 1H), 3.53-3.47 (m, 1H), 3.17-3.14 (m, 1H), 2.98 (br s, 2H), 2.61 (br s, 1H), 2.24 (br s, 2H), 2.08-2.03 (m, 4H), 1.96-1.78 (m, 5H), 1.75-1.65 (m, 3H), 1.08-1.02 (m, 1H) |
| 4th eluting isomer | methyl 3-[(2S)-1-phenylpropan-2-yl]-2-[(1r,4r)-4-(acetamidosulfonyl)cyclohexyl]-3H,6H,7H,8H,9H-imidazo[4,5-h]isoquinoline-8-carboxylate | 553 | 1H-NMR (CD3OD-d4, 400 MHz) δ (ppm): 7.69 (d, J = 6.4 Hz, 1H), 7.13-7.11 (m, 4H), 6.80 (br s, 1H), 5.00-4.95 (m, 2H), 4.87-4.85 (m, 1H), 3.78-3.73 (m, 5H), 3.50-3.44 (m, 2H), 3.19-3.16 (m, 1H), 2.98 (br s, 2H), 2.47-2.43 (m, 1H), 2.24-2.21 (m, 1H), 2.08-1.94 (m, 5H), 1.83 (d, J = 7.2 Hz, 3H), 1.78-1.41 (m, 4H), 0.83-0.78 (m, 1H) |

FIGURE 1 (continued)

| Structure | Name | MW | 1H-NMR |
|---|---|---|---|
| 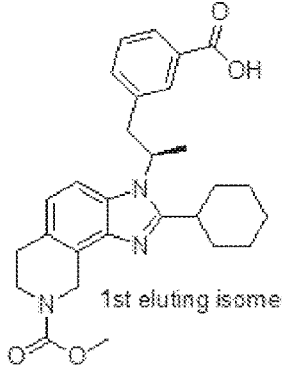 | 3-[(2R)-2-[2-cyclohexyl-8-(methoxycarbonyl)-3H,6H,7H,8H,9H-imidazo[4,5-h]isoquinolin-3-yl]propyl]benzoic acid | 476 | 1H-NMR (CD3OD, 400 MHz) δ (ppm): 7.78 (d, $J$ = 7.6 Hz, 1H), 7.71 (d, $J$ = 8 Hz, 1H), 7.64 (s, 1H), 7.18-7.11 (m, 2H), 6.88 (d, $J$ = 6.8 Hz, 1H), 4.95-4.90 (m, 3H), 3.80-3.78 (m, 5H), 3.59-3.51 (m, 1H), 3.29-3.25 (m, 1H), 3.01-2.98 (m, 2H), 2.44 (br s, 1H), 1.84-1.80 (m, 5H), 1.72-1.65 (m, 2H), 1.54-1.39 (m, 3H), 1.36-1.14 (m, 2H), 0.85-0.69 (m, 1H). |
| 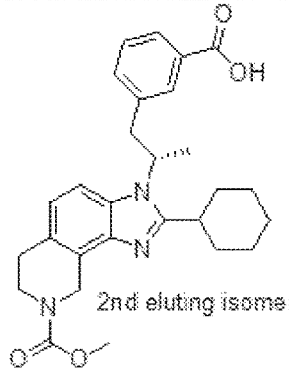 | 3-[(2S)-2-[2-cyclohexyl-8-(methoxycarbonyl)-3H,6H,7H,8H,9H-imidazo[4,5-h]isoquinolin-3-yl]propyl]benzoic acid | 476 | 1H-NMR (CD3OD, 400 MHz) δ (ppm): 7.78 (d, $J$ = 7.8 Hz, 1H), 7.71 (d, $J$ = 7.2 Hz, 1H), 7.65 (s, 1H), 7.18-7.11 (m, 2H), 6.88 (d, $J$ = 6 Hz, 1H), 4.95-4.91 (m, 3H), 3.80-3.78 (m, 5H), 3.59-3.51 (m, 1H), 3.29 -3.24 (m, 1H), 3.01-2.98 (m, 2H), 2.44 (br s, 1H), 1.84-1.79 (m, 5H), 1.72-1.65 (m, 2H), 1.55-1.42 (m, 3H), 1.39-1.14 (m, 2H), 0.81-0.73 (m, 1H). |
| 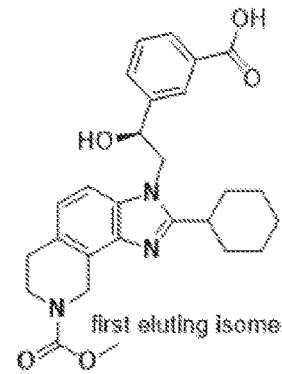 | 3-[(1S)-2-[2-cyclohexyl-8-(methoxycarbonyl)-3H,6H,7H,8H,9H-imidazo[4,5-h]isoquinolin-3-yl]-1-hydroxyethyl]benzoic acid | 478 | 1H-NMR-PH-FMA-PJ00200-100-0A (DMSO-$d6$, 400 MHz) δ (ppm): 12.98 (br s, 1H), 7.97 (s, 1H), 7.86 (d, $J$ = 7.6 Hz, 1H), 7.58-7.38 (m, 3H), 6.97 (d, $J$ = 8.4 Hz, 1H), 5.85 (d, $J$ = 4.0 Hz, 1H), 4.97 (d, $J$ = 4.0 Hz, 1H), 4.80 (s, 2H), 4.33 (d, $J$ = 5.2 Hz, 2H), 3.77-3.75 (m, 5H), 2.87 (s, 2H), 2.67-2.60 (m, 1H), 1.76-1.68 (m, 4H), 1.59-1.49 (m, 3H), 1.24-1.10 (m, 3H). |
| 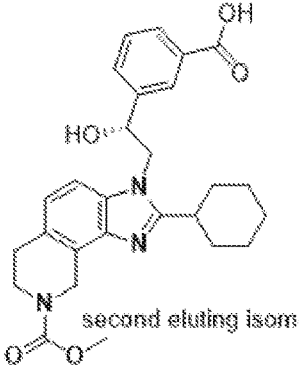 | 3-[(1R)-2-[2-cyclohexyl-8-(methoxycarbonyl)-3H,6H,7H,8H,9H-imidazo[4,5-h]isoquinolin-3-yl]-1-hydroxyethyl]benzoic acid | 478 | 1H-NMR-PH-FMA-PJ00200-100-0B (DMSO-$d6$, 400 MHz) δ (ppm): 12.97 (br s, 1H), 7.97 (s, 1H), 7.86 (d, $J$ = 7.6 Hz, 1H), 7.49-7.38 (m, 3H), 6.97 (d, $J$ = 7.6 Hz, 1H), 5.86 (d, $J$ = 3.6 Hz, 1H), 4.97 (d, $J$ = 7.6 Hz, 1H), 4.80 (s, 2H), 4.33 (d, $J$ = 5.2 Hz, 2H), 3.68 (br s, 5H), 2.87 (s, 2H), 2.68-2.55 (m, 1H), 1.73-1.68 (m, 4H), 1.59-1.49 (m, 3H), 1.26-1.24 (m, 3H). |

FIGURE 1 (continued)

| Structure | Name | MW | 1H-NMR |
|---|---|---|---|
| 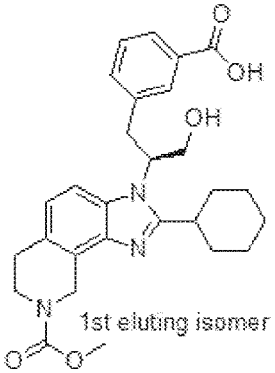 | 3-[(2S)-2-[2-cyclohexyl-8-(methoxycarbonyl)-3H,6H,7H,8H,9H-imidazo[4,5-h]isoquinolin-3-yl]-3-hydroxypropyl]benzoic acid | 492 | 1H-NMR (CD3OD, 400 MHz) δ (ppm): 7.79 (d, *J* = 8 Hz, 1H), 7.70-7.67 (m, 2H), 7.19-7.12 (m, 2H), 6.92 (d, *J* = 7.2 Hz, 1H), 4.96 (s, 2H), 4.82-4.75 (m, 1H), 4.36-4.31 (m, 1H), 4.16-4.12 (m, 1H), 3.78-3.77 (m, 5H), 3.53-3.47 (m, 1H), 3.00-2.97 (m, 2H), 2.50-2.45 (m, 1H), 1.92 (d, *J* = 12 Hz, 1H), 1.80 (d, *J* = 12.4 Hz, 1H), 1.71-1.63 (m, 2H), 1.58-1.12 (m, 5H), 0.75 (d, *J* = 12.8 Hz, 1H). |
| 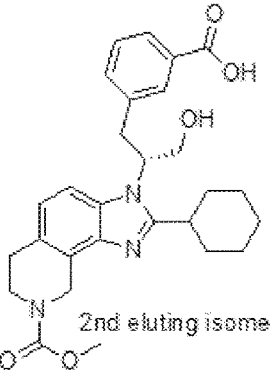 | 3-[(2R)-2-[2-cyclohexyl-8-(methoxycarbonyl)-3H,6H,7H,8H,9H-imidazo[4,5-h]isoquinolin-3-yl]-3-hydroxypropyl]benzoic acid | 492 | 1H-NMR (CD3OD, 400 MHz) δ (ppm): 7.79 (d, *J* = 7.2 Hz, 1H), 7.70-7.66 (m, 2H), 7.20-7.12 (m, 2H), 6.93 (d, *J* = 8 Hz, 1H), 4.96 (s, 2H), 4.82-4.75 (m, 1H), 4.36-4.31 (m, 1H), 4.16-4.12 (m, 1H), 3.78-3.77 (m, 5H), 3.53-3.47 (m, 1H), 3.00-2.98 (m, 2H), 2.51-2.45 (m, 1H), 1.92 (d, *J* = 10.8 Hz, 1H), 1.81 (d, *J* = 12.4 Hz, 1H), 1.72-1.63 (m, 2H), 1.58-1.12 (m, 5H), 0.75 (d, *J* = 12.8 Hz, 1H). |
| 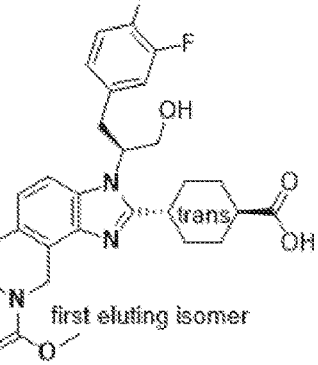 | (trans)-4-{3-[(2S)-1-(3,4-difluorophenyl)-3-hydroxypropan-2-yl]-8-(methoxycarbonyl)-3H,6H,7H,8H,9H-imidazo[4,5-h]isoquinolin-2-yl}cyclohexane-1-carboxylic acid first eluting isomer | 528 | 1H-NMR-PH-FMA-PJ00200-102-0A (CD3OD, 400 MHz) δ (ppm): 8.06 (d, *J* = 8.0 Hz, 1H), 7.46 (d, *J* = 8.4 Hz, 1H), 7.12-7.02 (m, 2H), 6.77 (s, 1H), 5.17 (br s, 1H), 4.95 (s, 2H), 4.44-4.38 (m, 1H), 4.13-4.09 (m, 1H), 3.83-3.80 (m, 5H), 3.58-3.51 (m, 1H), 3.43-3.38 (m, 1H), 3.08-3.06 (m, 3H), 3.43-2.37 (m, 1H), 2.18-2.08 (m, 3H), 1.79-1.61 (m, 3H), 1.54-1.45 (m, 1H), 1.07 (m, 2H). |

FIGURE 1 (continued)

| Structure | Name | MW | NMR |
|---|---|---|---|
| 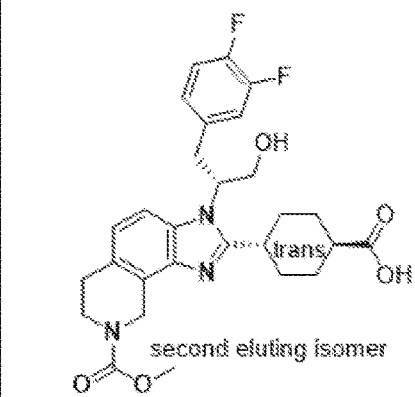 | (trans)-4-{3-[(2R)-1-(3,4-difluorophenyl)-3-hydroxypropan-2-yl]-8-(methoxycarbonyl)-3H,6H,7H,8H,9H-imidazo[4,5-h]isoquinolin-2-yl}cyclohexane-1-carboxylic acid | 528 | CD3OD, 400 MHz) δ (ppm): 7.69 (d, J = 8.0 Hz, 1H), 7.14 (d, J = 8.4 Hz, 1H), 7.05-6.98 (m, 1H), 6.84-6.80 (m, 1H), 6.62 (s, 1H), 4.97 (s, 2H), 4.78 (br s, 1H), 4.36-4.31 (m, 1H), 4.10-4.06 (m, 1H), 3.78 (br s, 5H), 3.48-3.41 (m, 1H), 3.22 (d, J = 2.0 Hz, 1H), 2.99 (s, 2H), 2.62-2.54 (m, 1H), 2.35-2.32 (m, 1H), 2.10- 1.98 (m, 3H), 1.73-1.54 (m, 3H), 1.38-1.31 (m, 1H), 0.98 (d, J = 14.8 Hz, 1H). |
| 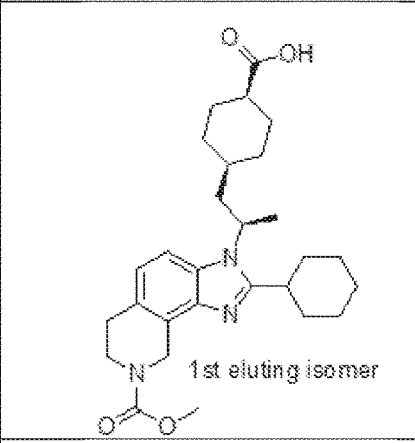 | (1s,4s)-4-[(2R)-2-[2-cyclohexyl-8-(methoxycarbonyl)-3H,6H,7H,8H,9H-imidazo[4,5-h]isoquinolin-3-yl]propyl]cyclohexane-1-carboxylic acid | 482 | 1H-NMR (CD3OD, 400 MHz) δ (ppm) 7.49 (d, J = 8 Hz, 1H), 7.02 (d, J = 8 Hz, 1H), 5.00 (s, 2H), 4.79 (br s, 1H), 3.80-3.76 (m, 5H), 3.15-3.02 (m, 1H), 2.95-2.93 (m, 2H), 2.46 (br s, 1H), 2.18 (br s, 1H), 1.97-1.78 (m, 10H), 1.75-1.62 (m, 4H), 1.58-1.26 (m, 7H), 1.19-1.07 (m, 2H). |
| 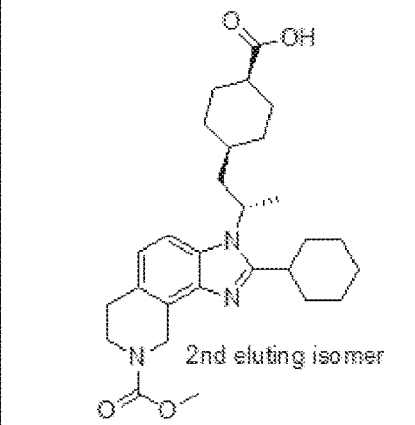 | (1s,4s)-4-[(2S)-2-[2-cyclohexyl-8-(methoxycarbonyl)-3H,6H,7H,8H,9H-imidazo[4,5-h]isoquinolin-3-yl]propyl]cyclohexane-1-carboxylic acid | 482 | 1H-NMR (CD3OD, 400 MHz) δ (ppm) 7.48 (br s, 1H), 7.02 (d, J = 7.6Hz, 1H), 5.00 (s, 2H), 4.87 (br s, 1H), 3.78 (br s, 5H), 3.03-2.85 (m, 3H), 2.16-2.08 (m, 2H), 1.94-1.78 (m, 11H), 1.64-1.62 (m, 3H), 1.52-1.41 (m, 4H), 1.30-1.15 (m, 2H), 1.09-0.90 (m, 3H). |

FIGURE 1 (continued)

| Structure | Name | Mass | NMR |
|---|---|---|---|
| 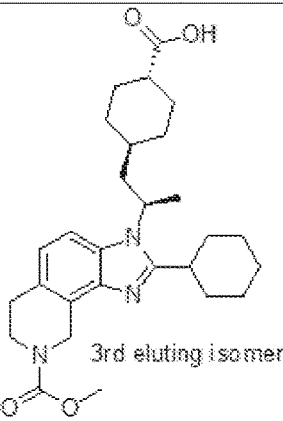 3rd eluting isomer | (1r,4r)-4-[(2R)-2-[2-cyclohexyl-8-(methoxycarbonyl)-3H,6H,7H,8H,9H-imidazo[4,5-h]isoquinolin-3-yl]propyl]cyclohexane-1-carboxylic acid | 482 | 1H-NMR (CD3OD, 400 MHz) δ (ppm) 7.49 (d, J = 6.8Hz, 1H), 7.01 (d, J = 8.4Hz, 1H), 5.00 (s, 2H), 4.79 (br s, 1H), 3.79-3.75 (m, 5H), 3.09-2.95 (m, 1H), 2.94-2.92 (m, 2H), 2.46 (br s, 1H), 2.17 (br s, 1H), 2.08-1.85 (m, 10H), 1.79-1.61 (m, 4H), 1.55-1.29 (m, 7H), 1.18-1.06 (m, 2H) |
| 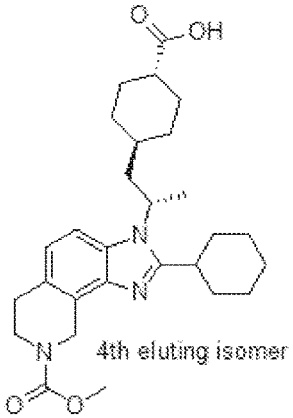 4th eluting isomer | (1r,4r)-4-[(2S)-2-[2-cyclohexyl-8-(methoxycarbonyl)-3H,6H,7H,8H,9H-imidazo[4,5-h]isoquinolin-3-yl]propyl]cyclohexane-1-carboxylic acid | 482 | 1H-NMR (CD3OD, 400 MHz) δ (ppm) 7.48 (br s, 1H), 7.02 (br s, 1H , 5.00 (s, 2H), 4.78 (br s, 1H), 3.86-3.79 (m, 5H), 3.06-2.85 (m, 3H), 2.16 (br s, 2H), 1.95-1.85 (m, 11H), 1.63-1.61 (m, 3H), 1.51-1.44 (m, 4H), 1.34-1.14 (m, 2H), 1.11-0.89 (m, 3H) |
| 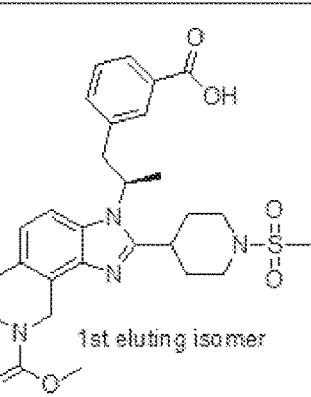 1st eluting isomer | 3-[(2R)-2-[2-(1-methanesulfonylpiperidin-4-yl)-8-(methoxycarbonyl)-3H,6H,7H,8H,9H-imidazo[4,5-h]isoquinolin-3-yl]propyl]benzoic acid | 555 | : 1H-NMR (CD3OD, 400 MHz) δ (ppm): 7.78-7.71 (m, 3H), 7.14-7.09 (m, 2H), 6.75 (d, J = 4.8 Hz, 1H), 4.98-4.94 (m, 3H), 3.86-3.73 (m, 6H), 3.66-3.63 (m, 1H), 3.57-3.51 (m, 1H), 3.30-3.23 (m, 1H), 2.99-2.96 (m, 2H), 2.94-2.87 (m, 4H), 2.63-2.55 (m, 2H), 1.86-1.80 (m, 6H), 0.82-0.80 (m, 1H) |

FIGURE 1 (continued)

| Structure | Name | MS | 1H-NMR |
|---|---|---|---|
| 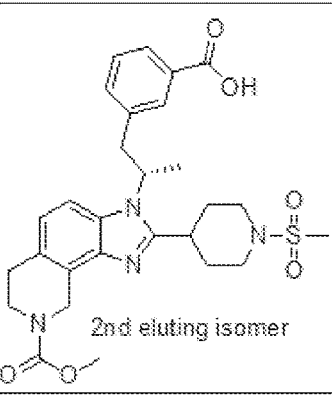 2nd eluting isomer | 3-[(2S)-2-[2-(1-methanesulfonylpiperidin-4-yl)-8-(methoxycarbonyl)-3H,6H,7H,8H,9H-imidazo[4,5-h]isoquinolin-3-yl]propyl]benzoic acid | 555 | 1H-NMR (CD3OD, 400 MHz) δ (ppm): 7.79 (d, J = 8 Hz, 1H), 7.73-7.68 (m, 2H), 7.19-7.13 (m, 2H), 6.89 (d, J = 6.8 Hz, 1H), 4.97-4.94 (m, 3H), 3.85-3.78 (m, 6H), 3.67-3.50 (m, 2H), 3.30-3.26 (m, 1H), 2.99-2.97 (m, 2H), 2.90-2.87 (m, 4H), 2.64-2.52 (m, 2H), 1.86-1.80 (m, 6H), 0.82-0.80 (m, 1H). |
| 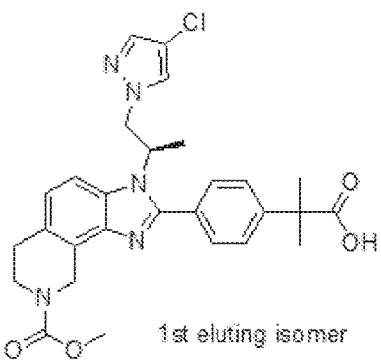 1st eluting isomer | 2-(4-{3-[(2R)-1-(4-chloro-1H-pyrazol-1-yl)propan-2-yl]-8-(methoxycarbonyl)-3H,6H,7H,8H,9H-imidazo[4,5-h]isoquinolin-2-yl}phenyl)-2-methylpropanoic acid | 536, 538 | 1H-NMR (Methanol-d4, 400 MHz) δ (ppm): 7.74 (d, J =8.4Hz, 1H), 7.56 (d, J =8.4 Hz, 2H), 7.26-7.21 (m, 4H), 6.86 (s, 1H), 5.05-4.94 (m, 3H), 4.89-4.84 (m, 1H), 4.46-4.42 (m, 1H), 3.86-3.80 (m, 2H), 3.78 (s, 3H), 3.01 (s, 3H), 1.82 (d, J = 6.8Hz, 3H), 1.63 (s, 6H). |
| 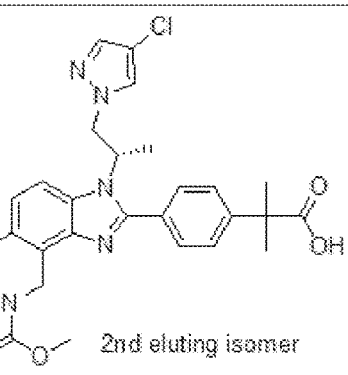 2nd eluting isomer | 2-(4-{3-[(2S)-1-(4-chloro-1H-pyrazol-1-yl)propan-2-yl]-8-(methoxycarbonyl)-3H,6H,7H,8H,9H-imidazo[4,5-h]isoquinolin-2-yl}phenyl)-2-methylpropanoic acid | 536, 538 | 1H-NMR (Methanol-d4, 400 MHz) δ (ppm): 7.74 (d, J = 8.4Hz, 1H), 7.56 (d, J =8.4 Hz, 2H), 7.26-7.21 (m, 4H), 6.86 (s, 1H), 5.05-4.94 (m, 3H), 4.90-4.84 (m, 1H), 4.46-4.42 (m, 1H), 3.86-3.80 (m, 2H), 3.78 (s, 3H), 3.01 (s, 2H), 1.82 (d, J = 6.8 Hz, 3H), 1.63 (s, 6H). |
| 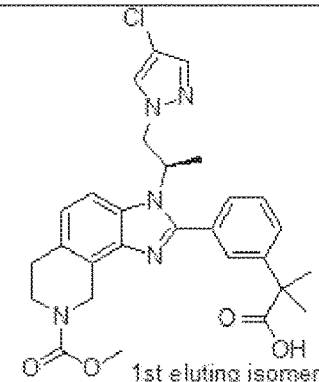 1st eluting isomer | 2-(3-{3-[(2R)-1-(4-chloro-1H-pyrazol-1-yl)propan-2-yl]-8-(methoxycarbonyl)-3H,6H,7H,8H,9H-imidazo[4,5-h]isoquinolin-2-yl}phenyl)-2-methylpropanoic acid | 536, 538 | (DMSO-d6, 400MHz) δ (ppm): 12.48 (br s, 1H), 7.77 (d, J = 8.4 Hz, 1H), 7.55-7.45 (m, 2H), 7.37-7.35 (m, 3H), 7.18 (d, J = 6.4 Hz, 1H), 7.12 (d, J = 8.4 Hz, 1H), 4.86-4.78 (m, 4H), 4.56-4.52 (m, 1H), 3.76-3.67 (m, 5H), 3.00-2.85 (m, 2H), 1.63 (d, J = 6.8 Hz, 3H), 1.54 (d, J = 2.8 Hz, 6H). |

FIGURE 1 (continued)

| Structure | Name | MS | NMR |
|---|---|---|---|
| 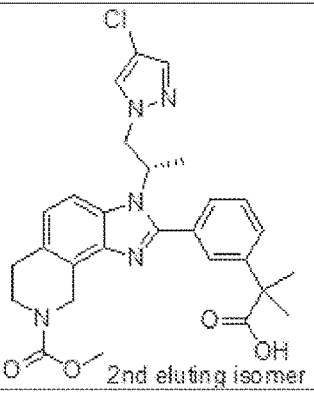 2nd eluting isomer | 2-(3-{3-[(2S)-1-(4-chloro-1H-pyrazol-1-yl)propan-2-yl]-8-(methoxycarbonyl)-3H,6H,7H,8H,9H-imidazo[4,5-h]isoquinolin-2-yl}phenyl)-2-methylpropanoic acid | 536, 538 | (DMSO-$d_6$, 400MHz) δ (ppm): 12.48 (br s, 1H), 7.77 (d, $J$ = 8.4 Hz, 1H), 7.53-7.45 (m, 2H), 7.37-7.35 (m, 3H), 7.18 (d, $J$ = 7.2 Hz, 1H), 7.12 (d, $J$ = 8.4 Hz, 1H), 4.86-4.78 (m, 4H), 4.56-4.52 (m, 1H), 3.76-3.67 (m, 5H), 3.00-2.85 (m, 2H), 1.63 (d, $J$ = 6.8 Hz, 3H), 1.54 (d, $J$ = 2.8 Hz, 6H). |
| 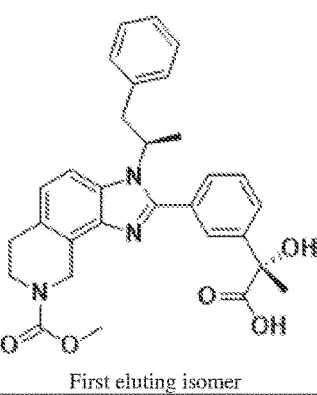 First eluting isomer | (2S)-2-hydroxy-2-(3-{8-(methoxycarbonyl)-3-[(2R)-1-phenylpropan-2-yl]-3H,6H,7H,8H,9H-imidazo[4,5-h]isoquinolin-2-yl}phenyl)propanoic acid | 514 | 1H-NMR (Methanol-$d_4$, 400 MHz) δ (ppm): 7.84 (d, $J$ = 8.4 Hz, 1H), 7.77 (d, $J$ = 8 Hz, 1H), 7.52 (d, 1H), 7.43-7.39 (m, 1H), 7.24 (d, $J$ = 8.4 Hz, 1H), 7.14-7.10 (m, 1H), 7.05-7.01 (m, 2H), 6.88 (d, $J$ = 7.6 Hz, 1H), 6.59 (d, $J$ = 7.2 Hz, 2H), 5.01-4.90 (m, 2H), 4.79-4.72 (m, 1H), 3.89-3.77 (m, 5H), 3.53-3.46 (m, 1H), 3.10-2.98 (m, 3H), 1.84 (d, $J$ = 6.8 Hz, 3H), 1.78 (s, 3H) |
| 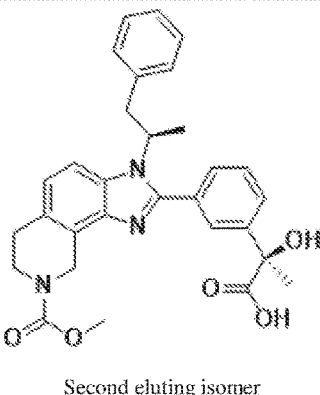 Second eluting isomer | (2R)-2-hydroxy-2-(3-{8-(methoxycarbonyl)-3-[(2R)-1-phenylpropan-2-yl]-3H,6H,7H,8H,9H-imidazo[4,5-h]isoquinolin-2-yl}phenyl)propanoic acid | 514 | 1H-NMR (Methanol-$d_4$, 400 MHz) δ (ppm): 7.83-7.78 (m, 2H), 7.51 (s, 1H), 7.41-7.37 (m, 1H), 7.24 (d, $J$ = 8.4 Hz, 1H), 7.14-7.10 (m, 1H), 7.04-7.01 (m, 2H), 6.86 (d, $J$ = 7.2 Hz, 1H), 6.56 (d, $J$ = 7.2 Hz, 2H), 5.02-4.91 (m, 2H), 4.76-4.72 (m, 1H), 3.89-3.77 (m, 5H), 3.52-3.46 (m, 1H), 3.07-2.96 (m, 3H), 1.85 (d, $J$ = 6.8 Hz, 3H), 1.77 (s, 3H). |

FIGURE 1 (continued)

| Structure | Name | MW | NMR |
|---|---|---|---|
| 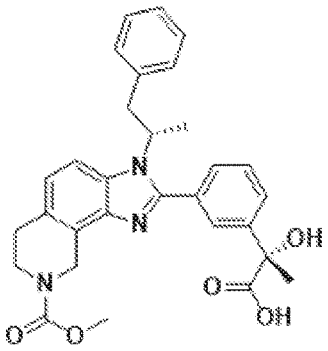 Third eluting isomer | (2S)-2-hydroxy-2-(3-[8-(methoxycarbonyl)-3-[(2S)-1-phenylpropan-2-yl]-3H,6H,7H,8H,9H-imidazo[4,5-h]isoquinolin-2-yl]phenyl)propanoic acid | 514 | 1H-NMR (Methanol-d4, 400 MHz) δ (ppm): 7.83-7.78 (m, 2H), 7.51 (s, 1H), 7.41-7.37 (m, 1H), 7.24 (d, J = 8 Hz, 1H), 7.14-7.10 (m, 1H), 7.05-7.01 (m, 2H), 6.86 (d, J = 7.6 Hz, 1H), 6.56 (d, J = 7.2 Hz, 2H), 5.02-4.91 (m, 2H), 4.76-4.71 (m, 1H), 3.90-3.77 (m, 5H), 3.52-3.46 (m, 1H), 3.07-3.03 (m, 3H), 1.85 (d, J = 6.8 Hz, 3H), 1.77 (s, 3H). |
| 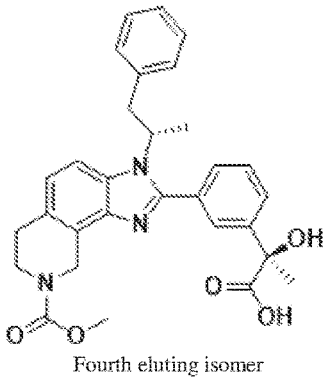 Fourth eluting isomer | (2R)-2-hydroxy-2-(3-[8-(methoxycarbonyl)-3-[(2S)-1-phenylpropan-2-yl]-3H,6H,7H,8H,9H-imidazo[4,5-h]isoquinolin-2-yl]phenyl)propanoic acid | 514 | 1H-NMR (Methanol-d4, 400 MHz) δ (ppm): 7.83 (d, J = 8 Hz, 1H), 7.77 (d, J = 7.6 Hz, 1H), 7.52 (s, 1H), 7.42-7.38 (m, 1H), 7.24 (d, J = 8.4 Hz, 1H), 7.13-7.10 (m, 1H), 7.05-7.01 (m, 2H), 6.89 (d, J = 7.6 Hz, 1H), 6.58 (d, J = 7.6 Hz, 2H), 5.01-4.90 (m, 2H), 4.77-4.72 (m, 1H), 3.86-3.76 (m, 5H), 3.51-3.45 (m, 1H), 3.09-3.01 (m, 3H), 1.83 (d, J = 6.4 Hz, 3H), 1.78 (s, 3H) |
| 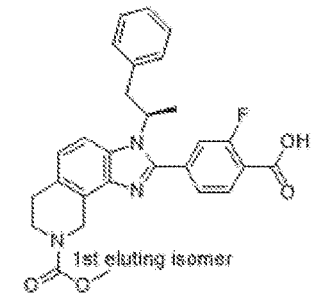 1st eluting isomer | 2-fluoro-4-[8-(methoxycarbonyl)-3-[(2R)-1-phenylpropan-2-yl]-3H,6H,7H,8H,9H-imidazo[4,5-h]isoquinolin-2-yl]benzoic acid | 488 | (CD3OD, 400MHz) δ (ppm): 7.96-7.92 (m, 1H), 7.86 (d, J = 8.0 Hz, 1H), 7.27 (d, J = 8.4 Hz, 1H), 7.19-7.16 (m, 1H), 7.08-7.05 (m, 2H), 6.92 (d, J = 8.0 Hz, 1H), 6.67 (d, J = 10.4 Hz, 1H), 6.55 (d, J = 6.8 Hz, 1H), 5.04-4.97 (m, 2H), 4.66 (br s, 1H), 3.86-3.79 (m, 5H), 3.54-3.48 (m, 1H), 3.08-3.04 (m, 3H), 1.90 (d, J = 6.4 Hz, 3H). |
| 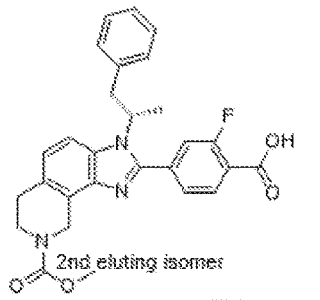 2nd eluting isomer | 2-fluoro-4-[8-(methoxycarbonyl)-3-[(2S)-1-phenylpropan-2-yl]-3H,6H,7H,8H,9H-imidazo[4,5-h]isoquinolin-2-yl]benzoic acid | 488 | (CD3OD, 400MHz) δ (ppm): 8.13-8.03 (m, 2H), 7.46 (br s, 1H), 7.23-7.15 (m, 1H), 7.12-7.08 (m, 2H), 7.00-6.95 (m, 1H), 6.79 (d, J = 10.4 Hz, 1H), 6.63-6.58 (m, 2H), 5.01-4.95 (m, 2H), 4.79 (br s, 1H), 3.89-3.81 (m, 2H), 3.80 (s, 3H), 3.56-3.49 (m, 1H), 3.17-3.01 (m, 3H), 1.96 (d, J = 6.4 Hz, 3H). |

FIGURE 1 (continued)

| Structure | Name | m/z | NMR |
|---|---|---|---|
| 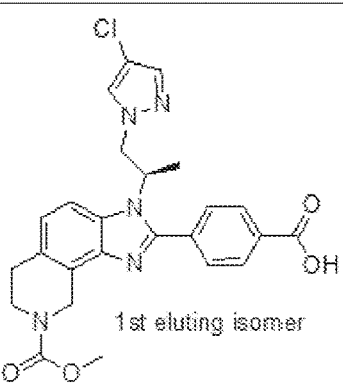 1st eluting isomer | 4-{3-[(2R)-1-(4-chloro-1H-pyrazol-1-yl)propan-2-yl]-8-(methoxycarbonyl)-3H,6H,7H,8H,9H-imidazo[4,5-h]isoquinolin-2-yl}benzoic acid | 494, 496 | 1H-NMR (DMSO-d6, 400 MHz) δ (ppm): 13.27 (br s, 1H), 8.04 (d, J = 8.4 Hz, 2H), 7.79 (d, J = 8.4Hz, 1H), 7.42-7.37 (m, 4H), 7.13 (d, J = 8.8 Hz, 1H), 4.92-4.78 (m, 4H), 4.55-4.50 (m, 1H), 3.78-3.67 (m, 5H), 2.92-2.87 (m, 2H), 1.67 (d, J = 6.8 Hz, 3H) |
| 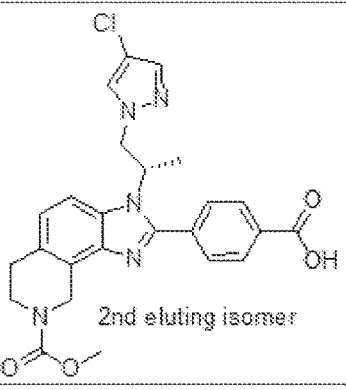 2nd eluting isomer | 4-{3-[(2S)-1-(4-chloro-1H-pyrazol-1-yl)propan-2-yl]-8-(methoxycarbonyl)-3H,6H,7H,8H,9H-imidazo[4,5-h]isoquinolin-2-yl}benzoic acid | 494, 496 | 1H-NMR (DMSO-d6, 400 MHz) δ (ppm): 13.34 (br s, 1H), 8.03 (d, J = 8.4 Hz, 2H), 7.79 (d, J = 8.4Hz, 1H), 7.42-7.37 (m, 4H), 7.13 (d, J = 8.4 Hz, 1H), 4.90-4.75 (m, 4H), 4.55-4.50 (m, 1H), 3.76-3.64 (m, 5H), 2.92-2.87 (m, 2H), 1.67 (d, J = 6.8 Hz, 3H) |
| 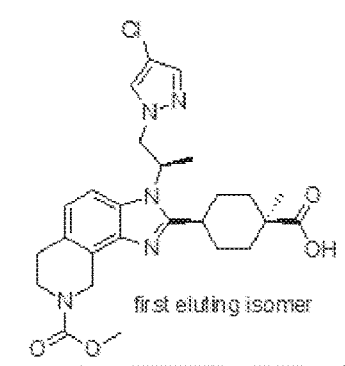 first eluting isomer | (1s,4s)-4-[3-[(2R)-1-(4-chloro-1H-pyrazol-1-yl)propan-2-yl]-8-(methoxycarbonyl)-3H,6H,7H,8H,9H-imidazo[4,5-h]isoquinolin-2-yl]-1-methylcyclohexane-1-carboxylic acid | 514 | 1H-NMR (CD3OD, 400 MHz) δ (ppm): 7.61-7.56 (m, 1H), 7.43 (s, 1H), 7.09 (d, J = 8.4 Hz, 1H), 7.01 (s, 1H), 5.11-5.04 (m, 1H), 4.96 (s, 2H), 4.82-4.80 (m, 1H), 4.59-4.55 (m, 1H), 3.80-3.75 (m, 5H), 2.97-2.95 (m, 2H), 2.51-2.45 (m, 1H), 2.31 (d, J = 12.8 Hz, 2H), 1.96-1.87 (m, 1H), 1.78-1.70 (m, 5H), 1.35-1.31 (m, 2H), 1.27-1.20 (m, 4H). |
| 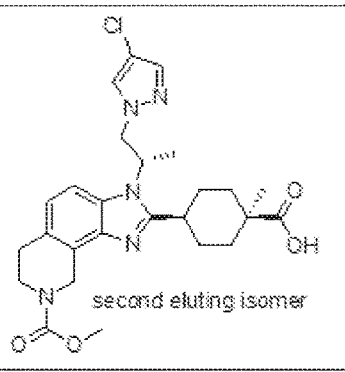 second eluting isomer | (1r,4r)-4-[3-[(2S)-1-(4-chloro-1H-pyrazol-1-yl)propan-2-yl]-8-(methoxycarbonyl)-3H,6H,7H,8H,9H-imidazo[4,5-h]isoquinolin-2-yl]-1-methylcyclohexane-1-carboxylic acid | 514 | 1H-NMR (CD3OD, 400 MHz) δ (ppm): 7.61-7.56 (m, 1H), 7.43 (s, 1H), 7.09 (d, J = 9.2 Hz, 1H), 7.01 (s, 1H), 5.09-5.04 (m, 1H), 4.97 (s, 2H), 4.82-4.80 (m, 1H), 4.59-4.55 (m, 1H), 3.80-3.75 (m, 5H), 2.97-2.95 (m, 2H), 2.47-2.45 (m, 1H), 2.31 (d, J = 12.8 Hz, 2H), 1.96-1.87 (m, 1H), 1.78-1.73 (m, 5H), 1.38-1.31 (m, 2H), 1.23-1.20 (m, 4H). |

FIGURE 1 (continued)

| Structure | Name | MW | NMR |
|---|---|---|---|
| 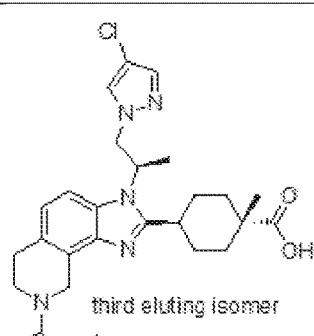 third eluting isomer | (1r,4r)-4-[3-[(2R)-1-(4-chloro-1H-pyrazol-1-yl)propan-2-yl]-8-(methoxycarbonyl)-3H,6H,7H,8H,9H-imidazo[4,5-h]isoquinolin-2-yl]-1-methylcyclohexane-1-carboxylic acid | 514 | 1H-NMR (CD3OD, 400 MHz) δ (ppm): 7.60 (d, $J$ = 8.4 Hz, 1H), 7.42 (s, 1H), 7.11 (d, $J$ = 8 Hz, 1H), 7.03 (s, 1H), 5.12-5.07 (m, 1H), 5.00 (s, 2H), 4.82-4.80 (m, 1H), 4.59-4.55 (m, 1H), 3.82-3.77 (m, 5H), 2.99-2.95 (m, 2H), 2.50 (br s, 1H), 2.05-1.89 (m, 2H), 1.86-1.62 (m, 8H), 1.36-1.24 (m, 4H). |
| 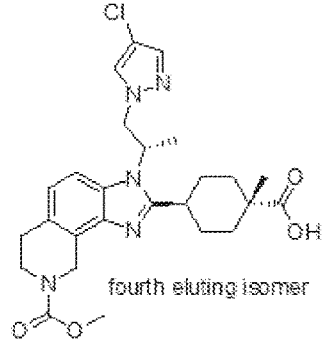 fourth eluting isomer | (1s,4s)-4-[3-[(2S)-1-(4-chloro-1H-pyrazol-1-yl)propan-2-yl]-8-(methoxycarbonyl)-3H,6H,7H,8H,9H-imidazo[4,5-h]isoquinolin-2-yl]-1-methylcyclohexane-1-carboxylic acid | 514 | 1H-NMR (CD3OD, 400 MHz) δ (ppm): 7.60 (d, $J$ = 8.4 Hz, 1H), 7.42 (s, 1H), 7.11 (d, $J$ = 8 Hz, 1H), 7.03 (s, 1H), 5.15-5.09 (m, 1H), 5.00 (s, 2H), 4.82-4.80 (m, 1H), 4.59-4.55 (m, 1H), 3.83-3.75 (m, 5H), 3.01-2.95 (m, 2H), 2.50 (br s, 1H), 2.05-1.86 (m, 2H), 1.82-1.72 (m, 8H), 1.38-1.25 (m, 4H). |
| 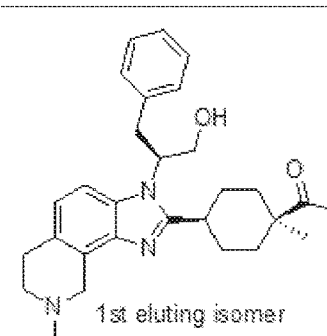 1st eluting isomer | (1s,4s)-4-[3-[(2S)-1-hydroxy-3-phenylpropan-2-yl]-8-(methoxycarbonyl)-3H,6H,7H,8H,9H-imidazo[4,5-h]isoquinolin-2-yl]-1-methylcyclohexane-1-carboxylic acid | 506 | CD3OD, 400 MHz) δ (ppm): 7.65 (d, $J$ = 4.0Hz, 1H), 7.14-7.09 (m, 4H), 6.82 (d, $J$ = 3.6Hz, 2H), 4.96 (s, 2H), 6.81-6.71 (m, 1H), 4.35-4.30 (m, 1H), 4.14-4.10 (m, 1H), 3.80-3.78 (s, 5H), 3.45-3.39 (m, 1H), 3.25-3.21 (m, 1H), 2.99-2.7 (m, 2H), 2.39-2.37 (m, 1H), 2.28-2.25 (m, 1H), 2.13-2.09 (m, 1H), 1.88-1.82 (m, 1H), 1.76-1.72 (m, 1H), 1.64-1.61 (m, 1H), 1.34-1.30 (m, 1H), 1.24 (s, 3H), 1.00-0.97 (m, 1H), 0.71-0.67 (m, 1H). |
| 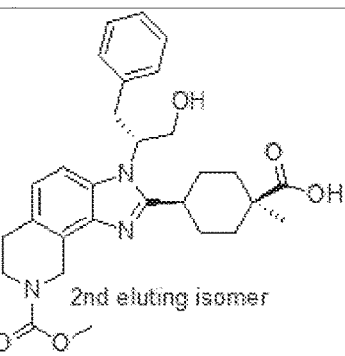 2nd eluting isomer | (1s,4s)-4-[3-[(2R)-1-hydroxy-3-phenylpropan-2-yl]-8-(methoxycarbonyl)-3H,6H,7H,8H,9H-imidazo[4,5-h]isoquinolin-2-yl]-1-methylcyclohexane-1-carboxylic acid | 506 | (CD3OD, 400 MHz) δ (ppm): 7.66 (d, $J$ = 4.0Hz, 1H), 7.14-7.11 (m, 4H), 6.82 (d, $J$ = 3.6Hz, 2H), 4.94 (s, 2H), 4.73-4.69 (m, 1H), 4.36-4.31 (m, 1H), 4.14-4.10 (m, 1H), 3.81-3.79 (m, 5H), 3.46-3.39 (m, 1H), 3.25-3.21 (m, 1H), 3.05-2.99 (m, 2H), 2.41-2.37 (m, 1H), 1.80-1.68 (m, 4H), 1.66-1.51 (m, 3H), 1.34-1.31 (m, 3H), 0.61-0.57 (m, 1H) |

FIGURE 1 (continued)

| Structure | Name | MW | NMR |
|---|---|---|---|
| 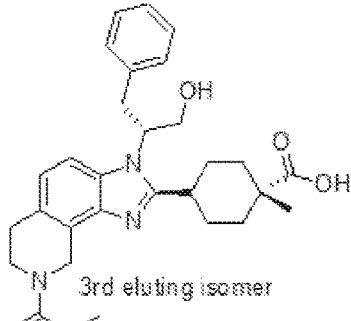 3rd eluting isomer | (1r,4r)-4-[3-[(2R)-1-hydroxy-3-phenylpropan-2-yl]-8-(methoxycarbonyl)-3H,6H,7H,8H,9H-imidazo[4,5-h]isoquinolin-2-yl]-1-methylcyclohexane-1-carboxylic acid | 506 | CD3OD, 400 MHz) δ (ppm): 7.65 (d, $J$ = 4.0Hz, 1H), 7.14-7.10 (m, 4H), 6.82 (d, $J$ = 3.6Hz, 1H), 4.96 (s, 2H), 4.75-4.67 (m, 1H), 4.35-4.30 (m, 1H), 4.14-4.10 (m, 1H), 3.79-3.76 (m, 5H), 3.45-3.39 (m, 1H), 3.25-3.21 (m, 1H), 3.00-2.97 (m, 2H), 2.41-2.38 (m, 1H), 2.29-2.24 (m, 1H), 2.13-2.09 (m, 1H), 1.84-1.81 (m, 1H), 1.73-1.69 (m, 1H), 1.61-1.58 (m, 1H), 1.32-1.30 (m, 1H), 1.24-1.18 (m, 3H), 1.00-0.97 (m, 1H), 0.70-0.68 (m, 1H). |
| 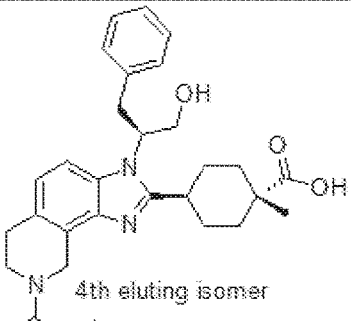 4th eluting isomer | (1r,4r)-4-[3-[(2S)-1-hydroxy-3-phenylpropan-2-yl]-8-(methoxycarbonyl)-3H,6H,7H,8H,9H-imidazo[4,5-h]isoquinolin-2-yl]-1-methylcyclohexane-1-carboxylic acid | 506 | CD3OD, 400 MHz) δ (ppm): 7.73 (d, $J$ = 4.0Hz, 1H), 7.18-7.13 (m, 4H), 6.84 (d, $J$ = 2.8Hz, 1H), 4.98 (s, 2H), 4.87-4.77 (m, 1H), 4.38-4.33 (m, 1H), 4.14-4.10 (m, 1H), 3.82-3.79 (m, 5H), 3.50-3.41 (m, 1H), 3.27-3.22 (m, 1H), 3.02-3.00 (m, 2H), 2.48-2.42 (m, 1H), 1.83-1.80 (m, 4H), 1.70-1.53 (m, 3H), 1.34-1.31 (m, 3H), 0.60-0.58 (m, 1H). |
| 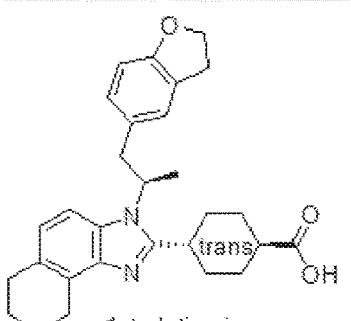 1st eluting isomer | (trans)-4-{3-[(2R)-1-(2,3-dihydro-1-benzofuran-5-yl)propan-2-yl]-8-(methoxycarbonyl)-3H,6H,7H,8H,9H-imidazo[4,5-h]isoquinolin-2-yl}cyclohexane-1-carboxylic acid | 518 | 1H-NMR (DMSO-$d6$, 400 MHz) δ (ppm): 12.06 (s, 1H), 7.64 (s, 1H), 7.05-6.97 (m, 1H), 6.85 (s, 1H), 6.53-6.51 (m, 2H), 4.77-4.66 (m, 3H), 4.44-4.41 (m, 2H), 3.71-3.60 (m, 5H), 3.27-3.01 (m, 4H), 2.87 (s, 2H), 2.25 (s, 1H), 1.95-1.78 (m, 3H), 1.62 (d, $J$ = 5.6 Hz, 3H), 1.56-1.49 (m, 3H), 1.30-1.24 (m, 1H), 1.13-1.04 (m, 1H). |
| 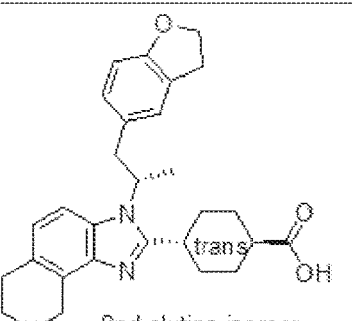 2nd eluting isomer | (trans)-4-{3-[(2S)-1-(2,3-dihydro-1-benzofuran-5-yl)propan-2-yl]-8-(methoxycarbonyl)-3H,6H,7H,8H,9H-imidazo[4,5-h]isoquinolin-2-yl}cyclohexane-1-carboxylic acid | 518 | 1H-NMR (DMSO-$d6$, 400 MHz) δ (ppm): 12.11 (s, 1H), 7.64 (s, 1H), 6.99 (br s, 1H), 6.91 (s, 1H), 6.53-6.51 (m, 2H), 4.78-4.66 (m, 3H), 4.45-4.41 (m, 2H), 3.73-3.62 (m, 5H), 3.21-3.11 (m, 2H), 3.09-3.01 (m, 2H), 2.88 (s, 2H), 2.28 (s, 1H), 1.97-1.78 (m, 3H), 1.62 (d, $J$ = 5.6 Hz, 3H), 1.56-1.49 (m, 3H), 1.30-1.24 (m, 1H), 1.13-1.04 (m, 1H) |

FIGURE 1 (continued)

| Structure | Name | MS | NMR |
|---|---|---|---|
| 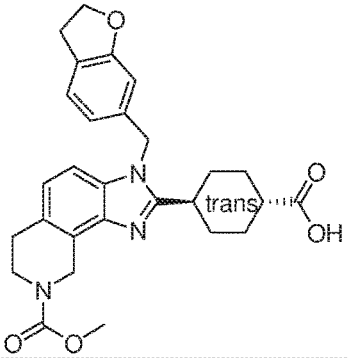 | (trans)-4-{3-[(2,3-dihydro-1-benzofuran-6-yl)methyl]-8-(methoxycarbonyl)-3H,6H,7H,8H,9H-imidazo[4,5-h]isoquinolin-2-yl}cyclohexane-1-carboxylic acid | 490 | 1H-NMR (DMSO-*d6*, 400 MHz) δ (ppm): 12.09 (s, 1H), 7.23 (d, *J* = 8.4 Hz, 1H), 7.13 (d, *J* = 7.6 Hz, 1H), 6.94 (d, *J* = 8.4 Hz, 1H), 6.49 (d, *J* = 7.6 Hz, 1H), 6.45 (s, 1H), 5.42 (s, 2H), 4.85-4.83 (m, 2H), 4.50-4.45 (m, 2H), 3.69-3.65 (m, 5H), 3.13-3.08 (m, 2H), 2.98-2.92 (m, 1H), 2.90-2.82 (m, 2H), 2.33-2.27 (m, 1H), 1.97-1.94 (m, 2H), 1.80-1.74 (m, 2H), 1.74-1.65 (m, 2H), 1.49-1.46 (m, 2H) |
| 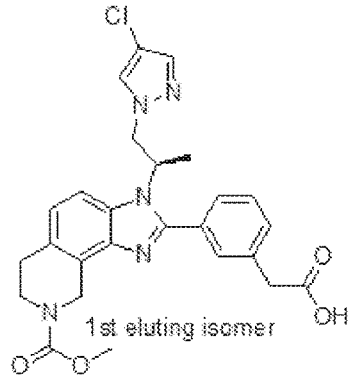 | 2-(3-{3-[1-(4-chloro-1H-pyrazol-1-yl)propan-2-yl]-8-(methoxycarbonyl)-3H,6H,7H,8H,9H-imidazo[4,5-h]isoquinolin-2-yl}phenyl)acetic acid | 508, 510 | (DMSO-*d6*, 400MHz) δ (ppm): 12.16 (br s, 1H), 7.76 (d, *J* = 8.4 Hz, 1H), 7.46-7.38 (m, 4H), 7.18-7.10 (m, 3H), 4.85-4.77 (m, 4H), 4.57-4.52 (m, 1H), 3.76-3.67 (m, 7H), 2.95-2.85 (m, 2H), 1.61 (d, *J* = 6.8 Hz, 3H). |
| 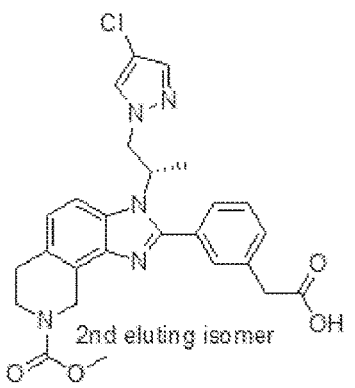 | 2-(3-{3-[1-(4-chloro-1H-pyrazol-1-yl)propan-2-yl]-8-(methoxycarbonyl)-3H,6H,7H,8H,9H-imidazo[4,5-h]isoquinolin-2-yl}phenyl)acetic acid | 508, 510 | (DMSO-*d6*, 400MHz) δ (ppm): 12.45 (br s, 1H), 7.76 (br s, 1H), 7.50-7.38 (m, 4H), 7.24-7.06 (m, 3H), 4.85-4.72 (m, 4H), 4.58-4.53 (m, 1H), 3.83-3.41 (m, 7H), 2.92 (br s, 2H), 1.61 (br s, 3H). |
| 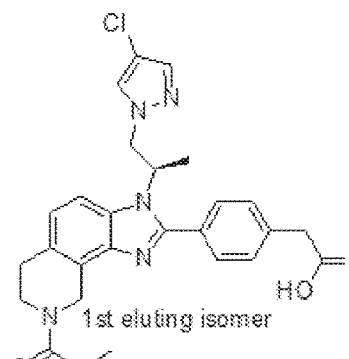 | 2-(4-{3-[(2R)-1-(4-chloro-1H-pyrazol-1-yl)propan-2-yl]-8-(methoxycarbonyl)-3H,6H,7H,8H,9H-imidazo[4,5-h]isoquinolin-2-yl}phenyl)acetic acid | 508, 510 | 1H-NMR (Methanol-*d4*, 400 MHz) δ (ppm): 7.73 (d, *J* = 8.8 Hz, 1H), 7.47 (d, *J* = 8 Hz, 2H), 7.26-7.21 (m, 4H), 6.88 (s, 1H), 5.05-4.95 (m, 4H), 4.47-4.42 (m, 1H), 3.88-3.77 (m, 5H), 3.72 (s, 2H), 3.05-1.95 (m, 2H), 1.81 (d, *J* = 6.8 Hz, 3H) |

FIGURE 1 (continued)

| Structure | Name | MS | 1H-NMR |
|---|---|---|---|
| 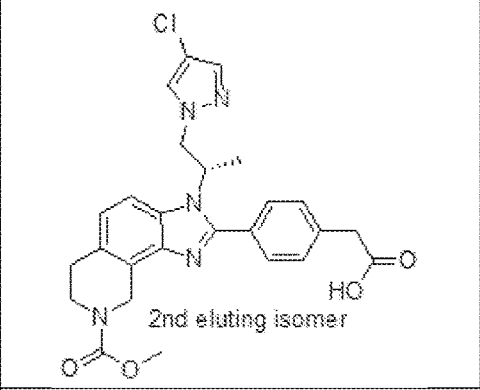 2nd eluting isomer | 2-(4-[3-[(2S)-1-(4-chloro-1H-pyrazol-1-yl)propan-2-yl]-8-(methoxycarbonyl)-3H,6H,7H,8H,9H-imidazo[4,5-h]isoquinolin-2-yl]phenyl)acetic acid | 508, 510 | 1H-NMR (Methanol-$d4$, 400 MHz) δ (ppm): 7.73 (d, $J$ = 8.4 Hz, 1H), 7.47 (d, $J$ = 7.6 Hz, 2H), 7.26-7.20 (m, 4H), 6.88 (s, 1H), 5.05-4.95 (m, 4H), 4.47-4.42 (m, 1H), 3.87-3.77 (m, 5H), 3.72 (s, 2H), 3.05-1.95 (m, 2H), 1.81 (d, $J$ = 7.2 Hz, 3H) |
| 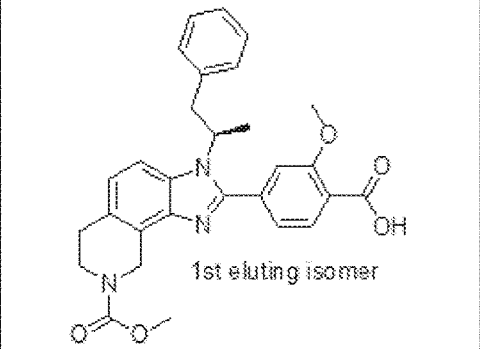 1st eluting isomer | 2-methoxy-4-[8-(methoxycarbonyl)-3-[(2R)-1-phenylpropan-2-yl]-3H,6H,7H,8H,9H-imidazo[4,5-h]isoquinolin-2-yl]benzoic acid | 500 | 1H-NMR (MeOD-$d4$, 400 MHz) δ (ppm): 7.83-7.79 (m, 2H), 7.25 (d, $J$ = 8.4 Hz, 1H), 7.15-7.12 (m, 1H), 7.05-7.02 (m, 2H), 6.70-6.68 (m, 2H), 6.53 (d, $J$ = 7.6 Hz, 2H), 5.04-4.92 (m, 2H), 4.77-4.70 (m, 1H), 3.96-3.89 (m, 4H), 3.88-3.78 (m, 4H), 3.59-3.47 (m, 1H), 3.05-3.02 (m, 3H), 1.90 (d, $J$ = 7.2 Hz, 3H) |
| 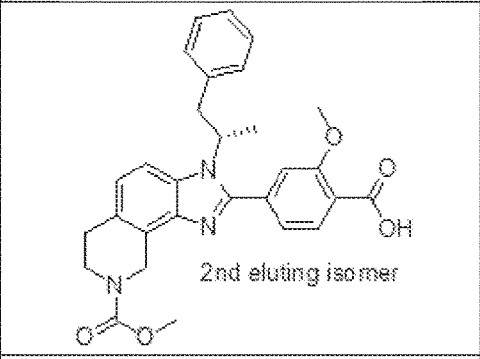 2nd eluting isomer | 2-methoxy-4-[8-(methoxycarbonyl)-3-[(2S)-1-phenylpropan-2-yl]-3H,6H,7H,8H,9H-imidazo[4,5-h]isoquinolin-2-yl]benzoic acid | 500 | 1H-NMR (MeOD-$d4$, 400 MHz) δ (ppm): 7.84 (d, $J$ = 8.4 Hz, 1H), 7.77 (d, $J$ = 7.6 Hz, 1H), 7.25 (d, $J$ = 8.4 Hz, 1H), 7.16-7.12 (m, 1H), 7.06-7.02 (m, 2H), 6.70-6.67 (m, 2H), 6.53 (d, $J$ = 7.6 Hz, 2H), 5.04-4.92 (m, 2H), 4.81-4.74 (m, 1H), 3.96-3.89 (m, 4H), 3.89-3.78 (m, 4H), 3.59-3.47 (m, 1H), 3.05-3.03 (m, 3H), 1.90 (d, $J$ = 6.8 Hz, 3H) |
| 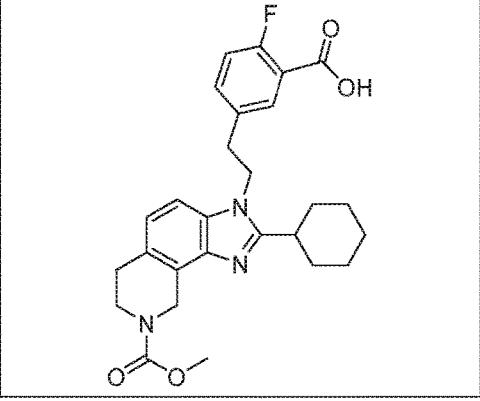 | 5-[2-[2-cyclohexyl-8-(methoxycarbonyl)-3H,6H,7H,8H,9H-imidazo[4,5-h]isoquinolin-3-yl]ethyl]-2-fluorobenzoic acid | 480 | 1H-NMR-PH-FMA-PJ00200-120-0 (MeOD-$d4$, 400MHz) δ (ppm): 7.54 (d, $J$ = 6.0 Hz, 1H), 7.36 (d, $J$ = 8.4 Hz, 1H), 7.11 (d, $J$ = 8.4 Hz, 1H), 7.02-6.98 (m, 2H), 4.98 (s, 2H), 4.55-4.52 (m, 2H), 3.78-3.75 (m, 5H), 3.18-3.15 (m, 2H), 2.98-2.95 (m, 2H), 2.52-2.46 (m, 1H), 1.81-1.80 (m, 2H), 1.74-1.68 (m, 1H), 1.65-1.60 (m, 2H), 1.53-1.50 (m, 2H), 1.31 (br s, 3H). |

FIGURE 1 (continued)

| Structure | Name | MW | 1H-NMR |
|---|---|---|---|
| 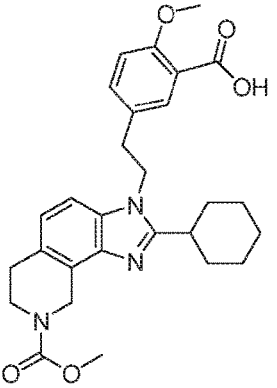 | 5-[2-[2-cyclohexyl-8-(methoxycarbonyl)-3H,6H,7H,8H,9H-imidazo[4,5-h]isoquinolin-3-yl]ethyl]-2-methoxybenzoic acid | 492 | 1H-NMR (DMSO-$d_6$, 400 MHz) δ (ppm): 12.54 (br s, 1H), 7.46 (s, 1H), 7.40 (d, $J$ = 8.8 Hz, 1H), 7.09 (d, $J$ = 8.4 Hz, 1H), 6.99 (d, $J$ = 8.8 Hz, 1H), 4.79 (s, 2H), 4.40-4.37 (m, 2H), 3.76 (s, 4H), 3.69-3.65 (m, 5H), 2.98-2.95 (m, 2H), 2.90-2.85 (m, 2H), 2.41-2.40 (m, 1H), 1.69-1.64 (m, 3H), 1.59-1.51 (m, 4H), 1.23 (br s, 3H) |
| 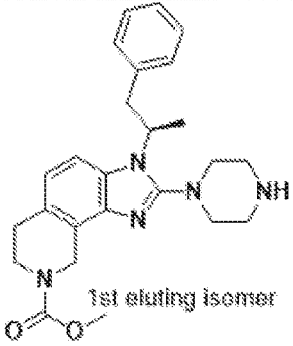 | methyl 3-[(2R)-1-phenylpropan-2-yl]-2-(piperazin-1-yl)-3H,6H,7H,8H,9H-imidazo[4,5-h]isoquinoline-8-carboxylate | 434 | 1H-NMR-PH-FMA-PJ00200-127-0A (CD3OD, 400 MHz) δ (ppm): 7.60 (d, $J$ = 8.4 Hz, 1H), 7.08 (d, $J$ = 6.0 Hz, 4H), 6.77 (d, $J$ = 3.6 Hz, 2H), 4.94-4.87 (m, 2H), 4.84-4.83 (m, 1H), 3.83-3.72 (m, 5H), 3.42-3.36 (m, 1H), 3.15-3.05 (m, 1H), 2.96-2.84 (m, 8H), 2.56-2.52 (m, 2H), 1.78 (d, $J$ = 6.4 Hz, 3H). |
| 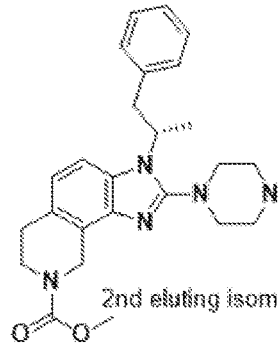 | methyl 3-[(2S)-1-phenylpropan-2-yl]-2-(piperazin-1-yl)-3H,6H,7H,8H,9H-imidazo[4,5-h]isoquinoline-8-carboxylate | 434 | 1H-NMR-PH-FMA-PJ00200-127-0B (CD3OD, 400 MHz) δ (ppm): 7.60 (d, $J$ = 8.0 Hz, 1H), 7.09 (d, $J$ = 6.4 Hz, 4H), 6.77 (d, $J$ = 3.6 Hz, 2H), 4.93-4.87 (m, 2H), 4.84-4.83 (m, 1H), 3.83-3.72 (m, 5H), 3.43-3.37 (m, 1H), 3.13-3.08 (m, 1H), 2.99-2.88 (m, 8H), 2.57-2.55 (m, 2H), 1.78 (d, $J$ = 5.6 Hz, 3H). |
| 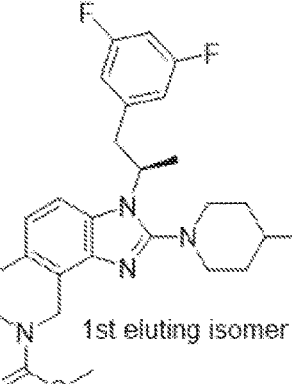 | 1-{3-[(2R)-1-(3,5-difluorophenyl)propan-2-yl]-8-(methoxycarbonyl)-3H,6H,7H,8H,9H-imidazo[4,5-h]isoquinolin-2-yl}piperidine-4-carboxylic acid | 513 | 1H-NMR (DMSO, 400 MHz) δ (ppm): 12.24 (br s, 1H), 7.54 (d, $J$ = 8.4 Hz, 1H), 6.97-6.93 (m, 2H), 6.55 (d, $J$ = 6.8 Hz, 1H), 4.76-4.69 (m, 3H), 3.70-3.57 (m, 5H), 3.32-3.26 (m, 2H), 3.17-3.10 (m, 2H), 2.87-2.82 (m, 3H), 2.68-2.66 (m, 2H), 2.40-2.34 (m, 1H), 1.90-1.75 (m, 3H), 1.67 (d, $J$ = 6.8 Hz, 3H), 1.64-1.50 (m, 1H). |

FIGURE 1 (continued)

| Structure | Name | MW | 1H-NMR |
|---|---|---|---|
| 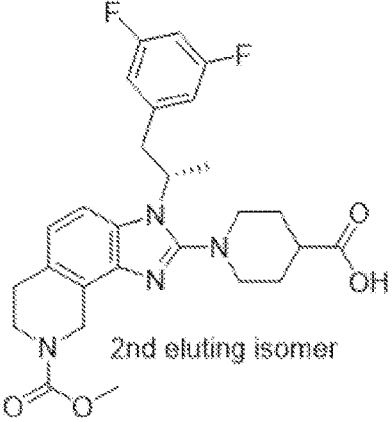 | 1-{3-[(2S)-1-(3,5-difluorophenyl)propan-2-yl]-8-(methoxycarbonyl)-3H,6H,7H,8H,9H-imidazo[4,5-h]isoquinolin-2-yl}piperidine-4-carboxylic acid | 513 | 1H-NMR (DMSO, 400 MHz) δ (ppm): 7.54 (d, $J$ = 8.4 Hz, 1H), 6.97-6.93 (m, 2H), 6.55 (d, $J$ = 7.2 Hz, 1H), 4.73-4.69 (m, 3H), 3.66-3.55 (m, 5H), 3.32-3.26 (m, 2H), 3.17-3.13 (m, 2H), 2.84-2.79 (m, 3H), 2.68-2.66 (m, 2H), 2.40-2.34 (m, 1H), 1.87-1.81 (m, 3H), 1.65 (d, $J$ = 6.8 Hz, 3H), 1.60-1.50 (m, 1H). |
| 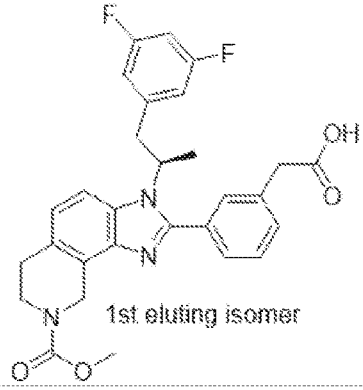 | 2-(3-{3-[(2R)-1-(3,5-difluorophenyl)propan-2-yl]-8-(methoxycarbonyl)-3H,6H,7H,8H,9H-imidazo[4,5-h]isoquinolin-2-yl}phenyl)acetic acid | 520 | 1H-NMR (DMSO, 400 MHz) δ (ppm): 12.46 (br s, 1H), 7.81 (d, $J$ = 8.4 Hz, 1H), 7.45-7.42 (m, 2H), 7.13-7.11 (m, 2H), 7.05 (s, 1H), 7.01-6.96 (m, 1H), 6.36 (d, $J$ = 6.4Hz, 2H), 4.84 (br s, 2H), 4.70-4.63 (m, 1H), 3.78-3.72 (m, 1H), 3.68-3.63 (m, 6H), 3.59-3.38 (m, 1H), 3.18-3.13 (m, 1H), 2.99-2.88 (m, 2H), 1.68 (d, $J$ = 6.8 Hz, 3H). |
| 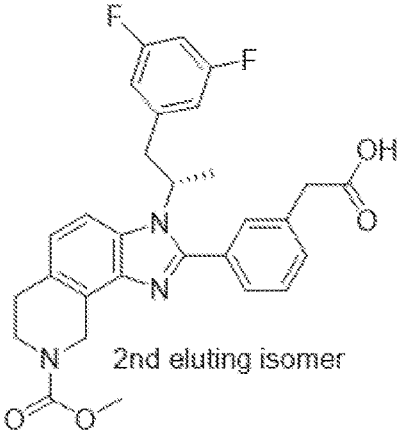 | 2-(3-{3-[(2S)-1-(3,5-difluorophenyl)propan-2-yl]-8-(methoxycarbonyl)-3H,6H,7H,8H,9H-imidazo[4,5-h]isoquinolin-2-yl}phenyl)acetic acid | 520 | 1H-NMR (DMSO, 400 MHz) δ (ppm): 12.48 (br s, 1H), 7.81 (d, $J$ = 8.0 Hz, 1H), 7.45-7.42 (m, 2H), 7.13-7.11 (m, 1H), 7.04 (s, 1H), 7.01-6.96 (m, 1H), 6.36 (d, $J$ = 7.2 Hz, 2H), 4.84 (br s, 2H), 4.70-4.64 (m, 1H) 3.76-3.69 (m, 1H), 3.67-3.63 (m, 6H), 3.48-3.38 (m, 1H), 3.18-3.13 (m, 1H), 2.97-2.88 (m, 2H), 1.68 (d, $J$ = 6.8 Hz, 3H). |

FIGURE 1 (continued)

INHIBITING CYCLIC AMP-RESPONSIVE ELEMENT-BINDING PROTEIN (CREB)

CROSS-REFERENCE TO RELATED APPLICATIONS

This application is a National Stage application of International Application No. PCT/US2020/022818, filed Mar. 13, 2020, which claims the benefit of U.S. Provisional Patent Application No. 62/819,108, filed Mar. 15, 2019, each of which is hereby incorporated herein by reference in its their entirety.

FIELD OF DISCLOSURE

The present disclosure relates to compounds and methods for the inhibition of p300 (also known as EP300 and KAT3B) binding protein of adenovirus E1A protein, and/or cyclic AMP-responsive element-binding protein (CREB) (CBP, also known as KAT3A), a cellular paralog of p300. The compounds are useful for the treatment of certain forms of cancer.

BACKGROUND OF DISCLOSURE

CBP/p300 are lysine acetyltransferases that catalyze the attachment of an acetyl group to a lysine side chain of histones and other protein substrates. p300 (also known as EP300 and KAT3B) is a protein with multiple domains that bind to diverse proteins including many DNA-binding transcription factors. The cyclic AMP-responsive element-binding protein (CREB) binding protein (CBP, also known as KAT3A) is a cellular paralog of p300. p300 and CBP share extensive sequence identity and functional similarity and are often referred to as CBP/p300. CBP/p300-catalyzed acetylation of histones and other proteins is pivotal to gene activation. Heightened p300 expression and activities have been observed in advanced human cancers such as prostate and in human primary breast cancer specimens. Chemical inhibition of CBP/p300 that possesses intrinsic acetyltransferase enzymatic activity is more feasible than blocking transcription factors with small molecules, as discovery of chemical inhibitors of transcription factors has proven extremely challenging.

Accordingly, there is a need for novel and potent compounds for inhibiting CBP/p300, useful as therapies for treating certain related forms of cancer.

SUMMARY OF DISCLOSURE

Applicants have discovered novel compounds and methods useful for inhibiting CBP/p300. The compounds and methods are useful for the treatment of certain related forms of cancer, such as certain forms of breast and prostate cancers.

Preferably, the compound is a CBP Inhibitor Compound of Formula (I):

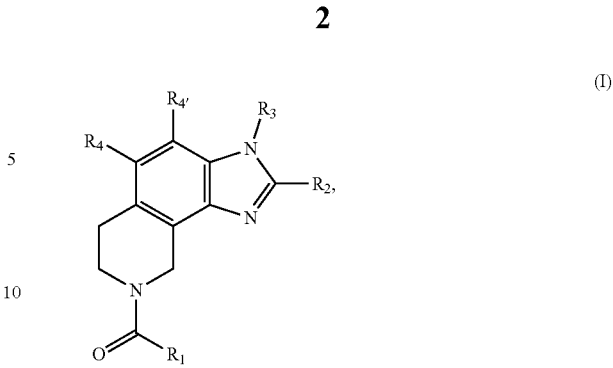

or a pharmaceutically acceptable salt thereof, wherein, $R_1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, aryl, —$OR_5$, —$N(R_5)_2$, or —$NHR_5$;

$R_2$ is —H, —$C_1$-$C_6$ alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, or aryl, wherein each alkyl, alkenyl, alkynyl, cycloalkyl, cycloalkenyl, heterocyclyl, heteroaryl, or aryl is optionally substituted with one or more $R_6$;

$R_3$ is —H, —$C_1$-$C_6$ alkyl, —$C_2$-$C_6$alkenyl, —$C_2$-$C_6$alkynyl, —$C_3$-$C_8$cycloalkyl, —$C_4$-$C_8$cycloalkenyl, spirocycloalkyl, spiroheterocyclyl, heterocyclyl, heteroaryl, or aryl, wherein each alkyl, alkenyl, alkynyl, cycloalkyl, cycloalkenyl, spirocycloalkyl, spiroheterocyclyl, heterocyclyl, heteroaryl, or aryl is optionally substituted with one or more $R_7$;

$R_4$ and $R_{4'}$ are each independently —H, halogen, —OH, —CN, —COOH, heterocycloalkyl, or —$NH_2$;

each $R_5$ is independently —$C_1$-$C_6$alkyl, —$C_3$-$C_8$cycloalkyl, heterocyclyl, aryl, or heteroaryl;

$R_6$ and $R_7$ are each independently, at each occurrence, —$C_1$-$C_6$alkyl, —$C_3$-$C_8$cycloalkyl, —$C_4$-$C_8$cycloalkenyl, heterocyclyl, aryl, spirocycloalkyl, spiroheterocyclyl, heteroaryl, —OH, halogen, oxo, —CN, —$SR_8$, —$OR_8$, —$(CH2)_n$—$OR_8$, —$NHR_8$, —$NR_8R_9$, —$S(O)_2NR_8R_9$, —$S(O)_2R_{8'}$, —$C(O)R_{8'}$, —$C(O)OR_8$, —$C(O)NR_8R_9$, —$C(O)NR_8S(O)_2R_{9'}$, —$NR_8C(O)R_{9'}$, —$NR_8S(O)_2R_{9'}$, —$S(O)R_{8'}$, —$S(O)NR_8R_9$, or —$NR_8S(O)R_{9'}$, wherein each alkyl, cycloalkyl, heterocyclyl, spirocycloalkyl, spiroheterocyclyl, heteroaryl, or aryl is optionally substituted with one or more $R_{10}$;

wherein any two $R_6$ or any two $R_7$, when on non-adjacent atoms, can combine to form a cycloalkyl or heterocyclyl;

wherein any two $R_6$ or any two $R_7$, when on adjacent atoms, can combine to form a cycloalkyl, heterocyclyl, aryl or heteroaryl;

$R_8$ and $R_9$ are each independently, at each occurrence, —H, —$C_1$-$C_6$alkyl, —$C(O)C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, aryl, heteroaryl, wherein each alkyl, alkenyl, alkynyl, cycloalkyl, cycloalkenyl, heterocyclyl, aryl, or heteroaryl is optionally substituted with one or more $R_{10}$ or $R_{11}$; or $R_8$ and $R_9$ may combine with the atom to which they are both attached to form a —$C_3$-$C_8$cycloalkyl, —$C_4$-$C_8$cycloalkenyl, spirocycloalkyl, spiroheterocyclyl, heterocyclyl, heteroaryl, or aryl, wherein the formed —$C_3$-$C_8$cycloalkyl, —$C_4$-$C_8$cycloalkenyl, spirocycloalkyl, spiroheterocyclyl, heterocyclyl, heteroaryl, or aryl is optionally substituted with one or more $R_{10}$ or $R_{11}$;

$R_{8'}$ and $R_{9'}$ are each independently, at each occurrence, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, aryl, heteroaryl, wherein each alkyl, alkenyl, alkynyl, cycloalkyl, cycloalkenyl, heterocyclyl, aryl, or heteroaryl is optionally substituted with one or more $R_{10}$ or $R_{11}$; or $R_8$ and $R_9$, may combine with the atom to which they are both attached to form a —$C_3$-$C_8$cycloalkyl, —$C_4$-$C_8$cycloalkenyl, spirocycloalkyl, spiroheterocyclyl, heterocyclyl, heteroaryl, or aryl, wherein the formed —$C_3$-$C_8$cycloalkyl, —$C_4$-$C_8$cycloalkenyl, spirocycloalkyl, spiroheterocyclyl, heterocyclyl, heteroaryl, or aryl is optionally substituted with one or more $R_{10}$ or $R_{11}$;

$R_{10}$ and $R_{11}$ are each independently, at each occurrence, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, aryl, —OH, halogen, oxo, —$NO_2$, —CN, —$NH_2$, —$OC_1$-$C_6$alkyl, —$OC_3$-$C_6$cycloalkyl, —Oaryl, —Oheteroaryl, —$NHC_1$-$C_6$alkyl, —$N(C_1$-$C_6$alkyl$)_2$, —$S(O)_2NH(C_1$-$C_6$alkyl), —$S(O)_2N(C_1$-$C_6$alkyl$)_2$, —$S(O)_2C_1$-$C_6$alkyl, —$C(O)C_1$-$C_6$alkyl, —$C(O)NH_2$, —$C(O)NH(C_1$-$C_6$alkyl), —$C(O)N(C_1$-$C_6$alkyl$)_2$, —$C(O)OH$, —$C(O)OC_1$-$C_6$alkyl, —$N(C_1$-$C_6$alkyl)$SO_2C_1$-$C_6$alkyl, —$S(O)(C_1$-$C_6$alkyl), —$S(O)N(C_1$-$C_6$alkyl$)_2$, or —$N(C_1$-$C_6$alkyl)$S(O)(C_1$-$C_6$alkyl), wherein each alkyl, alkenyl, alkynyl, cycloalkyl, cycloalkenyl, heterocyclyl, heteroaryl, or aryl is optionally substituted with one or more —$R_{12}$;

wherein any two $R_{10}$ or any two $R_{11}$, when on non-adjacent atoms, can combine to form a cycloalkyl or heterocyclyl;

wherein any two $R_{10}$ or any two $R_{11}$, when on adjacent atoms, can combine to form a cycloalkyl, heterocyclyl, aryl or heteroaryl; and $R_{12}$ is independently, at each occurrence, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, aryl, —OH, halogen, oxo, —$NO_2$, —CN, —$NH_2$, —$OC_1$-$C_6$alkyl, —$NHC_1$-$C_6$alkyl, —$N(C_1$-$C_6$alkyl$)_2$, —$S(O)_2NH(C_1$-$C_6$alkyl), —$S(O)_2N(C_1$-$C_6$alkyl$)_2$, —$S(O)_2C_1$-$C_6$alkyl, —$C(O)C_1$-$C_6$alkyl, —$C(O)NH_2$, —$C(O)NH(C_1$-$C_6$alkyl), —$C(O)N(C_1$-$C_6$alkyl$)_2$, —$C(O)OC_1$-$C_6$alkyl, —$N(C_1$-$C_6$alkyl)$SO_2C_1$-$C_6$alkyl, —$S(O)(C_1$-$C_6$alkyl), —$S(O)N(C_1$-$C_6$alkyl$)_2$, or —$N(C_1$-$C_6$alkyl)$S(O)(C_1$-$C_6$alkyl).

Another aspect of the present disclosure relates to a pharmaceutical composition comprising a compound of Formula (I), or a pharmaceutically acceptable salt thereof, and a pharmaceutically acceptable carrier. The pharmaceutically acceptable carrier can further include an excipient, diluent, or surfactant. The pharmaceutical composition can be effective for treating a disease or disorder associated with CBP/p300 modulation in a subject in need thereof. The pharmaceutical compositions can comprise the compounds of the present disclosure for use in treating diseases described herein. The compositions can contain at least one compound of the disclosure and a pharmaceutically acceptable carrier.

Another aspect of the present disclosure relates to a method of inhibiting one or more of CBP/p300-family bromodomains. The method can comprise administering to a patient in need thereof a therapeutically effective amount of a compound of Formula (I), or a pharmaceutically acceptable salt thereof.

BRIEF DESCRIPTION OF THE DRAWINGS

The present application contains one drawing for better understanding of the principles of the disclosure:

FIG. 1 illustrates additional CBP Inhibitor Compounds.

DETAILED DESCRIPTION

The present disclosure relates to compounds and compositions that are capable of modulating the activity of the CBP/p300 family bromodomains. The disclosure features methods of treating, preventing or ameliorating a disease or disorder in which CBP/p300 bromodomains play a role by administering to a patient in need thereof a therapeutically effective amount of a compound of Formula (I), or a pharmaceutically acceptable salt thereof. The methods of the present disclosure can be used in the treatment of a variety of CBP/p300 bromodomain dependent diseases and disorders by inhibiting the activity of a CBP/p300 bromodomains. Inhibition of CBP/p300 bromodomains provides a novel approach to the treatment of diseases including, but not limited to, cancer.

In certain embodiments, novel CBP Inhibitor Compounds are provided. Unless otherwise indicated, "CBP Inhibitor Compound" as used herein refers to a compound having a detectable CBP $IC_{50}$ value of when tested according to the HTRF biochemical Assay Protocol of Example 96 that is 1 micromolar or lower (e.g., between 0.001 and 1 micromolar, a CBP $IC_{50}$ value of less than 1 μM or a CBP $IC_{50}$ value of between 0.001 and 1 μM).

Unless otherwise indicated herein, all isomeric forms of specified chemical compounds are provided by the present disclosure, including mixtures thereof (e.g., S, R and racemic orientations at each chiral center). If the compound contains a double bond, the substituent may be in the E or Z configuration. If the compound contains a disubstituted cycloalkyl, the cycloalkyl substituent may have a cis- or trans configuration. All tautomeric forms are also intended to be included.

Compounds of Formula (I), unless otherwise indicated may exist in their tautomeric form. All such tautomeric forms are contemplated herein as part of the present disclosure.

The compounds of Formula (I), unless otherwise indicated, may contain one or more stereocenters, and, therefore, exist in different stereoisomeric forms. It is intended that unless otherwise indicated all stereoisomeric forms of the compounds of Formula (I) as well as mixtures thereof, including racemic mixtures, form part of the present disclosure. In addition, the present disclosure embraces all geometric and positional isomers. For example, if a compound of Formula (I), incorporates a double bond or a fused ring, both the cis- and trans-forms, as well as mixtures, are embraced within the scope of the disclosure. Each compound herein disclosed includes all the enantiomers that conform to the general structure of the compound. The compounds may be in a racemic or enantiomerically pure form, or any other form in terms of stereochemistry. The assay results may reflect the data collected for the racemic form, the enantiomerically pure form, or any other form in terms of stereochemistry.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this disclosure. Enantiomers can also be separated by use of a chiral HPLC column.

The compounds of Formula (I) may form salts which are also within the scope of this disclosure.

The disclosure is directed to compounds as described herein and pharmaceutically acceptable salts thereof. The disclosure also includes pharmaceutical compositions comprising one or more compounds as described herein, or a pharmaceutically acceptable salt thereof, and a pharmaceutically acceptable carrier. In some embodiments, pharmaceutical compositions reported herein can be provided in a unit dosage form (e.g., capsule, tablet or the like). In some embodiments, pharmaceutical compositions reported herein can be provided in an oral dosage form. In some embodiments, an oral dosage form of a compound of Formula (I) can be a capsule. In some embodiments, an oral dosage form of a compound of Formula (I) is a tablet. In some embodiments, an oral dosage form comprises one or more fillers, disintigrants, lubricants, glidants, anti-adherents and/or anti-statics. In some embodiments, an oral dosage form is prepared via dry blending. In some embodiments, an oral dosage form is a tablet and is prepared via dry granulation.

A CBP Inhibitor compound of the present disclosure can be dosed at a therapeutically effective level.

Compounds of the Disclosure

The present disclosure relates to compounds, or pharmaceutically acceptable salts or isomers thereof, capable of modulating CBP/p300 family bromodomains which are useful for the treatment of diseases and disorders associated with modulation of CBP/p300 family bromodomains. The disclosure further relates to compounds, or pharmaceutically acceptable salts or isomers thereof, which are useful for inhibiting CBP/p300 family bromodomains.

In some aspects, the disclosure relates to a compound of Formula (I)

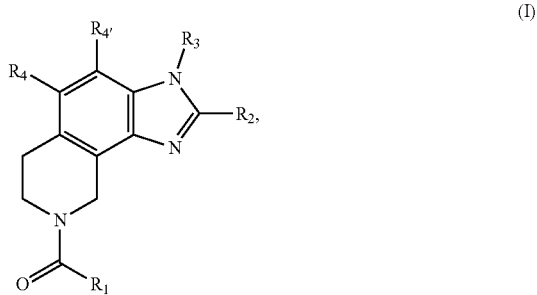

(I)

or a pharmaceutically acceptable salt thereof, wherein, $R_1$, $R_2$, $R_3$, $R_4$ and $R_4'$ are as defined above.

Preferably, a Compound of formula (I) can be a CBP Inhibitor Compound wherein $R_4$ and $R_4'$ are each hydrogen, and $R_1$ is —$OR_5$ and $R_5$ is methyl. For example, a compound of formula (I) can be a CBP Inhibitor Compound wherein $R_4$ and $R_4'$ are each hydrogen, $R_1$ is —$OR_5$ and $R_5$ is methyl and $R_2$ is ($C_5$-$C_6$)cycloalkyl (preferably, cyclohexyl) or 5-6 member heterocyclic ring substituted with one or more N, O or S heteroatom, either being optionally substituted with optionally substituted with one or more $R_6$. A Compound of formula (I) can be a CBP Inhibitor Compound wherein $R_4$ and $R_4'$ are each hydrogen, $R_1$ is —$OR_5$ and $R_5$ is methyl and $R_2$ is ($C_5$-$C_6$)cycloalkyl (preferably, cyclohexyl) optionally substituted with one or more $R_6$; and $R_6$ is —$C_1$-$C_6$alkyl optionally substituted with one or more $R_{10}$, —OH, halogen, oxo, —CN, —$SR_8$, —$OR_8$, —$(CH_2)_n$—$OR_8$, —$NHR_8$, —$NR_8R_9$, —$S(O)_2NR_8R_9$, —$S(O)_2R_8$, —$C(O)R_8$, —$C(O)OR_8$, —$C(O)NR_8R_9$, —$C(O)NR_8S(O)_2R_9'$, —$NR_8C(O)R_9'$, —$NR_8S(O)_2R_9'$, —$S(O)R_8$, —$S(O)NR_8R_9$, or —$NR_8S(O)R_9$ (preferably, $R_6$ is —$C(O)OR_8$, and $R_8$ is hydrogen). A Compound of formula (I) can be a CBP Inhibitor Compound wherein $R_4$ and $R_4'$ are each hydrogen, $R_1$ is —$OR_5$ and $R_5$ is methyl and $R_2$ is ($C_5$-$C_6$)cycloalkyl (preferably, cyclohexyl) optionally substituted with optionally substituted with one or more $R_6$ and $R_6$ is —$C_1$-$C_6$alkyl optionally substituted with one or more $R_{10}$, —OH, halogen, oxo, —CN, —$SR_8$, —$OR_8$, —$(CH_2)_n$—$OR_8$, —$NHR_8$, —$NR_8R_9$, —$S(O)_2NR_8R_9$, —$S(O)_2R_8'$, —$C(O)R_8'$, —$C(O)OR_8$, —$C(O)NR_8R_9$, —$C(O)NR_8S(O)_2R_9'$, —$NR_8C(O)R_9'$, —$NR_8S(O)_2R_9'$, —$S(O)R_8'$, —$S(O)NR_8R_9$, or —$NR_8S(O)R_9$ (preferably, $R_6$ is —$C(O)OR_8$, and $R_8$ is hydrogen).

Preferably, a Compound of formula (I) can be a CBP Inhibitor Compound wherein $R_2$ is ($C_5$-$C_6$)cycloalkyl (preferably, cyclohexyl) or 5-6 member heterocyclic ring substituted with one or more N, O or S heteroatom, either being optionally substituted with optionally substituted with one or more $R_6$.

Preferably, a Compound of formula (I) can be a CBP Inhibitor Compound wherein $R_3$ is —$C_1$-$C_4$ alkyl, substituted with one $R_7$ that is a mono or bicyclic ($C_5$-$C_{10}$)aryl (preferably a $C_5$-$C_6$ monocyclic aryl), (5-10 member)heteroaryl (preferably a 5-6 member monocyclic heteroaryl), ($C_3$-$C_{10}$)cycloalkyl (preferably $C_5$-$C_6$ monocyclic cycloalkyl), or a (3-10 member) heterocycloalkyl (preferably 5-6 member monocyclic heterocycloalkyl). In some examples, $R_3$ can be a —$C_1$-$C_4$ alkyl, substituted with one $R_7$ that is or a ($C_5$-$C_6$)aryl or (5-6 member)heteroaryl fused to a ($C_5$-$C_6$) cycloalkyl or (5-6 member)heterocycloalkyl comprising one or more O, N or S (e.g., $SO_2$) heteroatoms and optionally substituted with a second $R_7$ that is COOH.

Preferably, a Compound of formula (I) can be a CBP Inhibitor Compound wherein:

$R_1$ is —$OR_5$ and $R_5$ is methyl;

$R_2$ is ($C_5$-$C_6$)cycloalkyl (preferably, cyclohexyl) or 5-6 member heterocyclic ring substituted with one or more N, O or S heteroatom, either being optionally substituted with optionally substituted with one or more $R_6$.

$R_3$ is —$C_1$-$C_6$ alkyl, substituted with one $R_7$ that is an aryl (preferably phenyl) or an aryl or heteroaryl fused to a cycloalkyl or heterocycloalkyl;

$R_4$ and $R_4'$ are each hydrogen; and wherein $R_2$ is further substituted with an $R_6$ that is —COOH, or $R_3$ is substituted with a $R_7$ that is —COOH or $R_3$ is further substituted with a $R_7$ is a $C_6$-cycloalkyl or 6-member heterocycloalkyl substituted with a $R_{10}$ that is —COOH.

Preferably, a Compound of formula (I) can be a CBP Inhibitor Compound wherein:

$R_1$ is —$OR_5$ and $R_5$ is methyl;

$R_2$ is ($C_5$-$C_6$)cycloalkyl (preferably, cyclohexyl) or 5-6 member heterocyclic ring substituted with one or more N, O or S heteroatom, optionally substituted with one $R_6$ that is —COOH or H;

$R_3$ is —$C_1$-$C_4$ alkyl, substituted with one $R_7$ that is an aryl (preferably phenyl), cycloalkyl (preferably cyclohexyl), heterocycloalkyl or a ($C_5$-$C_6$)aryl or (5-6 member)heteroaryl fused to a ($C_5$-$C_6$)cycloalkyl or (5-6 member)heterocycloalkyl comprising one or more O, N or S (e.g., $SO_2$) heteroatoms and optionally substituted with a second $R_7$ that is COOH;

$R_4$ and $R_4'$ are each hydrogen; and wherein $R_2$ is a cycloalkyl or heterocycloalkyl substituted with a $R_6$ that is —COOH, or $R_3$ is an alkyl substituted with both a first $R_7$ that is a $C_6$ aryl or 6-member heteroaryl and a second $R_7$ that is —COOH;

$R_3$ is an alkyl substituted with a $R_7$ that is a $C_6$ cycloalkyl or 6-member heterocycloalkyl further substituted with a $R_{10}$ that is —COOH.

In some embodiments, the disclosure relates to a compound of formula (I), or a pharmaceutically acceptable salt thereof, wherein:

$R_1$ is —$C_1$-$C_6$alkyl, —$C_3$-$C_8$cycloalkyl, —$OR_5$, or —$NHR^5$;

$R_2$ is —$C_3$-$C_8$cycloalkyl, heterocyclyl, heteroaryl, or aryl, wherein each cycloalkyl, heterocyclyl, heteroaryl, or aryl is optionally substituted with one or more $R_6$;

$R_3$ is —$C_1$-$C_6$ alkyl, —$C_3$-$C_8$cycloalkyl, or heterocyclyl, wherein each alkyl, cycloalkyl, or heterocyclyl, is optionally substituted with one or more $R_7$;

$R_4$ and $R_{4'}$ are each independently —H, halogen, —CN, —$CH_2CN$, —COOH, or heterocycloalkyl;

each $R_5$ is independently —$C_1$-$C_6$alkyl;

$R_6$ and $R_7$ are each independently, at each occurrence, halogen, —$C_1$-$C_6$alkyl, —$C_3$-$C_8$cycloalkyl, -heterocyclyl, aryl, heteroaryl, —OH, oxo, —$OR_8$, —$NHR_8$, —$NR_8R_9$, —$S(O)_2NR_8R_9$, —$S(O)_2R_{8'}$, —$C(O)R_{8'}$, —$C(O)OR_{8'}$, —$C(O)NR_8S(O)_2R_{9'}$, wherein each alkyl, cycloalkyl, heterocyclyl, heteroaryl, or aryl is optionally substituted with one or more $R_{10}$;

wherein any two $R_6$ or any two $R_7$, when on non-adjacent atoms, can combine to form a cycloalkyl or heterocyclyl;

wherein any two $R_6$ or any two $R_7$, when on adjacent atoms, can combine to form an aryl;

$R_8$ and $R_9$ are each independently, at each occurrence, —H, —$C_1$-$C_6$alkyl, —$C(O)C_1$-$C_6$alkyl, or aryl, wherein each alkyl, or aryl is optionally substituted with one or more $R_{10}$ or $R_{11}$;

$R_{8'}$ and $R_{9'}$ are each independently, at each occurrence, —$C_1$-$C_6$alkyl or heterocyclyl, wherein each alkyl, or heterocyclyl is optionally substituted with one or more $R_{10}$ or $R_{11}$;

$R_{10}$ and $R_{11}$ are each independently, at each occurrence, —$C_1$-$C_6$alkyl, heteroaryl, aryl, —OH, halogen, —$OC_1$-$C_6$alkyl, or —C(O)OH, wherein each alkyl, or heteroaryl is optionally substituted with one or more —$R_{12}$;

wherein any two $R_{10}$ or any two $R_{11}$, when on adjacent atoms, can combine to form a heterocyclyl or aryl; and $R_{12}$ is independently, at each occurrence, —$C_1$-$C_6$alkyl, —OH, halogen, or —$OC_1$-$C_6$alkyl.

In some aspects, the disclosure relates to a compound of Formula (II)

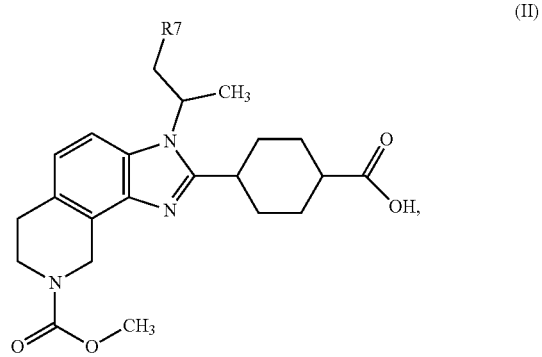

(II)

or a pharmaceutically acceptable salt thereof, wherein, $R_7$ is $C_6$aryl optionally substituted with one or more $R_{10}$, wherein $R_{10}$ is each independently —$C_1$-$C_3$alkyl —$O(C_1$-$C_3$alkyl), or halogen.

In some embodiments, the disclosure relates to a compound of Formula (III):

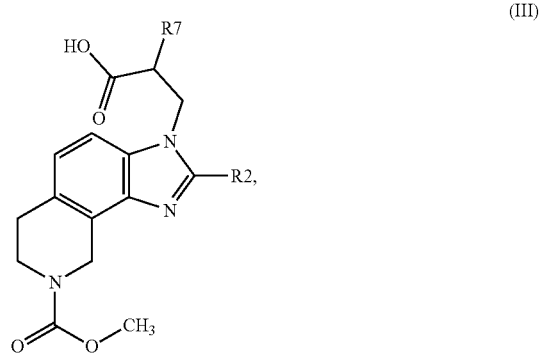

(III)

or a pharmaceutically acceptable salt thereof, wherein:

$R_2$ is —$C_5$-$C_6$cycloalkyl; and $R_7$ is $C_6$aryl optionally substituted with one or more $R_{10}$, wherein $R_{10}$ is each independently —$C_1$-$C_3$alkyl —$O(C_1$-$C_3$alkyl), or halogen.

In some embodiments, the disclosure relates to a compound of Formula (IV):

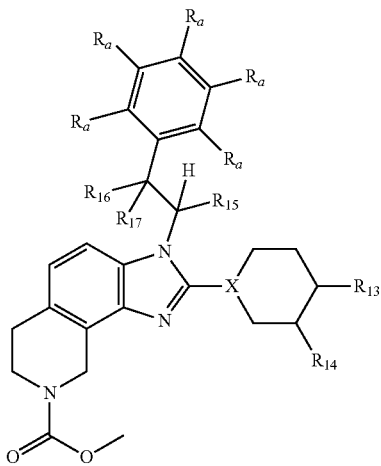

(IV)

or a pharmaceutically acceptable salt thereof, wherein:
each $R_a$ is independently selected from —H, halogen, —CH$_3$, —OCH$_3$, and —COOH;
X is CH or N;
$R_{13}$ is —H, —COOH, —OCH$_3$, or —(CO)NHSO$_2$CH$_3$;
$R_{14}$ is —H or —COOH;
$R_{15}$ is —H or —CH3;
$R_{16}$ is —H, halogen, —CH$_3$, —COOH, —CH$_2$COOH, or —(CO)NHSO$_2$CH$_3$; and
$R_{17}$ is —H or halogen.

It will be appreciated that throughout the present disclosure, unless otherwise indicated, reference to a compound of Formula (I) is intended to also include formula (II), formula (III), formula (IV), and compound species of such formulae disclosed herein.

In some embodiments, the disclosure relates to a compound of formula (I), or a pharmaceutically acceptable salt thereof, wherein:
$R_1$ is —C$_1$-C$_6$alkyl, —C$_3$cycloalkyl, —OR$_5$, or —NHR$^5$;
$R_2$ is —C$_4$-C$_6$cycloalkyl; 4-6 membered heterocyclyl; 6-membered heteroaryl; or C$_6$aryl; wherein each cycloalkyl, heterocyclyl, heteroaryl, or aryl is optionally substituted with one or more R$_6$;
$R_3$ is —C$_1$-C$_6$ alkyl, —C$_6$cycloalkyl, or 4-membered heterocyclyl, wherein each alkyl, cycloalkyl, or heterocyclyl, is optionally substituted with one or more R$_7$;
$R_4$ and $R_{4'}$ are each independently —H, halogen, —CN, —CH$_2$CN, —COOH, or 5-membered heterocycloalkyl;
$R_6$ is independently, at each occurrence, halogen, —C$_1$-C$_6$alkyl, 4-membered heterocyclyl, —OH, oxo, —OR$_8$, —NHR$_8$, —NR$_8$R$_9$, —S(O)$_2$NR$_8$R$_9$, —S(O)$_2$R$_{8'}$, —C(O)R$_8$, —C(O)OR$_8$, —C(O)NR$_8$S(O)$_2$R$_9$, wherein each alkyl or heterocyclyl is optionally substituted with one or more R$_{10}$;
$R_7$ is independently, at each occurrence, halogen, —C$_1$-C$_6$alkyl, —C$_6$cycloalkyl, -6-membered heterocyclyl, C$_6$aryl, 5-6 membered heteroaryl, —OH, halogen, oxo, —OR$_8$, —NHR$_8$, —NR$_8$R$_9$, —S(O)$_2$NR$_8$R$_9$, —S(O)$_2$R$_{8'}$, —C(O)R$_{8'}$, —C(O)OR$_8$, —C(O)NR$_8$S(O)$_2$R$_{9'}$, wherein each alkyl, cycloalkyl, heterocyclyl, heteroaryl, or aryl is optionally substituted with one or more R$_{10}$;
wherein any two $R_7$, when on adjacent atoms, can combine to form a 5-membered heterocycyl or C$_6$aryl;
$R_8$ and $R_9$ are each independently, at each occurrence, —H, —C$_1$-C$_6$alkyl, —C(O)C$_1$-C$_6$alkyl, or C$_6$aryl, wherein each alkyl is optionally substituted with one or more R$_{10}$ or R$_{11}$;

$R_{8'}$ and $R_{9'}$ are each independently, at each occurrence, —C$_1$-C$_6$alkyl or 4-membered heterocyclyl, wherein each alkyl is optionally substituted with one or more R$_{10}$ or R$_{11}$;
$R_{10}$ and $R_{11}$ are each independently, at each occurrence, —C$_1$-C$_6$alkyl, 5-membered heteroaryl, C$_6$aryl, —OH, halogen, —OC$_1$-C$_6$alkyl, or —C(O)OH, wherein each alkyl, or heteroaryl is optionally substituted with one or more —R$_{12}$;
wherein any two $R_{10}$ or any two $R_{11}$, when on adjacent atoms, can combine to form a 5-membered heterocyclyl or C$_6$aryl; and
$R_{12}$ is independently, at each occurrence, —C$_1$-C$_6$alkyl, —OH, halogen, or —OC$_1$-C$_6$alky.

In some embodiments, the disclosure relates to a compound of formula (I), or a pharmaceutically acceptable salt thereof, wherein:
$R_1$ is methyl;
$R_2$ is —C$_4$-C$_6$cycloalkyl; 6 membered heterocyclyl comprising 1-2 heteroatoms selected from N and O; 6-membered heteroaryl comprising one nitrogen; or C$_6$aryl; wherein each cycloalkyl, heterocyclyl, heteroaryl, or aryl is optionally substituted with one or more R$_6$;
$R_3$ is —C$_1$-C$_3$ alkyl optionally substituted with one or more R$_7$;
$R_4$ is —H or halogen;
$R_{4'}$ is —H, —CN, —CH2CN, —COOH, or 5-membered heterocycloalkyl;
$R_6$ is independently, at each occurrence, —C$_1$-C$_6$alkyl, —OR$_8$, —S(O)$_2$NR$_8$R$_9$, —S(O)$_2$R$_{8'}$, —C(O)R$_{8'}$, —C(O)OR$_8$, —C(O)NR$_8$S(O)$_2$R$_{9'}$, wherein each alkyl or heterocyclyl is optionally substituted with one or more R$_{10}$;
$R_7$ is independently, at each occurrence, halogen, —C$_1$-C$_6$alkyl, —C$_6$cycloalkyl, C$_6$aryl, 5-6 membered heteroaryl, —OH, —OR$_8$, —C(O)OR$_8$, or —C(O)NR$_8$S(O)$_2$R$_{9'}$, wherein each alkyl, cycloalkyl, heteroaryl, or aryl is optionally substituted with one or more R$_{10}$;
$R_8$ is independently, at each occurrence, —H, —C$_1$-C$_6$alkyl, —C(O)C$_1$-C$_6$alkyl, or C$_6$aryl, wherein each alkyl is optionally substituted with one or more R$_{10}$ or R$_{11}$;
$R_{8'}$ is independently, at each occurrence, —C$_1$-C$_6$alkyl or 4-membered heterocyclyl, wherein each alkyl is optionally substituted with one or more R$_{10}$ or R$_{11}$;
$R_{9'}$ is independently, at each occurrence, —C$_1$-C$_6$alkyl;
$R_{10}$ and $R_{11}$ are each independently, at each occurrence, —C$_1$-C$_6$alkyl, 5-membered heteroaryl, —OH, halogen, —OC$_1$-C$_6$alkyl, or —C(O)OH, wherein each alkyl is optionally substituted with one or more —R$_{12}$;
wherein any two $R_{10}$ or any two $R_{11}$, when on adjacent atoms, can combine to form a 5-membered heterocyclyl or C$_6$aryl;
and
$R_{12}$ is independently, at each occurrence, halogen.

In some embodiments, the disclosure relates to a compound of formula (I), or a pharmaceutically acceptable salt thereof, wherein $R_2$ is —C$_5$-C$_6$cycloalkyl; 6 membered heterocyclyl comprising 1-2 heteroatoms selected from N and O; or C$_6$aryl; wherein each cycloalkyl, heterocyclyl, heteroaryl, or aryl is optionally substituted with one or more R$_6$;
$R_{4'}$ is —H, —CN, —COOH, or 5-membered heterocycloalkyl;
$R_7$ is independently, at each occurrence, halogen, —C$_1$-C$_6$alkyl, —C$_6$cycloalkyl, C$_6$aryl, 5 membered heteroaryl, —OH, —C(O)OR$_8$, or —C(O)NR$_8$S(O)$_2$R$_{9'}$, wherein each alkyl, cycloalkyl, heteroaryl, or aryl is optionally substituted with one or more R$_{10}$;
$R_{10}$ and $R_{11}$ are each independently, at each occurrence, —C$_1$-C$_6$alkyl, 5-membered heteroaryl, —OH, halogen, —OC$_1$-C$_6$alkyl, or —C(O)OH, wherein each alkyl is optionally substituted with one or more R$_{12}$, wherein R$_{12}$ is fluorine.

In some embodiments, the disclosure relates to a compound of formula (I), or a pharmaceutically acceptable salt thereof, wherein R$_1$ is —OR$_5$.

In some embodiments, the disclosure relates to a compound of formula (I), or a pharmaceutically acceptable salt thereof, wherein R$_5$ is methyl.

In some embodiments, the disclosure relates to a compound of formula (I), or a pharmaceutically acceptable salt thereof, wherein R$_2$ is C$_4$-C$_6$ cycloalkyl.

In some embodiments, the disclosure relates to a compound of formula (I), or a pharmaceutically acceptable salt thereof, wherein R$_2$ is six-membered heterocyclyl.

In some embodiments, the disclosure relates to a compound of formula (I), or a pharmaceutically acceptable salt thereof, wherein R$_2$ is piperidinyl, tetrahydropyranyl, or piperazinyl.

In some embodiments, the disclosure relates to a compound of formula (I), or a pharmaceutically acceptable salt thereof, wherein R$_2$ is phenyl.

In some embodiments, the disclosure relates to a compound of formula (I), or a pharmaceutically acceptable salt thereof, wherein R$_2$ is six-membered heteroaryl.

In some embodiments, the disclosure relates to a compound of formula (I), or a pharmaceutically acceptable salt thereof, wherein R$_2$ is pyridinyl.

In some embodiments, the disclosure relates to a compound of formula (I), or a pharmaceutically acceptable salt thereof, wherein R$_3$ is C$_1$-C$_6$ alkyl substituted with phenyl and with methyl.

In some embodiments, the disclosure relates to a compound selected from any one of Tables 1-7, any one of Examples 2-7, and FIG. 1, or a pharmaceutically acceptable salt thereof. Many of the compounds in Tables 1-7, any one of Examples 2-7, and FIG. 1 were obtained as mixtures of stereoisomers, which were separated by HPLC according to the procedure described in Examples 2-7, or a similar method, to obtain the individual compounds in substantially pure form. For each compound, the order of elution is specified in the Tables, Examples, or FIGURE. The stereochemistry of each specific compound in the examples was arbitrarily assigned, as specified in the examples.

In some embodiments, the disclosure relates to a compound selected from any one of Tables 1-7, any one of Examples 2-7, and FIG. 1, or a pharmaceutically acceptable salt thereof, prepared by a method comprising: preparing the compound as a mixture of stereoisomers; separating the stereoisomers by chiral HPLC according to the procedure described in the corresponding Example; isolating one or more stereoisomers that are CBP Inhibitor Compounds; and optionally treating the isolated stereoisomer(s) with an acid or base to afford a pharmaceutically acceptable salt thereof. In some embodiments, the compound is the 1$^{st}$ eluting isomer. In some embodiments, the compound is the 2$^{nd}$ eluting isomer. In some embodiments, the compound is the 3$^{rd}$ eluting isomer. In some embodiments, the compound is the 4$^{th}$ eluting isomer. In some embodiments, the compound is the 5$^{th}$, 6$^{th}$, 7$^{th}$, or 8$^{th}$ eluting isomer.

In some embodiments, the disclosure relates to a CBP Inhibitor compound of the formula

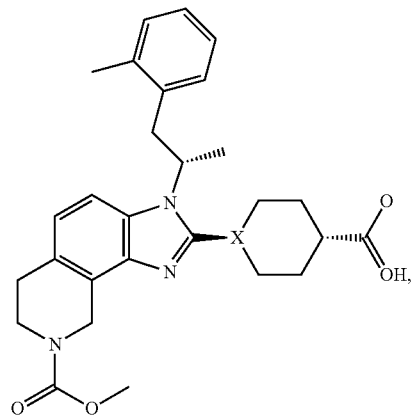

or a stereoisomer thereof, or a pharmaceutically acceptable salt thereof.

In some embodiments, the disclosure relates to a CBP Inhibitor compound of the formula

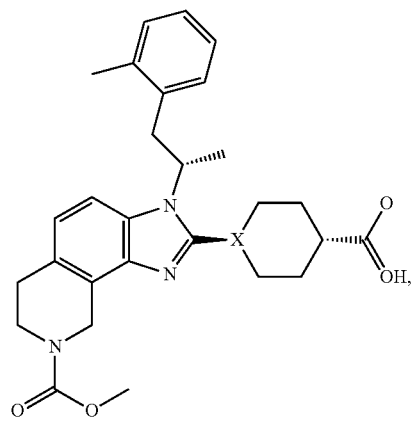

or a pharmaceutically acceptable salt thereof.

In some embodiments, the disclosure relates to a CBP Inhibitor compound of the formula

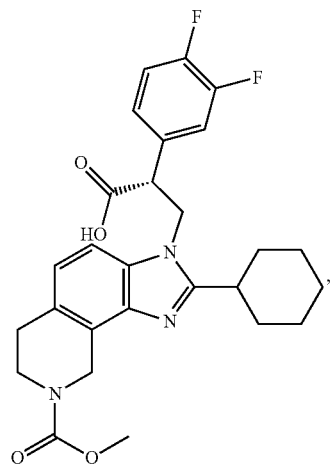 [SMILES: COC(=O)N1CCc2ccc3c(nc(C4CCCCC4)n3C[C@H](C(=O)O)c3ccc(F)c(F)c3)c2C1]

or a stereoisomer thereof, or a pharmaceutically acceptable salt thereof.

In some embodiments, the disclosure relates to a CBP Inhibitor compound of formula

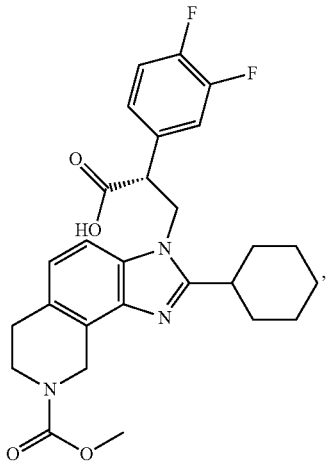

or a pharmaceutically acceptable salt thereof.

In some embodiments, the disclosure relates to a CBP Inhibitor compound of formula

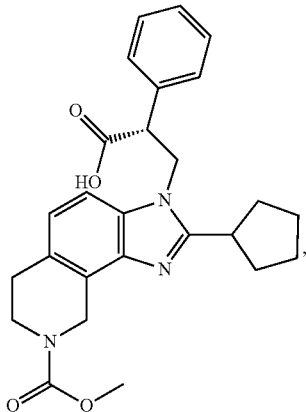 [SMILES: COC(=O)N1CCc2ccc3c(nc(C4CCCC4)n3C[C@H](C(=O)O)c3ccccc3)c2C1]

or a stereoisomer thereof, or a pharmaceutically acceptable salt thereof.

In some embodiments, the disclosure relates to a CBP Inhibitor compound of formula

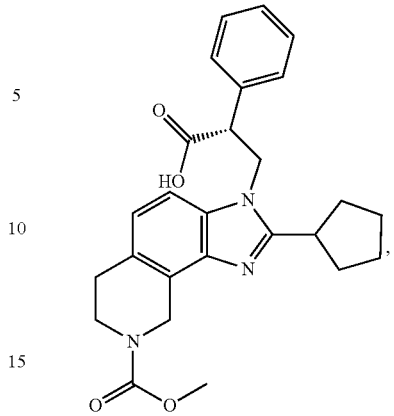

or a pharmaceutically acceptable salt thereof.

In some embodiments, the disclosure relates to a compound according to any of the embodiments set forth herein in non-salt form.

In some embodiments, the disclosure relates to a pharmaceutically acceptable salt of a compound according to any of the embodiments set forth herein.

Method of Synthesizing the Compounds

The compounds of the present disclosure may be made by a variety of methods, including standard chemistry. Suitable synthetic routes are depicted in the examples given below.

The compounds of the present disclosure, i.e., compounds of Formula (I), or a pharmaceutically acceptable salt thereof, may be prepared by methods known in the art of organic synthesis as set forth in part by the synthetic schemes depicted in the examples. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formula (I).

Those skilled in the art will recognize if a stereocenter exists in the compounds of Formula (I). Accordingly, the present disclosure includes both possible stereoisomers (unless otherwise indicated and/or specified in the synthesis) and includes not only racemic compounds but the individual enantiomers and/or diastereomers as well. Unless otherwise indicated, when a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

Methods of Using the Disclosed Compounds

One aspect of the present disclosure relates to a compound of Formula (I) for use in medicine. Another aspect of the present disclosure relates to a method of modulating one or more of CBP/p300-family bromodomains, comprising administering to a patient in need thereof a therapeutically effective amount of a compound of Formula (I). Another aspect of the present disclosure relates to a method of inhibiting one or more of CBP/p300-family bromodomains, comprising administering to a patient in need thereof a therapeutically effective amount of a compound of Formula (I). In another aspect, the present disclosure relates to a method of inhibiting one or more of CBP/p300-family bromodomains, comprising administering to a patient in need thereof a therapeutically effective amount of a pharmaceutical composition comprising a compound of Formula (I).

CBP Inhibitor Compounds are useful in the development of pharmaceutical compositions suitable for treatment of certain related forms of cancer. CBP Inhibitor Compounds are useful for treating disease states that are responsive to the inhibition of CBP. CREB binding protein (CBP) and EP300 (p300) are closely related multi-domain proteins that function as transcriptional co-activators. They carry acetyl-lysine binding bromodomains which impart a scaffolding or positioning function on these proteins and have proven to be suitable for the design of small molecule inhibitors of their biological function. These paralogs are highly homologous at the amino acid level and share many overlapping functions. They are histone acetyl transferases (HATs) which catalyze the post-translational modification of histone and non-histone proteins. As bromodomain carrying HATs these proteins function as epigenetic readers and writers. The non-histone protein substrates of CBP/p300 consist of numerous transcription factors including nuclear hormone receptors such as the androgen receptor (AR). CBP/p300 function as co-activators of AR-signaling by acetylation of the AR which activates its transcriptional activity and promotes its protein stability. In addition, they acetylate histone H3 at lysine 27 (Ac—H3K27) to provide a docking site for the bromodomain thus providing a scaffold to bridge the nuclear receptor to the basal transcriptional machinery. Acetylation of histone leads to the generation of a transcriptionally permissive environment on chromatin. The localization of CBP/p300 to AR dependent super-enhancers thus leads to increased localized Ac—H3K27 which further increases transcription at these loci.

EXAMPLES

Definitions used in the following Schemes and elsewhere herein are:
ACN acetonitrile
Ac$_2$O acetic anhydride
(±)BINAP (±)-2,2'-Bis(diphenylphosphino)-1,1'-binaphthalen
Boc tert-butoxycarbonyl
Brettphos Dicyclohexyl[3,6-dimethoxy-2',4',6'-tris(1-methylethyl)[1,1'-biphenyl]-2-yl]phosphine
Brettphos Pd G3 or 3$^{rd}$ generation BrettPhos precatalyst: Methanesulfonato(2-dicyclohexylphosphino-3,6-dimethoxy-2',4',6'-tri-i-propyl-1,1'-biphenyl)(2'-amino-1,1'-biphenyl-2-yl)palladium(II)
n-BuOH butanol
cm centimeter
DCE 1,2-dichloroethane
DCM dichloromethane or methylene chloride
D-CSA D-Camphorsulfonic acid
DEA diethylamine
DMC 2-Chloro-4,5-dihydro-1,3-dimethyl-1H-imidazolium chloride
DMP Dess-Martin periodinane
DMTMM 4-(4,6-Dimethoxy-1,3,5-triazin-2-yl)-4-methylmorpholinium chloride
DIEA N,N-diisopropylethylamine
DMAP 4-(dimethylamino)pyridine
DMF N,N-dimethylformamide
DMSO dimethylsulfoxide
DPPA diphenylphosphoryl azide
dppf bis(diphenylphosphino)ferrocene
EDC 1-Ethyl-(3-dimethylaminopropyl)carbodiimide hydrochloride
ES electrospray ionization
Et$_3$N triethylamine
EtOAc ethyl acetate
EtOH ethanol
FA formic acid
FCC flash column chromatography
h hours
HATU 2-(3H-[1,2,3]triazolo[4,5-b]pyridin-3-yl)-1,1,3,3-tetramethylisouronium hexafluorophosphate
HCl hydrogen chloride
HOAc acetic acid
HPLC high performance liquid chromatography
[Ir(COD)Cl]$_2$ chloro(1,5-cyclooctadiene)iridium(I) dimer
(i-Pr)$_2$NEt N,N-diisopropylethylamine
L liter
LCMS liquid chromatography/mass spectrometry
LDA lithium diisopropylamine
LRMS low resolution mass spectrometry
K$_2$CO$_3$ potassium carbonate
KHMDS Potassium hexamethyldisilazide
mCPBA 3-Chloroperoxybenzoic acid
MeOH methanol
mL milliliter
mmol millimole
mg milligram
MHz megahertz
MS mass spectrometry
m/z mass/charge ratio
NBS N-bromosuccinimide
NH$_4$Cl ammonium chloride
nm nanometer
NMM 4-methylmorpholine
NMR nuclear magnetic resonance
Pd$_2$(dba)$_3$ tris(dibenzylideneacetone)dipalladium
Ph$_3$P triphenylphosphine
PhCHO benzaldehyde
PhMe toluene
ppm parts per million
rt room temperature
RT retention time
(S)-(−)-MeO-BIPHEP (S)-(−)-2,2'-Bis(diphenylphosphino)-6,6'-dimethoxy-1,1'-biphenyl
SFC supercritical fluid chromatography
STAB sodium triacetoxyborohydride
TBS tert-Butyldimethylsilyl
TBDMS tert-Butyldimethylsilyl chloride
p-TSA para-toluenesulfonic anhydride
p-TsOH para-toluenesulfonic acid
TFA trifluoroacetic acid
TFAA trifluoroacetic anhydride
THF tetrahydrofuran
TMSCN trimethylsilyl cyanide
UV ultraviolet
XPhos 2-dicyclohexylphosphino-2',4',6'-triisopropylbiphenyl
ZnI$_2$ zinc iodide Materials Unless otherwise noted, all materials were obtained from commercial suppliers and were used without further purification. Anhydrous solvents were obtained from Sigma-Aldrich (Milwaukee, WI) and used directly. All reactions involving air- or moisture-sensitive reagents were performed under a nitrogen atmosphere and all reactions utilizing microwave irradiation were run on a Biotage Initiator EXP EU instrument.

Unless otherwise noted, mass-triggered HPLC purification and/or purity and low resolution mass spectral data were measured using either: (1) Waters Acquity ultra performance liquid chromatography (UPLC) system (Waters Acquity UPLC with Sample Organizer and Waters Micromass ZQ Mass Spectrometer) with UV detection at 220 nm and a low resonance electrospray positive ion mode (ESI) (Column: Acquity UPLC BEH C18 1.7 µm 2.1×50 mm; gradient: 5-100% Solvent B (95/5/0.09%: Acetonitrile/Water/Formic Acid) in Solvent A (95/5/0.1%: 10 mM Ammonium Formate/Acetonitrile/Formic Acid) for 2.2 min then 100-5% Solvent B in Solvent A for 0.01 min then hold at 5% Solvent B in Solvent A for 0.29 min) or (2) Waters HT2790 Alliance high performance liquid chromatography (HPLC) system (Waters 996 PDA and Waters ZQ Single Quad Mass Spectrometer) with UV detection at 220 nm and 254 nm and a low resonance electrospray ionization (positive/negative) mode (ESI) (Column: XBridge Phenyl or C18, 5 µm 4.6×50 mm; gradient: 5-95% Solvent B (95% methanol/5% water with 0.1% Formic Acid) in Solvent A (95% water/5% methanol with 0.1% Formic Acid) for 2.5 min then hold at 95% Solvent B in Solvent A for 1 min (purity and low resolution MS only).

Example 1: HTRF Biochemical Assay for CBP Activity

The assay was performed in a final volume of 6 µL in assay buffer containing 50 mM Hepes (pH 7.5, (0.5M Hepes, pH 7.5 solution; Teknova H1575)), 0.5 mM GSH, 0.01% BGG (0.22 µM filtered, Sigma, G7516-25G), 0.005% BSA (0.22 µM filtered, EMD Millipore Corporation, 126575) and 0.01% Triton X-100 (Sigma, T9284-10L). Nanoliter quantities of 10-point, 3-fold serial dilution in DMSO were pre-dispensed into 1536 assay plates (Corning, #3724BC) for a final test concentration of 33 µM to 1.7 nM, top to lowest dose, respectively. 3 µL of 2× Protein and 3 µL of 2× Peptide Ligand were added to assay plates (pre-stamped with compound). Plates were incubated for varying times at room temperature prior to measuring the signal. TR-FRET (Time-Resolved Fluorescence Resonance Energy Transfer) was measured on the PHERAstar (BMG, equipped with HTRF optic module [337/520/490]) or on the Envision (PerkinElmer, equipped with the TRF Laser unit, TRF dual mirror D400/D505 and emission filters M520 and M495). Data were reported as percent inhibition compared with control wells based on the following equation: % inh=1−((TR-FRET ratio−AveLow)/(AveHigh−AveLow)) where TR-FRET ratio=(Fluorescence at 520 nm/Fluorescence at 490 nm)*10000), AveLow=average TR-FRET ratio of no enzyme control (n=32), and AveHigh=average TR-FRET ratio of DMSO control (n=32). IC50 values were determined by curve fitting of the standard 4 parameter logistic fitting algorithm included in the Activity Base software package: IDBS XE Designer Model205. Data is fitted using the Levenburg Marquardt algorithm. $IC_{50}$ values are shown in Table 2, below. As set forth in Table 2 below, an $IC_{50}$ value of greater than or equal to 0.001 µM and less than or equal to 0.01 µM is marked "++++"; a value greater than 0.01 µM and less than or equal to 0.1 µM is marked "+++"; a value greater than 0.1 µM and less than or equal to 1 µM is marked "++"; and a value greater than 1 µM and less than 1000 µM is marked "+." Compounds that were not tested in a particular assay are marked "NT."

TABLE 1

| | | |
|---|---|---|
| | $IC_{50}$ Values | |
| Cpd. No. | Structure | BROMO $IC_{50}$ TRF TB CBP (µM gmean) |
| 1 | 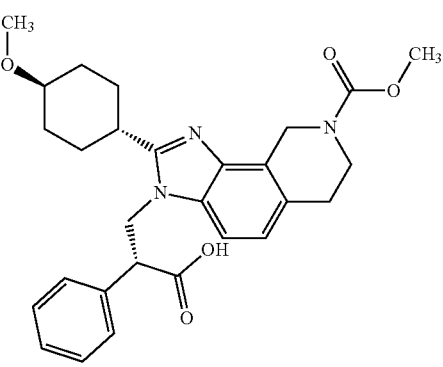 [SMILES: COC(=O)N1CCc2ccc3c(nc([C@H]4CC[C@H](OC)CC4)n3C[C@H](C(=O)O)c3ccccc3)c2C1] | ++++ |

TABLE 1-continued
IC$_{50}$ Values
| Cpd. No. | Structure | BROMO IC$_{50}$ TRF TB CBP (μM gmean) |
|---|---|---|
| 2 | 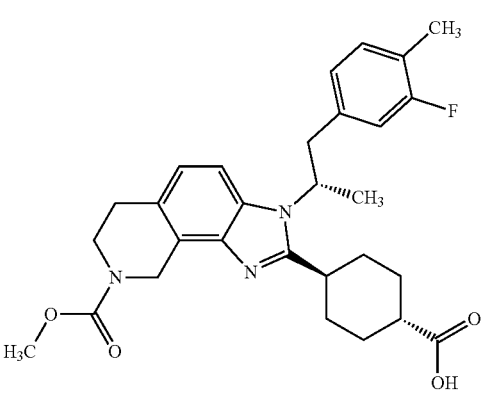 [SMILES: COC(=O)N1CCc2ccc3c(nc([C@H]4CC[C@H](C(=O)O)CC4)n3[C@@H](C)Cc3ccc(C)c(F)c3)c2C1] | ++++ |
| 3 | 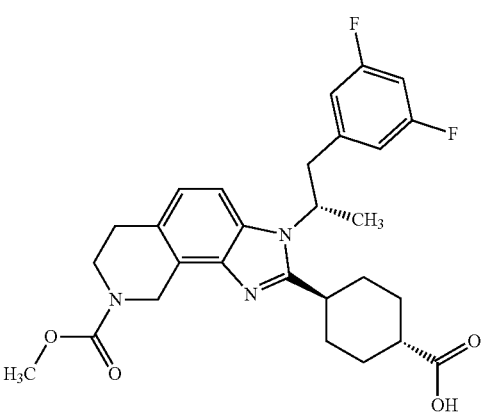 [SMILES: COC(=O)N1CCc2ccc3c(nc([C@H]4CC[C@H](C(=O)O)CC4)n3[C@@H](C)Cc3cc(F)cc(F)c3)c2C1] | ++++ |
| 4 | 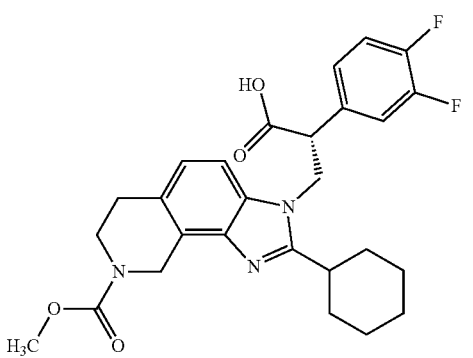 [SMILES: COC(=O)N1CCc2ccc3c(nc(C4CCCCC4)n3C[C@H](C(=O)O)c3ccc(F)c(F)c3)c2C1] | ++++ |

TABLE 1-continued

| | IC$_{50}$ Values | |
|---|---|---|
| Cpd. No. | Structure | BROMO IC$_{50}$ TRF TB CBP (µM gmean) |
| 5 | | ++++ |
| 6 | | ++++ |
| 7 | | ++++ |
| 8 | | ++++ |

TABLE 1-continued

| | | IC$_{50}$ Values |
|---|---|---|
| Cpd. No. | Structure | BROMO IC$_{50}$ TRF TB CBP (μM gmean) |
| 9 | *[chemical structure]* | ++++ |
| 10 | *[chemical structure]* | ++++ |
| 11 | *[chemical structure]* | ++++ |

TABLE 1-continued
| Cpd. No. | Structure | BROMO IC$_{50}$ TRF TB CBP (μM gmean) |
|---|---|---|
| 12 | 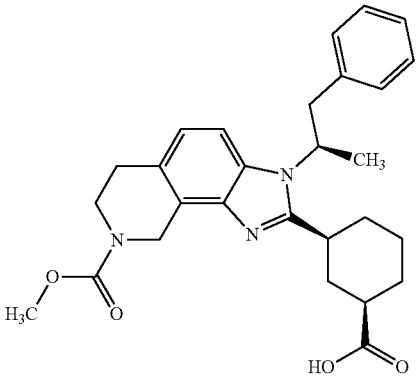 [SMILES: COC(=O)N1CCc2ccc3c(nc([C@H]4CCC[C@@H](C(=O)O)C4)n3[C@H](C)Cc3ccccc3)c2C1] | ++++ |
| 13 | 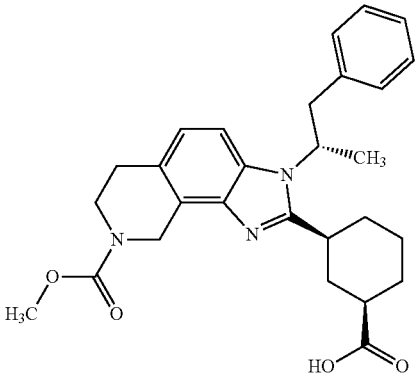 [SMILES: COC(=O)N1CCc2ccc3c(nc([C@H]4CCC[C@@H](C(=O)O)C4)n3[C@@H](C)Cc3ccccc3)c2C1] | ++++ |
| 14 | 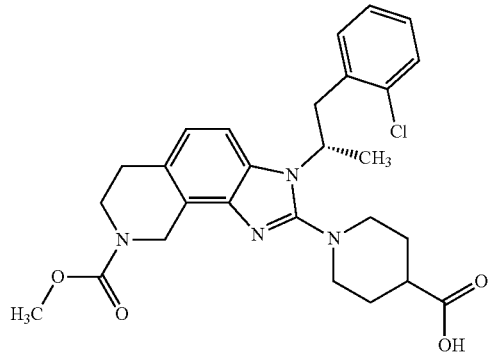 | ++++ |

TABLE 1-continued

| | IC$_{50}$ Values | |
|---|---|---|
| Cpd. No. | Structure | BROMO IC$_{50}$ TRF TB CBP (μM gmean) |
| 15 | | ++++ |
| 16 | | ++++ |
| 17 | | ++++ |

TABLE 1-continued

| | IC$_{50}$ Values | |
|---|---|---|
| Cpd. No. | Structure | BROMO IC$_{50}$ TRF TB CBP (μM gmean) |
| 18 | | ++++ |
| 19 | | ++++ |
| 20 | | ++++ |
| 21 | | ++++ |

TABLE 1-continued

| | IC₅₀ Values | |
|---|---|---|
| Cpd. No. | Structure | BROMO IC$_{50}$ TRF TB CBP (μM gmean) |
| 22 | *(structure)* | ++++ |
| 23 | *(structure)* | ++++ |
| 24 | *(structure)* | ++++ |
| 25 | *(structure)* | ++++ |

TABLE 1-continued

| Cpd. No. | Structure | IC$_{50}$ Values BROMO IC$_{50}$ TRF TB CBP (μM gmean) |
|---|---|---|
| 26 | 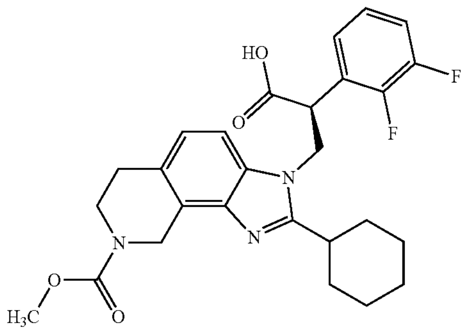 [SMILES: COC(=O)N1CCc2ccc3c(nc(C4CCCCC4)n3C[C@@H](C(=O)O)c3cccc(F)c3F)c2C1] | ++++ |
| 27 | 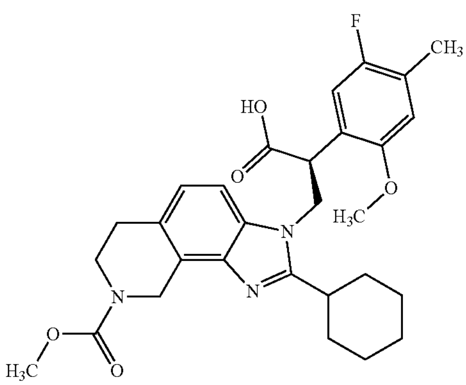 | ++++ |
| 28 | 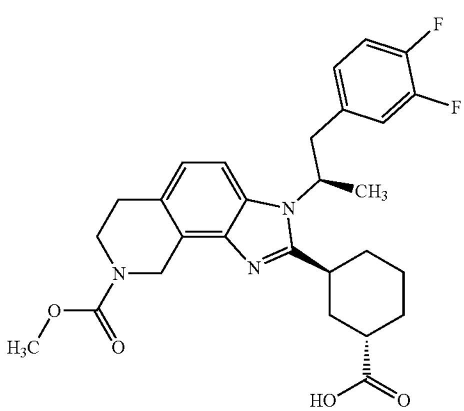 [SMILES: COC(=O)N1CCc2ccc3c(nc([C@H]4CCC[C@H](C(=O)O)C4)n3[C@H](C)Cc3ccc(F)c(F)c3)c2C1] | ++++ |

TABLE 1-continued

| Cpd. No. | Structure | BROMO IC$_{50}$ TRF TB CBP (μM gmean) |
|---|---|---|
| 29 | 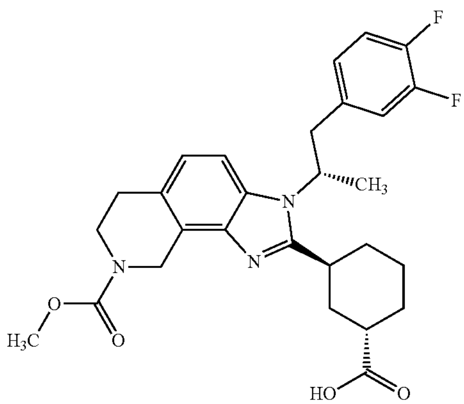 [SMILES: COC(=O)N1CCc2ccc3c(nc([C@H]4CCC[C@H](C(=O)O)C4)n3[C@@H](C)Cc3ccc(F)c(F)c3)c2C1] | ++++ |
| 30 | 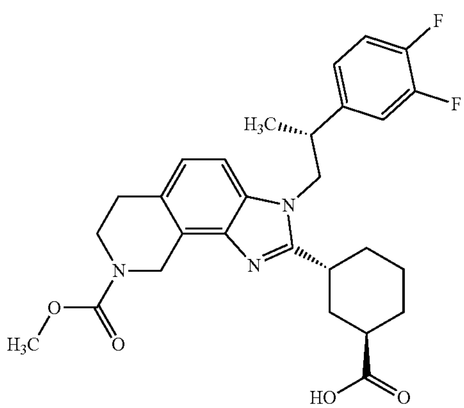 [SMILES: COC(=O)N1CCc2ccc3c(nc([C@@H]4CCC[C@@H](C(=O)O)C4)n3C[C@H](C)c3ccc(F)c(F)c3)c2C1] | ++++ |
| 31 | 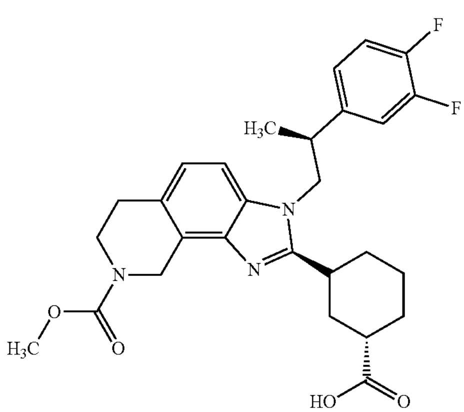 | ++++ |

TABLE 1-continued

| Cpd. No. | Structure | BROMO IC$_{50}$ TRF TB CBP (μM gmean) |
|---|---|---|
| 32 | 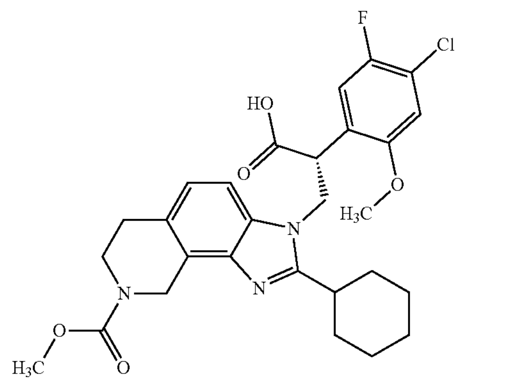 [SMILES: COC(=O)N1CCc2ccc3c(nc(C4CCCCC4)n3C[C@H](C(=O)O)c3cc(F)c(Cl)cc3OC)c2C1] | ++++ |
| 33 | 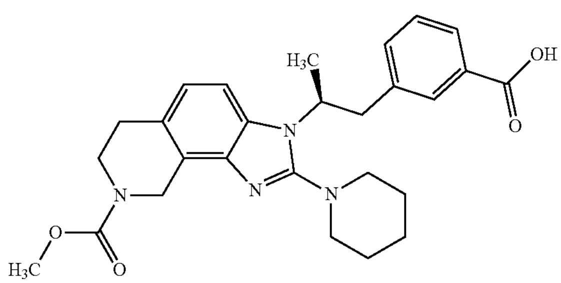 | ++++ |
| 34 | 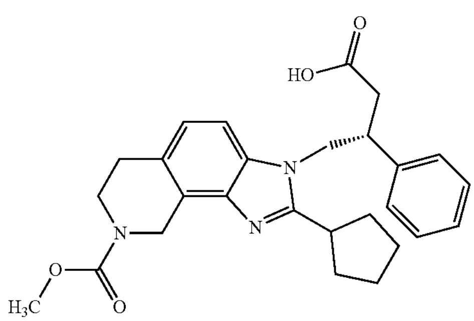 [SMILES: COC(=O)N1CCc2ccc3c(nc(C4CCCC4)n3C[C@H](CC(=O)O)c3ccccc3)c2C1] | ++++ |
| 35 | 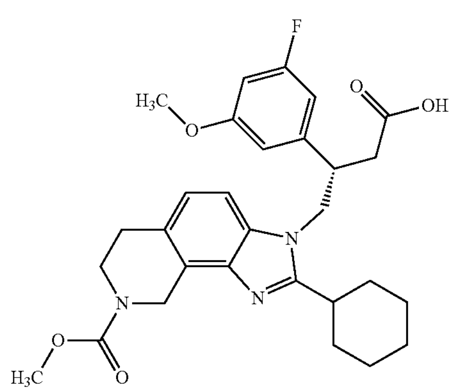 [SMILES: COC(=O)N1CCc2ccc3c(nc(C4CCCCC4)n3C[C@@H](CC(=O)O)c3cc(F)cc(OC)c3)c2C1] | ++++ |

TABLE 1-continued
| | IC$_{50}$ Values | |
|---|---|---|
| Cpd. No. | Structure | BROMO IC$_{50}$ TRF TB CBP (μM gmean) |
| 36 | 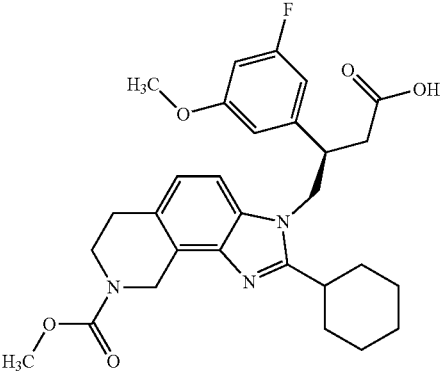 [SMILES: COC(=O)N1CCc2ccc3c(nc(C4CCCCC4)n3C[C@H](CC(=O)O)c3cc(F)cc(OC)c3)c2C1] | ++++ |
| 37 | 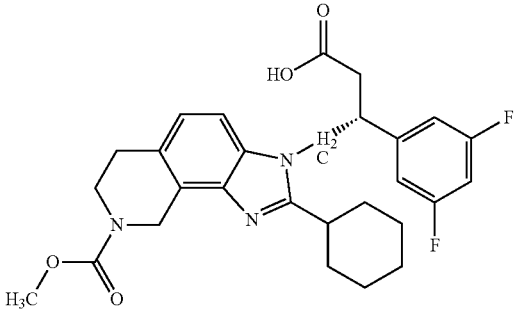 [SMILES: COC(=O)N1CCc2ccc3c(nc(C4CCCCC4)n3C[C@H](CC(=O)O)c3cc(F)cc(F)c3)c2C1] | ++++ |
| 38 | 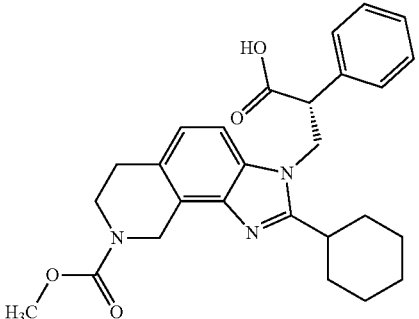 | ++++ |
| 39 | 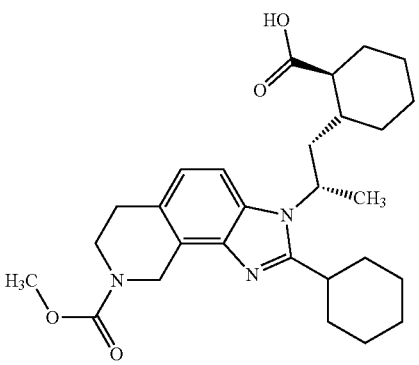 | ++++ |

TABLE 1-continued

| Cpd. No. | Structure | BROMO IC$_{50}$ TRF TB CBP (μM gmean) |
|---|---|---|
| 40 | 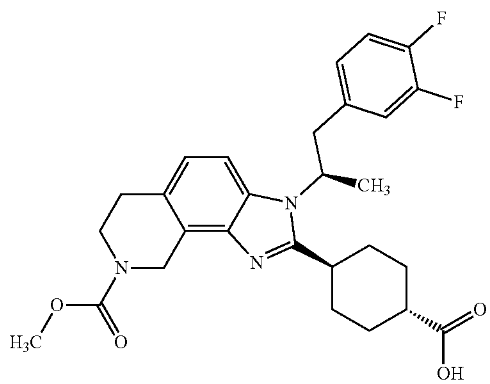 [SMILES: COC(=O)N1CCc2ccc3c(nc([C@H]4CC[C@H](C(=O)O)CC4)n3[C@H](C)Cc3ccc(F)c(F)c3)c2C1] | ++++ |
| 41 | 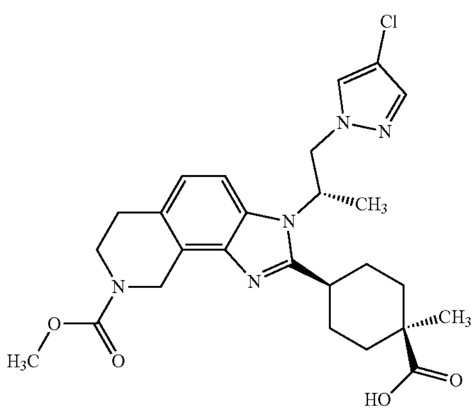 [SMILES: COC(=O)N1CCc2ccc3c(nc([C@H]4CC[C@@](C)(C(=O)O)CC4)n3[C@@H](C)Cn3cc(Cl)cn3)c2C1] | ++++ |
| 42 | 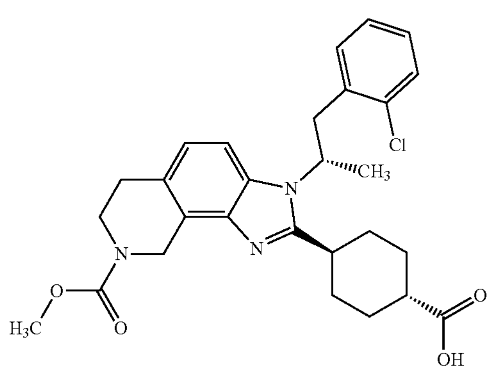 [SMILES: COC(=O)N1CCc2ccc3c(nc([C@H]4CC[C@H](C(=O)O)CC4)n3[C@@H](C)Cc3ccccc3Cl)c2C1] | ++++ |

TABLE 1-continued

| Cpd. No. | Structure | BROMO IC$_{50}$ TRF TB CBP (μM gmean) |
|---|---|---|
| 43 | 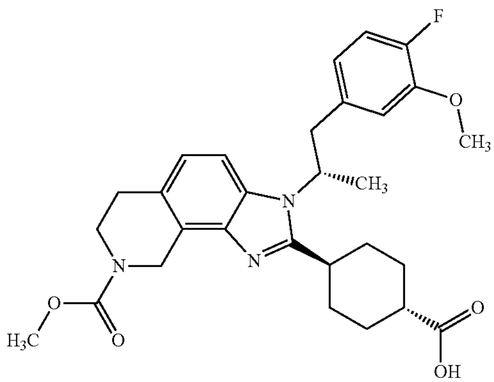 [SMILES: COC(=O)N1CCc2ccc3c(nc([C@H]4CC[C@H](C(=O)O)CC4)n3[C@@H](C)Cc3ccc(F)c(OC)c3)c2C1] | ++++ |
| 44 | 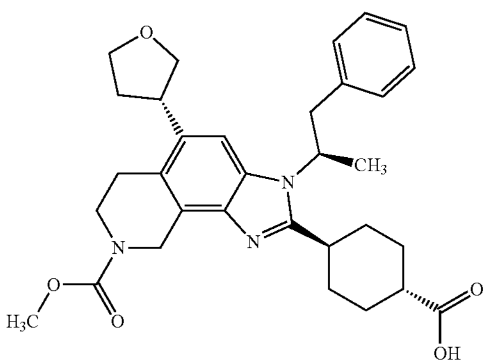 [SMILES: COC(=O)N1CCc2c([C@@H]3CCOC3)cc3c(nc([C@H]4CC[C@H](C(=O)O)CC4)n3[C@H](C)Cc3ccccc3)c2C1] | ++++ |
| 45 | 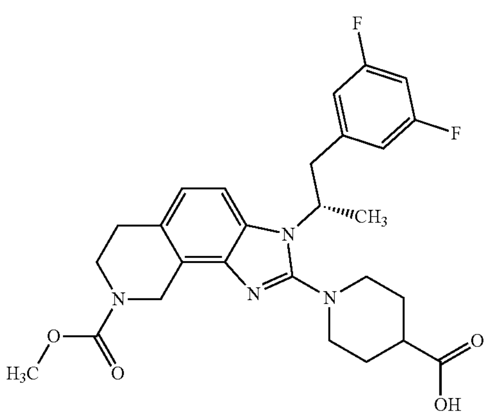 [SMILES: COC(=O)N1CCc2ccc3c(nc(N4CCC(C(=O)O)CC4)n3[C@@H](C)Cc3cc(F)cc(F)c3)c2C1] | ++++ |

TABLE 1-continued

| Cpd. No. | Structure | IC$_{50}$ Values BROMO IC$_{50}$ TRF TB CBP (μM gmean) |
|---|---|---|
| 46 | 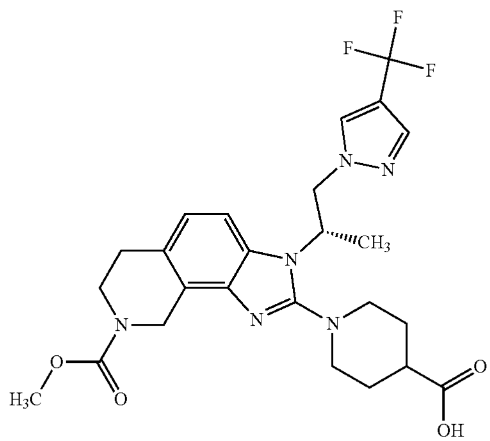 [SMILES: COC(=O)N1CCc2ccc3c(nc(N4CCC(C(=O)O)CC4)n3[C@@H](C)Cn3cc(C(F)(F)F)cn3)c2C1] | ++++ |
| 47 | 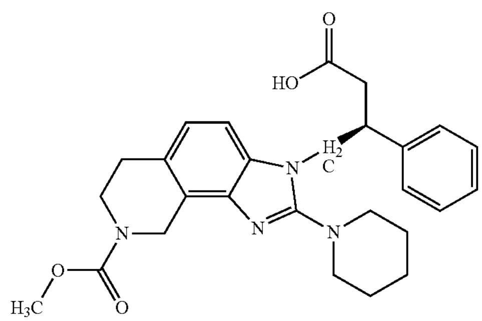 [SMILES: COC(=O)N1CCc2ccc3c(nc(N4CCCCC4)n3C[C@@H](CC(=O)O)c3ccccc3)c2C1] | ++++ |
| 48 | 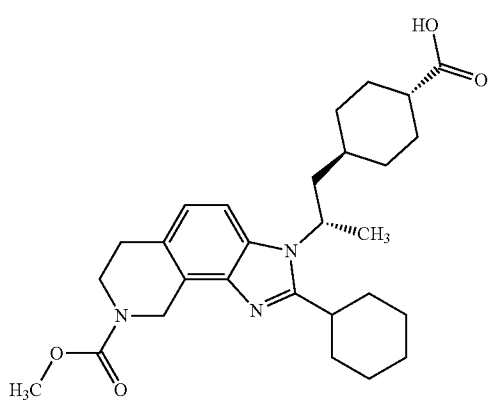 [SMILES: COC(=O)N1CCc2ccc3c(nc(C4CCCCC4)n3[C@@H](C)C[C@H]3CC[C@H](C(=O)O)CC3)c2C1] | ++++ |

TABLE 1-continued

| | IC$_{50}$ Values | |
|---|---|---|
| Cpd. No. | Structure | BROMO IC$_{50}$ TRF TB CBP (μM gmean) |
| 49 | | ++++ |
| 50 | | ++++ |
| 51 | | ++++ |
| 52 | | ++++ |

TABLE 1-continued

| Cpd. No. | Structure | BROMO IC$_{50}$ TRF TB CBP (μM gmean) |
|---|---|---|
| 53 | 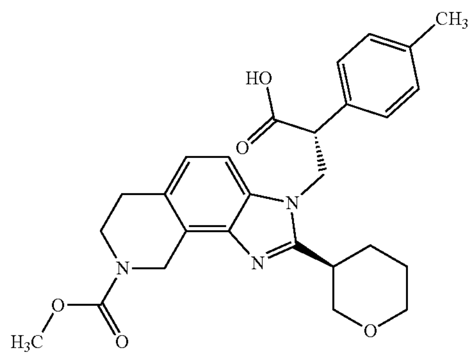 | ++++ |
| 54 | 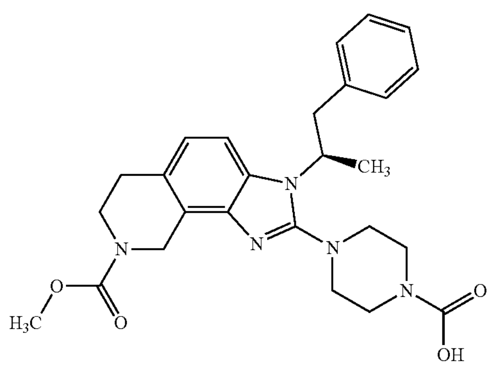 [SMILES: COC(=O)N1CCc2ccc3c(nc(N4CCN(C(=O)O)CC4)n3[C@H](C)Cc3ccccc3)c2C1] | ++++ |
| 55 | 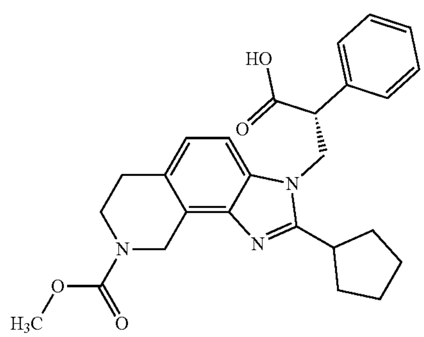 [SMILES: COC(=O)N1CCc2ccc3c(nc(C4CCCC4)n3C[C@H](C(=O)O)c3ccccc3)c2C1] | ++++ |
| 56 | 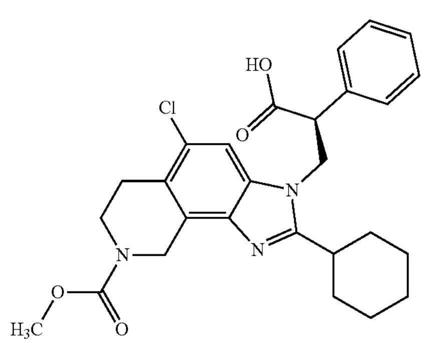 [SMILES: COC(=O)N1CCc2c(Cl)cc3c(nc(C4CCCCC4)n3C[C@@H](C(=O)O)c3ccccc3)c2C1] | ++++ |

TABLE 1-continued

| | IC$_{50}$ Values | |
|---|---|---|
| Cpd. No. | Structure | BROMO IC$_{50}$ TRF TB CBP (μM gmean) |
| 57 | | ++++ |
| 58 | | ++++ |
| 59 | | ++++ |

TABLE 1-continued

| Cpd. No. | Structure | BROMO IC$_{50}$ TRF TB CBP (μM gmean) |
|---|---|---|
| 60 | 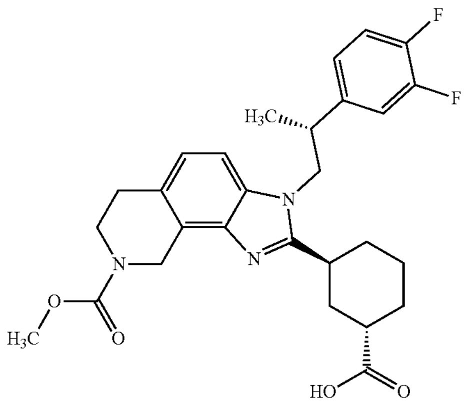 [SMILES: COC(=O)N1CCc2ccc3c(nc([C@H]4CCC[C@H](C(=O)O)C4)n3C[C@H](C)c3ccc(F)c(F)c3)c2C1] | ++++ |
| 61 | 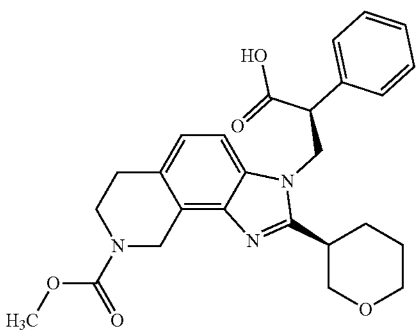 [SMILES: COC(=O)N1CCc2ccc3c(nc([C@H]4CCCOC4)n3C[C@@H](C(=O)O)c3ccccc3)c2C1] | ++++ |
| 62 | 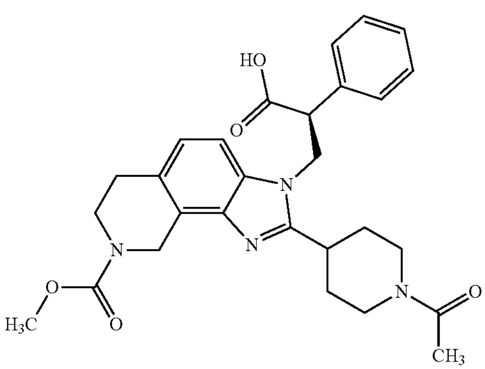 [SMILES: COC(=O)N1CCc2ccc3c(nc(C4CCN(C(C)=O)CC4)n3C[C@@H](C(=O)O)c3ccccc3)c2C1] | ++++ |
| 63 | 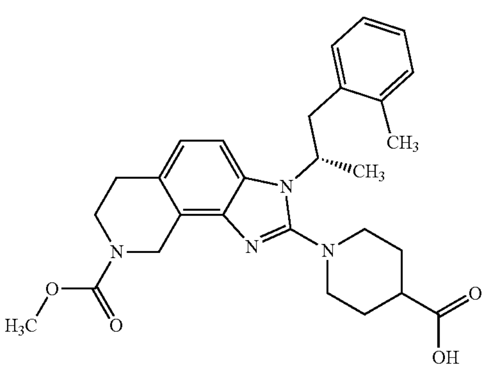 [SMILES: COC(=O)N1CCc2ccc3c(nc(N4CCC(C(=O)O)CC4)n3[C@@H](C)Cc3ccccc3C)c2C1] | ++++ |

TABLE 1-continued

| | IC$_{50}$ Values | |
|---|---|---|
| Cpd. No. | Structure | BROMO IC$_{50}$ TRF TB CBP (μM gmean) |
| 64 | | ++++ |
| 65 | | ++++ |
| 66 | | ++++ |
| 67 | | ++++ |

TABLE 1-continued

| Cpd. No. | Structure | BROMO IC$_{50}$ TRF TB CBP (μM gmean) |
|---|---|---|
| 68 | 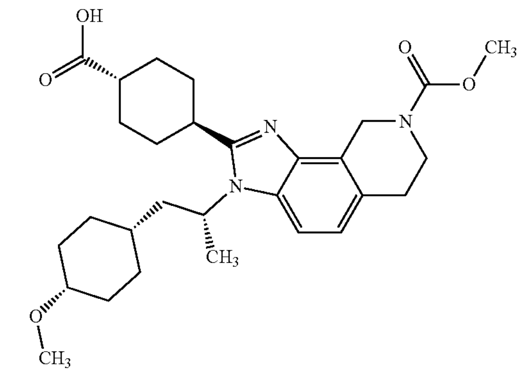 [SMILES: COC(=O)N1CCc2ccc3c(nc([C@H]4CC[C@H](C(=O)O)CC4)n3[C@H](C)C[C@H]3CC[C@@H](OC)CC3)c2C1] | ++++ |
| 69 | 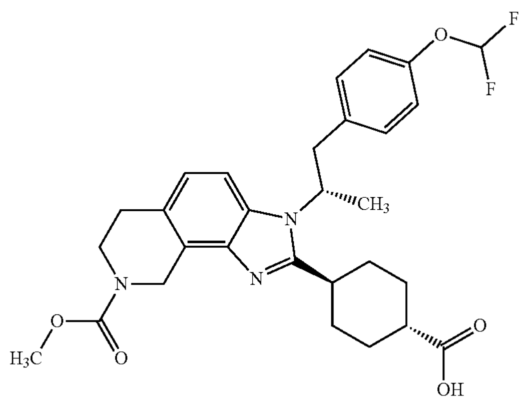 [SMILES: COC(=O)N1CCc2ccc3c(nc([C@H]4CC[C@H](C(=O)O)CC4)n3[C@@H](C)Cc3ccc(OC(F)F)cc3)c2C1] | ++++ |
| 70 | 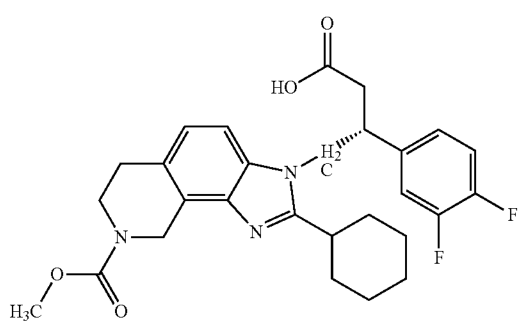 | ++++ |
| 71 | 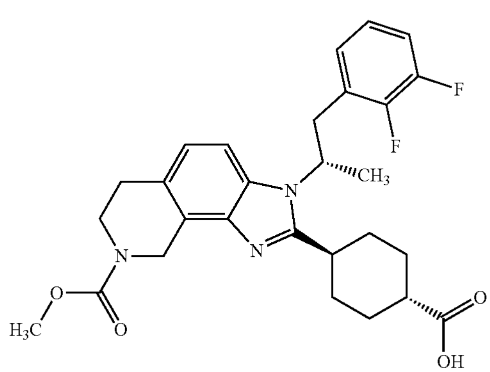 [SMILES: COC(=O)N1CCc2ccc3c(nc([C@H]4CC[C@H](C(=O)O)CC4)n3[C@@H](C)Cc3cccc(F)c3F)c2C1] | ++++ |

TABLE 1-continued

| Cpd. No. | Structure | BROMO IC$_{50}$ TRF TB CBP (μM gmean) |
|---|---|---|
| 72 | 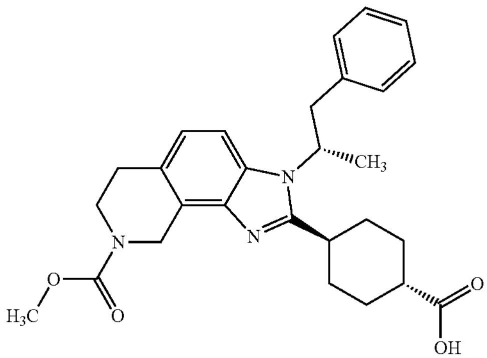 [SMILES: COC(=O)N1CCc2ccc3c(nc([C@H]4CC[C@H](C(=O)O)CC4)n3[C@@H](C)Cc3ccccc3)c2C1] | ++++ |
| 73 | 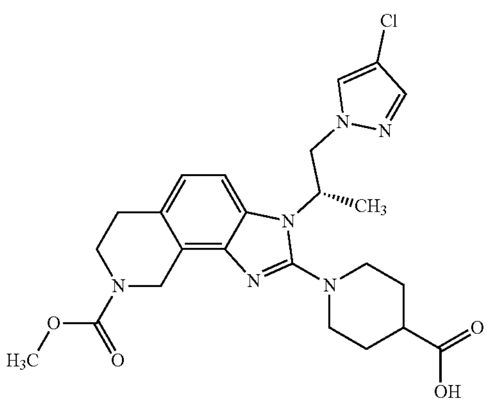 | ++++ |
| 74 | 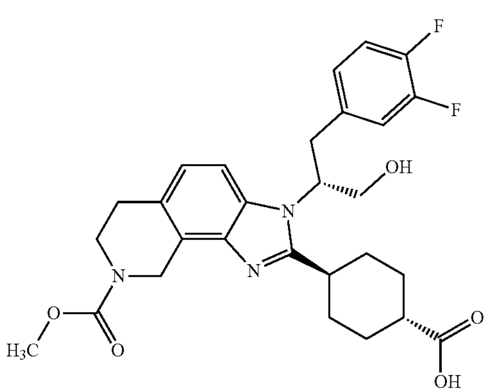 [SMILES: COC(=O)N1CCc2ccc3c(nc([C@H]4CC[C@H](C(=O)O)CC4)n3[C@@H](CO)Cc3ccc(F)c(F)c3)c2C1] | ++++ |

TABLE 1-continued

| Cpd. No. | Structure | BROMO IC$_{50}$ TRF TB CBP (μM gmean) |
|---|---|---|
| 75 | 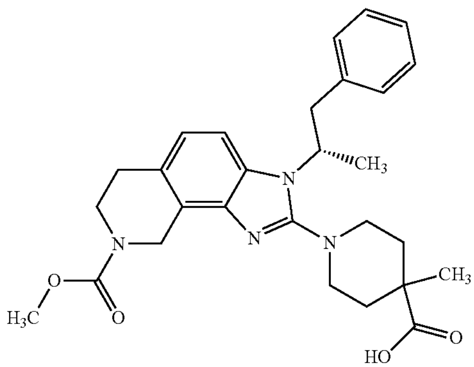 [SMILES: COC(=O)N1CCc2ccc3c(nc(N4CCC(C)(C(=O)O)CC4)n3[C@@H](C)Cc3ccccc3)c2C1] | ++++ |
| 76 | 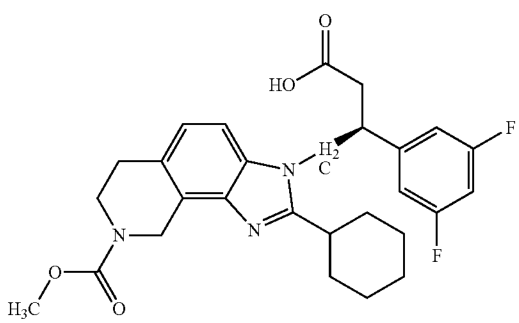 [SMILES: COC(=O)N1CCc2ccc3c(nc(C4CCCCC4)n3C[C@@H](CC(=O)O)c3cc(F)cc(F)c3)c2C1] | ++++ |
| 77 | 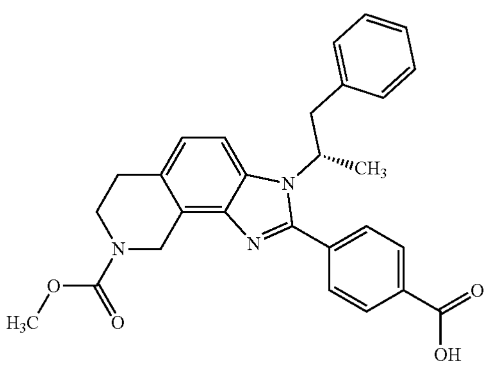 [SMILES: COC(=O)N1CCc2ccc3c(nc(-c4ccc(C(=O)O)cc4)n3[C@@H](C)Cc3ccccc3)c2C1] | ++++ |
| 78 | 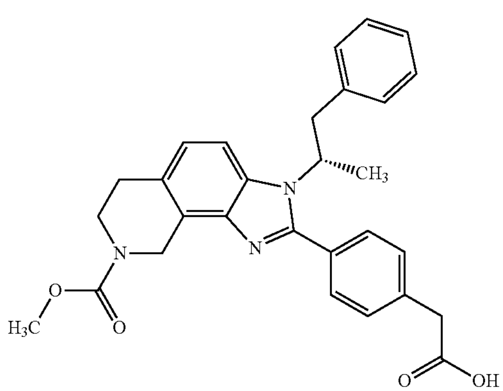 [SMILES: COC(=O)N1CCc2ccc3c(nc(-c4ccc(CC(=O)O)cc4)n3[C@@H](C)Cc3ccccc3)c2C1] | ++++ |

TABLE 1-continued

| Cpd. No. | Structure | IC$_{50}$ Values BROMO IC$_{50}$ TRF TB CBP (μM gmean) |
|---|---|---|
| 79 | 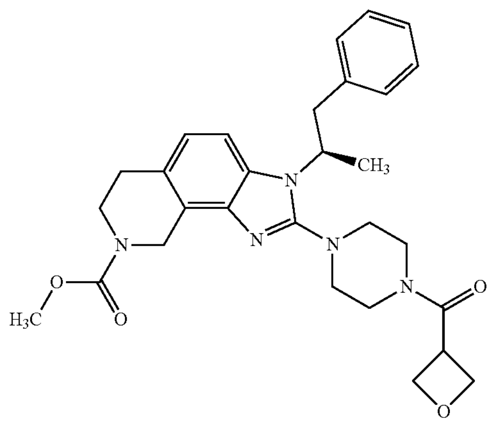 [SMILES: COC(=O)N1CCc2ccc3c(nc(N4CCN(C(=O)C5COC5)CC4)n3[C@H](C)Cc3ccccc3)c2C1] | ++++ |
| 80 | 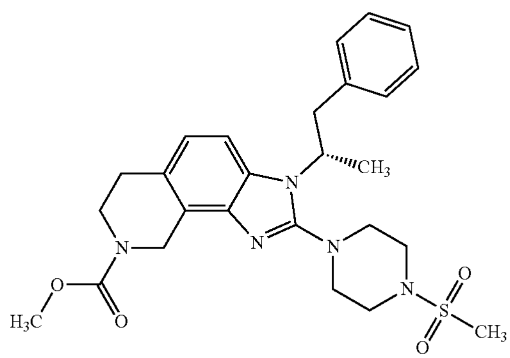 | ++++ |
| 81 | 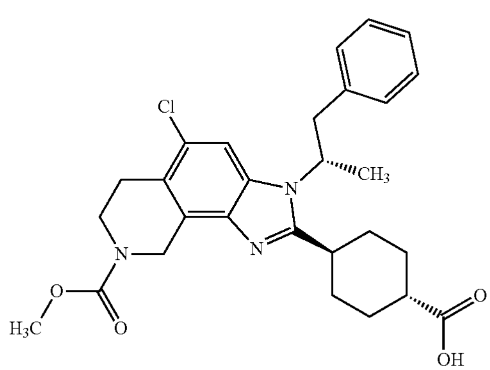 [SMILES: COC(=O)N1CCc2c(Cl)cc3c(nc([C@H]4CC[C@H](C(=O)O)CC4)n3[C@@H](C)Cc3ccccc3)c2C1] | ++++ |

TABLE 1-continued

| Cpd. No. | Structure | IC50 Values BROMO IC50 TRF TB CBP (μM gmean) |
|---|---|---|
| 82 | 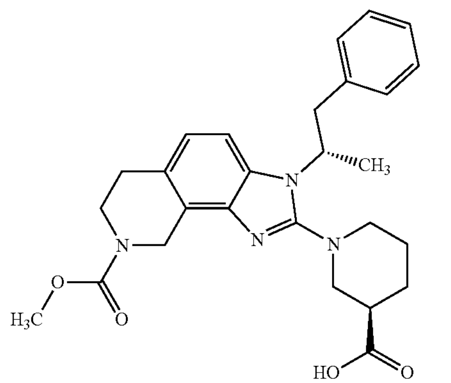 | ++++ |
| 83 | 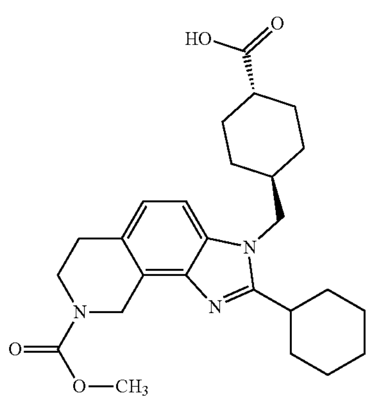 [SMILES: COC(=O)N1CCc2ccc3c(nc(C4CCCCC4)n3C[C@H]3CC[C@H](C(=O)O)CC3)c2C1] | ++++ |
| 84 | 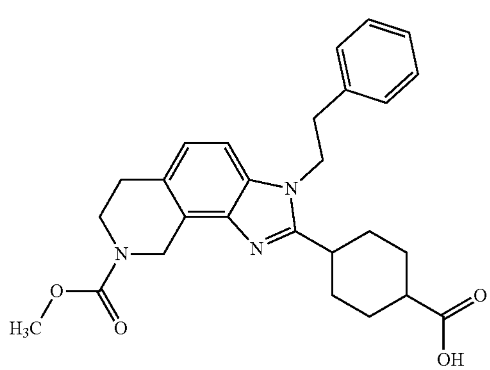 [SMILES: COC(=O)N1CCc2ccc3c(nc(C4CCC(C(=O)O)CC4)n3CCc3ccccc3)c2C1] | ++++ |

TABLE 1-continued

| | IC$_{50}$ Values | |
|---|---|---|
| Cpd. No. | Structure | BROMO IC$_{50}$ TRF TB CBP (μM gmean) |
| 85 | [Structure] | ++++ |
| 86 | [Structure] | ++++ |
| 87 | [Structure] | ++++ |
| 88 | [Structure] | ++++ |

TABLE 1-continued

| Cpd. No. | Structure | BROMO IC$_{50}$ TRF TB CBP (μM gmean) |
|---|---|---|
| 89 | 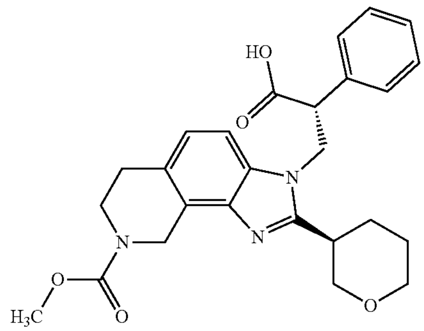 [SMILES: COC(=O)N1CCc2ccc3c(nc([C@H]4CCCOC4)n3C[C@H](C(=O)O)c3ccccc3)c2C1] | ++++ |
| 90 | 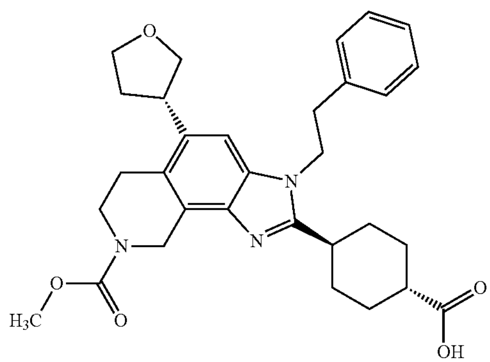 [SMILES: COC(=O)N1CCc2c([C@@H]3CCOC3)cc3c(nc([C@H]4CC[C@H](C(=O)O)CC4)n3CCc3ccccc3)c2C1] | ++++ |
| 91 | 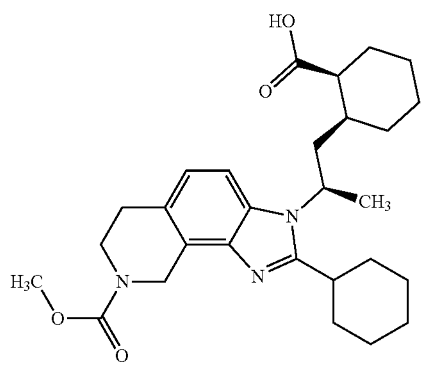 [SMILES: COC(=O)N1CCc2ccc3c(nc(C4CCCCC4)n3[C@H](C)C[C@@H]3CCCC[C@@H]3C(=O)O)c2C1] | ++++ |
| 92 | 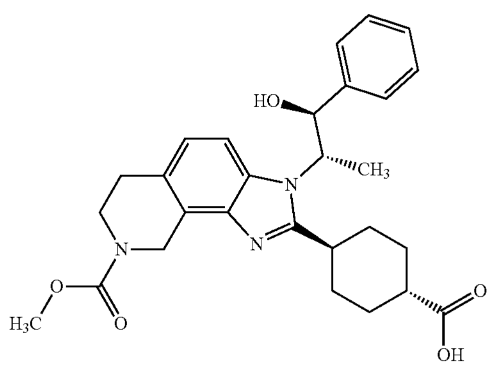 [SMILES: COC(=O)N1CCc2ccc3c(nc([C@H]4CC[C@H](C(=O)O)CC4)n3[C@@H](C)[C@@H](O)c3ccccc3)c2C1] | ++++ |

TABLE 1-continued

| | IC$_{50}$ Values | |
|---|---|---|
| Cpd. No. | Structure | BROMO IC$_{50}$ TRF TB CBP (μM gmean) |
| 93 | | ++++ |
| 94 | | ++++ |
| 95 | | ++++ |

TABLE 1-continued

| | IC$_{50}$ Values | |
|---|---|---|
| Cpd. No. | Structure | BROMO IC$_{50}$ TRF TB CBP (μM gmean) |
| 96 | | ++++ |
| 97 | | ++++ |
| 98 | | ++++ |
| 99 | | ++++ |

TABLE 1-continued

| Cpd. No. | Structure | BROMO IC$_{50}$ TRF TB CBP (μM gmean) |
|---|---|---|
| 100 | 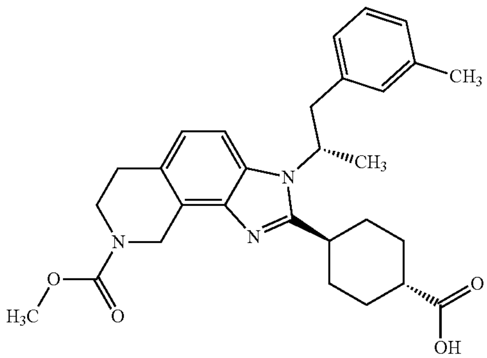 [SMILES: COC(=O)N1CCc2ccc3c(nc([C@H]4CC[C@H](C(=O)O)CC4)n3[C@@H](C)Cc3cccc(C)c3)c2C1] | ++++ |
| 101 | 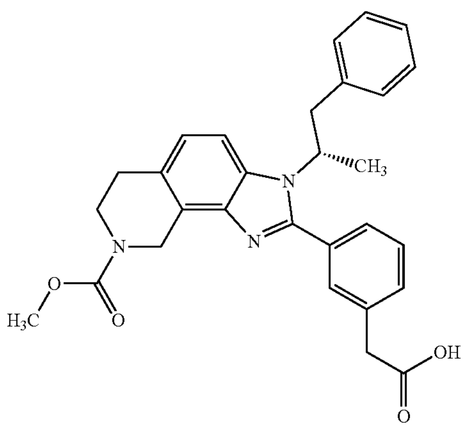 [SMILES: COC(=O)N1CCc2ccc3c(nc(-c4cccc(CC(=O)O)c4)n3[C@@H](C)Cc3ccccc3)c2C1] | ++++ |
| 102 | 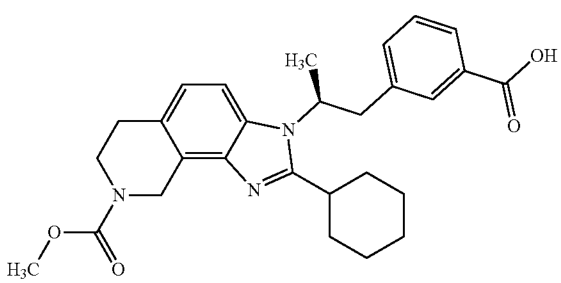 | ++++ |
| 103 | 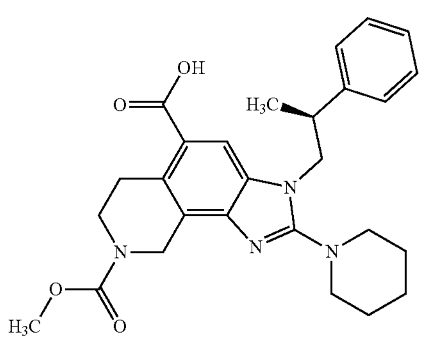 [SMILES: COC(=O)N1CCc2c(C(=O)O)cc3c(nc(N4CCCCC4)n3C[C@@H](C)c3ccccc3)c2C1] | ++++ |

TABLE 1-continued

| Cpd. No. | Structure | BROMO IC$_{50}$ TRF TB CBP (µM gmean) |
|---|---|---|
| 104 | 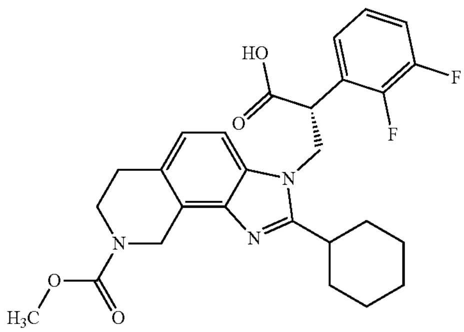 [SMILES: COC(=O)N1CCc2ccc3c(nc(C4CCCCC4)n3C[C@H](C(=O)O)c3cccc(F)c3F)c2C1] | ++++ |
| 105 | 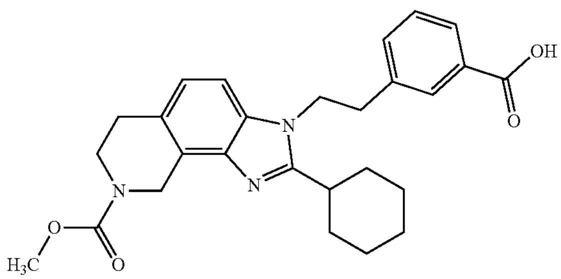 [SMILES: COC(=O)N1CCc2ccc3c(nc(C4CCCCC4)n3CCc3cccc(C(=O)O)c3)c2C1] | ++++ |
| 106 | 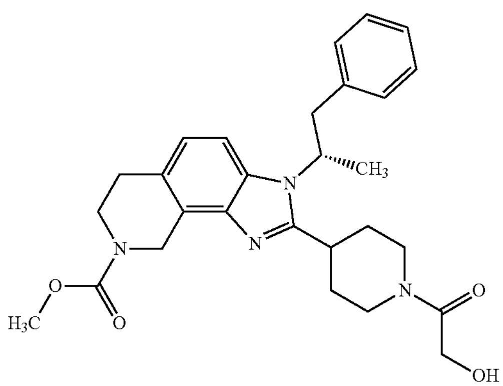 [SMILES: COC(=O)N1CCc2ccc3c(nc(C4CCN(C(=O)CO)CC4)n3[C@@H](C)Cc3ccccc3)c2C1] | ++++ |
| 107 | 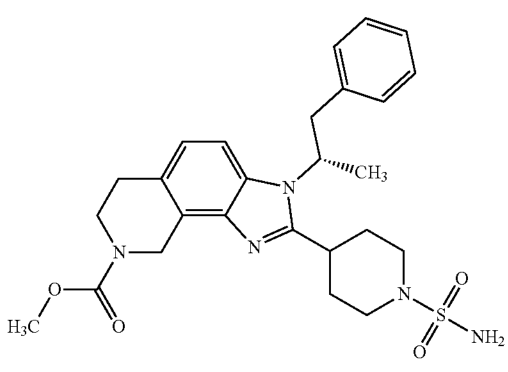 [SMILES: COC(=O)N1CCc2ccc3c(nc(C4CCN(S(N)(=O)=O)CC4)n3[C@@H](C)Cc3ccccc3)c2C1] | ++++ |

TABLE 1-continued

| | | IC$_{50}$ Values |
|---|---|---|
| Cpd. No. | Structure | BROMO IC$_{50}$ TRF TB CBP (μM gmean) |
| 108 | | ++++ |
| 109 | | ++++ |
| 110 | | ++++ |
| 111 | | ++++ |

TABLE 1-continued

| | IC$_{50}$ Values | |
|---|---|---|
| Cpd. No. | Structure | BROMO IC$_{50}$ TRF TB CBP (μM gmean) |
| 112 | (structure) | ++++ |
| 113 | (structure) | ++++ |
| 114 | (structure) | ++++ |

TABLE 1-continued

| | | IC$_{50}$ Values |
|---|---|---|
| Cpd. No. | Structure | BROMO IC$_{50}$ TRF TB CBP (µM gmean) |
| 115 | | ++++ |
| 116 | | ++++ |
| 117 | | ++++ |

TABLE 1-continued

| Cpd. No. | Structure | BROMO IC$_{50}$ TRF TB CBP (μM gmean) |
|---|---|---|
| 118 | 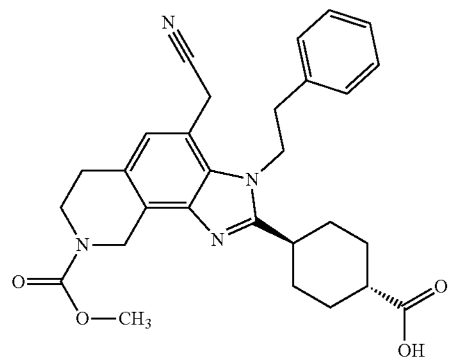 [SMILES: COC(=O)N1CCc2cc(CC#N)c3c(nc([C@H]4CC[C@H](C(=O)O)CC4)n3CCc3ccccc3)c2C1] | ++++ |
| 119 | 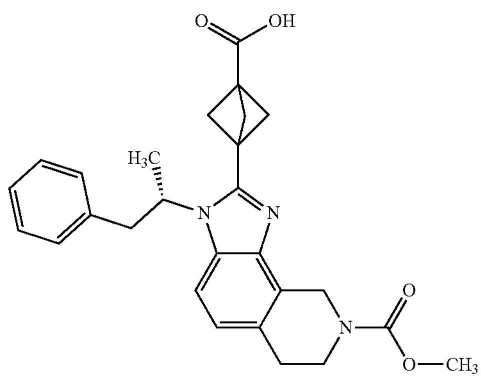 [SMILES: COC(=O)N1CCc2ccc3c(nc(C45CC(C(=O)O)(C4)C5)n3[C@@H](C)Cc3ccccc3)c2C1] | ++++ |
| 120 | 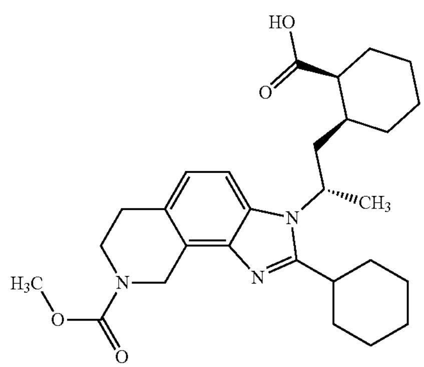 [SMILES: COC(=O)N1CCc2ccc3c(nc(C4CCCCC4)n3[C@@H](C)C[C@@H]3CCCC[C@@H]3C(=O)O)c2C1] | ++++ |
| 121 | 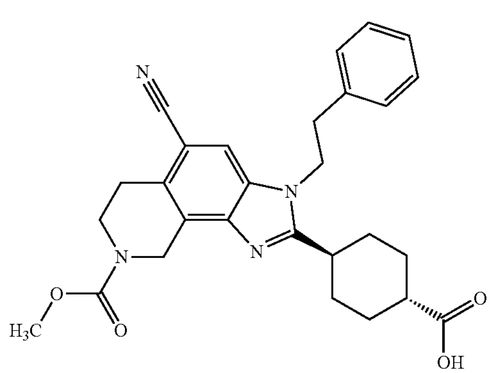 [SMILES: COC(=O)N1CCc2c(C#N)cc3c(nc([C@H]4CC[C@H](C(=O)O)CC4)n3CCc3ccccc3)c2C1] | ++++ |

TABLE 1-continued

| Cpd. No. | Structure | BROMO IC$_{50}$ TRF TB CBP (μM gmean) |
|---|---|---|
| 122 | 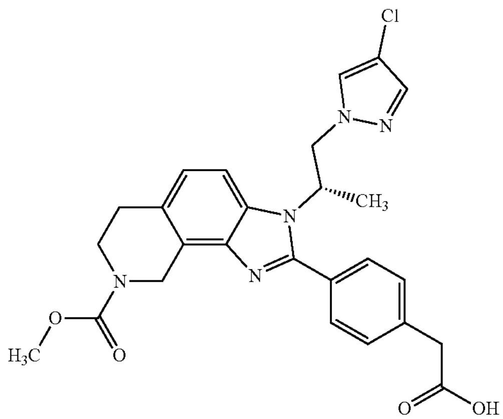 [SMILES: COC(=O)N1CCc2ccc3c(nc(-c4ccc(CC(=O)O)cc4)n3[C@@H](C)Cn3cc(Cl)cn3)c2C1] | ++++ |
| 123 | 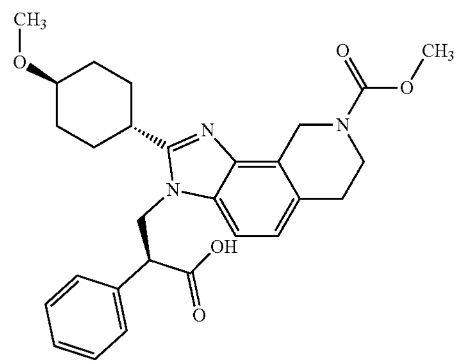 [SMILES: COC(=O)N1CCc2ccc3c(nc([C@H]4CC[C@H](OC)CC4)n3C[C@@H](C(=O)O)c3ccccc3)c2C1] | ++++ |
| 124 | 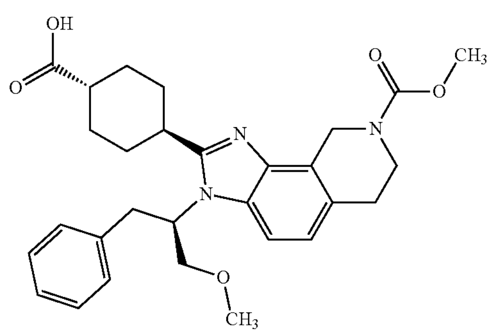 [SMILES: COC[C@@H](Cc1ccccc1)n1c2ccc3c(c2nc1[C@H]1CC[C@H](C(=O)O)CC1)CN(C(=O)OC)CC3] | ++++ |
| 125 | 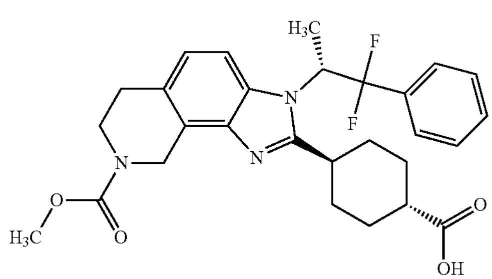 [SMILES: COC(=O)N1CCc2ccc3c(nc([C@H]4CC[C@H](C(=O)O)CC4)n3[C@H](C)C(F)(F)c3ccccc3)c2C1] | ++++ |

TABLE 1-continued

| Cpd. No. | Structure | BROMO IC$_{50}$ TRF TB CBP (μM gmean) |
|---|---|---|
| 126 | 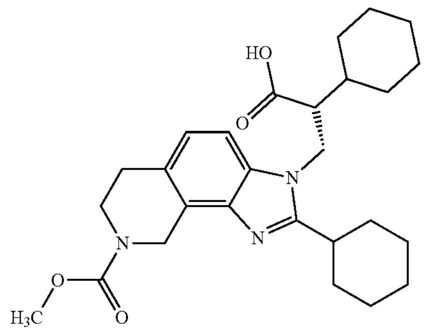 | ++++ |
| 127 | 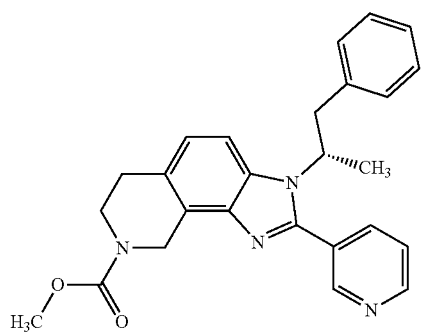 | ++++ |
| 128 | 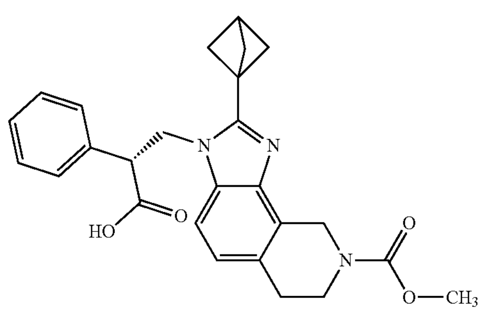 [SMILES: COC(=O)N1CCc2ccc3c(nc(C45CC(C4)C5)n3C[C@H](C(=O)O)c3ccccc3)c2C1] | ++++ |
| 129 | 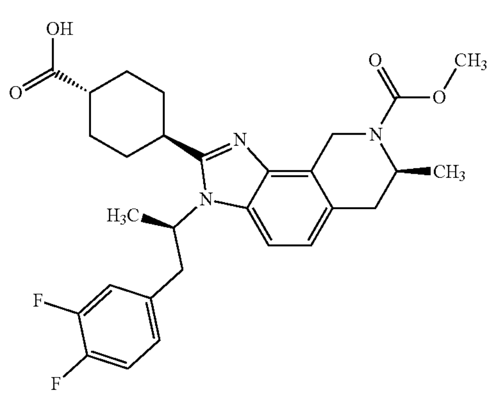 [SMILES: COC(=O)N1Cc2c(ccc3c2nc([C@H]2CC[C@H](C(=O)O)CC2)n3[C@H](C)Cc2ccc(F)c(F)c2)C[C@@H]1C] | ++++ |

TABLE 1-continued
| Cpd. No. | Structure | BROMO IC$_{50}$ TRF TB CBP (μM gmean) |
|---|---|---|
| 130 | 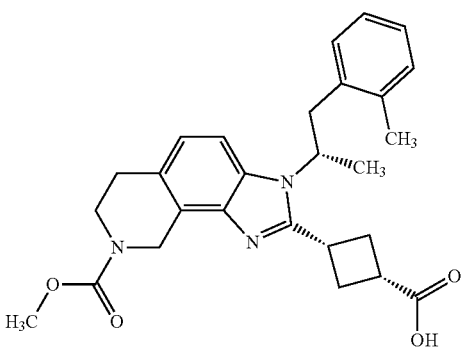 [SMILES: COC(=O)N1CCc2ccc3c(nc([C@H]4C[C@@H](C(=O)O)C4)n3[C@@H](C)Cc3ccccc3C)c2C1] | ++++ |
| 131 | 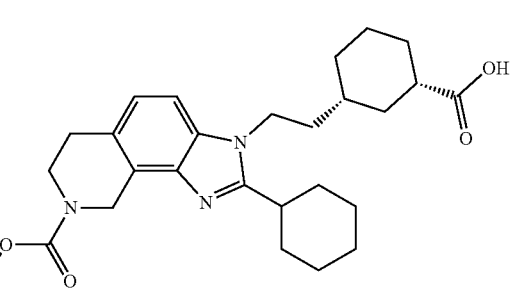 | ++++ |
| 132 | 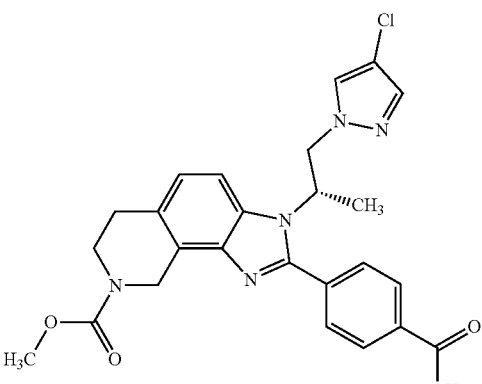 | ++++ |
| 133 | 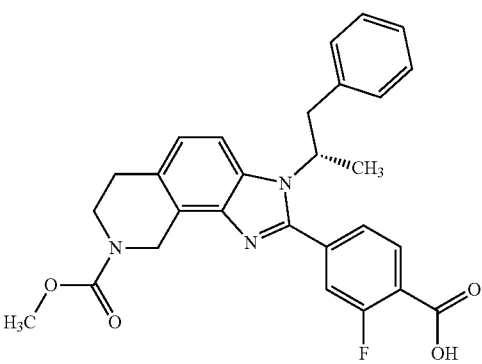 [SMILES: COC(=O)N1CCc2ccc3c(nc(-c4ccc(C(=O)O)c(F)c4)n3[C@@H](C)Cc3ccccc3)c2C1] | ++++ |

TABLE 1-continued

| Cpd. No. | Structure | BROMO IC$_{50}$ TRF TB CBP (µM gmean) |
|---|---|---|
| 134 | 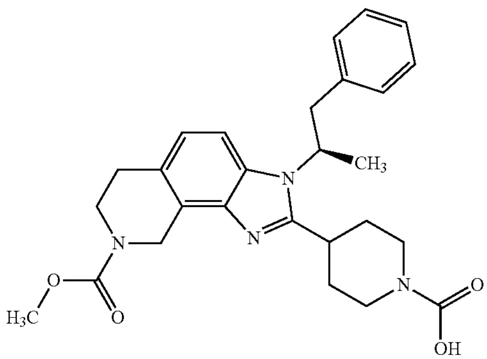 | ++++ |
| 135 | 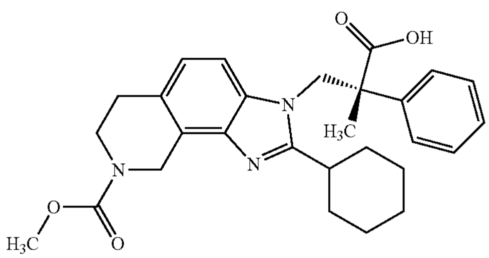 [SMILES: COC(=O)N1CCc2ccc3c(nc(C4CCCCC4)n3C[C@](C)(C(=O)O)c3ccccc3)c2C1] | ++++ |
| 136 | 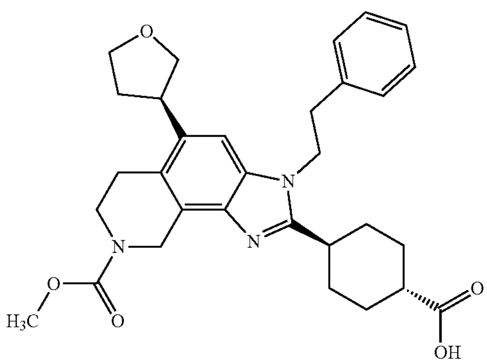 [SMILES: COC(=O)N1CCc2c([C@H]3CCOC3)cc3c(nc([C@H]4CC[C@H](C(=O)O)CC4)n3CCc3ccccc3)c2C1] | ++++ |
| 137 | 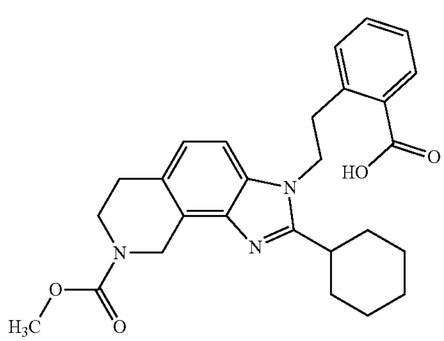 [SMILES: COC(=O)N1CCc2ccc3c(nc(C4CCCCC4)n3CCc3ccccc3C(=O)O)c2C1] | ++++ |

TABLE 1-continued

| Cpd. No. | Structure | BROMO IC$_{50}$ TRF TB CBP (μM gmean) |
|---|---|---|
| 138 | 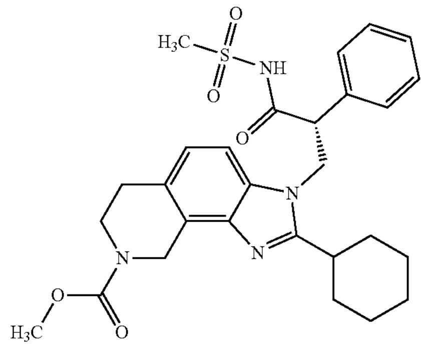 [SMILES: COC(=O)N1CCc2ccc3c(nc(C4CCCCC4)n3C[C@H](C(=O)NS(C)(=O)=O)c3ccccc3)c2C1] | ++++ |
| 139 | 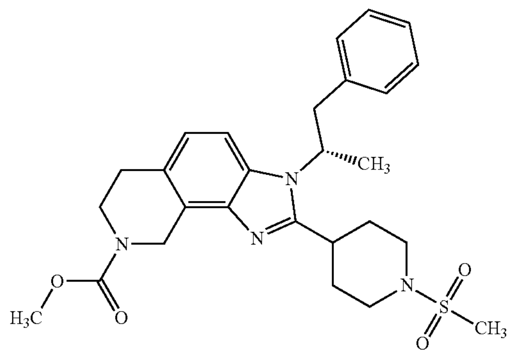 | ++++ |
| 140 | 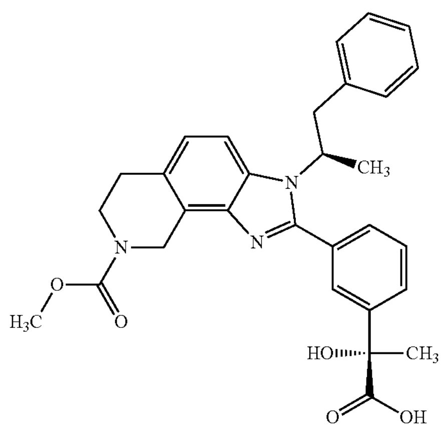 [SMILES: COC(=O)N1CCc2ccc3c(nc(-c4cccc([C@](C)(O)C(=O)O)c4)n3[C@H](C)Cc3ccccc3)c2C1] | ++++ |
| 141 | 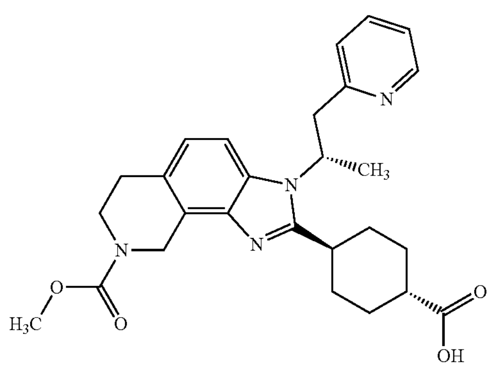 | ++++ |

TABLE 1-continued

| Cpd. No. | Structure | BROMO IC$_{50}$ TRF TB CBP (μM gmean) |
|---|---|---|
| 142 | 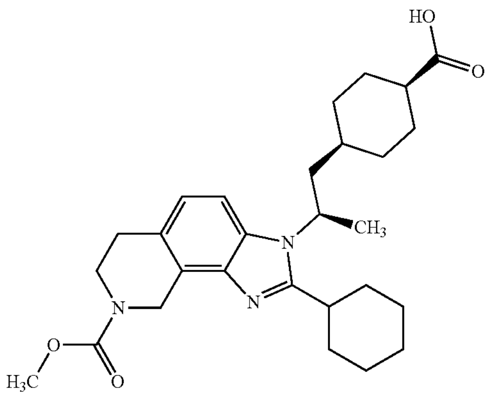 [SMILES: COC(=O)N1CCc2ccc3c(nc(C4CCCCC4)n3[C@H](C)C[C@H]3CC[C@@H](C(=O)O)CC3)c2C1] | ++++ |
| 143 | 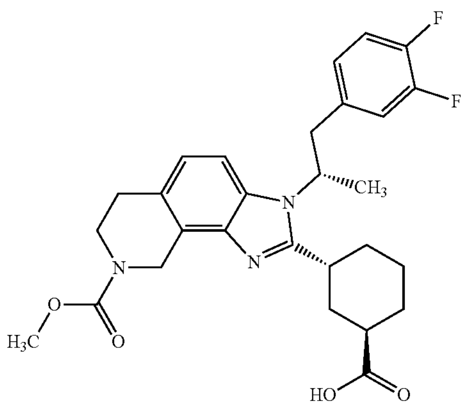 [SMILES: COC(=O)N1CCc2ccc3c(nc([C@@H]4CCC[C@@H](C(=O)O)C4)n3[C@@H](C)Cc3ccc(F)c(F)c3)c2C1] | ++++ |
| 144 | 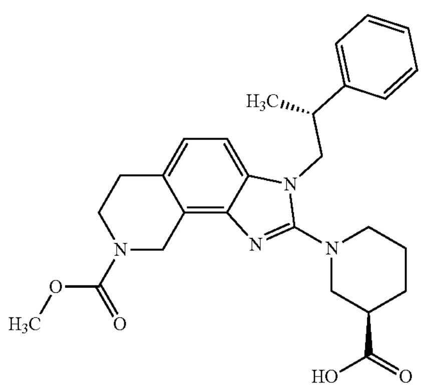 [SMILES: COC(=O)N1CCc2ccc3c(nc(N4CCC[C@@H](C(=O)O)C4)n3C[C@H](C)c3ccccc3)c2C1] | ++++ |
| 145 | 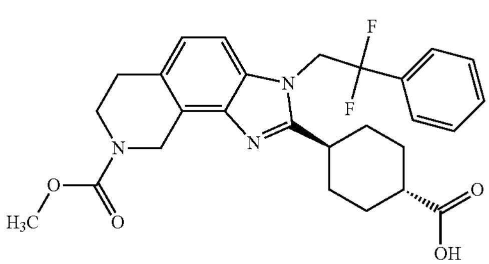 [SMILES: COC(=O)N1CCc2ccc3c(nc([C@H]4CC[C@H](C(=O)O)CC4)n3CC(F)(F)c3ccccc3)c2C1] | ++++ |

TABLE 1-continued

| Cpd. No. | Structure | BROMO IC$_{50}$ TRF TB CBP (μM gmean) |
|---|---|---|
| 146 | | ++++ |
| 147 | | ++++ |
| 148 | | ++++ |
| 149 | | ++++ |

TABLE 1-continued

| Cpd. No. | Structure | BROMO IC$_{50}$ TRF TB CBP (μM gmean) |
|---|---|---|
| 150 | 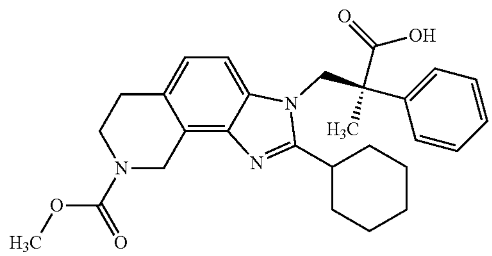 [SMILES: COC(=O)N1CCc2ccc3c(nc(C4CCCCC4)n3C[C@@](C)(C(=O)O)c3ccccc3)c2C1] | ++++ |
| 151 | 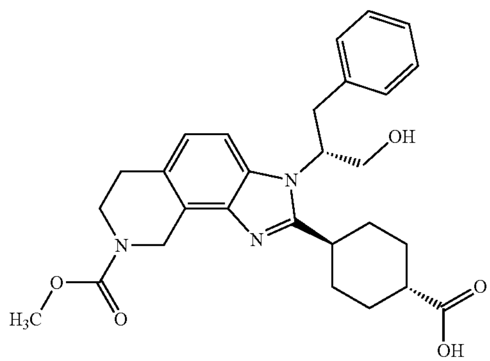 [SMILES: COC(=O)N1CCc2ccc3c(nc([C@H]4CC[C@H](C(=O)O)CC4)n3[C@@H](CO)Cc3ccccc3)c2C1] | ++++ |
| 152 | 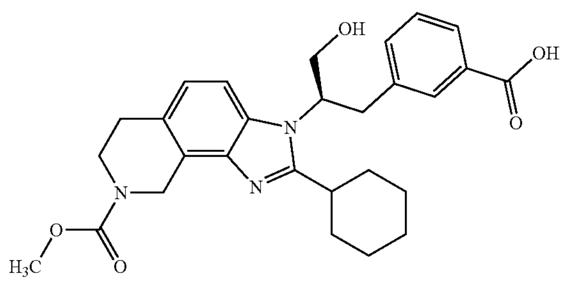 [SMILES: COC(=O)N1CCc2ccc3c(nc(C4CCCCC4)n3[C@@H](CO)Cc3cccc(C(=O)O)c3)c2C1] | ++++ |
| 153 | 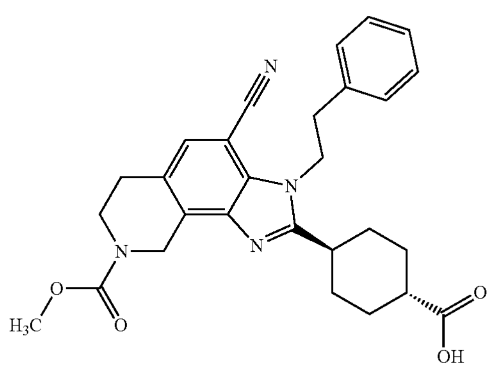 [SMILES: COC(=O)N1CCc2cc(C#N)c3c(nc([C@H]4CC[C@H](C(=O)O)CC4)n3CCc3ccccc3)c2C1] | ++++ |

TABLE 1-continued

| | IC$_{50}$ Values | |
|---|---|---|
| Cpd. No. | Structure | BROMO IC$_{50}$ TRF TB CBP (μM gmean) |
| 154 | *structure* | ++++ |
| 155 | *structure* | ++++ |
| 156 | *structure* | ++++ |
| 157 | *structure* | ++++ |

TABLE 1-continued

| | IC$_{50}$ Values | |
|---|---|---|
| Cpd. No. | Structure | BROMO IC$_{50}$ TRF TB CBP (μM gmean) |
| 158 | | ++++ |
| 159 | | ++++ |
| 160 | | ++++ |
| 161 | | ++++ |

TABLE 1-continued
| | IC$_{50}$ Values | |
|---|---|---|
| Cpd. No. | Structure | BROMO IC$_{50}$ TRF TB CBP (μM gmean) |
| 162 | 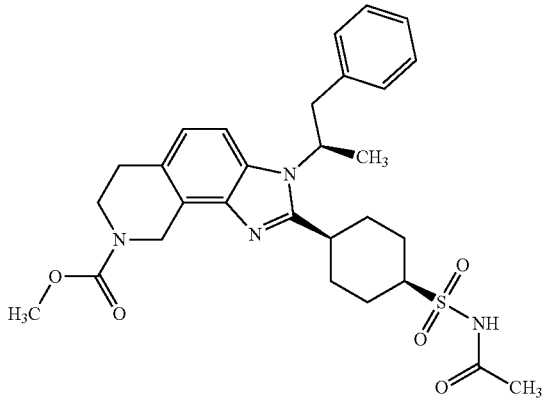 [SMILES: COC(=O)N1CCc2ccc3c(nc([C@H]4CC[C@@H](S(=O)(=O)NC(C)=O)CC4)n3[C@H](C)Cc3ccccc3)c2C1] | ++++ |
| 163 | 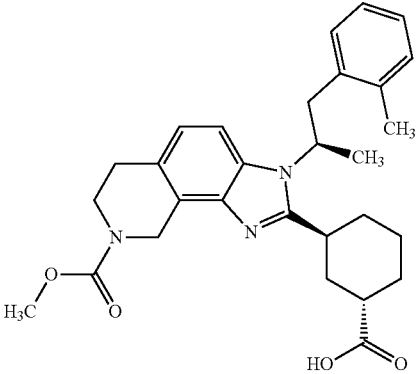 [SMILES: COC(=O)N1CCc2ccc3c(nc([C@H]4CCC[C@H](C(=O)O)C4)n3[C@H](C)Cc3ccccc3C)c2C1] | ++++ |
| 164 | 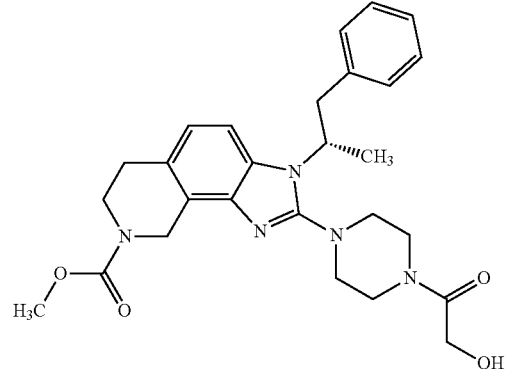 | ++++ |

TABLE 1-continued

| | | IC$_{50}$ Values |
|---|---|---|
| Cpd. No. | Structure | BROMO IC$_{50}$ TRF TB CBP (μM gmean) |
| 165 | | ++++ |
| 166 | | ++++ |
| 167 | | ++++ |
| 168 | | ++++ |

TABLE 1-continued

| | IC$_{50}$ Values | |
|---|---|---|
| Cpd. No. | Structure | BROMO IC$_{50}$ TRF TB CBP (μM gmean) |
| 169 | | ++++ |
| 170 | | ++++ |
| 171 | | ++++ |
| 172 | | ++++ |

TABLE 1-continued
| | | IC$_{50}$ Values |
|---|---|---|
| Cpd. No. | Structure | BROMO IC$_{50}$ TRF TB CBP (μM gmean) |
| 173 | 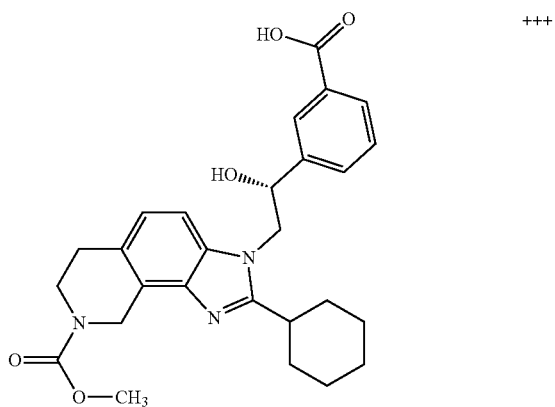 | +++ |
| 174 | 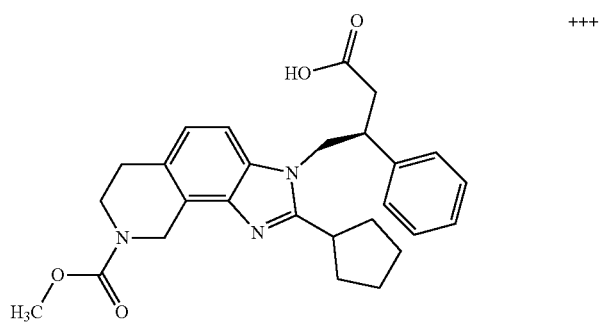 | +++ |
| 175 | 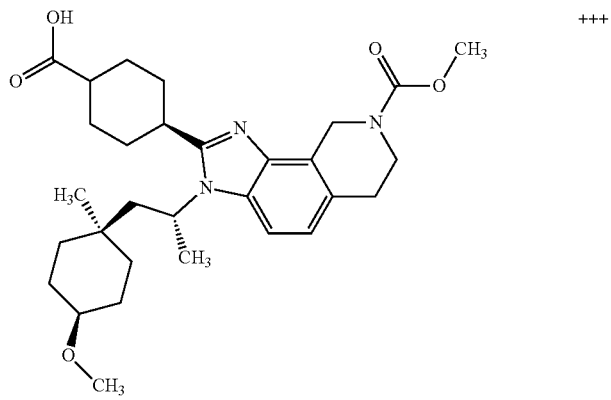 | +++ |

TABLE 1-continued
| | | IC$_{50}$ Values |
| --- | --- | --- |
| Cpd. No. | Structure | BROMO IC$_{50}$ TRF TB CBP (μM gmean) |
| 176 | 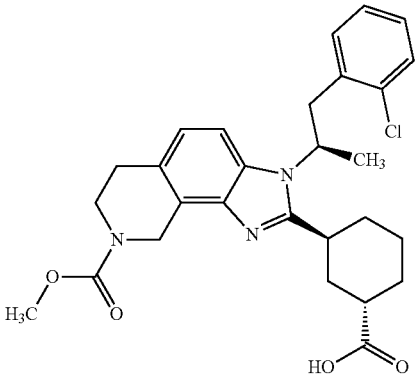 [SMILES: COC(=O)N1CCc2ccc3c(nc([C@H]4CCC[C@H](C(=O)O)C4)n3[C@H](C)Cc3ccccc3Cl)c2C1] | +++ |
| 177 | 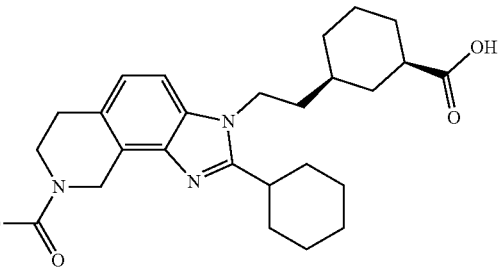 | +++ |
| 178 | 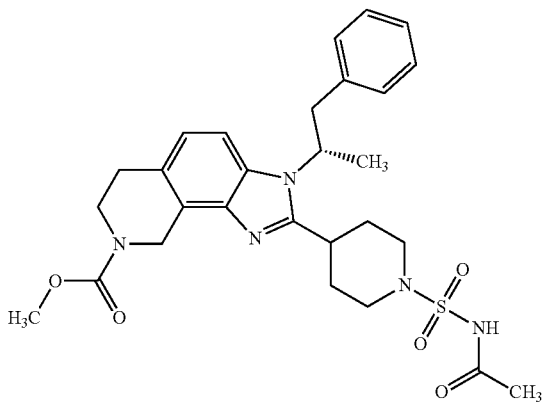 [SMILES: COC(=O)N1CCc2ccc3c(nc(C4CCN(S(=O)(=O)NC(C)=O)CC4)n3[C@@H](C)Cc3ccccc3)c2C1] | +++ |
| 179 | 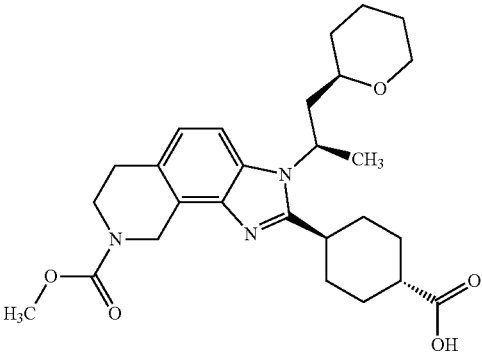 | +++ |

TABLE 1-continued

| | | IC$_{50}$ Values |
|---|---|---|
| Cpd. No. | Structure | BROMO IC$_{50}$ TRF TB CBP (μM gmean) |
| 180 | | +++ |
| 181 | | +++ |
| 182 | | +++ |
| 183 | | +++ |

TABLE 1-continued

| | IC$_{50}$ Values | |
|---|---|---|
| Cpd. No. | Structure | BROMO IC$_{50}$ TRF TB CBP (μM gmean) |
| 184 | | +++ |
| 185 | | +++ |
| 186 | | +++ |

TABLE 1-continued

| Cpd. No. | Structure | BROMO IC$_{50}$ TRF TB CBP (μM gmean) |
|---|---|---|
| 187 | 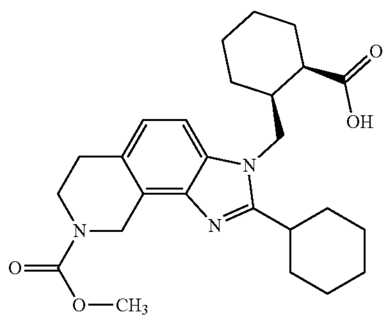 [SMILES: COC(=O)N1CCc2ccc3c(nc(C4CCCCC4)n3C[C@H]3CCCC[C@H]3C(=O)O)c2C1] | +++ |
| 188 | 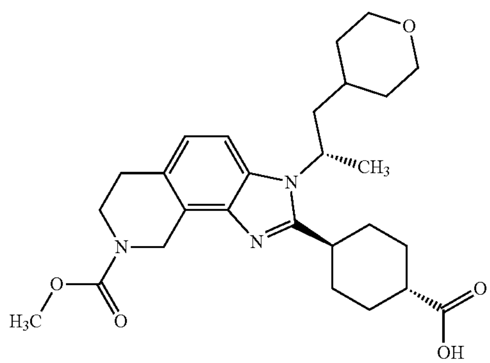 | +++ |
| 189 | 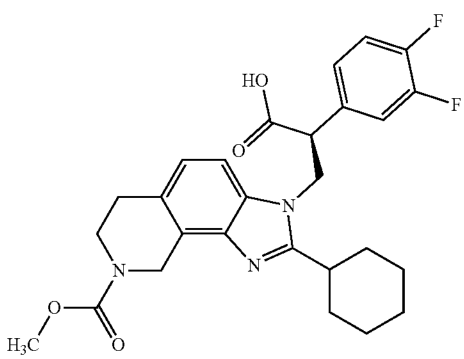 [SMILES: COC(=O)N1CCc2ccc3c(nc(C4CCCCC4)n3C[C@@H](C(=O)O)c3ccc(F)c(F)c3)c2C1] | +++ |
| 190 | 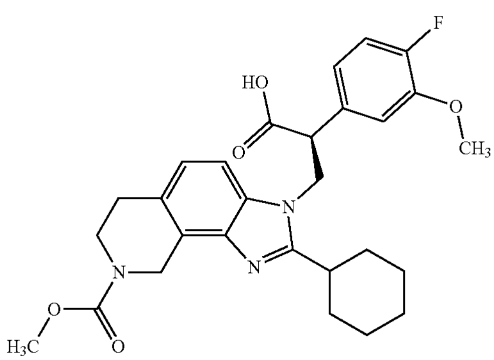 | +++ |

TABLE 1-continued

| Cpd. No. | Structure | IC₅₀ Values BROMO IC₅₀ TRF TB CBP (µM gmean) |
|---|---|---|
| 191 | 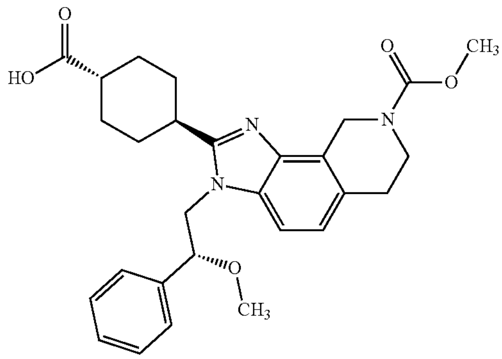 [SMILES: COC(=O)N1CCc2ccc3c(nc([C@H]4CC[C@H](C(=O)O)CC4)n3C[C@H](OC)c3ccccc3)c2C1] | +++ |
| 192 | 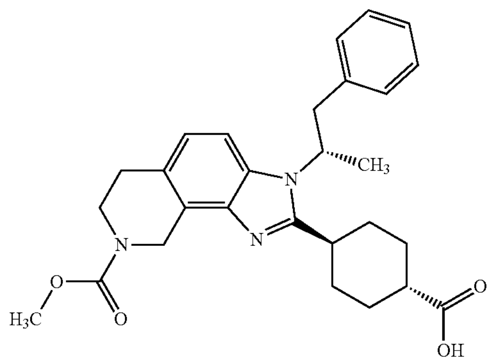 | +++ |
| 193 | 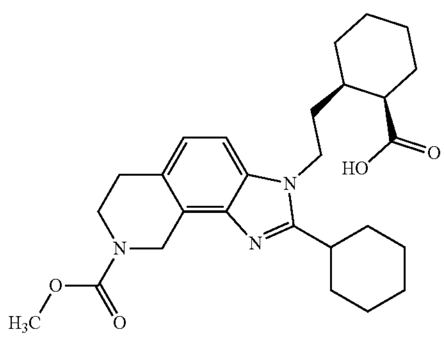 [SMILES: COC(=O)N1CCc2ccc3c(nc(C4CCCCC4)n3CC[C@H]3CCCC[C@H]3C(=O)O)c2C1] | +++ |
| 194 | 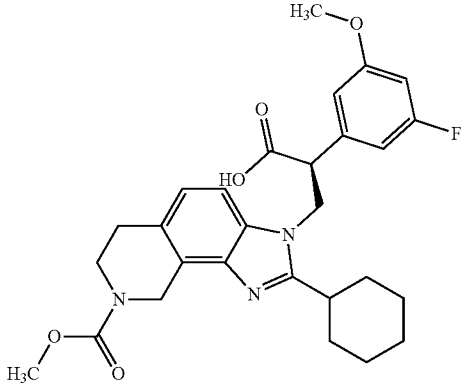 [SMILES: COC(=O)N1CCc2ccc3c(nc(C4CCCCC4)n3C[C@@H](C(=O)O)c3cc(F)cc(OC)c3)c2C1] | +++ |

TABLE 1-continued
| Cpd. No. | Structure | BROMO IC$_{50}$ TRF TB CBP (μM gmean) |
|---|---|---|
| 195 | 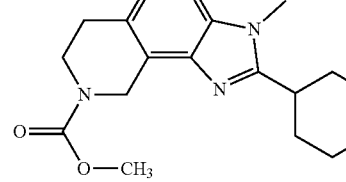 | +++ |
| 196 | 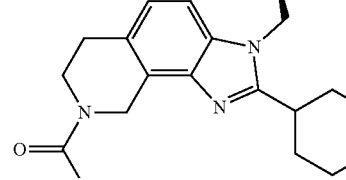 | +++ |
| 197 | 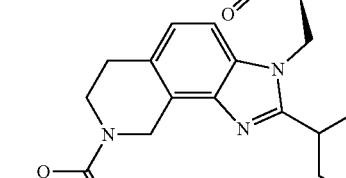 | +++ |
| 198 | 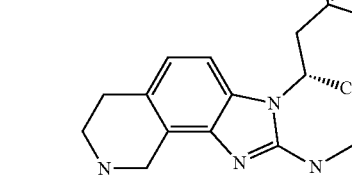 | +++ |

TABLE 1-continued

| | IC$_{50}$ Values | |
|---|---|---|
| Cpd. No. | Structure | BROMO IC$_{50}$ TRF TB CBP (μM gmean) |
| 199 | | +++ |
| 200 | | +++ |
| 201 | | +++ |

TABLE 1-continued

| | IC$_{50}$ Values | |
|---|---|---|
| Cpd. No. | Structure | BROMO IC$_{50}$ TRF TB CBP (μM gmean) |
| 202 | ![structure] | +++ |
| 203 | ![structure] | +++ |
| 204 | ![structure] | +++ |
| 205 | ![structure] | +++ |

TABLE 1-continued

| | IC$_{50}$ Values | |
|---|---|---|
| Cpd. No. | Structure | BROMO IC$_{50}$ TRF TB CBP (μM gmean) |
| 206 | | +++ |
| 207 | | +++ |
| 208 | | +++ |

TABLE 1-continued

| | IC$_{50}$ Values | |
|---|---|---|
| Cpd. No. | Structure | BROMO IC$_{50}$ TRF TB CBP (μM gmean) |
| 209 | | +++ |
| 210 | | +++ |
| 211 | | +++ |

TABLE 1-continued

| | IC$_{50}$ Values | |
|---|---|---|
| Cpd. No. | Structure | BROMO IC$_{50}$ TRF TB CBP (μM gmean) |
| 212 | | +++ |
| 213 | | +++ |
| 214 | | +++ |
| 215 | | +++ |

TABLE 1-continued
| Cpd. No. | Structure | BROMO IC$_{50}$ TRF TB CBP (µM gmean) |
|---|---|---|
| 216 | 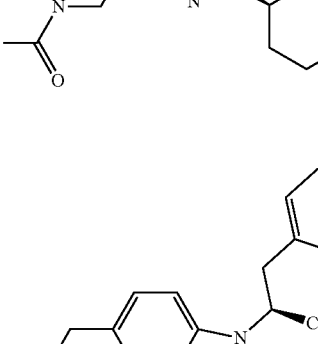 | +++ |
| 217 | 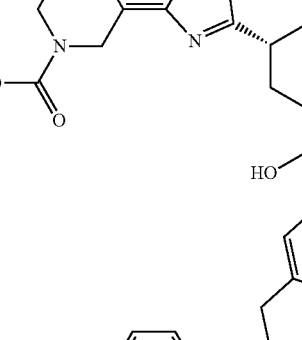 | +++ |
| 218 | 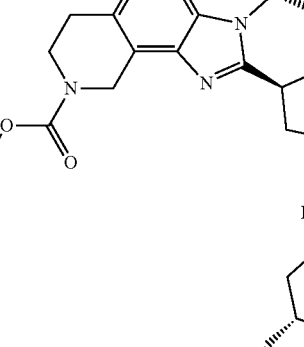 | +++ |
| 219 | 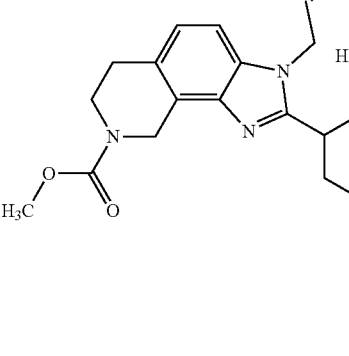 | +++ |

TABLE 1-continued

| Cpd. No. | Structure | BROMO IC$_{50}$ TRF TB CBP (μM gmean) |
|---|---|---|
| 220 | 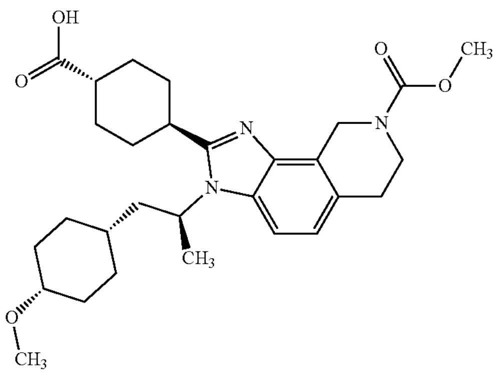 [SMILES: COC(=O)N1CCc2ccc3c(nc([C@H]4CC[C@H](C(=O)O)CC4)n3[C@@H](C)C[C@H]3CC[C@@H](OC)CC3)c2C1] | +++ |
| 221 | 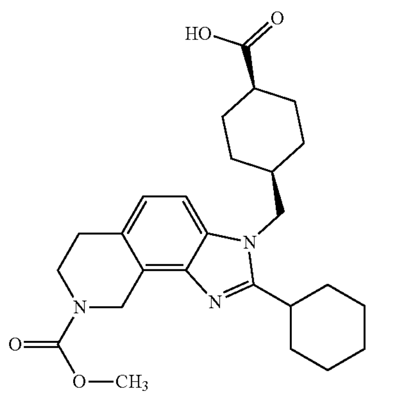 [SMILES: COC(=O)N1CCc2ccc3c(nc(C4CCCCC4)n3C[C@H]3CC[C@@H](C(=O)O)CC3)c2C1] | +++ |
| 222 | 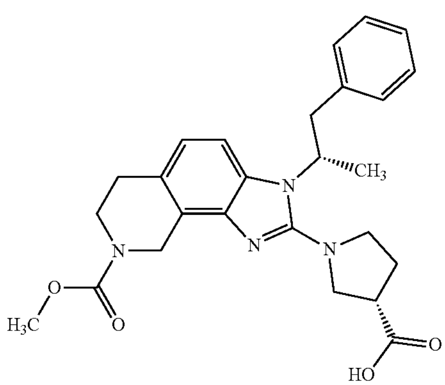 [SMILES: COC(=O)N1CCc2ccc3c(nc(N4CC[C@H](C(=O)O)C4)n3[C@@H](C)Cc3ccccc3)c2C1] | +++ |
| 223 | 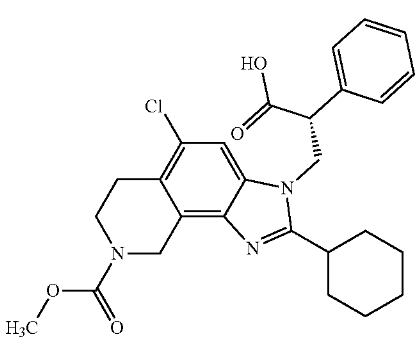 | +++ |

TABLE 1-continued

| Cpd. No. | Structure | IC$_{50}$ Values BROMO IC$_{50}$ TRF TB CBP (μM gmean) |
|---|---|---|
| 224 | 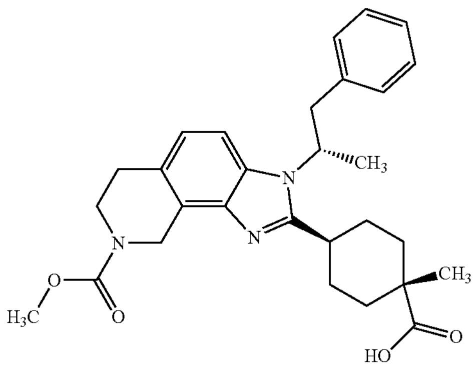 [SMILES: COC(=O)N1CCc2ccc3c(nc([C@H]4CC[C@](C)(C(=O)O)CC4)n3[C@@H](C)Cc3ccccc3)c2C1] | +++ |
| 225 | 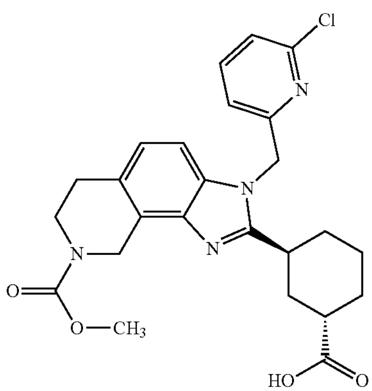 [SMILES: COC(=O)N1CCc2ccc3c(nc([C@H]4CCC[C@H](C(=O)O)C4)n3Cc3cccc(Cl)n3)c2C1] | +++ |
| 226 | 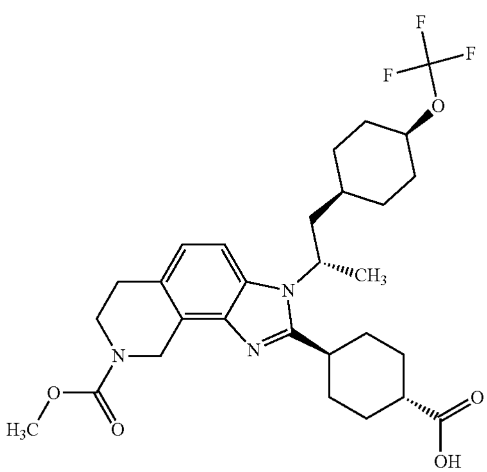 [SMILES: COC(=O)N1CCc2ccc3c(nc([C@H]4CC[C@H](C(=O)O)CC4)n3[C@@H](C)C[C@H]3CC[C@@H](OC(F)(F)F)CC3)c2C1] | +++ |

TABLE 1-continued
| | IC$_{50}$ Values | |
|---|---|---|
| Cpd. No. | Structure | BROMO IC$_{50}$ TRF TB CBP (μM gmean) |
| 227 | 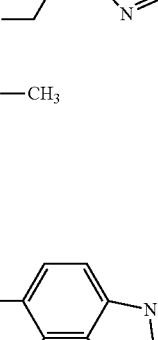 | +++ |
| 228 | 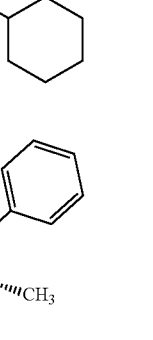 | +++ |
| 229 | 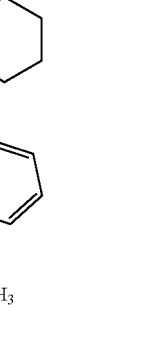 | +++ |
| 230 |  | +++ |

TABLE 1-continued

| Cpd. No. | Structure | BROMO IC$_{50}$ TRF TB CBP (μM gmean) |
|---|---|---|
| 231 | 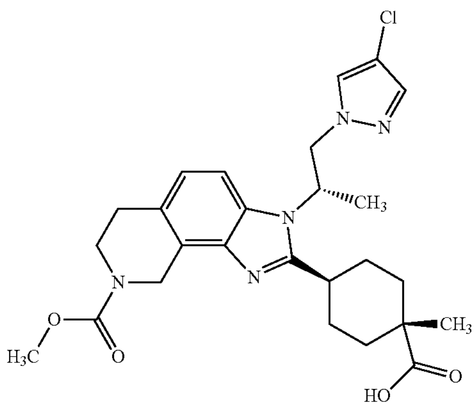 [SMILES: COC(=O)N1CCc2ccc3c(nc([C@H]4CC[C@](C)(C(=O)O)CC4)n3[C@@H](C)Cn3cc(Cl)cn3)c2C1] | +++ |
| 232 | 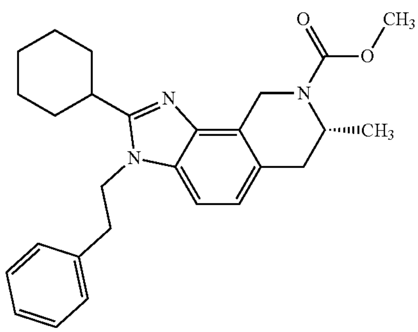 | +++ |
| 233 | 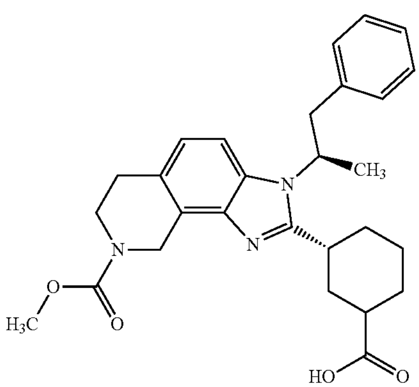 [SMILES: COC(=O)N1CCc2ccc3c(nc([C@@H]4CCCC(C(=O)O)C4)n3[C@H](C)Cc3ccccc3)c2C1] | +++ |
| 234 | 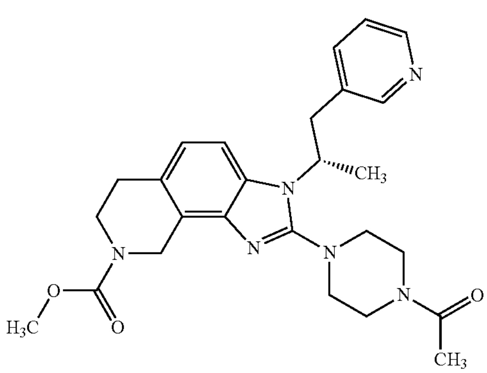 [SMILES: COC(=O)N1CCc2ccc3c(nc(N4CCN(C(C)=O)CC4)n3[C@@H](C)Cc3cccnc3)c2C1] | +++ |

TABLE 1-continued

| | | IC$_{50}$ Values | |
|---|---|---|---|
| Cpd. No. | Structure | | BROMO IC$_{50}$ TRF TB CBP (μM gmean) |
| 235 | | | +++ |
| 236 | | | +++ |
| 237 | | | +++ |
| 238 | | | +++ |

TABLE 1-continued

| | IC$_{50}$ Values | |
|---|---|---|
| Cpd. No. | Structure | BROMO IC$_{50}$ TRF TB CBP (μM gmean) |
| 239 | | +++ |
| 240 | | +++ |
| 241 | | +++ |
| 242 | | +++ |

TABLE 1-continued

| Cpd. No. | Structure | BROMO IC$_{50}$ TRF TB CBP (μM gmean) |
|---|---|---|
| 243 | 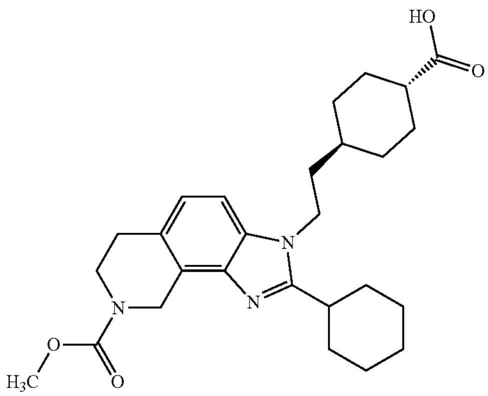 [SMILES: COC(=O)N1CCc2ccc3c(nc(C4CCCCC4)n3CC[C@H]3CC[C@H](C(=O)O)CC3)c2C1] | +++ |
| 244 | 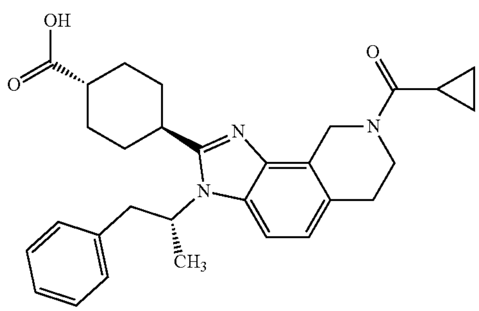 [SMILES: C[C@H](Cc1ccccc1)n1c2ccc3c(c2nc1[C@H]1CC[C@H](C(=O)O)CC1)CN(C(=O)C1CC1)CC3] | +++ |
| 245 | 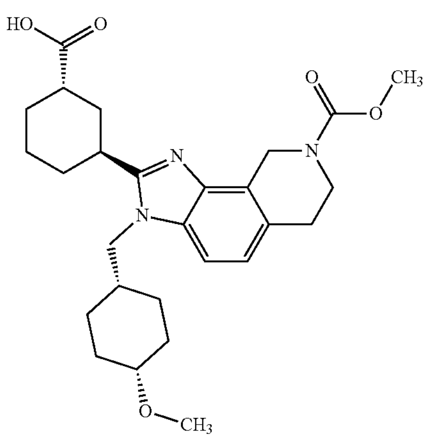 [SMILES: COC(=O)N1CCc2ccc3c(nc([C@H]4CCC[C@H](C(=O)O)C4)n3C[C@H]3CC[C@@H](OC)CC3)c2C1] | +++ |
| 246 | 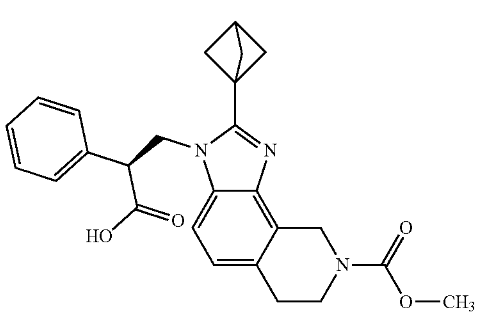 [SMILES: COC(=O)N1CCc2ccc3c(nc(C45CC(C4)C5)n3C[C@@H](C(=O)O)c3ccccc3)c2C1] | +++ |

TABLE 1-continued

| | IC$_{50}$ Values | |
|---|---|---|
| Cpd. No. | Structure | BROMO IC$_{50}$ TRF TB CBP (μM gmean) |
| 247 | | +++ |
| 248 | | +++ |
| 249 | | +++ |
| 250 | | +++ |

TABLE 1-continued

| | IC$_{50}$ Values | |
|---|---|---|
| Cpd. No. | Structure | BROMO IC$_{50}$ TRF TB CBP (μM gmean) |
| 251 | | +++ |
| 252 | | +++ |
| 253 | | +++ |
| 254 | | +++ |

TABLE 1-continued
| Cpd. No. | Structure | BROMO IC$_{50}$ TRF TB CBP (μM gmean) |
|---|---|---|
| 255 | 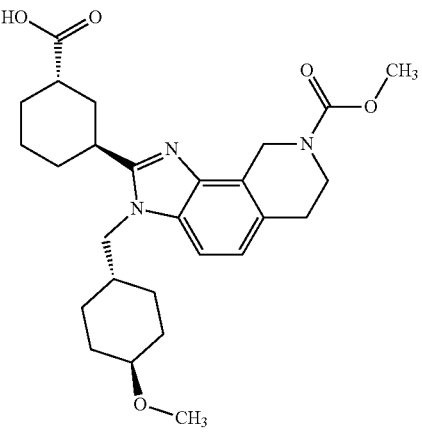 [SMILES: COC(=O)N1CCc2ccc3c(nc([C@H]4CCC[C@H](C(=O)O)C4)n3C[C@H]3CC[C@H](OC)CC3)c2C1] | +++ |
| 256 | 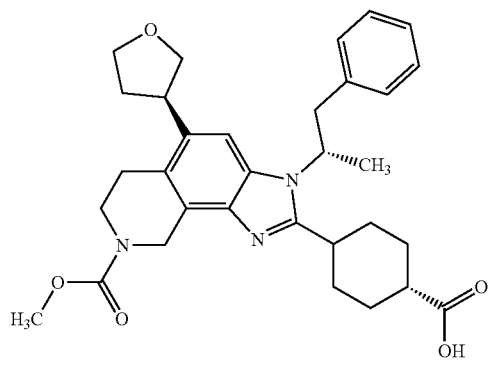 | +++ |
| 257 | 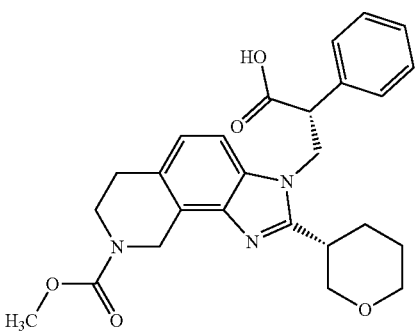 [SMILES: COC(=O)N1CCc2ccc3c(nc([C@@H]4CCCOC4)n3C[C@H](C(=O)O)c3ccccc3)c2C1] | +++ |

TABLE 1-continued
| | IC$_{50}$ Values | |
|---|---|---|
| Cpd. No. | Structure | BROMO IC$_{50}$ TRF TB CBP (μM gmean) |
| 258 | 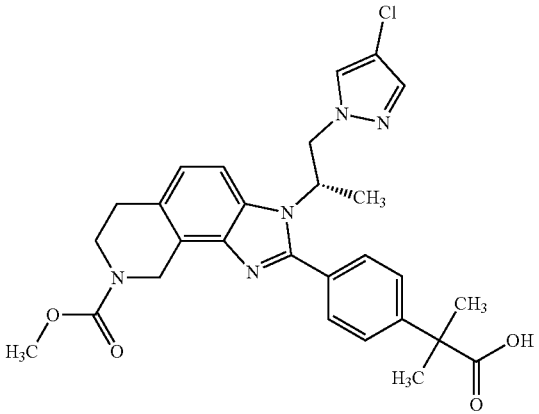 [SMILES: COC(=O)N1CCc2ccc3c(nc(-c4ccc(C(C)(C)C(=O)O)cc4)n3[C@@H](C)Cn3cc(Cl)cn3)c2C1] | +++ |
| 259 | 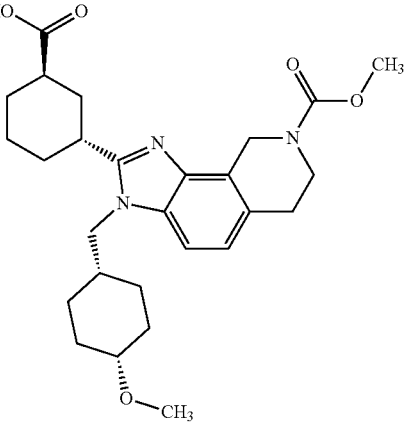 | +++ |
| 260 | 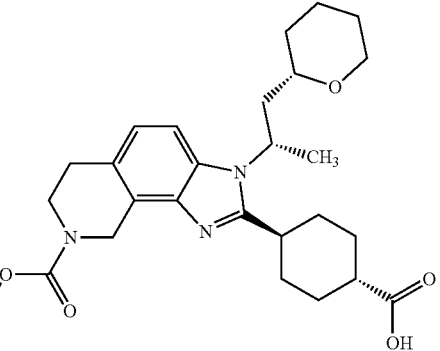 | +++ |

TABLE 1-continued

| | IC$_{50}$ Values | |
|---|---|---|
| Cpd. No. | Structure | BROMO IC$_{50}$ TRF TB CBP (μM gmean) |
| 261 | | +++ |
| 262 | | +++ |
| 263 | | +++ |

TABLE 1-continued

| Cpd. No. | Structure | BROMO IC$_{50}$ TRF TB CBP (μM gmean) |
|---|---|---|
| 264 | 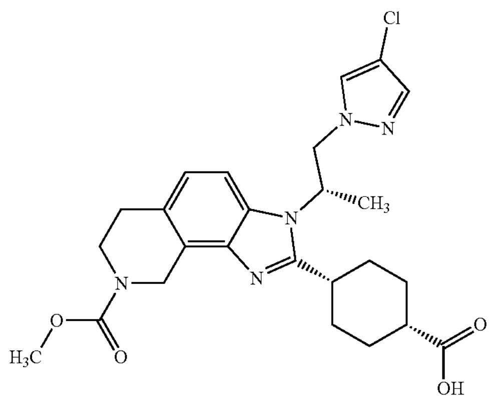 [SMILES: COC(=O)N1CCc2ccc3c(nc([C@H]4CC[C@@H](C(=O)O)CC4)n3[C@@H](C)Cn3cc(Cl)cn3)c2C1] | +++ |
| 265 | 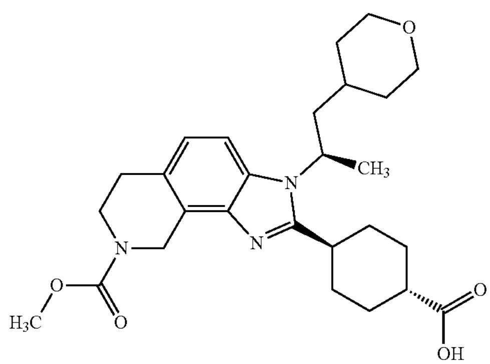 | +++ |
| 266 | 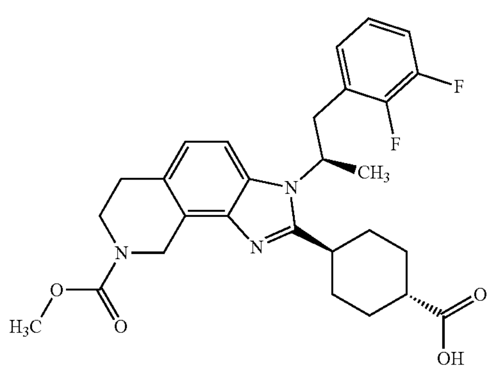 [SMILES: COC(=O)N1CCc2ccc3c(nc([C@H]4CC[C@H](C(=O)O)CC4)n3[C@H](C)Cc3cccc(F)c3F)c2C1] | +++ |

TABLE 1-continued

| | | IC₅₀ Values | |
|---|---|---|---|
| Cpd. No. | Structure | | BROMO IC₅₀ TRF TB CBP (μM gmean) |
| 267 | | | +++ |
| 268 | | | +++ |
| 269 | | | +++ |
| 270 | | | +++ |

TABLE 1-continued
| | IC$_{50}$ Values | |
|---|---|---|
| Cpd. No. | Structure | BROMO IC$_{50}$ TRF TB CBP (μM gmean) |
| 271 | 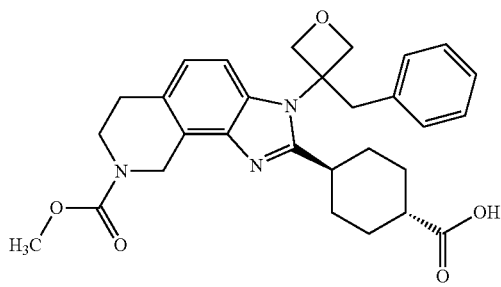 [SMILES: COC(=O)N1CCc2ccc3c(nc([C@H]4CC[C@H](C(=O)O)CC4)n3C3(Cc4ccccc4)COC3)c2C1] | +++ |
| 272 | 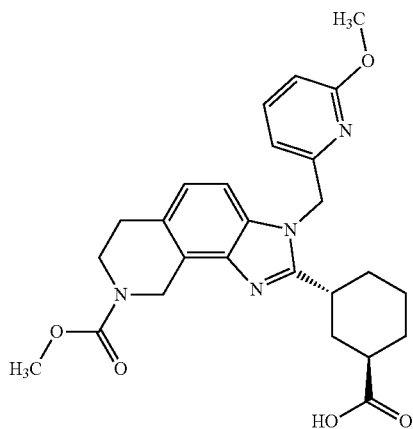 [SMILES: COC(=O)N1CCc2ccc3c(nc([C@@H]4CCC[C@@H](C(=O)O)C4)n3Cc3cccc(OC)n3)c2C1] | +++ |
| 273 | 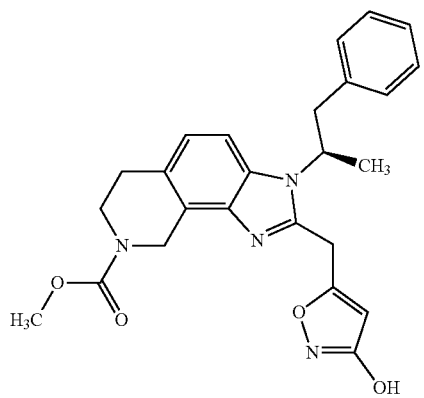 [SMILES: COC(=O)N1CCc2ccc3c(nc(Cc4cc(O)no4)n3[C@H](C)Cc3ccccc3)c2C1] | +++ |

TABLE 1-continued

| | IC$_{50}$ Values | |
|---|---|---|
| Cpd. No. | Structure | BROMO IC$_{50}$ TRF TB CBP (µM gmean) |
| 274 | (structure) | +++ |
| 275 | (structure) | +++ |
| 276 | (structure) | +++ |

TABLE 1-continued

| | IC$_{50}$ Values | |
|---|---|---|
| Cpd. No. | Structure | BROMO IC$_{50}$ TRF TB CBP (μM gmean) |
| 277 | | +++ |
| 278 | | +++ |
| 279 | | +++ |

TABLE 1-continued

| | IC$_{50}$ Values | |
|---|---|---|
| Cpd. No. | Structure | BROMO IC$_{50}$ TRF TB CBP (μM gmean) |
| 280 | | +++ |
| 281 | | +++ |
| 282 | | +++ |
| 283 | | +++ |

TABLE 1-continued

| | IC$_{50}$ Values | |
|---|---|---|
| Cpd. No. | Structure | BROMO IC$_{50}$ TRF TB CBP (μM gmean) |
| 284 | | +++ |
| 285 | | +++ |
| 286 | | +++ |

TABLE 1-continued

| | IC$_{50}$ Values | |
|---|---|---|
| Cpd. No. | Structure | BROMO IC$_{50}$ TRF TB CBP (µM gmean) |
| 287 | | +++ |
| 288 | | +++ |
| 289 | | +++ |

TABLE 1-continued

| Cpd. No. | Structure | BROMO IC$_{50}$ TRF TB CBP (μM gmean) |
|---|---|---|
| 290 | 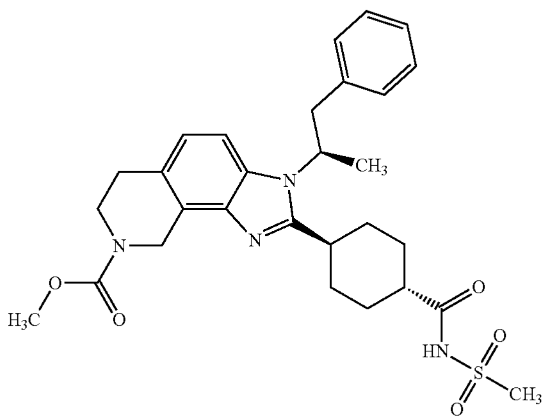 | ++ |
| 291 | 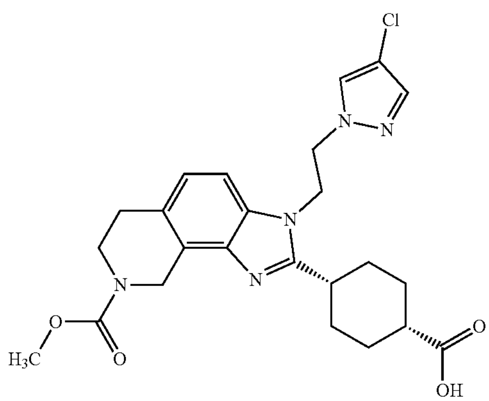 [SMILES: COC(=O)N1CCc2ccc3c(nc([C@H]4CC[C@@H](C(=O)O)CC4)n3CCn3cc(Cl)cn3)c2C1] | ++ |
| 292 | 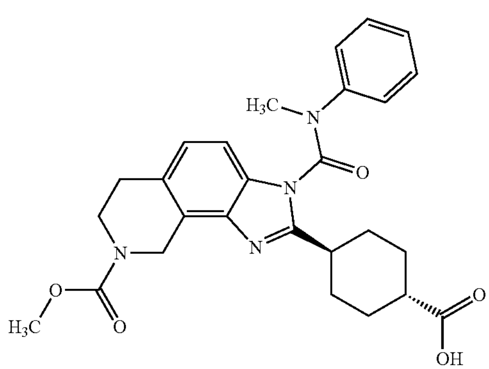 [SMILES: COC(=O)N1CCc2ccc3c(nc([C@H]4CC[C@H](C(=O)O)CC4)n3C(=O)N(C)c3ccccc3)c2C1] | ++ |

TABLE 1-continued

| Cpd. No. | Structure | BROMO IC$_{50}$ TRF TB CBP (μM gmean) |
|---|---|---|
| 293 | 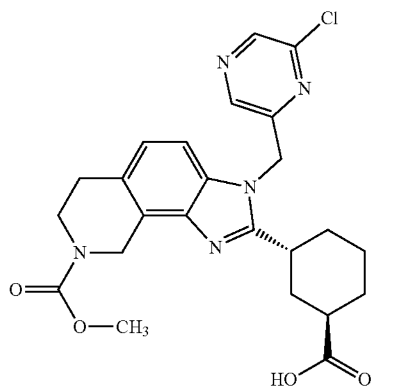 [SMILES: COC(=O)N1CCc2ccc3c(nc([C@@H]4CCC[C@@H](C(=O)O)C4)n3Cc3cncc(Cl)n3)c2C1] | ++ |
| 294 | 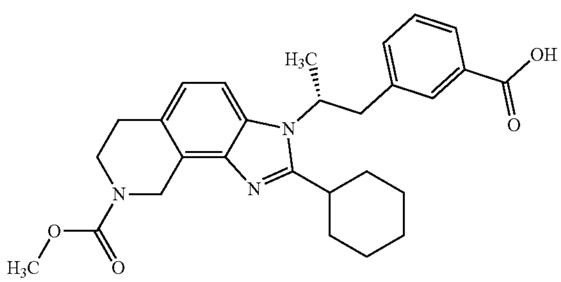 [SMILES: COC(=O)N1CCc2ccc3c(nc(C4CCCCC4)n3[C@H](C)Cc3cccc(C(=O)O)c3)c2C1] | ++ |
| 295 | 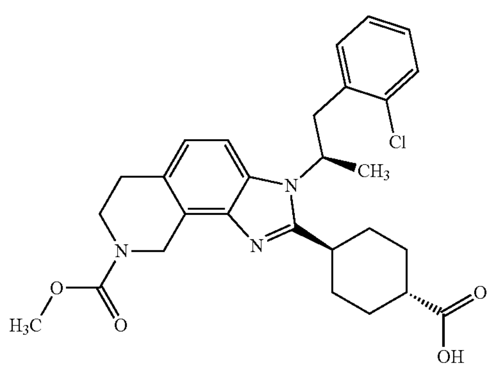 [SMILES: COC(=O)N1CCc2ccc3c(nc([C@H]4CC[C@H](C(=O)O)CC4)n3[C@H](C)Cc3ccccc3Cl)c2C1] | ++ |
| 296 | 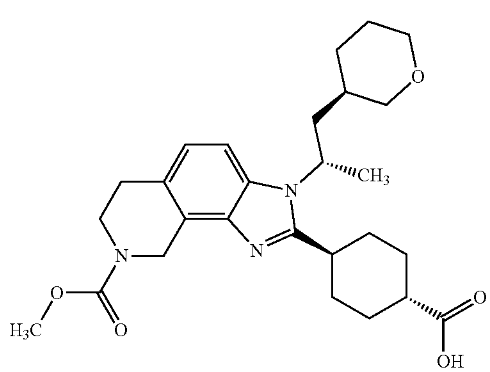 [SMILES: COC(=O)N1CCc2ccc3c(nc([C@H]4CC[C@H](C(=O)O)CC4)n3[C@@H](C)C[C@H]3CCCOC3)c2C1] | ++ |

TABLE 1-continued

| Cpd. No. | Structure | BROMO IC$_{50}$ TRF TB CBP (μM gmean) |
|---|---|---|
| 297 | 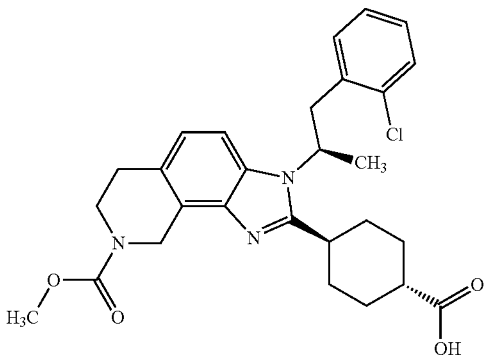 [SMILES: COC(=O)N1CCc2ccc3c(nc([C@H]4CC[C@H](C(=O)O)CC4)n3[C@H](C)Cc3ccccc3Cl)c2C1] | ++ |
| 298 | 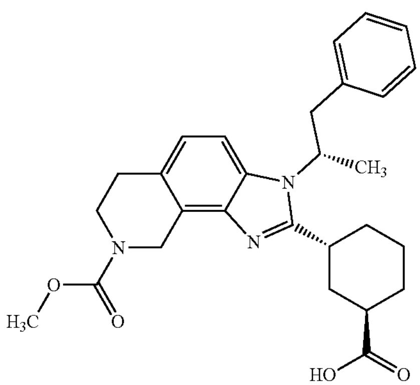 [SMILES: COC(=O)N1CCc2ccc3c(nc([C@@H]4CCC[C@@H](C(=O)O)C4)n3[C@@H](C)Cc3ccccc3)c2C1] | ++ |
| 299 | 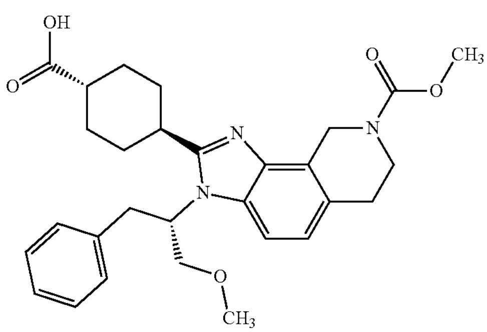 [SMILES: COC[C@H](Cc1ccccc1)n1c2ccc3c(c2nc1[C@H]1CC[C@H](C(=O)O)CC1)CN(C(=O)OC)CC3] | ++ |
| 300 | 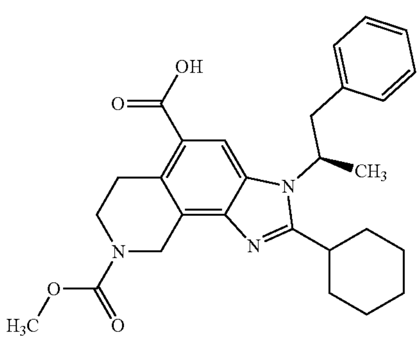 [SMILES: COC(=O)N1CCc2c(C(=O)O)cc3c(nc(C4CCCCC4)n3[C@H](C)Cc3ccccc3)c2C1] | ++ |

TABLE 1-continued
| | | IC$_{50}$ Values |
|---|---|---|
| Cpd. No. | Structure | BROMO IC$_{50}$ TRF TB CBP (μM gmean) |
| 301 | 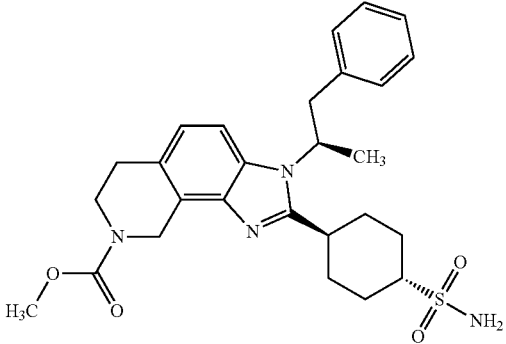 [SMILES: COC(=O)N1CCc2ccc3c(nc([C@H]4CC[C@H](S(N)(=O)=O)CC4)n3[C@H](C)Cc3ccccc3)c2C1] | ++ |
| 302 | 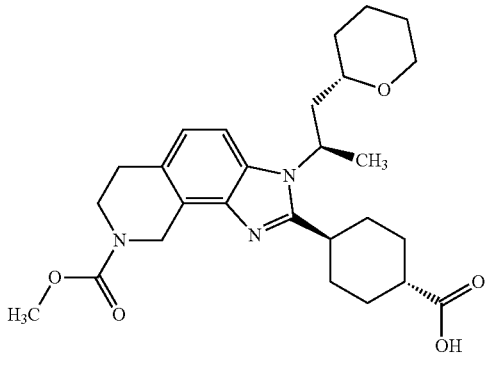 | ++ |
| 303 | 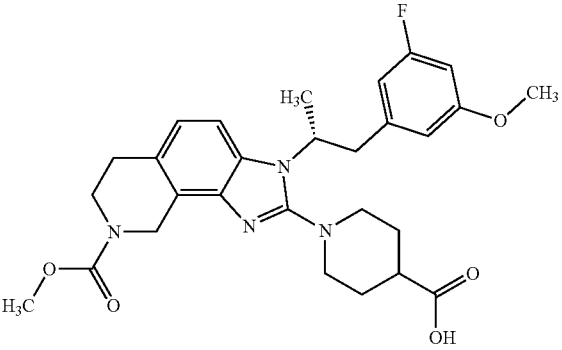 | |
| 304 | 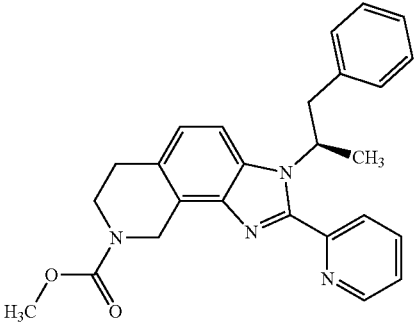 [SMILES: COC(=O)N1CCc2ccc3c(nc(-c4ccccn4)n3[C@H](C)Cc3ccccc3)c2C1] | ++ |

TABLE 1-continued

| | IC$_{50}$ Values | |
|---|---|---|
| Cpd. No. | Structure | BROMO IC$_{50}$ TRF TB CBP (µM gmean) |
| 305 | *(structure)* | ++ |
| 306 | *(structure)* | ++ |
| 307 | *(structure)* | ++ |

TABLE 1-continued

| Cpd. No. | Structure | BROMO IC$_{50}$ TRF TB CBP (μM gmean) |
|---|---|---|
| 308 | 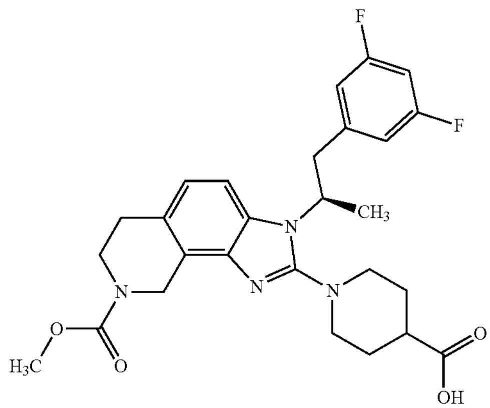 [SMILES: COC(=O)N1CCc2ccc3c(nc(N4CCC(C(=O)O)CC4)n3[C@H](C)Cc3cc(F)cc(F)c3)c2C1] | ++ |
| 309 | 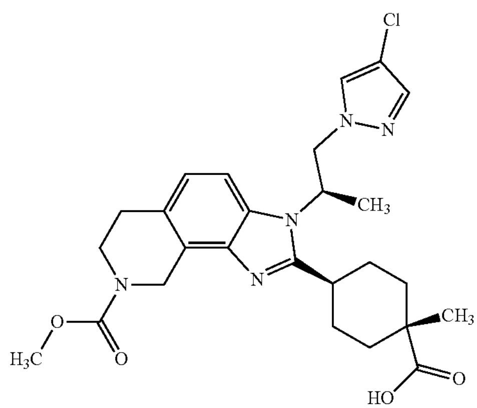 [SMILES: COC(=O)N1CCc2ccc3c(nc([C@H]4CC[C@](C)(C(=O)O)CC4)n3[C@H](C)Cn3cc(Cl)cn3)c2C1] | ++ |
| 310 | 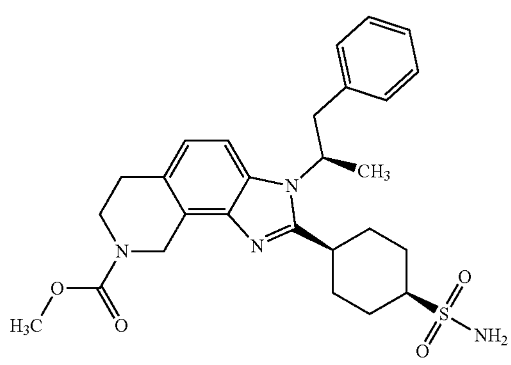 [SMILES: COC(=O)N1CCc2ccc3c(nc([C@H]4CC[C@@H](S(N)(=O)=O)CC4)n3[C@H](C)Cc3ccccc3)c2C1] | ++ |
| 311 | 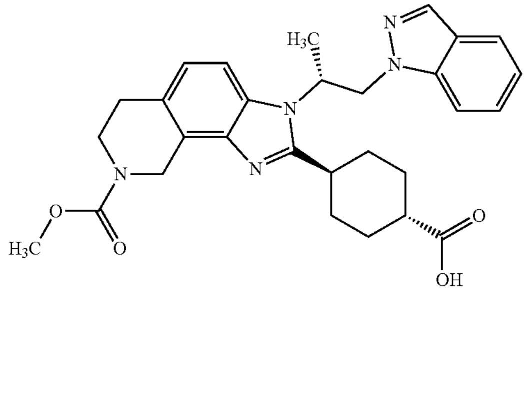 [SMILES: COC(=O)N1CCc2ccc3c(nc([C@H]4CC[C@H](C(=O)O)CC4)n3[C@H](C)Cn3ncc4ccccc43)c2C1] | ++ |

TABLE 1-continued

| Cpd. No. | Structure | BROMO IC$_{50}$ TRF TB CBP (μM gmean) |
|---|---|---|
| 312 | 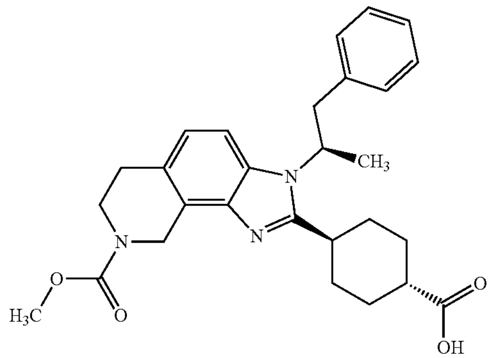 [SMILES: COC(=O)N1CCc2ccc3c(nc([C@H]4CC[C@H](C(=O)O)CC4)n3[C@H](C)Cc3ccccc3)c2C1] | ++ |
| 313 | 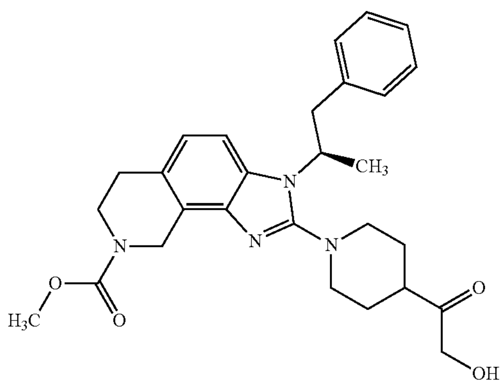 [SMILES: COC(=O)N1CCc2ccc3c(nc(N4CCC(C(=O)CO)CC4)n3[C@H](C)Cc3ccccc3)c2C1] | ++ |
| 314 | 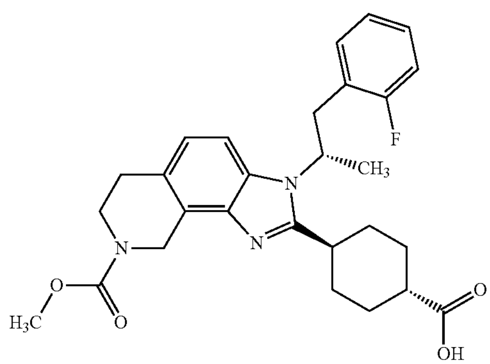 [SMILES: COC(=O)N1CCc2ccc3c(nc([C@H]4CC[C@H](C(=O)O)CC4)n3[C@@H](C)Cc3ccccc3F)c2C1] | ++ |
| 315 | 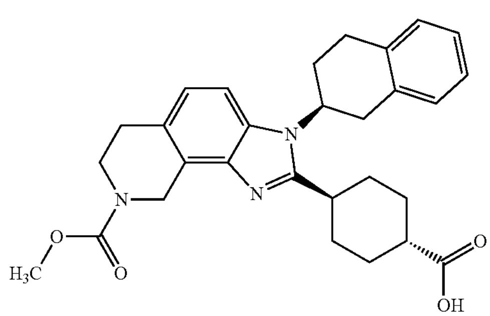 [SMILES: COC(=O)N1CCc2ccc3c(nc([C@H]4CC[C@H](C(=O)O)CC4)n3[C@H]3CCc4ccccc4C3)c2C1] | ++ |

TABLE 1-continued
| | IC$_{50}$ Values | |
|---|---|---|
| Cpd. No. | Structure | BROMO IC$_{50}$ TRF TB CBP (μM gmean) |
| 316 | 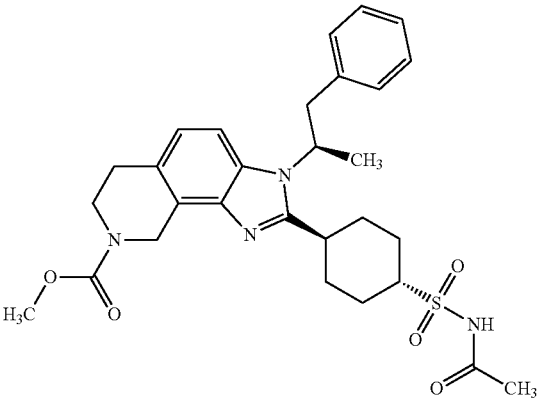 [SMILES: COC(=O)N1CCc2ccc3c(nc([C@H]4CC[C@H](S(=O)(=O)NC(C)=O)CC4)n3[C@H](C)Cc3ccccc3)c2C1] | ++ |
| 317 | 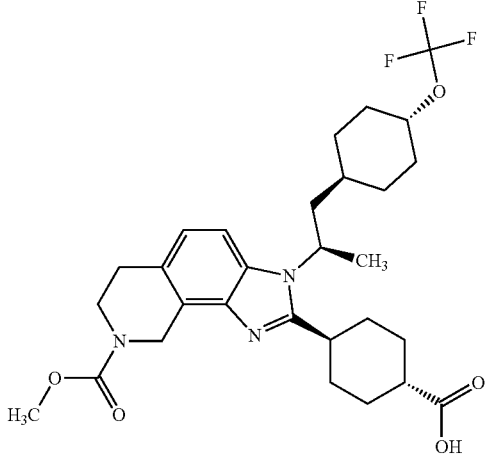 [SMILES: COC(=O)N1CCc2ccc3c(nc([C@H]4CC[C@H](C(=O)O)CC4)n3[C@H](C)C[C@H]3CC[C@H](OC(F)(F)F)CC3)c2C1] | ++ |
| 318 | 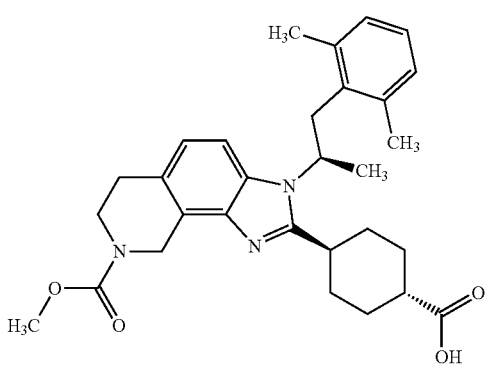 [SMILES: COC(=O)N1CCc2ccc3c(nc([C@H]4CC[C@H](C(=O)O)CC4)n3[C@H](C)Cc3c(C)cccc3C)c2C1] | ++ |

TABLE 1-continued

| Cpd. No. | Structure | BROMO IC$_{50}$ TRF TB CBP (µM gmean) |
|---|---|---|
| 319 | 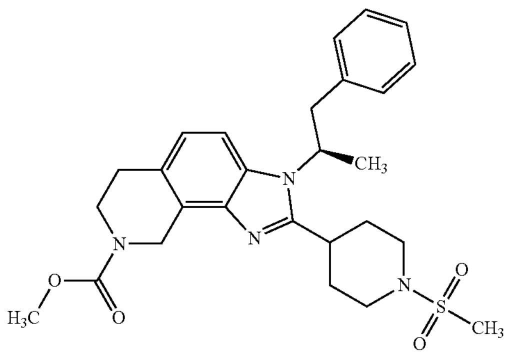 | ++ |
| 320 | 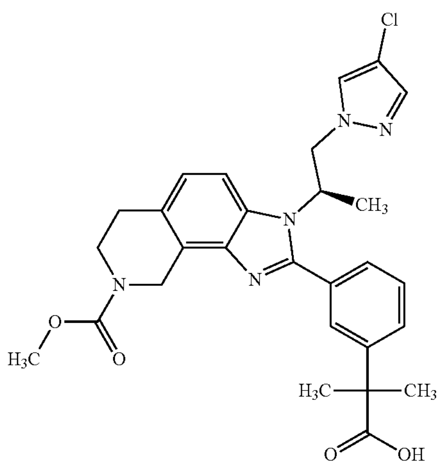 [SMILES: COC(=O)N1CCc2ccc3c(nc(-c4cccc(C(C)(C)C(=O)O)c4)n3[C@H](C)Cn3cc(Cl)cn3)c2C1] | ++ |
| 321 | 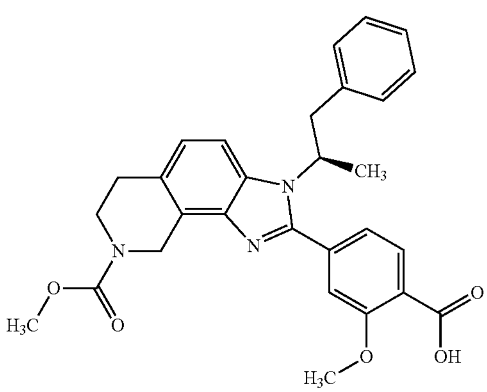 | ++ |

TABLE 1-continued

| Cpd. No. | Structure | BROMO IC$_{50}$ TRF TB CBP (µM gmean) |
|---|---|---|
| 322 | 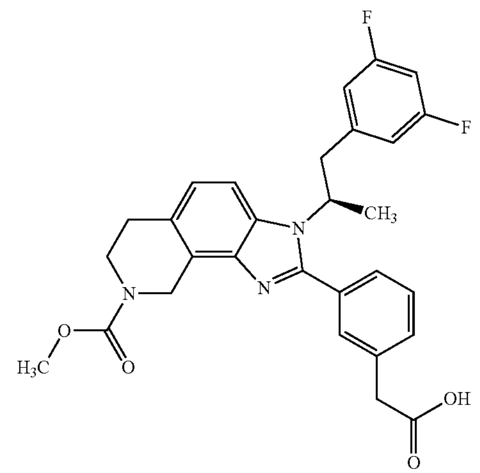 [SMILES: COC(=O)N1CCc2ccc3c(nc(-c4cccc(CC(=O)O)c4)n3[C@H](C)Cc3cc(F)cc(F)c3)c2C1] | ++ |
| 323 | 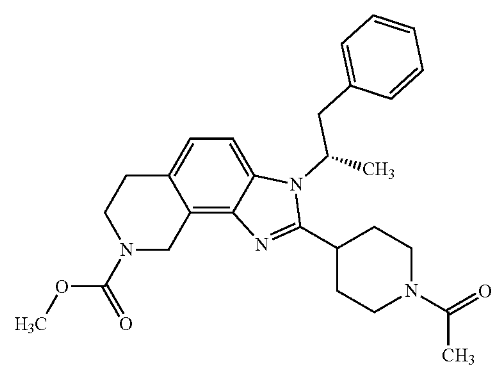 | ++ |
| 324 | 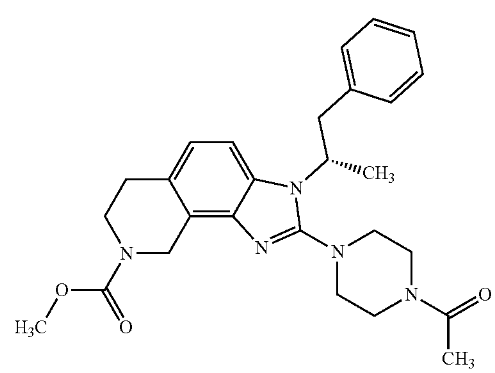 [SMILES: COC(=O)N1CCc2ccc3c(nc(N4CCN(C(C)=O)CC4)n3[C@@H](C)Cc3ccccc3)c2C1] | ++ |

TABLE 1-continued
| | IC$_{50}$ Values | |
|---|---|---|
| Cpd. No. | Structure | BROMO IC$_{50}$ TRF TB CBP (μM gmean) |
| 325 | 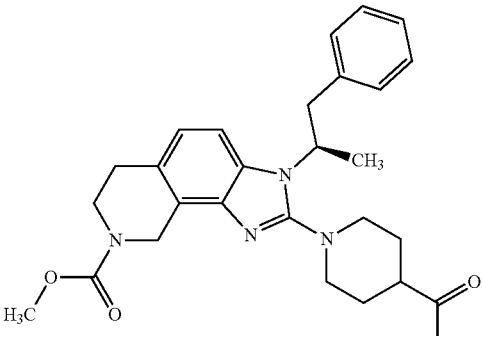 | ++ |
| 326 | 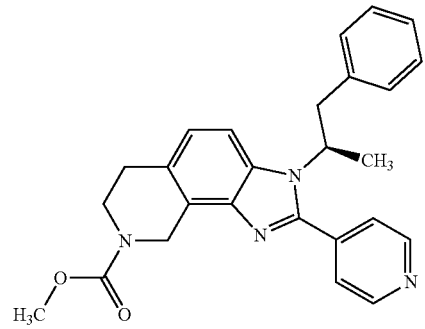 | ++ |
| 327 | 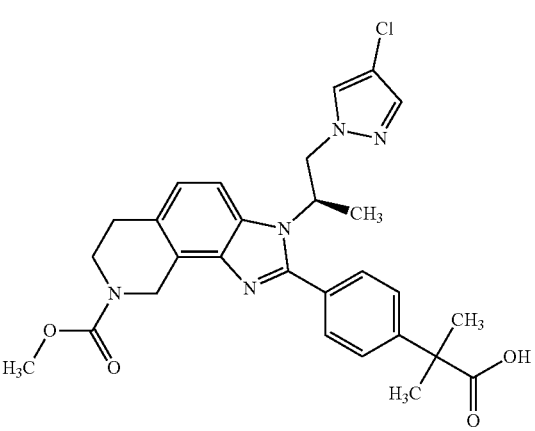 [SMILES: COC(=O)N1CCc2ccc3c(nc(-c4ccc(C(C)(C)C(=O)O)cc4)n3[C@H](C)Cn3cc(Cl)cn3)c2C1] | ++ |
| 328 | 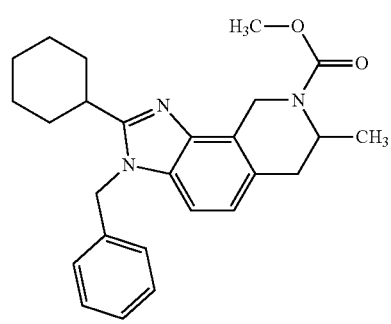 [SMILES: COC(=O)N1Cc2c(ccc3c2nc(C2CCCCC2)n3Cc2ccccc2)CC1C] | ++ |

TABLE 1-continued

| | | IC$_{50}$ Values |
|---|---|---|
| Cpd. No. | Structure | BROMO IC$_{50}$ TRF TB CBP (μM gmean) |
| 329 | | ++ |
| 330 | | ++ |
| 331 | | ++ |
| 332 | | ++ |

TABLE 1-continued

| Cpd. No. | Structure | BROMO IC$_{50}$ TRF TB CBP (μM gmean) |
|---|---|---|
| 333 | 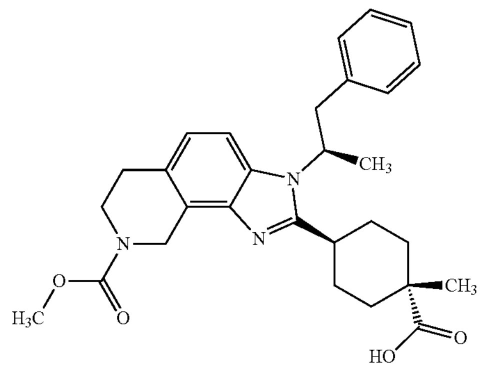 [SMILES: COC(=O)N1CCc2ccc3c(nc([C@H]4CC[C@](C)(C(=O)O)CC4)n3[C@H](C)Cc3ccccc3)c2C1] | ++ |
| 334 | 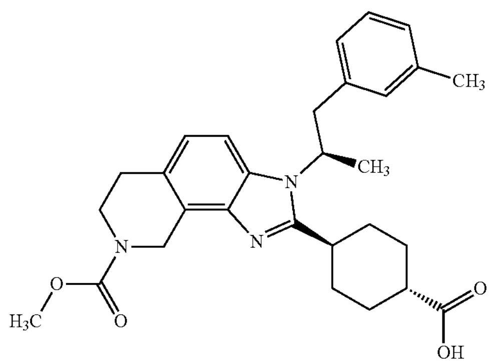 [SMILES: COC(=O)N1CCc2ccc3c(nc([C@H]4CC[C@H](C(=O)O)CC4)n3[C@H](C)Cc3cccc(C)c3)c2C1] | ++ |
| 335 | 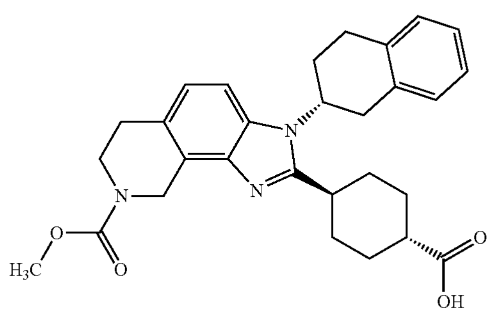 [SMILES: COC(=O)N1CCc2ccc3c(nc([C@H]4CC[C@H](C(=O)O)CC4)n3[C@@H]3CCc4ccccc4C3)c2C1] | ++ |
| 336 | 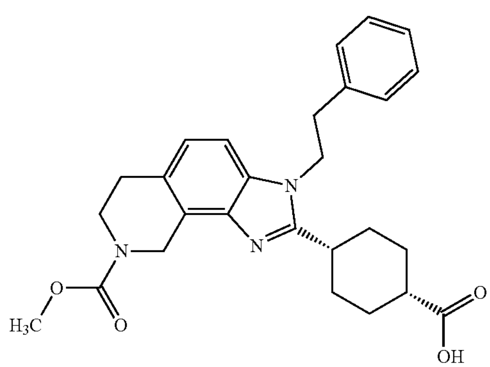 [SMILES: COC(=O)N1CCc2ccc3c(nc([C@H]4CC[C@@H](C(=O)O)CC4)n3CCc3ccccc3)c2C1] | ++ |

TABLE 1-continued

| Cpd. No. | Structure | BROMO IC$_{50}$ TRF TB CBP (μM gmean) |
|---|---|---|
| 337 | 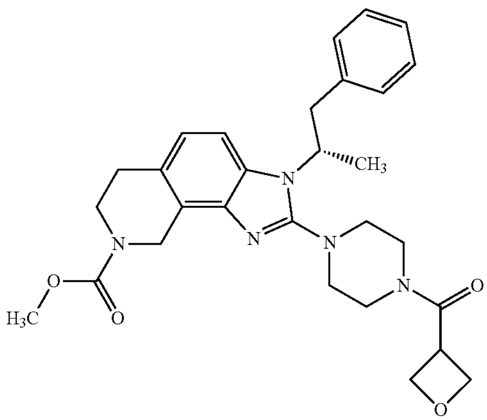 [SMILES: COC(=O)N1CCc2ccc3c(nc(N4CCN(C(=O)C5COC5)CC4)n3[C@@H](C)Cc3ccccc3)c2C1] | ++ |
| 338 | 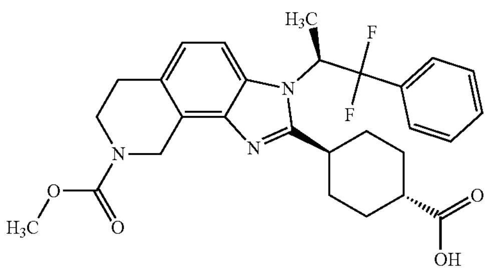 [SMILES: COC(=O)N1CCc2ccc3c(nc([C@H]4CC[C@H](C(=O)O)CC4)n3[C@@H](C)C(F)(F)c3ccccc3)c2C1] | ++ |
| 339 | 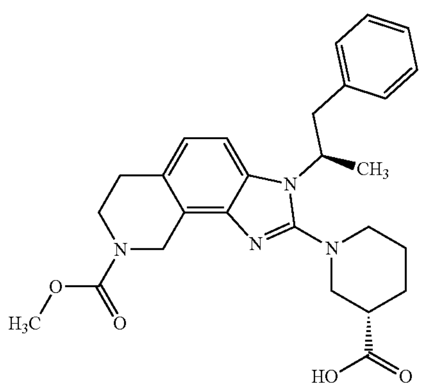 | ++ |
| 340 | 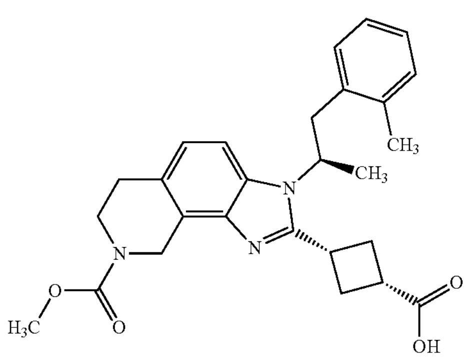 [SMILES: COC(=O)N1CCc2ccc3c(nc([C@H]4C[C@@H](C(=O)O)C4)n3[C@H](C)Cc3ccccc3C)c2C1] | ++ |

TABLE 1-continued

| | IC$_{50}$ Values | |
|---|---|---|
| Cpd. No. | Structure | BROMO IC$_{50}$ TRF TB CBP (μM gmean) |
| 341 | | ++ |
| 342 | | ++ |
| 343 | | ++ |
| 344 | | ++ |

TABLE 1-continued
| | | IC$_{50}$ Values |
|---|---|---|
| Cpd. No. | Structure | BROMO IC$_{50}$ TRF TB CBP (μM gmean) |
| 345 | 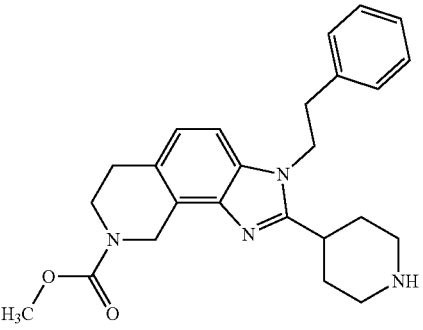 [SMILES: COC(=O)N1CCc2ccc3c(nc(C4CCNCC4)n3CCc3ccccc3)c2C1] | ++ |
| 346 | 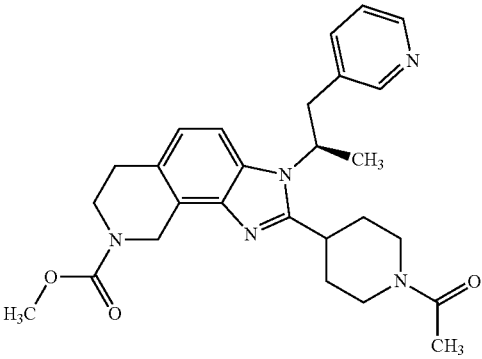 [SMILES: COC(=O)N1CCc2ccc3c(nc(C4CCN(C(C)=O)CC4)n3[C@H](C)Cc3cccnc3)c2C1] | ++ |
| 347 | 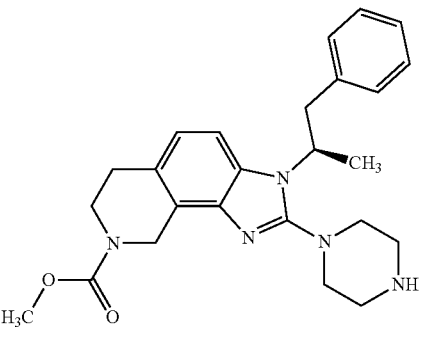 [SMILES: COC(=O)N1CCc2ccc3c(nc(N4CCNCC4)n3[C@H](C)Cc3ccccc3)c2C1] | + |
| 348 | 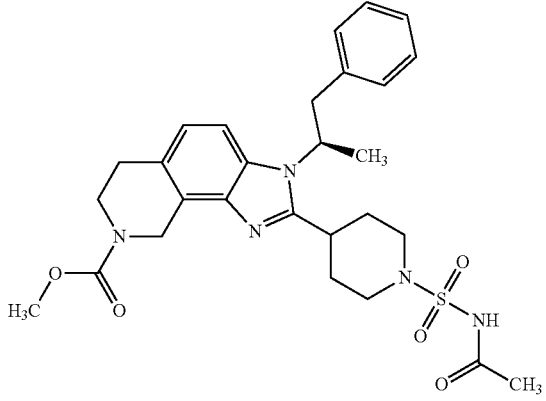 [SMILES: COC(=O)N1CCc2ccc3c(nc(C4CCN(S(=O)(=O)NC(C)=O)CC4)n3[C@H](C)Cc3ccccc3)c2C1] | + |

TABLE 1-continued
| Cpd. No. | Structure | BROMO IC$_{50}$ TRF TB CBP (μM gmean) |
|---|---|---|
| 349 | 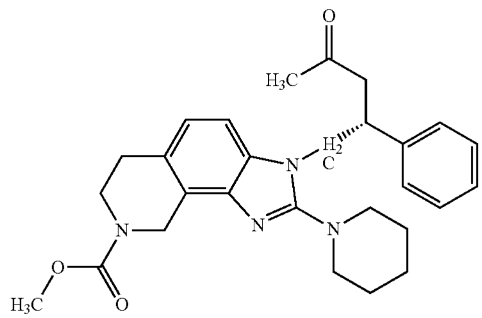 [SMILES: COC(=O)N1CCc2ccc3c(nc(N4CCCCC4)n3C[C@H](CC(C)=O)c3ccccc3)c2C1] | NT |
| 350 | 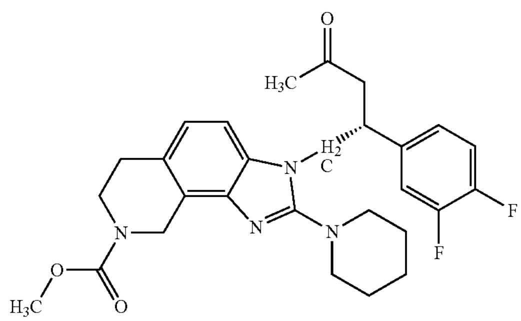 [SMILES: COC(=O)N1CCc2ccc3c(nc(N4CCCCC4)n3C[C@H](CC(C)=O)c3ccc(F)c(F)c3)c2C1] | NT |
| 351 | 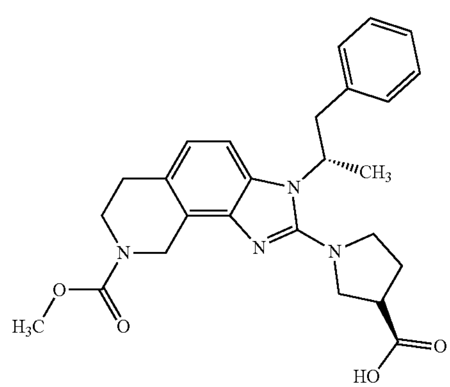 | NT |
Example 2: (trans)-4-[3-[(2R)-1-(3-fluoro-4-methylphenyl)propan-2-yl]-8-(methoxycarbonyl)-3H,6H,7H,8H,9H-imidazo[4,5-h]isoquinolin-2-yl]cyclohexane-1-carboxylic acid and (trans)-4-[3-[(2S)-1-(3-fluoro-4-methylphenyl)propan-2-yl]-8-(methoxycarbonyl)-3H,6H,7H,8H,9H-imidazo[4,5-h]isoquinolin-2-yl]cyclohexane-1-carboxylic acid
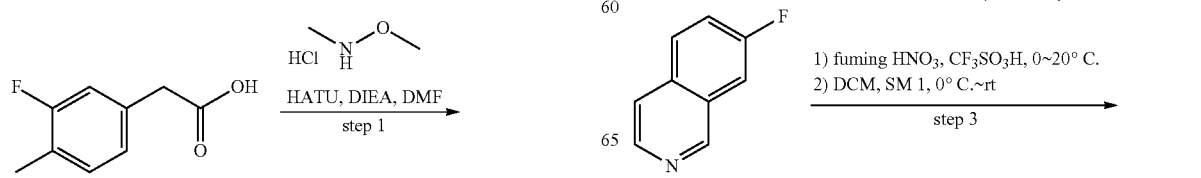

213
-continued
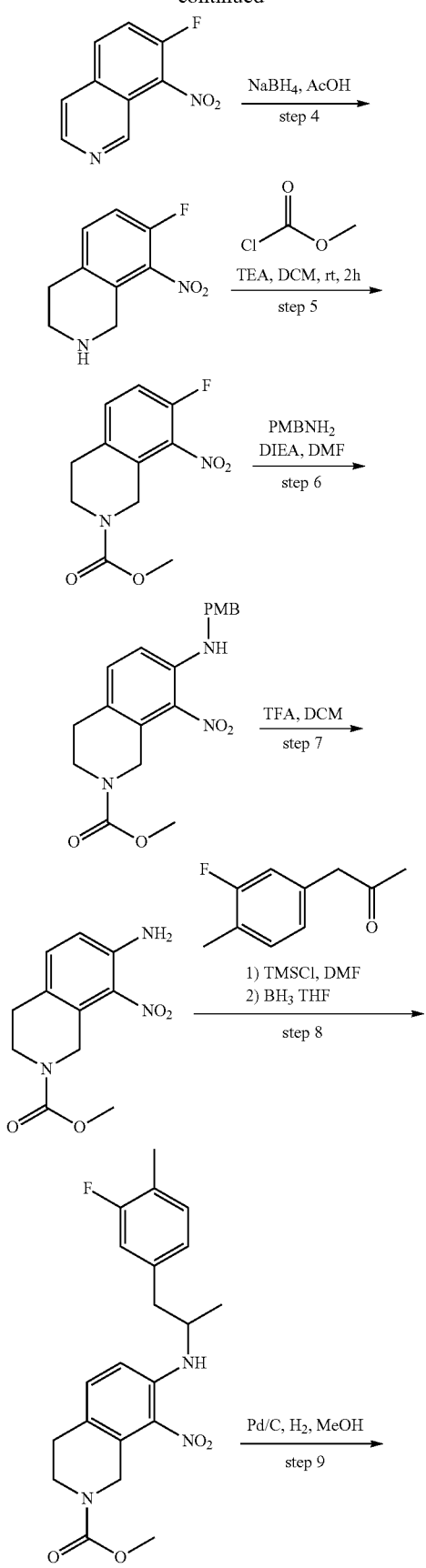
214
-continued
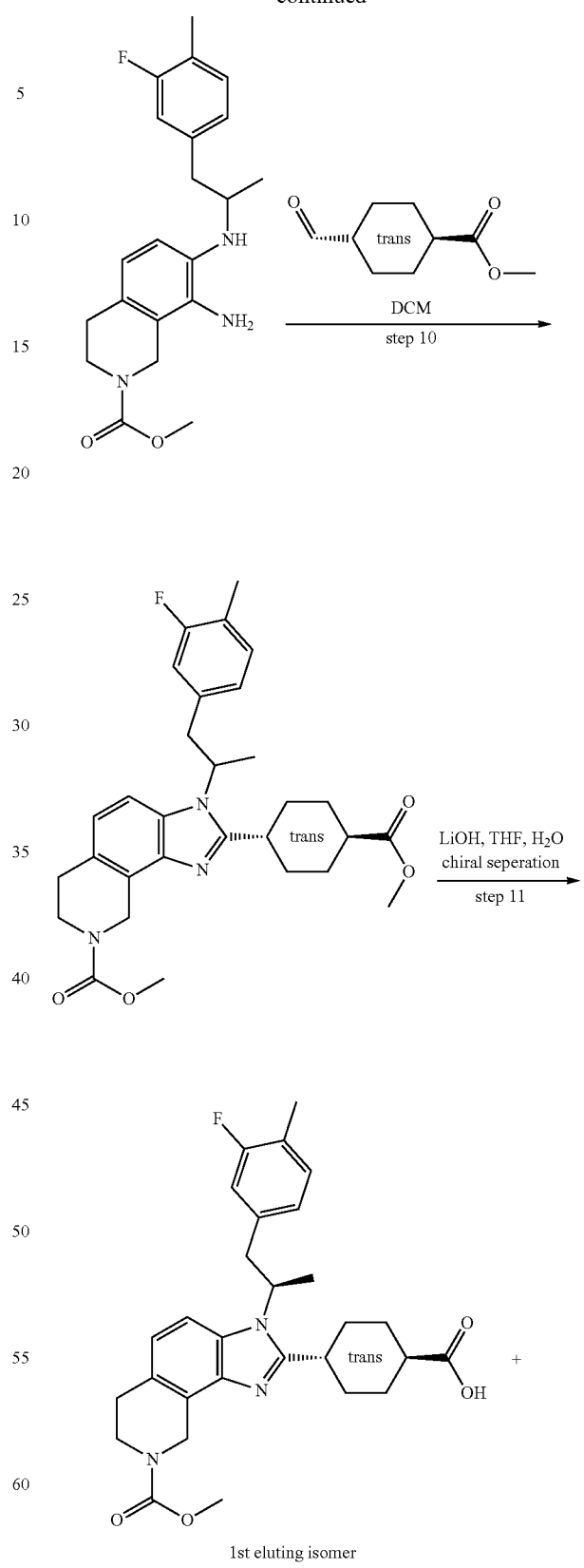
1st eluting isomer

-continued

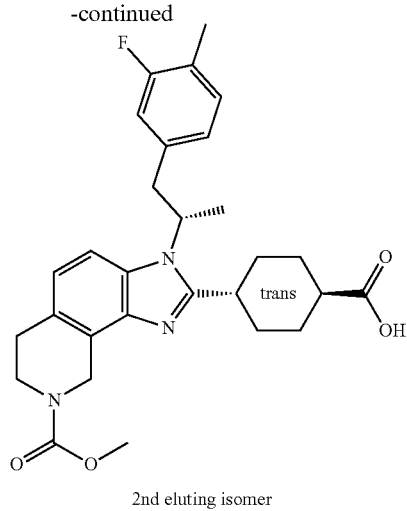

2nd eluting isomer

Step 1. 2-(3-fluoro-4-methylphenyl)-N-methoxy-N-methylacetamide

To a stirred solution of 2-(3-fluoro-4-methylphenyl)acetic acid (2.00 g, 11.6 mmol) in DMF (10 mL) was added HATU (5.47 g, 14.4 mmol), DIEA (6.20 g, 47.9 mmol) and N,O-dimethylhydroxylamine hydrochloride (1.80 g, 18.6 mmol). The resulting mixture was stirred for 1 h at 25° C. The mixture was diluted with water (50 mL) and was extracted with ethyl acetate (4×50 mL). The combined organic layers were washed with brine (150 mL), dried over anhydrous $Na_2SO_4$. After filtration, the filtrate was concentrated under reduced pressure. The residue was purified by silica gel column chromatography (eluting with 1:1 ethyl acetate/petroleum ether) to afford 2-(3-fluoro-4-methylphenyl)-N-methoxyacetamide as a yellow oil (417 mg, 18%). LCMS (ES, m/z): 212 [M+H]$^+$.

Step 2. 1-(3-fluoro-4-methylphenyl)propan-2-one

To a stirred mixture of 2-(3-fluoro-4-methylphenyl)-N-methoxy-N-methylacetamide (417 mg, 1.97 mmol) in THF (10 mL) was added $CH_3MgBr$ (1M in THF)(2.2 mL, 2.20 mmol) dropwise at 0° C. under nitrogen atmosphere. The resulting mixture was stirred for 2 h at 0° C. The reaction was quenched by the addition of sat. $NH_4Cl$ (aq.) (30 mL). The resulting mixture was extracted with ethyl acetate (3×30 mL), washed with brine (100 mL), dried over anhydrous $Na_2SO_4$. After filtration, the filtrate was concentrated under reduced pressure. The residue was purified by silica gel chromatography (eluting with 1:1 ethyl acetate/petroleum ether) to afford 1-(3-fluoro-4-methylphenyl) propan-2-one as a colorless oil (160 mg, 49%). LCMS (ES, m/z): 167 [M+H]$^+$.

Step 3. 7-fluoro-8-nitroisoquinoline

To a stirred mixture of $CF_3SO_3H$ (90.5 mL, 603 mmol) was added $HNO_3$ fuming (22.9 mL, 362 mmol) dropwise at −20° C. To the above mixture was added 7-fluoroisoquinoline (50.0 g, 340 mmol) in DCM (300 mL) dropwise over 30 min at 0° C. The resulting mixture was stirred for additional 3 h at room temperature (15° C.). The reaction was quenched with water/ice (500 mL). The mixture was neutralized to pH 7 with saturated $NaHCO_3$ (aq.). The resulting mixture was extracted with $CH_2Cl_2$ (3×1 L). The combined organic layers were washed with brine (1 L), dried over anhydrous $Na_2SO_4$, filtrated and concentrated under reduced pressure. The residue was purified by silica gel column chromatography (eluting with 3:1 ethyl acetate/petroleum ether) to afford 7-fluoro-8-nitroisoquinoline as a light yellow solid (56.6 g, 82%). LCMS (ES, m/z): 193[M+H]$^+$.

Step 4. 7-fluoro-8-nitro-1,2,3,4-tetrahydroisoquinoline

To a stirred mixture of 7-fluoro-8-nitroisoquinoline (51.0 g, 263 mmol) in acetic acid (1 L) was added $NaBH_4$ (30.1 g, 788 mmol) in portions for 30 min at 15° C. The resulting mixture was stirred for 2 h at 20° C. The reaction mixture was diluted with water/ice (1 L) and basified to pH 8 with potassium carbonate solids. The resulting mixture was extracted with ethyl acetate (3×2 L). The combined organic layers were washed with brine (2 L), dried over anhydrous $Na_2SO_4$, filtrated and concentrated under reduced pressure. The residue was purified by silica gel column chromatography (eluting with 1:10 MeOH/$CH_2Cl_2$) to afford 7-fluoro-8-nitro-1,2,3,4-tetrahydroisoquinoline as a yellow solid (42.3 g, 78%). LCMS (ES, m/z): 197 [M+H]$^+$.

Step 5. methyl 7-fluoro-8-nitro-1,2,3,4-tetrahydroisoquinoline-2-carboxylate To a stirred solution of 7-fluoro-8-nitro-1,2,3,4-tetrahydroisoquinoline (18.0 g, 90.8 mmol) and triethylamine (38.3 mL, 276 mmol) in DCM (250 mL) was added methyl carbonochloridate (17.3 g, 182 mmol) dropwise at 0° C. The resulting mixture was stirred for 2 h at 20° C. The reaction was quenched with water/ice (250 mL) at 20° C. The resulting mixture was extracted with $CH_2Cl_2$ (3×500 mL). The combined organic layers were washed with brine (500 mL), dried over anhydrous $Na_2SO_4$, filtrated and concentrated under reduced pressure. The residue was purified by silica gel column chromatography (eluting with 1:1 ethyl acetate/petroleum ether) to afford methyl 7-fluoro-8-nitro-1,2,3,4-tetrahydroisoquinoline-2-carboxylate as a yellow solid (18 g, 74%). LCMS (ES, m/z): 255[M+H]$^+$.

Step 6. methyl 7-{[(4-methoxyphenyl)methyl]amino}-8-nitro-1,2,3,4-tetrahydroisoquinoline-2-carboxylate To a stirred mixture of methyl 7-fluoro-8-nitro-1,2,3,4-tetrahydroisoquinoline-2-carboxylate (20 g, 77.9 mmol) and 1-(4-methoxyphenyl)methanamine (21.6 g, 156 mmol) in DMF (300 mL) was added ethylbis(propan-2-yl)amine (49.8 mL, 302 mmol). The resulting mixture was stirred for 12 h at 80° C. The mixture was allowed to cool down to room temperature, diluted with water (500 mL) and extracted with ethyl acetate (3×500 mL). The combined organic layers were washed with brine (6×500 mL), dried over anhydrous Na$_2$SO$_4$, filtrated and concentrated under reduced pressure to afford methyl 7-f{[(4-methoxyphenyl)methyl]amino}-8-nitro-1,2,3,4-tetrahydroisoquinoline-2-carboxylate as a yellow solid (22 g, 74%). LCMS (ES, m/z): 372[M+H]$^+$.

Step 7. methyl 7-amino-8-nitro-1,2,3,4-tetrahydroisoquinoline-2-carboxylate

To a stirred solution of methyl 7-{[(4-methoxyphenyl) methyl]amino}-8-nitro-1,2,3,4-tetrahydroisoquinoline-2-carboxylate (22.0 g, 58.6 mmol) in DCM 100 mL was added TFA (200 mL) dropwise at 10° C. The resulting mixture was stirred for 1 h at 20° C. The resulting mixture was concentrated under reduced pressure. The residue was diluted with water (50 mL). The mixture was neutralized to pH 7 with saturated NaHCO$_3$ (aq.). The resulting mixture was extracted with CH$_2$Cl$_2$ (3×100 mL). The combined organic layers were washed with brine (150 mL), dried over anhydrous Na$_2$SO$_4$, and concentrated under reduced pressure. The residue was purified by silica gel column chromatography (eluting with 1:3 ethyl acetate/petroleum ether) to afford methyl 7-amino-8-nitro-1,2,3,4-tetrahydroisoquinoline-2-carboxylate as a yellow solid (12 g, 77%). LCMS (ES, m/z): 252[M+H]$^+$.

Step 8. methyl 7-{[1-(3-fluoro-4-methylphenyl) propan-2-yl]amino}-8-nitro-1,2,3,4-tetrahydroisoquinoline-2-carboxylate To a mixture of methyl 7-amino-8-nitro-1,2,3,4-tetrahydroisoquinoline-2-carboxylate (162 mg, 0.63 mmol) and 1-(3-fluoro-4-methylphenyl)propan-2-one (160 mg, 0.96 mmol) in DMF (2 mL) was added TMSCl (174 mg, 1.61 mmol) and BH$_3$-THF (1M in THF) (0.96 mL, 0.96 mmol, 1M) dropwise at 0° C. The resulting mixture was stirred for 16 h at 25° C. The resulting mixture was diluted with water (20 mL). The mixture was basified to pH 8 with saturated NaHCO$_3$ (aq.) and extracted with ethyl acetate (3×30 mL). The combined organic layers were washed with brine (50 mL), dried over anhydrous Na$_2$SO$_4$. After filtration, the filtrate was concentrated under reduced pressure. The resulting mixture was concentrated under vacuum. The residue was purified by silica gel chromatography (eluting with 1:1 ethyl acetate/petroleum ether) to afford methyl 7-[[1-(3-fluoro-4-methylphenyl)propan-2-yl]amino]-8-nitro-1,2,3,4-tetrahydroisoquinoline-2-carboxylate (110 mg, 41%) as a yellow oil. LCMS (ES, m/z): 402 [M+H]$^+$.

Step 9. methyl 8-amino-7-{[1-(3-fluoro-4-methylphenyl)propan-2-yl]amino}-1,2,3,4-tetrahydroisoquinoline-2-carboxylate To a stirred mixture of methyl 7-[[11-(3-fluoro-4-methylphenyl)propan-2-yl]amino]-8-nitro-1,2,3,4-tetrahydroisoquinoline-2-carboxylate (110 mg, 0.27 mmol) in methanol (10 mL) was added Pd/C (50 mg, 10%). The resulting mixture was stirred for 16 h at 25° C. under hydrogen atmosphere. The solids were filtered out, the filtrate was concentrated under vacuum. The residue was purified by silica gel column chromatography, eluted with dichloromethane/methanol (10:1) to afford methyl 8-amino-7-[[1-(3-fluoro-4-methylphenyl)propan-2-yl]amino]-1,2,3,4-tetrahydroisoquinoline-2-carboxylate as a brown solid (80 mg, 77%). LCMS (ES, m/z): 372 [M+H]$^+$.

Step 10. methyl 3-[1-(3-fluoro-4-methylphenyl) propan-2-yl]-2-[(trans)-4-(methoxycarbonyl)cyclo hexyl]-3H,6H,7H,8H,9H-imidazo[4,5-h]isoquinoline-8-carboxylate A mixture of methyl 8-amino-7-[[1-(3-fluoro-4-methylphenyl)propan-2-yl]amino]-1,2,3,4-tetrahydroisoquinoline-2-carboxylate (80 mg, 0.22 mmol) and methyl (trans)-4-formylcyclohexane-1-carboxylate (46 mg, 0.27 mmol) in dichloromethane (2 mL) was stirred for 2 h at 25° C. The resulting mixture was concentrated under vacuum. The residue was purified by silica gel chromatography (eluting with 1:2 ethyl acetate/petroleum ether) to afford methyl 3-[1-(3-fluoro-4-methylphenyl)propan-2-yl]-2-[(trans)-4-(methoxycarbonyl)cyclohexyl]-3H,6H,7H,8H,9H-imidazo[4,5-h]isoquinoline-8-carboxylate as a colorless oil (84 mg, 73%). LCMS (ES, m/z): 522 [M+H]$^+$.

Step 11. (trans)-4-[3-[(2R)-1-(3-fluoro-4-methylphenyl)propan-2-yl]-8-(methoxycarbonyl)-3H,6H,7H, 8H,9H-imidazo[4,5-h]isoquinolin-2-yl]cyclohexane-1-carboxylic acid and (trans)-4-[3-[(2S)-1-(3-fluoro-4-methylphenyl)propan-2-yl]-8-(methoxycarbonyl)-3H,6H,7H,8H,9H-imidazo[4,5-h]isoquinolin-2-yl]cyclohexane-1-carboxylic acid To a stirred mixture of methyl 3-[1-(3-fluoro-4-methylphenyl)propan-2-yl]-2-[(trans)-4-(methoxycarbonyl)cyclohexyl]-3H,6H,7H,8H,9H-imidazo[4,5-h]isoquinoline-8-carboxylate (84 mg, 0.16 mmol) in THF (1 mL), MeOH (1 mL) and H$_2$O (1 mL) was added LiOH (20 mg, 0.81 mmol) at 0° C. The resulting mixture was stirred for 2 h at 25° C. The resulting mixture was concentrated under vacuum. The residue was purified by reverse flash chromatography (Column: C18 silica gel; Mobile phase, A: water (containing with 0.1% FA) and B: ACN (0% to 50% ACN in 20 min; Detector: 254 nm). The desired product was separated by Prep-Chiral-HPLC(Column: CHIRALPAK IG UL001, 20×250 mm, 5 um; Mobile Phase A:Hex (0.1% FA)-HPLC, Mobile Phase B: EtOH-HPLC; Flow rate: 20 mL/min; Gradient: 30 B to 30 B in 13 min; 220/254 nm; RT1:8.20; RT2:10.4) to afford (trans)-4-[3-[(2R)-1-(3-fluoro-4-methylphenyl)propan-2-yl]-8-(methoxycarbonyl)-3H,6H,7H,8H, 9H-imidazo[4,5-h]isoquinolin-2-yl]cyclohexane-1-carboxylic acid as a white solid (8.4 mg, 10%). And (trans)-4-[3-[(2S)-1-(3-fluoro-4-methylphenyl)propan-2-yl]-8-(methoxycarbonyl)-3H,6H,7H,8H,9H-imidazo[4,5-h]

isoquinolin-2-yl]cyclohexane-1-carboxylic acid as a white solid (9.0 mg, 11%).

The compounds in Table 2 below may be prepared by methods analogous to the method described in Example 2.

TABLE 2

| Compound No. | Structure | Compound name | MS (ESI, m/z) [M + H]⁺ | ¹H-NMR δ (ppm) |
|---|---|---|---|---|
| 283 | 1st eluting isomer | (trans)-4[3-[(2R)-1-(3-fluoro-4-methylphenyl)propan-2-yl]-8-(methoxycarbonyl)-3H,6H,7H,8H,9H-imidazo[4,5-h]isoquinolin-2-yl]cyclohexane-1-carboxylic acid | 508 | ¹H-NMR (CD₃OD, 400 MHz) δ (ppm): 7.67 (d, J = 8 Hz, 1H), 7.11 (d, J = 8.4 Hz, 1H), 6.99-6.95 (m, 1H), 6.53-6.47 (m, 2H), 4.97 (s, 2H), 3.79 (s, 6H), 3.47-3.40 (m, 1H), 3.16-3.13 (m, 1H), 2.98 (br s, 2H), 2.46 (br s, 1H), 2.34-2.32 (m, 1H), 2.14 (s, 3H), 2.08-2.05 (m, 1H), 1.95-1.85 (m, 2H), 1.80 (d, J = 6.8 Hz, 3H), 1.66-1.51 (m, 3H), 1.35-1.29 (m, 1H), 0.91-0.87 (m, 1H). |
| 2 | 2nd eluting isomer | (trans)-4-[3-[(2S)-1-(3-fluoro-4-methylphenyl)propan-2-yl]-8-(methoxycarbonyl)-3H,6H,7H,8H,9H-imidazo[4,5-h]isoquinolin-2-yl]cyclohexane-1-carboxylic acid | 508 | %). ¹H-NMR (CD₃OD, 400 MHz) δ (ppm): 7.66 (d, J = 8 Hz, 1H), 7.11 (d, J = 8 Hz, 1H), 6.98-6.94 (m, 1H), 6.53-6.46 (m, 2H), 4.97 (s, 2H), 3.81-3.78 (m, 5H), 3.46-3.40 (m, 1H), 3.17-3.12 (m, 1H), 2.98 (br s, 2H), 2.46 (br s, 1H), 2.31-2.28 (m, 1H), 2.14 (s, 3H), 2.08-2.05 (m, 1H), 1.96-1.85 (m, 2H), 1.80 (d, J = 7.2 Hz, 3H), 1.65-1.53 (m, 3H), 1.32-1.25 (m, 1H), 0.91-0.88 (m, 1H). |
| 325 | 1st eluting isomer | methyl 1-[8-(methoxycarbonyl)-3-[(2R)-1-phenylpropan-2-yl]-3H,6H,7H,8H,9H-imidazo[4,5-h]isoquinolin-2-yl]piperidine-4-carboxylate | 477 | 1H-NMR-PH-FMA-PJ00200-008-0A (CD3OD, 400 MHz) δ (ppm): 7.59 (d, J = 8.0 Hz, 1H), 7.10-7.06 (m, 4H), 6.78-6.76 (m, 2H), 4.88 (s, 2H), 4.85-4.81 (m, 1H), 3.80-3.75 (m, 5H), 3.42-3.39 (m, 1H), 3.22-3.08 (m, 2H), 2.97 (s, 2H), 2.81-2.75 (m, 2H), 2.44-2.40 (m, 2H), 1.96-1.94 (m, 1H), 1.86-1.77 (m, 5H), 1.64-1.57 (m, 1H). |

TABLE 2-continued

| Compound No. | Structure | Compound name | MS (ESI, m/z) [M + H]+ | 1H-NMR δ (ppm) |
|---|---|---|---|---|
| 5 | 2nd eluting isomer | methyl 1-[8-(methoxycarbonyl)-3-[(2S)-1-phenylpropan-2-yl]-3H,6H,7H,8H,9H-imidazo[4,5-h]isoquinolin-2-yl]piperidine-4-carboxylate | 477 | 1H-NMR-PH-FMA-PJ00200-008-0B (CD3OD, 400 MHz) δ (ppm): 7.59 (d, J = 8.0 Hz, 1H), 7.10-7.06 (m, 4H), 6.78-6.76 (m, 2H), 4.89 (s, 2H), 4.85-4.81 (m, 1H), 3.79-3.75 (m, 5H), 3.42-3.38 (m, 1H), 3.18-3.08 (m, 2H), 2.97 (s, 2H), 2.81-2.75 (m, 2H), 2.44-2.40 (m, 2H), 1.96-1.94 (m, 1H), 1.86-1.77 (m, 5H), 1.64-1.57 (m, 1H). |
| 16 | First eluting isomer | 1-{3-[(2R)-1-(3-fluoro-5-methoxyphenyl)propan-2-yl]-8-(methoxycarbonyl)-3H,6H,7H,8H,9H-imidazo[4,5-h]isoquinolin-2-yl}piperidine-4-carboxylic acid | 525 | 1H-NMR (Methanol-d4, 400 MHz) δ (ppm): 7.57 (d, J = 8.0 Hz, 1H), 7.08 (d, J = 8.0 Hz, 1H), 6.44-6.35 (m, 1H), 6.19 (d, J = 8.8 Hz, 1H), 5.89 (s, 1H), 4.90 (s, 2H), 4.87-4.75 (m, 1H), 3.83-3.71 (m, 5H), 3.48 (s, 3H), 3.36-3.21 (m, 2H), 3.08-3.00 (m, 1H), 3.00-2.86 (m, 3H), 2.83-2.71 (m, 1H), 2.64-2.58 (m, 1H), 2.49-2.37 (m, 1H), 2.02-1.85 (m, 3H), 1.82 (d, J = 6.8 Hz, 3H), 1.70-1.57 (m, 1H). |
| 303 | Second eluting isomer | 1-{3-[(2S)-1-(3-fluoro-5-methoxyphenyl)propan-2-yl]-8-(methoxycarbonyl)-3H,6H,7H,8H,9H-imidazo[4,5-h]isoquinolin-2-yl}piperidine-4-carboxylic acid | 525 | 1H-NMR (Methanol-d4, 400 MHz) δ (ppm): 7.57 (d, J = 8.4 Hz, 1H), 7.09 (d, J = 8.4 Hz, 1H), 6.44-6.35 (m, 1H), 6.18 (d, J = 9.2 Hz, 1H), 5.90 (s, 1H), 4.87 (s, 2H), 4.86-4.72 (m, 1H), 3.81-3.72 (m, 5H), 3.48 (s, 3H), 3.38-3.22 (m, 2H), 3.08-3.00 (m, 1H), 3.00-2.87 (m, 3H), 2.85-2.71 (m, 1H), 2.68-2.61 (m, 1H), 2.59-2.48 (m, 1H), 2.08-1.87 (m, 3H), 1.82 (d, J = 6.8 Hz, 3H), 1.81-1.53 (m, 1H). |

TABLE 2-continued

| Compound No. | Structure | Compound name | MS (ESI, m/z) [M + H]+ | 1H-NMR δ (ppm) |
|---|---|---|---|---|
| 284 | First eluting isomer | (1R,3R)-3-[8-(methoxycarbonyl)-3[(2R)-1-(2-methylphenyl)propan-2-yl]-3H,6H,7H,8H,9H-imidazo[4,5-h]isoquinolin-2-yl]cyclohexane-1-carboxylic acid | 490 | 1H-NMR (CD3OD, 400 MHz) δ (ppm): 7.70 (d, J = 8.4 Hz, 1H), 7.12-7.00 (m, 3H), 6.99-6.77 (m, 1H), 6.33(d, J = 7.6 Hz, 1H), 5.05-4.90 (m, 3H), 3.82-3.71 (m, 5H), 3.41-3.32 (m, 1H), 3.26-3.18 (m, 1H), 2.98-2.91 (m, 2H), 2.79-2.72 (m, 1H), 2.47-2.38 (m, 1H), 2.19-2.11 (m, 5H), 1.88 (d, J = 6.8 Hz, 3H), 1.72-1.41 (m, 4H), 1.26-1.04 (m, 1H), 0.92-0.81 (m, 1H). |
| 17 | Second eluting isomer | (1R,3R)-3-[8-(methoxycarbonyl)-3[(2S)-1-(2-methylphenyl)propan-2-yl]-3H,6H,7H,8H,9H-imidazo[4,5-h]isoquinolin-2-yl]cyclohexane-1-carboxylic acid | 490 | 1H-NMR (CD3OD, 400 MHz) δ (ppm): 7.71 (d, J = 8.0 Hz, 1H), 7.12-7.03 (m, 2H), 7.06-6.99 (m, 1H), 6.81-6.77 (m, 1H), 6.34 (d, J = 7.6 Hz, 1H), 5.02-4.91 (m, 3H), 3.85-3.73 (m, 5H), 3.42-3.33 (m, 1H), 3.24-3.20 (m, 1H), 2.98-2.93 (m, 2H), 2.77-2.72 (m, 1H), 2.48-2.35 (m, 1H), 2.24-2.11 (m, 5H), 1.88 (d, J = 6.8 Hz, 3H), 1.72-1.42 (m, 4H), 1.25-1.01 (m, 1H), 0.95-0.78 (m, 1H) |
| 163 | Third eluting isomer | (1S,3S)-3-[8-(methoxycarbonyl)-3-[(2R)-1-(2-methylphenyl)propan-2-yl]-3H,6H,7H,8H 9H-imidazo[4,5-h]isoquinolin-2-yl]cyclohexane-1-carboxylic acid | 490 | 1H-NMR (CD3OD, 400 MHz) δ (ppm): 7.78-7.71 (m, 1H), 7.21-7.08 (m, 2H), 7.07-6.95 (m, 1H), 7.84-7.76 (m, 1H), 6.45-6.39 (m, 1H), 5.04-4.92 (m, 3H), 3.82-3.76 (m, 5H), 3.56-3.42 (m, 1H), 3.21-3.05 (m, 1H), 3.04-2.97 (m, 2H), 2.71-2.62 (m, 1H), 2.38 (s, 3H), 2.08-2.02 (m, 1H), 2.00-0.90 (m, 11H). |

| Compound No. | Structure | Compound name | MS (ESI, m/z) [M + H]+ | 1H-NMR δ (ppm) |
|---|---|---|---|---|
| 18 | Fourth eluting isomer | (1S,3S)-3[8-(methoxycarbonyl)-3-[(2S)-1-(2-methylphenyl)propan-2-yl]-3H,6H,7H,8H,9H-imidazo[4,5-h]isoquinolin-2-yl]cyclohexane-1-carboxylic acid | 490 | 1H-NMR (CD3OD, 400 MHz) δ (ppm): 7.82-7.75 (m, 1H), 7.22-7.07 (m, 2H), 7.08-6.98 (m, 1H), 7.86-7.74 (m, 1H), 6.41-6.35 (m, 1H), 5.07-4.92 (m, 3H), 3.82-3.77 (m, 5H), 3.60-3.44 (m, 1H), 3.18-3.09 (m, 1H), 3.02-2.98 (m, 2H), 2.75-2.63 (m, 1H), 2.35 (s, 3H), 2.12-2.01 (m, 1H), 1.99-0.72 (m, 11H). |
| 263 | First eluting isomer | (1R,3R)-3-[3-[(2R)-1-(2-chlorophenyl)propan-2-yl]-8-(methoxycarbonyl)-3H,6H,7H,8H 9H-imidazo[4,5-h]isoquinolin-2-yl]cyclohexane-1-carboxylic acid | 510 | 1H-NMR (CD3OD, 400 MHz) δ (ppm): 7.71-7.68 (m, 1H), 7.34 (d, J =8.0 Hz, 1H), 7.16-7.11 (m, 2H) 6.92-6.89 (m, 1H), 6.53-6.45 (m, 1H), 5.25-5.13 (m, 1H), 5.00 (s, 2H), 3.82-3.78 5H), 3.58-3.35 (m, 2H), 3.04-2.91 (m, 2H), 2.87-2.64 (m, 2H), 2.23-2.13 (m, 2H), 1.91-1.82 (m, 3H), 1.75-1.46 (m, 4H), 1.31-1.24 (m, 1H), 0.93-0.85 (m, 1H). |
| 176 | Second eluting isomer | (1S,3S)-3-{3-[(2R)-1-(2-chlorophenyl)propan-2-yl[-8-(methoxycarbonyl)-3H,6H,7H,8H 9H-imidazo[4,5-h]isoquinolin-2-yl]cyclohexane 1-carboxylic acid | 510 | 1H-NMR (CD3OD, 400 MHz) δ (ppm): 7.69-7.67 (m, 1H), 7.39 (d, J = 7.6 Hz, 1H), 7.16-7.12 (m, 2H), 6.98-6.86 (m, 1H), 6.70-6.67 (m, 1H), 5.04-4.97 3H), 3.83-3.78 (m, 5H), 3.52-3.51 (m, 2H), 3.15-2.97 (m, 3H), 2.84-2.81 (m, 1H), 2.12-2.06 (m, 1H), 1.84-1.76 (m, 2H), 1.81-1.75 (m, 4H), 1.75-1.51 (m, 4H). |

TABLE 2-continued

| Compound No. | Structure | Compound name | MS (ESI, m/z) [M + H]+ | 1H-NMR δ (ppm) |
|---|---|---|---|---|
| 19 | 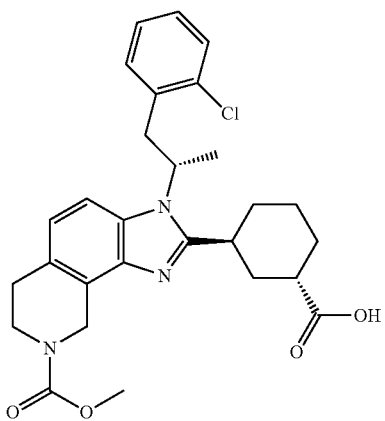 Third eluting isomer | (1S,3S)-3-{3-[(2R)-1-(2-chlorophenyl)propan-2-yl[-8-(methoxycarbonyl)-3H,6H,7H,8H 9H-imidazo[4,5-h]isoquinolin-2-yl]cyclohexane-1-carboxylic acid | 510 | 1H-NMR (CD3OD, 400 MHz) δ (ppm): 7.73-7.69 (m, 1H), 7.38 (d, J = 7.6 Hz, 1H), 7.16-7.12 (m, 2H), 6.96-6.90 (m, 1H), 6.67-6.62 (m, 1H), 5.03-4.97 (m, 3H), 3.83-3.78 (m, 5H), 3.52-3.48 (m, 2H), 3.15-2.97 (m, 3H), 2.82-2.78 (m, 1H), 2.09-2.04 (m, 1H), 1.99-1.82 (m, 2H), 1.91-1.56 (m, 8H). |
| 20 | 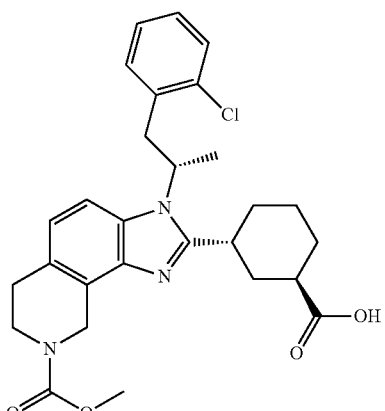 Fourth eluting isomer | (1R,3R)-3-{3-[(2S)-1-(2-chlorophenyl)propan-2-yl]-8-(methoxycarbonyl)-3H,6H,7H,8H, 9H-imidazo[4,5-h]isoquinolin-2-yl}cyclohexane-1-carboxylic acid | 510 | 1H-NMR (CD3OD, 400 MHz) δ (ppm): 7.71-7.68 (m, 1H), 7.34 (d, J = 8.0 Hz, 1H), 7.14-7.10 (m, 2H), 6.92-6.89 (m, 1H), 6.50-6.48 (m, 1H), 5.23-5.17 (m, 1H), 5.00 (s, 2H), 3.84-3.78 (m, 5H), 3.53-3.40 (m, 2H), 3.01-2.98 (m, 2H), 2.78-2.74 (m, 2H), 2.12-2.08 (m, 2H), 1.86 (d, J = 6.4 Hz, 3H), 1.75-1.48 (m, 4H), 1.33-1.30 (m, 1H), 0.96-0.89 (m, 1H). |
| 33 | 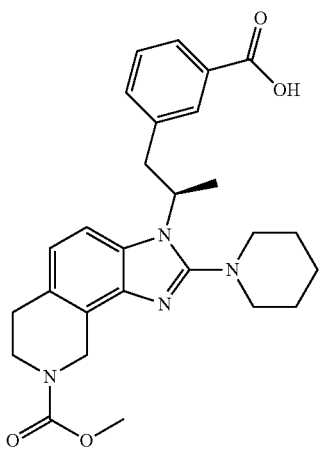 First eluting isomer | 3-[(2R)-2-[8-(methoxycarbonyl)-2-(piperidin-1-yl)-3H,6H,7H,8H, 9H-imidazo[4,5-h]isoquinolin-3-yl]propyl]benzoic acid | 477 | 1H NMR (400 MHz, CD3OD-d4) δ (ppm): 7.75 (d, J = 8.4 Hz, 1H), 7.60 (d, J = 8.0 Hz, 1H), 7.38 (s, 1H), 7.16 (t, J = 8.0 Hz, 1H), 7.09 (d, J = 8.4 Hz, 1H), 6.92 (d, J = 7.2 Hz, 1H), 4.91-4.77 (m, 3H), 3.82-3.71 (m, 5H), 3.45-3.32 (m, 1H), 3.18-3.13 (m, 1H), 3.03-2.95 (m, 4H), 2.62-2.55 (m, 2H), 1.85 (d, J = 6.8 Hz, 3H), 1.69-1.52 (m, 6H). |

TABLE 2-continued

| Compound No. | Structure | Compound name | MS (ESI, m/z) [M + H]+ | 1H-NMR δ (ppm) |
|---|---|---|---|---|
| 352 | ![structure] Second eluting isomer | 3-[(2S)-2-[8-(methoxycarbonyl)-2-(piperidin-1-yl)-3H,6H,7H,8H,9H-imidazo[4,5-h]isoquinolin-3-yl]propyl]benzoic acid | 477 | 1H NMR (400 MHz, CD3OD-d4) δ (ppm): 7.75 (d, J = 8.0 Hz, 1H), 7.58 (d, J = 8.4 Hz, 1H), 7.41 (s, 1H), 7.15 (t, J = 8.0 Hz, 1H), 7.07 (d, J = 8.4 Hz, 1H), 6.91 (d, J = 7.6 Hz, 1H), 4.91-4.79 (m, 3H), 3.83-3.71 (m, 5H), 3.45-3.32 (m, 1H), 3.18-3.13 (m, 1H), 3.02-2.91 (m, 4H), 2.62-2.51 (m, 2H), 1.84 (d, J = 6.8 Hz, 3H), 1.70-1.53 (m, 6H). |

Example 3: (1S,3S)-3-[8-(methoxycarbonyl)-3-[(2R)-1-phenylpropan-2-yl]-3H,6H,7H,8H,9H-imidazo[4,5-h]isoquinolin-2-yl]cyclohexane-1-carboxylic acid; (1S,3S)-3-[8-(methoxycarbonyl)-3-[(2S)-1-phenylpropan-2-yl]-3H,6H,7H,8H,9H-imidazo[4,5-h]isoquinolin-2-yl]cyclohexane-1-carboxylic acid; (1S,3R)-3-[8-(methoxycarbonyl)-3-[(2R)-1-phenylpropan-2-yl]-3H,6H,7H,8H,9H-imidazo[4,5-h]isoquinolin-2-yl]cyclohexane-1-carboxylic acid; (1S,3R)-3-[8-(methoxycarbonyl)-3-[(2S)-1-phenylpropan-2-yl]-3H,6H,7H,8H,9H-imidazo[4,5-h]isoquinolin-2-yl]cyclohexane-1-carboxylic acid; (1R,3S)-3-[8-(methoxycarbonyl)-3-[(2R)-1-phenylpropan-2-yl]-3H,6H,7H,8H,9H-imidazo[4,5-h]isoquinolin-2-yl]cyclohexane-1-carboxylic acid; (1R,3S)-3-[8-(methoxycarbonyl)-3-[(2S)-1-phenylpropan-2-yl]-3H,6H,7H,8H,9H-imidazo[4,5-h]isoquinolin-2-yl]cyclohexane-1-carboxylic acid; (1R,3R)-3-[8-(methoxycarbonyl)-3-[(2R)-1-phenylpropan-2-yl]-3H,6H,7H,8H,9H-imidazo[4,5-h]isoquinolin-2-yl]cyclohexane-1-carboxylic acid; and (1R,3R)-3-[8-(methoxycarbonyl)-3-[(2S)-1-phenylpropan-2-yl]-3H,6H,7H,8H,9H-imidazo[4,5-h]isoquinolin-2-yl]cyclohexane-1-carboxylic acid

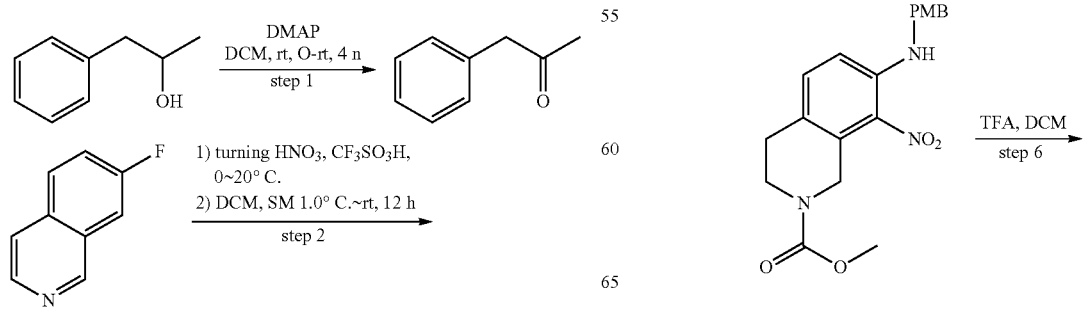

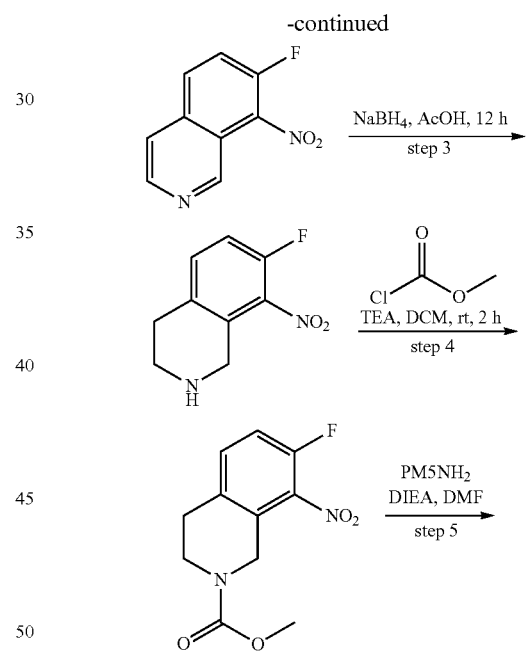

231
-continued
232
-continued
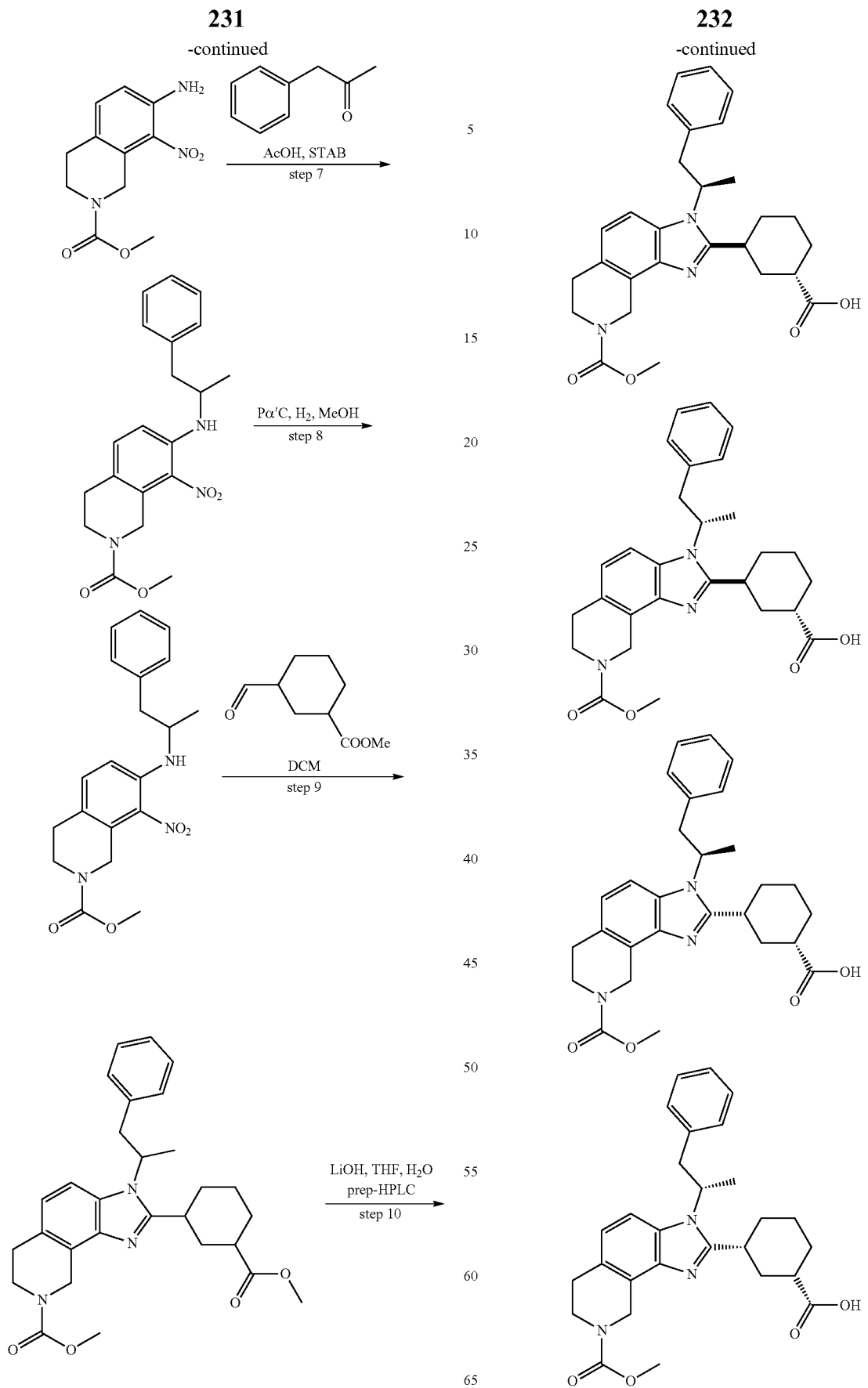

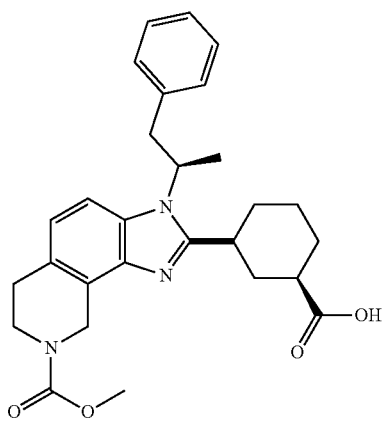

Step 1. 1-phenylpropan-2-one

To a stirred solution of 1-phenylpropan-2-ol (10.0 g, 73.42 mmol) in DCM (200 mL) was added DMP (62.3 g, 146.85 mmol) at 0° C. The resulting mixture was stirred for 4 h at room temperature and then concentrated under reduced pressure. The residue was dissolved in CH2Cl2 (300 mL). The resulting mixture was filtered, the filter cake was washed with CH2Cl2 (3×50 mL). The filtrate was concentrated under reduced pressure. The residue was purified by silica gel column chromatography (eluting with 3:1 ethyl acetate/petroleum ether) to afford 1-phenylpropan-2-one as a colorless liquid (6.7 g, 64.6%). 1H-NMR (DMSO-d6, 400 MHz) δ (ppm): 7.34-7.30 (m, 2H), 7.26-7.23 (m, 1H), 7.19 (d, J=8 Hz, 2H), 3.76 (s, 2H), 2.13 (s, 3H). LCMS (ES, m/z): 135 [M+H]$^+$.

Step 2. 7-fluoro-8-nitroisoquinoline

A solution of trifluoromethanesulfonic acid (87.8 mL, 573 mmol) and fuming nitric acid (22.2 mL, 344 mmol) was stirred for 30 min at 0° C. under nitrogen atmosphere. To the above was added 7-fluoroisoquinoline (50.0 g, 323 mmol) in dichloromethane (200 mL) dropwise over 30 min at 0° C. The resulting mixture was stirred for additional 4 h at room temperature. The mixture was neutralized to pH-7 with saturated sodium bicarbonate. The resulting mixture was extracted with dichloromethane (3×1000 mL), dried over anhydrous sodium sulfate, filtered, and concentrated under vacuum. The residue was purified by silica gel chromatography (eluting with 1:1 ethyl acetate/petroleum ether) to afford 7-fluoro-8-nitroisoquinoline as a yellow solid (60.0 g, 92%). LCMS (ES, m/z): 193 [M+H]$^+$.

Step 3. 7-fluoro-8-nitro-1,2,3,4-tetrahydroisoquinoline

A mixture of 7-fluoro-8-nitroisoquinoline (50.0 g, 247 mmol) and sodium borohydride (30.0 g, 777 mmol) in glacial acetic acid (200 mL) was stirred for 3 h at room temperature under the stream of nitrogen. The resulting mixture was diluted with water (150 mL). The mixture was neutralized to pH-7 with saturated sodium bicarbonate. The resulting mixture was extracted with dichloromethane (3×500 mL), dried over anhydrous sodium sulfate, filtered and concentrated under reduced pressure. The residue was purified by silica gel chromatography (eluting with 1:10 methanol/dichloromethane) to afford 7-fluoro-8-nitro-1,2,3,4-tetrahydroisoquinoline as a yellow solid (35 g, 69%). LCMS (ES, m/z): 197 [M+H]$^+$.

Step 4. methyl 7-fluoro-8-nitro-1,2,3,4-tetrahydroisoquinoline-2-carboxylate

A solution of 7-fluoro-8-nitro-1,2,3,4-tetrahydroisoquinoline (45.0 g, 228 mmol), methyl carbonochloridate (44.0 g, 456 mmol) and triethylamine (96 mL, 676 mmol) in dichloromethane (200 mL) was stirred for 2 h at room temperature. The resulting mixture was quenched with water (500 mL). The resulting mixture was extracted with dichloromethane (3×300 mL), dried over anhydrous sodium sulfate, filtered and concentrated under reduced pressure. The residue was purified by silica gel column chromatography (eluting with 1:1 ethyl acetate/petroleum ether) to afford methyl 7-fluoro-8-nitro-1,2,3,4-tetrahydroisoquinoline-2-carboxylate as a yellow solid (40.1 g, 69%). LCMS (ES, m/z): 255 [M+H]$^+$.

Step 5. methyl 7-[[(4-methoxyphenyl)methyl]amino]-8-nitro-1,2,3,4-tetrahydroisoquinoline-2-carboxylate A solution of methyl 7-fluoro-8-nitro-1,2,3,4-tetrahydroisoquinoline-2-carboxylate (30.0 g, 112 mmol), diisopropylethylamine (36.9 mL, 224 mmol) and 1-(4-methoxyphenyl)methanamine (31.5 g, 225 mmol) in N,N-dimethylformamide (200 mL) was stirred for 2 h at 80° C. under the stream of nitrogen. The mixture was allowed to cool down to room temperature and diluted with water (500 mL). The resulting mixture was extracted with dichloromethane (3×300 mL), dried over anhydrous sodium sulfate, filtered and concentrated under reduced pressure. The residue was purified by silica gel column chromatography (eluting with 1:1 ethyl acetate/petroleum ether) to afford methyl 7-[[(4-methoxyphenyl)methyl]amino]-8-nitro-1,2,3,4-tetrahydroisoquinoline-2-carboxylate as a yellow oil (34.0 g, 77%). LCMS (ES, m/z): 372 [M+H]$^+$.

Step 6. methyl 7-amino-8-nitro-1,2,3,4-tetrahydroisoquinoline-2-carboxylate

A solution of methyl 7-[[(4-methoxyphenyl)methyl]amino]-8-nitro-1,2,3,4-tetrahydroisoquinoline-2-carboxylate (34.0 g, 87 mmol) and trifluoroacetic acid (50 mL) in dichloromethane (150 mL) was stirred for 3 h at room temperature. The resulting mixture was concentrated under reduced pressure. The residue was purified by silica gel column chromatography (eluting with 1:1 ethyl acetate/petroleum ether) to afford methyl 7-amino-8-nitro-1,2,3,4-tetrahydroisoquinoline-2-carboxylate as a yellow solid (18 g, 78%). LCMS (ES, m/z): 252 [M+H]$^+$.

Step 7. Methyl 8-nitro-7-[(1-phenylpropan-2-yl)amino]-1,2,3,4-tetrahydroisoquinoline-2-carboxylate A solution of methyl 7-amino-8-nitro-1,2,3,4-tetrahydroisoquinoline-2-carboxylate (300 mg, 1.13 mmol) and 1-phenylpropan-2-one (317 mg, 2.25 mmol) in AcOH (10 mL) was stirred for 30 min at room temperature. To the above mixture was added NaBH(OAc)3 (1.3 g, 5.98 mmol) in portions at 0° C. The resulting mixture was stirred for 16 h at room temperature. The resulting mixture was diluted with water (20 mL) and extracted with ethyl acetate (3×20 mL). The combined organic phase was dried over anhydrous sodium sulfate, filtered and concentrated under vacuum. The resulting crude product was purified by silica gel chromatography (eluting with 1:1 ethyl acetate/petroleum ether) to afford methyl 8-nitro-7-[(1-phenylpropan-2-yl)amino]-1,2,3,4-tetrahydroisoquinoline-2-carboxylate as an orange solid (220 mg, 47%).
LCMS (ES, m/z) 370 [M+H]$^+$.

Step 8. Methyl 8-amino-7-[(1-phenylpropan-2-yl)amino]-1,2,3,4-tetrahydroisoquinoline-2-carboxylate A mixture of methyl 8-nitro-7-[(1-phenylpropan-2-yl)amino]-1,2,3,4-tetrahydroisoquinoline-2-carboxylate (250 mg, 0.64 mmol) and Pd/C (250 mg) in MeOH (10 mL) was stirred for 1 h at room temperature under hydrogen atmosphere. The resulting mixture was filtered out and concentrated under reduced pressure. The residue was purified by silica gel chromatography (eluting with 1:1 ethyl acetate/petroleum ether) to afford methyl 8-amino-7-[(1-phenylpropan-2-yl)amino]-1,2,3,4-tetrahydroisoquinoline-2-carboxylate as a light brown solid (150 mg, 62%). LCMS (ES, m/z) 340 [M+H]$^+$.

Step 9. Methyl 2-[3-(methoxycarbonyl)cyclohexyl]-3-(1-phenylpropan-2-yl)-3H,6H,7H,8H,9H-imidazo[4,5-h]isoquinoline-8-carboxylate A solution of methyl 8-amino-7-[(1-phenylpropan-2-yl)amino]-1,2,3,4-tetrahydroisoquinoline-2-carboxylate (2.00 g, 5.60 mmol) and methyl 3-formylcyclohexane-1-carboxylate (0.97 g, 5.60 mmol) in DCM (30 mL) was stirred for 16 h at room temperature. The resulting mixture was concentrated under reduced pressure. The residue was purified by silica gel chromatography (eluting with 1:1 ethyl acetate/petroleum ether) to afford methyl 2-[3-(methoxycarbonyl)cyclohexyl]-3-(1-phenylpropan-2-yl)-3H,6H,7H,8H,9H-imidazo[4,5-h]isoquinoline-8-carboxylate as a yellow solid (1.1 g, 38.13%). LCMS (ES, m/z) 490 [M+H]$^+$.

Step 10. (1S,3S)-3-[8-(methoxycarbonyl)-3-[(2R)-1-phenylpropan-2-yl]-3H,6H,7H,8H,9H-imidazo[4,5-h]isoquinolin-2-yl]cyclohexane-1-carboxylic acid; (1S,3S)-3-[8-(methoxycarbonyl)-3-[(2S)-1-phenylpropan-2-yl]-3H,6H,7H,8H,9H-imidazo[4,5-h]isoquinolin-2-yl]cyclohexane-1-carboxylic acid; (1S,3R)-3-[8-(methoxycarbonyl)-3-[(2R)-1-phenylpropan-2-yl]-3H,6H,7H,8H,9H-imidazo[4,5-h]isoquinolin-2-yl]cyclohexane-1-carboxylic acid; (1S,3R)-3-[8-(methoxycarbonyl)-3-[(2S)-1-phenylpropan-2-yl]-3H,6H,7H,8H,9H-imidazo[4,5-h]isoquinolin-2-yl]cyclohexane-1-carboxylic acid; (1R,3S)-3-[8-(methoxycarbonyl)-3-[(2R)-1-phenylpropan-2-yl]-3H,6H,7H,8H,9H-imidazo[4,5-h]isoquinolin-2-yl]cyclohexane-1-carboxylic acid; (1R,3S)-3-[8-(methoxycarbonyl)-3-[(2S)-1-phenylpropan-2-yl]-3H,6H,7H,8H,9H-imidazo[4,5-h]isoquinolin-2-yl]cyclohexane-1-carboxylic acid; (1R,3R)-3-[8-(methoxycarbonyl)-3-[(2R)-1-phenylpropan-2-yl]-3H,6H,7H,8H,9H-imidazo[4,5-h]isoquinolin-2-yl]cyclohexane-1-carboxylic acid; and (1R,3R)-3-[8-(methoxycarbonyl)-3-[(2S)-1-phenylpropan-2-yl]-3H,6H,7H,8H,9H-imidazo[4,5-h]isoquinolin-2-yl]cyclohexane-1-carboxylic acid A solution of methyl 2-[3-(methoxycarbonyl)cyclohexyl]-3-(1-phenylpropan-2-yl)-3H,6H,7H,8H,9H-imidazo[4,5-h]isoquinoline-8-carboxylate (1.2 g, 2.21 mmol) and LiOH (295 mg, 12.3 mmol) in THF (12 mL) and H2O (12 mL) was stirred for 16 h at 25° C. The resulting mixture was concentrated under vacuum. The crude product was purified by Prep-HPLC (Column: Xselect CSH OBD Column, 5 um, 30×150 mm; Mobile Phase, A: water (containing 0.05% TFA) and B: ACN (20% to 33% over 12 min); Detector: UV 254 nm). The product was separated by Prep-SFC (Column, CHIRALPAK AD, 3×100 cm, 3 um; Mobile phase, A: Hex (containing 20M NH3) and IPA (hold 20.0% ethanol to 80% over 40 min); Detector, UV 220/254 nm) to afford four eluting isomers. The first eluting isomer was separated by Prep-SFC (Column, CHIRALPAK AD, 3×100 cm, 3 um; Mobile phase, A: Hex (containing 20M NH3) and IPA (hold 10.0% ethanol to 50% over 4 min); Detector, UV 220/254 nm) to afford (1S,3S)-3-[8-(methoxycarbonyl)-3-[(2R)-1-phenylpropan-2-yl]-3H,6H,7H,8H,9H-imidazo[4,5-h]isoquinolin-2-yl]cyclohexane-1-carboxylic acid as a white solid (67.3 mg, 49.78%) and (1S,3S)-3-[8-(methoxycarbonyl)-3-[(2S)-1-phenylpropan-2-yl]-3H,6H,7H,8H,9H-imidazo[4,5-h]isoquinolin-2-yl]cyclohexane-1-carboxylic acid as a white solid (68.8 mg, 50.89%). The second eluting isomer was separated by Chiral-Prep-HPLC (Column, CHIRALPAK IC, 0.46×5 cm, 3 um; Mobile phase, A: Hex (containing 0.1% FA) and ethanol (hold 20.0% ethanol over 30 min); Detector, UV 220/254 nm) to afford (1S,3R)-3-[8-(methoxycarbonyl)-3-[(2R)-1-phenylpropan-2-yl]-3H,6H,7H,8H,9H-imidazo[4,5-h]isoquinolin-2-yl]cyclohexane-1-carboxylic acid as a white solid (7.7 mg, 5.75%) and (1R,3S)-3-[8-(methoxycarbonyl)-3-[(2S)-1-phenylpropan-2-yl]-3H,6H,7H,8H,9H-imidazo[4,5-h]isoquinolin-2-yl]cyclohexane-1-carboxylic acid as a white solid (8.9 mg, 6.65%). The third eluting isomer was separated by Chiral-Prep-HPLC (Column, CHIRALPAK IG, 0.46×5 cm, 3 um; Mobile phase, A: Hex (containing 0.1% FA) and ethanol (hold 30.0% ethanol over 30 min); Detector, UV 220/254 nm to afford (1S,3R)-3-[8-(methoxycarbonyl)-3-[(2S)-1-phenylpropan-2-yl]-3H,6H,7H,8H,9H-imidazo[4,5-h]isoquinolin-2-yl]cyclohexane-1-carboxylic acid as a white solid (7.9 mg, 5.90%) and (1R,3S)-3-[8-(methoxycarbonyl)-3-[(2R)-1-phenylpropan-2-yl]-3H,6H,7H,8H,9H-imidazo[4,5-h]isoquinolin-2-yl]cyclohexane-1-carboxylic acid as a white solid (8.0 mg, 5.98%). The fourth eluting isomer was separated by Prep-SFC (Column, CHIRALPAK IC, 3×100 cm, 3 um; Mobile phase, A: Hex (containing 20M NH3) and IPA (10% to 50.0% ethanol over 30 min); Detector, UV 220/254 nm to afford (1R,3R)-3-[8-(methoxycarbonyl)-3-[(2R)-1-phenylpropan-2-yl]-3H,6H,7H,8H,9H-imidazo[4,5-h]isoquinolin-2-yl]cyclohexane-1-carboxylic acid as a white solid (35.6 mg, 26.88%) and (1R,3R)-3-[8-(methoxycarbonyl)-3-[(2S)-1-phenylpropan-2-yl]-3H,6H,7H,8H,9H-imidazo[4,5-h]isoquinolin-2-yl]cyclohexane-1-carboxylic acid as a white solid (44.9 mg, 33.56%).

The compounds in Table 3 below may be prepared by methods analogous to the method described in Example 3.

TABLE 3

| Compound No. | Structure | Compound name | MS (ESI, m/z) [M + H]+ | 1H-NMR δ (ppm) |
|---|---|---|---|---|
| 353 | First eluting isomer | (1S,3S)-3-[8-(methoxycarbonyl)-3-[(2R)-1-phenylpropan-2-yl]-3H,6H,7H,8H,9H-imidazo[4,5-h]isoquinolin-2-yl]cyclohexane-1-carboxylic acid | 476 | 1H-NMR (CD3OD, 400 MHz) δ (ppm): 7.70-7.68 (m, 1H), 7.12-7.10 (m, 4H), 6.85-6.73 (m, 2H), 5.02-4.85 (m, 3H), 3.83-3.73 (m, 5H), 3.49-3.40 (m, 1H), 3.20-3.11 (m, 1H), 3.02-2.98 (m, 2H), 2.51-2.41 (m, 1H), 2.20-2.07 (m, 1H), 2.01-1.87 (m, 2H), 1.85-1.73 (m, 4H), 1.68-1.56 (m, 1H), 1.55-1.35 (m, 3H), 1.10-0.95 (m, 1H). |
| 354 | Second eluting isomer | (1S,3S)-3-[8-(methoxycarbonyl)-3-[(2S)-1-phenylpropan-2-yl]-3H,6H,7H,8H,9H-imidazo[4,5-h]isoquinolin-2-yl]cyclohexane-1-carboxylic acid | 476 | 1H-NMR (CD3OD, 400 MHz) δ (ppm): 7.70-7.67 (m, 1H), 7.11-7.10 (m, 4H), 6.84-6.79 (m, 2H), 5.01-4.81 (m, 3H), 3.84-3.74 (m, 5H), 3.48-3.42 (m, 1H), 3.22-3.12 (m, 1H), 3.03-2.94 (m, 2H), 2.51-2.41 (m, 1H), 2.17-2.05 (m, 1H), 1.99-1.87 (m, 2H), 1.85-1.74 (m, 4H), 1.71-1.58 (m, 1H), 1.55-1.32 (m, 3H), 1.10-0.98 (m, 1H). |

TABLE 3-continued

| Compound No. | Structure | Compound name | MS (ESI, m/z) [M + H]⁺ | ¹H-NMR δ (ppm) |
|---|---|---|---|---|
| 233 | Third eluting isomer | (1S,3R)-3-[8-(methoxycarbonyl)-3-[(2R)-1-phenylpropan-2-yl]-3H,6H,7H,8H,9H-imidazo[4,5-h]isoquinolin-2-yl]cyclohexane-1-carboxylic acid | 476 | ¹H-NMR (CD3OD, 400 MHz) δ (ppm): 7.72-7.67 (m, 1H), 7.12-7.05 (m, 4H), 6.81-6.73 (m, 2H), 5.07-5.01 (m, 1H), 4.89 (s, 2H), 3.85-3.72 (m, 5H), 3.50-3.35 (m, 1H), 3.18-3.11 (m, 1H), 3.02-2.93 (m, 2H), 2.81-2.76 (m, 1H), 2.62-2.52 (m, 1H), 2.20-2.10 (m, 2H), 1.84 (d, J = 6.4 Hz, 3H), 1.70-1.45 (m, 4H), 1.30-1.11 (m, 1H), 1.05-0.92 (m, 1H). |
| 203 | Fourth eluting isomer | (1S,3R)-3-[8-(methoxycarbonyl)-3-[(2S)-1-phenylpropan-2-yl]-3H,6H,7H,8H,9H-imidazo[4,5-h]isoquinolin-2-yl]cyclohexane-1-carboxylic acid | 476 | ¹H-NMR (CD3OD, 400 MHz) δ (ppm): 7.78-7.60 (m, 1H), 7.12-7.05 (m, 4H), 6.95-6.88 (m, 2H), 5.00-4.88 (m, 3H), 3.82-3.73 (m, 5H), 3.55-3.46 (m, 1H), 3.28-3.21 (m, 1H), 3.19-3.07 (m, 1H), 3.01-2.93 (m, 1H), 2.78-2.71 (m, 1H), 2.11-2.08 (m, 1H), 1.86-1.78 (m, 1H), 1.77-1.69 (m, 5H), 1.67-1.52 (m, 4H). |
| 12 | Fifth eluting isomer | (1R,3S)-3-[8-(methoxycarbonyl)-3-[(2R)-1-phenylpropan-2-yl]-3H,6H,7H,8H,9H-imidazo[4,5-h]isoquinolin-2-yl]cyclohexane-1-carboxylic acid | 476 | ¹H-NMR (CD3OD, 400 MHz) δ (ppm): 7.85-7.62 (m, 1H), 7.10-7.09 (m, 4H), 6.93-6.86 (m, 2H), 5.05-4.92 (m, 3H), 3.82-3.73 (m, 5H), 3.67-3.55 (m, 1H), 3.28-3.19 (m, 1H), 3.18-3.04 (m, 1H), 3.01-2.90 (m, 2H), 2.78-2.69 (m, 1H), 2.26-2.02 (m, 1H), 1.90-1.70 (m, 6H), 1.69-1.42 (m, 4H). |

TABLE 3-continued

| Compound No. | Structure | Compound name | MS (ESI, m/z) [M + H]⁺ | ¹H-NMR δ (ppm) |
|---|---|---|---|---|
| 13 | Sixth eluting isomer | (1R,3S)-3-[8-(methoxycarbonyl)-3-[(2S)-1-phenylpropan-2-yl]-3H,6H,7H,8H,9H-imidazo[4,5-h]isoquinolin-2-yl]cyclohexane-1-carboxylic acid | 476 | ¹H-NMR (CD3OD, 400 MHz) δ (ppm): 7.79-7.50 (m, 1H), 7.17-7.05 (m, 4H), 6.82-6.74 (m, 2H), 5.07-4.92 (m, 3H), 3.83-3.72 (m, 5H), 3.50-3.40 (m, 1H), 3.21-3.05 (m, 1H), 3.03-2.92 (m, 2H), 2.82-2.75 (m, 1H), 2.65-2.45 (m, 1H), 2.30-2.05 (m, 2H), 1.84 (d, J = 6.4 Hz, 3H), 1.75-1.41 (m, 4H), 1.28-1.10 (m, 1H), 1.04-0.95 (m, 1H). |
| 298 | Seventh eluting isomer | (1R,3R)-3-[8-(methoxycarbonyl)-3-[(2R)-1-phenylpropan-2-yl]-3H,6H,7H,8H,9H-imidazo[4,5-h]isoquinolin-2-yl]cyclohexane-1-carboxylic acid | 476 | ¹H-NMR (CD3OD, 400 MHz) δ (ppm): 7.90-7.46 (m, 1H), 7.30-6.95 (m, 4H), 6.85-6.74 (m, 2H), 5.01-4.95 (m, 2H), 4.90-4.80 (m, 1H), 3.84-3.73 (m, 5H), 3.52-3.40 (m, 1H), 3.25-3.12 (m, 1H), 3.03-2.91 (m, 2H), 2.60-2.25 (m, 2H), 2.12-1.91 (m, 2H), 1.82 (d, J = 6.8 Hz, 3H), 1.80-1.61 (m, 2H), 1.53-1.30 (m, 2H), 1.29-1.06 (m, 1H), 0.83-0.61 (m, 1H). |
| 99 | Eighth eluting isomer | (1R,3R)-3-[8-(methoxycarbonyl)-3-[(2S)-1-phenylpropan-2-yl]-3H,6H,7H,8H,9H-imidazo[4,5-h]isoquinolin-2-yl]cyclohexane-1-carboxylic acid | 476 | ¹H-NMR (CD3OD, 400 MHz) δ (ppm): 7.89-7.50 (m, 1H), 7.29-7.00 (m, 4H), 6.5-6.77 (m, 2H), 5.01-4.90 (m, 2H), 4.89-4.80 (m, 1H), 3.83-3.72 (m, 5H), 3.58-3.39 (m, 1H), 3.25-3.12 (m, 1H), 3.02-2.84 (m, 2H), 2.60-2.30 (m, 2H), 2.12-1.90 (m, 2H), 1.82 (d, J = 6.8 Hz, 3H), 1.80-1.57 (m, 2H), 1.52-1.31 (m, 2H), 1.29-1.06 (m, 1H), 0.83-0.70 (m, 1H). |

TABLE 3-continued

| Compound No. | Structure | Compound name | MS (ESI, m/z) [M + H]+ | 1H-NMR δ (ppm) |
|---|---|---|---|---|
| 15 | First eluting isomer | methyl 3-[(2R)-1-phenylpropan-2-yl]-2-[(1r,4r)-4-(methanesulfinyl-carbamoyl)cyclohexyl]-3H,6H,7H,8H,9H-imidazo[4,5-h]isoquinoline-8-carboxylate | 553 | 1H-NMR (CD3OD, 400 MHz) δ (ppm): 7.78-7.64 (m, 1H), 7.17-7.06 (m, 4H), 6.88-6.73 (m, 2H), 5.01-4.92 (m, 2H), 4.90-4.80 (m, 1H), 3.85-3.77 (m, 5H), 3.54-3.40 (m, 1H), 3.28 (s, 3H), 3.25-3.13 (m, 1H), 3.01-2.88 (m, 2H), 2.55-2.21 (m, 2H), 2.10-2.03 (m, 1H), 1.91-1.70 (m, 5H), 1.69-1.42 (m, 3H), 1.40-1.21 (m, 1H), 0.88-0.72 (m, 1H). |
| 290 | Second eluting isomer | methyl 3-[(2S)-1-phenylpropan-2-yl]-2-[(1r,4r)-4-(methanesulfinyl-carbamoyl)cyclohexyl]-3H,6H,7H,8H,9H-imidazo[4,5-h]isoquinoline-8-carboxylate | 553 | 1H-NMR (CD3OD, 400 MHz) δ (ppm): 7.75-7.64 (m, 1H), 7.18-7.07 (m, 4H), 6.89-6.73 (m, 2H), 5.01-4.95 (m, 2H), 4.90-4.80 (m, 1H), 3.87-3.73 (m, 5H), 3.61-3.41 (m, 1H), 3.27 (s, 3H), 3.23-3.12 (m, 1H), 3.04-2.90 (m, 2H), 2.52-2.21 (m, 2H), 2.05-1.91 (m, 1H), 1.90-1.72 (m, 5H), 1.70-1.45 (m, 3H), 1.39-1.20 (m, 1H), 0.85-0.64 (m, 1H). |

Example 4: 1-{3-[(2R)-1-(2-chlorophenyl)propan-2-yl]-8-(methoxycarbonyl)-3H,6H,7H,8H,9H-imidazo[4,5-h]isoquinolin-2-yl}piperidine-4-carboxylic acid and 1-{3-[(2S)-1-(2-chlorophenyl)propan-2-yl]-8-(methoxycarbonyl)-3H,6H,7H,8H,9H-imidazo[4,5-h]isoquinolin-2-yl}piperidine-4-carboxylic acid

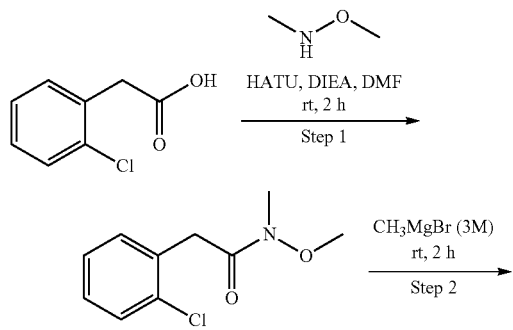

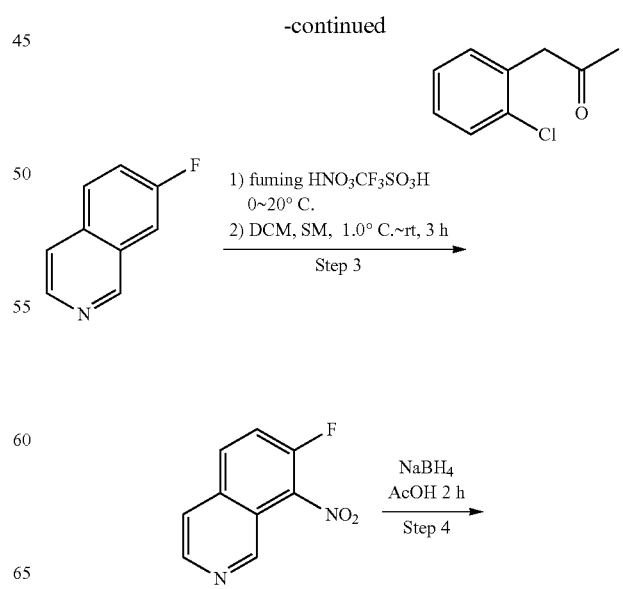

245
-continued
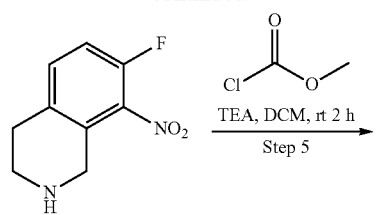
Step 5: methyl chloroformate, TEA, DCM, rt 2 h
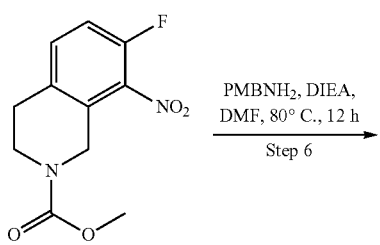
Step 6: PMBNH₂, DIEA, DMF, 80° C., 12 h
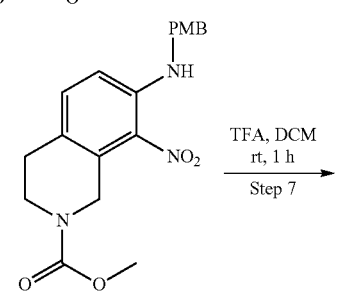
Step 7: TFA, DCM, rt, 1 h
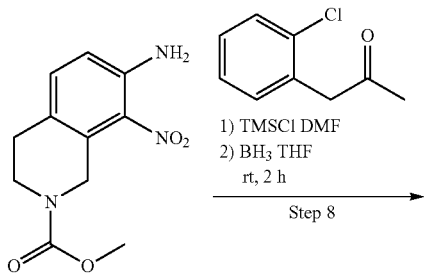
Step 8: 1) TMSCl DMF 2) BH₃ THF, rt, 2 h
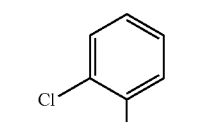
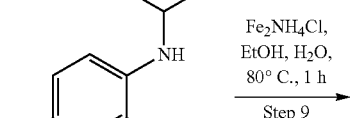
Step 9: Fe₂NH₄Cl, EtOH, H₂O, 80° C., 1 h
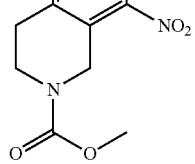
246
-continued
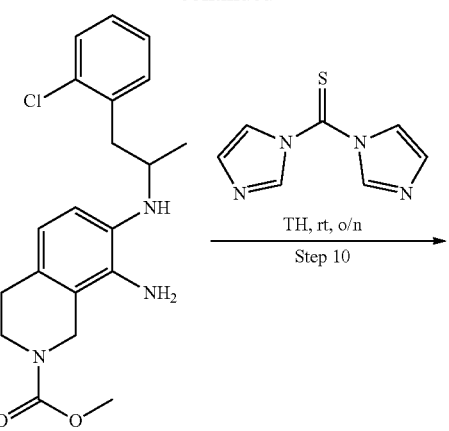
Step 10: TH, rt, o/n
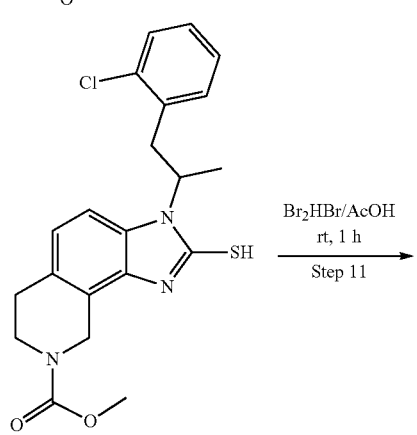
Step 11: Br₂HBr/AcOH, rt, 1 h
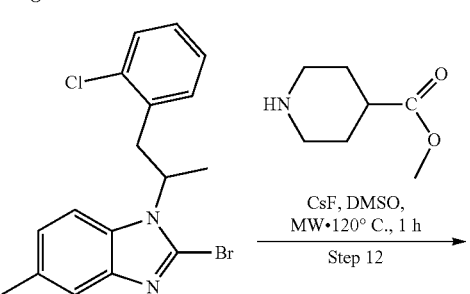
Step 12: methyl piperidine-4-carboxylate, CsF, DMSO, MW•120° C., 1 h
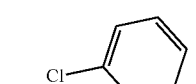
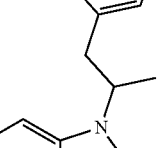
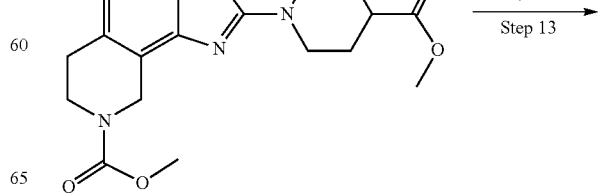
Step 13: LiOH, H₂O, MeOH, THF, rt, 1 h -continued

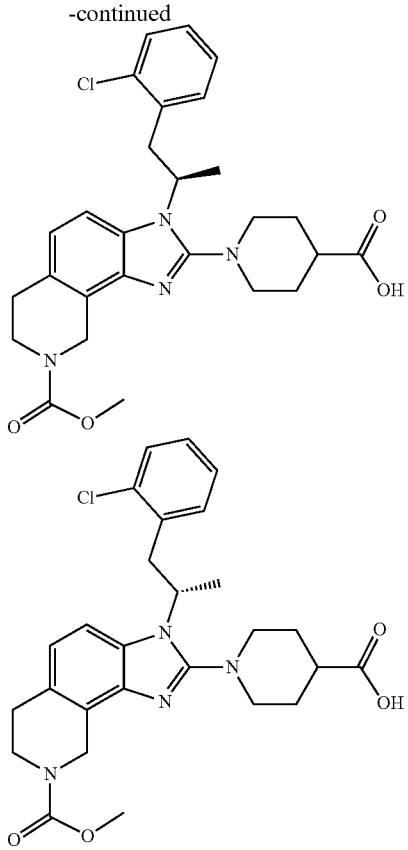

Step 1. 2-(2-chlorophenyl)-N-methoxy-N-methylacetamide

A mixture of 2-(2-chlorophenyl)acetic acid (5 g, 29.31 mmol), methoxy(methyl)amine (4.31 g, 43.97 mmol), HATU (13 g, 35.17 mmol) and DIEA (15 g, 117.24 mmol) in DMF (100 mL) was stirred for 2 h at room temperature. The resulting mixture was diluted with brine (100 mL) and extracted with ethyl acetate (3×50 mL). The combined organic layers were dried over anhydrous Na2SO4. After filtration, the filtrate was concentrated under reduced pressure. The residue was purified by silica gel column chromatography (eluting with 1:3 ethyl acetate/petroleum ether) to afford 2-(2-chlorophenyl)-N-methoxy-N-methylacetamide as a colorless oil (5.8 g, 93%). LCMS (ES, m/z): 214, 216[M+H]$^+$.

Step 2. 1-(2-chlorophenyl)propan-2-one

To a stirred solution of 2-(2-chlorophenyl)-N-methoxy-N-methylacetamide (2 g, 8.89 mmol) in THF (50 mL) was added CH3MgBr (3 M in THF) (6.83 mL) dropwise at 0° C. The resulting mixture was stirred for 2 h at room temperature. The reaction was quenched with sat. NH4Cl (aq.) at 0° C. The resulting mixture was diluted with ethyl acetate (50 mL) and washed with brine (50 mL), dried over anhydrous Na2SO4. After filtration, the filtrate was concentrated under reduced pressure. The residue was purified by silica gel column chromatography (eluting with 1:3 ethyl acetate/ petroleum ether) to afford 1-(2-chlorophenyl)propan-2-one as a light yellow oil (500 mg, 31%). LCMS (ES, m/z): 169, 171 [M+H]$^+$.

Step 3. 7-fluoro-8-nitroisoquinoline

A solution of trifluoromethanesulfonic acid (87.8 mL, 573 mmol) and fuming nitric acid (22.2 mL, 344 mmol) was stirred for 30 min at 0° C. under nitrogen atmosphere. To the above was added 7-fluoroisoquinoline (50.0 g, 323 mmol) in dichloromethane (200 mL) dropwise over 30 min at 0° C. The resulting mixture was stirred for additional 4 h at room temperature. The mixture was neutralized to pH-7 with saturated sodium bicarbonate. The resulting mixture was extracted with dichloromethane (3×1000 mL), dried over anhydrous sodium sulfate, filtered, and concentrated under vacuum. The residue was purified by silica gel chromatography (eluting with 1:1 ethyl acetate/petroleum ether) to afford 7-fluoro-8-nitroisoquinoline as a yellow solid (60.0 g, 92%). LCMS (ES, m/z): 193 [M+H]$^+$.

Step 4. 7-fluoro-8-nitro-1,2,3,4-tetrahydroisoquinoline

A mixture of 7-fluoro-8-nitroisoquinoline (50.0 g, 247 mmol) and sodium borohydride (30.0 g, 777 mmol) in glacial acetic acid (200 mL) was stirred for 3 h at room temperature under the stream of nitrogen. The resulting mixture was diluted with water (150 mL). The mixture was neutralized to pH-7 with saturated sodium bicarbonate. The resulting mixture was extracted with dichloromethane (3×500 mL), dried over anhydrous sodium sulfate, filtered and concentrated under reduced pressure. The residue was purified by silica gel chromatography (eluting with 1:10 methanol/dichloromethane) to afford 7-fluoro-8-nitro-1,2,3,4-tetrahydroisoquinoline as a yellow solid (35 g, 69%). LCMS (ES, m/z): 197 [M+H]$^+$.

Step 5. methyl 7-fluoro-8-nitro-1,2,3,4-tetrahydroisoquinoline-2-carboxylate A solution of 7-fluoro-8-nitro-1,2,3,4-tetrahydroisoquinoline (45.0 g, 228 mmol), methyl carbonochloridate (44.0 g, 456 mmol) and triethylamine (96 mL, 676 mmol) in dichloromethane (200 mL) was stirred for 2 h at room temperature. The resulting mixture was quenched with water (500 mL). The resulting mixture was extracted with dichloromethane (3×300 mL), dried over anhydrous sodium sulfate, filtered and concentrated under reduced pressure. The residue was purified by silica gel column chromatography (eluting with 1:1 ethyl acetate/petroleum ether) to afford methyl 7-fluoro-8-nitro-1,2,3,4-tetrahydroisoquinoline-2-carboxylate as a yellow solid (40.1 g, 69%). LCMS (ES, m/z): 255 [M+H]$^+$.

Step 6. methyl 7-[[(4-methoxyphenyl)methyl]amino]-8-nitro-1,2,3,4-tetrahydroisoquinoline-2-carboxylate A solution of methyl 7-fluoro-8-nitro-1,2,3,4-tetrahydroisoquinoline-2-carboxylate (30.0 g, 112 mmol), diisopropylethylamine (36.9 mL, 224 mmol) and 1-(4-methoxyphenyl)methanamine (31.5 g, 225 mmol) in N,N-dimethylformamide (200 mL) was stirred for 2 h at 80° C. under the stream of nitrogen. The mixture was allowed to cool down to room temperature and diluted with water (500 mL). The resulting mixture was extracted with dichloromethane (3×300 mL), dried over anhydrous sodium sulfate, filtered and concentrated under reduced pressure. The residue was purified by silica gel column chromatography (eluting with 1:1 ethyl acetate/petroleum ether) to afford methyl 7-[[(4-methoxyphenyl)methyl]amino]-8-nitro-1,2,3, 4-tetrahydroisoquinoline-2-carboxylate as a yellow oil (34.0 g, 77%). LCMS (ES, m/z): 372 [M+H]⁺.

Step 7. methyl 7-amino-8-nitro-1,2,3,4-tetrahydroisoquinoline-2-carboxylate

A solution of methyl 7-[[(4-methoxyphenyl)methyl]amino]-8-nitro-1,2,3,4-tetrahydroisoquinoline-2-carboxylate (34.0 g, 87 mmol) and trifluoroacetic acid (50 mL) in dichloromethane (150 mL) was stirred for 3 h at room temperature. The resulting mixture was concentrated under reduced pressure. The residue was purified by silica gel column chromatography (eluting with 1:1 ethyl acetate/petroleum ether) to afford methyl 7-amino-8-nitro-1,2,3,4-tetrahydroisoquinoline-2-carboxylate as a yellow solid (18 g, 78%). LCMS (ES, m/z): 252 [M+H]⁺.

Step 8. Methyl 7-{[1-(2-chlorophenyl)propan-2-yl]amino}-8-nitro-1,2,3,4-tetrahydroisoquinoline-2-carboxylate To a stirred solution of methyl 7-amino-8-nitro-1,2,3,4-tetrahydroisoquinoline-2-carboxylate (500 mg, 1.891 mmol) and 1-(2-chlorophenyl)propan-2-one (403 mg, 2.269 mmol) in DMF (5 mL) was added TMSCl (540 mg, 4.726 mmol) dropwise at room temperature. The resulting mixture was stirred for 30 min at room temperature. To the above mixture was added BH3-THF (1 M in THF, 1.99 mL) dropwise at 0° C. The resulting mixture was stirred for additional 1 h at room temperature. The reaction was quenched with water/ice at 0° C. The resulting mixture was diluted with ethyl acetate (20 mL) and washed with saturated NaHCO₃ (aq.) (20 mL) and brine (20 mL), dried over anhydrous Na2SO4. After filtration, the filtrate was concentrated under reduced pressure. The residue was purified by silica gel column chromatography (eluting with 1:1 ethyl acetate/petroleum ether) to afford methyl 7-[[1-(2-chlorophenyl)propan-2-yl]amino]-8-nitro-1,2,3,4-tetrahydroisoquinoline-2-carboxylate as a brown solid (500 mg, 62%). LCMS (ES, m/z) 404, 406 [M+H]⁺.

Step 9. Methyl 8-amino-7-{[1-(2-chlorophenyl)propan-2-yl]amino}-1,2,3,4-tetrahydroisoquinoline-2-carboxylate A mixture of methyl 7-[[1-(2-chlorophenyl)propan-2-yl]amino]-8-nitro-1,2,3,4-tetrahydroisoquinoline-2-carboxylate (900 mg, 2.117 mmol), NH4Cl (596 mg, 10.59 mmol) and Fe (622 mg, 10.59 mmol) in mixed solvent of EtOH (15 mL) and H2O (5 mL) was stirred for 1 h at 80° C. The mixture was allowed to cool down to room temperature and concentrated under vacuum. The resulting mixture was diluted with ethyl acetate (20 mL) and washed with saturated NaHCO₃ (20 mL) and brine (20 mL), dried over anhydrous Na2SO4. After filtration, the filtrate was concentrated under reduced pressure to afford methyl 8-amino-7-[[1-(2-chlorophenyl)propan-2-yl]amino]-1,2,3,4-tetrahydroisoquinoline-2-carboxylate as a brown solid (800 mg, crude). LCMS (ES, m/z) 374, 376 [M+H]⁺.

Step 10. Methyl 3-[1-(2-chlorophenyl)propan-2-yl]-2-sulfanyl-3H,6H,7H,8H,9H-imidazo[4,5-h]isoquinoline-8-carboxylate A solution of methyl 8-amino-7-[[1-(2-chlorophenyl)propan-2-yl]amino]-1,2,3,4-tetrahydroisoquinoline-2-carboxylate (400 mg, 1.016 mmol) and 1-(1H-imidazole-1-carbothioyl)-1H-imidazole (381 mg, 2.033 mmol) in THF (10 mL) was stirred for 16 h at room temperature. The resulting mixture was concentrated under reduced pressure. The residue was purified by silica gel column chromatography (eluting with 1:1 ethyl acetate/petroleum ether) to afford methyl 3-[1-(2-chlorophenyl)propan-2-yl]-2-sulfanyl-3H,6H,7H,8H,9H-imidazo[4,5-h]isoquinoline-8-carboxylate as a white solid (300 mg, 67%). LCMS (ES, m/z) 416, 418 [M+H]⁺.

Step 11. Methyl 2-bromo-3-[1-(2-chlorophenyl)propan-2-yl]-3H,6H,7H,8H,9H-imidazo[4,5-h]isoquinoline-8-carboxylate To a stirred solution of methyl 3-[1-(2-chlorophenyl)propan-2-yl]-2-sulfanyl-3H,6H,7H,8H,9H-imidazo[4,5-h]isoquinoline-8-carboxylate (400 mg, 0.914 mmol) in mixed solvent of HBr (3 mL) and AcOH (9 mL) was added Br2 (768 mg, 4.568 mmol) dropwise at 0° C. The resulting mixture was stirred for 1 h at room temperature and concentrated under reduced pressure. The residue was purified by silica gel column chromatography (eluting with 1:1 ethyl acetate/petroleum ether) to afford methyl 2-bromo-3-[1-(2-chlorophenyl)propan-2-yl]-3H,6H,7H,8H,9H-imidazo[4,5-h]isoquinoline-8-carboxylate as a white solid (260 mg, 58%). LCMS (ES, m/z) 462, 464, 466 [M+H]⁺.

Step 12. Methyl 1-{3-[1-(2-chlorophenyl)propan-2-yl]-8-(methoxycarbonyl)-3H,6H,7H,8H,9H-imidazo[4,5-h]isoquinolin-2-yl}piperidine-4-carboxylate A mixture of methyl 2-bromo-3-[1-(2-chlorophenyl)propan-2-yl]-3H,6H,7H,8H,9H-imidazo[4,5-h]isoquinoline-8-carboxylate (300 mg, 0.616 mmol), methyl piperidine-4-carboxylate (186 mg, 1.232 mmol) and CsF (394 mg, 2.463 mmol) in DMSO (10 mL) was irradiated with microwave radiation for 2 h at 120° C. The mixture was allowed to cool down to room temperature. The crude product was purified by reverse phase flash with the following conditions (Column: C18 Column, 40 g, 20-35 nm; Mobile Phase, A: water (containing 0.1% FA) and B: CH3CN (30% to 75% over 32 min); Detector: UV 254/220 nm) to afford methyl 1-[3-[1-(2-chlorophenyl)propan-2-yl]-8-(methoxycarbonyl)-3H,6H,7H,8H,9H-imidazo[4,5-h]isoquinolin-2-yl]piperidine-4-carboxylate as a white solid (240 mg, 71%). LCMS (ES, m/z) 525, 527 [M+H]⁺.

Step 13. 1-{3-[(2R)-1-(2-chlorophenyl)propan-2-yl]-8-(methoxycarbonyl)-3H,6H,7H,8H,9H-imidazo[4,5-h]isoquinolin-2-yl}piperidine-4-carboxylic acid and 1-{3-[(2S)-1-(2-chlorophenyl)propan-2-yl]-8-(methoxycarbonyl)-3H,6H,7H,8H,9H-imidazo[4,5-h]isoquinolin-2-yl}piperidine-4-carboxylic acid To a stirred solution of methyl 1-[3-[1-(2-chlorophenyl)propan-2-yl]-8-(methoxycarbonyl)-3H,6H,7H,8H,9H-imidazo[4,5-h]isoquinolin-2-yl]piperidine-4-carboxylate (200 mg, 0.362 mmol) in mixed solvent of MeOH (5 mL) and THF (5 mL) was added LiOH (46 mg, 1.809 mmol) in H2O (5 mL) at room temperature. The resulting mixture was stirred for 1 h at room temperature. The crude product was purified by Prep-HPLC with the following conditions (Column: XBridge Shield RP18 OBD Column 30×150 mm, 5 um; Mobile Phase A: water (10 mM NH4HCO3), Mobile Phase B: CH3CN (5% to 95% over 7 min); 254 nm; Rt: 5.8 min) to afford racemic product and separated by Chiral-HPLC (Column: CHIRALPAK IG, 2.0 cm, 25 cm L (5 um);

Mobile Phase A: Hex (0.1% FA), Mobile Phase B: EtOH (40% to 40% over 12 min); 254/220 nm; Rt1: 6.726; Rt2: 9.099) to afford 1-[3-[(2R)-1-(2-chlorophenyl)propan-2-yl]-8-(methoxycarbonyl)-3H,6H,7H,8H,9H-imidazo[4,5-h]isoquinolin-2-yl]piperidine-4-carboxylic acid as a light yellow solid (55.4 mg, 28.46%) and 1-[3-[(2S)-1-(2-chlorophenyl)propan-2-yl]-8-(methoxycarbonyl)-3H,6H,7H,8H,9H-imidazo[4,5-h]isoquinolin-2-yl]piperidine-4-carboxylic acid as a light yellow solid (53.3 mg, 27.38%).

The compounds in Table 4 below may be prepared by methods analogous to the method described in Example 4.

TABLE 4

| Compound No. | Structure | Compound name | MS (ESI, m/z) [M + H]+ | 1H-NMR δ (ppm) |
|---|---|---|---|---|
| 355 | First eluting isomer | 1-[3-[(2R)-1-(2-chlorophenyl)propan-2-yl]-8-(methoxycarbonyl)-3H,6H,7H,8H,9H-imidazo[4,5-h]isoquinolin-2-yl]piperidine-4-carboxylic acid | 511, 513 | 1H-NMR (Methanol-d4, 400 MHz) δ (ppm): 7.60 (d, J = 8.4 Hz, 1H), 7.40-7.34 (m, 1H), 7.16-7.05 (m, 2H), 6.87-6.79 (m, 1H), 6.22 (d, J = 7.6 Hz, 1H), 5.07-4.96 (m, 1H), 4.88 (d, J = 4.0 Hz, 2H), 3.88-3.65 (m, 5H), 3.42-3.28 (m, 2H), 3.24-3.15 (m, 1H), 3.03-2.92 (m, 2H), 2.88-2.78 (m, 1H), 2.76-2.63 (m, 1H), 2.47-2.31 (m, 2H), 2.03-1.80 (m, 6H), 1.70-1.55 (m, 1H) |
| 14 | Second eluting isomer | 1-[3-[(2S)-1-(2-chlorophenyl)propan-2-yl]-8-(methoxycarbonyl)-3H,6H,7H,8H,9H-imidazo[4,5-h]isoquinolin-2-yl]piperidine-4-carboxylic acid | 511, 513 | 1H-NMR (Methanol-d4, 400 MHz) δ (ppm): 7.60 (d, J = 8.4 Hz, 1H), 7.37 (d, J = 8.0 Hz, 1H), 7.19-7.05 (m, 2H), 6.87-6.79 (m, 1H), 6.22 (d, J = 7.6 Hz, 1H), 5.07-4.96 (m, 1H), 4.89-4.83 (m, 2H), 3.89-3.68 (m, 5H), 3.42-3.29 (m, 2H), 3.22-3.16 (m, 1H), 2.98-2.92 (m, 2H), 2.88-2.78 (m, 1H), 2.74-2.64 (m, 1H), 2.47-2.32 (m, 2H), 2.01-1.86 (m, 3H), 1.83 (d, J = 7.2 Hz, 3H), 1.70-1.55 (m, 1H). |
| 307 | 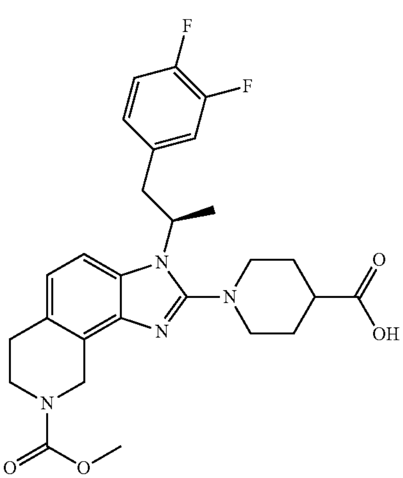 [SMILES: COC(=O)N1CCc2ccc3c(nc(N4CCC(C(=O)O)CC4)n3[C@H](C)Cc3ccc(F)c(F)c3)c2C1] | 1-[3-[(2R)-1-(3,4-difluorophenyl)propan-2-yl]-8-(methoxycarbonyl)-3H,6H,7H,8H,9H-imidazo[4,5-h]isoquinolin-2-yl]piperidine-4-carboxylic acid | 513 | 1H-NMR (CD3OD, 400 MHz) δ (ppm): 7.54 (d, J = 8.4 Hz, 1H), 7.05 (d, J = 8.4 Hz, 1H), 7.08-7.01 (m, 1H), 6.78-6.66 (m, 1H), 6.48-6.41 (m, 1H), 4.87 (s, 2H), 4.85-4.76 (m, 1H), 3.85-3.72 (m, 5H), 3.30-3.20 (m, 1H), 3.19-3.05 (m, 1H), 3.01-2.90 (m, 3H), 2.85-2.62 (m, 2H), 3.51-2.40 (m, 1H), 2.11-1.85 (m, 3H), 1.81 (d, J = 7.2 Hz, 3H), 1.72-1.55 (m, 1H), 1.40-1.30 (m, 1H). |

TABLE 4-continued

| Compound No. | Structure | Compound name | MS (ESI, m/z) [M + H]+ | 1H-NMR δ (ppm) |
|---|---|---|---|---|
| | First eluting isomer | | | |
| 23 | 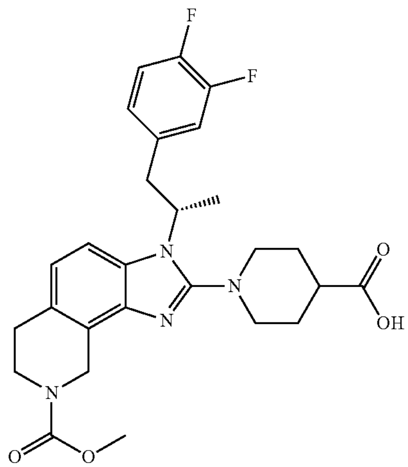 [SMILES: COC(=O)N1CCc2ccc3c(nc(N4CCC(C(=O)O)CC4)n3[C@@H](C)Cc3ccc(F)c(F)c3)c2C1] | 1-[3-[(2S)-1-(3,4-difluorophenyl)propan-2-yl]-8-(methoxycarbonyl)-3H,6H,7H,8H,9H-imidazo[4,5-h]isoquinolin-2-yl]piperidine-4-carboxylic acid | 513 | 1H-NMR (CD3OD, 400 MHz) δ (ppm): 7.55 (d, J = 8.4 Hz, 1H), 7.06 (d, J = 8.4 Hz, 1H), 7.09-7.01 (m, 1H), 6.80-6.62 (m, 1H), 6.53-6.40 (m, 1H), 4.87 (s, 2H), 4.85-4.77 (m, 1H), 3.84-3.71 (m, 5H), 3.33-3.21 (m, 1H), 3.19-3.07 (m, 1H), 3.02-2.90 (m, 3H), 2.80-2.71 (m, 1H), 2.68-2.62 (m, 1H), 2.49-2.38 (m, 1H), 2.08-1.85 (m, 3H), 1.81 (d, J = 7.6 Hz, 3H), 1.75-1.58 (m, 1H), 1.40-1.30 (m, 1H). |
| | Second eluting isomer | | | |
| 145 | 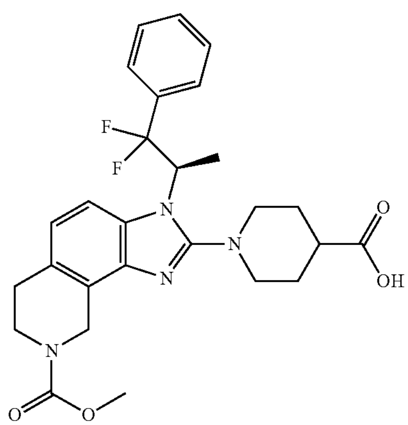 [SMILES: COC(=O)N1CCc2ccc3c(nc(N4CCC(C(=O)O)CC4)n3[C@H](C)C(F)(F)c3ccccc3)c2C1] | 1-[3-[(2R)-1,1-difluoro-1-phenylpropan-2-yl]-8-(methoxycarbonyl)-3H,6H,7H,8H,9H-imidazo[4,5-h]isoquinolin-2-yl]piperidine-4-carboxylic acid | 513 | 1H-NMR (CD3OD, 400 MHz) δ (ppm): 7.58 (d, J = 8.4 Hz, 1H), 7.45-7.33 (m, 1H), 7.31-7.22 (m, 2H), 7.11-7.06 (m, 3H), 5.23-5.09 (m, 1H), 4.85 (s, 2H), 3.86-3.70 (m, 5H), 3.16-3.10 (m, 1H), 2.95-2.91 (m, 2H), 2.89-2.82 (m, 1H), 2.71-2.62 (m, 1H), 2.49-2.41 (m, 1H), 2.35-2.26 (m, 1H), 2.05-1.81 (m, 6H), 1.72-1.58 (m, 1H). |
| | first eluting isomer | | | |
| 24 | 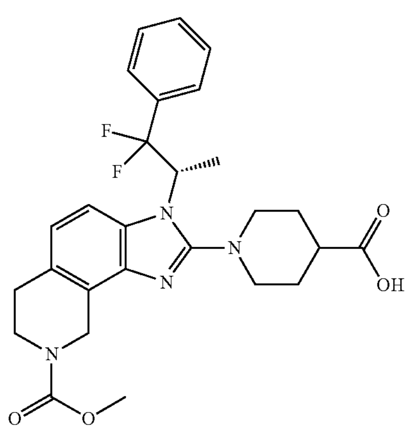 [SMILES: COC(=O)N1CCc2ccc3c(nc(N4CCC(C(=O)O)CC4)n3[C@@H](C)C(F)(F)c3ccccc3)c2C1] | 1-[3-[(2S)-1,1-difluoro-1-phenylpropan-2-yl]-8-(methoxycarbonyl)-3H,6H,7H,8H,9H-imidazo[4,5-h]isoquinolin-2-yl]piperidine-4-carboxylic acid | 513 | 1H-NMR (CD3OD, 400 MHz) δ (ppm): 7.58 (d, J = 8.4 Hz, 1H), 7.44-7.36 (m, 1H), 7.31-7.22 (m, 2H), 7.11-7.05 (m, 3H), 5.24-5.09 (m, 1H), 4.85 (s, 2H), 3.84-3.68 (m, 5H), 3.13-3.10 (m, 1H), 2.95-2.92 (m, 2H), 2.89-2.82 (m, 1H), 2.71-2.62 (m, 1H), 2.48-2.41 (m, 1H), 2.35-2.26 (m, 1H), 2.03-1.81 (m, 6H), 1.71-1.59 (m, 1H). |
| | second eluting isomer | | | |

TABLE 4-continued

| Compound No. | Structure | Compound name | MS (ESI, m/z) [M + H]⁺ | ¹H-NMR δ (ppm) |
|---|---|---|---|---|
| 148 | 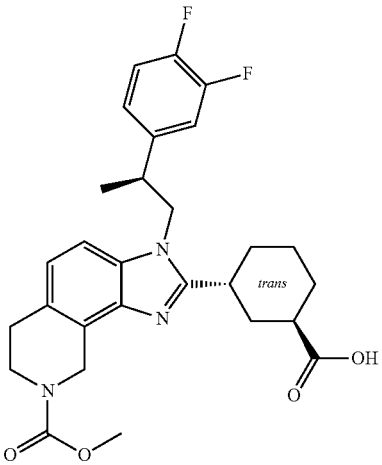 [SMILES: COC(=O)N1CCc2ccc3c(nc([C@@H]4CCC[C@@H](C(=O)O)C4)n3C[C@@H](C)c3ccc(F)c(F)c3)c2C1]<br>First eluting isomer | (1R,3R)-3-[3-[(2S)-2-(3,4-difluorophenyl)propyl]-8-(methoxycarbonyl)-3H,6H,7H,8H,9H-imidazo[4,5-h]isoquinolin-2-yl]cyclohexane-1-carboxylic acid | 512 | ¹H-NMR (CD3OD, 400 MHz) δ (ppm): 7.34 (d, J = 8.0 Hz, 1H), 7.24-6.91 (m, 3H), 6.79-6.51 (m, 1H), 5.02 (s, 2H), 4.51-4.30 (m, 2H), 3.87-3.68 (m, 5H), 3.00-2.90 (m, 2H), 2.89-2.73 (m, 1H), 2.71-2.58 (m, 1H), 2.34-1.98 (m, 2H), 1.91-1.52 (m, 4H), 1.49 (d, J = 6.8 Hz, 3H), 1.43-1.12 (m, 3H). |
| 30 | 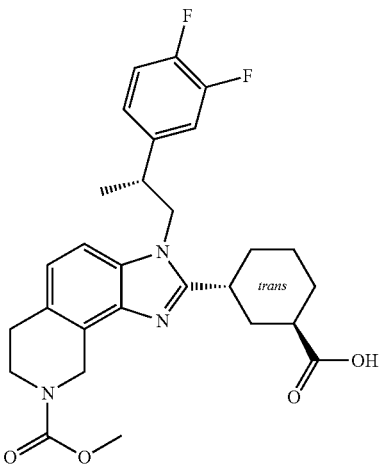 [SMILES: COC(=O)N1CCc2ccc3c(nc([C@@H]4CCC[C@@H](C(=O)O)C4)n3C[C@H](C)c3ccc(F)c(F)c3)c2C1]<br>Second eluting isomer | (1S,3S)-3[3-[(2R)-2-(3,4-difluorophenyl)propyl]-8-(methoxycarbonyl)-3H,6H,7H,8H,9H-imidazo[4,5-h]isoquinolin-2-yl]cyclohexane-1-carboxylic acid | 512 | ¹H-NMR (CD3OD, 400 MHz) δ (ppm): 7.31-7.19 (m, 2H), 7.18-7.09 (m, 1H), 7.08-6.95 (m, 2H), 4.99 (s, 2H), 4.58-4.42 (m, 1H), 4.39-4.20 (m, 1H), 3.80-3.65 (m, 5H), 3.51-3.38 (m, 1H), 3.30-3.20 (m, 1H), 3.00-2.80 (m, 3H), 2.30-2.00 (m, 2H), 1.99-1.41 (m, 6H), 1.19 (d, J = 6.4 Hz, H). |
| 28 | 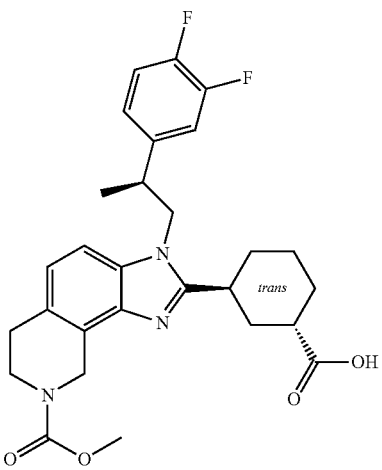 [SMILES: COC(=O)N1CCc2ccc3c(nc([C@H]4CCC[C@H](C(=O)O)C4)n3C[C@@H](C)c3ccc(F)c(F)c3)c2C1]<br>Third eluting isomer | (1R,3R)-3-[3-[(2R)-2-(3,4-difluorophenyl)propyl]-8-(methoxycarbonyl)-3H,6H,7H,8H,9H-imidazo[4,5-h]isoquinolin-2-yl]cyclohexane-1-carboxylic acid | 512 | ¹H-NMR (CD3OD, 400 MHz) δ (ppm): 7.34 (d, J = 8.4 Hz, 1H), 7.20-6.88 (m, 3H), 6.82-6.50 (m, 1H), 5.02 (s, 2H), 4.50-4.29 (m, 2H), 3.81-3.69 (m, 5H), 3.00-2.87 (m, 2H), 2.86-2.72 (m, 1H), 2.72-2.52 (m, 1H), 2.36-2.08 (m, 2H), 1.90-1.51 (m, 4H), 1.48 (d, J = 6.8 Hz, 3H), 1.35-1.14 (m, 3H). |

TABLE 4-continued

| Compound No. | Structure | Compound name | MS (ESI, m/z) [M + H]⁺ | ¹H-NMR δ (ppm) |
|---|---|---|---|---|
| 29 | Fourth eluting isomer | (1S,3S)-3-[3-[(2S)-2-(3,4-difluorophenyl)propyl]-8-(methoxycarbonyl)-3H,6H,7H,8H,9H-imidazo[4,5-h]isoquinolin-2-yl]cyclohexane-1-carboxylic acid | 512 | ¹H-NMR (CD3OD, 400 MHz) δ (ppm): 7.30-7.18 (m, 2H), 7.17-7.09 (m, 1H), 7.07-6.80 (m, 2H), 4.99 (s, 2H), 4.59-4.42 (m, 1H), 4.38-4.18 (m, 1H), 3.82-3.70 (m, 5H), 3.53-3.38 (m, 1H), 3.31-3.19 (m, 1H), 3.00-2.78 (m, 3H), 2.30-2.01 (m, 2H), 2.00-1.68 (m, 5H), 1.62-1.46 (m, 1H), 1.28 (d, J = 6.8 Hz, 3H). |
| 356 | first eluting isomer | (1R,3R)-3-[3-[(2R)-1-(3,4-difluorophenyl)propan-2-yl]-8-(methoxycarbonyl)-3H,6H,7H,8H,9H-imidazo[4,5-h]isoquinolin-2-yl]cyclohexane-1-carboxylic acid | 512 | ¹H-NMR (CD₃OD, 400 MHz) δ (ppm): 7.67 (d, J = 8.4 Hz, 1H), 7.11 (d, J = 8.0 Hz, 1H), 7.13-6.90 (m, 1H), 6.85-6.62 (m, 1H), 6.50-6.30 (m, 1H), 5.19-5.00 (m, 1H), 4.97 (s, 2H), 3.85-3.67 (m, 5H), 3.27-3.13 (m, 1H), 3.09-2.89 (m, 2H), 2.89-2.65 (m, 2H), 2.25-2.12 (m, 2H), 1.85-1.44 (m, 7H), 1.42-0.98 (m, 3H). |
| 357 | second eluting isomer | (1R,3R)-3-[3-[(2S)-1-(3,4-difluorophenyl)propan-2-yl]-8-(methoxycarbonyl)-3H,6H,7H,8H,9H-imidazo[4,5-h]isoquinolin-2-yl]cyclohexane-1-carboxylic acid | 512 | ¹H-NMR (CD₃OD, 400 MHz) δ (ppm): 7.95-7.50 (m, 1H), 7.11 (d, J = 7.6 Hz, 1H), 7.02-6.97 (m, 1H), 6.90-6.60 (m, 2H), 5.03-4.98 (m, 3H), 3.82-3.71 (m, 5H), 3.60-3.39 (m, 1H), 3.29-3.19 (m, 1H), 3.19-3.05 (m, 1H), 3.01-2.88 (m, 2H), 2.85 2.70 (m, 1H), 2.31-2.02 (m, 1H), 1.89-1.50 (m, 9H), 1.38-1.19 (m, 1H). |

TABLE 4-continued

| Compound No. | Structure | Compound name | MS (ESI, m/z) [M + H]+ | 1H-NMR δ (ppm) |
|---|---|---|---|---|
| 31 | third eluting isomer | (1S,3S)-3-[3-[(2R)-1-(3,4-difluorophenyl)propan-2-yl]-8-(methoxycarbonyl)-3H,6H,7H,8H,9H-imidazo[4,5-h]isoquinolin-2-yl]cyclohexane-1-carboxylic acid | 512 | 1H-NMR (CD3OD, 400 MHz) δ (ppm): 7.95-7.45 (m, 1H), 7.11 (d, J = 8.0 Hz, 1H), 7.05-6.94 (m, 1H), 6.91-6.56 (m, 2H), 5.03-4.91 (m, 3H), 3.82-3.69 (m, 5H), 3.59-3.41 (m, 1H), 3.29-3.19 (m, 1H), 3.19-3.04 (m, 1H), 2.97-2.75 (m, 3H), 2.32-2.02 (m, 1H), 1.97-1.42 (m, 9H), 1.33-1.25 (m, 1H). |
| 60 | fourth eluting isomer | (1S,3S)-3-[3-[(2S)-1-(3,4-difluorophenyl)propan-2-yl]-8-(methoxycarbonyl)-3H,6H,7H,8H,9H-imidazo[4,5-h]isoquinolin-2-yl]cyclohexane-1-carboxylic acid | 512 | 1H-NMR (CD3OD, 400 MHz) δ (ppm): 7.82-7.48 (m, 1H), 7.11 (d, J = 8.0 Hz, 1H), 7.03-6.85 (m, 1H), 6.85-6.61 (m, 1H), 6.61-6.32 (m, 1H), 5.12-5.01 (m, 1H), 4.97 (s, 2H), 3.86-3.72 (m, 5H), 3.49-3.38 (m, 1H), 3.25-3.12 (m, 1H), 3.05-2.50 (m, 4H), 2.24-2.09 (m, 1H), 1.87-1.40 (m, 7H), 1.40-1.00 (m, 3H). |

Example 5: (2S)-3-[2-cyclohexyl-8-(methoxycarbonyl)-3H,6H,7H,8H,9H-imidazo[4,5-h]isoquinolin-3-yl]-2-(5-fluoro-2-methoxyphenyl)propanoic acid and (2R)-3-[2-cyclohexyl-8-(methoxycarbonyl)-3H,6H,7H,8H,9H-imidazo[4,5-h]isoquinolin-3-yl]-2-(5-fluoro-2-methoxyphenyl)propanoic acid

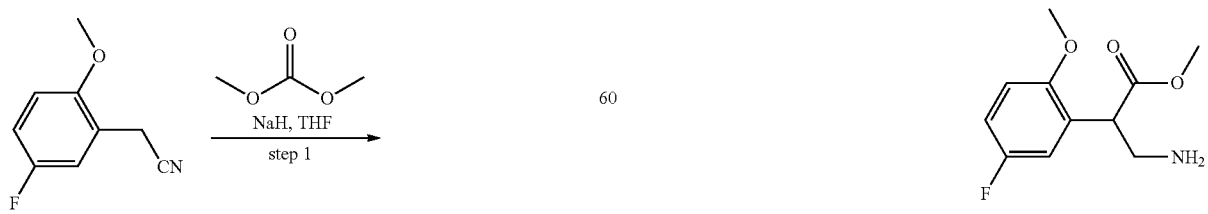

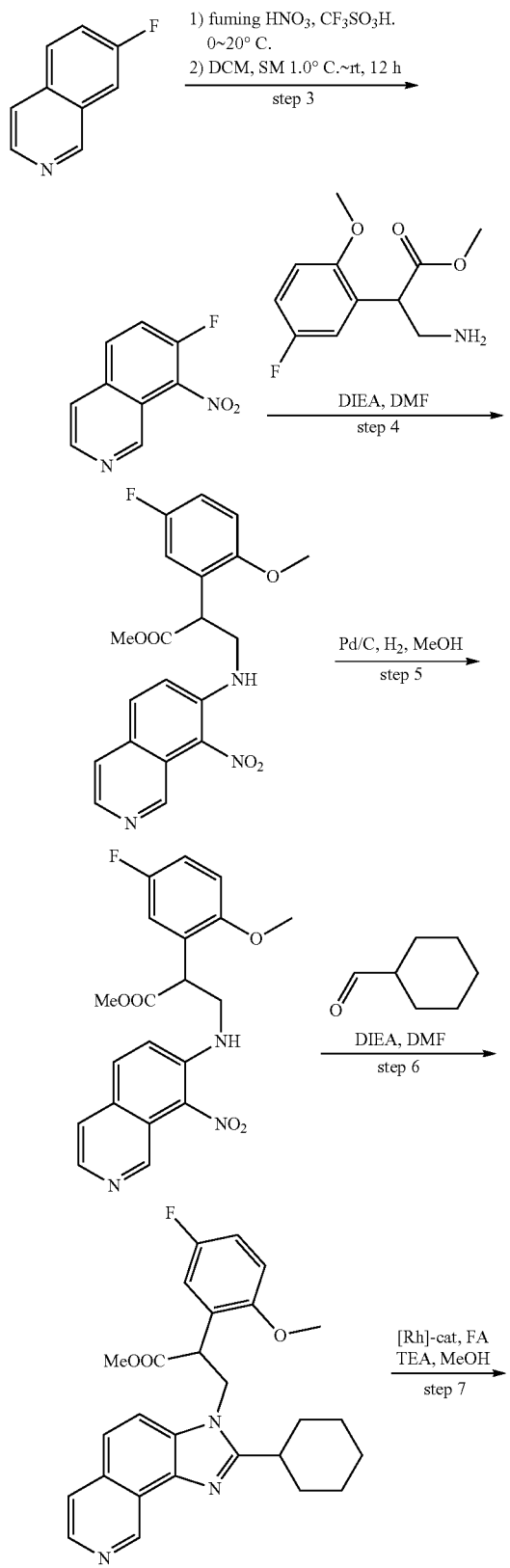
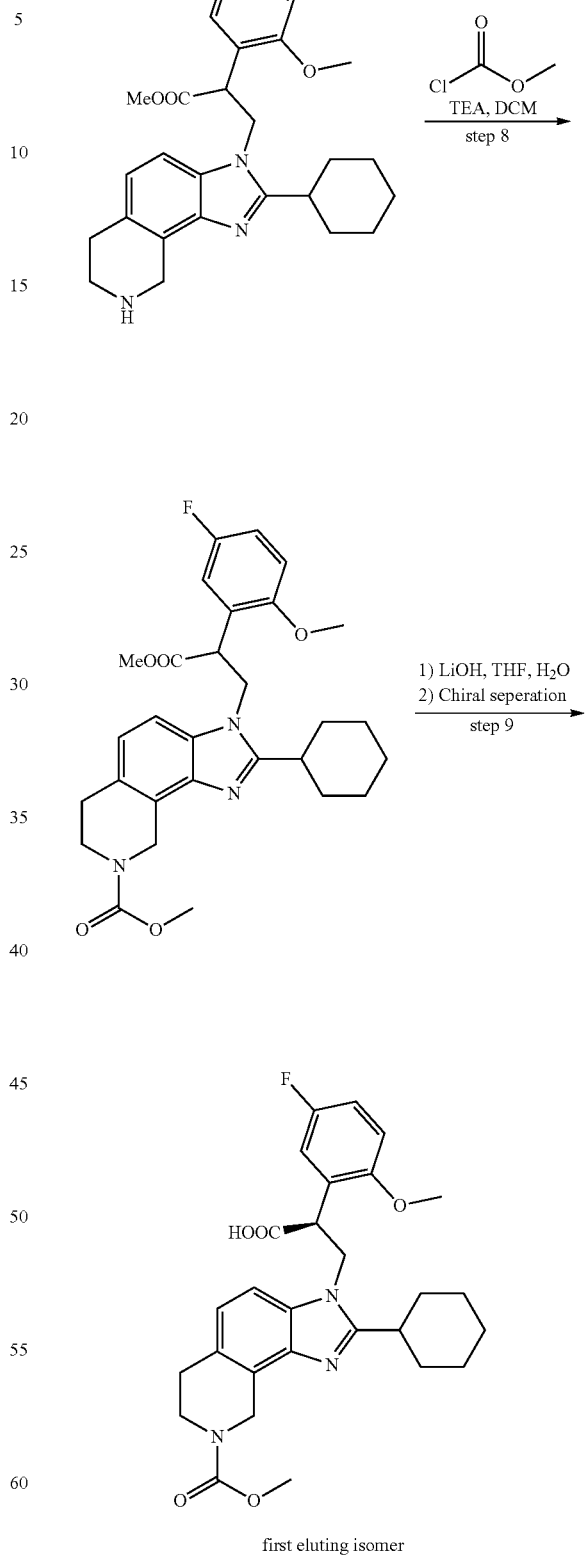
first eluting isomer

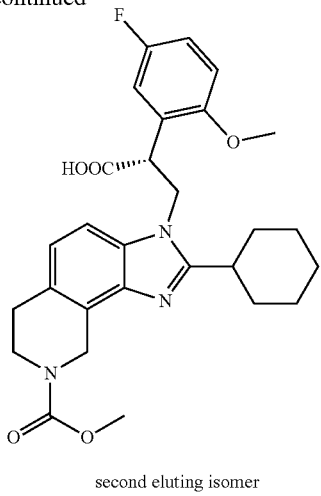

second eluting isomer

Step 1. methyl 2-cyano-2-(5-fluoro-2-methoxyphenyl)acetate

A stirred solution of 2-(5-fluoro-2-methoxyphenyl)acetonitrile (500 mg, 3.03 mmol) in THF (10 mL) was added NaH (242 mg, 10.084 mmol, 3.33 equiv) in portions at 0° C. The mixture was stirred for 30 min at 0° C., and then to them was added dimethyl carbonate (545 mg, 6.05 mmol) at 25° C. The resulting mixture was stirred for 4 h at 25° C. The resulting mixture was diluted with water (80 mL) and extracted with ethyl acetate (3×60 mL). The combined organic layers were washed with brine (1×100 mL), dried over anhydrous sodium sulfate. After filtration, the filtrate was concentrated under reduced pressure. The residue was purified by silica gel column chromatography (eluting with 1:5 ethyl acetate/petroleum ether) to afford methyl 2-cyano-2-(5-fluoro-2-methoxyphenyl)acetate as a white solid (640 mg, 90%). LCMS (ES, m/z): 224[M+H]$^+$.

Step 2. methyl 3-amino-2-(5-fluoro-2-methoxyphenyl)propanoate

A stirred solution of methyl 2-cyano-2-(5-fluoro-2-methoxyphenyl)acetate (620 mg, 2.78 mmol) in MeOH (30 mL) was added PtO2 (620 mg, 2.73 mmol) and HCl (6M) (1.5 mL). The resulting mixture was stirred for 2 h at 25° C. under hydrogen atmosphere. The resulting mixture was filtered. The filter cake was washed with MeOH (3×10 mL). The filtrate was concentrated under reduced pressure. This resulted in methyl 3-amino-2-(5-fluoro-2-methoxyphenyl) propanoate as a light yellow oil (564 mg, crude). LCMS (ES, m/z): 228[M+H]$^+$.

Step 3. 7-fluoro-8-nitroisoquinoline

A solution of trifluoromethanesulfonic acid (87.8 mL, 573 mmol) and fuming nitric acid (22.2 mL, 344 mmol) was stirred for 30 min at 0° C. under nitrogen atmosphere. To the above was added 7-fluoroisoquinoline (50.0 g, 323 mmol) in dichloromethane (200 mL) dropwise over 30 min at 0° C. The resulting mixture was stirred for additional 4 h at room temperature. The mixture was neutralized to pH-7 with saturated sodium bicarbonate. The resulting mixture was extracted with dichloromethane (3×1000 mL), dried over anhydrous sodium sulfate, filtered, and concentrated under vacuum. The residue was purified by silica gel chromatography (eluting with 1:1 ethyl acetate/petroleum ether) to afford 7-fluoro-8-nitroisoquinoline as a yellow solid (60.0 g, 92%). LCMS (ES, m/z): 193 [M+H]$^+$.

Step 4. methyl 2-(5-fluoro-2-methoxyphenyl)-3-[(8-nitroisoquinolin-7-yl)amino]propanoate A stirred solution of 7-fluoro-8-nitroisoquinoline (254 mg, 1.32 mmol) in DMF (10 mL) was added DIEA (597 mg, 4.62 mmol) and methyl methyl 3-amino-2-(5-fluoro-2-methoxyphenyl)propanoate (300 mg, 1.34 mmol). The resulting mixture was stirred for 1 h at 60° C. The resulting mixture was diluted with brine (50 mL) and extracted with ethyl acetate (3×50 mL). The combined organic layers were washed with water (1×100 mL), dried over anhydrous sodium sulfate. After filtration, the filtrate was concentrated under reduced pressure. The residue was purified by silica gel column chromatography (eluting with 1:1 ethyl acetate/petroleum ether) to afford methyl 2-(5-fluoro-2-methoxyphenyl)-3-[(8-nitroisoquinolin-7-yl)amino]propanoate as a yellow solid (390 mg, 70.18%). LCMS (ES, m/z): 400 [M+H]$^+$.

Step 5. methyl 3-[(8-aminoisoquinolin-7-yl)amino]-2-(5-fluoro-2-methoxyphenyl)propanoate A stirred solution of methyl 2-(5-fluoro-2-methoxyphenyl)-3-[(8-nitroisoquinolin-7-yl)amino]propanoate (390 mg, 0.97 mmol) in MeOH (10 mL) was added Pd/C (39 mg, 10%). The mixture was stirred for 16 h at 25° C. under hydrogen atmosphere. The resulting mixture was filtered. The filter cake was washed with MeOH (3×10 mL). The filtrate was concentrated under reduced pressure to afford methyl 3-[(8-aminoisoquinolin-7-yl)amino]-2-(5-fluoro-2-methoxyphenyl)propanoate as a dark yellow solid (260 mg, 68%). LCMS (ES, m/z): 370 [M+H]$^+$.

Step 6. methyl 3-{2-cyclohexyl-3H-imidazo[4,5-h]isoquinolin-3-yl}-2-(5-fluoro-2-methoxyphenyl) propanoate A stirred solution of methyl 3-[(8-aminoisoquinolin-7-yl)amino]-2-(5-fluoro-2-methoxyphenyl)propanoate (260 mg, 0.70 mmol) in DCM (10 mL) was added cyclohexanecarbaldehyde (158 mg, 1.41 mmol). The resulting mixture was stirred for 16 h at 25° C. The resulting mixture was concentrated under reduced pressure and purified by silica gel column chromatography (eluted with 1:3 ethyl acetate/petroleum ether) to afford methyl 3-{2-cyclohexyl-3H-imidazo[4,5-h]isoquinolin-3-yl}-2-(5-fluoro-2-methoxyphenyl)propanoate as a dark green solid (310 mg, 91%). LCMS (ES, m/z): 462[M+H]$^+$.

Step 7. methyl 3-{2-cyclohexyl-3H,6H,7H,8H,9H-imidazo[4,5-h]isoquinolin-3-yl}-2-(5-fluoro-2-methoxyphenyl) propanoate A stirred solution of formic acid (139 mg, 2.96 mmol) and MeOH (10 mL) was added TEA (102 mg, 0.99 mmol). To the above mixture was added methyl 3-{2-cyclohexyl-3H-imidazo[4,5-h]isoquinolin-3-yl}-2-(5-fluoro-2-methoxyphenyl)propanoate (310 mg, 0.64 mmol) and (4S,5S)-2-chloro-2-methyl-1-(4-methylbenzenesulfonyl)-4,5-diphenyl-1,3-diaza-2-rhodacyclopentane; 1,2,3,4,5-pentamethylcyclopentane (44 mg, 0.06 mmol). The resulting mixture was stirred for additional 16 h at 25° C. The resulting mixture was concentrated under reduced pressure. The residue was purified by reversed phase column (Column, C18 column, 40 g; mobile phase, water with 0.1% NH4HCO3 and ACN (10% up to 80% ACN in 40 min); Detector, UV 254/220 nm). This resulted in methyl 3-{2-cyclohexyl-3H,6H,7H,8H,9H-imidazo[4,5-h]isoquinolin-3-yl}-2-(5-fluoro-2-methoxyphenyl) propanoate as a brown solid (300 mg, 96%). LCMS (ES, m/z): 466 [M+H]+.

Step 8. methyl 2-cyclohexyl-3-[2-(5-fluoro-2-methoxyphenyl)-3-methoxy-3-oxopropyl]-3H,6H, 7H,8H,9H-imidazo [4,5-h]isoquinoline-8-carboxylate A stirred solution of methyl 3-[2-cyclohexyl-3H,6H,7H, 8H,9H-imidazo[4,5-h]isoquinolin-3-yl]-2-(5-fluoro-2-methoxyphenyl)propanoate (300 mg, 0.64 mmol) in DCM (20 mL) was added TEA (251 mg, 2.48 mmol) and methyl carbonochloridate (133 mg, 1.41 mmol) dropwise at 0° C. The mixture was stirred for 2 h at 25° C. The resulting mixture was concentrated under reduced pressure, diluted with water (50 mL) and extracted with ethyl acetate (3×30 mL). The combined organic layers were washed with brine (1×50 mL), dried over anhydrous sodium sulfate. After filtration, the filtrate was concentrated under reduced pressure. The residue was purified by silica gel column chromatography (eluted with 1:1 ethyl acetate/petroleum ether) to afford methyl 2-cyclohexyl-3-[2-(5-fluoro-2-methoxyphenyl)-3-methoxy-3-oxopropyl]-3H,6H,7H,8H,9H-imidazo[4,5-h]isoquinoline-8-carboxylate as a light yellow solid (218 mg, 61%). LCMS (ES, m/z) 524 [M+H]+.

Step 9. (2S)-3-[2-cyclohexyl-8-(methoxycarbonyl)-3H, 6H,7H,8H,9H-imidazo[4,5-h]isoquinolin-3-yl]-2-(5-fluoro-2-methoxyphenyl)propanoic acid, (2R)-3-[2-cyclohexyl-8-(methoxycarbonyl)-3H, 6H,7H,8H,9H-imidazo[4,5-h] isoquinolin-3-yl]-2-(5-fluoro-2-methoxyphenyl)propanoic acid A mixture of methyl 2-cyclohexyl-3-[2-(5-fluoro-2-methoxyphenyl)-3-methoxy-3-oxopropyl]-3H,6H,7H,8H, 9H-imidazol[4,5-h]isoquinoline-8-carboxylate (50 mg, 0.09 mmol) and LiOH (24 mg, 0.98 mmol) in TH (2 mL) and H2O (2 mL) was stirred for 1 h at 60° C. The mixture was allowed to cool down to 25° C. and concentrated under reduced pressure. The residue was purified by Prep-HPLC (Column, XBridge Prep OBD C18 Column, 30×150 mm 5 urn; mobile phase, water (10 mmol/L NH4HCO3) and ACN (10% up to 37% in 7 mic); 254/220 nm, RT, 7.43 min). The product was separated by Chiral-Prep-HPLC (Column, CHIRAL ART Cellulose-SB, 2×25 cm, 5 um; mobile phase, Hex (0.10% FA) and EtOH (hold 20% in 22 min, (RT1, 13.416; RT2, 16.777); 254/220 nm to afford (2S)-3-[2-cyclohexyl-8-(methoxycarbonyl)-3H,6H,7H,8H,9H-imidazo[4,5-h]isoquinolin-3-yl]-2-(5-fluoro-2-methoxyphenyl)propanoic acid as a white solid (9.5 mg, 20%) and (2R)-3-[2-cyclohexyl-8-(methoxycarbonyl)-3H,6H,7H, 8H,9H-imidazo[4,5-h]isoquinolin-3-yl]-2-(5-fluoro-2-methoxyphenyl)propanoic acid as a white solid (13.7 mg, 29%).

The compounds in Table 5 below may be prepared by methods analogous to the method described in Example 5.

TABLE 5

| Compound No. | Structure | Compound name | MS (ESI, m/z) [M + H]+ | 1H-NMR δ (ppm) |
| --- | --- | --- | --- | --- |
| 11 | first eluting isomer | (2S)-3-[2-cyclohexyl-8-(methoxycarbonyl)-3H,6H,7H,8H, 9H-imidazo[4,5-h]isoquinolin-3-yl]-2-(5-fluoro-2-methoxyphenyl) propanoic acid | 510 | 1H-NMR (DMSO-d6, 400 MHz) δ (ppm): 7.33 (d, J = 8.0 Hz, 1H), 7.11-7.15 (m, 1H), 7.00-6.91 (m, 3H), 4.77-4.71 (m, 3H), 4.47-4.41 (m, 1H), 4.33-4.30 (m, 1H), 3.67-3.62 (m, 5H), 3.61 (s, 3H), 2.87-2.84 (m, 2H), 2.68-2.58 (m, 1H), 1.78-1.70 (m, 4H), 1.54-1.47 (m, 2H), 1.40-1.14 (m, 4H). |

TABLE 5-continued

| Compound No. | Structure | Compound name | MS (ESI, m/z) [M + H]+ | 1H-NMR δ (ppm) |
|---|---|---|---|---|
| 241 | 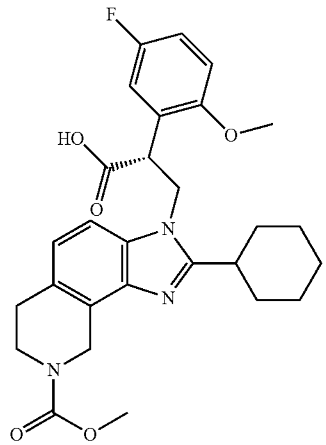 [SMILES: COC(=O)N1CCc2ccc3c(nc(C4CCCCC4)n3C[C@H](C(=O)O)c3cc(F)ccc3OC)c2C1] | (2R)-3-[2-cyclohexyl-8-(methoxycarbonyl)-3H,6H,7H,8H,9H-imidazo[4,5-h]isoquinolin-3-yl]-2-(5-fluoro-2-methoxyphenyl) propanoic acid | 510 | 1H-NMR (DMSO-d6, 400 MHz) δ (ppm): 12.81 (br, 1H), 7.33 (d, J = 8.4 Hz, 1H), 7.11-7.06 (m, 1H), 7.00-6.91 (m, 3H), 4.77-4.71 (m, 3H), 4.47-4.41 (m, 1H), 4.33-4.29 (m, 1H), 3.67-3.62 (m, 5H), 3.61 (s, 3H), 2.87-2.84 (m, 2H), 2.58-2.51 (m, 1H), 1.88-1.75 (s, 2H), 1.74-1.65 (m, 2H), 1.61-1.39 (m, 2H), 1.37-1.15 (m, 4H). |
| | second eluting isomer | | | |
| 4 | 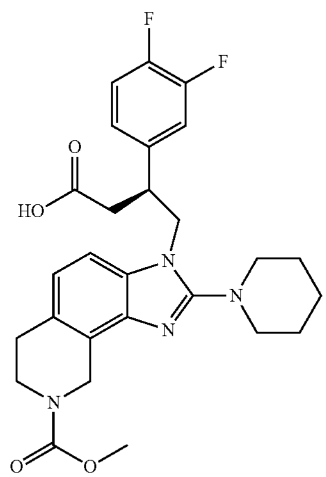 [SMILES: COC(=O)N1CCc2ccc3c(nc(N4CCCCC4)n3C[C@@H](CC(=O)O)c3ccc(F)c(F)c3)c2C1] | (3S)-4-[2-cyclohexyl-8-(methoxycarbonyl)-3H,6H,7H,8H,9H-imidazo[4,5-h]isoquinolin-3-yl]-3-(3,4-difluorophenyl) butanoic acid | 512 | 1H NMR (400 MHz, Methanol-d4) δ (ppm): 7.45 (d, J = 8.4 Hz, 1H), 7.11-6.98 (m, 3H), 6.70-6.62 (m, 1H), 4.94 (s, 2H), 4.61-4.51 (m, 1H), 4.42-4.30 (m, 1H), 3.82-3.75 (m, 5H), 3.70-3.59 (m, 1H), 3.04-2.90 (m, 3H), 2.84-2.73 (m, 1H), 2.55-2.47 (m, 1H), 1.86-1.78 (m, 2H), 1.78-1.70 (m, 2H), 1.69-1.49 (m, 2H), 1.50-1.36 (m, 1H), 1.37-1.14 (m, 2H), 1.04-0.95 (m, 1H) |
| | First eluting isomer | | | |
| 189 | 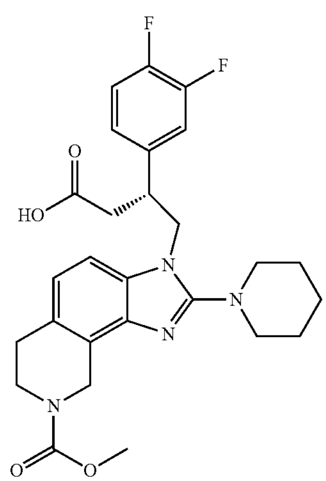 [SMILES: COC(=O)N1CCc2ccc3c(nc(N4CCCCC4)n3C[C@H](CC(=O)O)c3ccc(F)c(F)c3)c2C1] | (3R)-4-[2-cyclohexyl-8-(methoxycarbonyl)-3H,6H,7H,8H,9H-imidazo[4,5-h]isoquinolin-3-yl]-3-(3,4-difluorophenyl) butanoic acid | 512 | 1H NMR (400 MHz, Methanol-d4) δ (ppm): 7.45 (d, J = 8.4 Hz, 1H), 7.13-6.95 (m, 3H), 6.74-6.65 (m, 1H), 4.94 (s, 2H), 4.62-4.55 (m, 1H), 4.42-4.31 (m, 1H), 3.81-3.76 (m, 5H), 3.73-3.61 (m, 1H), 3.04-2.91 (m, 3H), 2.84-2.72 (m, 1H), 2.58-2.46 (m, 1H), 1.87-1.78 (m, 2H), 1.77-1.72 (m, 2H), 1.71-1.52 (m, 2H), 1.551-1.38 (m, 1H), 1.37-1.21 (m, 2H), 1.08-0.97 (m, 1H). |
| | Second eluting isomer | | | |

TABLE 5-continued

| Compound No. | Structure | Compound name | MS (ESI, m/z) [M + H]+ | 1H-NMR δ (ppm) |
|---|---|---|---|---|
| 138 | First eluting isomer | methyl 2-cyclohexyl-3-[(2S)-2-(methanesulfon-ylcarbamoyl)-2-phenylethyl]-3H,6H,7H,8H,9H-imidazo[4,5-h]isoquinoline-8-carboxylate | 539 | 1H-NMR-(CD3OD, 400 MHz) δ (ppm): 7.47 (d, J = 8.4 Hz, 1H), 7.37-7.31 (m, 3H), 7.16-7.12 (m, 3H), 4.97 (s, 2H), 4.63-4.57 (m, 1H), 4.22-4.14 (m, 1H), 3.78 (s, 3H), 3.77-3.72 (m, 2H), 3.16 (s, 3H), 3.02-2.92 (m, 2H), 2.71-2.58 (m, 1H), 1.95-1.81 (m, 2H), 1.80-1.72 (m, 2H), 1.66-1.52 (m, 2H), 1.50-1.36 (m, 1H), 1.35-1.15 (m, 3H), 1.13-1.05 (m, 1H). |
| 22 | Second eluting isomer | methyl 2-cyclohexyl-3-[(2R)-2-(methanesulfon-ylcarbamoyl)-2-phenylethyl]-3H,6H,7H,8H,9H-imidazo[4,5-h]isoquinoline-8-carboxylate | 539 | 1H-NMR-(CD3OD, 400 MHz) δ (ppm): 7.48 (d, J = 8.4 Hz, 1H), 7.35-7.30 (m, 3H), 7.20-7.12 (m, 3H), 4.97 (s, 2H), 4.65-4.54 (m, 1H), 4.21-4.16 (m, 1H), 3.78 (s, 3H), 3.77-3.72 (m, 2H), 3.17 (s, 3H), 2.98 (t, J = 6.4 Hz, 2H), 2.71-2.55 (m, 1H), 1.93-1.81 (m, 2H), 1.79-1.71 (m, 2H), 1.67-1.52 (m, 2H), 1.51-1.40 (m, 1H), 1.38-1.20 (m, 3H), 1.18-1.06 (m, 1H). |
| 32 | First eluting isomer | (2S)-2-(4-chloro-5-fluoro-2-methoxyphenyl)-3-[2-cyclohexyl-8-(methoxycarbonyl)-3H,6H,7H,8H,9H-imidazo[4,5-h]isoquinolin-3-yl]propanoic acid | 544 | 1H-NMR (CD3OD, 400 MHz) δ (ppm): 7.41 (d, J = 28.0 Hz, 1H), 7.16 (d, J = 8.0 Hz, 1H), 7.05 (d, J = 6.0 Hz, 2H), 4.97 (s, 3H), 4.67-4.58 (m, 1H), 4.48-4.40 (m, 1H), 3.81-3.75 (m, 5H), 3.61 (s, 3H), 3.02-2.94 (m, 2H), 2.82-2.65 (m, 1H), 1.93-1.77 (m, 4H), 1.75-1.58 (m, 2H), 1.52-1.22 (m, 4H). |

TABLE 5-continued

| Compound No. | Structure | Compound name | MS (ESI, m/z) [M + H]+ | 1H-NMR δ (ppm) |
|---|---|---|---|---|
| 229 | *Second eluting isomer* | (2R)-2-(4-chloro-5-fluoro-2-methoxyphenyl)-3-[2-cyclohexyl-8-(methoxycarbonyl)-3H,6H,7H,8H,9H-imidazo[4,5-h]isoquinolin-3-yl]propanoic acid | 544 | 1H-NMR (CDCl$_3$, 400 MHz) δ (ppm): 7.55-7.36 (m, 1H), 7.27-7.19 (m, 1H), 7.158-7.09 (m, 1H), 6.82-6.76 (m, 1H), 5.08-4.92 (m, 2H), 4.88-4.78 (m, 1H), 4.59-4.50 (m, 1H), 4.43-4.32 (m, 1H), 3.88-3.65 (m, 5H), 3.59 (s, 3H), 2.96-2.87 (m, 2H), 2.90-2.75 (m, 1H), 1.90-1.48 (m, 6H), 1.41-0.96 (m, 4H). |
| 10 | *First eluting isomer* | (3S)-4-[2-cyclohexyl-8-(methoxycarbonyl)-3H,6H,7H,8H,9H-imidazo[4,5-h]isoquinolin-3-yl]-3-(3-fluoro-5-methoxyphenyl)butanoic acid | 524 | 1H-NMR (Methanol-d$_4$, 400 MHz) δ (ppm): 7.56 (d, J = 8.0 Hz, 1H), 7.11 (d, J = 8.4 Hz, 1H), 6.56-6.49 (m, 1H), 6.39-6.31 (m, 1H), 6.26 (s, 1H), 4.97 (s, 2H), 4.63-4.55 (m, 1H), 4.44-4.33 (m, 1H), 3.84-3.71 (m, 5H), 3.69-3.56 (m, 4H), 3.07-2.91 (m, 3H), 2.87-2.75 (m, 1H), 2.56-2.44 (m, 1H), 1.89-1.69 (m, 4H), 1.71-1.15 (m, 5H), 1.07-0.96 (m, 1H). |
| 194 | *Second eluting isomer* | (3R)-4-[2-cyclohexyl-8-(methoxycarbonyl)-3H,6H,7H,8H,9H-imidazo[4,5-h]isoquinolin-3-yl]-3-(3-fluoro-5-methoxyphenyl)butanoic acid | 524 | 1H-NMR (Methanol-d$_4$, 400 MHz) δ (ppm): 7.55 (d, J = 8.4 Hz, 1H), 7.10 (d, J = 8.4 Hz, 1H), 6.56-6.49 (m, 1H), 6.41-6.35 (m, 1H), 6.25 (s, 1H), 4.97 (s, 2H), 4.63-4.55 (m, 1H), 4.44-4.33 (m, 1H), 3.84-3.71 (m, 5H), 3.69-3.56 (m, 4H), 3.09-2.91 (m, 3H), 2.87-2.75 (m, 1H), 2.56-2.44 (m, 1H), 1.89-1.69 (m, 4H), 1.69-1.13 (m, 5H), 1.05-0.97 (m, 1H). |

Example 6: (1R,4R)-4-[3-(2,2-difluoro-2-phenylethyl)-8-(methoxycarbonyl)-3H,6H,7H,8H,9H-imidazo[4,5-h]isoquinolin-2-yl]cyclohexane-)-carboxylic acid

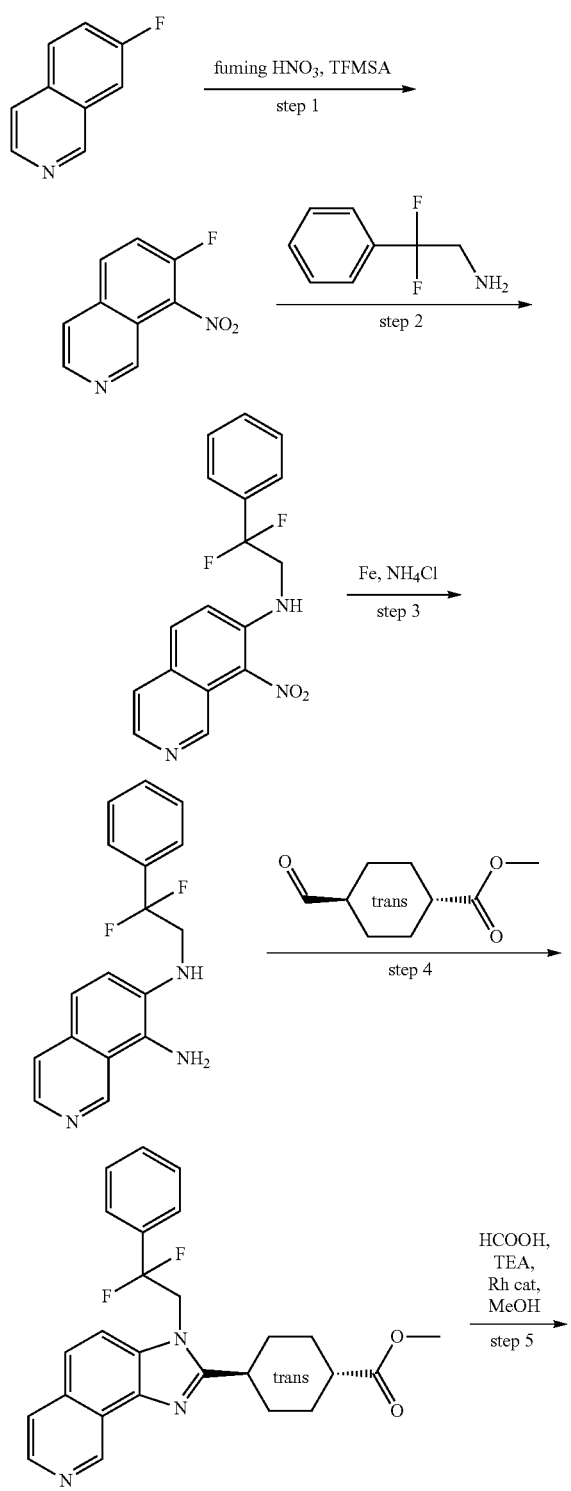

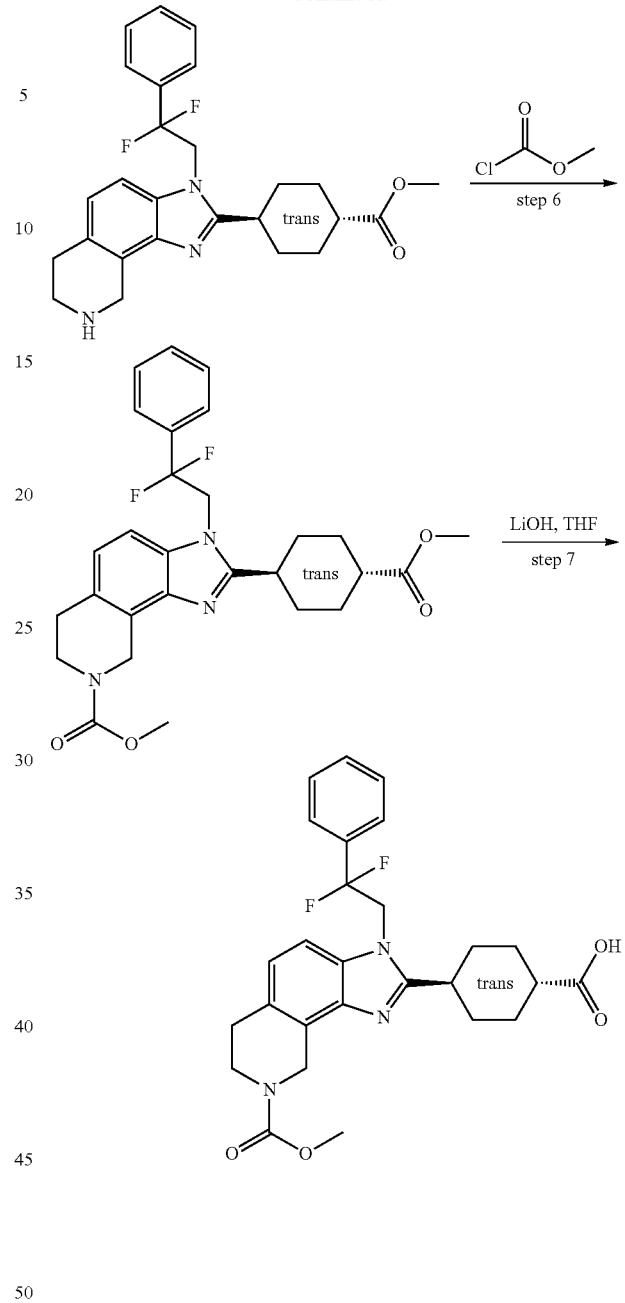

Step 1. 7-fluoro-8-nitroisoquinoline

A solution of trifluoromethanesulfonic acid (87.8 mL, 573 mmol) and fuming nitric acid (22.2 mL, 344 mmol) was stirred for 30 min at 0° C. under nitrogen atmosphere. To the above was added 7-fluoroisoquinoline (50.0 g, 323 mmol) in dichloromethane (200 mL) dropwise over 30 min at 0° C. The resulting mixture was stirred for additional 4 h at room temperature. The mixture was neutralized to pH~7 with saturated sodium bicarbonate. The resulting mixture was extracted with dichloromethane (3×1000 mL), dried over anhydrous sodium sulfate, filtered, and concentrated under vacuum. The residue was purified by silica gel chromatography (eluting with 1:1 ethyl acetate/petroleum ether) to afford 7-fluoro-8-nitroisoquinoline as a yellow solid (60.0 g, 92%). LCMS (ES, m/z): 193 [M+H]+.

Step 2. N-(2,2-difluoro-2-phenylethyl)-8-nitroisoquinolin-7-amine

A mixture of 7-fluoro-8-nitroisoquinoline (1 g, 4.684 mmol), DIEA (3.19 g, 23.419 mmol) and 2,2-difluoro-2-phenylethan-1-amine (1.13 g, 7.026 mmol) in DMF (15 mL) was stirred for 2 h at room temperature. The resulting mixture was diluted with water (50 mL). The resulting solution was extracted with ethyl acetate (3×40 mL). The combined organic layers were washed with brine (100 mL), dried over anhydrous sodium sulfate and concentrated under vacuum. The residue was purified by silica gel chromatography (eluting with 1:2 ethyl acetate/petroleum ether) to afford (1.3 g, 75.85%) of N-(2,2-difluoro-2-phenylethyl)-8-nitroisoquinolin-7-amine as a yellow solid. LCMS (ES, m/z): 330[M+H]$^+$.

Step 3. N-(2,2-difluoro-2-phenylethyl)isoquinoline-7,8-diamine

A mixture of N-(2,2-difluoro-2-phenylethyl)-8-nitroisoquinolin-7-amine (2 g, 5.466 mmol), NH4Cl (1.79 g, 32.796 mmol) and Fe (4.67 g, 81.990 mmol) in THF (15 mL), EtOH (15 mL) and H2O (5 mL) was stirred for 2 h at 80° C. The reaction mixture was cooled to room temperature. The solids were filtered out and washed with THF (2×30 mL). The filtrate was concentrated under vacuum. This resulted in (2.0 g, crude) of N-(2,2-difluoro-2-phenylethyl)isoquinoline-7,8-diamine as a red solid. LCMS (ES, m/z): 300[M+H]$^+$.

Step 4. methyl (1r,4r)-4-[3-(2,2-difluoro-2-phenylethyl)-3H-imidazo[4,5-h]isoquinolin-2-yl]cyclohexane-1-carboxylate A mixture of N-(2,2-difluoro-2-phenylethyl)isoquinoline-7,8-diamine (500 mg, 1.503 mmol) and methyl (1r,4r)-4-formylcyclohexane-1-carboxylate (522.22 mg, 3.007 mmol) in DCM (15 mL) was stirred for 30 min at room temperature. The mixture was concentrated under reduced pressure. The residue was purified by silica gel chromatography (eluting with 1:2 ethyl acetate/petroleum ether) to afford methyl (1r,4r)-4-[3-(2,2-difluoro-2-phenylethyl)-3H-imidazo[4,5-h]isoquinolin-2-yl]cyclohexane-1-carboxylate (518 mg, 68.99%) as a brown solid. LCMS (ES, m/z): 450 [M+H]$^+$.

Step 5. methyl (1r,4r)-4-[3-(2,2-difluoro-2-phenylethyl)-3H,6H,7H,8H,9H-imidazo[4,5-h]isoquinolin-2-yl]cyclohexane-1-carboxylate A mixture of methyl (1r,4r)-4-[3-(2,2-difluoro-2-phenylethyl)-3H-imidazo[4,5-h]isoquinolin-2-yl]cyclohexane-1-carboxylate (498 mg, 0.997 mmol), Rh cat (49.8 mg, 0.076 mmol), TEA (151.35 mg, 1.496 mmol) and HCOOH (413.03 mg, 8.974 mmol) in MeOH (10 mL) was stirred for overnight at room temperature. The solids were filtered out and washed with MeOH (2×10 mL). The filtrate was concentrated under reduced pressure. The residue was purified by reverse phase chromatography with the following conditions: column, C18 silica gel; mobile phase, A: water (5% NH4HCO3) and B: ACN (5% ACN to 80% in 45 min); detector, UV 254 nm to yield methyl (1r,4r)-4-[3-(2,2-difluoro-2-phenylethyl)-3H,6H,7H,8H,9H-imidazo[4,5-h]isoquinolin-2-yl]cyclohexane-1-carboxylate (318 mg, 63.29%) as a brown solid. LCMS (ES, m/z): 454 [M+H]$^+$.

Step 6. methyl 3-(2,2-difluoro-2-phenylethyl)-2-[(1r,4r)-4-(methoxycarbonyl)cyclohexyl]-3H,6H,7H,8H,9H-imidazo[4,5-h]isoquinoline-8-carboxylate A mixture of methyl (1r,4r)-4-[3-(2,2-difluoro-2-phenylethyl)-3H,6H,7H,8H,9H-imidazo[4,5-h]isoquinolin-2-yl]cyclohexane-1-carboxylate (300 mg, 0.595 mmol), methyl carbonochloridate (118.43 mg, 1.191 mmol) and TEA (190.23 mg, 1.786 mmol) in DCM (10 mL) was stirred for 1 h at room temperature. The mixture was concentrated under reduced pressure. The residue was purified by silica gel chromatography (eluting with 1:2 ethyl acetate/petroleum ether) to afford methyl 3-(2,2-difluoro-2-phenylethyl)-2-[(1r,4r)-4-(methoxycarbonyl)cyclohexyl]-3H,6H,7H,8H,9H-imidazo[4,5-h]isoquinoline-8-carboxylate (289 mg, 93.00%) as a light yellow solid. LCMS (ES, m/z): 512 [M+H]$^+$.

Step 7. (1r,4r)-4-[3-(2,2-difluoro-2-phenylethyl)-8-(methoxycarbonyl)-3H,6H,7H,8H,9H-imidazo[4,5-h]isoquinolin-2-yl]cyclohexane-1-carboxylic acid A mixture of methyl 3-(2,2-difluoro-2-phenylethyl)-2-[(1r,4r)-4-(methoxycarbonyl)cyclohexyl]-3H,6H,7H,8H,9H-imidazo[4,5-h]isoquinoline-8-carboxylate (273 mg, 0.523 mmol) and LiOH (63.90 mg, 2.615 mmol) in THF (10 mL) and H$_2$O (5 mL) was stirred for 4 h at room temperature. The mixture was concentrated under vacuum. The residue was purified by reverse phase chromatography with the following conditions: column, C18 silica gel; mobile phase, A: water (5% NH4HCO3) and B: ACN (20% ACN to 40% in 15 min); detector, UV 254 nm to afford (1r,4r)-4-[3-(2,2-difluoro-2-phenylethyl)-8-(methoxycarbonyl)-3H,6H,7H,8H,9H-imidazo[4,5-h]isoquinolin-2-yl]cyclohexane-1-carboxylic acid (65 mg, 24.48%) as a white solid. LCMS (ES, m/z): 498 [M+H]$^+$.

The compounds in Table 6 below may be prepared by methods analogous to the method described in Example 6.

TABLE 6

| Compound No. | Structure | Compound name | MS (ESI, m/z) [M + H]+ | 1H-NMR δ (ppm) |
|---|---|---|---|---|
| 145 | 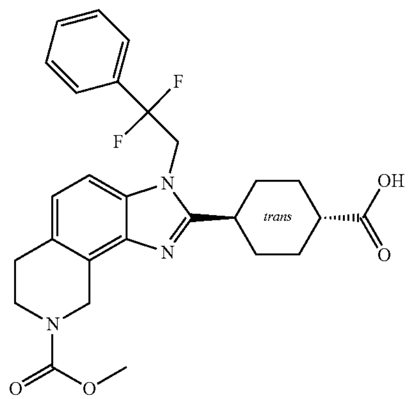 [SMILES: COC(=O)N1CCc2ccc3c(nc([C@H]4CC[C@H](C(=O)O)CC4)n3CC(F)(F)c3ccccc3)c2C1] | (1r,4r)-4-[3-(2,2-difluoro-2-phenylethyl)-8-(methoxycarbonyl)-3H,6H,7H,8H,9H-imidazo[4,5-h]isoquinolin-2-yl]cyclohexane-1-carboxylic acid | 498 | 1H-NMR (CD3OD, 400 MHz) δ (ppm): 7.53-7.43 (m, 3H), 7.37-7.31 (m, 3H), 7.04 (d, J = 8.4 Hz, 1H), 5.02-4.85 (m, 4H), 3.98-3.62 (m, 5H), 2.94 (s, 2H), 3.69-3.44 (m, 1H), 3.42-3.24 (m, 1H), 2.16-1.94 (m, 2H), 1.82-1.65 (m, 2H), 1.64-1.52 (m, 2H), 1.51-1.44 (m, 2H) |
| 358 | First eluting isomer | (2S)-3-[2-cyclohexyl-8-(methoxycarbonyl)-3H,6H,7H,8H,9H-imidazo[4,5-h]isoquinolin-difluorophenyl)propanoic acid | 498 | 1H NMR (400 MHz, CD3OD-d4) δ (ppm): 7.38 (d, J = 8.4 Hz, 1H), 7.24-7.07 (m, 4H), 5.02-4.97 (m, 3H), 4.72-4.63 (m, 1H), 4.48-4.44 (m, 1H), 3.83-3.72 (m, 5H), 2.98-2.95 (m, 2H), 2.88-2.71 (m, 1H), 1.94-1.64 (m, 6H), 1.49-1.24 (m, 4H). |
| 26 | Second eluting isomer | (2R)-3-[2-cyclohexyl-8-(methoxycarbonyl)-3H,6H,7H,8H,9H-imidazo-[4,5-h]isoquinolin-3-yl]-2-(2,3-difluorophenyl)propanoic acid | 498 | 1H NMR (400 MHz, CD3OD-d4) δ (ppm): 7.34 (d, J = 8.0 Hz, 1H), 7.18-7.07 (m, 4H), 4.97-4.90 (m, 3H), 4.64-4.58 (m, 1H), 4.40-4.38 (m, 1H), 3.84-3.75 (m, 5H), 2.97-2.94 (m, 2H), 2.79-2.65 (m, 1H), 1.92-1.86 (m, 2H), 1.80-1.71 (m, 2H), 1.71-1.64 (m, 2H), 1.55-1.41 (m, 1H), 1.40-1.19 (m, 3H). |

Example 7: (2S)-3-[2-cyclohexyl-8-(methoxycarbonyl)-3H,6H,7H,8H,9H-imidazo[4,5-h]isoquinolin-3-yl]-2-(5-fluoro-2-methoxy-4-methylphenyl)propanoic acid and (2R)-3-[2-cyclohexyl-8-(methoxycarbonyl)-3H,6H,7H,8H,9H-imidazo[4,5-h]isoquinolin-3-yl]-2-(5-fluoro-2-methoxy-4-methylphenyl)propanoic acid
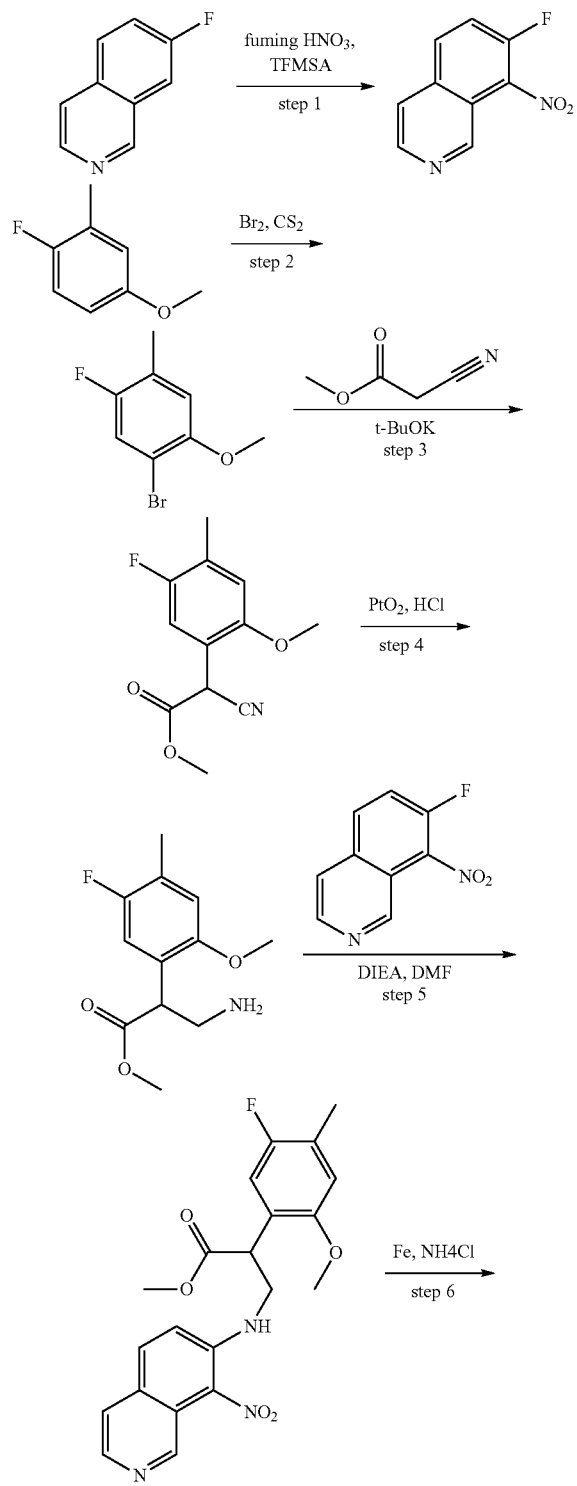
-continued
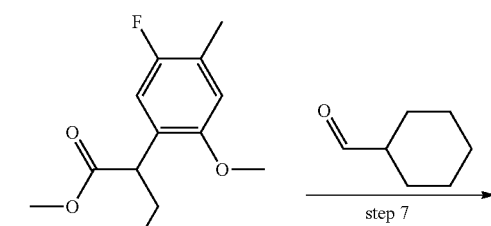
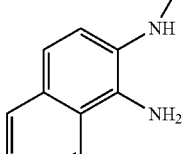
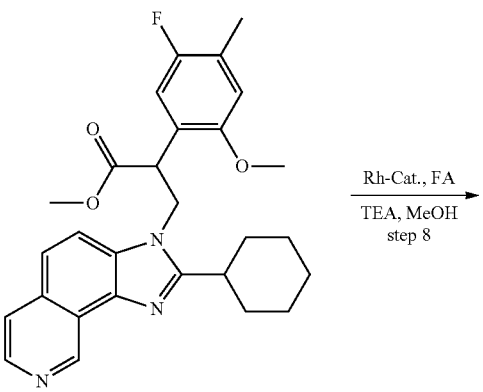
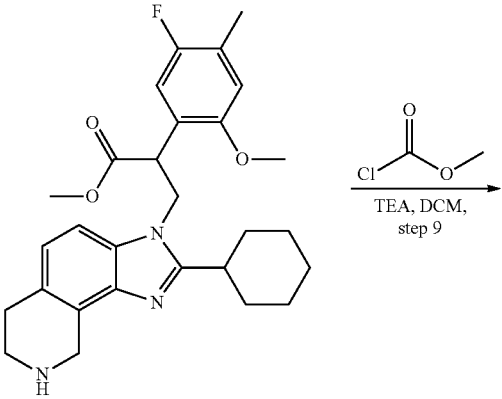

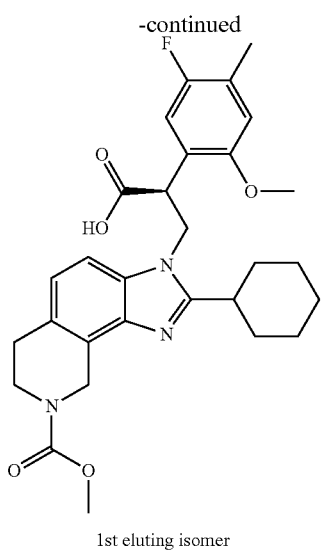

1st eluting isomer

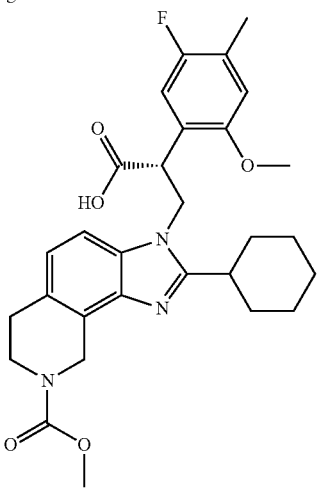

2nd eluting isomer

Step 1. 7-fluoro-8-nitroisoquinoline

A solution of trifluoromethanesulfonic acid (87.8 mL, 573 mmol) and fuming nitric acid (22.2 mL, 344 mmol) was stirred for 30 min at 0° C. under nitrogen atmosphere. To the above was added 7-fluoroisoquinoline (50.0 g, 323 mmol) in dichloromethane (200 mL) dropwise over 30 min at 0° C. The resulting mixture was stirred for additional 4 h at room temperature. The mixture was neutralized to pH-7 with saturated sodium bicarbonate. The resulting mixture was extracted with dichloromethane (3×1000 mL), dried over anhydrous sodium sulfate, filtered, and concentrated under vacuum. The residue was purified by silica gel chromatography (eluting with 1:1 ethyl acetate/petroleum ether) to afford 7-fluoro-8-nitroisoquinoline as a yellow solid (60.0 g, 92%). LCMS (ES, m/z): 193 [M+H]$^+$.

Step 2.
1-bromo-5-fluoro-2-methoxy-4-methylbenzene

A solution of 1-fluoro-4-methoxy-2-methylbenzene (5 g, 34.961 mmol) and Br2 (5.82 g, 0.035 mmol) in CS$_2$ (20 mL) was stirred for 16 h at room temperature. The resulting mixture was diluted with water (100 mL) and was extracted with DCM (3×80 mL), dried over anhydrous sodium sulfate and concentrated under reduced pressure. The residue was purified by silica gel column chromatography (eluting with 1:5 ethyl acetate/petroleum ether) to afford 1-bromo-5-fluoro-2-methoxy-4-methylbenzene (6 g, 70.51%) as a yellow oil. LCMS (ES, m/z): 219, 221 [M+H]$^+$.

Step 3. methyl 2-cyano-2-(5-fluoro-2-methoxy-4-methylphenyl)acetate

A solution of 1-bromo-5-fluoro-2-methoxy-4-methylbenzene (5.00 g, 21.684 mmol), t-BuOK (7.37 g, 65.053 mmol), Pd2(dba)3 (2.03 g, 2.168 mmol), X-Phos (2.15 g, 4.337 mmol) and methyl 2-cyanoacetate (3.32 g, 32.500 mmol) in 1,2-dimethoxy-ethan (20 mL) was stirred for 5 h at 120° C. under nitrogen atmosphere. The resulting mixture was diluted with water (100 mL) and was extracted with EtOAc (3×100 mL), dried over anhydrous sodium sulfate and concentrated under reduced pressure. The residue was purified by silica gel column chromatography (eluting with 1:1 ethyl acetate/petroleum ether) to afford methyl 2-cyano-2-(5-fluoro-2-methoxy-4-methylphenyl)acetate (2.5 g, 43.74%) as a yellow oil. LCMS (ES, m/z): 238 [M+H]$^+$.

Step 4. methyl 3-amino-2-(5-fluoro-2-methoxy-4-methylphenyl)propanoate

To a solution of methyl 2-cyano-2-(5-fluoro-2-methoxy-4-methylphenyl)acetate (500 mg, 2.002 mmol) and PtO2 (50.00 mg, 0.211 mmol) in MeOH (10 mL) and HCl (1 mL) was stirred for 4 h under hydrogen atmosphere with a hydrogen balloon. The solids were filtered out. The resulting mixture was diluted with water (50 mL). The mixture was basified to pH 7 with saturated NaHCO$_3$ (aq.). The resulting mixture was extracted with EtOAc (3×50 mL), dried over anhydrous sodium sulfate and concentrated under reduced pressure. The residue was purified by silica gel column chromatography (eluting with 3:1 ethyl acetate/petroleum ether) to afford methyl 3-amino-2-(5-fluoro-2-methoxy-4-methylphenyl)propanoate (315 mg, crude) as a white solid. LCMS (ES, m/z): 242 [M+H]$^+$.

Step 5. methyl 2-(5-fluoro-2-methoxy-4-methylphenyl)-3-[(8-nitroisoquinolin-7-yl)amino]propanoate A solution of methyl 3-amino-2-(5-fluoro-2-methoxy-4-methylphenyl)propanoate (315.00 mg, 1.240 mmol),7-fluoro-8-nitroisoquinoline (124.13 mg, 0.620 mmol) and DIEA (490.74 mg, 3.721 mmol) in DMF (8 mL) was stirred for 1 h at 80° C. The mixture was allowed to cool down to room temperature. The resulting mixture was diluted with water (30 mL). The resulting mixture was extracted with EtOAc (3×30 mL). The combined organic layers were washed with brine (2×20 mL), dried over anhydrous sodium sulfate and concentrated under reduced pressure. The residue was purified by silica gel column chromatography (eluting with 1:1 ethyl acetate/petroleum ether) to afford methyl 2-(5-fluoro-2-methoxy-4-methylphenyl)-3-[(8-nitroisoquinolin-7-yl)amino]propanoate (300 mg, 55.58%) as a yellow solid. LCMS (ES, m/z): 414 [M+H]$^+$.

Step 6. methyl 3-[(8-aminoisoquinolin-7-yl)amino]-2-(5-fluoro-2-methoxy-4-methylphenyl)propanoate A mixture of methyl 3-[(3-carboximidoyl-2-nitrophenyl)amino]-2-(5-fluoro-2-methoxy-4-methylphenyl)propanoate (300.00 mg, 0.740 mmol), Fe (417.22 mg, 7.396 mmol) and NH4Cl (403.71 mg, 7.396 mmol) in THF (10 mL), EtOH (10 mL) and water (3 mL) was stirred for 1 h at 80° C. The mixture was allowed to cool down to room temperature. The solids were filtered out. The filtrate was concentrated under reduced pressure. The resulting mixture was diluted with water (30 mL). The resulting mixture was extracted with EtOAc (3×30 mL). The combined organic layers were washed with brine (2×20 mL), dried over anhydrous sodium sulfate and concentrated under reduced pressure. This resulted in methyl 3-[(8-aminoisoquinolin-7-yl)amino]-2-(5-fluoro-2-methoxy-4-methylphenyl)propanoate (280 mg, crude) as a yellow solid. LCMS (ES, m/z): 384 [M+H]$^+$.

Step 7. methyl 3-[2-cyclohexyl-3H-imidazo[4,5-h]isoquinolin-3-yl]-2-(5-fluoro-2-methoxy-4-methylphenyl) propanoate A mixture of methyl 3-[(8-aminoisoquinolin-7-yl)amino]-2-(5-fluoro-2-methoxy-4-methylphenyl)propanoate (593.00 mg, 1.500 mmol) and cyclohexanecarbaldehyde (515.14 mg, 4.501 mmol) in DCM (10.00 mL) was stirred for 1 h at room temperature. The resulting mixture was concentrated under reduced pressure. The residue was purified by silica gel column chromatography (eluting with 1:1 ethyl acetate/petroleum ether) to afford methyl 3-[2-cyclohexyl-3H-imidazo[4,5-h]isoquinolin-3-yl]-2-(5-fluoro-2-methoxy-4-methylphenyl)propanoate (400 mg, 53.26%) as a yellow solid. LCMS (ES, m/z): 476 [M+H]$^+$.

Step 8. methyl 3-[2-cyclohexyl-3H,6H,7H,8H,9H-imidazo[4,5-h]isoquinolin-3-yl]-2-(5-fluoro-2-methoxy-4-methylphenyl)propanoate To a stirred solution methyl 3-([8-[(1-cyclohexylethylidene)amino]isoquinolin-7-yl]amino)-2-(5-fluoro-2-methoxy-4-methylphenyl)propanoate (431.00 mg, 0.842 mmol) and TEA (129.04 mg, 1.262 mmol) in MeOH (10 mL) were added FA (175.98 mg, 3.787 mmol) and Rh cat (57.07 mg, 0.084 mmol). The mixture was stirred at room temperature for overnight under nitrogen atmosphere. The resulting mixture was concentrated under vacuum. The residue was purified by silica gel column chromatography (eluting with 1:10 MeOH/DCM) to afford methyl 3-[2-cyclohexyl-3H,6H,7H, 8H,9H-imidazo[4,5-h]isoquinolin-3-yl]-2-(5-fluoro-2-methoxy-4-methylphenyl)propanoate (399 mg, 96.87%) as a yellow solid. LCMS (ES, m/z): 480[M+H]$^+$.

Step 9. methyl 2-cyclohexyl-3-[2-(5-fluoro-2-methoxy-4-methylphenyl)-3-methoxy-3-oxopropyl]-3H,6H,7H,8H,9H-imidazo[4,5-h]isoquinoline-8-carboxylate To a stirred solution of methyl 3-[2-cyclohexyl-3H,6H,7H,8H,9H-imidazo[4,5-h]isoquinolin-3-yl]-2-(5-fluoro-2-methoxy-4-methylphenyl)propanoate (340.00 mg, 0.695 mmol) and TEA (217.43 mg, 2.084 mmol) in DCM (10 mL) were added methyl carbonochloridate (132.62 mg, 1.389 mmol) dropwise. The resulting mixture was stirred for 1 h at room temperature. The resulting mixture was diluted with water (20 mL) and was extracted with EtOAc (3×50 mL), dried over anhydrous sodium sulfate and concentrated under reduced pressure. The residue was purified by silica gel column chromatography (eluting with 1:1 ethyl acetate/petroleum ether) to afford methyl 2-cyclohexyl-3-[2-(5-fluoro-2-methoxy-4-methylphenyl)-3-methoxy-3-oxopropyl]-3H,6H,7H,8H,9H-imidazo [4,5-h]isoquinoline-8-carboxylate (202 mg, 51.38%) as a white solid. LCMS (ES, m/z): 538[M+H]$^+$.

Step 10. (2S)-3-[2-cyclohexyl-8-(methoxycarbonyl)-3H,6H,7H,8H,9H-imidazo[4,5-h]isoquinolin-3-yl]-2-(5-fluoro-2-methoxy-4-methylphenyl)propanoic acid and (2R)-3-[2-cyclohexyl-8-(methoxycarbonyl)-3H,6H,7H,8H,9H-imidazo[4,5-h]isoquinolin-3-yl]-2-(5-fluoro-2-methoxy-4-methylphenyl)propanoic acid A mixture of methyl 2-cyclohexyl-3-[2-(5-fluoro-2-methoxy-4-methylphenyl)-3-methoxy-3-oxopropyl]-3H, 6H,7H,8H,9H-imidazo[4,5-h]isoquinoline-8-carboxylate (182.00 mg, 0.325 mmol) and LiOH (38.91 mg, 1.625 mmol) in H2O (4 mL) and THF (12 mL) was stirred for 16 h at room temperature. The resulting mixture was concentrated under reduced pressure. The crude product was purified by Prep-HPLC with the following conditions: Column, XBridge Prep 0.1BD C18 Column, 30×150 mm 5 um; mobile phase, Water (10 MMOL/L NH4HCO3) and ACN (40% ACN up to 60% in 7 min); Detector, UV 254 nm. The product was separated by Chiral-Prep-HPLC with the following conditions: Column, (R,R)-WHELK-01-Kromasil, 5 cm×25 cm (5 um); mobile phase, Hex (0.1% FA) and EtOH (hold 15% EtOH in 21 min); Detector, UV 254 nm to afford (2S)-3-[2-cyclohexyl-8-(methoxycarbonyl)-3H,6H,7H,8H, 9H-imidazo[4,5-h]isoquinolin-3-yl]-2-(5-fluoro-2-methoxy-4-methylphenyl)propanoic acid (29.4 mg, 17.11%) as a white solid and (2R)-3-[2-cyclohexyl-8-(methoxycarbonyl)-3H,6H,7H,8H,9H-imidazo[4,5-h]isoquinolin-3-yl]-2-(5-fluoro-2-methoxy-4-methylphenyl)propanoic acid (27.8 mg, 16.34%) as a white solid.

The compounds in Table 7 below may be prepared by methods analogous to the method described in Example 7.

TABLE 7

| Compound No. | Structure | Compound name | MS (ESI, m/z) [M + H]+ | 1H-NMR δ (ppm) |
|---|---|---|---|---|
| 278 | First eluting isomer | (2S)-3-[2-cyclohexyl-8-(methoxycarbonyl)-3H,6H,7H,8H,9H-imidazo[4,5-h]isoquinolin-3-yl]-2-(5-fluoro-2-methoxy-4-methylphenyl) propanoic acid | 524 | 1H-NMR (CD3OD, 400 MHz) δ (ppm): 7.40 (d, J = 8.0 Hz, 1H), 7.12 (d, J = 8.4 Hz, 1H), 6.77 (d, J = 6.4 Hz, 2H), 4.97 (s, 2H), 4.89-4.81 (m, 1H), 4.63-4.50 (m, 1H), 4.41-4.31 (m, 1H), 3.82-3.75 (m, 5H), 3.54 (s, 3H), 2.98-2.90 (m, 2H), 2.70-2.58 (m, 1H), 2.22 (s, 3H), 1.89-1.72 (m, 3H), 1.71-1.49 (m, 3H), 1.50-1.20 (m, 3H), 1.19-1.10 (m, 1H). |
| 27 | Second eluting isomer | (2R)-3-[2-cyclohexyl-8-(methoxycarbonyl)-3H,6H,7H,8H,9H-imidazo[4,5-h]isoquinolin-3-yl]-2-(5-fluoro-2-methoxy-4-methylphenyl) propanoic acid | 524 | 1H-NMR (CD3OD, 400 MHz) δ (ppm): 7.39 (d, J = 8.4 Hz, 1H), 7.12 (d, J = 8.4 Hz, 1H), 6.77 (d, J = 6.4 Hz, 2H), 4.98 (s, 2H), 4.88-4.80 (m, 1H), 4.59-4.53 (m, 1H), 4.43-4.35 (m, 1H), 3.83-3.70 (m, 5H), 3.54 (s, 3H), 3.10-2.85 (m, 2H), 2.70-2.55 (m, 1H), 2.22 (s, 3H), 1.92-1.75 (m, 4H), 1.75-1.50 (m, 2H), 1.49-1.21 (m, 3H), 1.20-1.06 (m, 1H). |
| 34 | First eluting isomer | (3S)-4-[2-cyclopentyl-8-(methoxycarbonyl)-6H,7H,9H-imidazo[4,5-h]isoquinolin-3-yl]-3-phenylbutanoic acid | 462 | 1H-NMR (CD3OD, 400 MHz) δ (ppm): 7.864 (d, J = 8.4 Hz, 1H), 7.42 (d, J = 8.4 Hz, 1H), 7.27-7.26 (m, 3 H), 7.07-7.05 (m, 2H), 4.93-4.91 (m, 3H), 4.71-4.65 (m, 1H), 3.83-3.82 (m, 5H), 3.79-3.77 (m, 1H), 3.19-3.12 (m, 2H), 3.06-3.03 (m, 2H), 2.92-2.86 (m, 1H), 2.30-2.27 (m, 1H), 1.92-1.88 (m, 2H), 1.78-1.76 (m, 2H), 1.62-1.57 (m, 2H), 1.33-1.24 (m, 1H). |

TABLE 7-continued

| Compound No. | Structure | Compound name | MS (ESI, m/z) [M + H]+ | $^1$H-NMR δ (ppm) |
|---|---|---|---|---|
| 174 | 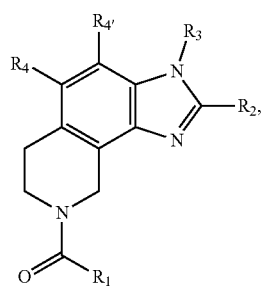<br>Second eluting isomer | (3R)-4-[2-cyclopentyl-8-(methoxycarbonyl)-6H,7H,9H-imidazo[4,5-h]isoquinolin-3-yl]-3-phenylbutanoic acid | 462 | $^1$H-NMR (CD$_3$OD, 400 MHz) δ (ppm): 7.86-7.84 (d, J = 28.4 Hz, 1H), 7.43-7.41 (d, J = 9.2 Hz, 1H), 7.27-7.26 (m, 3H), 7.07-7.05 (m, 2H), 4.93-4.91 (m, 3H), 4.71-4.65 (m, 1H), 3.83-3.82 (m, 5H), 3.79-3.77 (m, 1H), 3.19-3.12 (m, 2H), 3.06-3.03 (m, 2H), 2.92-2.86 (m, 1H), 2.30-2.27 (m, 1H), 1.92-1.88 (m, 2H), 1.78-1.76 (m, 2H), 1.62-1.57 (m, 2H), 1.38-1.22 (m, 1H). |

The compounds in FIG. 1 were prepared using standard chemical manipulations and procedures similar to those described in Examples 2-7.

The invention claimed is:

1. A compound of Formula (I):

(I)

or a pharmaceutically acceptable salt thereof, wherein:
R$_1$ is —C$_1$-C$_6$alkyl, —C$_3$-C$_8$cycloalkyl,—OR$_5$, or —NHR$^5$;
R$_2$ is —C$_3$-C$_8$cycloalkyl, heterocyclyl, heteroaryl, or aryl, wherein each cycloalkyl, heterocyclyl, heteroaryl, or aryl is optionally substituted with one or more R$_6$;
R$_3$ is —C$_1$-C$_6$ alkyl,—C$_3$-C$_8$cycloalkyl, or heterocyclyl, wherein each alkyl, cycloalkyl, or heterocyclyl, is optionally substituted with one or more R$_7$;
R$_4$ and R$_{4'}$ are each independently —H, halogen, —CN, —CH$_2$CN, —COOH, or heterocycloalkyl;
each R$_5$ is independently —C$_1$-C$_6$alkyl;
R$_6$ and R$_7$ are each independently, at each occurrence, halogen, —C$_1$-C$_6$alkyl, —C$_3$-C$_8$cycloalkyl, -heterocyclyl, aryl, heteroaryl, —OH, oxo, —OR$_8$,— NHR$_8$, —NR$_8$R$_9$, —S(O)$_2$NR$_8$R$_9$, —S(O)$_2$R$_{8'}$, —C(O)R$_8$, —C(O)OR$_8$, —C(O)NR$_8$S(O)$_2$R$_{9'}$, wherein each alkyl, cycloalkyl, heterocyclyl, heteroaryl, or aryl is optionally substituted with one or more R$_{10}$;

wherein any two R$_6$ or any two R$_7$, when on non-adjacent atoms, can combine to form a cycloalkyl or heterocyclyl;

wherein any two R$_6$ or any two R$_7$, when on adjacent atoms, can combine to form an aryl or heterocyclyl;

R$_8$ and R$_9$ are each independently, at each occurrence, —H, —C$_1$-C$_6$alkyl, —C(O)C$_1$-C$_6$alkyl, or aryl, wherein each alkyl, or aryl is optionally substituted with one or more R$_{10}$ or R$_{11}$;

R$_{8'}$ and R$_{9'}$ are each independently, at each occurrence, —C$_1$-C$_6$alkyl or heterocyclyl, wherein each alkyl, or heterocyclyl is optionally substituted with one or more R$_{10}$ or R$_{11}$;

R$_{10}$ and R$_{11}$ are each independently, at each occurrence, —C$_1$-C$_6$alkyl, heteroaryl, aryl, —OH, halogen, —OC$_1$-C$_6$alkyl, or —C(O)OH, wherein each alkyl, or heteroaryl is optionally substituted with one or more —R$_{12}$;

wherein any two R$_{10}$ or any two R$_{11}$, when on adjacent atoms, can combine to form a heterocyclyl or aryl; and R$_{12}$ is independently, at each occurrence, —C$_1$-C$_6$alkyl, —OH, halogen, or —OC$_1$-C$_6$alkyl.

2. The compound of claim 1, or the pharmaceutically acceptable salt thereof, wherein:
R$_1$ is —C$_1$-C$_6$alkyl, -C$_3$cycloalkyl,—OR$_5$, or —NHR$^5$;
R$_2$ is —C$_4$-C$_6$cycloalkyl; 4-6 membered heterocyclyl; 6-membered heteroaryl; or C$_6$aryl;
wherein each cycloalkyl, heterocyclyl, heteroaryl, or aryl is optionally substituted with one or more R$_6$;
R$_3$ is —C$_1$-C$_6$ alkyl, —C$_6$cycloalkyl, or 4-membered heterocyclyl, wherein each alkyl, cycloalkyl, or heterocyclyl, is optionally substituted with one or more R$_7$;
R$_4$ and R$_{4'}$ are each independently —H, halogen, —CN, —CH$_2$CN, —COOH, or 5-membered heterocycloalkyl;

R₆ is independently, at each occurrence, halogen, —C₁-C₆alkyl, 4-membered heterocyclyl, —OH, oxo, —OR₈, —NHR₈, —NR₈R₉, —S(O)₂NR₈R₉', —S(O)₂R₈', —C(O)R₈', —C(O)OR₈, —C(O)NR₈S(O)₂R₉', wherein each alkyl or heterocyclyl is optionally substituted with one or more R₁₀;

R₇ is independently, at each occurrence, halogen, —C₁-C₆alkyl, -C₆cycloalkyl, -6-membered heterocyclyl, C₆aryl, 5-6 membered heteroaryl, —OH, halogen, oxo, —OR₈, —NHR₈, —NR₈R₉, —S(O)₂NR₈R₉', —S(O)₂R₈', —C(O)R₈', —C(O)OR₈, —C(O)NR₈S(O)₂R₉', wherein each alkyl, cycloalkyl, heterocyclyl, heteroaryl, or aryl is optionally substituted with one or more R₁₀;

wherein any two R₇, when on adjacent atoms, can combine to form a 5-membered heterocycyl or C₆aryl;

R₈ and R₉ are each independently, at each occurrence, —H, —C₁-C₆alkyl, —C(O)C₁-C₆alkyl, or C₆aryl, wherein each alkyl is optionally substituted with one or more R₁₀ or R₁₁;

R₈' and R₉' are each independently, at each occurrence, —C₁-C₆alkyl or 4-membered heterocyclyl, wherein each alkyl is optionally substituted with one or more R₁₀ or R₁₁;

R₁₀ and R₁₁ are each independently, at each occurrence, —C₁-C₆alkyl, 5-membered heteroaryl, C₆aryl, —OH, halogen, —OC₁-C₆alkyl, or —C(O)OH, wherein each alkyl, or heteroaryl is optionally substituted with one or more —R₁₂;

wherein any two R₁₀ or any two R₁₁, when on adjacent atoms, can combine to form a 5-membered heterocyclyl or C₆aryl; and R₁₂ is independently, at each occurrence, —C₁-C₆alkyl, —OH, halogen, or —OC₁-C₆alkyl.

3. The compound of claim 2, or the pharmaceutically acceptable salt thereof, wherein:

R₁ is methyl;

R₂ is —C₄-C₆cycloalkyl; 6 membered heterocyclyl comprising 1-2 heteroatoms selected from N and O; 6-membered heteroaryl comprising one nitrogen; or C₆aryl; wherein each cycloalkyl, heterocyclyl, heteroaryl, or aryl is optionally substituted with one or more R₆;

R₃ is —C₁-C₃ alkyl optionally substituted with one or more R₇;

R₄ is —H or halogen;

R₄' is —H, —CN, —CH₂CN, —COOH, or 5-membered heterocycloalkyl;

R₆ is independently, at each occurrence, —C₁-C₆alkyl, —OR₈, —S(O)₂NR₈R₉', —S(O)₂R₈', —C(O)R₈', —C(O)OR₈, —C(O)NR₈S(O)₂R₉', wherein each alkyl or heterocyclyl is optionally substituted with one or more R₁₀;

R₇ is independently, at each occurrence, halogen, —C₁-C₆alkyl, -C₆cycloalkyl, C₆aryl, 5-6 membered heteroaryl, —OH, —OR₈, —C(O)OR₈, or —C(O)NR₈S(O)₂R₉', wherein each alkyl, cycloalkyl, heteroaryl, or aryl is optionally substituted with one or more R₁₀;

R₈ is independently, at each occurrence, —H, —C₁-C₆alkyl, —C(O)C₁-C₆alkyl, or C₆aryl, wherein each alkyl is optionally substituted with one or more R₁₀ or R₁₁;

R₈' is independently, at each occurrence, —C₁-C₆alkyl or 4-membered heterocyclyl, wherein each alkyl is optionally substituted with one or more R₁₀ or R₁₁;

R₉' is independently, at each occurrence, —C₁-C₆alkyl;

R₁₀ and R₁₁ are each independently, at each occurrence, —C₁-C₆alkyl, 5-membered heteroaryl, —OH, halogen, —OC₁-C₆alkyl, or —C(O)OH, wherein each alkyl is optionally substituted with one or more —R₁₂;

wherein any two R₁₀ or any two R₁₁, when on adjacent atoms, can combine to form a 5-membered heterocyclyl or C₆aryl; and R₁₂ is independently, at each occurrence, halogen.

4. The compound of claim 3, or the pharmaceutically acceptable salt thereof, wherein:

R₂ is —C₅-C₆cycloalkyl; 6 membered heterocyclyl comprising 1-2 heteroatoms selected from N and O; or C₆aryl; wherein each cycloalkyl, heterocyclyl, heteroaryl, or aryl is optionally substituted with one or more R₆;

R₄' is —H, —CN, —COOH, or 5-membered heterocycloalkyl;

R₇ is independently, at each occurrence, halogen, —C₁-C₆alkyl, -C₆cycloalkyl, C₆aryl, 5-membered heteroaryl, —OH, —C(O)OR₈, or —C(O)NR₈S(O)₂R₉', wherein each alkyl, cycloalkyl, heteroaryl, or aryl is optionally substituted with one or more R₁₀;

R₁₀ and R₁₁ are each independently, at each occurrence, —C₁-C₆alkyl, 5-membered heteroaryl, —OH, halogen, —OC₁-C₆alkyl, or —C(O)OH, wherein each alkyl is optionally substituted with one or more R₁₂, wherein R₁₂ is fluorine.

5. The compound of claim 1, or the pharmaceutically acceptable salt thereof, wherein R₁ is —OR₅, and optionally wherein R₅ is methyl.

6. The compound of claim 1, or the pharmaceutically acceptable salt thereof, wherein R₂ is C₄-C₆ cycloalkyl, phenyl, six-membered heterocyclyl, or six-membered heteroaryl, optionally wherein:
the six-membered heterocyclyl is selected from the group consisting of piperidinyl, tetrahydropyranyl, and piperazinyl; or
the six-membered heteroaryl is pyridinyl.

7. The compound of claim 1, or the pharmaceutically acceptable salt thereof, wherein R₃ is:
C₁-C₆ alkyl substituted with phenyl and with methyl; or
C₂ alkyl substituted with phenyl and at least one of halogen, —CH₃, —COOH, —CH₂COOH, or —C(O)NHSO₂CH₃, wherein the phenyl is optionally substituted with 1 to 3 substituents independently selected from the group consisting of halogen, —CH₃, —OCH₃, and —COOH.

8. The compound of claim 1, or the pharmaceutically acceptable salt thereof, wherein the compound is:

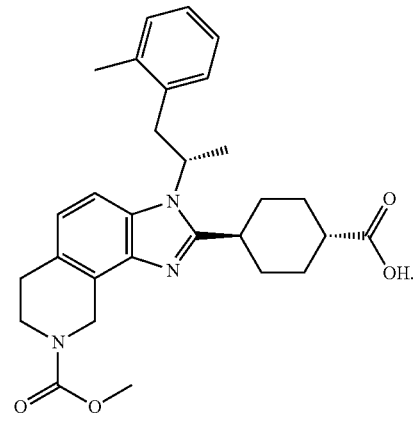 [SMILES: COC(=O)N1CCc2ccc3c(nc([C@H]4CC[C@H](C(=O)O)CC4)n3[C@@H](C)Cc3ccccc3C)c2C1]

9. The compound of claim 1, or the pharmaceutically acceptable salt thereof, wherein the compound is:

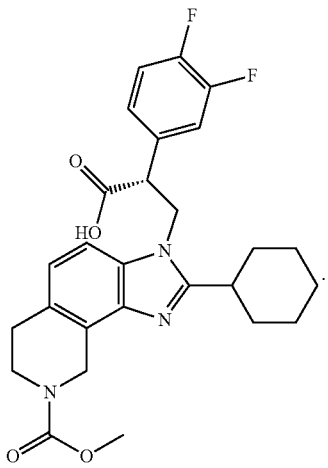

10. The compound of claim 1, or the pharmaceutically acceptable salt thereof, wherein the compound is:

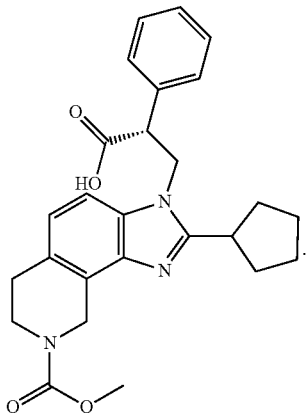 [SMILES: COC(=O)N1CCc2ccc3c(nc(C4CCCC4)n3C[C@H](C(=O)O)c3ccccc3)c2C1]

11. The compound of claim 1, wherein the compound is of Formula (II):

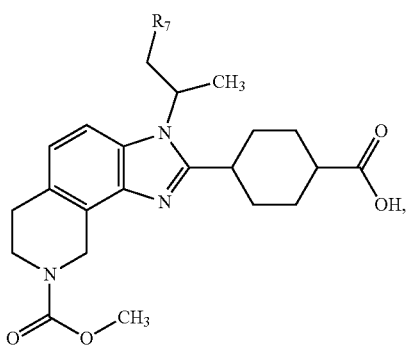

(II)

or a pharmaceutically acceptable salt thereof, wherein $R_7$ is phenyl optionally substituted with one or more $R_{10}$, wherein each $R_{10}$ is independently selected from —$C_1$-$C_3$alkyl, —O($C_1$-$C_3$alkyl), and halogen.

12. The compound of claim 1, wherein the compound is of Formula (III):

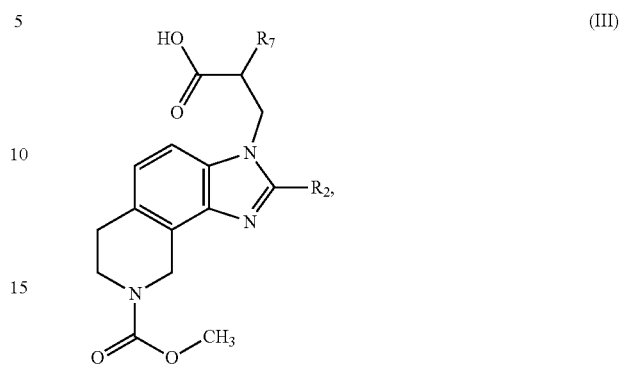

(III)

or a pharmaceutically acceptable salt thereof, wherein:

$R_2$ is —$C_5$-$C_6$cycloalkyl; and $R_7$ is phenyl optionally substituted with one or more $R_{10}$, wherein each $R_{10}$ is independently selected from —$C_1$-$C_3$alkyl —O($C_1$-$C_3$alkyl), and halogen.

13. The compound of claim 1, wherein the compound is of Formula (IV):

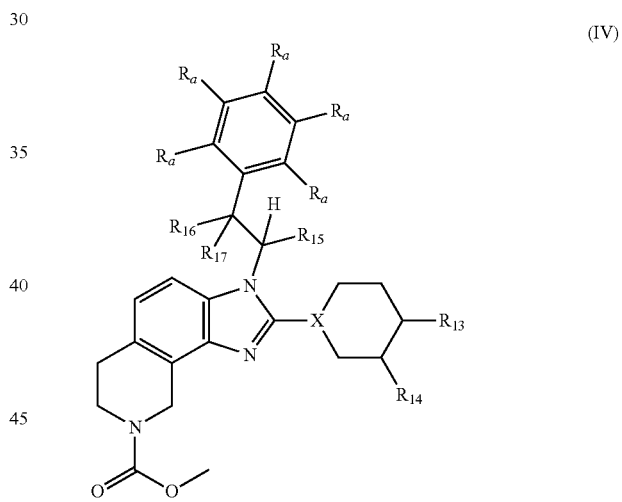

(IV)

or a pharmaceutically acceptable salt thereof, wherein:

each $R_a$ is independently selected from —H, halogen, —$CH_3$, —$OCH_3$, and —COOH;

X is CH or N;

$R_{13}$ is —H, —COOH, —$OCH_3$, or —(CO)NHSO$_2$CH$_3$;

$R_{15}$ is —H or —$CH_3$;

$R_{16}$ is —H, halogen, —$CH_3$, —COOH, —$CH_2$COOH, or —(CO)NHSO$_2$CH$_3$; and $R_{17}$ is —H or halogen.

14. A compound of Formula (I):

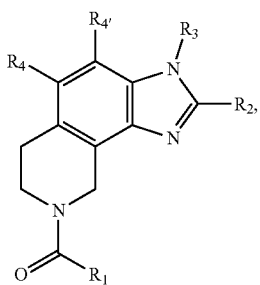

or a pharmaceutically acceptable salt thereof, wherein:

$R_1$ is —$C_1$-$C_6$alkyl;

$R_2$ is —$C_3$-$C_8$cycloalkyl, or 3-8 member heterocyclyl comprising one or more O, S or N heteroatoms, wherein each cycloalkyl, or heterocycloalkyl is optionally substituted with one or more $R_6$;

$R_3$ is —$C_1$-$C_6$ alkyl substituted with one or more one $R_7$, and optionally additionally substituted with a COOH;

$R_4$ and $R_{4'}$ are each independently —H;

$R_6$ is each independently, at each occurrence, —$C_1$-$C_6$alkyl optionally substituted with one or more $R_{10}$, —OH, halogen, oxo, —CN, —$SR_8$, —$OR_8$, —($CH_2$)--$OR_8$, —$NHR_8$, —$NR_8R_9$, —$S(O)_2NR_8R_9$, —$S(O)_2R_{8'}$, —$C(O)R_{8'}$, —$C(O)OR_8$, —$C(O)NR_8R_9$, —$C(O)NR_8S(O)_2R_{9'}$, —$NR_8C(O)R_{9'}$, —$NR_8S(O)_2R_{9'}$, —$S(O)R_{8'}$, —$S(O)NR_8R_9$, or —$NR_8S(O)R_9$;

$R_7$ that is a mono or bicyclic ($C_5$-$C_{10}$)aryl, (5-10 member)heteroaryl, ($C_3$-$C_{10}$)cycloalkyl, or a (3-10 member) heterocycloalkyl optionally substituted with one or more $R_{10}$;

$R_8$ and $R_9$ is each independently, at each occurrence, H, or ($C_1$-$C_4$) alkyl optionally substituted with one or more $R_{10}$;

$R_{10}$ is each independently, at each occurrence, —OH, halogen, oxo, —$NO_2$, —CN, —$NH_2$, methyl or methoxy.

15. The compound of claim 14, wherein $R_2$ is —$C_5$-$C_6$ cycloalkyl or 5-6 member heterocyclyl comprising one or more O, S or N heteroatoms, wherein each cycloalkyl, or heterocycloalkyl is optionally substituted with one or more $R_6$;

optionally wherein $R_2$ is —$C_6$ cycloalkyl optionally substituted with one or more $R_6$.

16. The compound of claim 14, wherein $R_3$ is:

—$C_1$-$C_4$ alkyl substituted with one $R_7$, and $R_7$ is a $C_5$-$C_6$ monocyclic aryl, a 5-6 member monocyclic heteroaryl, a $C_5$-$C_6$ monocyclic cycloalkyl, or a 5-6 member monocyclic heterocycloalkyl; or —$C_1$-$C_6$ alkyl substituted with —COOH.

17. The compound of claim 14, wherein $R_3$ is —$C_1$-$C_6$ alkyl not substituted with COOH, and either $R_7$ or $R_2$ is substituted with one —COOH.

18. The compound of claim 14, wherein $R_1$ is methyl.

19. A compound or a pharmaceutically acceptable salt thereof, wherein the compound is selected from:

| | (Currently amended) A compound or a pharmaceutically acceptable salt thereof, wherein the compound is selected from |
|---|---|
| Compound No. | Structure |
| 1 | <br> |
| 2 | <br> |

-continued
(Currently amended) A compound or a pharmaceutically acceptable salt thereof, wherein the compound is selected from
| Compound No. | Structure |
|---|---|
| 3 | 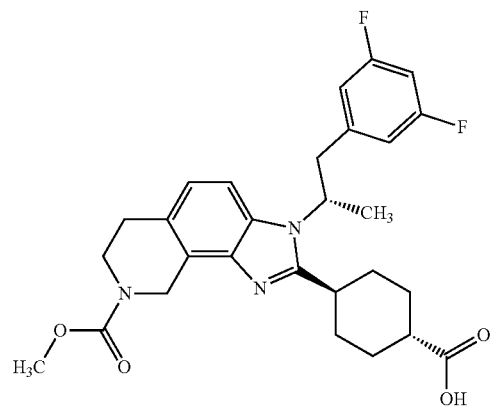 [SMILES: COC(=O)N1CCc2ccc3c(nc([C@H]4CC[C@H](C(=O)O)CC4)n3[C@@H](C)Cc3cc(F)cc(F)c3)c2C1] |
| 4 | 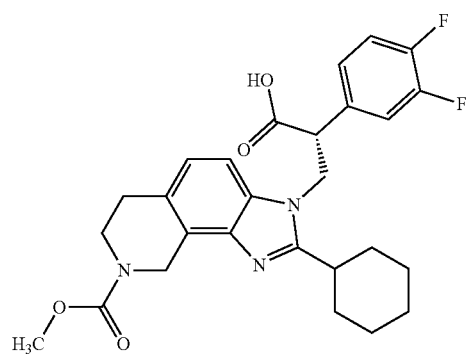 [SMILES: COC(=O)N1CCc2ccc3c(nc(C4CCCCC4)n3C[C@H](C(=O)O)c3ccc(F)c(F)c3)c2C1] |
| 5 | 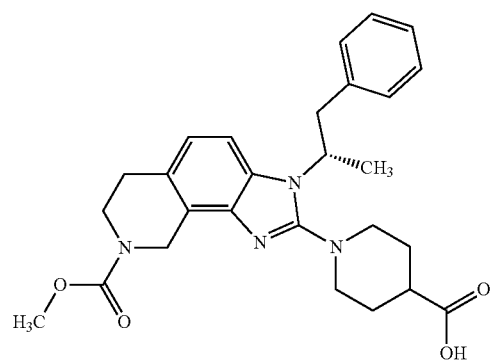 |
| 6 | 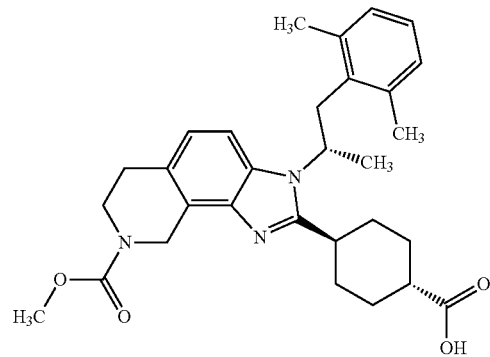 [SMILES: COC(=O)N1CCc2ccc3c(nc([C@H]4CC[C@H](C(=O)O)CC4)n3[C@@H](C)Cc3c(C)cccc3C)c2C1] |

-continued
(Currently amended) A compound or a pharmaceutically acceptable salt thereof, wherein the compound is selected from
| Compound No. | Structure |
| --- | --- |
| 7 | 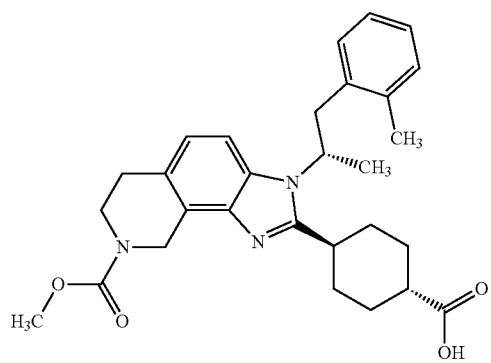 |
| 8 | 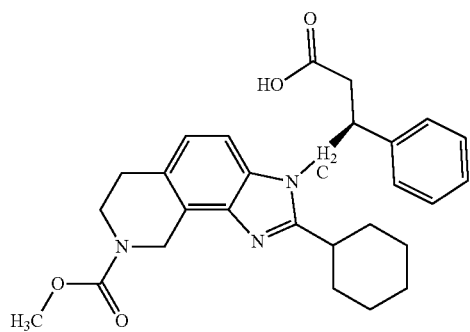 [SMILES: COC(=O)N1CCc2ccc3c(nc(C4CCCCC4)n3C[C@@H](CC(=O)O)c3ccccc3)c2C1] |
| 9 | 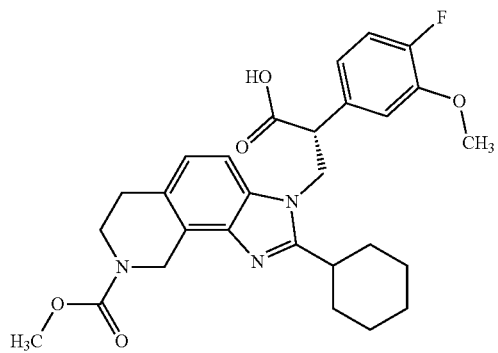 |
| 10 | 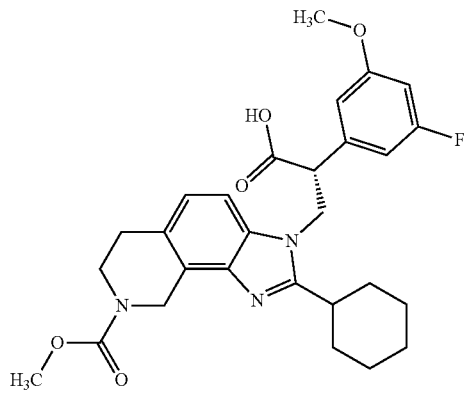 [SMILES: COC(=O)N1CCc2ccc3c(nc(C4CCCCC4)n3C[C@H](C(=O)O)c3cc(F)cc(OC)c3)c2C1] |

(Currently amended) A compound or a pharmaceutically acceptable salt thereof, wherein the compound is selected from

| Compound No. | Structure |
|---|---|
| 11 | 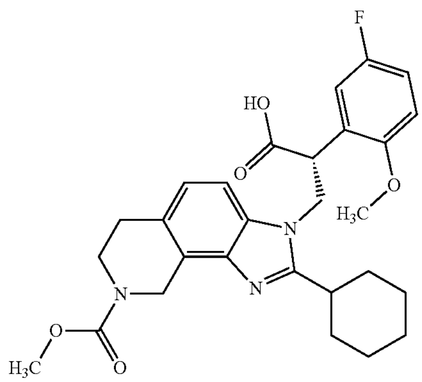 [SMILES: COC(=O)N1CCc2ccc3c(nc(C4CCCCC4)n3C[C@H](C(=O)O)c3cc(F)ccc3OC)c2C1] |
| 12 | 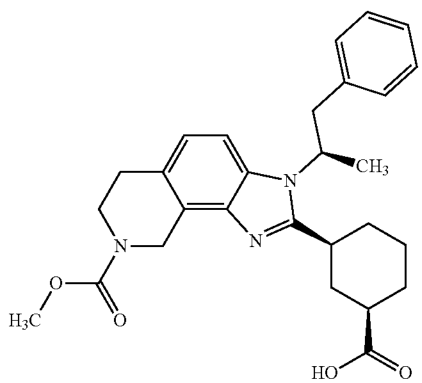 [SMILES: COC(=O)N1CCc2ccc3c(nc([C@H]4CCC[C@@H](C(=O)O)C4)n3[C@H](C)Cc3ccccc3)c2C1] |
| 13 | 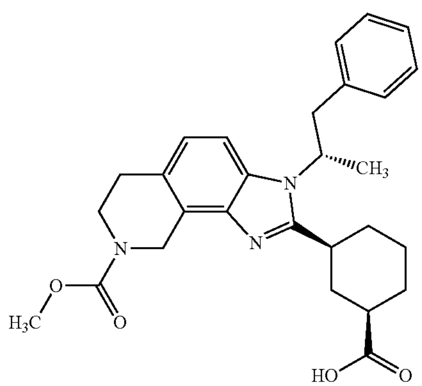 [SMILES: COC(=O)N1CCc2ccc3c(nc([C@H]4CCC[C@@H](C(=O)O)C4)n3[C@@H](C)Cc3ccccc3)c2C1] |
| 14 | 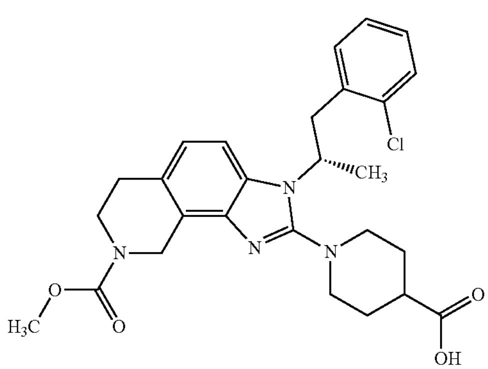 |

(Currently amended) A compound or a pharmaceutically acceptable salt thereof, wherein the compound is selected from
| Compound No. | Structure |
|---|---|
| 15 | 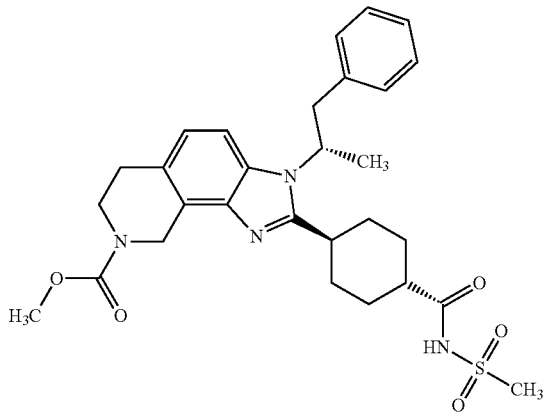 |
| 16 | 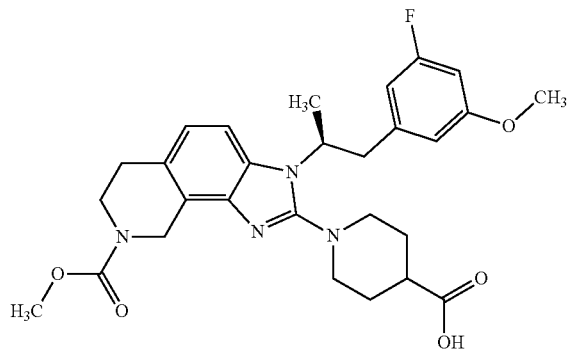 |
| 17 | 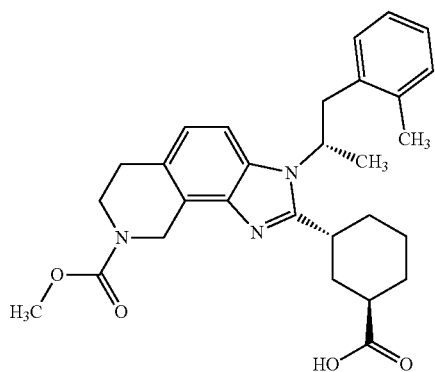 |
| 18 | 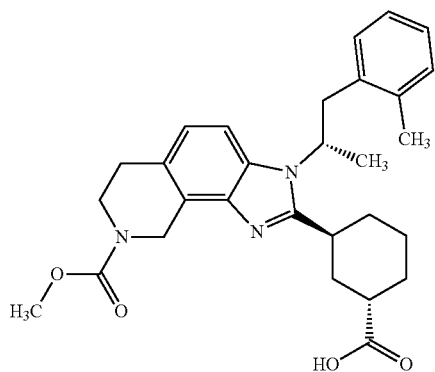 [SMILES: COC(=O)N1CCc2ccc3c(nc([C@H]4CCC[C@H](C(=O)O)C4)n3[C@@H](C)Cc3ccccc3C)c2C1] |

(Currently amended) A compound or a pharmaceutically acceptable salt thereof, wherein the compound is selected from
| Compound No. | Structure |
|---|---|
| 19 | 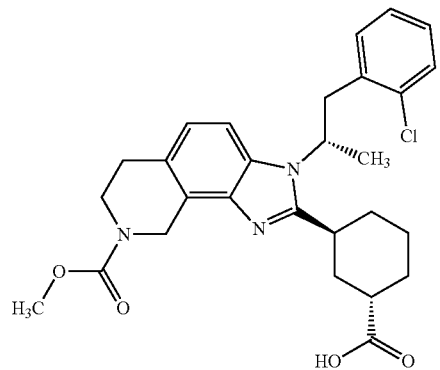 |
| 20 | 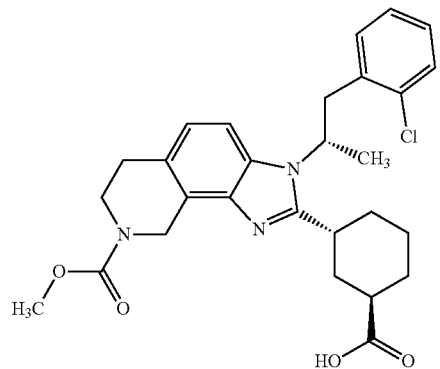 [SMILES: COC(=O)N1CCc2ccc3c(nc([C@@H]4CCC[C@@H](C(=O)O)C4)n3[C@@H](C)Cc3ccccc3Cl)c2C1] |
| 21 | 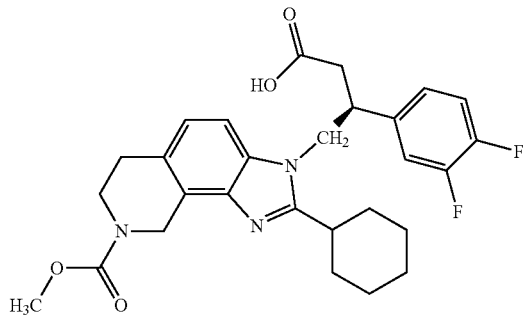 [SMILES: COC(=O)N1CCc2ccc3c(nc(C4CCCCC4)n3C[C@@H](CC(=O)O)c3ccc(F)c(F)c3)c2C1] |
| 22 | 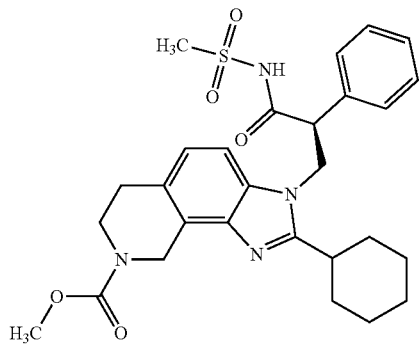 [SMILES: COC(=O)N1CCc2ccc3c(nc(C4CCCCC4)n3C[C@@H](C(=O)NS(C)(=O)=O)c3ccccc3)c2C1] |

(Currently amended) A compound or a pharmaceutically acceptable salt thereof, wherein the compound is selected from
| Compound No. | Structure |
|---|---|
| 23 | 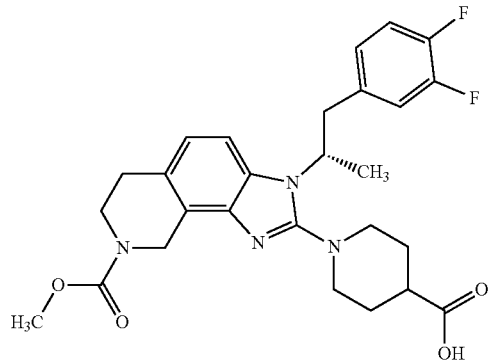 [SMILES: COC(=O)N1CCc2ccc3c(nc(N4CCC(C(=O)O)CC4)n3[C@@H](C)Cc3ccc(F)c(F)c3)c2C1] |
| 24 | 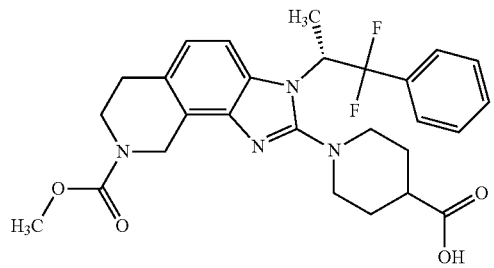 [SMILES: COC(=O)N1CCc2ccc3c(nc(N4CCC(C(=O)O)CC4)n3[C@H](C)C(F)(F)c3ccccc3)c2C1] |
| 25 | 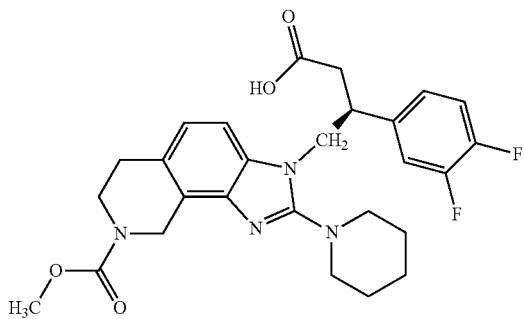 |
| 26 | 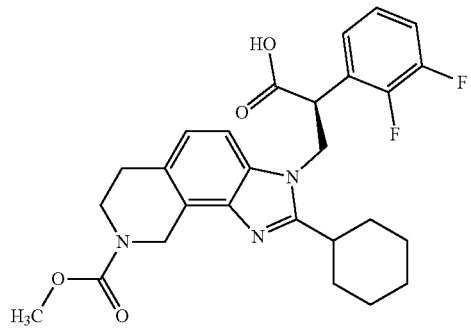 [SMILES: COC(=O)N1CCc2ccc3c(nc(C4CCCCC4)n3C[C@@H](C(=O)O)c3cccc(F)c3F)c2C1] |

-continued
(Currently amended) A compound or a pharmaceutically acceptable salt thereof, wherein the compound is selected from
| Compound No. | Structure |
|---|---|
| 27 | 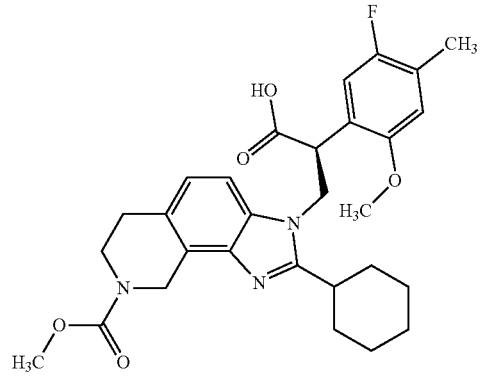 |
| 28 | 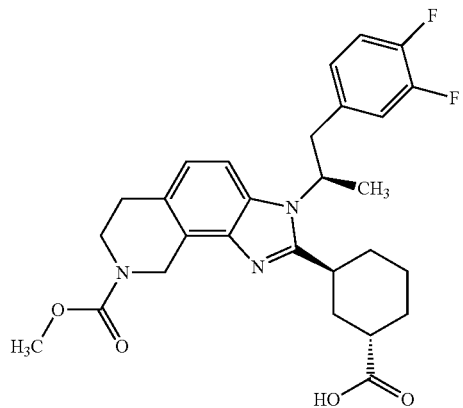 [SMILES: COC(=O)N1CCc2ccc3c(nc([C@H]4CCC[C@H](C(=O)O)C4)n3[C@H](C)Cc3ccc(F)c(F)c3)c2C1] |
| 29 | 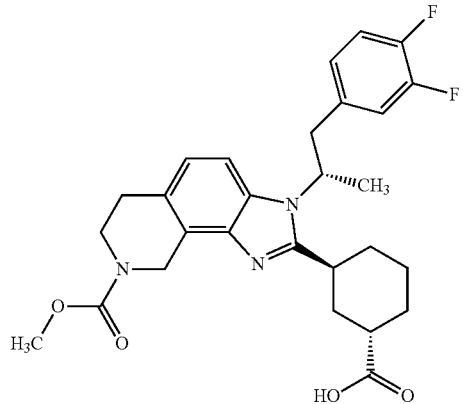 [SMILES: COC(=O)N1CCc2ccc3c(nc([C@H]4CCC[C@H](C(=O)O)C4)n3[C@@H](C)Cc3ccc(F)c(F)c3)c2C1] |

-continued
(Currently amended) A compound or a pharmaceutically acceptable salt thereof, wherein the compound is selected from
| Compound No. | Structure |
|---|---|
| 30 | 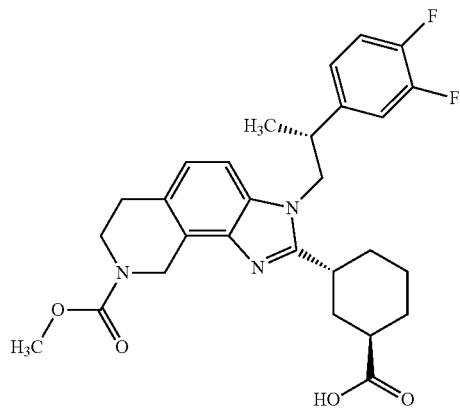 [SMILES: COC(=O)N1CCc2ccc3c(nc([C@@H]4CCC[C@@H](C(=O)O)C4)n3C[C@H](C)c3ccc(F)c(F)c3)c2C1] |
| 31 | 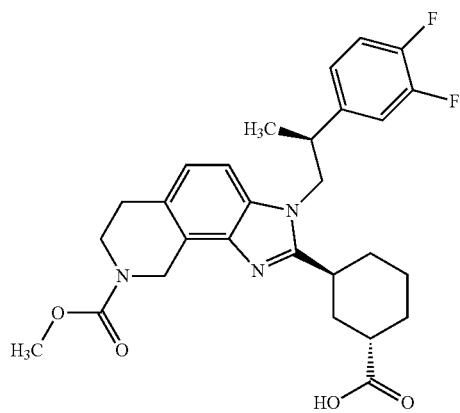 [SMILES: COC(=O)N1CCc2ccc3c(nc([C@H]4CCC[C@H](C(=O)O)C4)n3C[C@@H](C)c3ccc(F)c(F)c3)c2C1] |
| 32 | 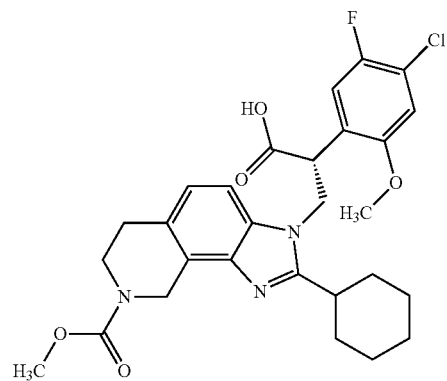 [SMILES: COC(=O)N1CCc2ccc3c(nc(C4CCCCC4)n3C[C@H](C(=O)O)c3cc(F)c(Cl)cc3OC)c2C1] |
| 33 | 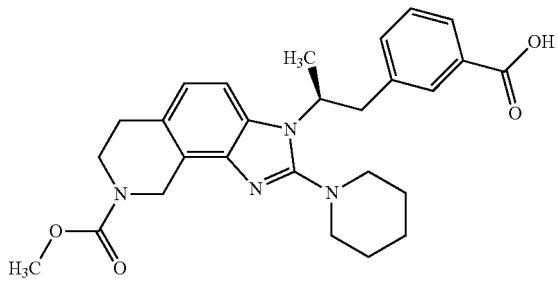 [SMILES: COC(=O)N1CCc2ccc3c(nc(N4CCCCC4)n3[C@@H](C)Cc3cccc(C(=O)O)c3)c2C1] |

-continued
(Currently amended) A compound or a pharmaceutically acceptable salt thereof, wherein the compound is selected from
| Compound No. | Structure |
|---|---|
| 34 | 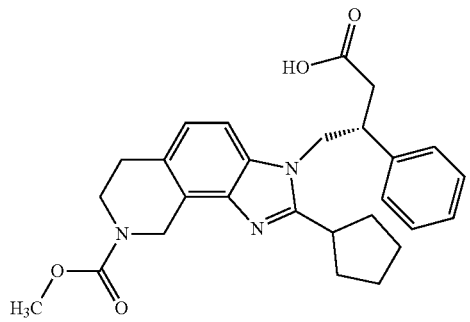 [SMILES: COC(=O)N1CCc2ccc3c(nc(C4CCCC4)n3C[C@H](CC(=O)O)c3ccccc3)c2C1] |
| 35 | 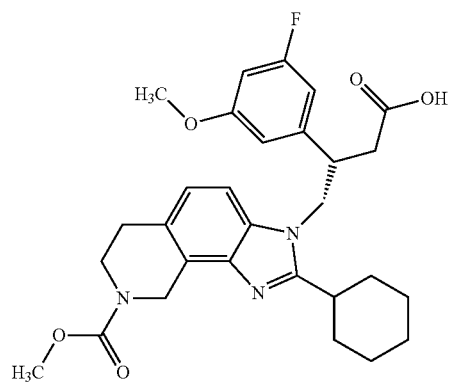 |
| 36 | 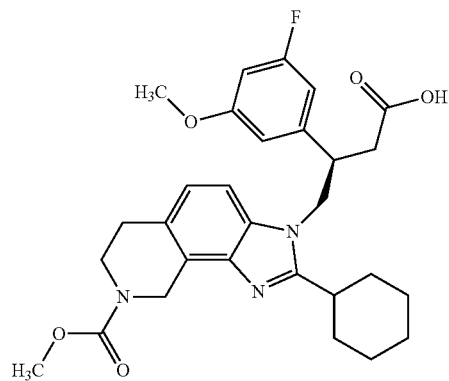 [SMILES: COC(=O)N1CCc2ccc3c(nc(C4CCCCC4)n3C[C@H](CC(=O)O)c3cc(F)cc(OC)c3)c2C1] |
| 37 | 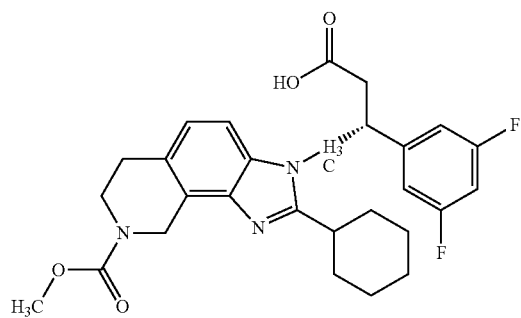 [SMILES: COC(=O)N1CCc2ccc3c(nc(C4CCCCC4)n3C[C@H](CC(=O)O)c3cc(F)cc(F)c3)c2C1] |

-continued
(Currently amended) A compound or a pharmaceutically acceptable salt thereof, wherein the compound is selected from
| Compound No. | Structure |
|---|---|
| 38 | 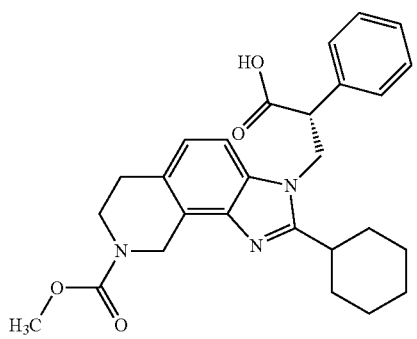 [SMILES: COC(=O)N1CCc2ccc3c(nc(C4CCCCC4)n3C[C@H](C(=O)O)c3ccccc3)c2C1] |
| 39 | 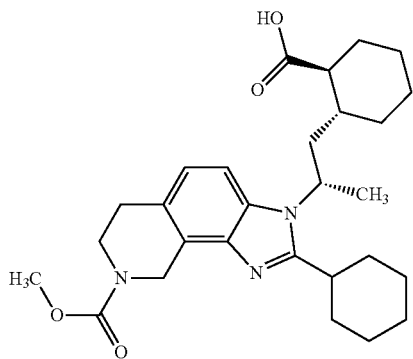 [SMILES: COC(=O)N1CCc2ccc3c(nc(C4CCCCC4)n3[C@@H](C)C[C@H]3CCCC[C@@H]3C(=O)O)c2C1] |
| 40 | 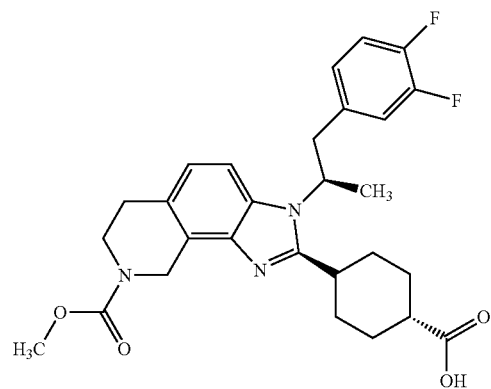 |
| 41 | 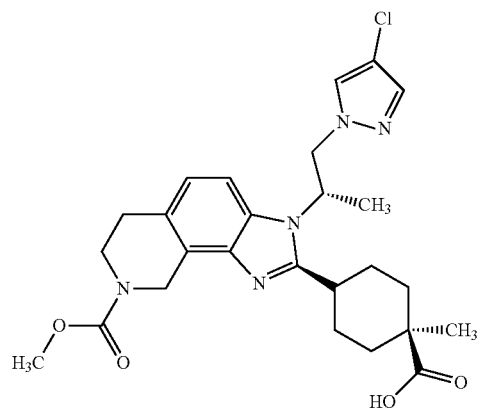 |

315
-continued
(Currently amended) A compound or a pharmaceutically acceptable salt thereof, wherein the compound is selected from
| Compound No. | Structure |
|---|---|
| 42 | 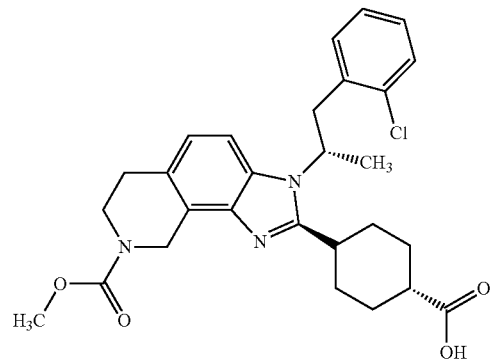 |
| 43 | 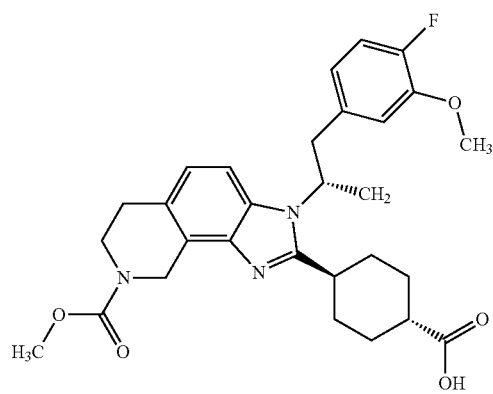 [SMILES: COC(=O)N1CCc2ccc3c(nc([C@H]4CC[C@H](C(=O)O)CC4)n3[C@@H](C)Cc3ccc(F)c(OC)c3)c2C1] |
| 44 | 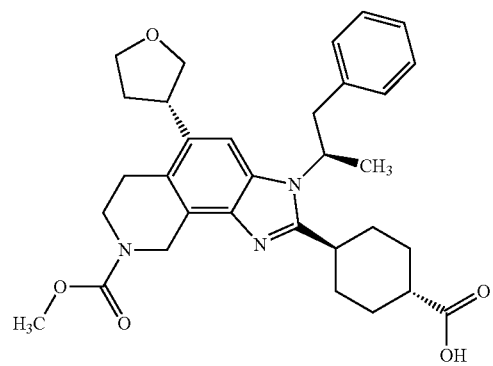 [SMILES: COC(=O)N1CCc2c([C@@H]3CCOC3)cc3c(nc([C@H]4CC[C@H](C(=O)O)CC4)n3[C@H](C)Cc3ccccc3)c2C1] |
| 45 | 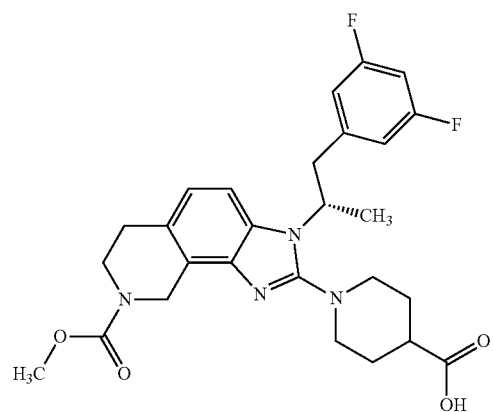 [SMILES: COC(=O)N1CCc2ccc3c(nc(N4CCC(C(=O)O)CC4)n3[C@@H](C)Cc3cc(F)cc(F)c3)c2C1] |

| Compound No. | Structure |
|---|---|
| 46 | 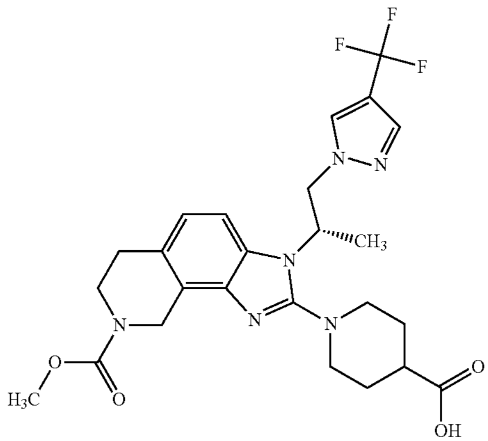 [SMILES: COC(=O)N1CCc2ccc3c(nc(N4CCC(C(=O)O)CC4)n3[C@@H](C)Cn3cc(C(F)(F)F)cn3)c2C1] |
| 47 | 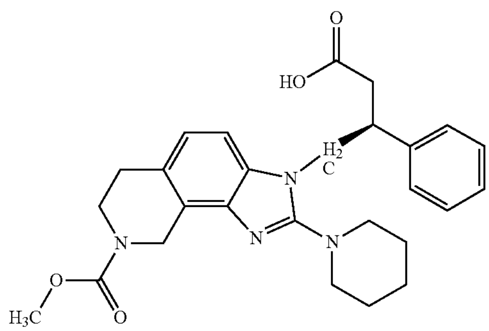 [SMILES: COC(=O)N1CCc2ccc3c(nc(N4CCCCC4)n3C[C@@H](CC(=O)O)c3ccccc3)c2C1] |
| 48 | 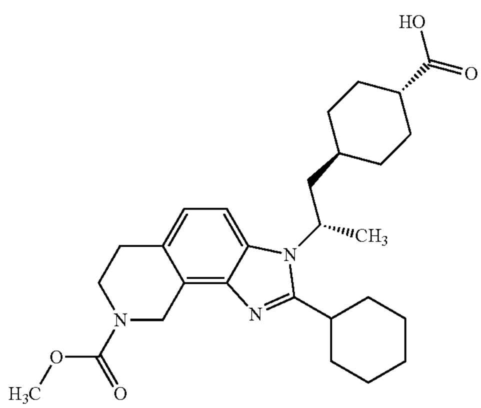 [SMILES: COC(=O)N1CCc2ccc3c(nc(C4CCCCC4)n3[C@@H](C)C[C@H]3CC[C@H](C(=O)O)CC3)c2C1] |
| 49 | 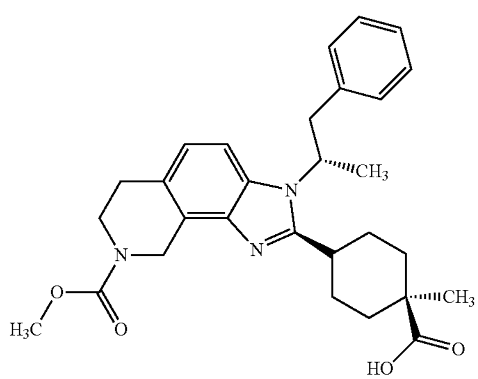 |

(Currently amended) A compound or a pharmaceutically acceptable salt thereof, wherein the compound is selected from -continued
(Currently amended) A compound or a pharmaceutically acceptable salt thereof, wherein the compound is selected from
| Compound No. | Structure |
|---|---|
| 50 | 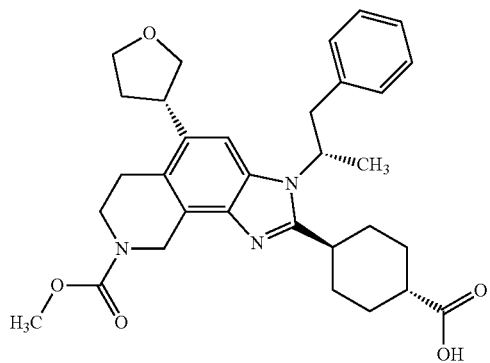 [SMILES: COC(=O)N1CCc2c([C@@H]3CCOC3)cc3c(nc([C@H]4CC[C@H](C(=O)O)CC4)n3[C@@H](C)Cc3ccccc3)c2C1] |
| 51 | 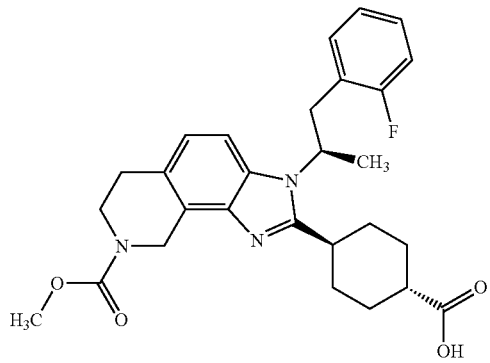 [SMILES: COC(=O)N1CCc2ccc3c(nc([C@H]4CC[C@H](C(=O)O)CC4)n3[C@H](C)Cc3ccccc3F)c2C1] |
| 52 | 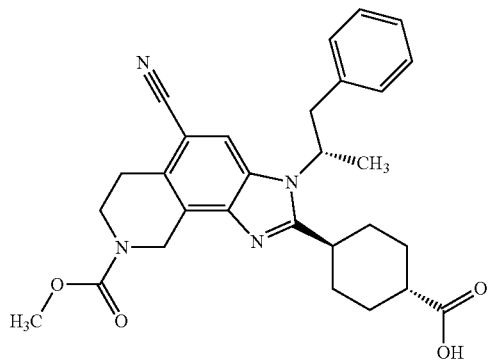 [SMILES: COC(=O)N1CCc2c(C#N)cc3c(nc([C@H]4CC[C@H](C(=O)O)CC4)n3[C@@H](C)Cc3ccccc3)c2C1] |
| 53 | 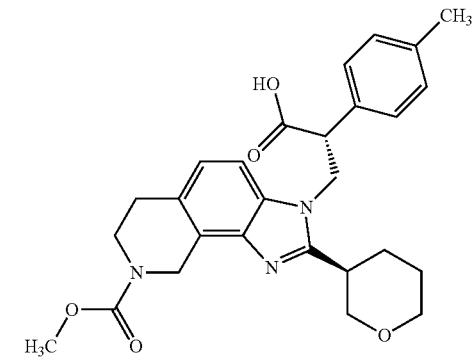 |

-continued (Currently amended) A compound or a pharmaceutically acceptable salt thereof, wherein the compound is selected from

| Compound No. | Structure |
|---|---|
| 54 | 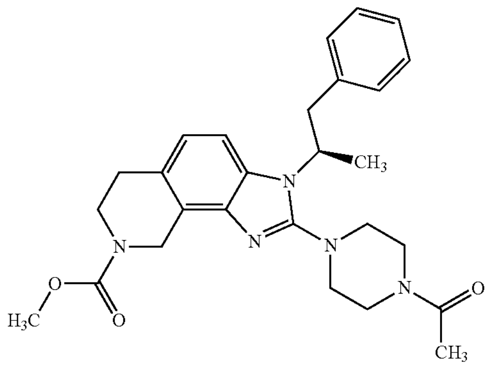 [SMILES: COC(=O)N1CCc2ccc3c(nc(N4CCN(C(C)=O)CC4)n3[C@H](C)Cc3ccccc3)c2C1] |
| 55 | 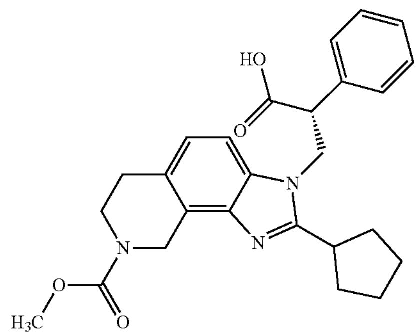 [SMILES: COC(=O)N1CCc2ccc3c(nc(C4CCCC4)n3C[C@H](C(=O)O)c3ccccc3)c2C1] |
| 56 | 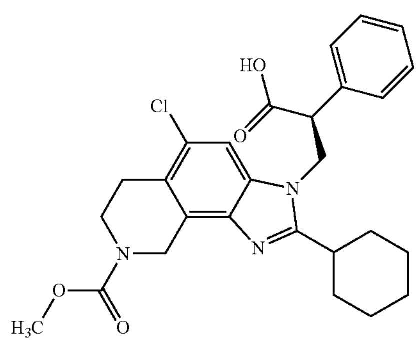 [SMILES: COC(=O)N1CCc2c(Cl)cc3c(nc(C4CCCCC4)n3C[C@@H](C(=O)O)c3ccccc3)c2C1] |
| 57 | 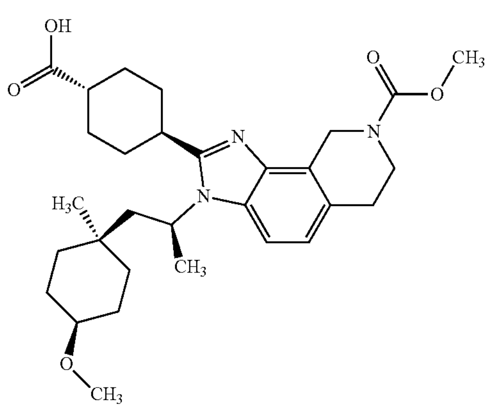 [SMILES: COC(=O)N1CCc2ccc3c(nc([C@H]4CC[C@H](C(=O)O)CC4)n3[C@@H](C)C[C@]3(C)CC[C@H](OC)CC3)c2C1] |

(Currently amended) A compound or a pharmaceutically acceptable salt thereof, wherein the compound is selected from

| Compound No. | Structure |
|---|---|
| 58 | 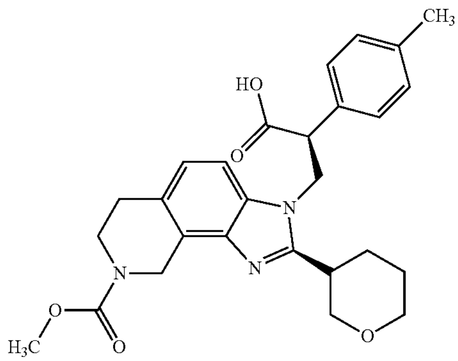 |
| 59 | 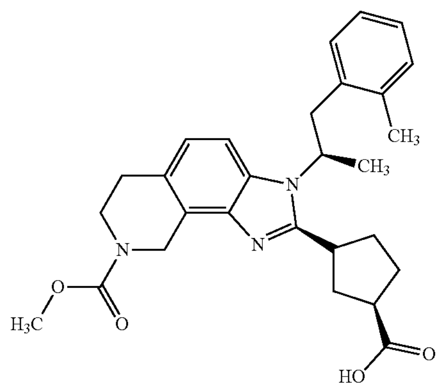 |
| 60 | 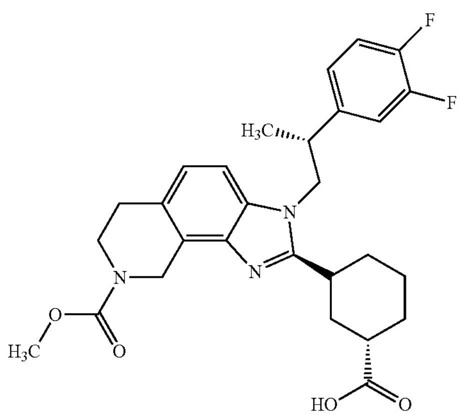 |
| 61 | 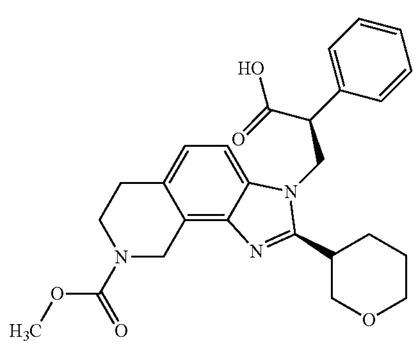 |

325
-continued
(Currently amended) A compound or a pharmaceutically acceptable salt thereof, wherein the compound is selected from
| Compound No. | Structure |
|---|---|
| 62 | 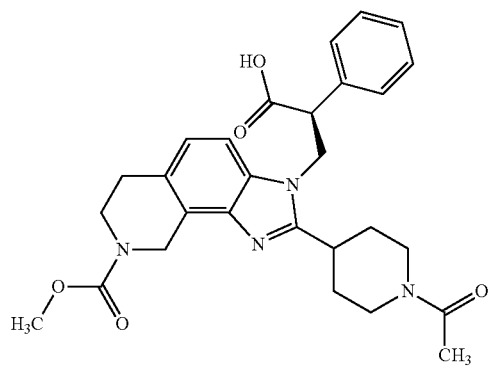 [SMILES: COC(=O)N1CCc2ccc3c(nc(C4CCN(C(C)=O)CC4)n3C[C@@H](C(=O)O)c3ccccc3)c2C1] |
| 63 | 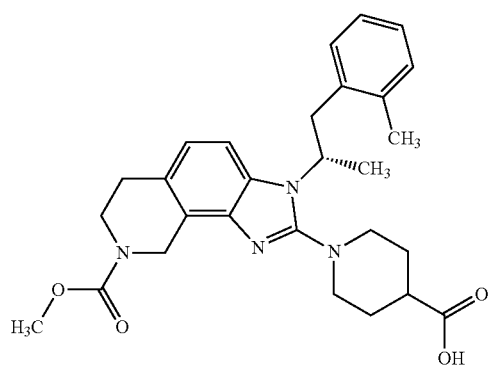 [SMILES: COC(=O)N1CCc2ccc3c(nc(N4CCC(C(=O)O)CC4)n3[C@@H](C)Cc3ccccc3C)c2C1] |
| 64 | 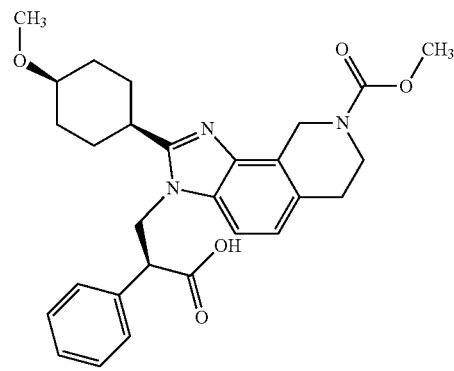 [SMILES: COC(=O)N1CCc2ccc3c(nc([C@H]4CC[C@@H](OC)CC4)n3C[C@@H](C(=O)O)c3ccccc3)c2C1] |
| 65 | 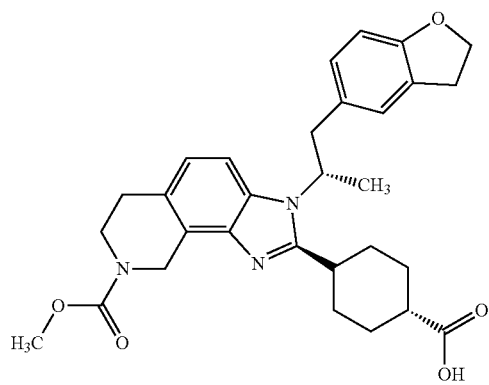 |

-continued (Currently amended) A compound or a pharmaceutically acceptable salt thereof, wherein the compound is selected from

| Compound No. | Structure |
|---|---|
| 66 | 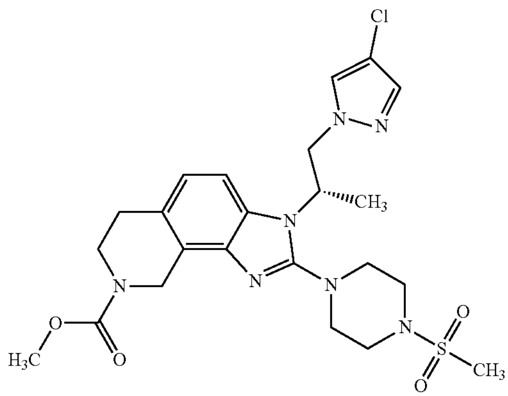 |
| 67 | 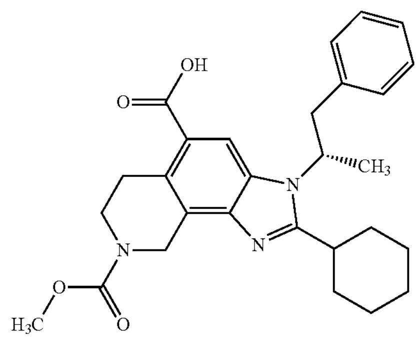 [SMILES: COC(=O)N1CCc2c(C(=O)O)cc3c(nc(C4CCCCC4)n3[C@@H](C)Cc3ccccc3)c2C1] |
| 68 | 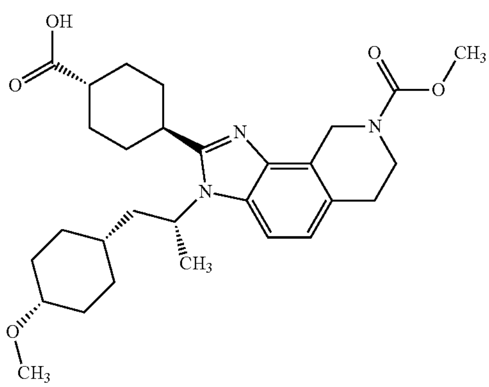 [SMILES: COC(=O)N1CCc2ccc3c(nc([C@H]4CC[C@H](C(=O)O)CC4)n3[C@H](C)C[C@H]3CC[C@@H](OC)CC3)c2C1] |
| 69 | 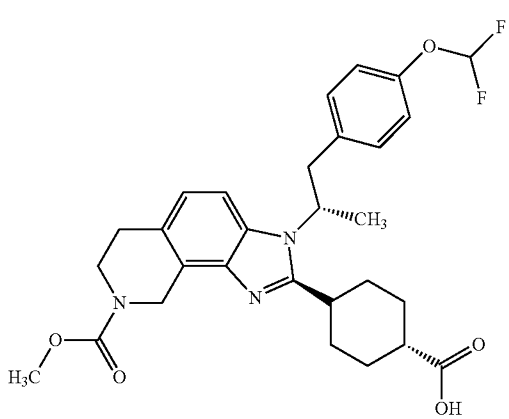 |

-continued (Currently amended) A compound or a pharmaceutically acceptable salt thereof, wherein the compound is selected from

| Compound No. | Structure |
|---|---|
| 70 | 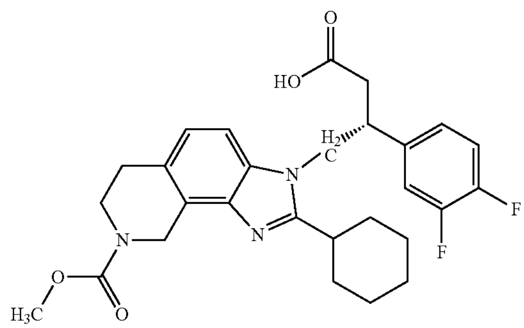 [SMILES: COC(=O)N1CCc2ccc3c(nc(C4CCCCC4)n3C[C@H](CC(=O)O)c3ccc(F)c(F)c3)c2C1] |
| 71 | 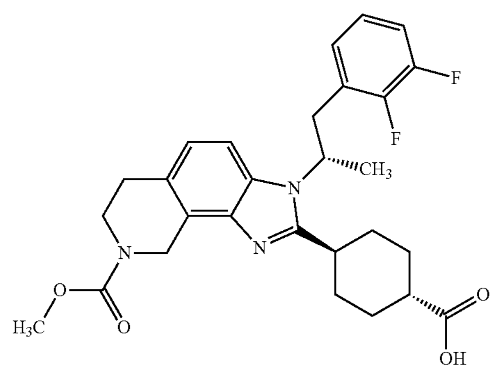 [SMILES: COC(=O)N1CCc2ccc3c(nc([C@H]4CC[C@H](C(=O)O)CC4)n3[C@@H](C)Cc3cccc(F)c3F)c2C1] |
| 72 | 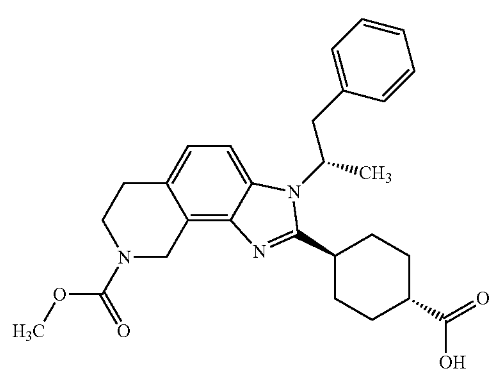 [SMILES: COC(=O)N1CCc2ccc3c(nc([C@H]4CC[C@H](C(=O)O)CC4)n3[C@@H](C)Cc3ccccc3)c2C1] |
| 73 | 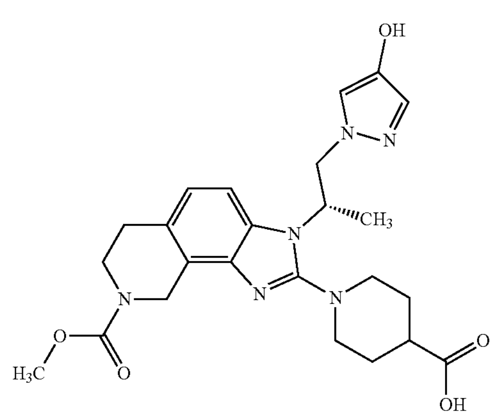 [SMILES: COC(=O)N1CCc2ccc3c(nc(N4CCC(C(=O)O)CC4)n3[C@@H](C)Cn3cc(O)cn3)c2C1] |

331
-continued
(Currently amended) A compound or a pharmaceutically acceptable salt thereof, wherein the compound is selected from
| Compound No. | Structure |
|---|---|
| 74 | 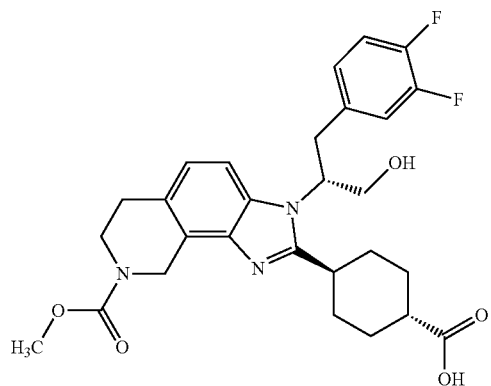 [SMILES: COC(=O)N1CCc2ccc3c(nc([C@H]4CC[C@H](C(=O)O)CC4)n3[C@@H](CO)Cc3ccc(F)c(F)c3)c2C1] |
| 75 | 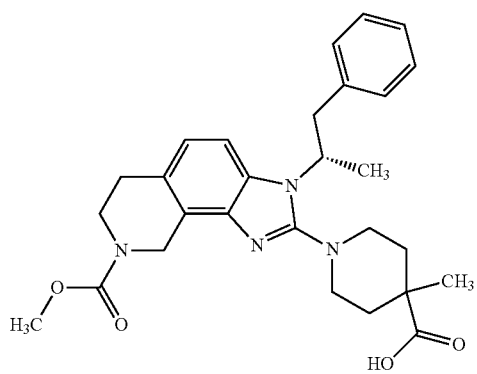 [SMILES: COC(=O)N1CCc2ccc3c(nc(N4CCC(C)(C(=O)O)CC4)n3[C@@H](C)Cc3ccccc3)c2C1] |
| 76 | 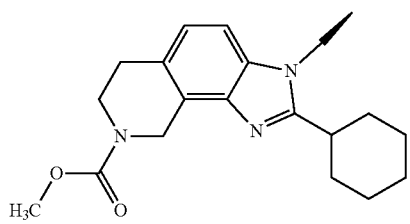 |
| 77 | 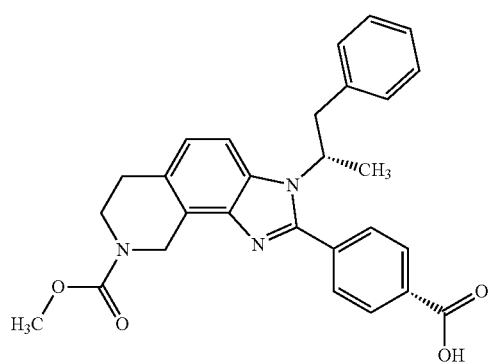 |

(Currently amended) A compound or a pharmaceutically acceptable salt thereof, wherein the compound is selected from
| Compound No. | Structure |
|---|---|
| 78 | 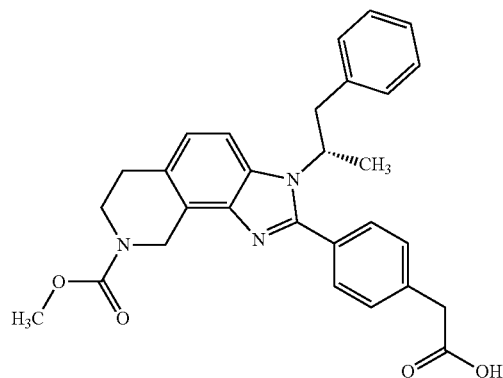 [SMILES: COC(=O)N1CCc2ccc3c(nc(-c4ccc(CC(=O)O)cc4)n3[C@@H](C)Cc3ccccc3)c2C1] |
| 79 | 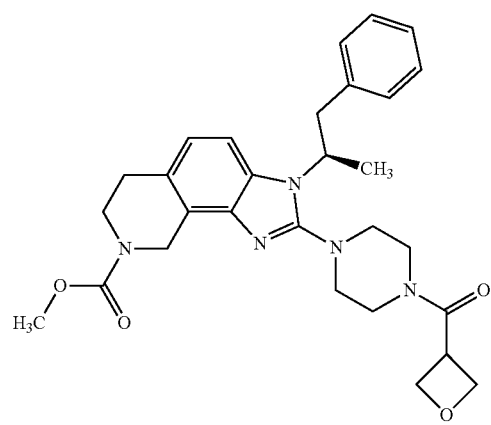 [SMILES: COC(=O)N1CCc2ccc3c(nc(N4CCN(C(=O)C5COC5)CC4)n3[C@H](C)Cc3ccccc3)c2C1] |
| 80 | 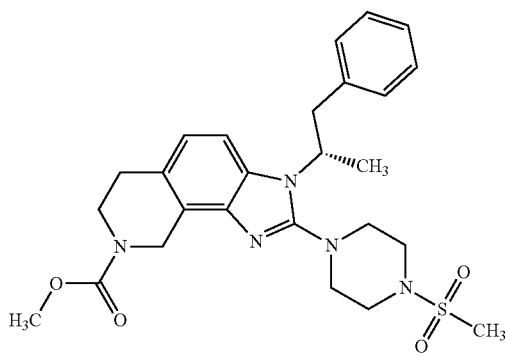 |
| 81 | 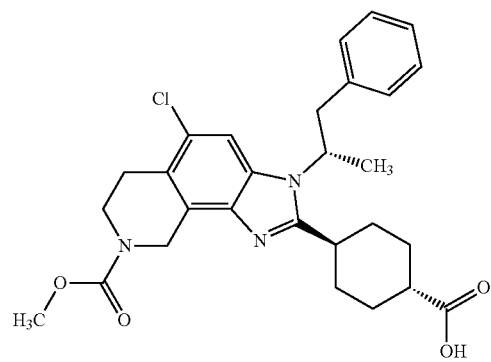 [SMILES: COC(=O)N1CCc2c(Cl)cc3c(nc([C@H]4CC[C@H](C(=O)O)CC4)n3[C@@H](C)Cc3ccccc3)c2C1] |

(Currently amended) A compound or a pharmaceutically acceptable salt thereof, wherein the compound is selected from
| Compound No. | Structure |
|---|---|
| 82 | 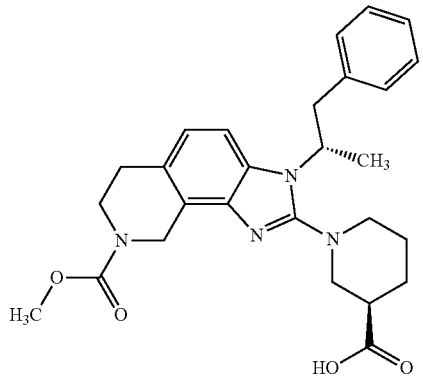 [SMILES: COC(=O)N1CCc2ccc3c(nc(N4CCC[C@@H](C(=O)O)C4)n3[C@@H](C)Cc3ccccc3)c2C1] |
| 83 | 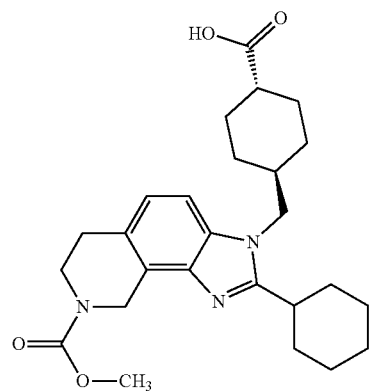 [SMILES: COC(=O)N1CCc2ccc3c(nc(C4CCCCC4)n3C[C@H]3CC[C@H](C(=O)O)CC3)c2C1] |
| 84 | 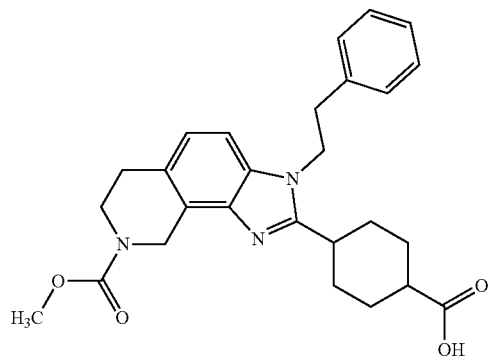 |
| 85 | 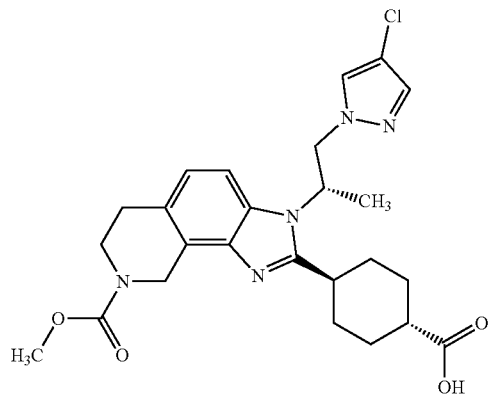 |

| Compound No. | Structure |
|---|---|
| 86 | 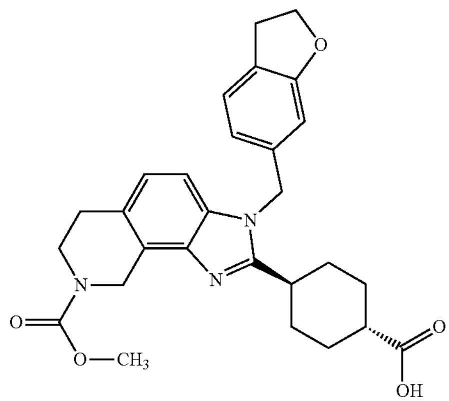 [SMILES: COC(=O)N1CCc2ccc3c(nc([C@H]4CC[C@H](C(=O)O)CC4)n3Cc3ccc4c(c3)OCC4)c2C1] |
| 87 | 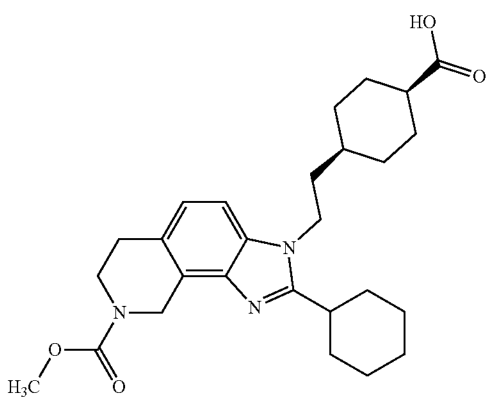 [SMILES: COC(=O)N1CCc2ccc3c(nc(C4CCCCC4)n3CC[C@H]3CC[C@@H](C(=O)O)CC3)c2C1] |
| 88 | 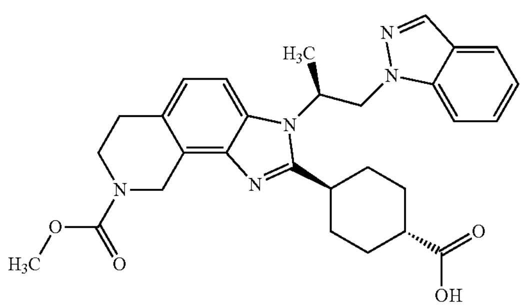 [SMILES: COC(=O)N1CCc2ccc3c(nc([C@H]4CC[C@H](C(=O)O)CC4)n3[C@@H](C)Cn3ncc4ccccc43)c2C1] |
| 89 | 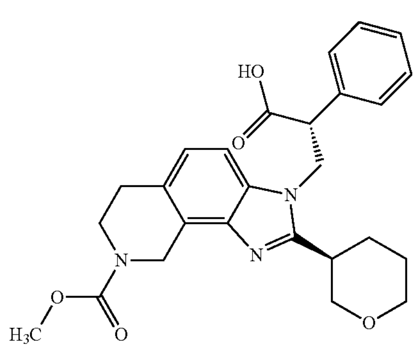 [SMILES: COC(=O)N1CCc2ccc3c(nc([C@H]4CCCOC4)n3C[C@H](C(=O)O)c3ccccc3)c2C1] |

(Currently amended) A compound or a pharmaceutically acceptable salt thereof, wherein the compound is selected from (Currently amended) A compound or a pharmaceutically acceptable salt thereof, wherein the compound is selected from
| Compound No. | Structure |
|---|---|
| 90 | 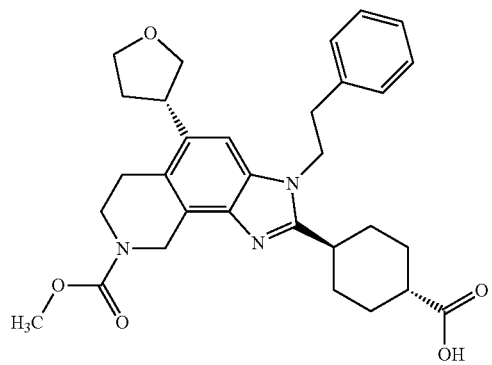 [SMILES: COC(=O)N1CCc2c([C@@H]3CCOC3)cc3c(nc([C@H]4CC[C@H](C(=O)O)CC4)n3CCc3ccccc3)c2C1] |
| 91 | 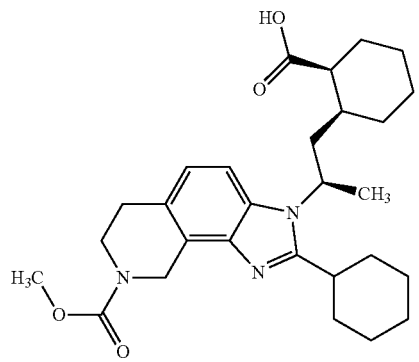 [SMILES: COC(=O)N1CCc2ccc3c(nc(C4CCCCC4)n3[C@H](C)C[C@@H]3CCCC[C@@H]3C(=O)O)c2C1] |
| 92 | 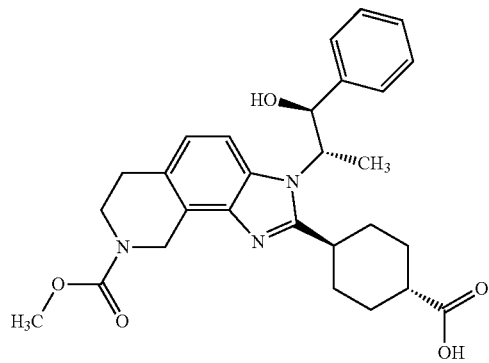 [SMILES: COC(=O)N1CCc2ccc3c(nc([C@H]4CC[C@H](C(=O)O)CC4)n3[C@@H](C)[C@@H](O)c3ccccc3)c2C1] |
| 93 | 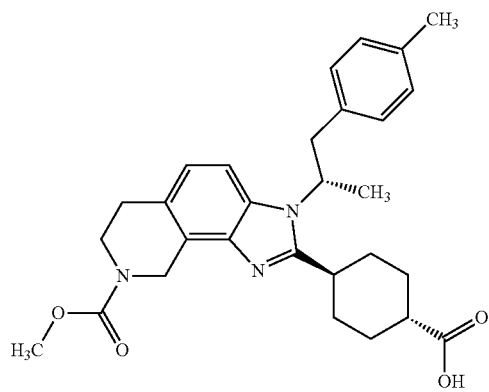 [SMILES: COC(=O)N1CCc2ccc3c(nc([C@H]4CC[C@H](C(=O)O)CC4)n3[C@@H](C)Cc3ccc(C)cc3)c2C1] |

-continued
(Currently amended) A compound or a pharmaceutically acceptable salt thereof, wherein the compound is selected from
| Compound No. | Structure |
|---|---|
| 94 | 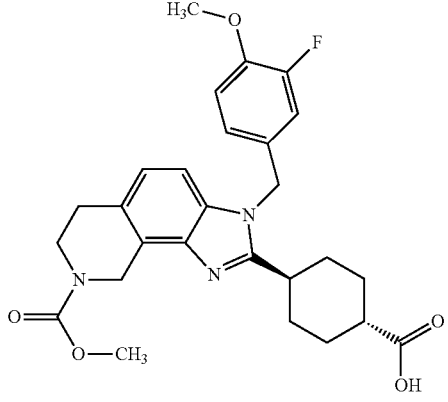 [SMILES: COC(=O)N1CCc2ccc3c(nc([C@H]4CC[C@H](C(=O)O)CC4)n3Cc3ccc(OC)c(F)c3)c2C1] |
| 95 | 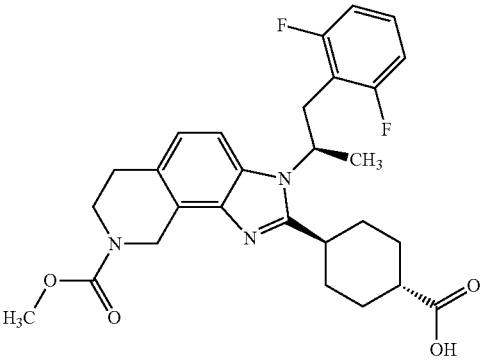 [SMILES: COC(=O)N1CCc2ccc3c(nc([C@H]4CC[C@H](C(=O)O)CC4)n3[C@H](C)Cc3c(F)cccc3F)c2C1] |
| 96 | 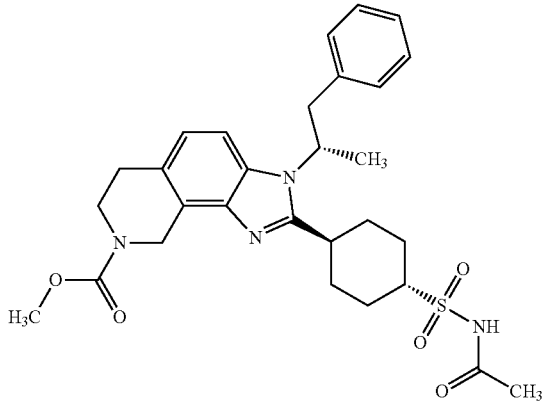 [SMILES: COC(=O)N1CCc2ccc3c(nc([C@H]4CC[C@H](S(=O)(=O)NC(C)=O)CC4)n3[C@@H](C)Cc3ccccc3)c2C1] |
| 97 | 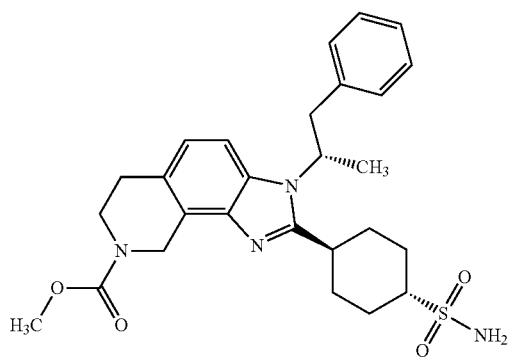 [SMILES: COC(=O)N1CCc2ccc3c(nc([C@H]4CC[C@H](S(N)(=O)=O)CC4)n3[C@@H](C)Cc3ccccc3)c2C1] |

(Currently amended) A compound or a pharmaceutically acceptable salt thereof, wherein the compound is selected from
| Compound No. | Structure |
|---|---|
| 98 | 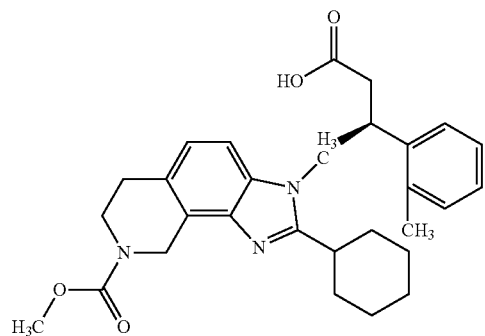 |
| 99 | 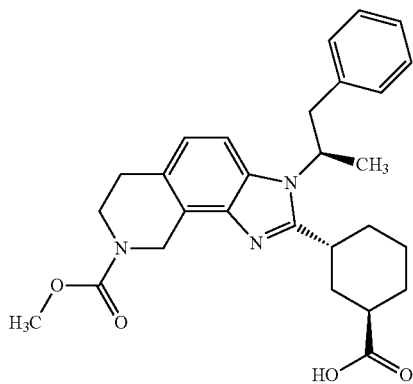 [SMILES: COC(=O)N1CCc2ccc3c(nc([C@@H]4CCC[C@@H](C(=O)O)C4)n3[C@H](C)Cc3ccccc3)c2C1] |
| 100 | 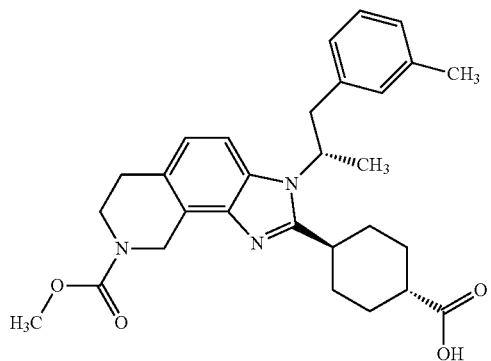 [SMILES: COC(=O)N1CCc2ccc3c(nc([C@H]4CC[C@H](C(=O)O)CC4)n3[C@@H](C)Cc3cccc(C)c3)c2C1] |
| 101 | 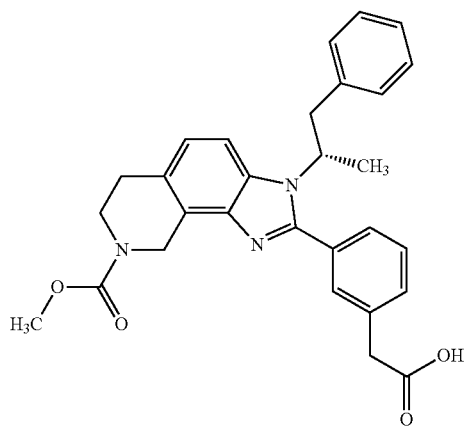 [SMILES: COC(=O)N1CCc2ccc3c(nc(-c4cccc(CC(=O)O)c4)n3[C@@H](C)Cc3ccccc3)c2C1] |

-continued
(Currently amended) A compound or a pharmaceutically acceptable salt thereof, wherein the compound is selected from
| Compound No. | Structure |
|---|---|
| 102 | 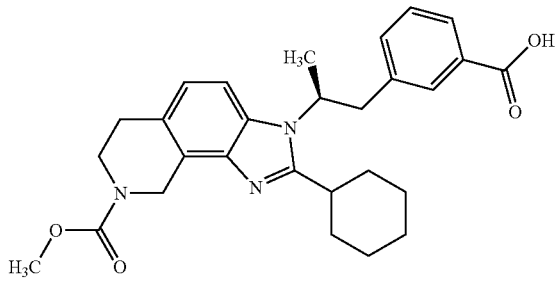 |
| 103 | 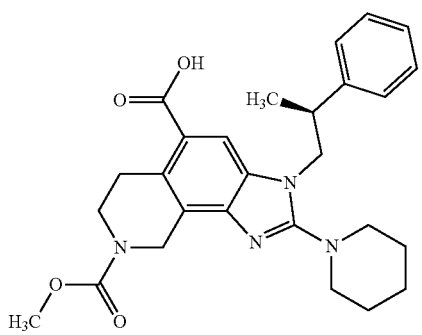 [SMILES: COC(=O)N1CCc2c(C(=O)O)cc3c(nc(N4CCCCC4)n3C[C@@H](C)c3ccccc3)c2C1] |
| 104 | 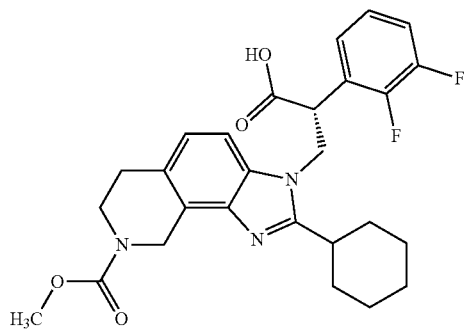 |
| 105 | 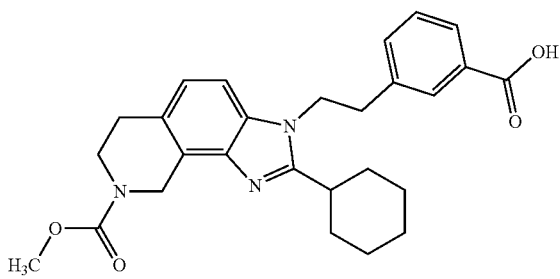 [SMILES: COC(=O)N1CCc2ccc3c(nc(C4CCCCC4)n3CCc3cccc(C(=O)O)c3)c2C1] |

-continued
(Currently amended) A compound or a pharmaceutically acceptable salt thereof, wherein the compound is selected from
| Compound No. | Structure |
|---|---|
| 106 | 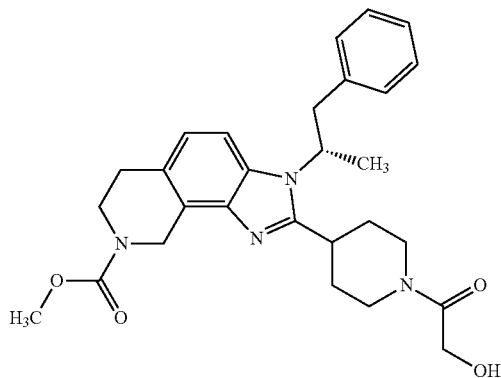 [SMILES: COC(=O)N1CCc2ccc3c(nc(C4CCN(C(=O)CO)CC4)n3[C@@H](C)Cc3ccccc3)c2C1] |
| 107 | 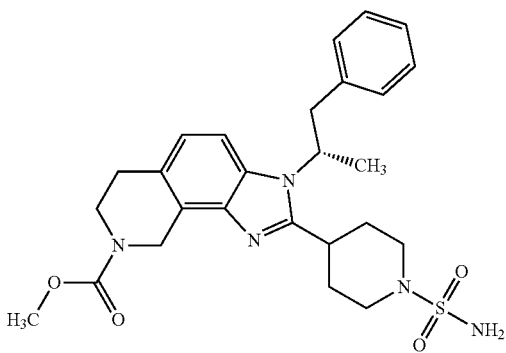 [SMILES: COC(=O)N1CCc2ccc3c(nc(C4CCN(S(N)(=O)=O)CC4)n3[C@@H](C)Cc3ccccc3)c2C1] |
| 108 | 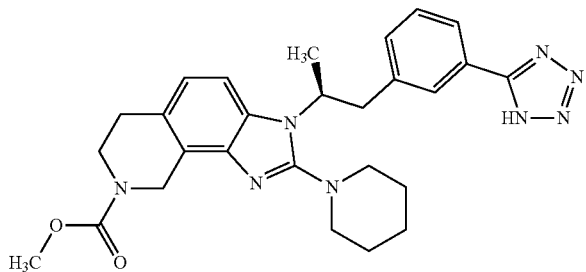 [SMILES: COC(=O)N1CCc2ccc3c(nc(N4CCCCC4)n3[C@@H](C)Cc3cccc(-c4nnn[nH]4)c3)c2C1] |
| 109 | 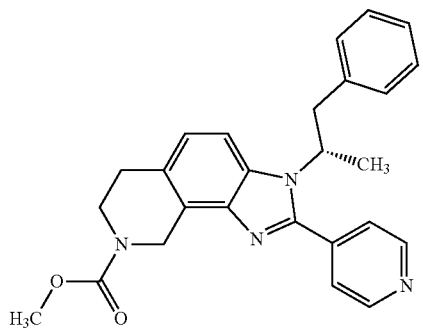 [SMILES: COC(=O)N1CCc2ccc3c(nc(-c4ccncc4)n3[C@@H](C)Cc3ccccc3)c2C1] |

(Currently amended) A compound or a pharmaceutically acceptable salt thereof, wherein the compound is selected from
| Compound No. | Structure |
|---|---|
| 110 | 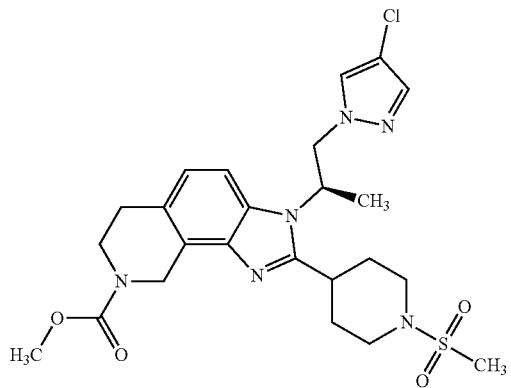 |
| 111 | 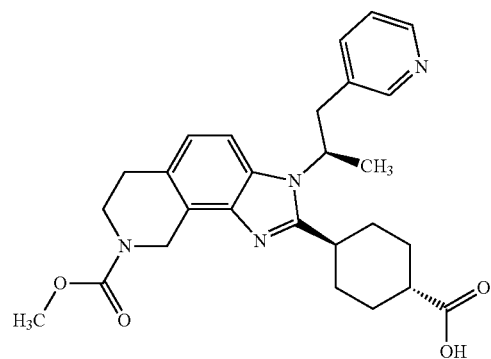 |
| 112 | 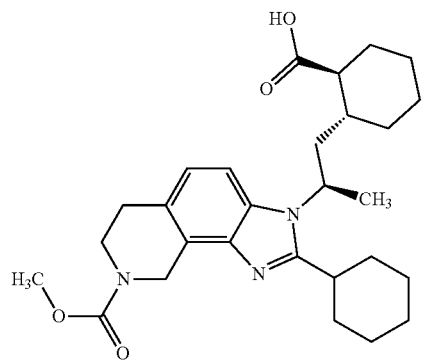 [SMILES: COC(=O)N1CCc2ccc3c(nc(C4CCCCC4)n3[C@H](C)C[C@H]3CCCC[C@@H]3C(=O)O)c2C1] |

(Currently amended) A compound or a pharmaceutically acceptable salt thereof, wherein the compound is selected from
| Compound No. | Structure |
|---|---|
| 113 | 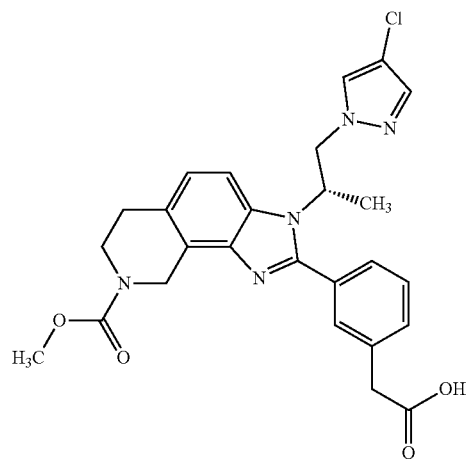 [SMILES: COC(=O)N1CCc2ccc3c(nc(-c4cccc(CC(=O)O)c4)n3[C@@H](C)Cn3cc(Cl)cn3)c2C1] |
| 114 | 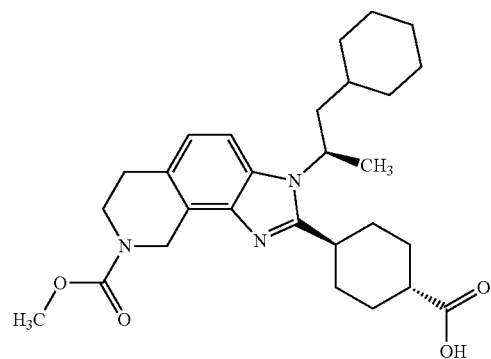 |
| 115 | 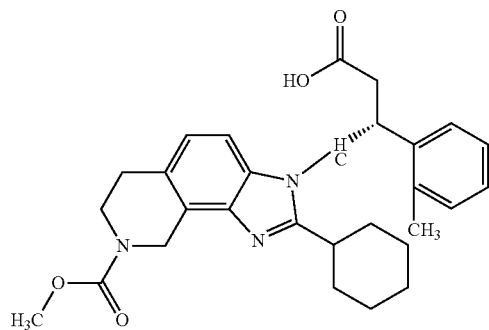 [SMILES: COC(=O)N1CCc2ccc3c(nc(C4CCCCC4)n3C[C@H](CC(=O)O)c3ccccc3C)c2C1] |

-continued (Currently amended) A compound or a pharmaceutically acceptable salt thereof, wherein the compound is selected from

| Compound No. | Structure |
|---|---|
| 116 | 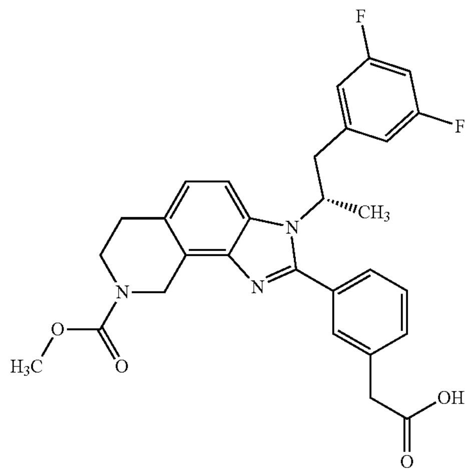 [SMILES: COC(=O)N1CCc2ccc3c(nc(-c4cccc(CC(=O)O)c4)n3[C@@H](C)Cc3cc(F)cc(F)c3)c2C1] |
| 117 | 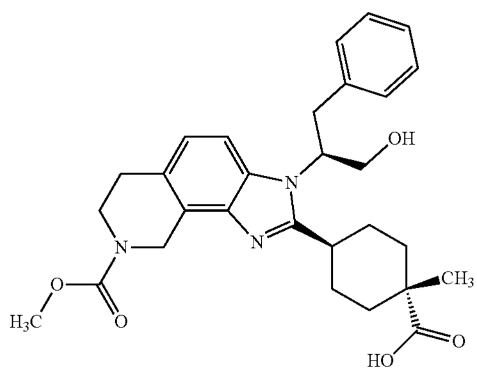 [SMILES: COC(=O)N1CCc2ccc3c(nc([C@H]4CC[C@](C)(C(=O)O)CC4)n3[C@H](CO)Cc3ccccc3)c2C1] |
| 118 | 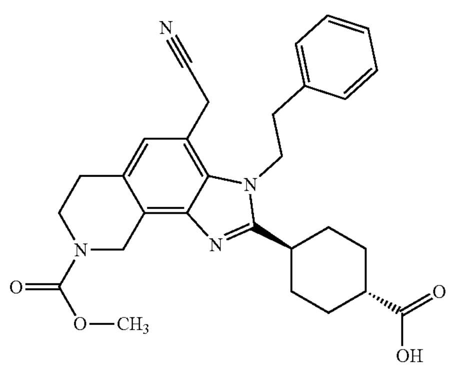 [SMILES: COC(=O)N1CCc2cc(CC#N)c3c(nc([C@H]4CC[C@H](C(=O)O)CC4)n3CCc3ccccc3)c2C1] |

| Compound No. | Structure |
|---|---|
| 119 | 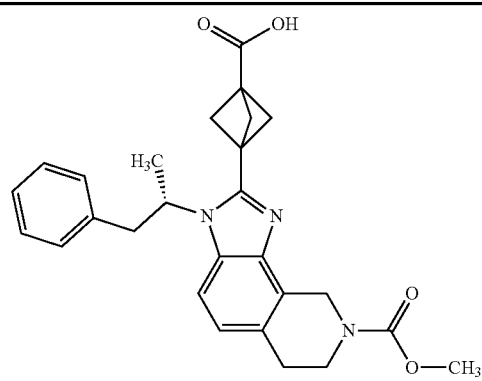 |
| 120 | 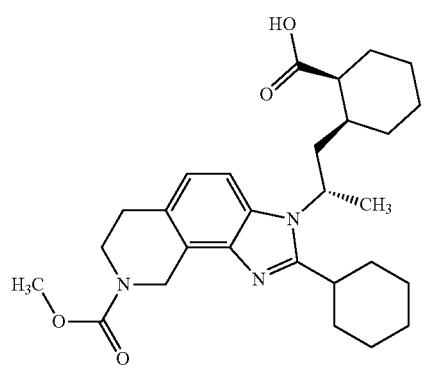 [SMILES: COC(=O)N1CCc2ccc3c(nc(C4CCCCC4)n3[C@@H](C)C[C@@H]3CCCC[C@@H]3C(=O)O)c2C1] |
| 121 | 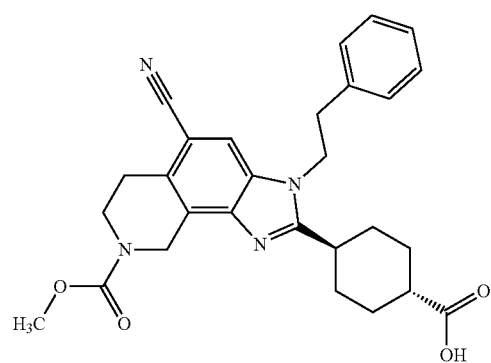 [SMILES: COC(=O)N1CCc2c(C#N)cc3c(nc([C@H]4CC[C@H](C(=O)O)CC4)n3CCc3ccccc3)c2C1] |
| 122 | 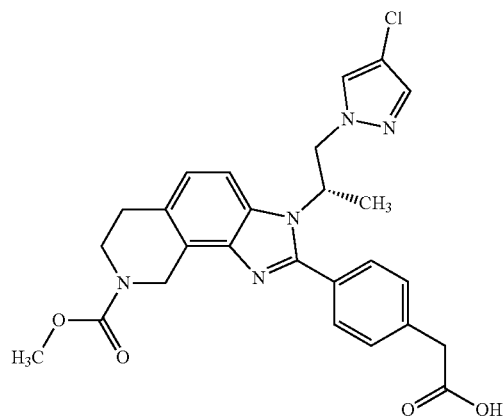 [SMILES: COC(=O)N1CCc2ccc3c(nc(-c4ccc(CC(=O)O)cc4)n3[C@@H](C)Cn3cc(Cl)cn3)c2C1] |

-continued (Currently amended) A compound or a pharmaceutically acceptable salt thereof, wherein the compound is selected from

| Compound No. | Structure |
|---|---|
| 123 | 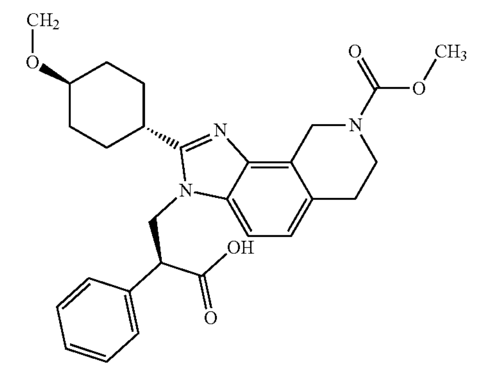 [SMILES: COC(=O)N1CCc2ccc3c(nc([C@H]4CC[C@H](OC)CC4)n3C[C@@H](C(=O)O)c3ccccc3)c2C1] |
| 124 | 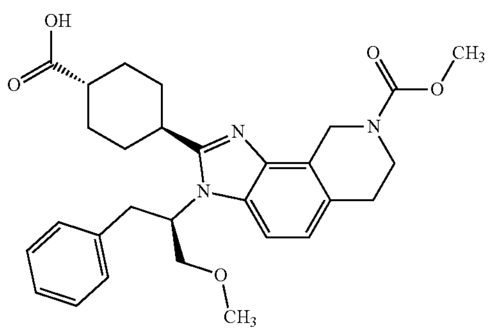 [SMILES: COC[C@@H](Cc1ccccc1)n1c2ccc3c(c2nc1[C@H]1CC[C@H](C(=O)O)CC1)CN(C(=O)OC)CC3] |
| 125 | 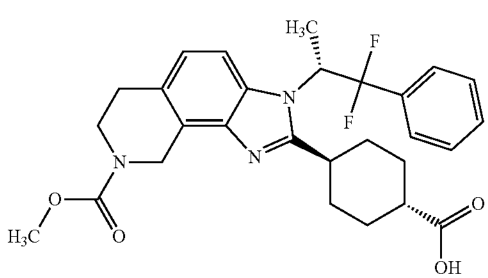 [SMILES: COC(=O)N1CCc2ccc3c(nc([C@H]4CC[C@H](C(=O)O)CC4)n3[C@H](C)C(F)(F)c3ccccc3)c2C1] |
| 126 | 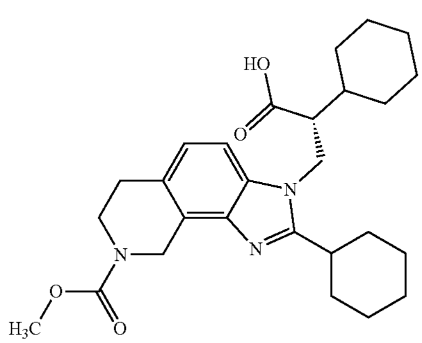 |

-continued
(Currently amended) A compound or a pharmaceutically acceptable salt thereof, wherein the compound is selected from
| Compound No. | Structure |
|---|---|
| 127 | 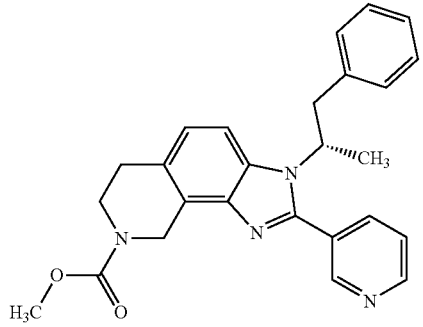 |
| 128 | 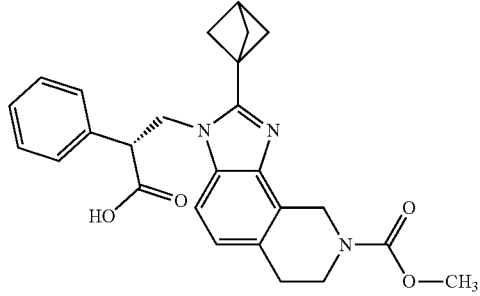 [SMILES: COC(=O)N1CCc2ccc3c(nc(C45CC(C4)C5)n3C[C@H](C(=O)O)c3ccccc3)c2C1] |
| 129 | 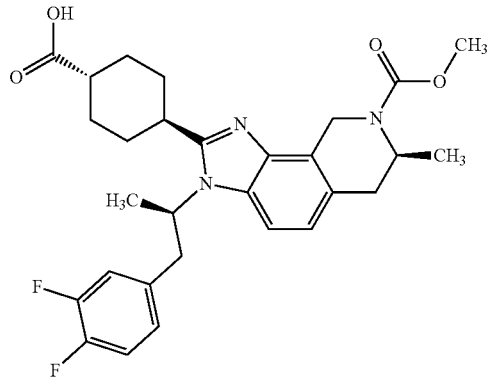 [SMILES: COC(=O)N1Cc2c(ccc3c2nc([C@H]2CC[C@H](C(=O)O)CC2)n3[C@H](C)Cc2ccc(F)c(F)c2)C[C@@H]1C] |
| 130 | 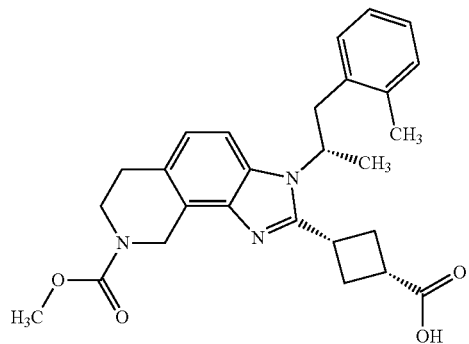 [SMILES: COC(=O)N1CCc2ccc3c(nc([C@H]4C[C@@H](C(=O)O)C4)n3[C@@H](C)Cc3ccccc3C)c2C1] |

361
-continued
(Currently amended) A compound or a pharmaceutically acceptable salt thereof, wherein the compound is selected from
| Compound No. | Structure |
|---|---|
| 131 | 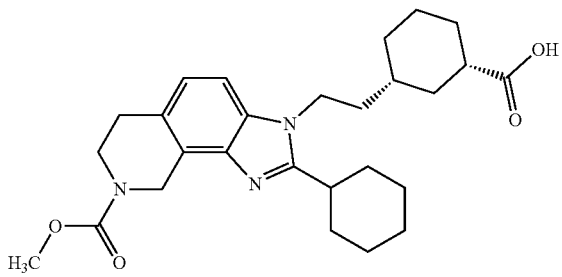 [SMILES: COC(=O)N1CCc2ccc3c(nc(C4CCCCC4)n3CC[C@@H]3CCC[C@H](C(=O)O)C3)c2C1] |
| 132 | 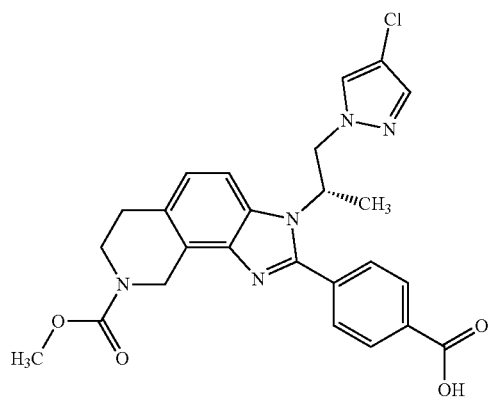 [SMILES: COC(=O)N1CCc2ccc3c(nc(-c4ccc(C(=O)O)cc4)n3[C@@H](C)Cn3cc(Cl)cn3)c2C1] |
| 133 | 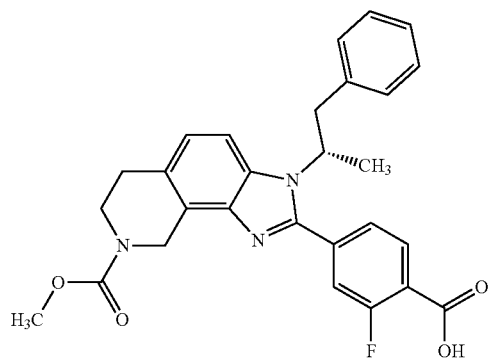 |
| 134 | 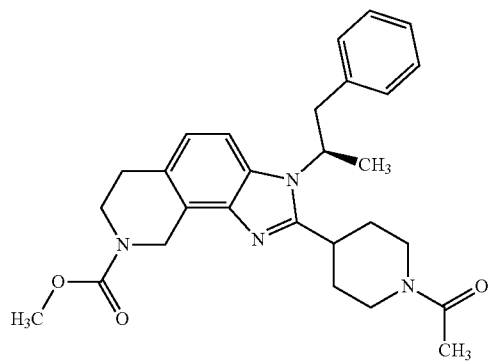 |

(Currently amended) A compound or a pharmaceutically acceptable salt thereof, wherein the compound is selected from
| Compound No. | Structure |
|---|---|
| 135 | 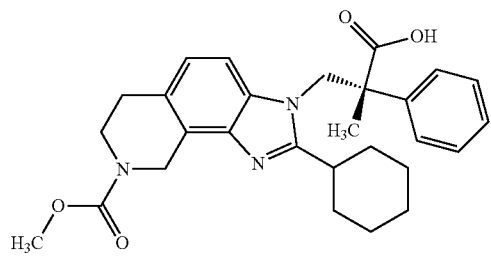 |
| 136 | 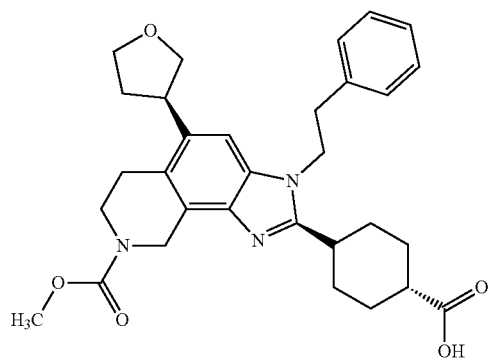 |
| 137 | 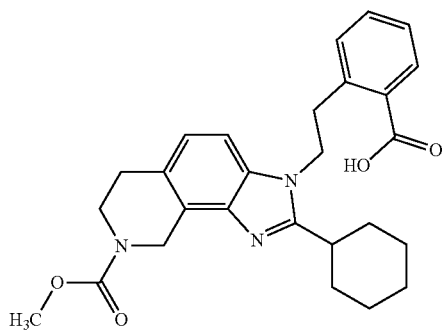 |
| 138 | 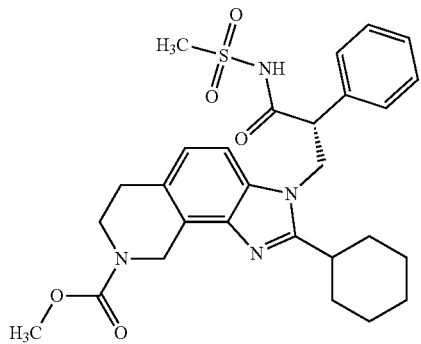 [SMILES: COC(=O)N1CCc2ccc3c(nc(C4CCCCC4)n3C[C@H](C(=O)NS(C)(=O)=O)c3ccccc3)c2C1] |

(Currently amended) A compound or a pharmaceutically acceptable salt thereof, wherein the compound is selected from

| Compound No. | Structure |
|---|---|
| 139 | 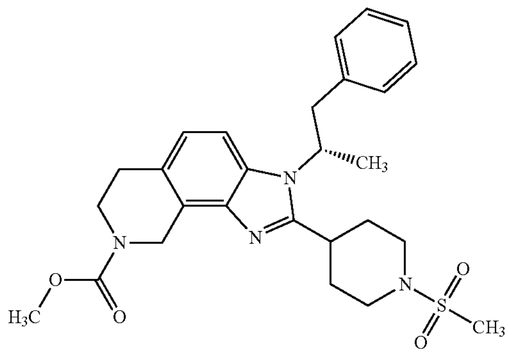 |
| 140 | 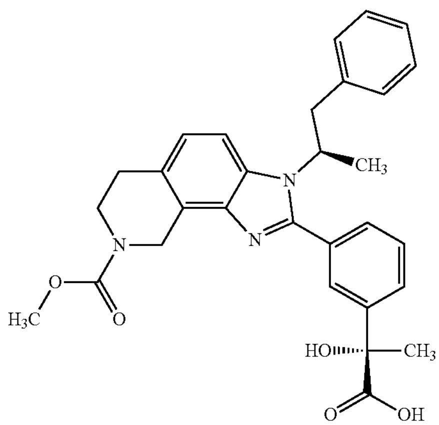 [SMILES: COC(=O)N1CCc2ccc3c(nc(-c4cccc([C@](C)(O)C(=O)O)c4)n3[C@H](C)Cc3ccccc3)c2C1] |
| 141 | 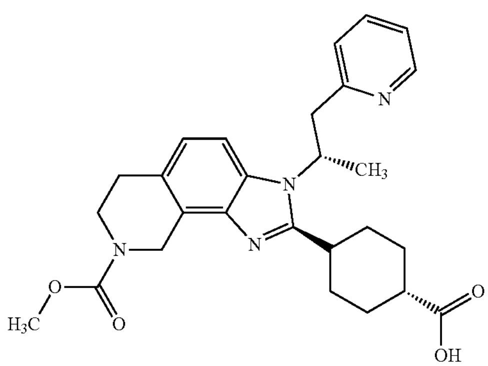 |
| 142 | 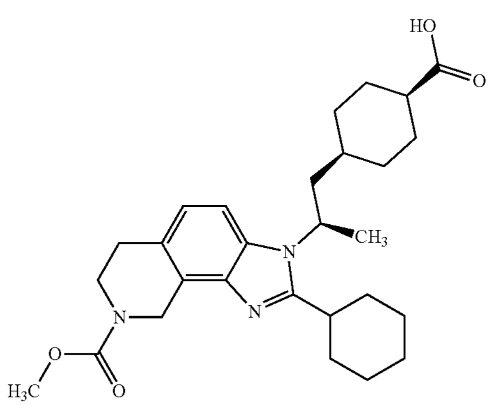 [SMILES: COC(=O)N1CCc2ccc3c(nc(C4CCCCC4)n3[C@H](C)C[C@H]3CC[C@@H](C(=O)O)CC3)c2C1] |

| (Currently amended) A compound or a pharmaceutically acceptable salt thereof, wherein the compound is selected from |  |
|---|---|
| Compound No. | Structure |
| 143 | 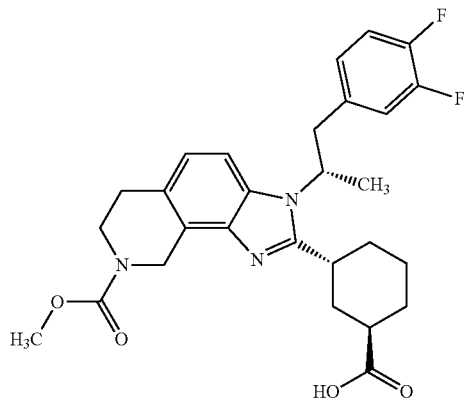 [SMILES: COC(=O)N1CCc2ccc3c(nc([C@@H]4CCC[C@@H](C(=O)O)C4)n3[C@@H](C)Cc3ccc(F)c(F)c3)c2C1] |
| 144 | 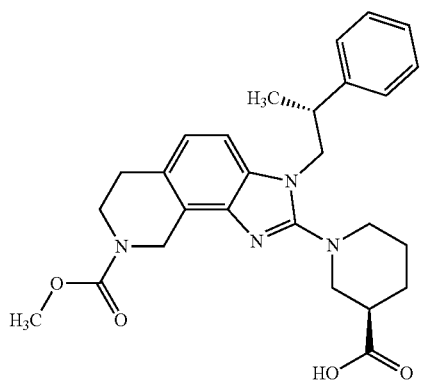 [SMILES: COC(=O)N1CCc2ccc3c(nc(N4CCC[C@@H](C(=O)O)C4)n3C[C@H](C)c3ccccc3)c2C1] |
| 145 | 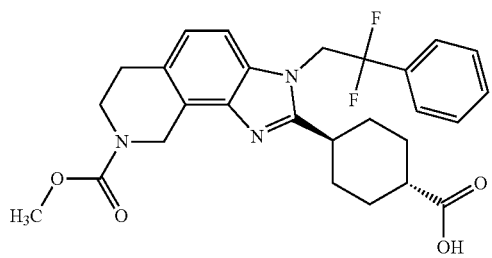 [SMILES: COC(=O)N1CCc2ccc3c(nc([C@H]4CC[C@H](C(=O)O)CC4)n3CC(F)(F)c3ccccc3)c2C1] |
| 146 | 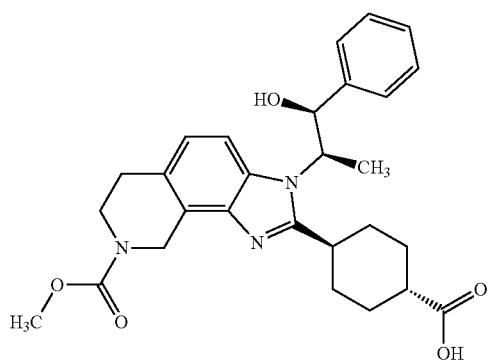 [SMILES: COC(=O)N1CCc2ccc3c(nc([C@H]4CC[C@H](C(=O)O)CC4)n3[C@H](C)[C@@H](O)c3ccccc3)c2C1] |

-continued
(Currently amended) A compound or a pharmaceutically acceptable salt thereof, wherein the compound is selected from
| Compound No. | Structure |
|---|---|
| 147 | 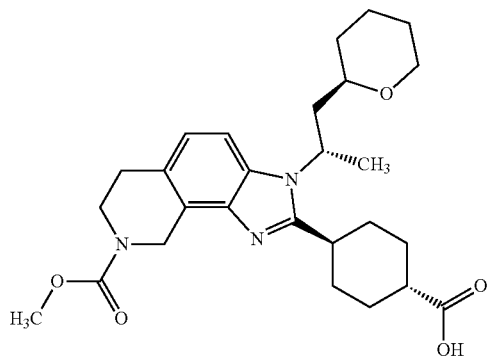 |
| 148 | 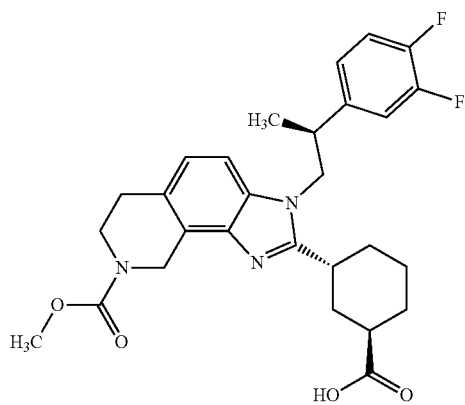 [SMILES: COC(=O)N1CCc2ccc3c(nc([C@@H]4CCC[C@@H](C(=O)O)C4)n3C[C@@H](C)c3ccc(F)c(F)c3)c2C1] |
| 149 | 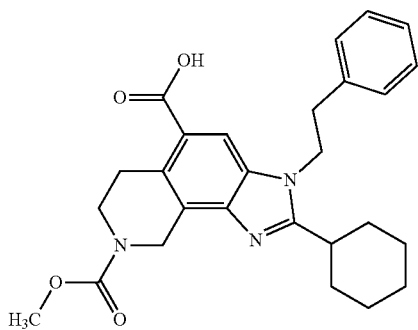 [SMILES: COC(=O)N1CCc2c(C(=O)O)cc3c(nc(C4CCCCC4)n3CCc3ccccc3)c2C1] |
| 150 | 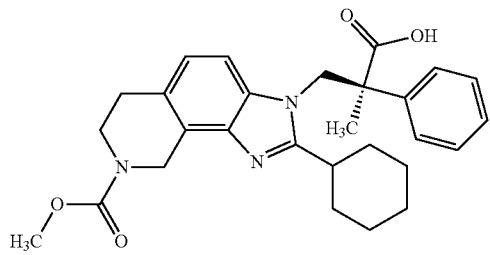 [SMILES: COC(=O)N1CCc2ccc3c(nc(C4CCCCC4)n3C[C@@](C)(C(=O)O)c3ccccc3)c2C1] |

-continued
(Currently amended) A compound or a pharmaceutically acceptable salt thereof, wherein the compound is selected from
| Compound No. | Structure |
|---|---|
| 151 | 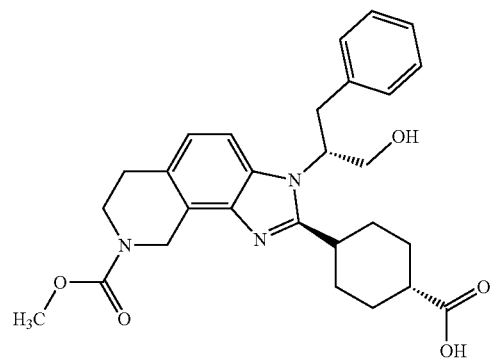 |
| 152 | 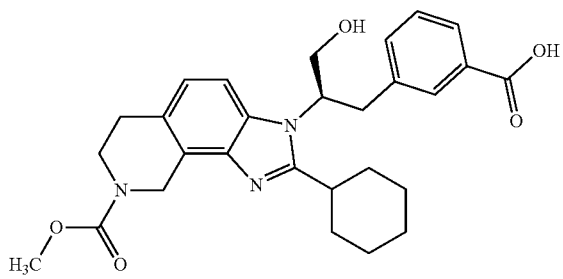 [SMILES: COC(=O)N1CCc2ccc3c(nc(C4CCCCC4)n3[C@@H](CO)Cc3cccc(C(=O)O)c3)c2C1] |
| 153 | 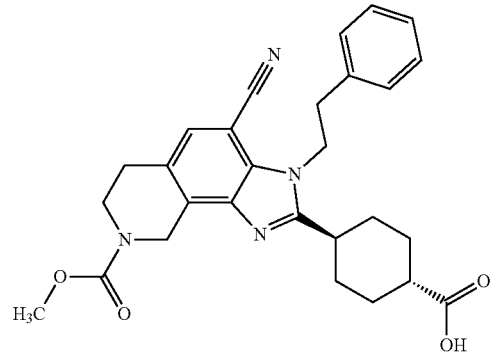 [SMILES: COC(=O)N1CCc2cc(C#N)c3c(nc([C@H]4CC[C@H](C(=O)O)CC4)n3CCc3ccccc3)c2C1] |
| 154 | 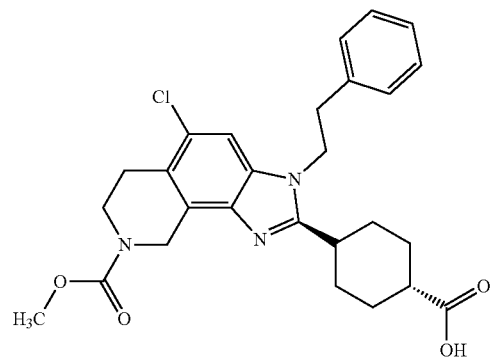 |

-continued (Currently amended) A compound or a pharmaceutically acceptable salt thereof, wherein the compound is selected from

| Compound No. | Structure |
|---|---|
| 155 | 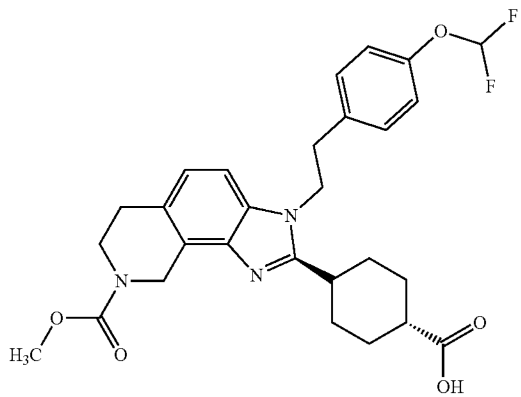 |
| 156 | 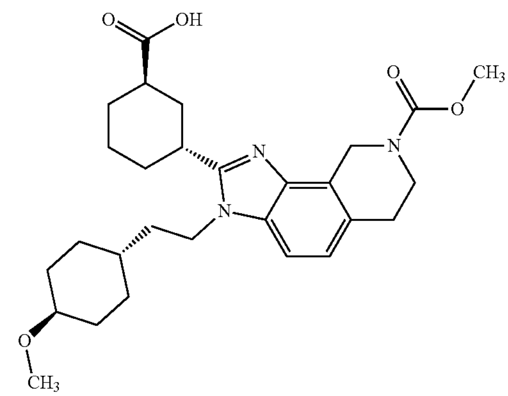 [SMILES: COC(=O)N1CCc2ccc3c(nc([C@@H]4CCC[C@@H](C(=O)O)C4)n3CC[C@H]3CC[C@H](OC)CC3)c2C1] |
| 157 | 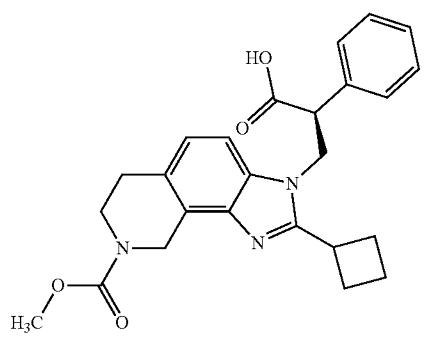 [SMILES: COC(=O)N1CCc2ccc3c(nc(C4CCC4)n3C[C@@H](C(=O)O)c3ccccc3)c2C1] |
| 158 | 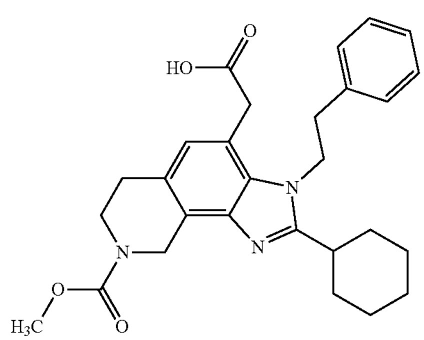 [SMILES: COC(=O)N1CCc2cc(CC(=O)O)c3c(nc(C4CCCCC4)n3CCc3ccccc3)c2C1] |

375
-continued
(Currently amended) A compound or a pharmaceutically
acceptable salt thereof, wherein the compound is selected from
| Compound No. | Structure |
|---|---|
| 159 | 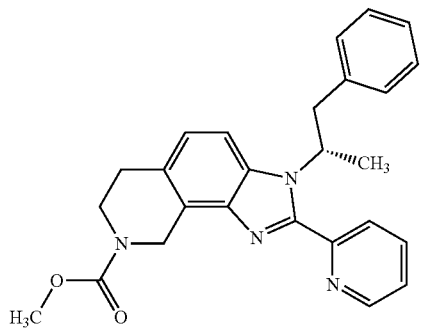 |
| 160 | 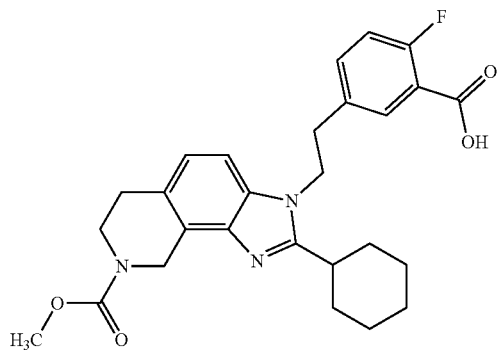 [SMILES: COC(=O)N1CCc2ccc3c(nc(C4CCCCC4)n3CCc3ccc(F)c(C(=O)O)c3)c2C1] |
| 161 | 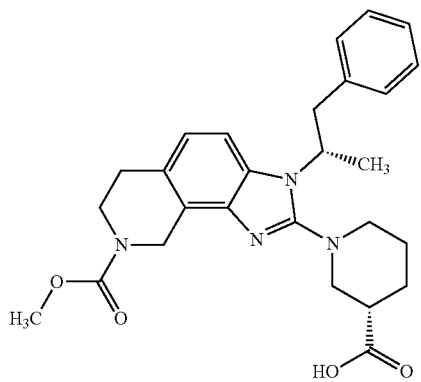 [SMILES: COC(=O)N1CCc2ccc3c(nc(N4CCC[C@H](C(=O)O)C4)n3[C@@H](C)Cc3ccccc3)c2C1] |
| 162 | 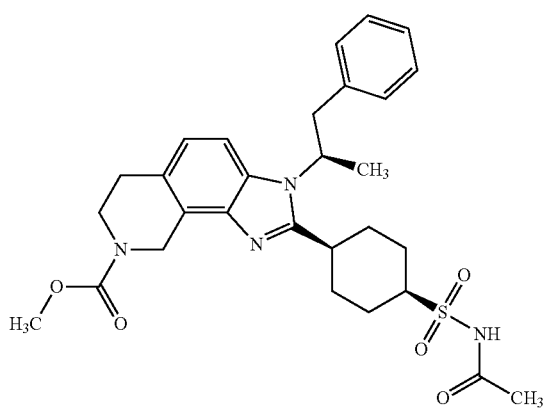 |

-continued (Currently amended) A compound or a pharmaceutically acceptable salt thereof, wherein the compound is selected from

| Compound No. | Structure |
|---|---|
| 163 | 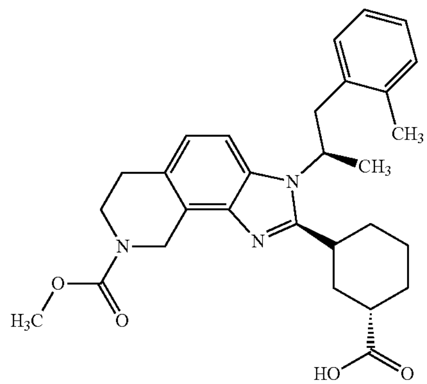 |
| 164 | 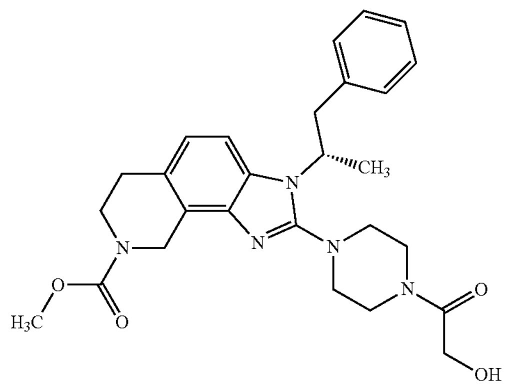 [SMILES: COC(=O)N1CCc2ccc3c(nc(N4CCN(C(=O)CO)CC4)n3[C@@H](C)Cc3ccccc3)c2C1] |
| 165 | 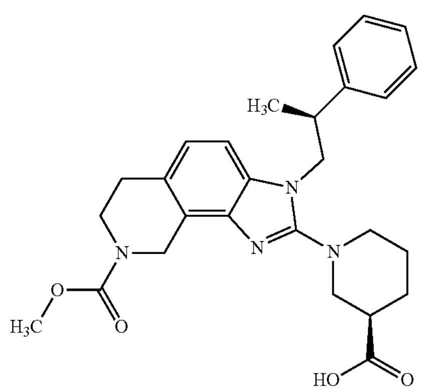 [SMILES: COC(=O)N1CCc2ccc3c(nc(N4CCC[C@@H](C(=O)O)C4)n3C[C@@H](C)c3ccccc3)c2C1] |
| 166 | 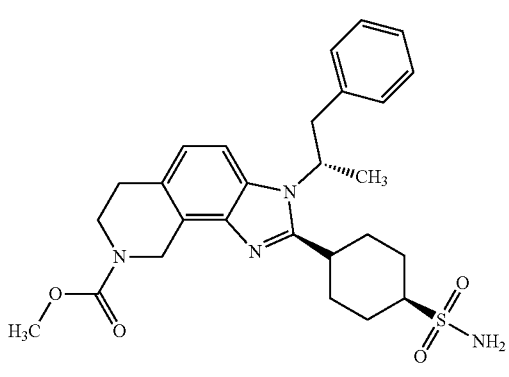 |

(Currently amended) A compound or a pharmaceutically acceptable salt thereof, wherein the compound is selected from

| Compound No. | Structure |
|---|---|
| 167 | 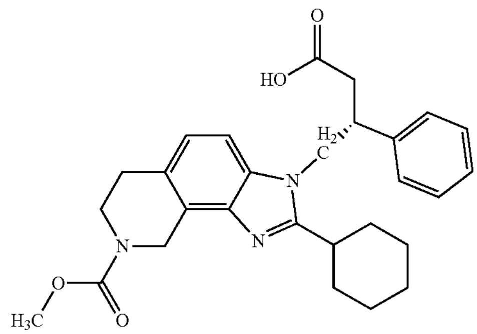 [SMILES: COC(=O)N1CCc2ccc3c(nc(C4CCCCC4)n3C[C@H](CC(=O)O)c3ccccc3)c2C1] |
| 168 | 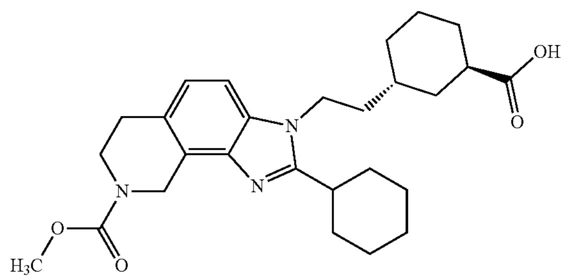 [SMILES: COC(=O)N1CCc2ccc3c(nc(C4CCCCC4)n3CC[C@@H]3CCC[C@@H](C(=O)O)C3)c2C1] |
| 169 | 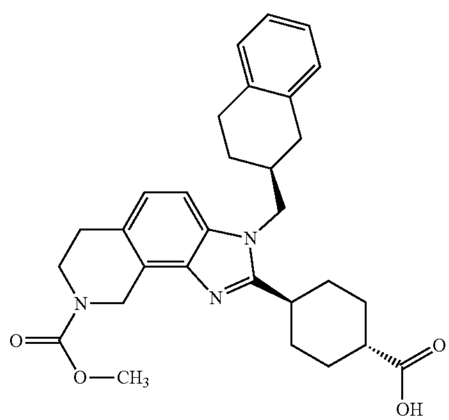 [SMILES: COC(=O)N1CCc2ccc3c(nc([C@H]4CC[C@H](C(=O)O)CC4)n3C[C@H]3CCc4ccccc4C3)c2C1] |
| 170 | 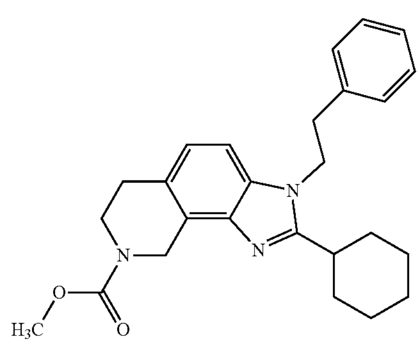 [SMILES: COC(=O)N1CCc2ccc3c(nc(C4CCCCC4)n3CCc3ccccc3)c2C1] |

381
382
-continued
(Currently amended) A compound or a pharmaceutically acceptable salt thereof, wherein the compound is selected from
| Compound No. | Structure |
|---|---|
| 171 | 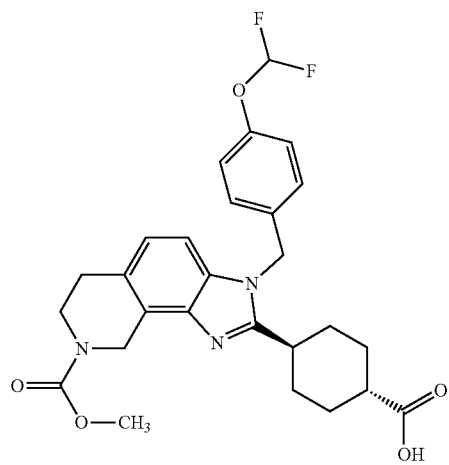 [SMILES: COC(=O)N1CCc2ccc3c(nc([C@H]4CC[C@H](C(=O)O)CC4)n3Cc3ccc(OC(F)F)cc3)c2C1] |
| 172 | 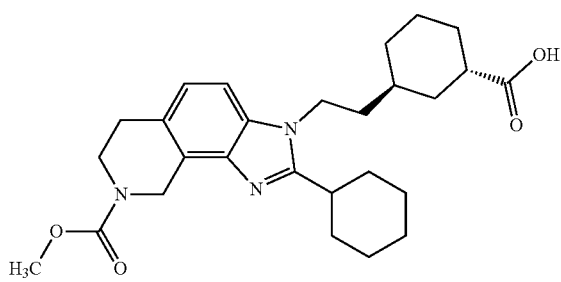 [SMILES: COC(=O)N1CCc2ccc3c(nc(C4CCCCC4)n3CC[C@H]3CCC[C@H](C(=O)O)C3)c2C1] |
| 173 | 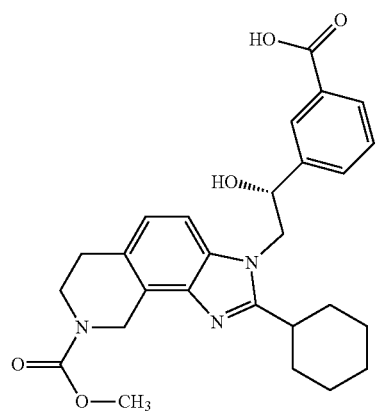 [SMILES: COC(=O)N1CCc2ccc3c(nc(C4CCCCC4)n3C[C@H](O)c3cccc(C(=O)O)c3)c2C1] |
| 174 | 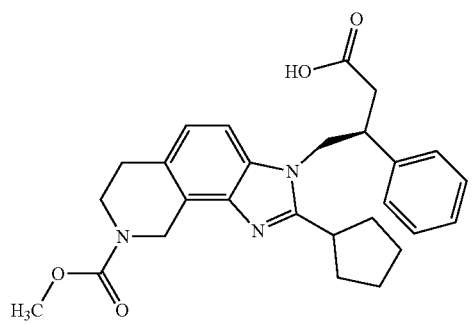 [SMILES: COC(=O)N1CCc2ccc3c(nc(C4CCCC4)n3C[C@@H](CC(=O)O)c3ccccc3)c2C1] |

-continued
(Currently amended) A compound or a pharmaceutically acceptable salt thereof, wherein the compound is selected from
| Compound No. | Structure |
|---|---|
| 175 | 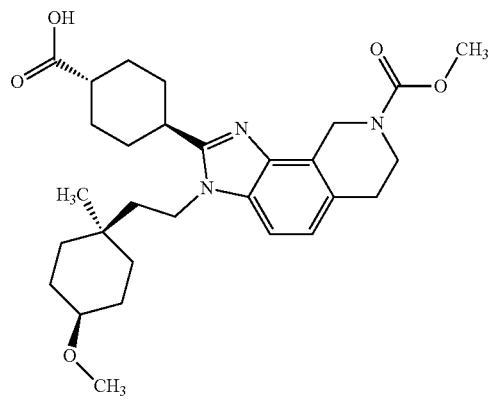 [SMILES: COC(=O)N1CCc2ccc3c(nc([C@H]4CC[C@H](C(=O)O)CC4)n3CC[C@]3(C)CC[C@H](OC)CC3)c2C1] |
| 176 | 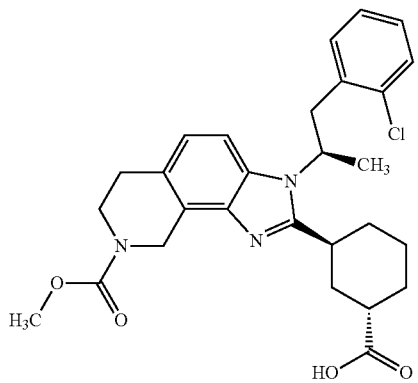 [SMILES: COC(=O)N1CCc2ccc3c(nc([C@H]4CCC[C@H](C(=O)O)C4)n3[C@H](C)Cc3ccccc3Cl)c2C1] |
| 177 | 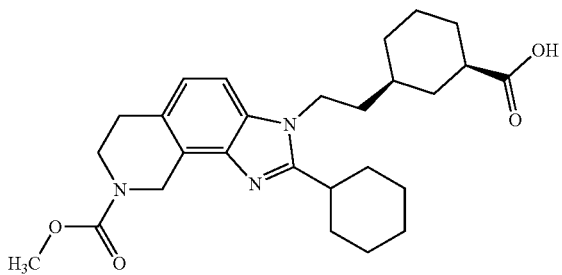 [SMILES: COC(=O)N1CCc2ccc3c(nc(C4CCCCC4)n3CC[C@H]3CCC[C@@H](C(=O)O)C3)c2C1] |
| 178 | 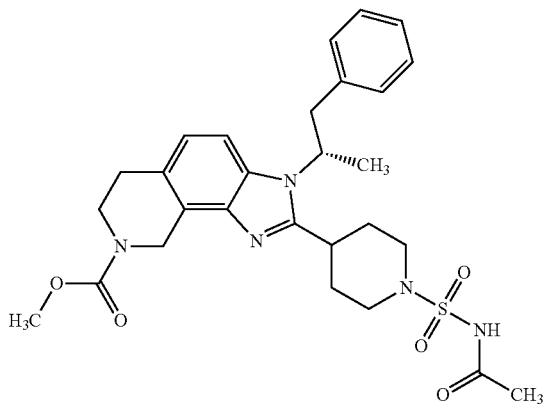 [SMILES: COC(=O)N1CCc2ccc3c(nc(C4CCN(S(=O)(=O)NC(C)=O)CC4)n3[C@@H](C)Cc3ccccc3)c2C1] |

(Currently amended) A compound or a pharmaceutically acceptable salt thereof, wherein the compound is selected from
| Compound No. | Structure |
|---|---|
| 179 | 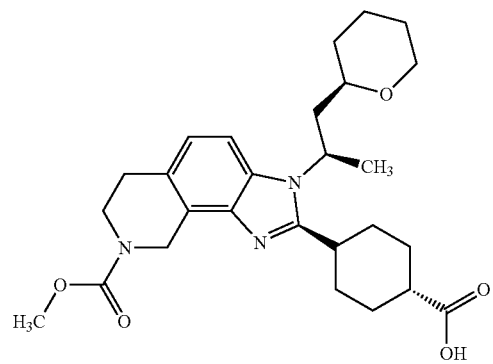 |
| 180 | 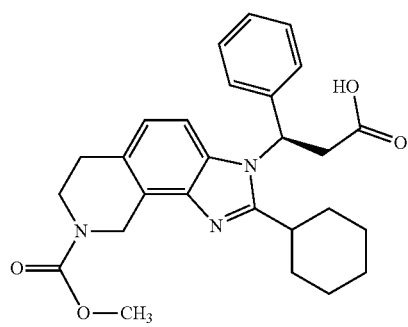 [SMILES: COC(=O)N1CCc2ccc3c(nc(C4CCCCC4)n3[C@H](CC(=O)O)c3ccccc3)c2C1] |
| 181 | 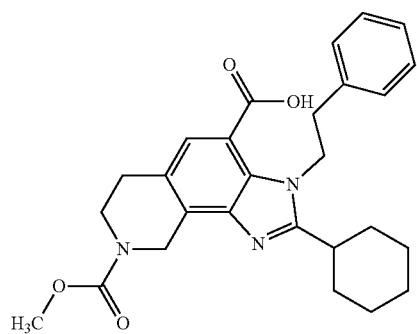 [SMILES: COC(=O)N1CCc2cc(C(=O)O)c3c(nc(C4CCCCC4)n3CCc3ccccc3)c2C1] |
| 182 | 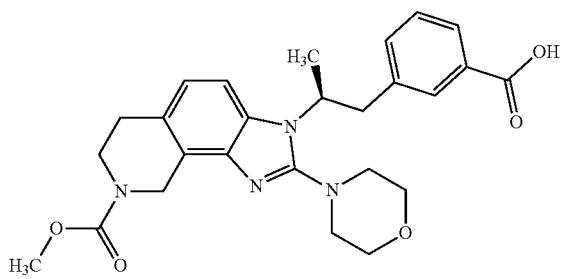 [SMILES: COC(=O)N1CCc2ccc3c(nc(N4CCOCC4)n3[C@@H](C)Cc3cccc(C(=O)O)c3)c2C1] |

(Currently amended) A compound or a pharmaceutically acceptable salt thereof, wherein the compound is selected from
| Compound No. | Structure |
|---|---|
| 183 | 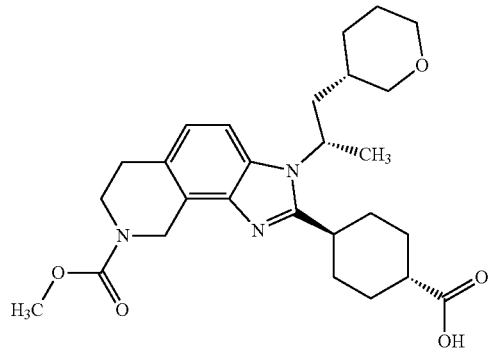 [SMILES: COC(=O)N1CCc2ccc3c(nc([C@H]4CC[C@H](C(=O)O)CC4)n3[C@@H](C)C[C@@H]3CCCOC3)c2C1] |
| 184 | 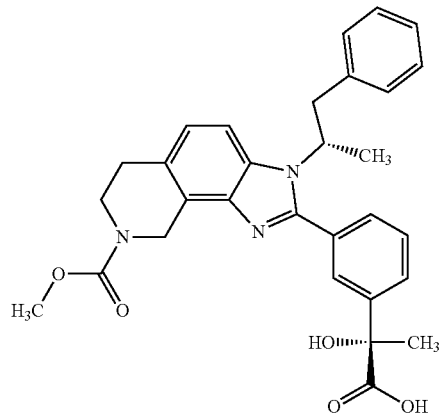 [SMILES: COC(=O)N1CCc2ccc3c(nc(-c4cccc([C@](C)(O)C(=O)O)c4)n3[C@@H](C)Cc3ccccc3)c2C1] |
| 185 | 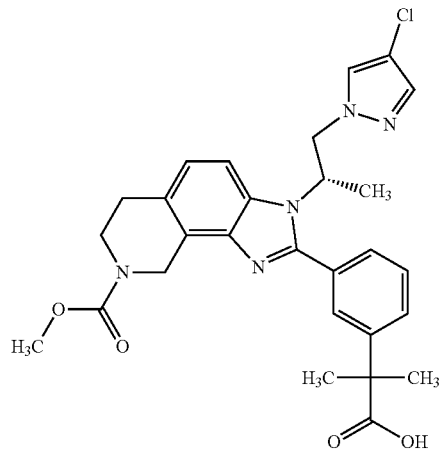 [SMILES: COC(=O)N1CCc2ccc3c(nc(-c4cccc(C(C)(C)C(=O)O)c4)n3[C@@H](C)Cn3cc(Cl)cn3)c2C1] |

(Currently amended) A compound or a pharmaceutically acceptable salt thereof, wherein the compound is selected from
| Compound No. | Structure |
|---|---|
| 186 | 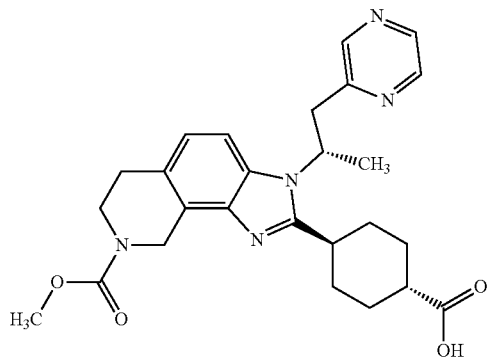 [SMILES: COC(=O)N1CCc2ccc3c(nc([C@H]4CC[C@H](C(=O)O)CC4)n3[C@@H](C)Cc3cnccn3)c2C1] |
| 187 | 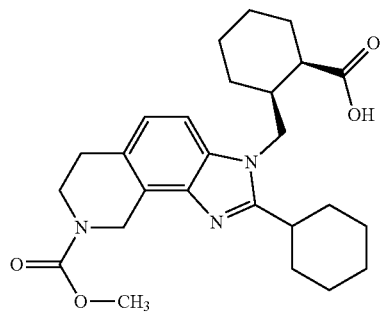 [SMILES: COC(=O)N1CCc2ccc3c(nc(C4CCCCC4)n3C[C@H]3CCCC[C@H]3C(=O)O)c2C1] |
| 188 | 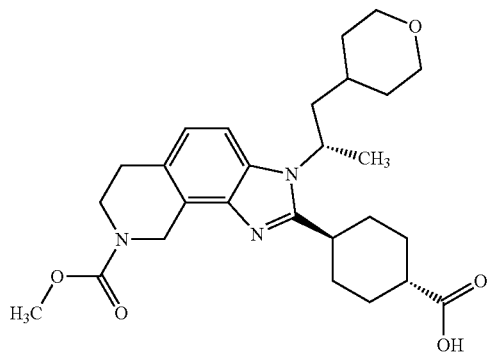 [SMILES: COC(=O)N1CCc2ccc3c(nc([C@H]4CC[C@H](C(=O)O)CC4)n3[C@@H](C)CC3CCOCC3)c2C1] |
| 189 | 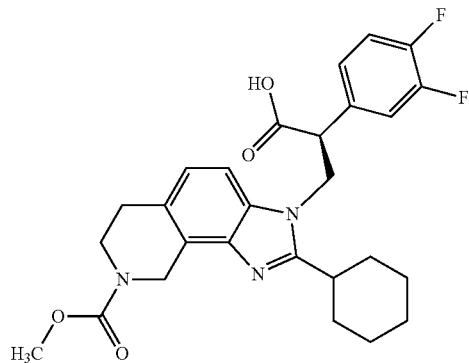 [SMILES: COC(=O)N1CCc2ccc3c(nc(C4CCCCC4)n3C[C@@H](C(=O)O)c3ccc(F)c(F)c3)c2C1] |

-continued
(Currently amended) A compound or a pharmaceutically acceptable salt thereof, wherein the compound is selected from
| Compound No. | Structure |
|---|---|
| 190 | 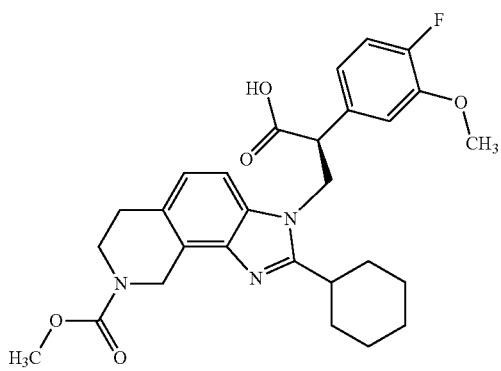 |
| 191 | 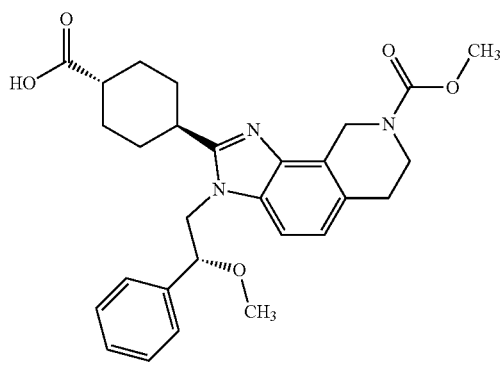 [SMILES: COC(=O)N1CCc2ccc3c(nc([C@H]4CC[C@H](C(=O)O)CC4)n3C[C@H](OC)c3ccccc3)c2C1] |
| 192 | 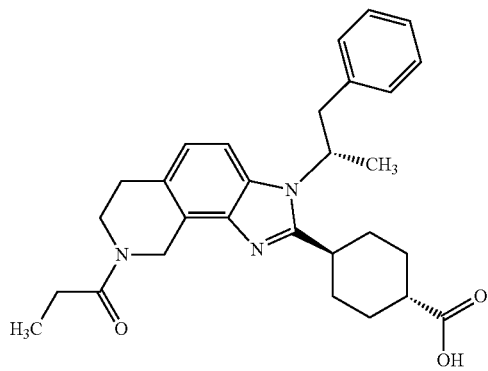 [SMILES: CCC(=O)N1CCc2ccc3c(nc([C@H]4CC[C@H](C(=O)O)CC4)n3[C@@H](C)Cc3ccccc3)c2C1] |
| 193 | 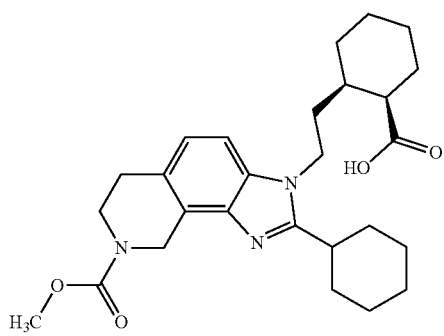 |

393
-continued
(Currently amended) A compound or a pharmaceutically acceptable salt thereof, wherein the compound is selected from
| Compound No. | Structure |
|---|---|
| 194 | 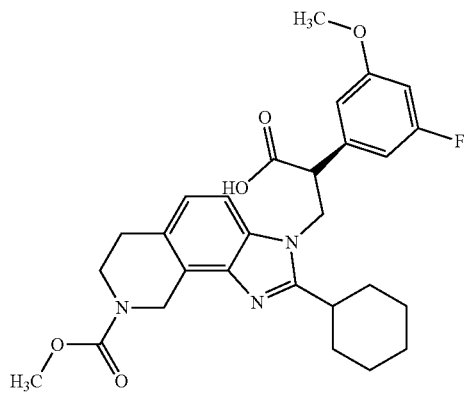 |
| 195 | 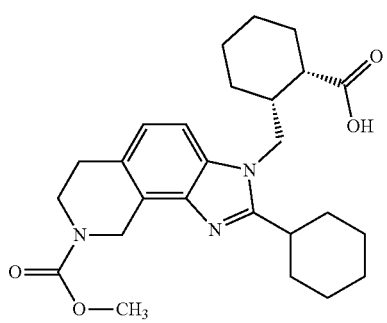 [SMILES: COC(=O)N1CCc2ccc3c(nc(C4CCCCC4)n3C[C@@H]3CCCC[C@@H]3C(=O)O)c2C1] |
| 196 | 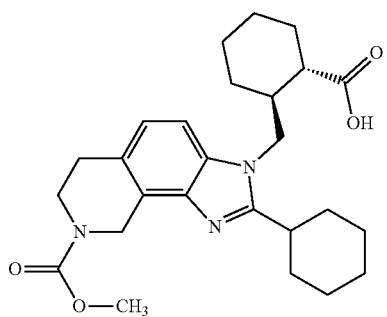 [SMILES: COC(=O)N1CCc2ccc3c(nc(C4CCCCC4)n3C[C@H]3CCCC[C@@H]3C(=O)O)c2C1] |
| 197 | 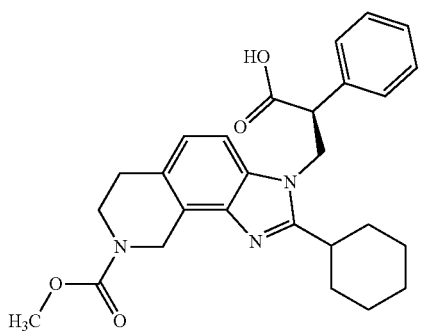 [SMILES: COC(=O)N1CCc2ccc3c(nc(C4CCCCC4)n3C[C@@H](C(=O)O)c3ccccc3)c2C1] |

-continued
(Currently amended) A compound or a pharmaceutically acceptable salt thereof, wherein the compound is selected from
| Compound No. | Structure |
|---|---|
| 198 | 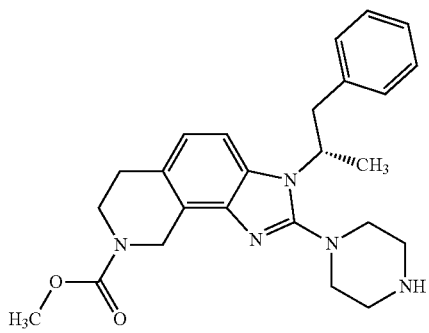 [SMILES: COC(=O)N1CCc2ccc3c(nc(N4CCNCC4)n3[C@@H](C)Cc3ccccc3)c2C1] |
| 199 | 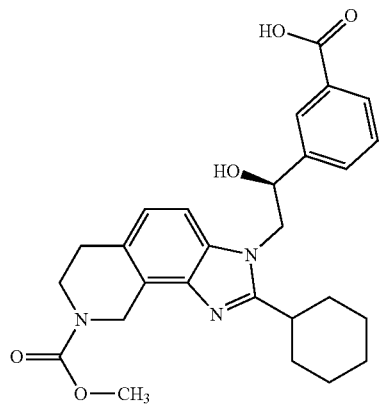 [SMILES: COC(=O)N1CCc2ccc3c(nc(C4CCCCC4)n3C[C@@H](O)c3cccc(C(=O)O)c3)c2C1] |
| 200 | 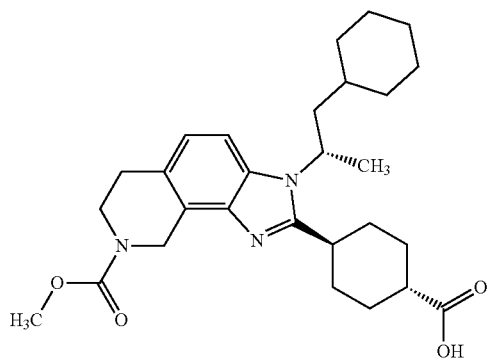 |
| 201 | 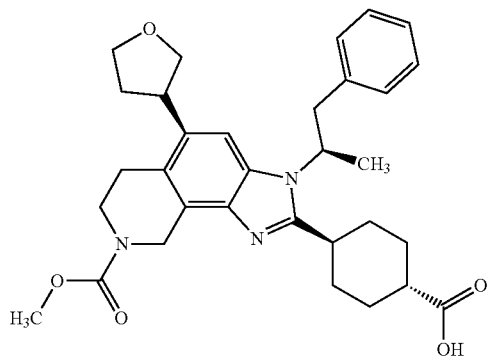 |

-continued
(Currently amended) A compound or a pharmaceutically acceptable salt thereof, wherein the compound is selected from
| Compound No. | Structure |
|---|---|
| 202 | 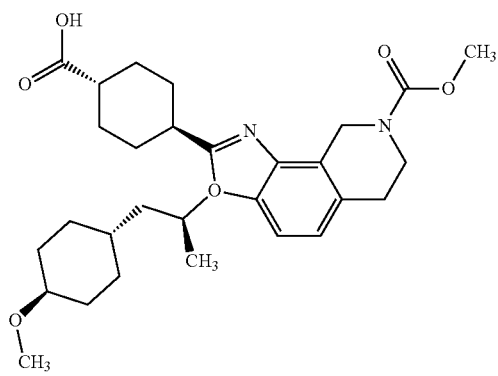 |
| 203 | 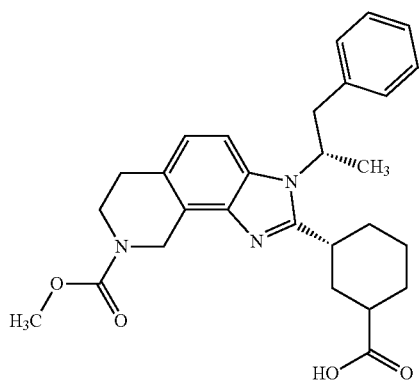 [SMILES: COC(=O)N1CCc2ccc3c(nc([C@@H]4CCCC(C(=O)O)C4)n3[C@@H](C)Cc3ccccc3)c2C1] |
| 204 | 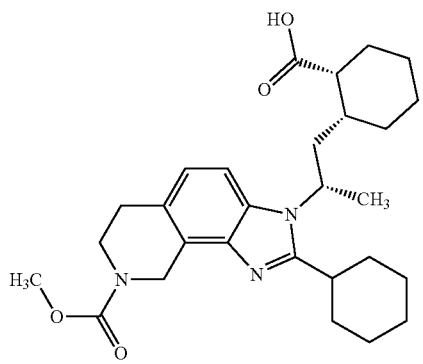 [SMILES: COC(=O)N1CCc2ccc3c(nc(C4CCCCC4)n3[C@@H](C)C[C@H]3CCCC[C@H]3C(=O)O)c2C1] |
| 205 | 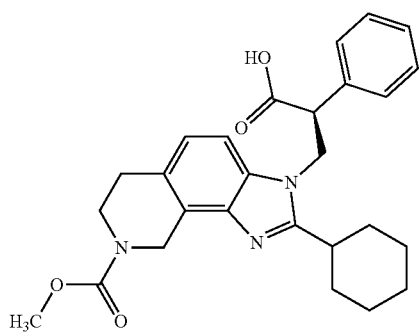 [SMILES: COC(=O)N1CCc2ccc3c(nc(C4CCCCC4)n3C[C@@H](C(=O)O)c3ccccc3)c2C1] |

-continued (Currently amended) A compound or a pharmaceutically acceptable salt thereof, wherein the compound is selected from

| Compound No. | Structure |
|---|---|
| 206 | 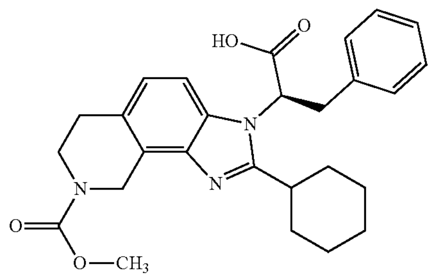 [SMILES: COC(=O)N1CCc2ccc3c(nc(C4CCCCC4)n3[C@H](Cc3ccccc3)C(=O)O)c2C1] |
| 207 | 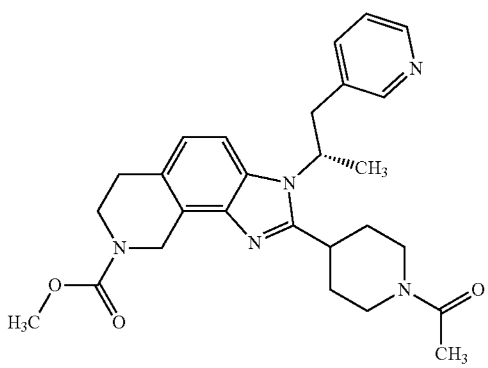 |
| 208 | 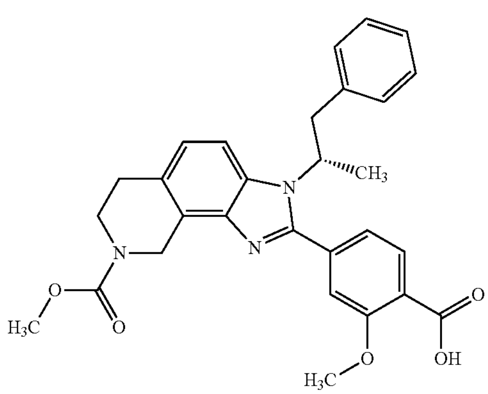 [SMILES: COC(=O)N1CCc2ccc3c(nc(-c4ccc(C(=O)O)c(OC)c4)n3[C@@H](C)Cc3ccccc3)c2C1] |
| 209 | 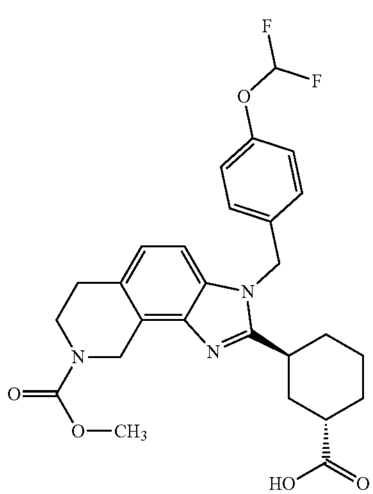 [SMILES: COC(=O)N1CCc2ccc3c(nc([C@H]4CCC[C@H](C(=O)O)C4)n3Cc3ccc(OC(F)F)cc3)c2C1] |

-continued
(Currently amended) A compound or a pharmaceutically acceptable salt thereof, wherein the compound is selected from
| Compound No. | Structure |
|---|---|
| 210 | 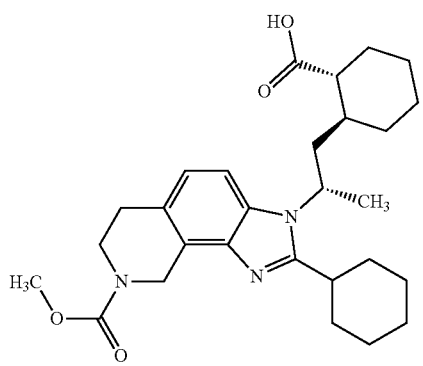 [SMILES: COC(=O)N1CCc2ccc3c(nc(C4CCCCC4)n3[C@@H](C)C[C@@H]3CCCC[C@H]3C(=O)O)c2C1] |
| 211 | 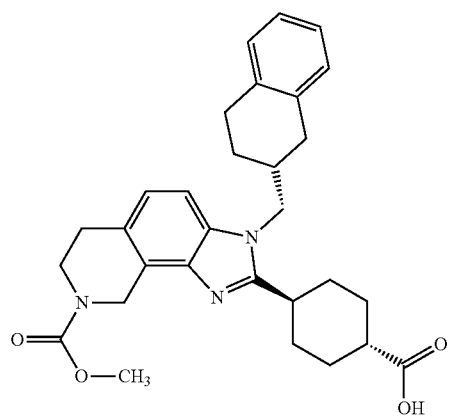 |
| 212 | 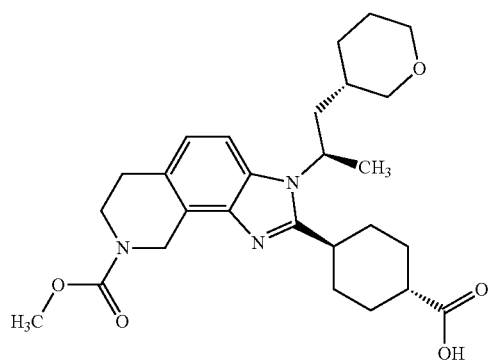 [SMILES: COC(=O)N1CCc2ccc3c(nc([C@H]4CC[C@H](C(=O)O)CC4)n3[C@H](C)C[C@@H]3CCCOC3)c2C1] |
| 213 | 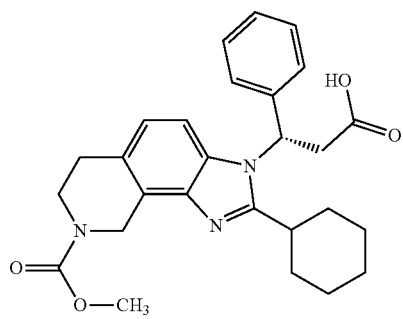 [SMILES: COC(=O)N1CCc2ccc3c(nc(C4CCCCC4)n3[C@@H](CC(=O)O)c3ccccc3)c2C1] |

-continued
(Currently amended) A compound or a pharmaceutically acceptable salt thereof, wherein the compound is selected from
| Compound No. | Structure |
|---|---|
| 214 | 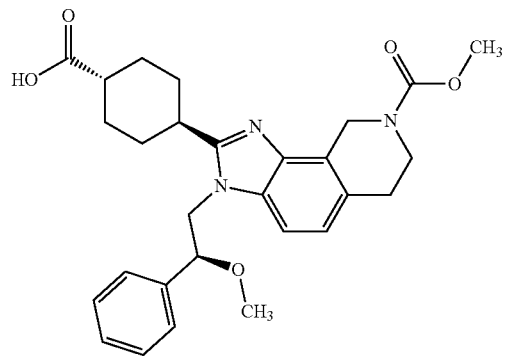 [SMILES: COC(=O)N1CCc2ccc3c(nc([C@H]4CC[C@H](C(=O)O)CC4)n3C[C@@H](OC)c3ccccc3)c2C1] |
| 215 | 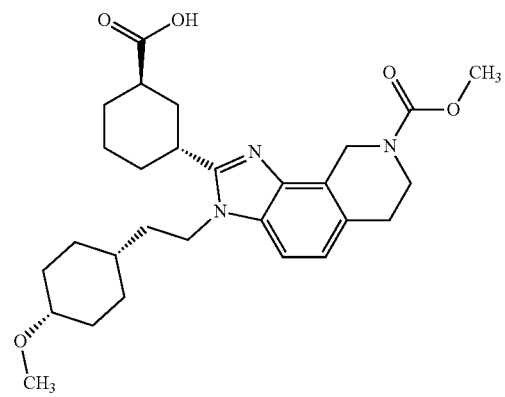 [SMILES: COC(=O)N1CCc2ccc3c(nc([C@@H]4CCC[C@@H](C(=O)O)C4)n3CC[C@H]3CC[C@@H](OC)CC3)c2C1] |
| 216 | 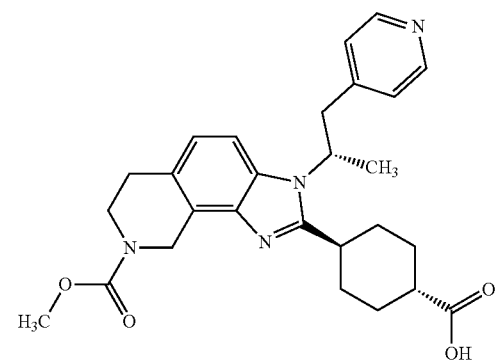 [SMILES: COC(=O)N1CCc2ccc3c(nc([C@H]4CC[C@H](C(=O)O)CC4)n3[C@@H](C)Cc3ccncc3)c2C1] |
| 217 | 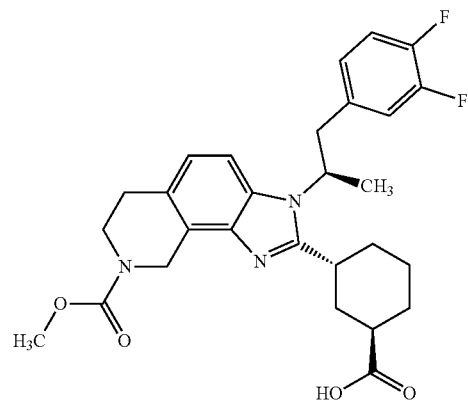 [SMILES: COC(=O)N1CCc2ccc3c(nc([C@@H]4CCC[C@@H](C(=O)O)C4)n3[C@H](C)Cc3ccc(F)c(F)c3)c2C1] |

-continued
(Currently amended) A compound or a pharmaceutically acceptable salt thereof, wherein the compound is selected from
| Compound No. | Structure |
|---|---|
| 218 | 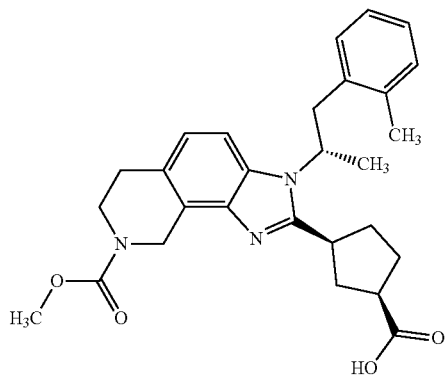 [SMILES: COC(=O)N1CCc2ccc3c(nc([C@H]4CC[C@@H](C(=O)O)C4)n3[C@@H](C)Cc3ccccc3C)c2C1] |
| 219 | 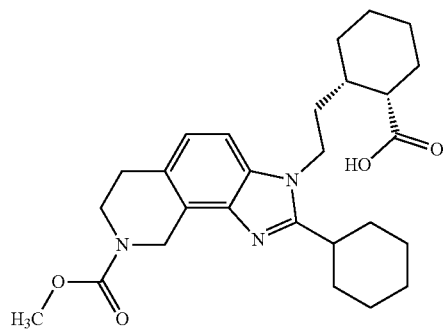 [SMILES: COC(=O)N1CCc2ccc3c(nc(C4CCCCC4)n3CC[C@@H]3CCCC[C@@H]3C(=O)O)c2C1] |
| 220 | 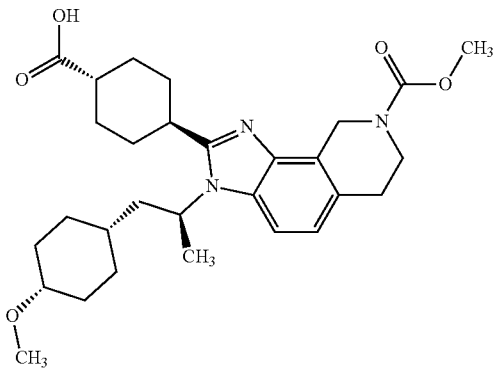 [SMILES: COC(=O)N1CCc2ccc3c(nc([C@H]4CC[C@H](C(=O)O)CC4)n3[C@@H](C)C[C@H]3CC[C@@H](OC)CC3)c2C1] |
| 221 | 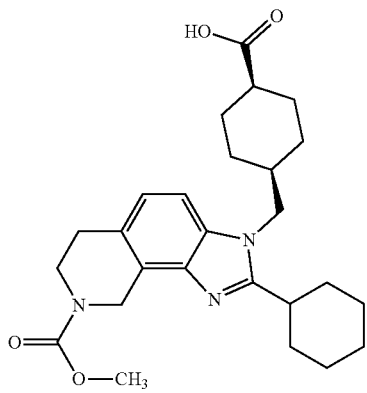 [SMILES: COC(=O)N1CCc2ccc3c(nc(C4CCCCC4)n3C[C@H]3CC[C@@H](C(=O)O)CC3)c2C1] |

407
-continued
(Currently amended) A compound or a pharmaceutically
acceptable salt thereof, wherein the compound is selected from
| Compound No. | Structure |
|---|---|
| 222 | 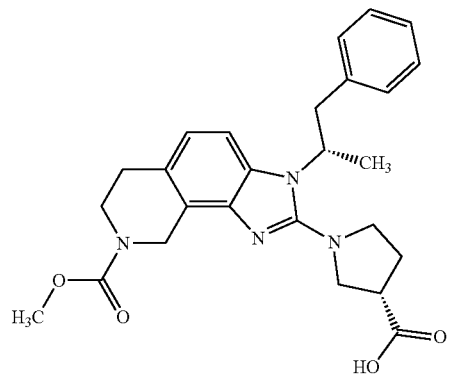 [SMILES: COC(=O)N1CCc2ccc3c(nc(N4CC[C@H](C(=O)O)C4)n3[C@@H](C)Cc3ccccc3)c2C1] |
| 223 | 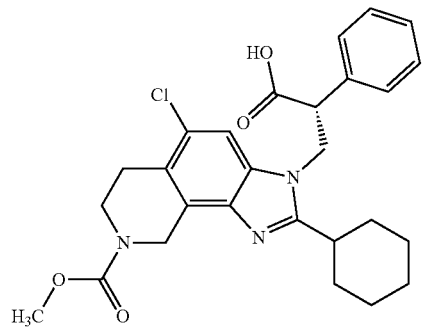 [SMILES: COC(=O)N1CCc2c(Cl)cc3c(nc(C4CCCCC4)n3C[C@H](C(=O)O)c3ccccc3)c2C1] |
| 224 | 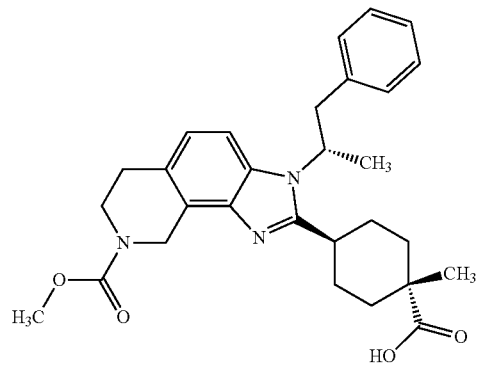 [SMILES: COC(=O)N1CCc2ccc3c(nc([C@H]4CC[C@](C)(C(=O)O)CC4)n3[C@@H](C)Cc3ccccc3)c2C1] |
| 225 | 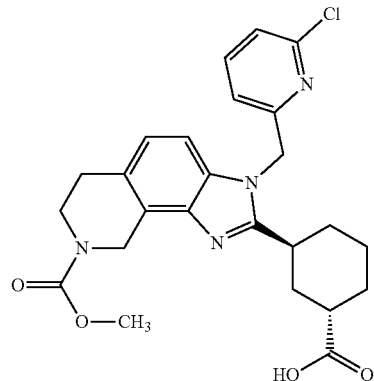 [SMILES: COC(=O)N1CCc2ccc3c(nc([C@H]4CCC[C@H](C(=O)O)C4)n3Cc3cccc(Cl)n3)c2C1] |

409
-continued
(Currently amended) A compound or a pharmaceutically acceptable salt thereof, wherein the compound is selected from
| Compound No. | Structure |
|---|---|
| 226 | 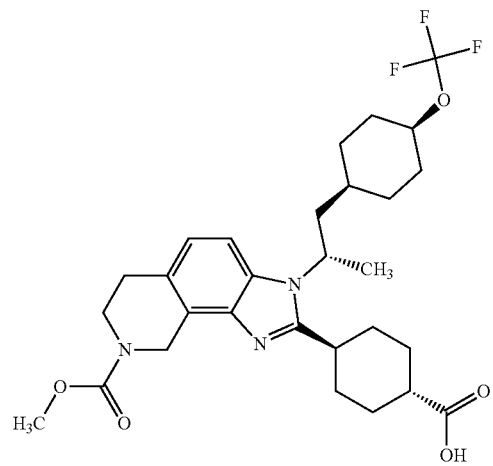 [SMILES: COC(=O)N1CCc2ccc3c(nc([C@H]4CC[C@H](C(=O)O)CC4)n3[C@@H](C)C[C@H]3CC[C@@H](OC(F)(F)F)CC3)c2C1] |
| 227 | 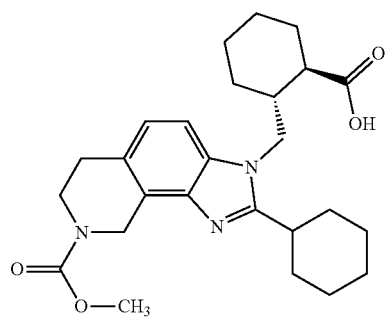 [SMILES: COC(=O)N1CCc2ccc3c(nc(C4CCCCC4)n3C[C@@H]3CCCC[C@H]3C(=O)O)c2C1] |
| 228 | 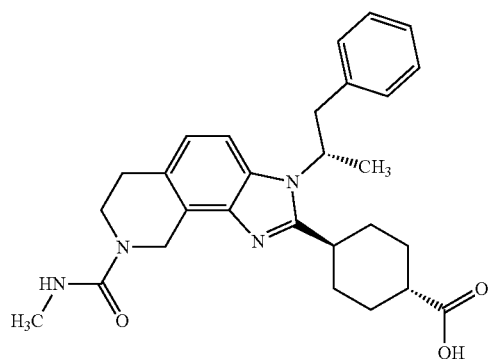 [SMILES: CNC(=O)N1CCc2ccc3c(nc([C@H]4CC[C@H](C(=O)O)CC4)n3[C@@H](C)Cc3ccccc3)c2C1] |
| 229 | 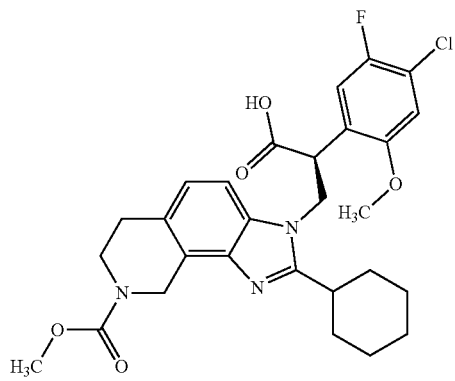 [SMILES: COC(=O)N1CCc2ccc3c(nc(C4CCCCC4)n3C[C@@H](C(=O)O)c3cc(F)c(Cl)cc3OC)c2C1] |

-continued
(Currently amended) A compound or a pharmaceutically acceptable salt thereof, wherein the compound is selected from
| Compound No. | Structure |
|---|---|
| 230 | 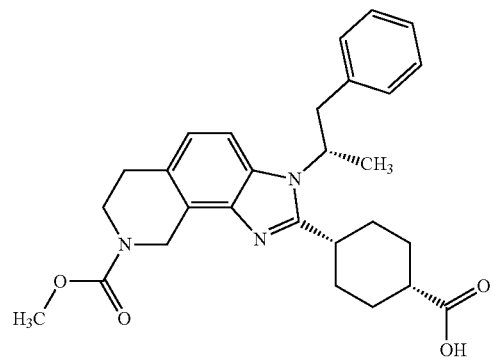 [SMILES: COC(=O)N1CCc2ccc3c(nc([C@H]4CC[C@@H](C(=O)O)CC4)n3[C@@H](C)Cc3ccccc3)c2C1] |
| 231 | 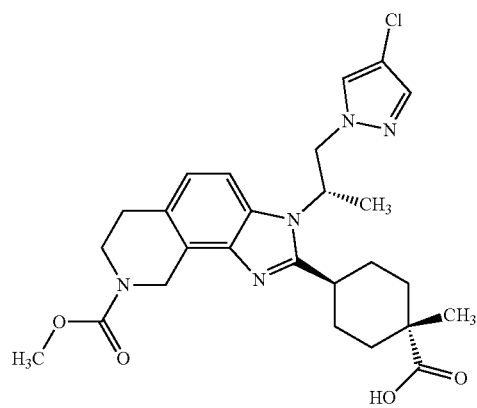 [SMILES: COC(=O)N1CCc2ccc3c(nc([C@H]4CC[C@](C)(C(=O)O)CC4)n3[C@@H](C)Cn3cc(Cl)cn3)c2C1] |
| 232 | 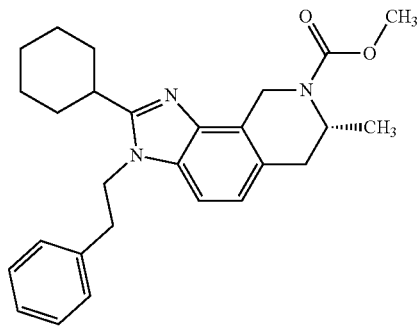 [SMILES: COC(=O)N1Cc2c(ccc3c2nc(C2CCCCC2)n3CCc2ccccc2)C[C@H]1C] |
| 233 | 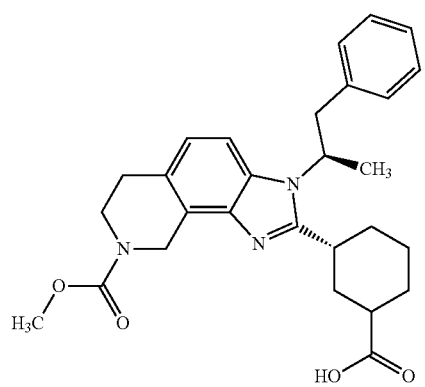 [SMILES: COC(=O)N1CCc2ccc3c(nc([C@@H]4CCCC(C(=O)O)C4)n3[C@H](C)Cc3ccccc3)c2C1] |

-continued
(Currently amended) A compound or a pharmaceutically acceptable salt thereof, wherein the compound is selected from
| Compound No. | Structure |
|---|---|
| 234 | 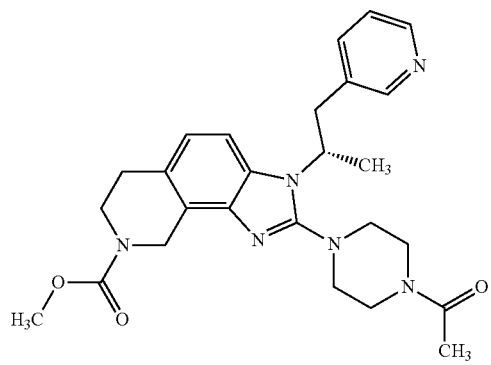 |
| 235 | 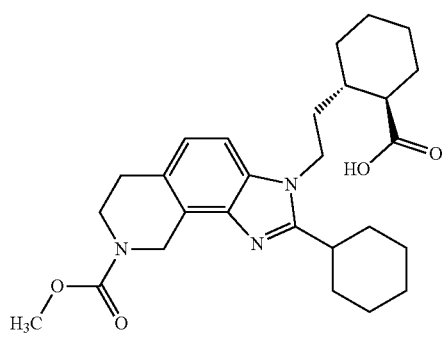 [SMILES: COC(=O)N1CCc2ccc3c(nc(C4CCCCC4)n3CC[C@@H]3CCCC[C@H]3C(=O)O)c2C1] |
| 236 | 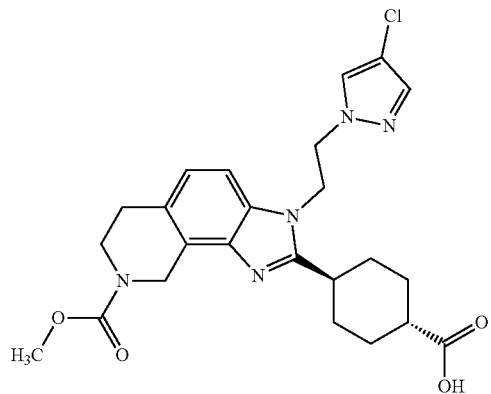 [SMILES: COC(=O)N1CCc2ccc3c(nc([C@H]4CC[C@H](C(=O)O)CC4)n3CCn3cc(Cl)cn3)c2C1] |
| 237 | 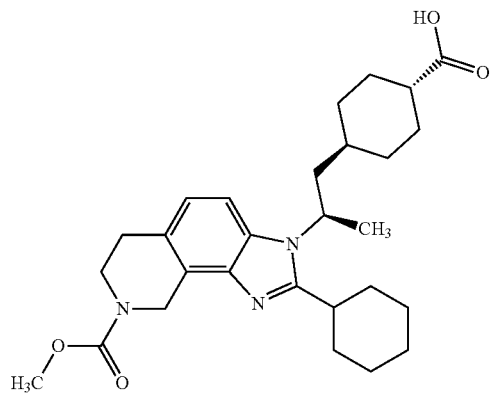 [SMILES: COC(=O)N1CCc2ccc3c(nc(C4CCCCC4)n3[C@H](C)C[C@H]3CC[C@H](C(=O)O)CC3)c2C1] |

415
416
-continued
(Currently amended) A compound or a pharmaceutically acceptable salt thereof, wherein the compound is selected from
| Compound No. | Structure |
|---|---|
| 238 | 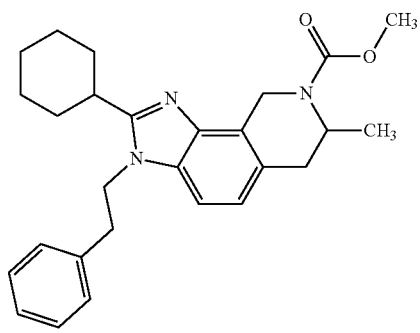 |
| 239 | 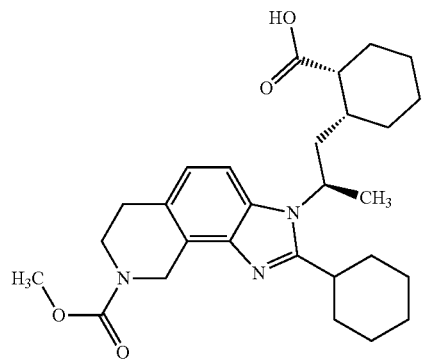 [SMILES: COC(=O)N1CCc2ccc3c(nc(C4CCCCC4)n3[C@H](C)C[C@H]3CCCC[C@H]3C(=O)O)c2C1] |
| 240 | 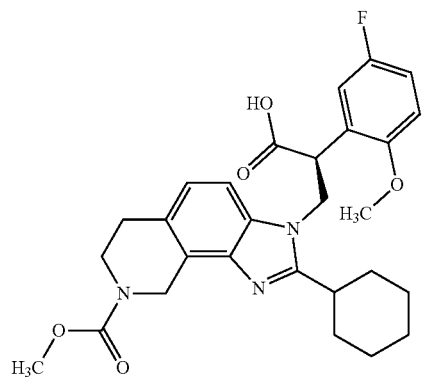 [SMILES: COC(=O)N1CCc2ccc3c(nc(C4CCCCC4)n3C[C@@H](C(=O)O)c3cc(F)ccc3OC)c2C1] |
| 241 | 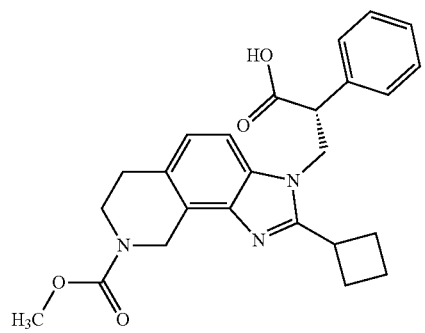 [SMILES: COC(=O)N1CCc2ccc3c(nc(C4CCC4)n3C[C@H](C(=O)O)c3ccccc3)c2C1] |

-continued
(Currently amended) A compound or a pharmaceutically acceptable salt thereof, wherein the compound is selected from
| Compound No. | Structure |
|---|---|
| 242 | 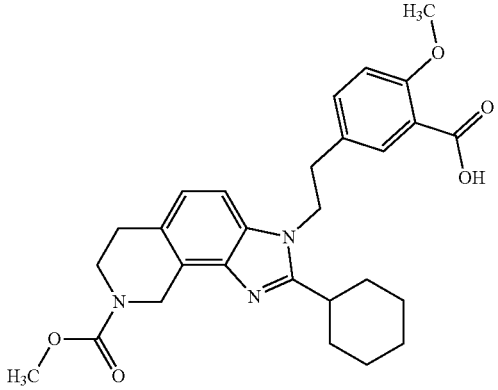 [SMILES: COC(=O)N1CCc2ccc3c(nc(C4CCCCC4)n3CCc3ccc(OC)c(C(=O)O)c3)c2C1] |
| 243 | 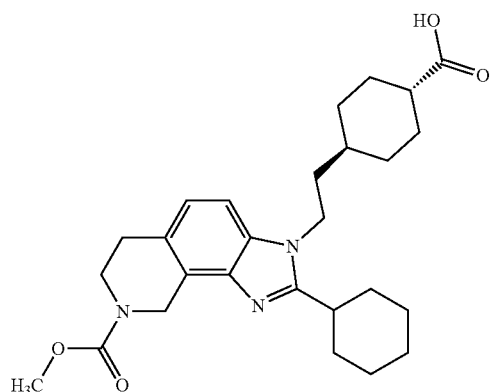 |
| 244 | 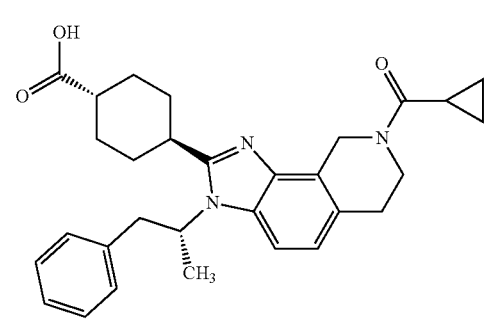 [SMILES: C[C@H](Cc1ccccc1)n1c2ccc3c(c2nc1[C@H]1CC[C@H](C(=O)O)CC1)CN(C(=O)C1CC1)CC3] |
| 245 | 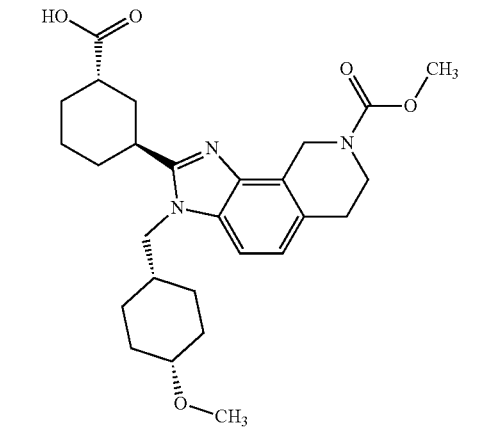 [SMILES: COC(=O)N1CCc2ccc3c(nc([C@H]4CCC[C@H](C(=O)O)C4)n3C[C@H]3CC[C@@H](OC)CC3)c2C1] |

(Currently amended) A compound or a pharmaceutically acceptable salt thereof, wherein the compound is selected from
| Compound No. | Structure |
|---|---|
| 246 | 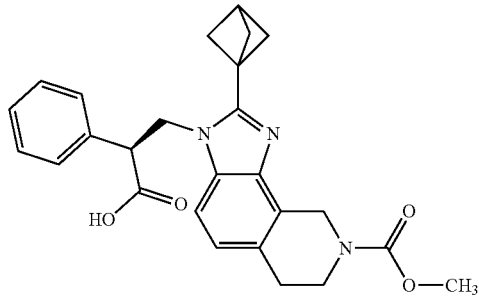 [SMILES: COC(=O)N1CCc2ccc3c(nc(C45CC(C4)C5)n3C[C@@H](C(=O)O)c3ccccc3)c2C1] |
| 247 | 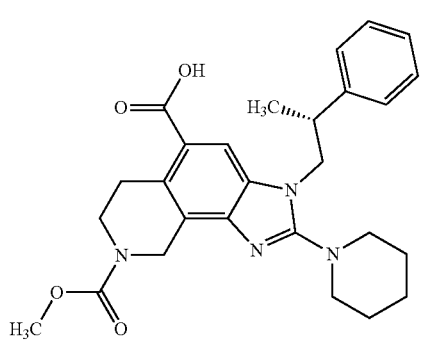 [SMILES: COC(=O)N1CCc2c(C(=O)O)cc3c(nc(N4CCCCC4)n3C[C@H](C)c3ccccc3)c2C1] |
| 248 | 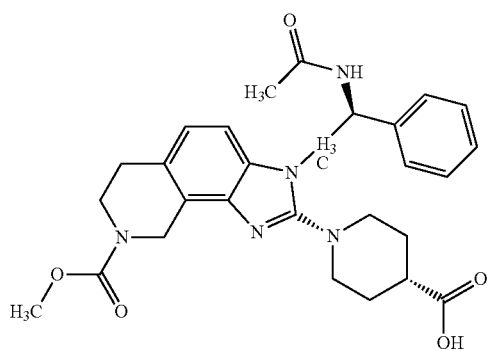 |
| 249 | 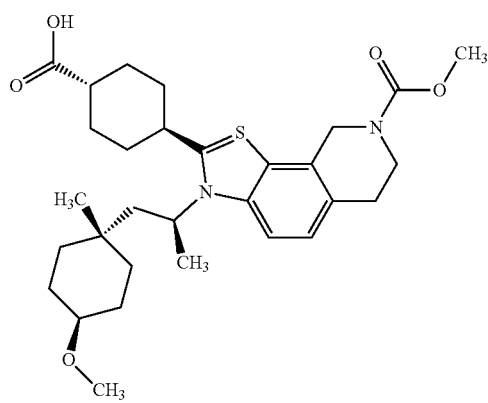 |

421

-continued (Currently amended) A compound or a pharmaceutically acceptable salt thereof, wherein the compound is selected from

| Compound No. | Structure |
|---|---|
| 250 | 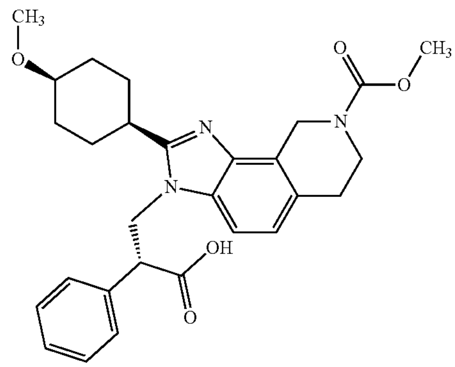 [SMILES: COC(=O)N1CCc2ccc3c(nc([C@H]4CC[C@@H](OC)CC4)n3C[C@H](C(=O)O)c3ccccc3)c2C1] |
| 251 | 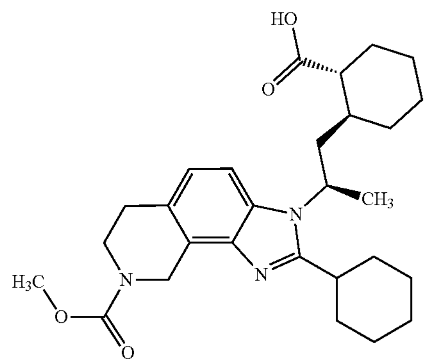 [SMILES: COC(=O)N1CCc2ccc3c(nc(C4CCCCC4)n3[C@H](C)C[C@@H]3CCCC[C@H]3C(=O)O)c2C1] |
| 252 | 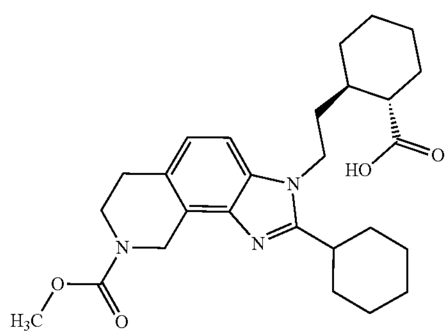 [SMILES: COC(=O)N1CCc2ccc3c(nc(C4CCCCC4)n3CC[C@H]3CCCC[C@@H]3C(=O)O)c2C1] |
| 253 | 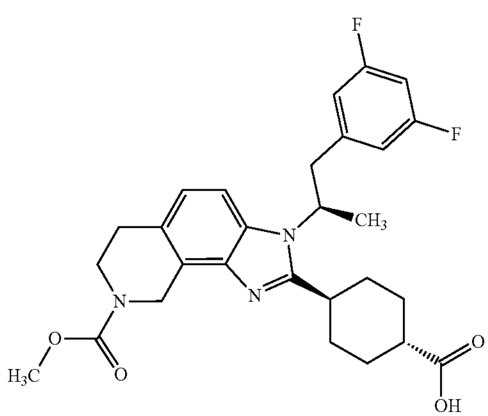 [SMILES: COC(=O)N1CCc2ccc3c(nc([C@H]4CC[C@H](C(=O)O)CC4)n3[C@H](C)Cc3cc(F)cc(F)c3)c2C1] |

-continued
(Currently amended) A compound or a pharmaceutically acceptable salt thereof, wherein the compound is selected from
| Compound No. | Structure |
|---|---|
| 254 | 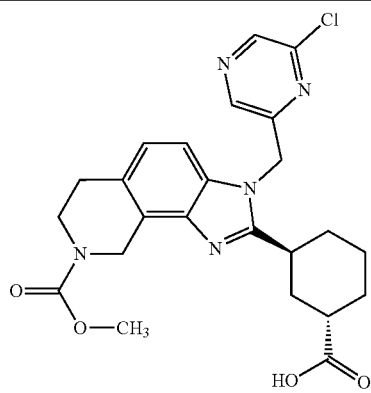 |
| 255 | 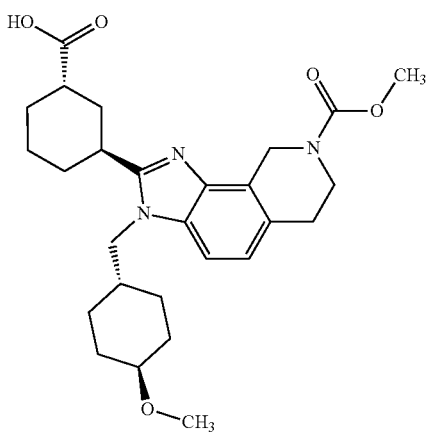 [SMILES: COC(=O)N1CCc2ccc3c(nc([C@H]4CCC[C@H](C(=O)O)C4)n3C[C@H]3CC[C@H](OC)CC3)c2C1] |
| 256 | 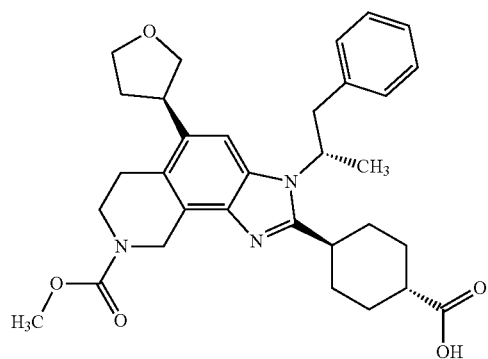 [SMILES: COC(=O)N1CCc2c([C@H]3CCOC3)cc3c(nc([C@H]4CC[C@H](C(=O)O)CC4)n3[C@@H](C)Cc3ccccc3)c2C1] |
| 257 | 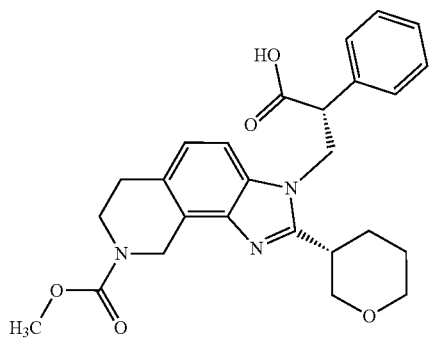 [SMILES: COC(=O)N1CCc2ccc3c(nc([C@@H]4CCCOC4)n3C[C@H](C(=O)O)c3ccccc3)c2C1] |

(Currently amended) A compound or a pharmaceutically acceptable salt thereof, wherein the compound is selected from
| Compound No. | Structure |
|---|---|
| 258 | 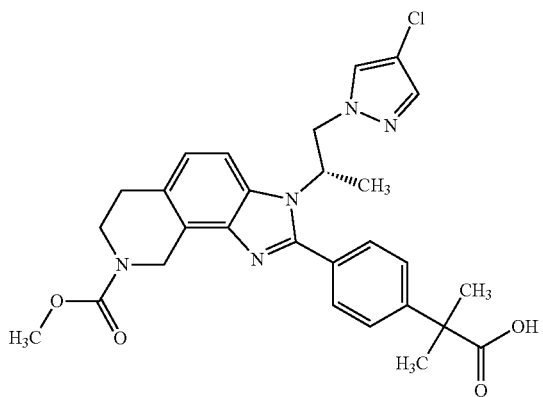 [SMILES: COC(=O)N1CCc2ccc3c(nc(-c4ccc(C(C)(C)C(=O)O)cc4)n3[C@@H](C)Cn3cc(Cl)cn3)c2C1] |
| 259 | 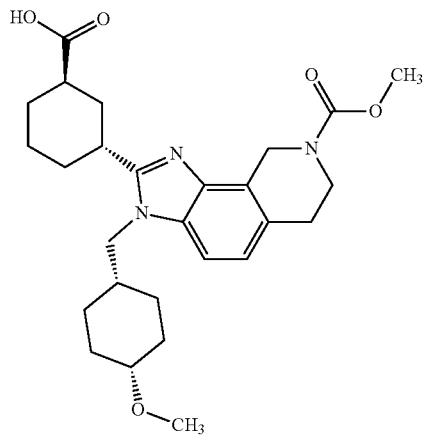 [SMILES: COC(=O)N1CCc2ccc3c(nc([C@@H]4CCC[C@@H](C(=O)O)C4)n3C[C@H]3CC[C@@H](OC)CC3)c2C1] |
| 260 | 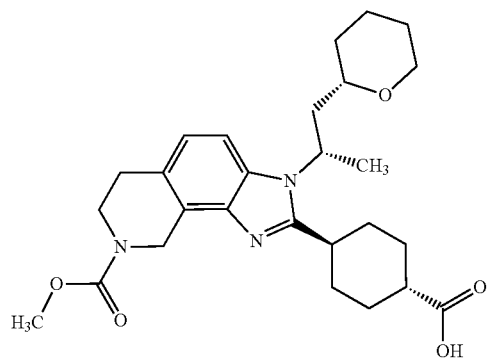 [SMILES: COC(=O)N1CCc2ccc3c(nc([C@H]4CC[C@H](C(=O)O)CC4)n3[C@@H](C)C[C@@H]3CCCCO3)c2C1] |

(Currently amended) A compound or a pharmaceutically acceptable salt thereof, wherein the compound is selected from
| Compound No. | Structure |
|---|---|
| 261 | 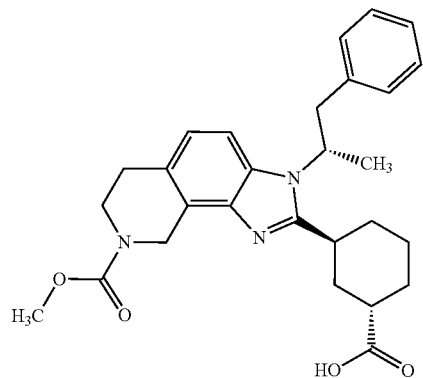 [SMILES: COC(=O)N1CCc2ccc3c(nc([C@H]4CCC[C@H](C(=O)O)C4)n3[C@@H](C)Cc3ccccc3)c2C1] |
| 262 | 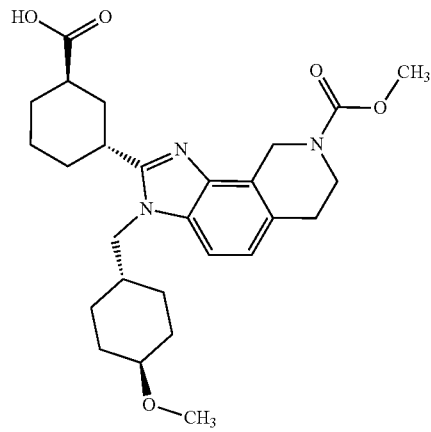 [SMILES: COC(=O)N1CCc2ccc3c(nc([C@@H]4CCC[C@@H](C(=O)O)C4)n3C[C@H]3CC[C@H](OC)CC3)c2C1] |
| 263 | 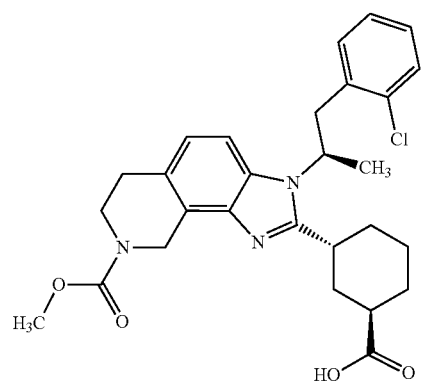 [SMILES: COC(=O)N1CCc2ccc3c(nc([C@@H]4CCC[C@@H](C(=O)O)C4)n3[C@H](C)Cc3ccccc3Cl)c2C1] |

| Compound No. | Structure |
|---|---|
| 264 | *(structure shown)* |
| 265 | *(structure shown)* |
| 266 | *(structure shown)* |
| 267 | *(structure shown)* |

(Currently amended) A compound or a pharmaceutically acceptable salt thereof, wherein the compound is selected from -continued (Currently amended) A compound or a pharmaceutically acceptable salt thereof, wherein the compound is selected from

| Compound No. | Structure |
|---|---|
| 268 | 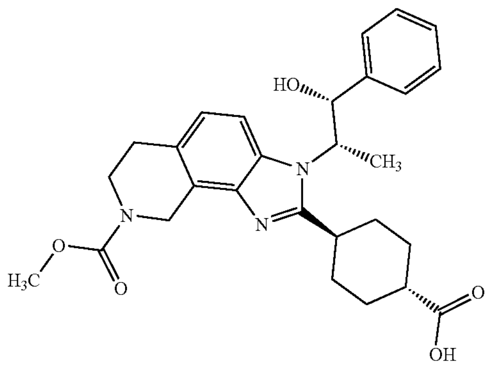 [SMILES: COC(=O)N1CCc2ccc3c(nc([C@H]4CC[C@H](C(=O)O)CC4)n3[C@@H](C)[C@H](O)c3ccccc3)c2C1] |
| 269 | 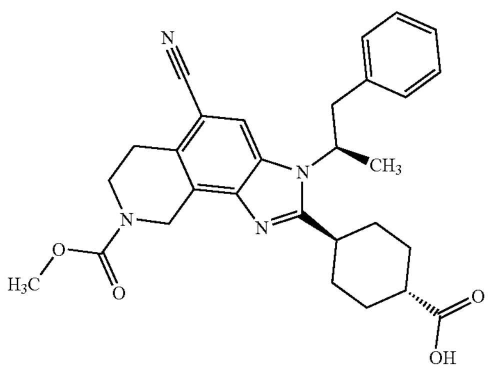 [SMILES: COC(=O)N1CCc2c(C#N)cc3c(nc([C@H]4CC[C@H](C(=O)O)CC4)n3[C@H](C)Cc3ccccc3)c2C1] |
| 270 | 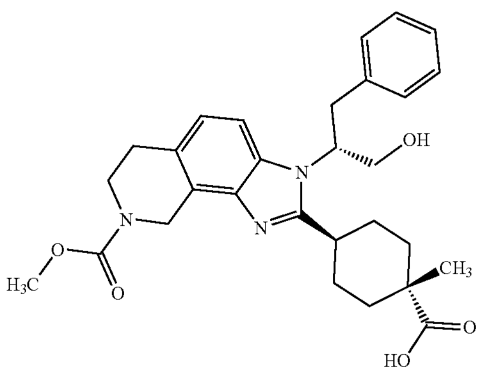 [SMILES: COC(=O)N1CCc2ccc3c(nc([C@H]4CC[C@](C)(C(=O)O)CC4)n3[C@@H](CO)Cc3ccccc3)c2C1] |
| 271 | 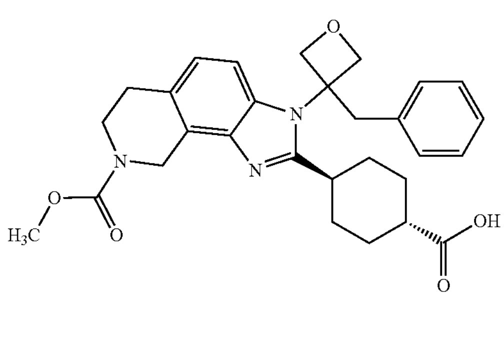 [SMILES: COC(=O)N1CCc2ccc3c(nc([C@H]4CC[C@H](C(=O)O)CC4)n3C3(Cc4ccccc4)COC3)c2C1] |

433
434
-continued
(Currently amended) A compound or a pharmaceutically acceptable salt thereof, wherein the compound is selected from
| Compound No. | Structure |
|---|---|
| 272 | 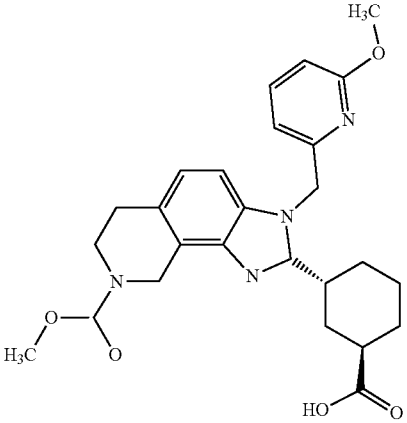 [SMILES: COCOCN1CCc2ccc3c(c2C1)NC([C@@H]1CCC[C@@H](C(=O)O)C1)N3Cc1cccc(OC)n1] |
| 273 | 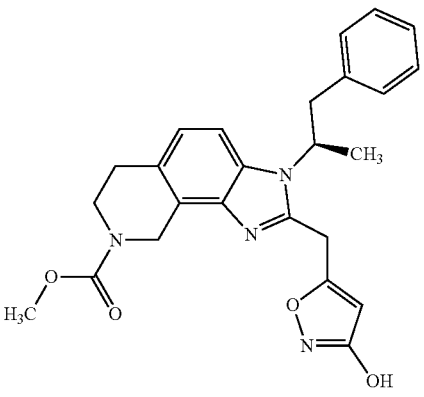 [SMILES: COC(=O)N1CCc2ccc3c(nc(Cc4cc(O)no4)n3[C@H](C)Cc3ccccc3)c2C1] |
| 274 | 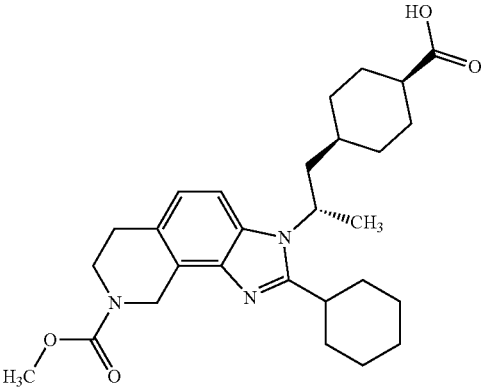 [SMILES: COC(=O)N1CCc2ccc3c(nc(C4CCCCC4)n3[C@@H](C)C[C@H]3CC[C@@H](C(=O)O)CC3)c2C1] |

-continued
(Currently amended) A compound or a pharmaceutically acceptable salt thereof, wherein the compound is selected from
| Compound No. | Structure |
|---|---|
| 275 | 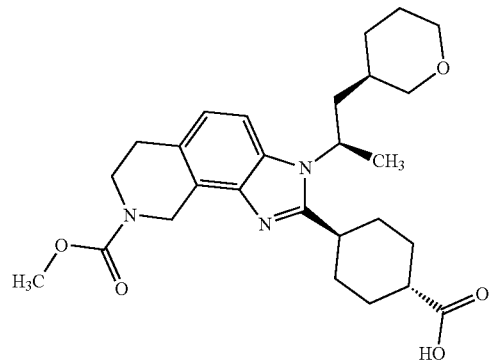 [SMILES: COC(=O)N1CCc2ccc3c(nc([C@H]4CC[C@H](C(=O)O)CC4)n3[C@H](C)C[C@H]3CCCOC3)c2C1] |
| 276 | 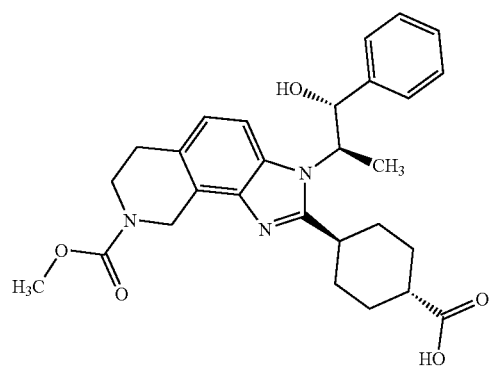 [SMILES: COC(=O)N1CCc2ccc3c(nc([C@H]4CC[C@H](C(=O)O)CC4)n3[C@H](C)[C@H](O)c3ccccc3)c2C1] |
| 277 | 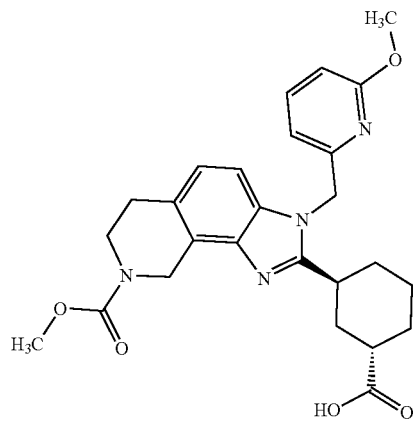 [SMILES: COC(=O)N1CCc2ccc3c(nc([C@H]4CCC[C@H](C(=O)O)C4)n3Cc3cccc(OC)n3)c2C1] |
| 278 | 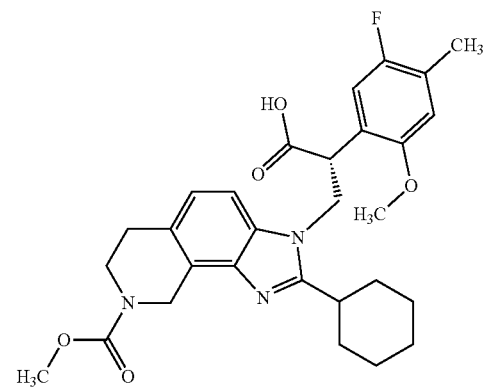 |

437
-continued
(Currently amended) A compound or a pharmaceutically acceptable salt thereof, wherein the compound is selected from
| Compound No. | Structure |
|---|---|
| 279 | 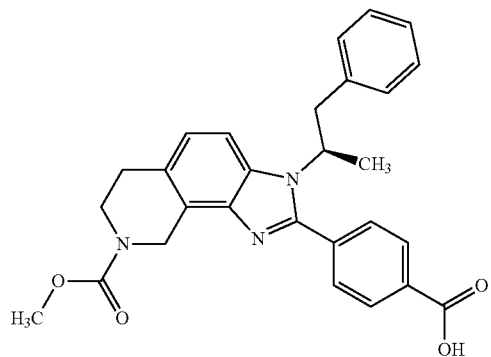 [SMILES: COC(=O)N1CCc2ccc3c(nc(-c4ccc(C(=O)O)cc4)n3[C@H](C)Cc3ccccc3)c2C1] |
| 280 | 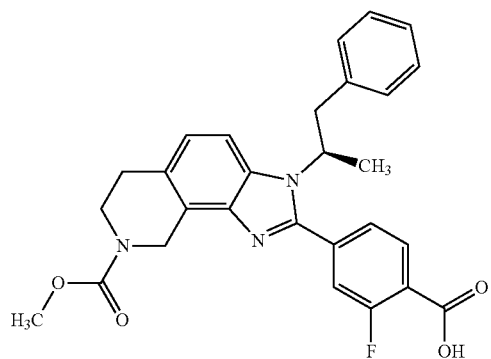 [SMILES: COC(=O)N1CCc2ccc3c(nc(-c4ccc(C(=O)O)c(F)c4)n3[C@H](C)Cc3ccccc3)c2C1] |
| 281 | 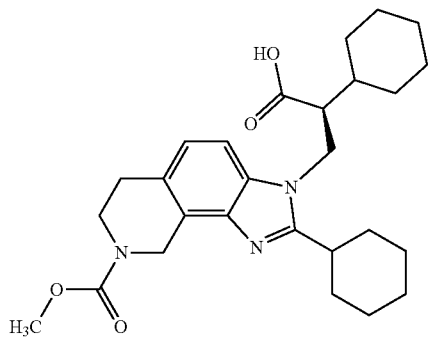 [SMILES: COC(=O)N1CCc2ccc3c(nc(C4CCCCC4)n3C[C@@H](C(=O)O)C3CCCCC3)c2C1] |
| 282 | 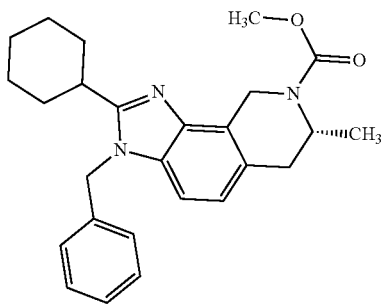 [SMILES: COC(=O)N1Cc2c(ccc3c2nc(C2CCCCC2)n3Cc2ccccc2)C[C@H]1C] |

439 440
-continued
(Currently amended) A compound or a pharmaceutically acceptable salt thereof, wherein the compound is selected from
| Compound No. | Structure |
|---|---|
| 283 | 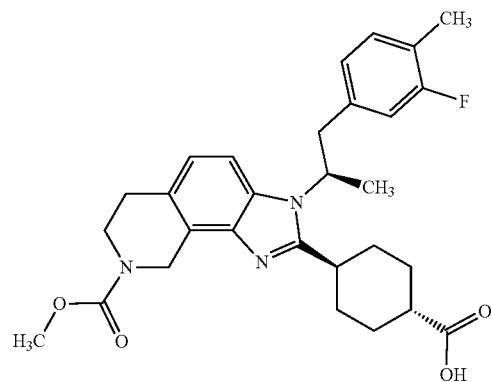 [SMILES: COC(=O)N1CCc2ccc3c(nc([C@H]4CC[C@H](C(=O)O)CC4)n3[C@H](C)Cc3ccc(C)c(F)c3)c2C1] |
| 284 | 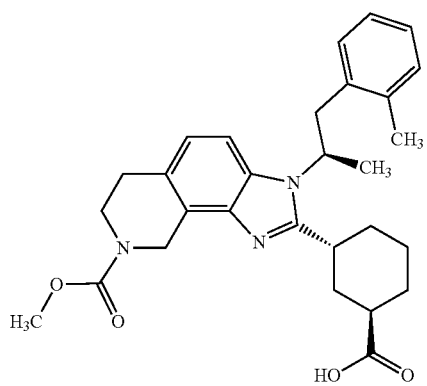 [SMILES: COC(=O)N1CCc2ccc3c(nc([C@@H]4CCC[C@@H](C(=O)O)C4)n3[C@H](C)Cc3ccccc3C)c2C1] |
| 285 | 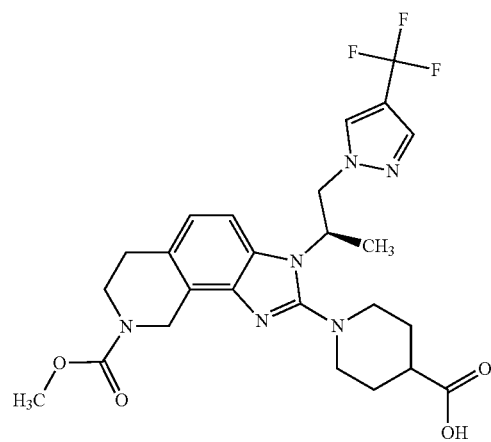 [SMILES: COC(=O)N1CCc2ccc3c(nc(N4CCC(C(=O)O)CC4)n3[C@H](C)Cn3cc(C(F)(F)F)cn3)c2C1] |

441
(Currently amended) A compound or a pharmaceutically acceptable salt thereof, wherein the compound is selected from
| Compound No. | Structure |
|---|---|
| 286 | 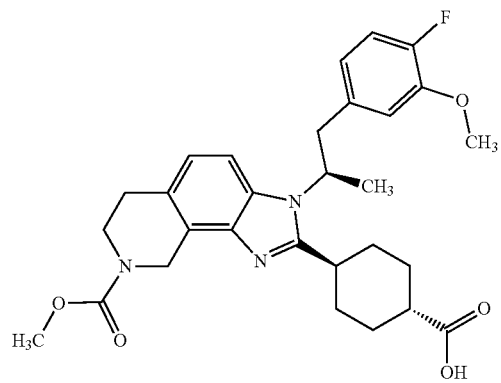 [SMILES: COC(=O)N1CCc2ccc3c(nc([C@H]4CC[C@H](C(=O)O)CC4)n3[C@H](C)Cc3ccc(F)c(OC)c3)c2C1] |
| 287 | 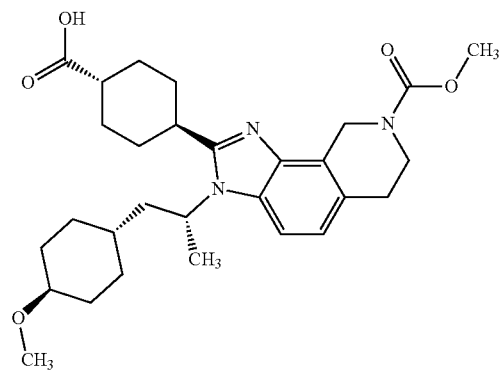 [SMILES: COC(=O)N1CCc2ccc3c(nc([C@H]4CC[C@H](C(=O)O)CC4)n3[C@H](C)C[C@H]3CC[C@H](OC)CC3)c2C1] |
| 288 | 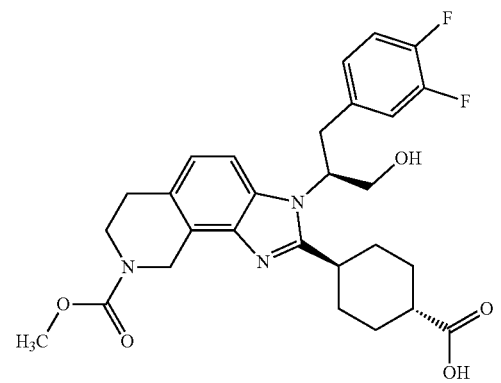 [SMILES: COC(=O)N1CCc2ccc3c(nc([C@H]4CC[C@H](C(=O)O)CC4)n3[C@H](CO)Cc3ccc(F)c(F)c3)c2C1] |
| 289 | 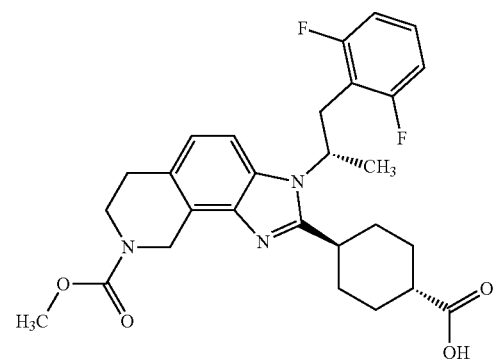 [SMILES: COC(=O)N1CCc2ccc3c(nc([C@H]4CC[C@H](C(=O)O)CC4)n3[C@@H](C)Cc3c(F)cccc3F)c2C1] |

(Currently amended) A compound or a pharmaceutically acceptable salt thereof, wherein the compound is selected from
| Compound No. | Structure |
|---|---|
| 290 | 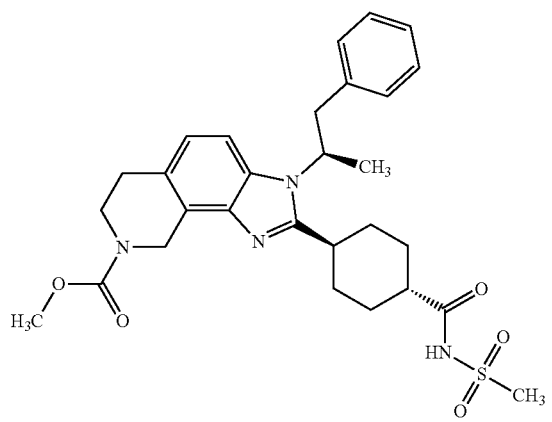 |
| 291 | 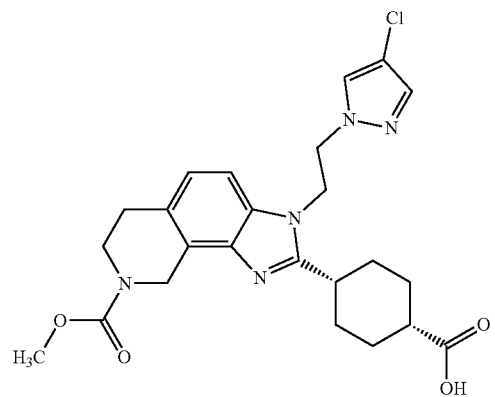 [SMILES: COC(=O)N1CCc2ccc3c(nc([C@H]4CC[C@@H](C(=O)O)CC4)n3CCn3cc(Cl)cn3)c2C1] |
| 292 | 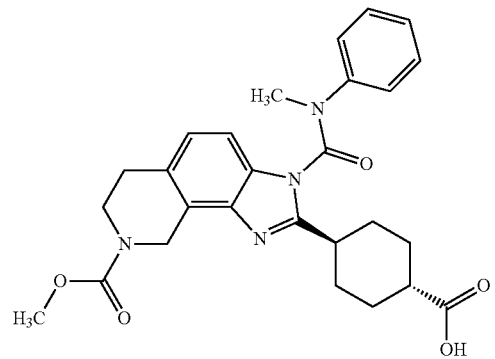 [SMILES: COC(=O)N1CCc2ccc3c(nc([C@H]4CC[C@H](C(=O)O)CC4)n3C(=O)N(C)c3ccccc3)c2C1] |

(Currently amended) A compound or a pharmaceutically acceptable salt thereof, wherein the compound is selected from
| Compound No. | Structure |
|---|---|
| 293 | 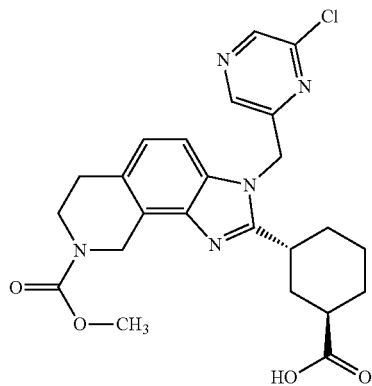 [SMILES: COC(=O)N1CCc2ccc3c(nc([C@@H]4CCC[C@@H](C(=O)O)C4)n3Cc3cncc(Cl)n3)c2C1] |
| 294 | 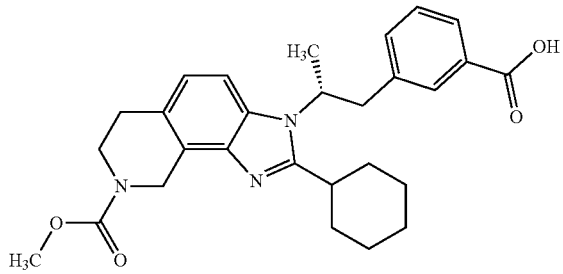 [SMILES: COC(=O)N1CCc2ccc3c(nc(C4CCCCC4)n3[C@H](C)Cc3cccc(C(=O)O)c3)c2C1] |
| 295 | 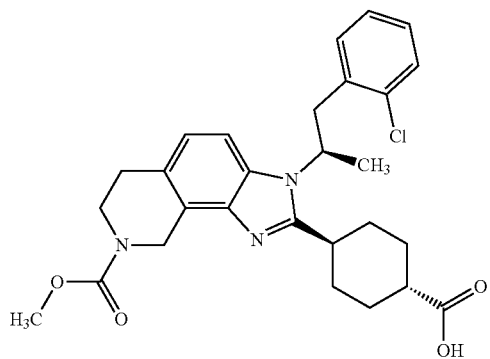 |
| 296 | 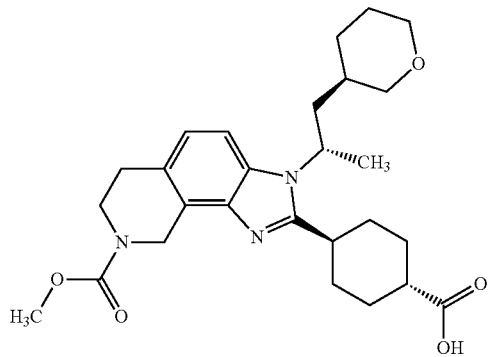 |

-continued
(Currently amended) A compound or a pharmaceutically acceptable salt thereof, wherein the compound is selected from
| Compound No. | Structure |
|---|---|
| 297 | 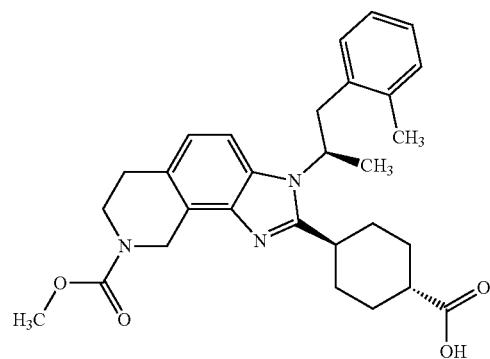 |
| 298 | 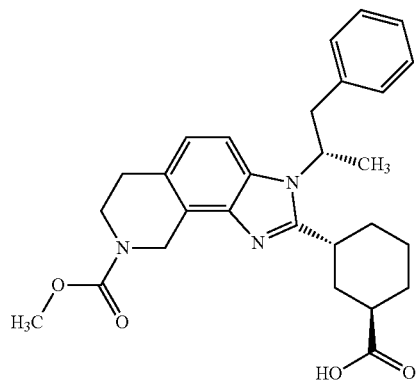 [SMILES: COC(=O)N1CCc2ccc3c(nc([C@@H]4CCC[C@@H](C(=O)O)C4)n3[C@@H](C)Cc3ccccc3)c2C1] |
| 299 | 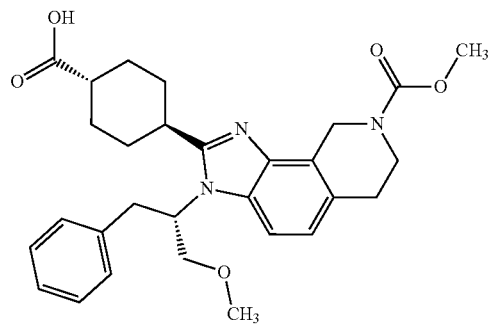 [SMILES: COC[C@H](Cc1ccccc1)n1c2ccc3c(c2nc1[C@H]1CC[C@H](C(=O)O)CC1)CN(C(=O)OC)CC3] |
| 300 | 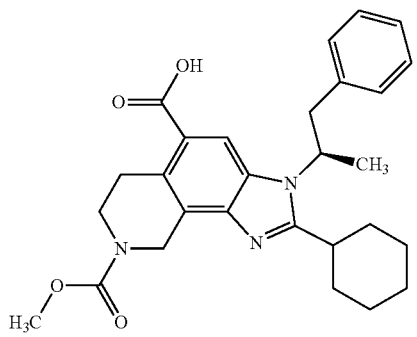 |

-continued
(Currently amended) A compound or a pharmaceutically acceptable salt thereof, wherein the compound is selected from
| Compound No. | Structure |
|---|---|
| 301 | 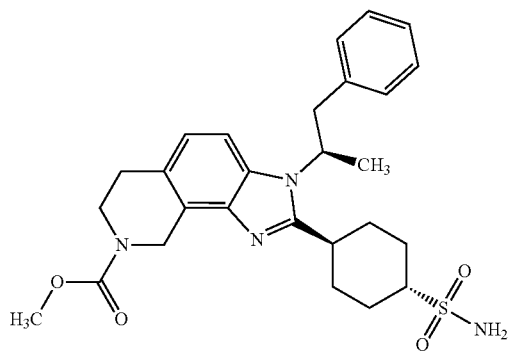 [SMILES: COC(=O)N1CCc2ccc3c(nc([C@H]4CC[C@H](S(N)(=O)=O)CC4)n3[C@H](C)Cc3ccccc3)c2C1] |
| 302 | 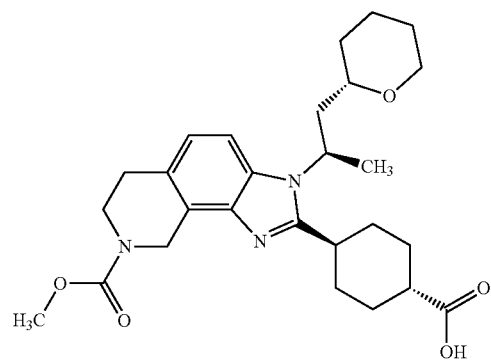 |
| 303 | 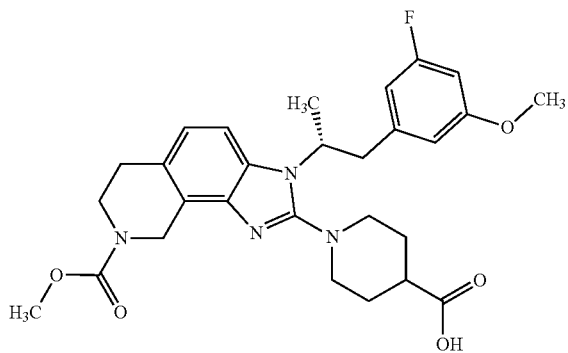 |
| 304 | 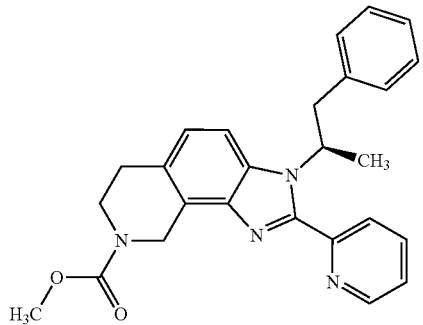 [SMILES: COC(=O)N1CCc2ccc3c(nc(-c4ccccn4)n3[C@H](C)Cc3ccccc3)c2C1] |

-continued
(Currently amended) A compound or a pharmaceutically acceptable salt thereof, wherein the compound is selected from
| Compound No. | Structure |
|---|---|
| 305 | 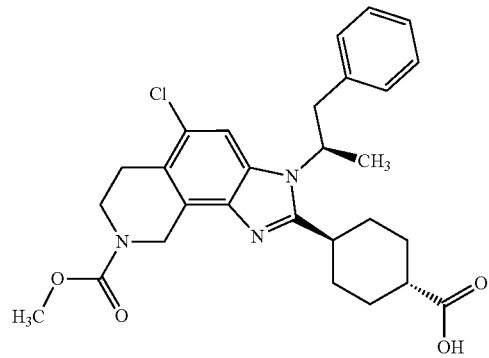 [SMILES: COC(=O)N1CCc2c(Cl)cc3c(nc([C@H]4CC[C@H](C(=O)O)CC4)n3[C@H](C)Cc3ccccc3)c2C1] |
| 306 | 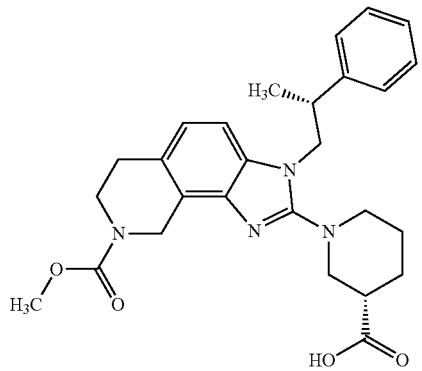 [SMILES: COC(=O)N1CCc2ccc3c(nc(N4CCC[C@H](C(=O)O)C4)n3C[C@H](C)c3ccccc3)c2C1] |
| 307 | 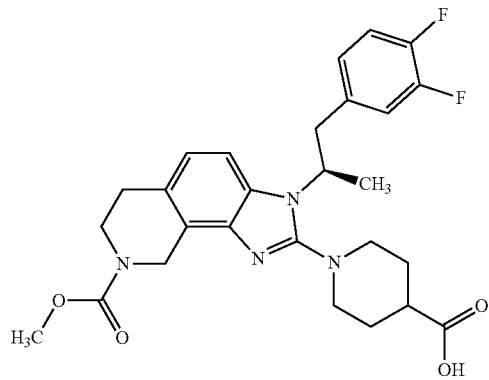 [SMILES: COC(=O)N1CCc2ccc3c(nc(N4CCC(C(=O)O)CC4)n3[C@H](C)Cc3ccc(F)c(F)c3)c2C1] |
| 308 | 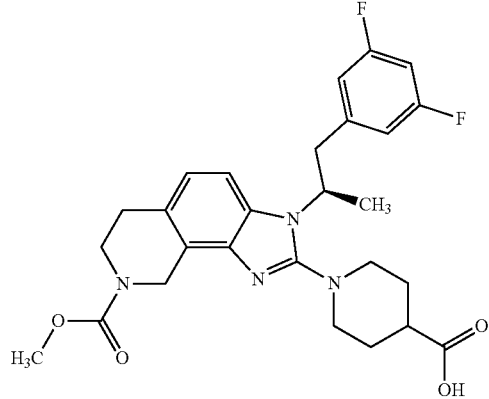 [SMILES: COC(=O)N1CCc2ccc3c(nc(N4CCC(C(=O)O)CC4)n3[C@H](C)Cc3cc(F)cc(F)c3)c2C1] |

453
-continued
(Currently amended) A compound or a pharmaceutically acceptable salt thereof, wherein the compound is selected from
| Compound No. | Structure |
|---|---|
| 309 | 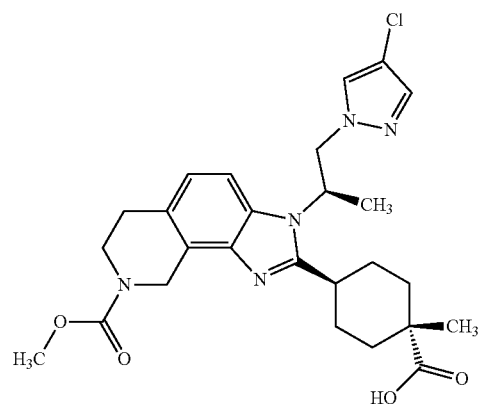 [SMILES: COC(=O)N1CCc2ccc3c(nc([C@H]4CC[C@](C)(C(=O)O)CC4)n3[C@H](C)Cn3cc(Cl)cn3)c2C1] |
| 310 | 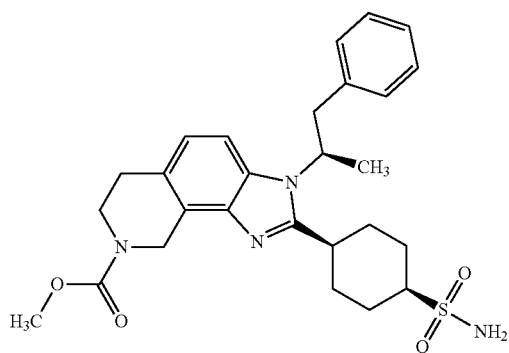 [SMILES: COC(=O)N1CCc2ccc3c(nc([C@H]4CC[C@@H](S(N)(=O)=O)CC4)n3[C@H](C)Cc3ccccc3)c2C1] |
| 311 | 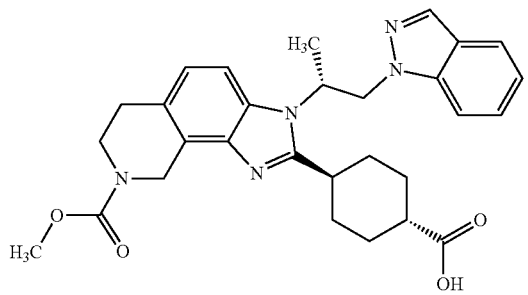 [SMILES: COC(=O)N1CCc2ccc3c(nc([C@H]4CC[C@H](C(=O)O)CC4)n3[C@H](C)Cn3ncc4ccccc43)c2C1] |
| 312 | 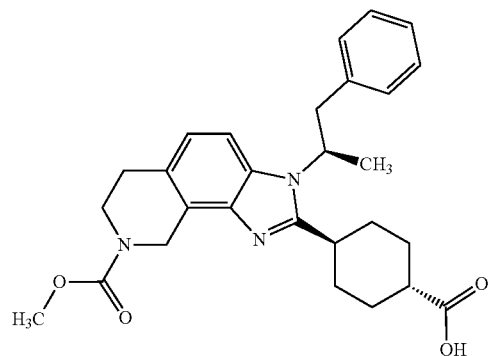 |

-continued
(Currently amended) A compound or a pharmaceutically acceptable salt thereof, wherein the compound is selected from
| Compound No. | Structure |
|---|---|
| 313 | 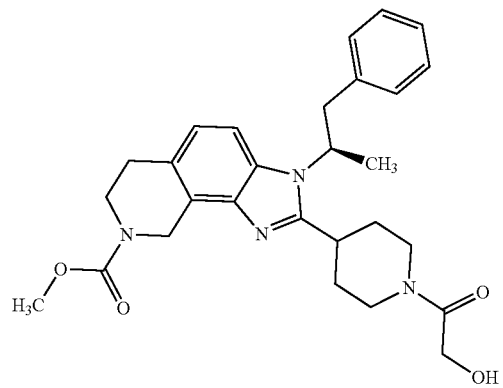 [SMILES: COC(=O)N1CCc2ccc3c(nc(C4CCN(C(=O)CO)CC4)n3[C@H](C)Cc3ccccc3)c2C1] |
| 314 | 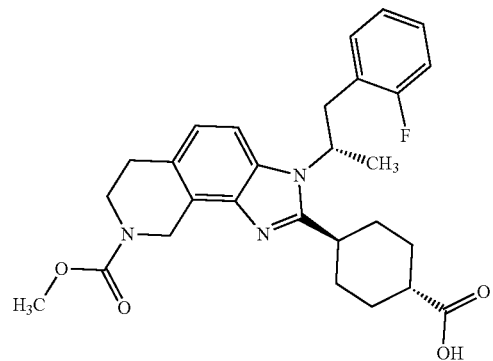 [SMILES: COC(=O)N1CCc2ccc3c(nc([C@H]4CC[C@H](C(=O)O)CC4)n3[C@@H](C)Cc3ccccc3F)c2C1] |
| 315 | 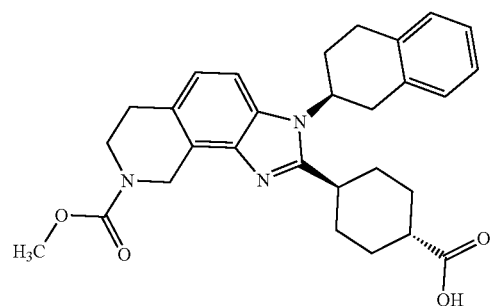 [SMILES: COC(=O)N1CCc2ccc3c(nc([C@H]4CC[C@H](C(=O)O)CC4)n3[C@H]3CCc4ccccc4C3)c2C1] |
| 316 | 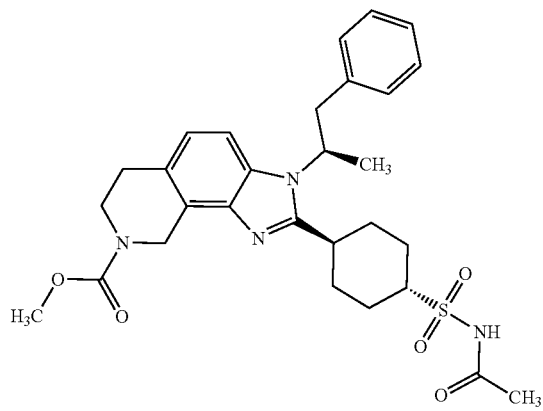 [SMILES: COC(=O)N1CCc2ccc3c(nc([C@H]4CC[C@H](S(=O)(=O)NC(C)=O)CC4)n3[C@H](C)Cc3ccccc3)c2C1] |

(Currently amended) A compound or a pharmaceutically acceptable salt thereof, wherein the compound is selected from
| Compound No. | Structure |
|---|---|
| 317 | 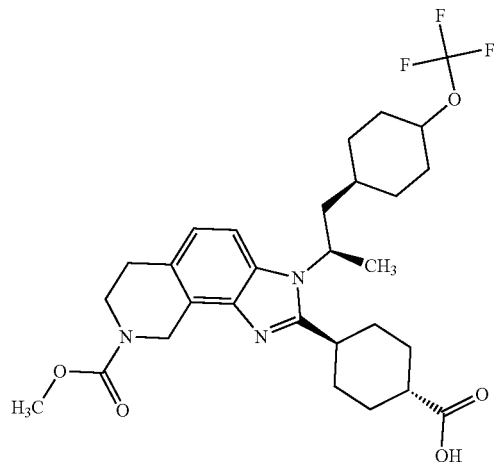 |
| 318 | 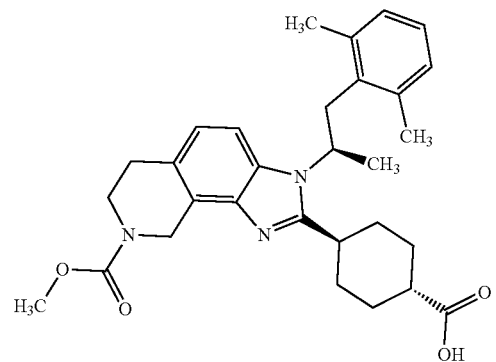 [SMILES: COC(=O)N1CCc2ccc3c(nc([C@H]4CC[C@H](C(=O)O)CC4)n3[C@H](C)Cc3c(C)cccc3C)c2C1] |
| 319 | 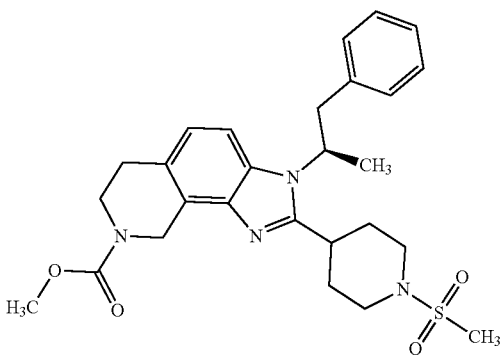 |

-continued
(Currently amended) A compound or a pharmaceutically acceptable salt thereof, wherein the compound is selected from
| Compound No. | Structure |
|---|---|
| 320 | 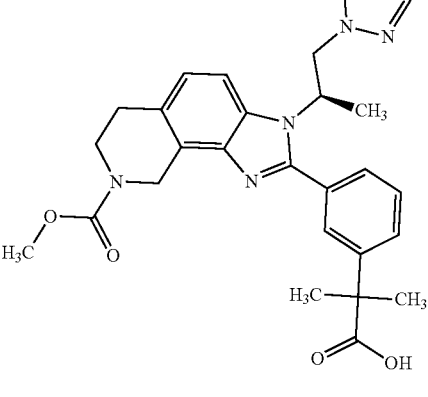 |
| 321 | 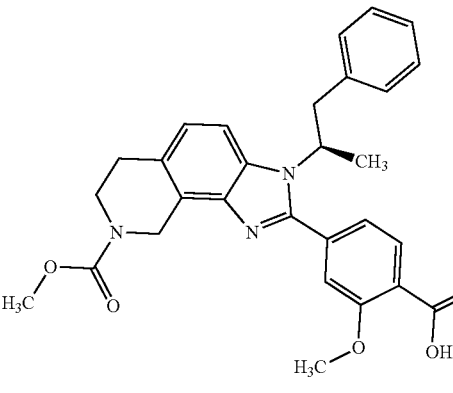 |
| 322 | 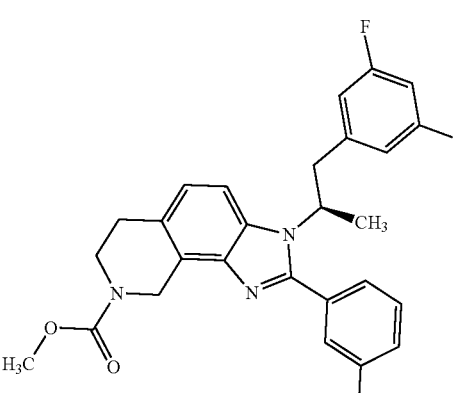 |

461                                                                462
-continued (Currently amended) A compound or a pharmaceutically
acceptable salt thereof, wherein the compound is selected from

| Compound No. | Structure |
|---|---|
| 323 | 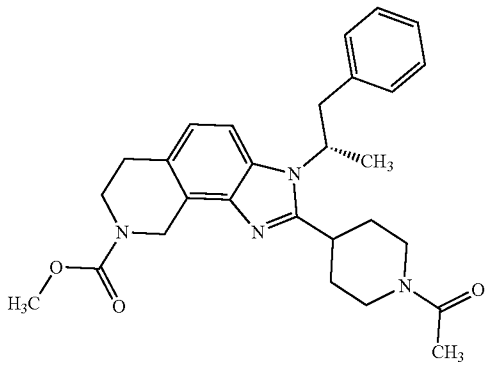 [SMILES: COC(=O)N1CCc2ccc3c(nc(N4CCN(C(C)=O)CC4)n3[C@@H](C)Cc3ccccc3)c2C1] |
| 324 | 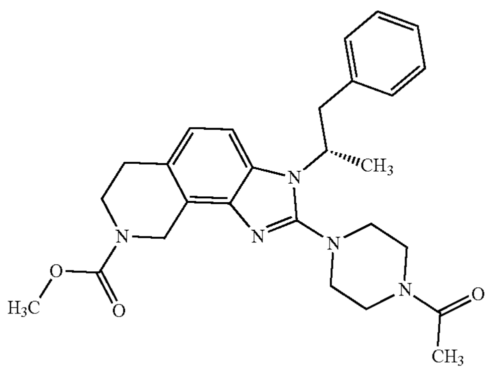 |
| 325 | 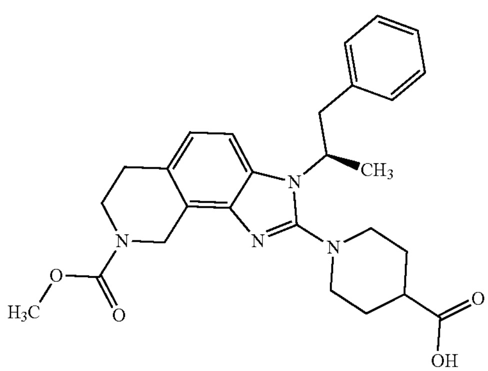 [SMILES: COC(=O)N1CCc2ccc3c(nc(N4CCC(C(=O)O)CC4)n3[C@H](C)Cc3ccccc3)c2C1] |
| 326 | 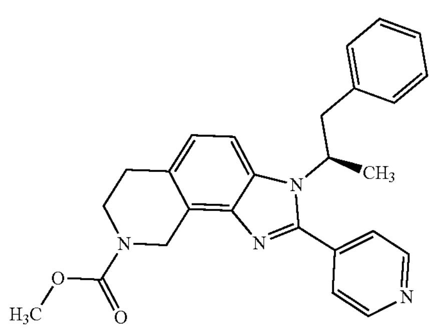 [SMILES: COC(=O)N1CCc2ccc3c(nc(-c4ccncc4)n3[C@H](C)Cc3ccccc3)c2C1] |

-continued (Currently amended) A compound or a pharmaceutically acceptable salt thereof, wherein the compound is selected from

| Compound No. | Structure |
|---|---|
| 327 | 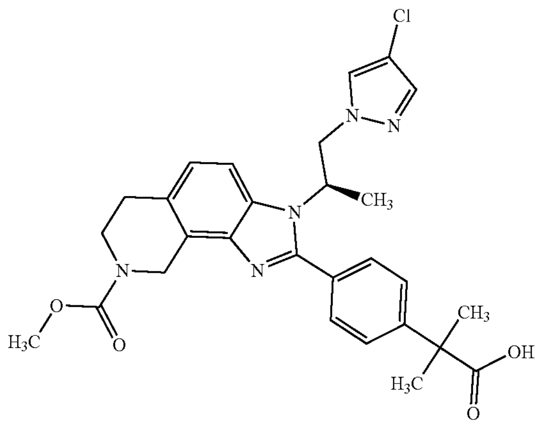 [SMILES: COC(=O)N1CCc2ccc3c(nc(-c4ccc(C(C)(C)C(=O)O)cc4)n3[C@H](C)Cn3cc(Cl)cn3)c2C1] |
| 328 | 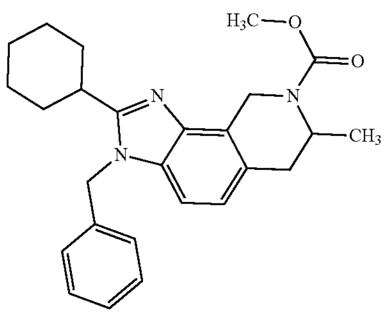 [SMILES: COC(=O)N1Cc2c(ccc3c2nc(C2CCCCC2)n3Cc2ccccc2)CC1C] |
| 329 | 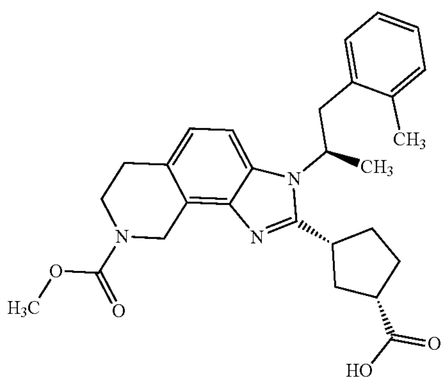 [SMILES: COC(=O)N1CCc2ccc3c(nc([C@@H]4CC[C@H](C(=O)O)C4)n3[C@H](C)Cc3ccccc3C)c2C1] |
| 330 | 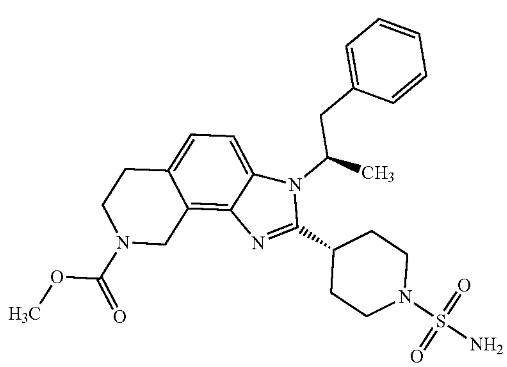 |

-continued
(Currently amended) A compound or a pharmaceutically acceptable salt thereof, wherein the compound is selected from
| Compound No. | Structure |
|---|---|
| 331 | 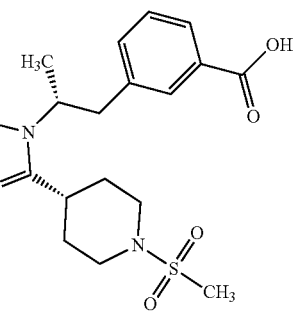 |
| 332 | 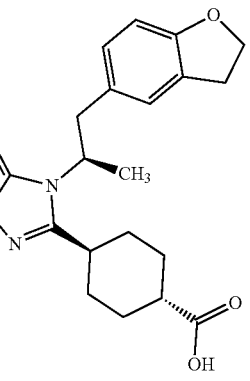 |
| 333 | 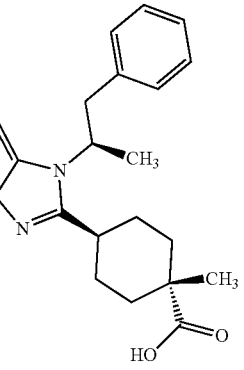 |
| 334 | 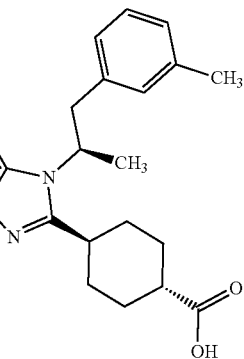 |

-continued (Currently amended) A compound or a pharmaceutically acceptable salt thereof, wherein the compound is selected from

| Compound No. | Structure |
|---|---|
| 335 | 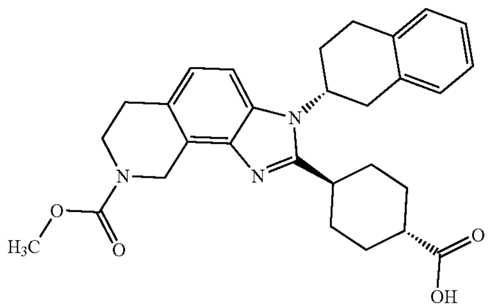 [SMILES: COC(=O)N1CCc2ccc3c(nc([C@H]4CC[C@H](C(=O)O)CC4)n3[C@@H]3CCc4ccccc4C3)c2C1] |
| 336 | 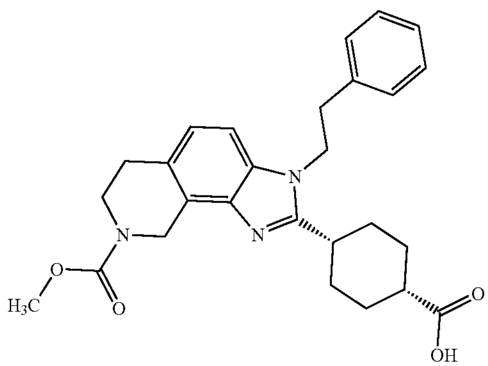 [SMILES: COC(=O)N1CCc2ccc3c(nc([C@H]4CC[C@@H](C(=O)O)CC4)n3CCc3ccccc3)c2C1] |
| 337 | 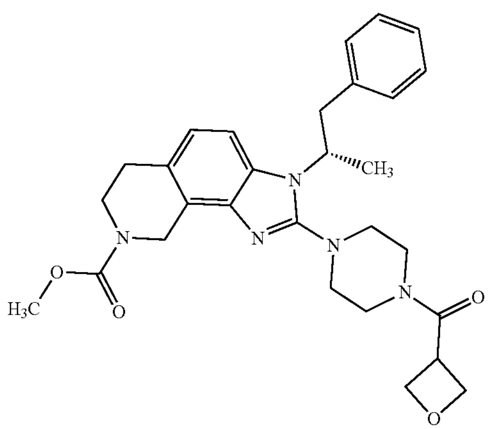 [SMILES: COC(=O)N1CCc2ccc3c(nc(N4CCN(C(=O)C5COC5)CC4)n3[C@@H](C)Cc3ccccc3)c2C1] |
| 338 | 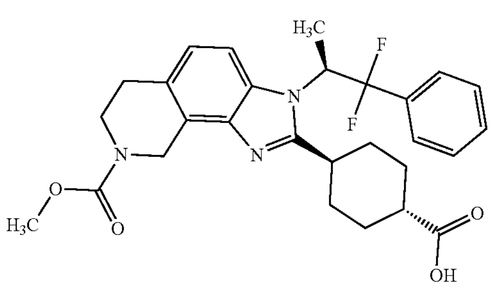 [SMILES: COC(=O)N1CCc2ccc3c(nc([C@H]4CC[C@H](C(=O)O)CC4)n3[C@@H](C)C(F)(F)c3ccccc3)c2C1] |

-continued (Currently amended) A compound or a pharmaceutically acceptable salt thereof, wherein the compound is selected from

| Compound No. | Structure |
|---|---|
| 339 | 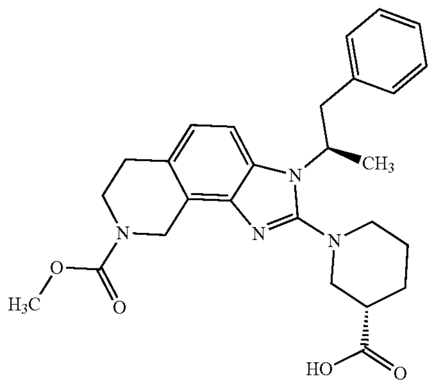 [SMILES: COC(=O)N1CCc2ccc3c(nc(N4CCC[C@H](C(=O)O)C4)n3[C@H](C)Cc3ccccc3)c2C1] |
| 340 | 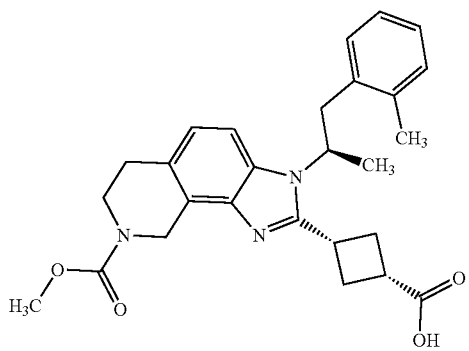 [SMILES: COC(=O)N1CCc2ccc3c(nc([C@H]4C[C@@H](C(=O)O)C4)n3[C@H](C)Cc3ccccc3C)c2C1] |
| 341 | 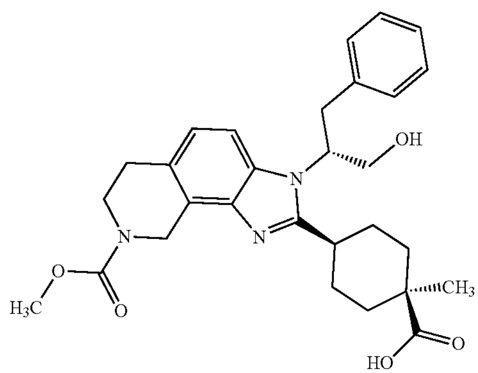 [SMILES: COC(=O)N1CCc2ccc3c(nc([C@H]4CC[C@@](C)(C(=O)O)CC4)n3[C@@H](CO)Cc3ccccc3)c2C1] |
| 342 | 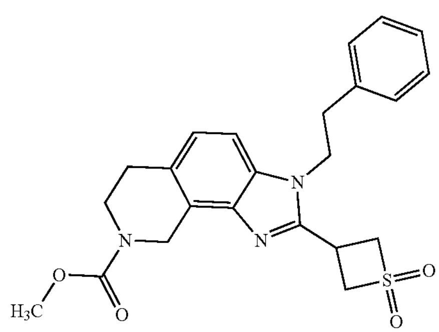 [SMILES: COC(=O)N1CCc2ccc3c(nc(C4CS(=O)(=O)C4)n3CCc3ccccc3)c2C1] |

-continued
(Currently amended) A compound or a pharmaceutically acceptable salt thereof, wherein the compound is selected from
| Compound No. | Structure |
|---|---|
| 343 | 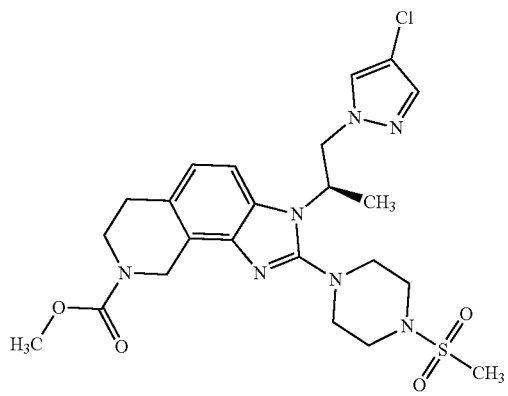 |
| 344 | 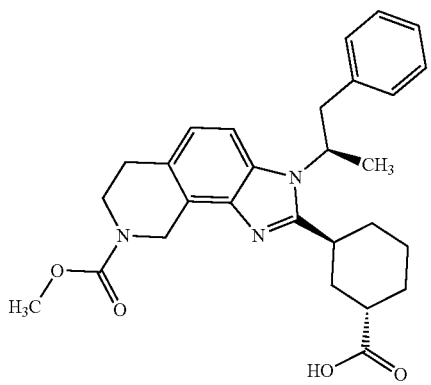 [SMILES: COC(=O)N1CCc2ccc3c(nc([C@H]4CCC[C@H](C(=O)O)C4)n3[C@H](C)Cc3ccccc3)c2C1] |
| 345 | 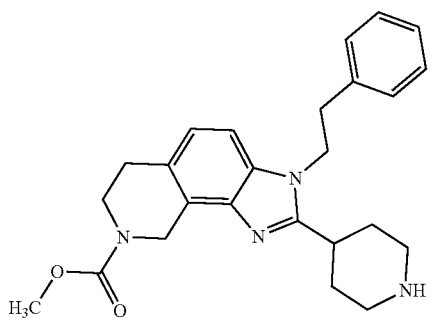 [SMILES: COC(=O)N1CCc2ccc3c(nc(C4CCNCC4)n3CCc3ccccc3)c2C1] |
| 346 | 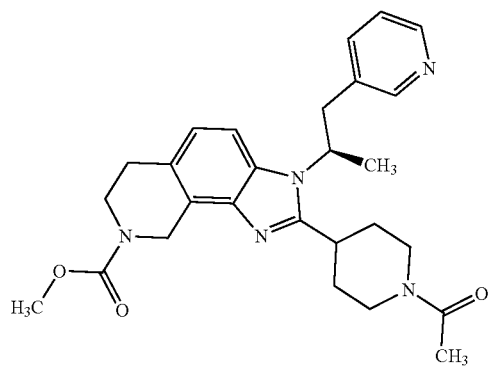 [SMILES: COC(=O)N1CCc2ccc3c(nc(C4CCN(C(C)=O)CC4)n3[C@H](C)Cc3cccnc3)c2C1] |

-continued
(Currently amended) A compound or a pharmaceutically acceptable salt thereof, wherein the compound is selected from
| Compound No. | Structure |
|---|---|
| 347 | 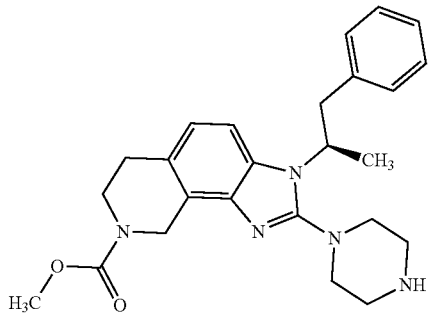 [SMILES: COC(=O)N1CCc2ccc3c(nc(N4CCNCC4)n3[C@H](C)Cc3ccccc3)c2C1] |
| 348 | 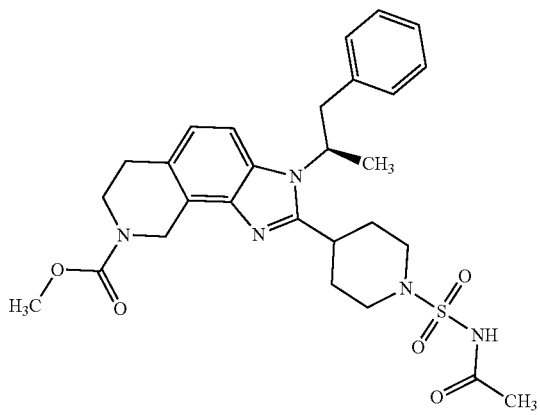 [SMILES: COC(=O)N1CCc2ccc3c(nc(C4CCN(S(=O)(=O)NC(C)=O)CC4)n3[C@H](C)Cc3ccccc3)c2C1] |
| 349 | 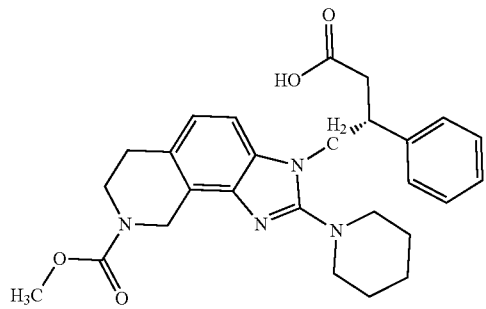 [SMILES: COC(=O)N1CCc2ccc3c(nc(N4CCCCC4)n3C[C@H](CC(=O)O)c3ccccc3)c2C1] |
| 350 | 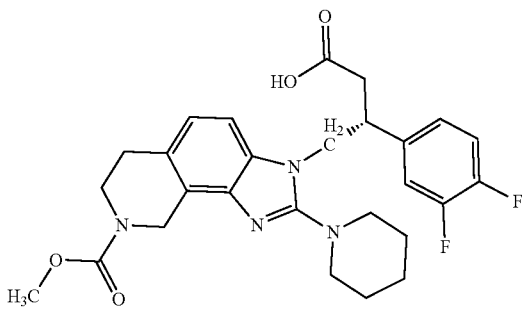 [SMILES: COC(=O)N1CCc2ccc3c(nc(N4CCCCC4)n3C[C@H](CC(=O)O)c3ccc(F)c(F)c3)c2C1] |

(Currently amended) A compound or a pharmaceutically acceptable salt thereof, wherein the compound is selected from
| Compound No. | Structure |
|---|---|
| 351 | 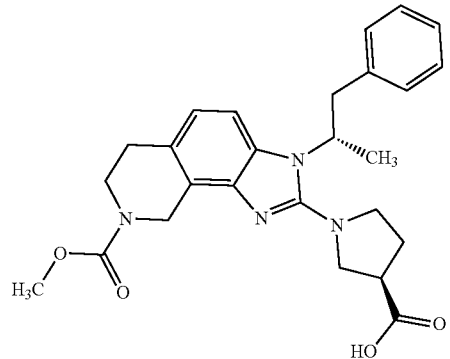 [SMILES: COC(=O)N1CCc2ccc3c(nc(N4CC[C@@H](C(=O)O)C4)n3[C@@H](C)Cc3ccccc3)c2C1] |
| 352 | 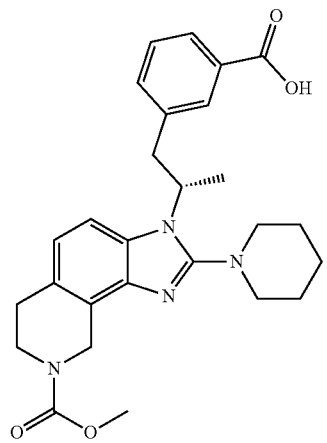 [SMILES: COC(=O)N1CCc2ccc3c(nc(N4CCCCC4)n3[C@@H](C)Cc3cccc(C(=O)O)c3)c2C1] |
| 353 | 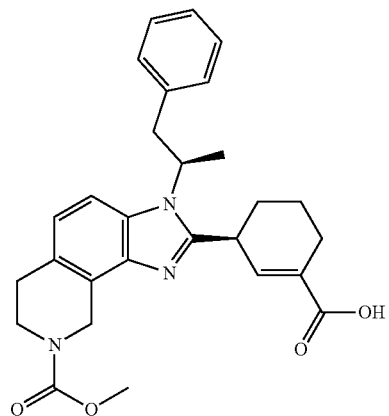 [SMILES: COC(=O)N1CCc2ccc3c(nc([C@@H]4C=C(C(=O)O)CCC4)n3[C@H](C)Cc3ccccc3)c2C1] |

(Currently amended) A compound or a pharmaceutically acceptable salt thereof, wherein the compound is selected from
| Compound No. | Structure |
|---|---|
| 354 | 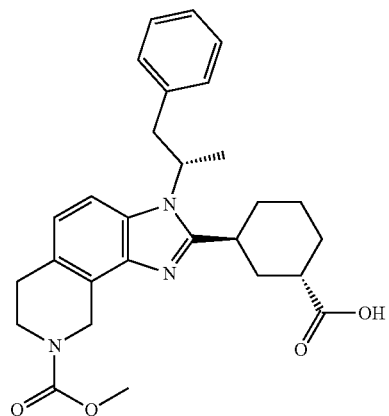 [SMILES: COC(=O)N1CCc2ccc3c(nc([C@H]4CCC[C@H](C(=O)O)C4)n3[C@@H](C)Cc3ccccc3)c2C1] |
| 355 | 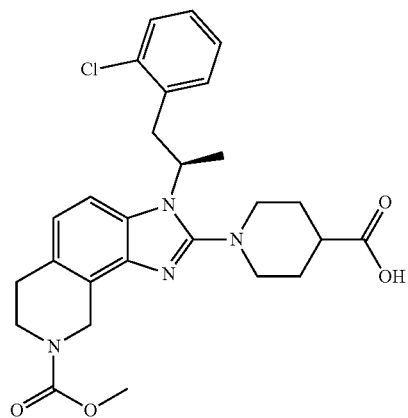 [SMILES: COC(=O)N1CCc2ccc3c(nc(N4CCC(C(=O)O)CC4)n3[C@H](C)Cc3ccccc3Cl)c2C1] |
| 356 | 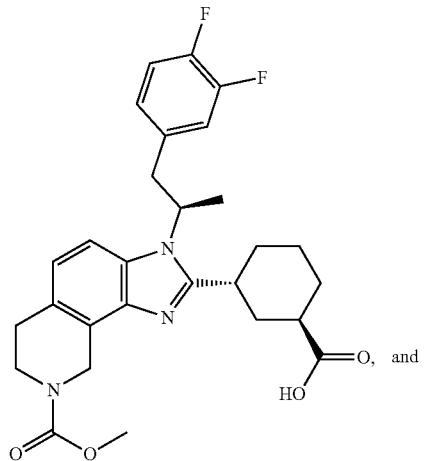 [SMILES: COC(=O)N1CCc2ccc3c(nc([C@@H]4CCC[C@@H](C(=O)O)C4)n3[C@H](C)Cc3ccc(F)c(F)c3)c2C1], and |

| | (Currently amended) A compound or a pharmaceutically acceptable salt thereof, wherein the compound is selected from |
|---|---|
| Compound No. | Structure |
| 357 | [Structure: a tetrahydroisoquinoline fused benzimidazole bearing an N-substituent of (S)-1-(3,4-difluorophenyl)propan-2-yl, a 2-substituent of (1S,3R)-3-carboxycyclohexyl, and the tetrahydroisoquinoline nitrogen carrying a methoxycarbonyl (methyl carbamate) group] |

* * * * *

UNITED STATES PATENT AND TRADEMARK OFFICE
CERTIFICATE OF CORRECTION

| | | |
|---|---|---|
| PATENT NO. | : 12,351,577 B2 | Page 1 of 1 |
| APPLICATION NO. | : 17/439646 | |
| DATED | : July 8, 2025 | |
| INVENTOR(S) | : Schiller et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 722 days.

Signed and Sealed this
Sixteenth Day of December, 2025

John A. Squires
*Director of the United States Patent and Trademark Office*